(12) United States Patent
Londesbrough et al.

(10) Patent No.: US 12,377,112 B2
(45) Date of Patent: Aug. 5, 2025

(54) METHODS OF TREATING NEUROCOGNITIVE DISORDERS, CHRONIC PAIN AND REDUCING INFLAMMATION

(71) Applicant: COMPASS PATHFINDER LIMITED, Altrincham (GB)

(72) Inventors: Derek John Londesbrough, Hartlepool (GB); Christopher Brown, Gateshead (GB); Julian Scott Northen, South Shields (GB); Gillian Moore, Sedgefield (GB); Hemant Kashinath Patil, Surrey (GB); David E. Nichols, Chapel Hill, NC (US); Hans Ake Eriksson, Altrincham (GB); George Goldsmith, Altrincham (GB); Ekaterina Malievskaia, Altrincham (GB); Manon Cecile Elisabeth Veraart, Altrincham (GB); Tobias Patrick Whelan, Altrincham (GB); Lars Christian Wilde, Altrincham (GB)

(73) Assignee: Compass Pathfinder Limited, Altrincham (GB)

( * ) Notice: Subject to any disclaimer, the term of this patent is extended or adjusted under 35 U.S.C. 154(b) by 871 days.

(21) Appl. No.: 17/604,606

(22) PCT Filed: Apr. 17, 2020

(86) PCT No.: PCT/IB2020/053684
§ 371 (c)(1),
(2) Date: Oct. 18, 2021

(87) PCT Pub. No.: WO2020/212948
PCT Pub. Date: Oct. 22, 2020

(65) Prior Publication Data
US 2022/0169668 A1    Jun. 2, 2022

Related U.S. Application Data

(60) Provisional application No. 62/946,159, filed on Dec. 10, 2019, provisional application No. 62/893,611, (Continued)

(51) Int. Cl.
| | | |
|---|---|---|
| *A61K 31/675* | (2006.01) | |
| *A61K 9/00* | (2006.01) | |
| *A61K 9/20* | (2006.01) | |
| *A61K 9/48* | (2006.01) | |
| *A61K 31/661* | (2006.01) | |
| *A61P 25/00* | (2006.01) | |

(Continued)

(52) U.S. Cl.
CPC .......... *A61K 31/675* (2013.01); *A61K 9/0053* (2013.01); *A61K 9/20* (2013.01); *A61K 9/48* (2013.01); *A61K 31/661* (2013.01); *A61P 25/00* (2018.01); *A61P 25/04* (2018.01); *A61P 25/08* (2018.01); *A61P 25/16* (2018.01); *A61P 25/20* (2018.01); *A61P 25/22* (2018.01); *A61P 25/24* (2018.01); *A61P 25/28* (2018.01); *C07F 9/5728* (2013.01); *C07B 2200/13* (2013.01)

(58) Field of Classification Search
CPC ...... A61K 31/675; A61K 9/0053; A61K 9/20; A61K 9/48; A61K 31/661; A61K 45/06; A61P 25/00; A61P 25/04; A61P 25/08; A61P 25/16; A61P 25/20; A61P 25/22; A61P 25/24; A61P 25/28; A61P 31/4045; A61P 1/00; A61P 25/06; A61P 25/30; A61P 29/00; A61P 9/10; A61P 1/04; A61P 1/12; A61P 1/16; A61P 3/10; A61P 9/12; A61P 11/00; A61P 17/00; A61P 19/04; A61P 25/18; A61P 37/08; C07F 9/5728; C07B 2200/13
See application file for complete search history.

(56) References Cited

U.S. PATENT DOCUMENTS

| | | |
|---|---|---|
| 3,075,992 A | 1/1963 | Albert et al. |
| 3,183,172 A | 5/1965 | Roger et al. |

(Continued)

FOREIGN PATENT DOCUMENTS

| | | |
|---|---|---|
| AU | 2016208412 A1 | 8/2016 |
| AU | 2018203524 A1 | 6/2018 |

(Continued)

OTHER PUBLICATIONS

Howard Jacobs, Samata Singhi, Jack Gladstein,Medical Comorbidities in Pediatric Headache,Seminars in Pediatric Neurology, vol. 23, Issue 1,2016,pp. 60-67,ISSN 1071-9091, https://doi.org/10.1016/j.spen.2016.02.001. (Year: 2016).*
White SW, Oswald D, Ollendick T, Scahill L. Anxiety in children and adolescents with autism spectrum disorders. Clin Psychol Rev. Apr. 2009;29(3):216-29. doi: 10.1016/j.cpr.2009.01.003. Epub Jan. 25, 2009. PMID: 19223098; PMCID: PMC2692135. (Year: 2009).*
https://www.medicalnewstoday.com/articles/315303 Written by Jayne Leonard on May 15, 2017 (Year: 2017).*

(Continued)

*Primary Examiner* — Joseph K McKane
*Assistant Examiner* — Anna Grace Kuckla
(74) *Attorney, Agent, or Firm* — COOLEY LLP

(57) ABSTRACT

The disclosure provides methods for treating a subject in need thereof comprising administering to the subject a therapeutically-effective dose of psilocybin. The methods described herein may be used to treat a variety of diseases, disorders, and conditions. For example, the methods may be used to treat neurocognitive disorders (e.g., Alzheimer's disease, Parkinson's disease), ADHD, Epilepsy, Autism, Sleep-wake disorders, Chronic pain, Inflammatory Disorders, IBD, Stroke, ALS, and/or Multiple Sclerosis.

27 Claims, 96 Drawing Sheets

Related U.S. Application Data filed on Aug. 29, 2019, provisional application No. 62/893,110, filed on Aug. 28, 2019, provisional application No. 62/835,480, filed on Apr. 17, 2019, provisional application No. 62/835,478, filed on Apr. 17, 2019, provisional application No. 62/835,460, filed on Apr. 17, 2019, provisional application No. 62/835,458, filed on Apr. 17, 2019, provisional application No. 62/835,479, filed on Apr. 17, 2019, provisional application No. 62/835,476, filed on Apr. 17, 2019, provisional application No. 62/835,449, filed on Apr. 17, 2019, provisional application No. 62/835,474, filed on Apr. 17, 2019, provisional application No. 62/835,477, filed on Apr. 17, 2019, provisional application No. 62/835,465, filed on Apr. 17, 2019, provisional application No. 62/835,450, filed on Apr. 17, 2019, provisional application No. 62/835,464, filed on Apr. 17, 2019, provisional application No. 62/835,472, filed on Apr. 17, 2019, provisional application No. 62/835,482, filed on Apr. 17, 2019, provisional application No. 62/835,485, filed on Apr. 17, 2019, provisional application No. 62/835,484, filed on Apr. 17, 2019, provisional application No. 62/835,481, filed on Apr. 17, 2019.

(51) Int. Cl.

| | | |
|---|---|---|
| *A61P 25/04* | (2006.01) | |
| *A61P 25/08* | (2006.01) | |
| *A61P 25/16* | (2006.01) | |
| *A61P 25/20* | (2006.01) | |
| *A61P 25/22* | (2006.01) | |
| *A61P 25/24* | (2006.01) | |
| *A61P 25/28* | (2006.01) | |
| *C07F 9/572* | (2006.01) | |

(56) References Cited

U.S. PATENT DOCUMENTS

| | | |
|---|---|---|
| 3,192,111 A | 6/1965 | Albert et al. |
| 4,499,096 A | 2/1985 | Lotsof |
| 4,587,243 A | 5/1986 | Lotsof |
| 4,721,612 A | 1/1988 | Janoff et al. |
| 5,145,677 A | 9/1992 | Von Eichborn et al. |
| 5,264,443 A | 11/1993 | Jarreau et al. |
| 5,468,486 A | 11/1995 | Reddick et al. |
| 5,482,706 A | 1/1996 | Igari et al. |
| 5,545,617 A | 8/1996 | Dartt et al. |
| 5,573,776 A | 11/1996 | Harrison et al. |
| 5,626,863 A | 5/1997 | Hubbell et al. |
| 5,629,307 A | 5/1997 | Olney |
| 5,643,586 A | 7/1997 | Perricone |
| 5,696,125 A | 12/1997 | Altura et al. |
| 5,725,871 A | 3/1998 | Illum |
| 5,736,161 A | 4/1998 | Garces et al. |
| 5,785,989 A | 7/1998 | Stanley et al. |
| 5,804,592 A | 9/1998 | Volicer |
| 5,827,819 A | 10/1998 | Yatvin et al. |
| 5,871,710 A | 2/1999 | Bogdanov et al. |
| 5,874,477 A | 2/1999 | McConnell et al. |
| 5,879,690 A | 3/1999 | Perricone |
| 5,902,815 A | 5/1999 | Olney et al. |
| 5,914,129 A | 6/1999 | Mauskop |
| 5,922,341 A | 7/1999 | Smith et al. |
| 5,925,634 A | 7/1999 | Olney |
| 5,935,925 A | 8/1999 | Weinshank et al. |
| 5,942,241 A | 8/1999 | Chasin et al. |
| 5,942,503 A | 8/1999 | Jung et al. |
| 5,958,919 A | 9/1999 | Olney et al. |
| 6,037,346 A | 3/2000 | Doherty, Jr. et al. |
| 6,121,264 A | 9/2000 | Sakamoto et al. |
| 6,126,924 A | 10/2000 | Scales-Medeiros et al. |
| 6,204,245 B1 | 3/2001 | Siegel et al. |
| 6,217,904 B1 | 4/2001 | Midha et al. |
| 6,228,864 B1 | 5/2001 | Smith et al. |
| 6,294,550 B1 | 9/2001 | Place et al. |
| 6,323,236 B2 | 11/2001 | McElroy |
| 6,348,456 B1 | 2/2002 | Mash et al. |
| 6,380,176 B2 | 4/2002 | Takahashi et al. |
| 6,383,471 B1 | 5/2002 | Chen et al. |
| 6,444,665 B1 | 9/2002 | Helton et al. |
| 6,479,074 B2 | 11/2002 | Murdock et al. |
| 6,489,341 B1 | 12/2002 | Jerussi |
| 6,495,154 B1 | 12/2002 | Tam et al. |
| 6,495,498 B2 | 12/2002 | Niemiec et al. |
| 6,500,459 B1 | 12/2002 | Chhabra et al. |
| 6,541,043 B2 | 4/2003 | Lang |
| 6,544,998 B2 | 4/2003 | Mylari |
| 6,592,901 B2 | 7/2003 | Durig et al. |
| 6,604,698 B2 | 8/2003 | Verhoff et al. |
| 6,635,279 B2 | 10/2003 | Kolter et al. |
| 6,693,135 B2 | 2/2004 | Yeager et al. |
| 6,720,348 B2 | 4/2004 | Mylari |
| 6,814,976 B1 | 11/2004 | Hille et al. |
| 6,893,662 B2 | 5/2005 | Dittmar et al. |
| 6,913,768 B2 | 7/2005 | Couch et al. |
| 6,962,717 B1 | 11/2005 | Huber et al. |
| 6,977,070 B2 | 12/2005 | Dugger, III |
| 6,979,447 B2 | 12/2005 | Jameson et al. |
| 7,045,543 B2 | 5/2006 | Yatvin et al. |
| 7,084,156 B2 | 8/2006 | DeVita et al. |
| 7,186,293 B2 | 3/2007 | Cunningham |
| 7,220,737 B1 | 5/2007 | Mash |
| 7,229,784 B2 | 6/2007 | Holtzman et al. |
| 7,241,797 B2 | 7/2007 | Horseman |
| 7,294,649 B2 | 11/2007 | Hui et al. |
| 7,384,651 B2 | 6/2008 | Hille et al. |
| 7,517,900 B2 | 4/2009 | Pendri et al. |
| 7,638,651 B2 | 12/2009 | Gant et al. |
| 7,666,877 B2 | 2/2010 | Baenteli et al. |
| 7,670,627 B2 | 3/2010 | Shefer et al. |
| 7,671,030 B2 | 3/2010 | Mickle et al. |
| 7,678,770 B2 | 3/2010 | Mickle et al. |
| 7,754,710 B2 | 7/2010 | Mash |
| 7,772,222 B2 | 8/2010 | Mickle |
| 7,799,337 B2 | 9/2010 | Levin |
| 7,833,546 B2 | 11/2010 | Petereit et al. |
| 7,838,034 B2 | 11/2010 | Kugelmann et al. |
| 7,981,441 B2 | 7/2011 | Pantelidis et al. |
| 8,008,285 B2 | 8/2011 | Roberts et al. |
| 8,067,028 B2 | 11/2011 | Bennett |
| 8,101,661 B2 | 1/2012 | Mickle |
| 8,263,561 B2 | 9/2012 | Saeed |
| 8,318,210 B2 | 11/2012 | Tengler et al. |
| 8,318,813 B2 | 11/2012 | Sanfilippo |
| 8,329,663 B2 | 12/2012 | Griffin |
| 8,362,007 B1 | 1/2013 | Mash et al. |
| 8,445,016 B2 | 5/2013 | Santerre et al. |
| 8,512,751 B2 | 8/2013 | Rariy et al. |
| 8,574,604 B2 | 11/2013 | Esfand et al. |
| 8,617,607 B2 | 12/2013 | Moses et al. |
| 8,673,351 B2 | 3/2014 | Andrýsek et al. |
| 8,742,096 B2 | 6/2014 | Moriarty et al. |
| 8,747,832 B2 | 6/2014 | Uhrich et al. |
| 8,754,119 B2 | 6/2014 | Scheller et al. |
| 8,784,835 B2 | 7/2014 | Austin |
| 8,785,500 B2 | 7/2014 | Charney et al. |
| 8,846,100 B2 | 9/2014 | Shojaei et al. |
| 8,852,638 B2 | 10/2014 | Luk et al. |
| 8,859,579 B2 | 10/2014 | Sewell |
| 8,859,622 B1 | 10/2014 | Bristol et al. |
| 8,906,413 B2 | 12/2014 | Chang et al. |
| 8,906,847 B2 | 12/2014 | Cleemann et al. |
| 8,921,393 B2 | 12/2014 | Weiner et al. |
| 8,962,697 B2 | 2/2015 | Laronde et al. |
| 8,980,308 B2 | 3/2015 | Horstmann et al. |
| 8,980,880 B1 | 3/2015 | King et al. |
| 9,737,759 B2 | 8/2017 | Mrowka et al. |
| 9,878,138 B2 | 1/2018 | Altschul et al. |
| 10,058,253 B2 | 8/2018 | Parton et al. |

(56) References Cited

U.S. PATENT DOCUMENTS

| | | |
|---|---|---|
| 10,058,584 B2 | 8/2018 | Young et al. |
| 10,064,856 B2 | 9/2018 | Bosse et al. |
| 10,085,994 B2 | 10/2018 | Lozinsky et al. |
| 10,148,534 B2 | 12/2018 | Lazarescu et al. |
| 10,183,001 B1 | 1/2019 | King et al. |
| 10,231,651 B2 | 3/2019 | Deng et al. |
| 10,254,298 B1 | 4/2019 | Koh |
| 10,519,175 B2 | 12/2019 | Londesbrough et al. |
| 10,596,378 B2 | 3/2020 | Rustick |
| 10,729,706 B2 | 8/2020 | Kucuksen et al. |
| 10,738,268 B2 | 8/2020 | Leo |
| 10,947,257 B2 | 3/2021 | Londesbrough et al. |
| 10,954,259 B1 | 3/2021 | Londesbrough et al. |
| 11,149,044 B2 | 10/2021 | Londesbrough et al. |
| 11,180,517 B2 | 11/2021 | Londesbrough et al. |
| 11,447,510 B2 | 9/2022 | Londesbrough et al. |
| 11,505,564 B2 | 11/2022 | Derek et al. |
| 11,564,935 B2 | 1/2023 | Londesbrough et al. |
| 11,629,159 B2 | 4/2023 | Londesbrough et al. |
| 11,738,035 B2 | 8/2023 | Londesbrough et al. |
| 11,851,451 B2 | 12/2023 | Londesbrough et al. |
| 11,865,126 B2 | 1/2024 | Londesbrough et al. |
| 11,939,346 B2 | 3/2024 | Londesbrough et al. |
| 2001/0004644 A1 | 6/2001 | Levin |
| 2002/0015730 A1 | 2/2002 | Hoffmann et al. |
| 2002/0019421 A1 | 2/2002 | Biberman |
| 2002/0044962 A1 | 4/2002 | Cherukuri et al. |
| 2002/0137785 A1 | 9/2002 | Kindness et al. |
| 2003/0013689 A1 | 1/2003 | Helton et al. |
| 2003/0049308 A1 | 3/2003 | Theobald et al. |
| 2003/0051728 A1 | 3/2003 | Lloyd et al. |
| 2003/0082225 A1 | 5/2003 | Mason |
| 2003/0096831 A1 | 5/2003 | Stone et al. |
| 2003/0099711 A1 | 5/2003 | Meadows et al. |
| 2003/0114512 A1 | 6/2003 | Collier, Jr. et al. |
| 2003/0119884 A1 | 6/2003 | Epstein et al. |
| 2003/0135202 A1 | 7/2003 | Harper et al. |
| 2003/0144220 A1 | 7/2003 | Obach |
| 2003/0153552 A1 | 8/2003 | Mash et al. |
| 2003/0171435 A1 | 9/2003 | Pouletty et al. |
| 2003/0180357 A1 | 9/2003 | Martino et al. |
| 2003/0203912 A1 | 10/2003 | May et al. |
| 2003/0224057 A1 | 12/2003 | Martin-Letellier et al. |
| 2003/0235617 A1 | 12/2003 | Martino et al. |
| 2004/0006043 A1 | 1/2004 | Margalit et al. |
| 2004/0023952 A1 | 2/2004 | Leventhal |
| 2004/0024038 A1 | 2/2004 | Ebert et al. |
| 2004/0029860 A1 | 2/2004 | Gil-Ad et al. |
| 2004/0077540 A1 | 4/2004 | Quay |
| 2004/0132780 A1 | 7/2004 | Allen et al. |
| 2004/0186155 A1 | 9/2004 | Dayno et al. |
| 2004/0214215 A1 | 10/2004 | Yu et al. |
| 2004/0224942 A1 | 11/2004 | Weiner et al. |
| 2005/0009815 A1 | 1/2005 | DeVita et al. |
| 2005/0014786 A1 | 1/2005 | Sun et al. |
| 2005/0026842 A1 | 2/2005 | Simon |
| 2005/0070501 A1 | 3/2005 | Neurath et al. |
| 2005/0096396 A1 | 5/2005 | Davis et al. |
| 2005/0106220 A1 | 5/2005 | Inagawa et al. |
| 2005/0148673 A1 | 7/2005 | Harbut et al. |
| 2005/0176790 A1 | 8/2005 | Bartholomaus et al. |
| 2005/0203011 A1 | 9/2005 | Ron |
| 2005/0209218 A1 | 9/2005 | Meyerson et al. |
| 2005/0215521 A1 | 9/2005 | Lalji et al. |
| 2005/0215571 A1 | 9/2005 | Romano |
| 2005/0222270 A1 | 10/2005 | Olney et al. |
| 2005/0233010 A1 | 10/2005 | Satow |
| 2005/0245460 A1 | 11/2005 | Meyerson et al. |
| 2005/0245617 A1 | 11/2005 | Meyerson et al. |
| 2005/0255091 A1 | 11/2005 | Loomis |
| 2005/0260258 A1 | 11/2005 | Ficht et al. |
| 2005/0261278 A1 | 11/2005 | Weiner et al. |
| 2005/0265955 A1 | 12/2005 | Raman et al. |
| 2005/0288375 A1 | 12/2005 | Hobden et al. |
| 2006/0019963 A1 | 1/2006 | Barnette et al. |
| 2006/0025387 A1 | 2/2006 | Hochman |
| 2006/0030625 A1 | 2/2006 | Hart et al. |
| 2006/0034872 A1 | 2/2006 | Woolf |
| 2006/0045865 A1 | 3/2006 | Jacob et al. |
| 2006/0051408 A1 | 3/2006 | Parente Duena et al. |
| 2006/0067937 A1 | 3/2006 | Karumanchi et al. |
| 2006/0093679 A1 | 5/2006 | Mayer et al. |
| 2006/0110327 A1 | 5/2006 | Emigh et al. |
| 2006/0135403 A1 | 6/2006 | Gervais et al. |
| 2006/0183744 A1 | 8/2006 | Rohrer et al. |
| 2006/0229293 A1 | 10/2006 | Lotsof |
| 2006/0240014 A1 | 10/2006 | Sukhatme |
| 2006/0240043 A1 | 10/2006 | Meyerson et al. |
| 2006/0241172 A1 | 10/2006 | Zhou et al. |
| 2006/0264508 A1 | 11/2006 | Stone |
| 2006/0270592 A1 | 11/2006 | Ousler, III et al. |
| 2007/0053954 A1 | 3/2007 | Rowe et al. |
| 2007/0059367 A1 | 3/2007 | Cherukuri |
| 2007/0065463 A1 | 3/2007 | Aung-Din |
| 2007/0066996 A1 | 3/2007 | Katzman et al. |
| 2007/0092586 A1 | 4/2007 | Cutler |
| 2007/0099977 A1 | 5/2007 | Nudelman et al. |
| 2007/0100000 A1 | 5/2007 | Epstein et al. |
| 2007/0190130 A1 | 8/2007 | Mark et al. |
| 2007/0190142 A1 | 8/2007 | Breitenbach et al. |
| 2007/0203216 A1 | 8/2007 | Ebert et al. |
| 2007/0207222 A1 | 9/2007 | Yu et al. |
| 2007/0213394 A1 | 9/2007 | Beguin et al. |
| 2008/0015181 A1 | 1/2008 | Roberts et al. |
| 2008/0026014 A1 | 1/2008 | Michel |
| 2008/0026189 A1 | 1/2008 | Lin et al. |
| 2008/0066741 A1 | 3/2008 | LeMahieu et al. |
| 2008/0075789 A1 | 3/2008 | Vawter et al. |
| 2008/0103127 A1 | 5/2008 | Haas |
| 2008/0103165 A1 | 5/2008 | Barlow et al. |
| 2008/0103179 A1 | 5/2008 | Tam et al. |
| 2008/0103199 A1 | 5/2008 | Haas |
| 2008/0193540 A1 | 8/2008 | Soula et al. |
| 2008/0207600 A1 | 8/2008 | Goldstein et al. |
| 2008/0226715 A1 | 9/2008 | Cha et al. |
| 2008/0233201 A1 | 9/2008 | Royere et al. |
| 2008/0241255 A1 | 10/2008 | Rose et al. |
| 2008/0255096 A1 | 10/2008 | Knipper-Breer et al. |
| 2008/0260844 A1 | 10/2008 | Soula et al. |
| 2009/0036468 A1 | 2/2009 | Samoriski et al. |
| 2009/0041838 A1 | 2/2009 | Guimberteau et al. |
| 2009/0069308 A1 | 3/2009 | Deregnaucourt et al. |
| 2009/0105222 A1 | 4/2009 | Kranzler et al. |
| 2009/0143435 A1 | 6/2009 | Ebert et al. |
| 2009/0156581 A1 | 6/2009 | Dillon et al. |
| 2009/0169566 A1 | 7/2009 | Rawlin et al. |
| 2009/0176792 A1 | 7/2009 | Gant et al. |
| 2009/0186099 A1 | 7/2009 | Dugger, III |
| 2009/0198145 A1 | 8/2009 | Chow |
| 2009/0232898 A1 | 9/2009 | Pettersson et al. |
| 2009/0252786 A1 | 10/2009 | Hanz |
| 2009/0259039 A1 | 10/2009 | Bristol et al. |
| 2009/0285916 A1 | 11/2009 | Haritou |
| 2009/0291137 A1 | 11/2009 | Guimberteau et al. |
| 2009/0298814 A1 | 12/2009 | Nudelman et al. |
| 2010/0016280 A1 | 1/2010 | Nichols et al. |
| 2010/0098722 A1 | 4/2010 | Bachmann et al. |
| 2010/0152108 A1 | 6/2010 | Hung et al. |
| 2010/0166889 A1 | 7/2010 | Sanfilippo |
| 2010/0179221 A1 | 7/2010 | Nagel et al. |
| 2010/0189818 A1 | 7/2010 | Tsai |
| 2010/0216964 A1 | 8/2010 | Zech et al. |
| 2010/0255094 A1 | 10/2010 | Jackson et al. |
| 2010/0266701 A1 | 10/2010 | Guimberteau et al. |
| 2010/0303903 A1 | 12/2010 | Hackett |
| 2011/0038915 A1 | 2/2011 | Gonzalez |
| 2011/0053859 A1 | 3/2011 | Deadwyler et al. |
| 2011/0077239 A1 | 3/2011 | Knipper et al. |
| 2011/0091508 A1 | 4/2011 | Esfand et al. |
| 2011/0111029 A1 | 5/2011 | Schmitz et al. |
| 2011/0118189 A1 | 5/2011 | Farr et al. |
| 2011/0144209 A1 | 6/2011 | Zachar |
| 2011/0207718 A1 | 8/2011 | Bird |
| 2011/0217289 A1 | 9/2011 | Kolter et al. |

(56) References Cited

U.S. PATENT DOCUMENTS

| | | |
|---|---|---|
| 2011/0245261 A1 | 10/2011 | Lagarde et al. |
| 2011/0274634 A1 | 11/2011 | Rieth et al. |
| 2011/0306596 A1 | 12/2011 | Rao et al. |
| 2012/0058125 A1 | 3/2012 | Strittmatter et al. |
| 2012/0059066 A1 | 3/2012 | Bartholomaus et al. |
| 2012/0108510 A1 | 5/2012 | Young et al. |
| 2012/0129834 A1 | 5/2012 | Hughes et al. |
| 2012/0135960 A2 | 5/2012 | Mouthon et al. |
| 2012/0159656 A1 | 6/2012 | Gerber et al. |
| 2012/0282255 A1 | 11/2012 | Plucinski |
| 2012/0302590 A1 | 11/2012 | Bhide et al. |
| 2012/0302592 A1 | 11/2012 | Johnson et al. |
| 2013/0045979 A1 | 2/2013 | Sanfilippo |
| 2013/0116215 A1 | 5/2013 | Coma et al. |
| 2013/0276799 A1 | 10/2013 | Davidson et al. |
| 2013/0281401 A1 | 10/2013 | Turner |
| 2013/0295170 A1 | 11/2013 | Dordunoo |
| 2014/0093577 A1 | 4/2014 | Tengler et al. |
| 2014/0099336 A1 | 4/2014 | Woiwode et al. |
| 2014/0100282 A1 | 4/2014 | Wong |
| 2014/0148491 A1 | 5/2014 | Valia et al. |
| 2014/0178480 A1 | 6/2014 | King et al. |
| 2014/0187655 A1 | 7/2014 | Mash et al. |
| 2014/0220150 A1 | 8/2014 | Stamets |
| 2014/0255522 A1 | 9/2014 | Lozinsky et al. |
| 2014/0288056 A1 | 9/2014 | Friedhoff |
| 2014/0294923 A1 | 10/2014 | Cartt et al. |
| 2014/0315837 A1 | 10/2014 | Mash et al. |
| 2014/0356428 A1 | 12/2014 | Barnscheid et al. |
| 2014/0364367 A1 | 12/2014 | Cotter |
| 2015/0011644 A1 | 1/2015 | Leech |
| 2015/0094466 A1 | 4/2015 | Moriarty |
| 2015/0099741 A1 | 4/2015 | Li et al. |
| 2015/0118301 A1 | 4/2015 | Haswani et al. |
| 2015/0118327 A1 | 4/2015 | Sewell |
| 2015/0196533 A1 | 7/2015 | Mao et al. |
| 2015/0216799 A1 | 8/2015 | Farber |
| 2015/0231300 A1 | 8/2015 | Lozinsky et al. |
| 2015/0258114 A1 | 9/2015 | Friedhoff |
| 2016/0051476 A1 | 2/2016 | Pilgaonkar et al. |
| 2016/0331725 A1 | 11/2016 | Gillessen et al. |
| 2016/0338945 A1 | 11/2016 | Knight |
| 2016/0340334 A1 | 11/2016 | Knight |
| 2017/0086727 A1 | 3/2017 | Dagum |
| 2017/0258382 A1 | 9/2017 | Dagum |
| 2017/0258383 A1 | 9/2017 | Dagum |
| 2017/0276676 A1 | 9/2017 | Slotman |
| 2017/0287348 A1 | 10/2017 | Mosher et al. |
| 2017/0348303 A1 | 12/2017 | Bosse et al. |
| 2018/0021326 A1 | 1/2018 | Stamets |
| 2018/0036303 A1 | 2/2018 | Raz |
| 2018/0104490 A1 | 4/2018 | Rustick |
| 2018/0147142 A1 | 5/2018 | Knight |
| 2018/0221396 A1 | 8/2018 | Chadeayne |
| 2018/0343812 A1 | 12/2018 | Leo |
| 2018/0344743 A1 | 12/2018 | Lozinsky et al. |
| 2018/0353434 A1 | 12/2018 | Hatanaka et al. |
| 2018/0354995 A1 | 12/2018 | Gudkov et al. |
| 2019/0105313 A1 | 4/2019 | Stamets |
| 2019/0142851 A1 | 5/2019 | Chadeayne |
| 2019/0187163 A1 | 6/2019 | Koh |
| 2019/0192498 A1 | 6/2019 | Stamets |
| 2019/0246591 A1 | 8/2019 | Leo |
| 2020/0078368 A1 | 3/2020 | Lehmann et al. |
| 2020/0093416 A1 | 3/2020 | Rogers et al. |
| 2020/0101041 A1 | 4/2020 | Kleidon |
| 2020/0147038 A1 | 5/2020 | Russ et al. |
| 2020/0215297 A1 | 7/2020 | Rabin et al. |
| 2020/0375967 A1 | 12/2020 | Stamets |
| 2021/0015833 A1 | 1/2021 | LaRosa et al. |
| 2021/0267966 A1 | 9/2021 | Petcavich |
| 2022/0088041 A1 | 3/2022 | Londesbrough et al. |
| 2022/0402949 A1 | 12/2022 | Londesbrough et al. |
| 2023/0000883 A1 | 1/2023 | Londesbrough et al. |
| 2023/0023092 A1 | 1/2023 | Londesbrough et al. |
| 2023/0119714 A1 | 4/2023 | Londesbrough et al. |
| 2023/0124137 A1 | 4/2023 | Londesbrough et al. |
| 2023/0330117 A1 | 10/2023 | Londesbrough et al. |
| 2024/0197758 A1 | 6/2024 | Elder et al. |
| 2024/0199660 A1 | 6/2024 | Londesbrough et al. |
| 2024/0252521 A1 | 8/2024 | Londesbrough et al. |

FOREIGN PATENT DOCUMENTS

| | | |
|---|---|---|
| CA | 672478 A | 10/1963 |
| CA | 2338326 A1 | 2/2000 |
| CA | 2416650 A1 | 1/2002 |
| CA | 2422730 A1 | 3/2002 |
| CA | 2492823 A1 | 3/2003 |
| CA | 2492826 A1 | 3/2003 |
| CA | 2487849 A1 | 1/2004 |
| CA | 2489410 A1 | 1/2004 |
| CA | 2498938 A1 | 4/2004 |
| CA | 2517675 A1 | 10/2004 |
| CA | 2541090 A1 | 5/2005 |
| CA | 2594451 A1 | 6/2007 |
| CA | 3050679 A1 | 7/2018 |
| CN | 103535561 A | 1/2014 |
| CN | 103549133 A | 2/2014 |
| CN | 103751943 A | 4/2014 |
| CN | 103773056 A | 5/2014 |
| CN | 107252080 A | 10/2017 |
| CN | 108619214 A | 10/2018 |
| EP | 0152379 A2 | 8/1985 |
| EP | 0218479 A2 | 4/1987 |
| EP | 0493380 B1 | 10/1997 |
| EP | 0628042 B1 | 8/2001 |
| EP | 0554352 B1 | 3/2003 |
| EP | 0932416 B1 | 6/2005 |
| EP | 1944017 A2 | 7/2008 |
| EP | 2106799 A1 | 10/2009 |
| EP | 1774968 B1 | 12/2011 |
| EP | 1861427 B1 | 8/2012 |
| EP | 2142185 B1 | 8/2012 |
| EP | 2525226 A1 | 11/2012 |
| EP | 2649989 A1 | 10/2013 |
| EP | 2053919 B1 | 12/2013 |
| EP | 2183227 B1 | 9/2014 |
| EP | 2023900 B1 | 12/2014 |
| EP | 2818177 A1 | 12/2014 |
| EP | 2481740 B1 | 11/2015 |
| EP | 3151906 B1 | 12/2019 |
| ES | 2693502 T3 | 12/2018 |
| FI | 20176142 A1 | 6/2019 |
| FI | 20185254 A1 | 9/2019 |
| GB | 911946 A | 12/1962 |
| GB | 912714 A | 12/1962 |
| HR | P20050421 A2 | 12/2005 |
| IE | 24138 L | 8/1959 |
| JP | S5576859 A | 6/1980 |
| JP | S5728046 A | 2/1982 |
| JP | 4174016 B2 | 10/2008 |
| JP | 2013233437 A | 11/2013 |
| MX | 2014005372 A | 7/2014 |
| TW | 201605856 A | 2/2016 |
| WO | WO-9728798 A1 | 8/1997 |
| WO | WO-9728799 A1 | 8/1997 |
| WO | WO-9728800 A1 | 8/1997 |
| WO | WO-9729121 A1 | 8/1997 |
| WO | WO-9747285 A1 | 12/1997 |
| WO | WO-9850027 A1 | 11/1998 |
| WO | WO-9859234 A1 | 12/1998 |
| WO | WO-9903458 A1 | 1/1999 |
| WO | WO-9909828 A1 | 3/1999 |
| WO | WO-9948501 A1 | 9/1999 |
| WO | WO-9966909 A2 | 12/1999 |
| WO | WO-0003679 A2 | 1/2000 |
| WO | WO-0003701 A1 | 1/2000 |
| WO | WO-0003746 A2 | 1/2000 |
| WO | WO-0006139 A2 | 2/2000 |
| WO | WO-0056403 A1 | 9/2000 |
| WO | WO-0113935 A2 | 3/2001 |
| WO | WO-0126642 A2 | 4/2001 |
| WO | WO-0152832 A1 | 7/2001 |

(56) References Cited

FOREIGN PATENT DOCUMENTS

| | | |
|---|---|---|
| WO | WO-0167890 A2 | 9/2001 |
| WO | WO-0172839 A2 | 10/2001 |
| WO | WO-0182915 A2 | 11/2001 |
| WO | WO-0205851 A2 | 1/2002 |
| WO | WO-0224865 A2 | 3/2002 |
| WO | WO-03016903 A2 | 2/2003 |
| WO | WO-03024480 A2 | 3/2003 |
| WO | WO-03024481 A2 | 3/2003 |
| WO | WO-03026564 A2 | 4/2003 |
| WO | WO-03041645 A2 | 5/2003 |
| WO | WO-03045353 A1 | 6/2003 |
| WO | WO-03047551 A1 | 6/2003 |
| WO | WO03066030 A2 | 8/2003 |
| WO | WO-2004000275 A1 | 12/2003 |
| WO | WO-2004007538 A2 | 1/2004 |
| WO | WO-2004009116 A2 | 1/2004 |
| WO | WO-2004014429 A1 | 2/2004 |
| WO | WO-2004025268 A2 | 3/2004 |
| WO | WO-2004032900 A1 | 4/2004 |
| WO | WO-2004071431 A2 | 8/2004 |
| WO | WO-2004084940 A1 | 10/2004 |
| WO | WO-2004111185 A2 | 12/2004 |
| WO | WO-2005039502 A2 | 5/2005 |
| WO | WO-2005039546 A2 | 5/2005 |
| WO | WO-2005058319 A1 | 6/2005 |
| WO | WO-2005067930 A2 | 7/2005 |
| WO | WO-2005102390 A2 | 11/2005 |
| WO | WO-2006006858 A1 | 1/2006 |
| WO | WO-2006047032 A2 | 5/2006 |
| WO | WO-2006079999 A2 | 8/2006 |
| WO | WO-2006121552 A2 | 11/2006 |
| WO | WO-2006127418 A1 | 11/2006 |
| WO | WO-2007050697 A2 | 5/2007 |
| WO | WO-2007066240 A2 | 6/2007 |
| WO | WO-2007067519 A2 | 6/2007 |
| WO | WO-2007085898 A2 | 8/2007 |
| WO | WO-2007092043 A2 | 8/2007 |
| WO | WO-2007101884 A1 | 9/2007 |
| WO | WO-2008009125 A1 | 1/2008 |
| WO | WO-2008010223 A2 | 1/2008 |
| WO | WO-2008023261 A1 | 2/2008 |
| WO | WO-2008026046 A1 | 3/2008 |
| WO | WO-2008038291 A1 | 4/2008 |
| WO | WO-2008039179 A1 | 4/2008 |
| WO | WO-2008119097 A1 | 10/2008 |
| WO | WO-2008122990 A1 | 10/2008 |
| WO | WO-2008130638 A2 | 10/2008 |
| WO | WO-2009018338 A2 | 2/2009 |
| WO | WO-2009021055 A1 | 2/2009 |
| WO | WO-2009050354 A1 | 4/2009 |
| WO | WO-2009055001 A2 | 4/2009 |
| WO | WO-2009061436 A1 | 5/2009 |
| WO | WO-2009079765 A1 | 7/2009 |
| WO | WO-2009091605 A2 | 7/2009 |
| WO | WO-2009097596 A1 | 8/2009 |
| WO | WO-2009102805 A1 | 8/2009 |
| WO | WO-2009109428 A2 | 9/2009 |
| WO | WO-2009118179 A1 | 10/2009 |
| WO | WO-2009118763 A1 | 10/2009 |
| WO | WO-2009149252 A1 | 12/2009 |
| WO | WO-2010099522 A1 | 9/2010 |
| WO | WO-2010123577 A2 | 10/2010 |
| WO | WO-2010124089 A2 | 10/2010 |
| WO | WO-2011027060 A2 | 3/2011 |
| WO | WO-2011028875 A1 | 3/2011 |
| WO | WO-2011045443 A1 | 4/2011 |
| WO | WO-2011045769 A2 | 4/2011 |
| WO | WO-2011048494 A2 | 4/2011 |
| WO | WO-2011072398 A1 | 6/2011 |
| WO | WO-2011097269 A1 | 8/2011 |
| WO | WO-2011109809 A2 | 9/2011 |
| WO | WO-2011116189 A1 | 9/2011 |
| WO | WO-2011138142 A1 | 11/2011 |
| WO | WO-2011143254 A2 | 11/2011 |
| WO | WO-2011158964 A1 | 12/2011 |
| WO | WO-2012012764 A1 | 1/2012 |
| WO | WO-2012022928 A2 | 2/2012 |
| WO | WO-2012031125 A2 | 3/2012 |
| WO | WO-2012039660 A1 | 3/2012 |
| WO | WO-2012045118 A1 | 4/2012 |
| WO | WO-2012054815 A1 | 4/2012 |
| WO | WO-2012063257 A2 | 5/2012 |
| WO | WO-2012066537 A2 | 5/2012 |
| WO | WO-2012074588 A2 | 6/2012 |
| WO | WO-2012077110 A2 | 6/2012 |
| WO | WO-2012085919 A2 | 6/2012 |
| WO | WO-2012110537 A1 | 8/2012 |
| WO | WO-2012134436 A1 | 10/2012 |
| WO | WO-2012137971 A1 | 10/2012 |
| WO | WO-2012158892 A2 | 11/2012 |
| WO | WO-2012177962 A1 | 12/2012 |
| WO | WO-2013004999 A1 | 1/2013 |
| WO | WO-2013040471 A2 | 3/2013 |
| WO | WO-2013068949 A1 | 5/2013 |
| WO | WO-2013083710 A1 | 6/2013 |
| WO | WO-2013085849 A2 | 6/2013 |
| WO | WO-2013085850 A2 | 6/2013 |
| WO | WO-2013085922 A1 | 6/2013 |
| WO | WO-2013091900 A1 | 6/2013 |
| WO | WO-2013097947 A1 | 7/2013 |
| WO | WO-2013112163 A1 | 8/2013 |
| WO | WO-2013112757 A1 | 8/2013 |
| WO | WO-2013169355 A1 | 11/2013 |
| WO | WO-2014015993 A1 | 1/2014 |
| WO | WO-2014031958 A1 | 2/2014 |
| WO | WO-2014035473 A1 | 3/2014 |
| WO | WO-2014064703 A1 | 5/2014 |
| WO | WO-2014078857 A1 | 5/2014 |
| WO | WO-2014093277 A1 | 6/2014 |
| WO | WO-2014098877 A1 | 6/2014 |
| WO | WO-2014117089 A1 | 7/2014 |
| WO | WO-2014140925 A2 | 9/2014 |
| WO | WO-2014143085 A1 | 9/2014 |
| WO | WO-2014145126 A2 | 9/2014 |
| WO | WO-2014146082 A1 | 9/2014 |
| WO | WO-2014153099 A2 | 9/2014 |
| WO | WO-2014176556 A1 | 10/2014 |
| WO | WO-2014186623 A2 | 11/2014 |
| WO | WO-2014190440 A1 | 12/2014 |
| WO | WO-2014195872 A1 | 12/2014 |
| WO | WO-2015004245 A1 | 1/2015 |
| WO | WO-2015006315 A1 | 1/2015 |
| WO | WO-2015034846 A1 | 3/2015 |
| WO | WO-2015061125 A1 | 4/2015 |
| WO | WO-2015065546 A2 | 5/2015 |
| WO | WO-2015066344 A1 | 5/2015 |
| WO | WO-2015134405 A1 | 9/2015 |
| WO | WO-2015112168 A2 | 11/2015 |
| WO | WO-2015187289 A1 | 12/2015 |
| WO | WO-2016161138 A1 | 10/2016 |
| WO | WO-2016176177 A1 | 11/2016 |
| WO | WO-2016178053 A1 | 11/2016 |
| WO | WO-2017023679 A1 | 2/2017 |
| WO | WO-2018035477 A1 | 2/2018 |
| WO | WO-2018135943 A1 * | 7/2018 ........... A61K 31/352 |
| WO | WO-2018141063 A1 | 8/2018 |
| WO | WO-2018145219 A1 | 8/2018 |
| WO | WO-2018148605 A1 | 8/2018 |
| WO | WO-2018184206 A1 | 10/2018 |
| WO | WO-2018195455 A1 | 10/2018 |
| WO | WO-2018223044 A1 | 12/2018 |
| WO | WO-2019073379 A1 | 4/2019 |
| WO | WO-2019079742 A1 | 4/2019 |
| WO | WO-2019081764 A1 | 5/2019 |
| WO | WO-2019099745 A1 | 5/2019 |
| WO | WO-2019109124 A1 | 6/2019 |
| WO | WO-2019122525 A1 | 6/2019 |
| WO | WO-2019144140 A1 | 7/2019 |
| WO | WO-2019161050 A1 | 8/2019 |
| WO | WO-2019173797 A1 | 9/2019 |
| WO | WO-2019180309 A1 | 9/2019 |
| WO | WO-2019213551 A1 | 11/2019 |
| WO | WO-2019246532 A1 | 12/2019 |
| WO | WO-2020024060 A1 | 2/2020 |

(56) References Cited

FOREIGN PATENT DOCUMENTS

| WO | WO-2020041329 A1 | 2/2020 |
|---|---|---|
| WO | WO-2020053196 A1 | 3/2020 |
| WO | WO-2020142259 A1 | 7/2020 |
| WO | WO-2020157569 A1 | 8/2020 |
| WO | WO-2020212948 A1 | 10/2020 |
| WO | WO-2020212951 A1 | 10/2020 |
| WO | WO-2020212952 A1 | 10/2020 |
| WO | WO-2022207746 A1 | 10/2022 |

OTHER PUBLICATIONS

The Association of Depression and Anxiety with Pain: A Study from NESDA de Heer EW, Gerrits MMJG, Beekman ATF, Dekker J, van Marwijk HWJ, et al. (2014) The Association of Depression and Anxiety with Pain: A Study from Nesda. PLOS ONE 9(10): e106907. https://doi.org/10.1371/journal.pone.0106907 (Year: 2014).*

David W. Dodick, Catherine C. Turkel, Ronald E. DeGryse, Hans-Christoph Diener, Richard B. Lipton, Sheena K. Aurora, Marissa E. Nolan, Stephen D. Silb, Assessing Clinically Meaningful Treatment Effects in Controlled Trials: Chronic Migraine as an Example, The Journal of Pain, vol. 16, 2, 2015, 164-175 (Year: 2015).*

Meinzer MC, Chronis-Tuscano A. ADHD and the Development of Depression: Commentary on the Prevalence, Proposed Mechanisms, and Promising Interventions. Curr Dev Disord Rep. Mar. 2017;4(1):1-4. doi: 10.1007/s40474-017-0106-1. Epub Feb. 27, 2017. PMID: 33282629; PMCID: PMC7717502. (Year: 2017).*

Magnuson KM, Constantino JN. Characterization of depression in children with autism spectrum disorders. J Dev Behav Pediatr. May 2011;32(4):332-40. doi: 10.1097/DBP.0b013e318213f56c. PMID: 21502871; PMCID: PMC3154372. (Year: 2011).*

Sheng J, Liu S, Wang Y, Cui R, Zhang X. The Link between Depression and Chronic Pain: Neural Mechanisms in the Brain. Neural Plast. 2017;2017:9724371. doi: 10.1155/2017/9724371. Epub Jun. 19, 2017. PMID: 28706741; PMCID: PMC5494581. (Year: 2017).*

Chen MH, Pan TL, Hsu JW, Huang KL, Su TP, Li CT, Lin WC, Tsai SJ, Chang WH, Chen TJ, Bai YM. Attention-deficit hyperactivity disorder comorbidity and antidepressant resistance among patients with major depression: A nationwide longitudinal study. Eur Neuropsychopharmacol. Nov. 2016;26(11):1760-1767. (Year: 2016).*

Anonymous: "Compass Pathways announces positive outcome of 25mg COMP360 psilocybin therapy as adjunct to SRI antidepressants in open-label treatment-resistant depression study", Dec. 13, 2021 (Dec. 13, 2021), XP093033918., 7 pages.

Anonymous: "Psilocybin in Depression Resistant to Standard Treatments—Full Text View—ClinicalTrials.gov", Jul. 13, 2021 (Jul. 13, 2021), XP093024023, Retrieved from the Internet: URL:https://clinicaltrials.gov/ct2/show/NCT04959253?term=depression&cond=psilocybin&draw=2&rank=11 [retrieved on Feb. 15, 2023], 5 pages.

Becker Anna M. et al: "Acute Effects of Psilocybin After Escitalopram or Placebo Pretreatment in a Randomized, Double-Blind, Placebo-Controlled, Crossover Study in Healthy Subjects", Clinical Pharmacology and Therapeutics, vol. 111, No. 4, Nov. 22, 2021 (Nov. 22, 2021), pp. 886-895, XP093033911.

Fekadu et al., "Standardisation framework for the Maudsley staging method for treatment resistance in depression," BMC Psychiatry (Apr. 11, 2018) 18:100, 13 pages.

*Freedom To Operate, Inc. v. Compass Pathways Limited.* Case PGR2022-00012, U.S. Pat. No. 10,947,257. and *Freedom To Operate, Inc. v. Compass Pathways Limited.* Case PGR2022-00018, U.S. Pat. No. 10,954,259; Paper No. 21, Order Denying Petitioners Request on Rehearing, dated May 23, 2023, 9 pages.

Greyson, B., The Near-Death Experience Scale, The Journal of Nervous and Mental Disease, 171:369-375 (1983).

Halberstadt et al., "Correlation between the potency of hallucinogens in the mouse head-twitch response assay and their behavioral and subjective effects in other species," Neuropharmacology. May 1, 2020;167:107933, pp. 1-35. doi: 10.1016/j.neuropharm.2019.107933. Epub Jan. 7, 2020.

International Search Report and Written Opinion for International Application No. PCT/US2022/052368 dated Mar. 30, 2023, 14 Pages.

International Search Report and Written Opinion for PCT/US2022/048713 dated Feb. 24, 2023, 17 pages.

International Search Report and Written Opinion issued in International Patent Application No. PCT/EP2021/079287, mailed Feb. 3, 2022, with Notification of Transmittal; 17 pages.

Jones, S.A.V., et al., "Psychedelics as a Treatment for Alzheimer's Disease Dementia," Frontiers in Synaptic Neuroscience, Aug. 21, 2020, vol. 12, pp. 34.

Mertens, L.J., et al., "Therapeutic mechanisms of psilocybin: Changes in amygdala and prefrontal functional connectivity during emotional processing after psilocybin for treatment-resistant depression," Journal of Psychopharmacology, Feb. 2020, vol. 34(2), pp. 167-180.

Aaron, M. (2017) "Open Your Mind: Merging Psychedelic Therapy with Sex Therapy" Psychology Today [online]. Retrieved from: https://www.psychologytoday.com/us/blog/standard-deviations/201710/open-your-mind-merging-psychedelic-therapy-sex-therapy, retrieved Oct. 24, 2017, 4 pages.

Abramovitch, A. et al. (Jul./Aug. 2015). Comorbidity Between Attention Deficit/Hyperactivity Disorder and Obsessive-Compulsive Disorder Across the Lifespan: A Systematic and Critical Review. Harvard Review of Psychiatry, 23(4):245-262.

Adams, K.S. and Breden Crouse, E.L. (2014). Melatonin agonists in the management of sleep disorders: A focus on ramelteon and tasimelteon. Ment Health Clin, 4:59-64. https://doi.org/10.9740/mhc.n190087.

Adams, T.G. et al. (Apr. 2017). Intranasal ketamine and cognitive-behavioral therapy for treatment-refractory obsessive-compulsive disorder. Journal of Clinical Psychopharmacology, 37(2):269-271. HHS Public Access Author Manuscript; available in PMC Apr. 1, 2018, 4 pages.

Adelow, C. et al. (2012). Hospitalization for psychiatric disorders before and after onset of unprovoked seizures/epilepsy. Neurology, 78(6), 396-401. https://doi.org/10.1212/WNL.0b013e318245f461.

Advokat, C. and M. Scheithauer (May 2013). Attention-deficit hyperactivity disorder (ADHD) stimulant medications as cognitive enhancers. Front Neurosci, 7:Article 92, 8 pages.

Agh, T. et al. (2015). Epidemiology, health-related quality of life and economic burden of binge eating disorder: a systematic literature review. Eating and Weight Disorders, 20:1-12.

Agin-Liebes, G.I. et al. (2020). Long-term follow-up of psilocybin-assisted psychotherapy for psychiatric and existential distress in patients with life-threatening cancer. J Psychopharmacol [online]; retrieved from: https://doi.org/10.1177/0269881119897615, 12 pages.

Aguglia, A., Signorelli, M. S., Albert, U., & Maina, G. (2018). The impact of general medical conditions in obsessive-compulsive disorder. Psychiatry Investigation, 15(3):246-253. https://doi.org/10.30773/pi.2017.06.17.2.

Alayadhi, L.Y. et al. (2016). High-resolution SNP genotyping platform identified recurrent and novel CNVs in autism multiplex families. Neuroscience, 339:561-570.

Albelda, N., & Joel, D. (2012). Current animal models of obsessive compulsive disorder: An update. Neuroscience, 211:83-106. https://doi.org/10.1016/j.neuroscience.2011.08.070.

Alcaro, A., and J. Panksepp (2011). The Seeking mind: Primal neuro-affective substrates for appetitive incentive states and their pathological dynamics in addictions and depression. Neurosci Biobehav Rev, 35:1805-1820. https://doi.org/10.1016/j.neubiorev.2011.03.002.

Alderson, R.M. et al. (2013) Attention-deficit/hyperactivity disorder (ADHD) and working memory in adults: A meta-analytic review. Neuropsychology, 27(3):287-302.

Allam, J.S., Collop, N., 2018. Central Sleep Apnea Syndrome (Idiopathic CSA, Cheyne-Stokes Respiration, CSA due to a drug or substance, High-altitude Periodic breathing, CSA due to a medical condition other than Cheyne-Stokes). Pulmonology Advisor (2018): pp. 1-14. Retrieved from: https://www.pulmonologyadvisor.com/home/decision-support-in-medicine/pulmonary-medicine/central-sleep-apnea-syndrome-idiopathic-csa-cheyne-stokes-respiration-csa-

(56) References Cited

OTHER PUBLICATIONS due-to-a-drug-or-substance-high-altitude-periodic-breathing-csa-due-to-a-medical-condition-ot (accessed Jul. 30, 2020).

Allen, G. and E. Courchesne (Jan. 1, 2001). Attention function and dysfunction in autism. Frontiers in Bioscience, 6:d105-119.

Alonso, P., Lopez-Sola, C., Real, E., Segalas, C., & Menchon, J. M. (2015). Animal models of obsessive-compulsive disorder: Utility and limitations. In Neuropsychiatric Disease and Treatment, 11:1939-1955. https://doi.org/10.2147/NDT.S62785.

Alvarez, A.J. et al. (2009) "Polymorph Screening: Comparing a Semi-Automated Approach with a High Throughput Method" Crystal Growth and Design, 9:4181-4188.

Alzheimer's Association (2019). Alzheimer's Disease Facts and Figures. Alzheimers Dement, 15(3):321-387, with Appendices, 90 total pages.

Alzheimer's Association (2019). FDA-approved treatments for Alzheimer's. TS-0087. 5 pages.

American Parkinson Disease Association. (2019). Medications for Parkinson's. Retrieved from https://www.apdaparkinson.org/what-is-parkinsons/treatment-medication/medication/; retrieved on Jul. 30, 2020, 18 pages.

American Psychiatric Association (2013) Binge-eating disorder. In: Diagnostic and Statistical Manual of Mental Disorders. 5th ed. Arlington, VA: American Psychiatric Association; p. 350-353.

American Psychiatric Association (2013). Diagnostic and statistical manual of mental disorders (5th ed.). American Journal of Psychiatry. https://doi.org/10.1176/appi.books.9780890425596.744053, 970 pages.

American Psychiatric Association (2013). Sleep-Wake Disorders. In: Diagnostic and Statistical Manual of Mental Disorders. 5th Edition. [online]. Retrieved from: https://doi.org/10.1176/appi.books.9780890425596.dsm12, 2 pages.

Amiri, S. et al. (2008) Modafinil as a treatment for Attention-Deficit/Hyperactivity Disorder in children and adolescents: A double blind, randomized clinical trial. Prog Neuro-Psychopharmacol Biol Psychiatry. 32(1):145-149.

Amodeo, D.A. et al. (2012). Differences in BTBR T+ tf/J and C57BL/6J mice on probabilistic reversal learning and stereotyped behaviors. Behavioural Brain Research,227(1):64-72. NIH Public Access Author Manuscript, available Mar. 1, 2012, 19 pages.

Andermann, F. (1987). Migraine-epilepsy relationships. Epilepsy Research, 1(4):213-226. https://doi.org/10.1016/0920-1211(87)90028-3.

Andersson, M. et al. (2017) Psychoactive substances as a last resort—a qualitative study of self-treatment of migraine and cluster headaches. Harm Reduction Journal, 14:60, DOI:10.1186/s12954-017-0186-6, 11 pages.

Andres-Pepina, S. et al. (2019). Long-term outcome and psychiatric comorbidity of adolescent-onset anorexia nervosa. Clinical Child Psychology and Psychiatry [online]. Retrieved from: https://doi.org/10.1177/1359104519827629, 12 pages.

Angst, J., Gamma, A., Endrass, J., Goodwin, R., Ajdacic, V., Eich, D., & Rossler, W. (2004). Obsessive-compulsive severity spectrum in the community: Prevalence, comorbidity, and course. European Archives of Psychiatry and Clinical Neuroscience, 254(3):156-164. https://doi.org/10.1007/s00406-004-0459-4.

Anwar, M.A. et al. (2013). Negative regulatory approaches to the attenuation of Toll-like receptor signaling. Experimental & Molecular Medicine, 45(2):e11, 14 pages. https://doi.org/10.1038/emm.2013.28.

Ara, A. et al. (2016). Sleep disturbances and substance use disorders: A bi-directional relationship. Psychiatr Ann, 46(7):408-412.

Arcelus, J., Mitchell, A. J., Wales, J., & Nielsen, S. (Jul. 2011). Mortality rates in patients with anorexia nervosa and other eating disorders. A meta-analysis of 36 studies. Archives of General Psychiatry, 68(7):724-731. https://doi.org/10.1001/archgenpsychiatry.2011.74.

Armstrong, M.J. and M.S. Okun (2020). Diagnosis and Treatment of Parkinson Disease. A Review. JAMA, 323(6):548-560.

Arzt, E. et al. (1991). Serotonin inhibition of tumor necrosis factor—αsynthesis by human monocytes. Life Sciences, 48(26):2557-2562.

Asnis, G.M. et al. (2016). Pharmacotherapy treatment options for insomnia: A primer for clinicians. Int J Mol Sci, 17:50, 11 pages. https://doi.org/10.3390/ijms17010050.

Attia, E., Kaplan, A. S., Walsh, B. T., Gershkovich, M., Yilmaz, Z., Musante, D., & Wang, Y. (2011). Olanzapine versus placebo for out-patients with anorexia nervosa. Psychological Medicine, 41(10):2177-2182. https://doi.org/10.1017/S0033291711000390.

Auger, R.R. et al. (2005). Risks of high-dose stimulants in the treatment of disorders of excessive somnolence: A case-control study. Sleep, 28(6):667-672.

Avidan, A.Y. (2012). Comorbidities of central nervous system hypersomnia. Sleep Med Clin, 7:291-302.

Ayaz, G. et al. (2017). Evaluation of 5-HT7 Receptor Trafficking on In Vivo and In Vitro Model of Lipopolysaccharide (LPS)-Induced Inflammatory Cell Injury in Rats and LPS-Treated A549 Cells. Biochemical Genetics, 55(1):34-47.

Babu, C.S. et al. (2009). Co-morbidities in people living with epilepsy: Hospital based case-control study from a resource-poor setting. Epilepsy Research, 86(2-3):146-152.

Baglioni, C. et al. (2016). Sleep and mental disorders: A meta-analysis of polysomnographic research. Psychol Bull, 142:969-990. HHS Public Access Author Manuscript, available Sep. 1, 2017, 56 pages.

Bahi, Camile (Sep. 2020) "Antidepressants and Psychedelics—What Do We Know and What Could Be the Risks?", Mind Foundation [online]. Retrieved from the Internet: URL:https://mindfoundation.org/psychedelic-antidepressant-interactions/[retrieved on Jan. 20, 2022]; 12 printed pages.

Bai, D. et al. (Jul. 17, 2019). Association of Genetic and Environmental Factors With Autism in a 5-Country Cohort. JAMA Psychiatry, 76(10):1035-1043.

Baio, J. (Mar. 30, 2012). Prevalence of autism spectrum disorders—Autism and developmental disabilities monitoring network, 14 sites, United States, 2008. Morbidity and Mortality Weekly Report (MMWR), 61(3):1-24.

Baker, L.A. et al. (2006) Behavioral Genetics: The Science of Antisocial Behavior. Law Contemp Probl, 69(1-2):7-46. NIH Public Access Author Manuscript, 37 pages.

Bandeen-Roche, K. et al. (2009). Measuring Systemic Inflammatory Regulation in Older Adults: Evidence and Utility. Rejuvenation Research, 12(6):403-410.

Bandelow, B. and S. Michaelis (2015). Epidemiology of anxiety disorders in the 21st century. Dialogues Clin Neurosci, 17:327-335.

Banks, W.A. et al. (1994). Penetration of interleukin-6 across the murine blood-brain barrier. Neuroscience Letters, 179(1-2):53-56.

Barnes, D.T. (1970). The uses and abuses of L.S.D. and other hallucinogenic drugs. The Australian and New Zealand Journal of Psychiatry, 4(4):170-173.

Barnes, P. J. (2006). How corticosteroids control inflammation: Quintiles Prize Lecture 2005. British Journal of Pharmacology, 148(3):245-254.

Barnes, T.R.E. (1989) A Rating Scale for Drug-Induced Akathisia. Br J Psychiatry, 154:672-676.

Baron-Cohen, S. et al. (2000) The amygdala theory of autism. Neurosci Biobehav Rev, 24(3):355-364.

Barrett, F.S. et al. (Nov. 2015) Validation of the revised Mystical Experience Questionnaire in experimental sessions with psilocybin. Journal of Psychopharmacology. 29:1182-1190. HHS Public Access Author Manuscript, 20 pages.

Barrett, F.S. et al. (Dec. 2016) The Challenging Experience Questionnaire: Characterization of challenging experiences with psilocybin mushrooms. Journal of Psychopharmacology, 30(12):1279-1295. HHS Public Access Author Manuscript, 42 pages.

Barrett, F.S. et al. (Nov. 2018) Serotonin 2A Receptor Signaling Underlies LSD-Induced Alteration of the Neural Response to Dynamic Changes in Music. Cerebral Cortex, 28:3939-3950.

Basetti and Aldrich, "Idiopathic hypersomnia. A series of 42 patients," Brain, (1997) 120(8): 1423-1435.

(56) References Cited

OTHER PUBLICATIONS

Bateman, R.J. et al. (Aug. 30, 2012). Clinical and biomarker changes in dominantly inherited Alzheimer's disease. The New England Journal of Medicine, 367(9):795-804.
Bech, P. et al. (1978) The mania rating scale: scale construction and inter-observer agreement. Neuropharmacology. 17(6):430-431.
Becker, D. and Grilo, C. (2015). Comorbidity of mood and substance use disorders in patients with binge-eating disorder: Associations with personality disorder and eating disorder pathology. Journal of Psychosomatic Research, 79(2), pp. 159-164.
Becker, P.M. (2006). Insomnia: Prevalence, Impact, Pathogenesis, Differential Diagnosis, and Evaluation. Psychiatr Clin North Am, 26:855-870.
Bell, R.F. and E.A. Kalso (2018) Ketamine for pain management. Pain Reports, 3:e674, 8 pages.
Belli, H et al. (2012). Dissociative symptoms and dissociative disorder comorbidity in patients with obsessive-compulsive disorder. Comprehensive Psychiatry, 53(7):975-980.
Bello, N. and Yeomans, B. (2018). Safety of pharmacotherapy options for bulimia nervosa and binge eating disorder. Expert Opinion on Drug Safety, 17(1), pp. 17-23.
Belzeaux, R et al. (Feb. 2018). Focusing on the Opioid System for Addiction Biomarker Discovery. Trends in Molecular Medicine, 24(2), pp. 206-220.
Benzon, H.T et al. (2013) Preface. Practical Management of Pain, 5th Edition. Philadelphia, PA: Elsevier Mosby; 13 total pages.
Berg, A.T. (Jan. 2011). Epilepsy, cognition, and behavior: The clinical picture. Epilepsia, 52(Suppl 1):7-12. NIH Public Access Author Manuscript, available Jan. 1, 2012, 8 pages.
Berg, A.T et al. (2008). Residual cognitive effects of uncomplicated idiopathic and cryptogenic epilepsy. Epilepsy & Behavior, 13(4):614-619.
Berg, D. et al. (Nov. 12, 2015). MDS research criteria for prodromal Parkinson's disease. Movement Disorders, 30(12):1600-1609.
Berlin, H.A. et al. (2011). Double-blind, placebo-controlled trial of topiramate augmentation in treatment-resistant obsessive-compulsive disorder. Journal of Clinical Psychiatry, 72(5):716-721. https://doi.org/10.4088/JCP.09m05266gre.
Berthold-Losleben, M. & H. Himmerich (2008). The TNF-alpha System: Functional Aspects in Depression, Narcolepsy and Psychopharmacology. Current Neuropharmacology, 6(3):193-202.
Besnard, J. et al. (Dec. 13, 2012) Automated design of ligands to polypharmacological profiles. Nature, 492(7428):215-220. https://doi.org/10.1038/nature11691.
Bhidayasiri, R. & P. Martinez-Martin (2017). Clinical Assessments in Parkinson's Disease: Scales and Monitoring. 132:129-182.
Billiard, M. & Bentley, A. (2004). Is insomnia best categorized as a symptom or a disease? Sleep Med. 5(Suppl 1):S35-S40. https://doi.org/10.1016/S1389-9457(04)90006-8.
Billiard, M. (2008). Narcolepsy: Current treatment options and future approaches. Neuropsychiatr Dis Treat, 4(3):557-566.
Binukumar, B.K. et al. (2015). Peptide TFP5/TP5 derived from Cdk5 activator P35 provides neuroprotection in the MPTP model of Parkinson's disease. Molecular Biology of the Cell, 26(24):4478-4491. https://doi.org/10.1091/mbc.E15-06-0415.
Bird, A.D. & Cuntz, H. (Jun. 4, 2019). Dissecting Sholl Analysis into Its Functional Components. Cell Reports, 27(10):3081-3096.
Bison, S. et al. (2009). Differential behavioral, physiological, and hormonal sensitivity to LPS challenge in rats. International Journal of Interferon, Cytokine and Mediator Research, 1:1-13. https://doi.org/10.2147/IJICMR.S4273.
Black, D.W. (2015) The Natural History of Antisocial Personality Disorder. The Canadian Journal of Psychiatry. 60(7):309-314.
Blair, J.B. et al. (2000) Effect of Ring Fluorination on the Pharmacology of Hallucinogenic Tryptamines. J Med Chem, 43(24):4701-4710. https://doi.org/10.1021/jm000339w.
Blasio, A. et al. (2014). Opioid system in the medial prefrontal cortex mediates binge-like eating. Addiction Biology, 19(4), pp. 652-662.
Blum, A. (2014). HMG-COA reductase inhibitors (statins), inflammation, and endothelial progenitor cells—New mechanistic insights of atherosclerosis. BioFactors, 40(3), 295-302. https://doi.org/10.1002/biof.1157.
Bogenschutz et al. (2015) Psilocybin-assisted treatment for alcohol dependence: A proof-of-concept study. J Psychopharmacol, 29:289-299.
Bonnet, M.H. et al. (1990). The effect of triazolam on arousal and respiration in central sleep apnea patients. Sleep, 13:31-41.
Borovcanin, M.M. et al. (Nov. 6, 2017). Interleukin-6 in Schizophrenia—Is There a Therapeutic Relevance? Frontiers in Psychiatry, 8:Article 221, 10 pages. https://doi.org/10.3389/fpsyt.2017.00221.
Bortolato, B. et al. (2015). The Involvement of TNF-alpha in Cognitive Dysfunction Associated with Major Depressive Disorder: An Opportunity for Domain Specific Treatments. Current Neuropharmacology, 13(5):558-576.
Bosanac, P. et al. (2005). Serotonergic and dopaminergic systems in anorexia nervosa: a role for atypical antipsychotics? Australian and New Zealand Journal of Psychiatry, 39(3):146-153.
Bossers, K. et al. (2009). Analysis of gene expression in Parkinson's disease: possible involvement of neurotrophic support and axon guidance in dopaminergic cell death. Brain Pathology, 19(1):91-107.
Boszormenyi, Z. (1961) Psilocybin and diethyltryptamine: Two tryptamine hallucinogens. In: Rothlin E (ed) neuropsychopharmacology, vol. II. Elsevier, Amsterdam, pp. 226-229.
Braak, H. et al. (2003). Staging of brain pathology related to sporadic Parkinson's disease. Neurobiology of Aging, 24(2):197-211.
Bradley, T.D. and Phillipson, E.A. (1992). Central sleep apnea. Clin. Chest Med, 13(3):493-505 (abstract).
Bradley, T.D. et al. (1986). Clinical and physiologic heterogeneity of the central sleep apnea syndrome. Am. Rev. Respir. Dis., 134:217-221.
Braga, R.J. et al. (2013). Anxiety comorbidity in schizophrenia. Psychiatry Res, 210:1-7.
Brakoulias, V. et al. (2017). Comorbidity, age of onset and suicidality in obsessive-compulsive disorder (OCD): An international collaboration. Comprehensive Psychiatry, 76:79-86.
Brandt, C. & Mula, M. (2016). Anxiety disorders in people with epilepsy. Epilepsy Behav., 59:87-91. https://doi.org/10.1016/j.yebeh.2016.03.020.
Brandt, R.B. et al. (2020) Pharmacotherapy for Cluster Headache. CNS Drugs, 34:171-184, doi.org/10.1007/s40263-019-00696-2.
Brasure, M. et al. (2015). Management of Insomnia Disorder. Comparative Effectiveness Review No. 159. (Prepared by the Minnesota Evidence-based Practice Center under Contract No. 290-2012-00016-I). AHRQ Publication No. 15(16)-EHC027-EF. Rockville, MD: Agency for Healthcare Research and Quality. Dec. 2015 [online]. Retrieved from: www.effectivehealthcare.ahrq.gov/reports/final.cfm, 288 pages.
Bratland-Sanda, S. et al. (2019). Defining compulsive exercise in eating disorders: Acknowledging the exercise paradox and exercise obsessions. Journal of Eating Disorders, 7(1):8, https://doi.org/10.1186/s40337-019-0238-2, 3 pages.
Brawman-Mintzer, O. et al. (1993). Psychiatric comorbidity in patients with generalized anxiety disorder. Am. J. Psychiatry, 150:1216-1218.
Brockmeyer, T. et al. (2017) Advances in the treatment of anorexia nervosa: A review of established and emerging interventions. Psychological Medicine, 48(8):1228-1256. Cambridge University Press. https://doi.org/10.1017/S0033291717002604.
Brown, C. M., & Stokes, M.A. (2020). Intersection of Eating Disorders and the Female Profile of Autism. Child and Adolescent Psychiatric Clinics of North America, 29:409-417.
Brown, R.T. et al. (2017). Pharmacokinetics of Escalating Doses of Oral Psilocybin in Healthy Adults. Clinical Pharmacokinetics, 56(12):1543-1554. https://doi.org/10.1007/s40262-017-0540-6.
Brown, T.A. et al. (2001). Current and Lifetime Comorbidity of the DSM-IV Anxiety and Mood Disorders in a Large Clinical Sample. J. Abnorm. Psychol., 110:585-599.
Brownley, K. et al. (2016). Binge-Eating Disorder in Adults. Annals of Internal Medicine, 165(6):409-420.

(56) References Cited

OTHER PUBLICATIONS

Bruce, S.E. et al. (2005). Influence of psychiatric comorbidity on recovery and recurrence in generalized anxiety disorder, social phobia, and panic disorder: A 12-year prospective study. Am. J. Psychiatry, 162:1179-1187. NIH Public Access Author Manuscript, available in PMC Feb. 6, 2012, 16 pages.
Buescher, A.V. S. et al. (2014). Costs of autism spectrum disorders in the United Kingdom and the United States. JAMA Pediatrics, 168(8):721-728.
Bulik, C.M. et al. (1997). Eating disorders and antecedent anxiety disorders: a controlled study. Acta Psychiatr. Scand. 96, 101-107. https://doi.org/10.1111/j.1600-0447.1997.tb09913.x.
Burgess, E. et al. (2016). Effects of transcranial direct current stimulation (tDCS) on binge-eating disorder. International Journal of Eating Disorders, 49(10), pp. 930-936.
Burt, D.R. et al. (1976). Binding interactions of lysergic acid diethylamide and related agents with dopamine receptors in the brain. Molecular Pharmacology, 12(4):631-638.
Buscemi, N. et al. (Jun. 2005). Manifestations and management of chronic insomnia in adults: summary. In: AHRQ Evidence Report Summaries. Rockville (MD): Agency for Healthcare Research and Quality (US); 1998-2005. 125. https://doi.org/10.1037/e439752005-001, 11 pages.
Buxbaum, J.D., & Hof, P.R. (2013). Introduction. In the Neuroscience of Autism Spectrum Disorders. Elsevier, 7 pages. https://doi.org/10.1016/C2011-0-04170-4.
Buysse, D.J. et al. (1989). The Pittsburgh Sleep Quality Index: A New Instrument for Psychiatric Practice and Research. Psychiatry Res, 28:193-213.
Cabarkapa S. et al. (Aug. 13, 2019) Co-morbid obsessive-compulsive disorder and attention deficit hyperactivity disorder: Neurobiological commonalities and treatment implications. Front Psychiatry, 10:Article 557, 4 pages.
Cahill, C.M., & Rogers, J.T. (Sep. 19, 2008). Interleukin (IL) 1β Induction of IL-6 Is Mediated by a Novel Phosphatidylinositol 3-Kinase-dependent AKT/IκB Kinase α Pathway Targeting Activator Protein-1. Journal of Biological Chemistry, 283(38):25900-25912.
Caira, M. R., "Crystalline polymorphism of organic compounds", Topics in Current Chemistry (1998); 198: 163-208.
Callahan, P. M., & Appel, J.B. (1988). Differences in the stimulus properties of 3,4-methylenedioxyamphetamine and 3,4-methylenedioxymethamphetamine in animals trained to discriminate hallucinogens from saline. J Pharmacol Exp Ther, 246(3):866-870.
Calvin, A.D. et al. (2010). Advanced heart failure and nocturnal hypoxaemia due to central sleep apnoea are associated with increased serum erythropoietin. Eur. J. Heart Fail., 12:354-359. https://doi.org/10.1093/eurjhf/hfq005.
Campolongo, M. et al. (2018) Sociability deficits after prenatal exposure to valproic acid are rescued by early social enrichment. Molecular Autism, 9:36, https://doi.org/10.1186/s13229-018-0221-9, 17 pages.
Canellas, F. et al. (2014). Dual cases of type 1 narcolepsy with schizophrenia and other psychotic disorders. J. Clin. Sleep Med., 10(9):1011-1018. https://doi.org/10.5664/jcsm.4040.
Carhart-Harris et al., "Psilocybin for treatment-resistant depression: fMRI-measured brain mechanisms," Scientific Reports, 2017, 7:13187, 11 pages.
Carhart-Harris, R. et al. (2012). Implications for psychedelic-assisted psychotherapy: functional magnetic resonance imaging study with psilocybin. British Journal of Psychiatry, 200(3):238-244.
Carhart-Harris, R.L. et al. (May 17, 2016) "Psilocybin with psychological support for treatment-resistant depression: an open-label feasibility study" Lancet Psychiatry, 3:619-627.
Carhart-Harris, R.L. et al. (2018) "Psilocybin with psychological support for treatment-resistant depression: six-month follow-up" Psychopharmacology, 235:399-408.
Carlsson, T. et al. (2011). Systemic administration of neuregulin-1β1 protects dopaminergic neurons in a mouse model of Parkinson's disease. Journal of Neurochemistry, 117(6), 1066-1074. https://doi.org/10.1111/j.1471-4159.2011.07284.x.
Carosi, J. M., & Sargeant, T. J. (2019). Rapamycin and Alzheimer disease: a double-edged sword? Autophagy, 15(8):1460-1462. https://doi.org/10.1080/15548627.2019.1615823.
Carter, O.L. (2005) Using psilocybin to investigate the relationship between attention, working memory, and the serotonin 1A and 2A receptors. J Cogn Neurosci., 17(10):1497-1508.
Cashman, J.N. (1996). The mechanisms of action of NSAIDs in analgesia. Drugs, 52(Suppl. 5):13-23. https://doi.org/10.2165/00003495-199600525-00004.
Cassano, G.B. et al. (2002). Psychopharmacology of anxiety disorders. Dialogues Clin. Neurosci., 4(3):271-285.
Cavalli, E. et al. (2019). The neuropathic pain: An overview of the current treatment and future therapeutic approaches. Intl J Immunopathol Pharmacol, 33:1-10; DOI: 10.1177/2058738419838383.
Chang, A. et al. (Jun. 3, 2020). Capsaicin. StatPearls. NCBI Bookshelf [online]. Retrieved from: https://www.ncbi.nlm.nih.gov/books/NBK459168/?report=printable; retrieved on Jul. 30, 2020, 4 pages.
Chang, S. et al. (2015). Disease monitoring in inflammatory bowel disease. World Journal of Gastroenterology, 21(40):11246-11259.
Chang, T.-T. and Yen, Y.-C. (2010). Cytokines and Major Psychiatric Disorders. Taiwanese Journal of Psychiatry, 24(4):257-268.
Chang, Y.C. et al. (2017). Behavioral phenotyping for autism spectrum disorders in mice. Current Protocols in Toxicology. 72:11.22.1-11.22.21, doi: 10.1002/cptx.19.
Charles, P. et al. (1999). Regulation of Cytokines, Cytokine Inhibitors, and Acute-Phase Proteins Following Anti-TNF-α Therapy in Rheumatoid Arthritis. The Journal of Immunology, 163(3):1521-1528. http://www.jimmunol.org/content/163/3/1521.
Chelminski, P.R. et al. (Jan. 2005) A primary care, multi-disciplinary disease management program for opioid-treated patients with chronic non-cancer pain and a high burden of psychiatric comorbidity. BMC Health Serv Res, 5:3, doi:10.1186/1472-6963-5-3, 13 pages.
Cheng, Z. et al. (2019). Ethnic differences in eating disorder prevalence, risk factors, and predictive effects of risk factors among young women. Eating Behaviors, 32, pp. 23-30.
Chieffi, S. et al. (2017). Orexin system: The key for a healthy life. Front. Physiol., 8:357, doi: 10.3389/fphys.2017.00357, 9 pages.
Choi, G.B. et al. (2016). The maternal interleukin-17a pathway in mice promotes autism-like phenotypes in offspring. Science, 351(6276):933-939.
Chrem, Mendez, P. et al. (2019). Biomarkers for Alzheimer's disease. Where we stand and where we are headed. Medicina (Buenos Aires), 79:546-551.
Citrome, L. (2014). Suvorexant for insomnia: A systematic review of the efficacy and safety profile for this newly approved hypnotic—What is the number needed to treat, number needed to harm and likelihood to be helped or harmed? Int. J. Clin. Pract., 68(12):1429-1441. https://doi.org/10.1111/ijcp.12568.
Citrome, L. (2019). Binge eating disorder revisited: what's new, what's different, what's next. CNS Spectrums, 24, pp. 4-12.
Ciz, M. et al. (2007). Serotonin modulates the oxidative burst of human phagocytes via various mechanisms. Platelets, 18(8):583-590. https://doi.org/10.1080/09537100701471865.
Clark, B. (1968). Some early observations on the use of psilocybin in psychiatric patients. Brit. J. Soc. Psychiatry, 2:21-25.
Clemmensen, C. et al. (2012). The microtubule-associated protein 1A (MAP1A) is an early molecular target of soluble Aβ-peptide. Cellular and Molecular Neurobiology, 32(4):561-566.
ClinicalTrials.gov, "Effects of Psilocybin in Major Depressive Disorder", NCT03181529, First posted Jun. 8, 2017, pp. 1-6.
clinicaltrials.gov, "Effects of SERT Inhibition on the Subjective Response to Psilocybin in Healthy Subjects", Study NCT03912974, Submitted Feb. 28, 2020. Retrieved from the Internet: URL:https://www.clinicaltrials.gov/ct2/history/NCT03912974?V_4=View#StudyPageTop [retrieved on Jan. 21, 2022]; 7 printed pages.
Cloez-Tayarani, I. et al. (2003). Differential effect of serotonin on cytokine production in lipopolysaccharide-stimulated human periph-

(56) References Cited

OTHER PUBLICATIONS eral blood mononuclear cells: Involvement of 5-hydroxytryptamine$_{2a}$ receptors. International Immunology, 15(2), 233-240. https://doi.org/10.1093/intimm/dxg027.
Coley, A.A., & Gao, W.J. (2019). PSD-95 deficiency disrupts PFC-associated function and behavior during neurodevelopment. Scientific Reports, 9:9486, https://doi.org/10.1038/s41598-019-45971-w, 13 pages.
Collins, K.L. Et al. (2018). A review of current theories and treatments for phantom limb pain. J Clin Invest, 128(6):2168-2176. https://doi.org/10.1172/JCI94003.
Colloca, L. et al. (2017) Neuropathic pain. Nat Rev Dis Primers, 3:17002, doi:10.1038/nrdp.2017.2, 45 pages.
Connolly, J. et al. (Sep. 2015). ADHD & Pharmacotherapy: Past, Present and Future. Ther Innoc Regul Sci., 49(5):632-642. HHS Public Access, available in PMC Sep. 1, 2016, 19 pages.
Cooper, C.M. et al. (2015) Tianeptine in an experimental medicine model of antidepressant action. Journal of Psychopharmacology, 29(5):582-590.
Coric, V. et al. (2005). Riluzole augmentation in treatment-resistant obsessive-compulsive disorder: An open-label trial. Biological Psychiatry, 58(5):424-428. https://doi.org/10.1016/j.biopsych.2005.04.043.
Cornillie, F. et al. (2001) Infliximab induces potent anti-inflammatory and local immunomodulatory activity but no systemic immune suppression in patients with Crohn's disease. Alimentary Pharmacology and Therapeutics, 15(4), 463-473. https://doi.org/10.1046/j.1365-2036.2001.00956.x.
Cossrow, N. et al. (2016). Estimating the Prevalence of Binge Eating Disorder in a Community Sample From the United States: Comparing DSM-IV-TR and DSM-5 Criteria. The Journal of Clinical Psychiatry, 77(8), pp. e968-e974.
Costa-Mattioli, M., & Monteggia, L.M. (2013). mTOR complexes in neurodevelopmental and neuropsychiatric disorders. Nature Neuroscience, 16(11):1537-1543.
Cowie, M.R. et al. (2015) Adaptive servo-ventilation for central sleep apnea in systolic heart failure. N. Engl. J. Med., 373:1095-1105. doi.org/10.1056/NEJMoa1506459.
Croall, I.D. et al. (2020). Cognitive Deficit and White Matter Changes in Persons with Celiac Disease: a Population-Based Study. Gastroenterology. 158:2112-2122.
Crow, S.J. et al. (2009). Increased mortality in bulimia nervosa and other eating disorders. American Journal of Psychiatry, 166(12):1342-1346.
Crowson, C. S. et al. (2009). Which Measure of Inflammation to Use? A Comparison of Erythrocyte Sedimentation Rate and C-Reactive Protein Measurements from Randomized Clinical Trials of Golimumab in Rheumatoid Arthritis. The Journal of Rheumatology, 36(8):1606-1610. https://doi.org/10.3899/jrheum.081188.
Cruccu, G. (2017) A Review of Neuropathic Pain: From Guidelines to Clinical Practice. Pain Ther, 6(Suppl 1):S35-S42.
Cryan, J.F. & Sweeney, F.F. (2011). The age of anxiety: Role of animal models of anxiolytic action in drug discovery. British Journal of Pharmacology, 164:1129-1161.
Csicsvari, J. et al. (2003). Mechanisms of gamma oscillations in the hippocampus of the behaving rat. Neuron, 37:311-322.
Culbert, K.M. et al. (2015). Research Review: What we have learned about the causes of eating disorders—A synthesis of sociocultural, psychological, and biological research. Journal of Child Psychology and Psychiatry, 56:11, pp. 1141-1164. https://doi.org/10.1111/jcpp.12441.
Curatolo, P. et al. (2010) The neurobiological basis of ADHD. Ital J Pediatr, 36:79, http://www.ijponline.net/content/36/1/79, 7 pages.
Cuthbert, P.C. et al. (2007). Synapse-associated protein 102/dlgh3 couples the NMDA receptor to specific plasticity pathways and learning strategies. Journal of Neuroscience, 27(10):2673-2682. https://doi.org/10.1523/JNEUROSCI.4457-06.2007.
Da Silveira, D.X. et al. (2005). Ayahuasca in adolescence: A preliminary psychiatric assessment. Journal of Psychoactive Drugs, 37:2, 129-133. https://doi.org/10.1080/02791072.2005.10399792.
Dahan, A. et al. (Oct. 2014) Comorbidities and the Complexities of Chronic Pain. Anesthesiology, 121(4):675-677.
Dalic, L., & Cook, M. (2016). Managing drug-resistant epilepsy: challenges and solutions. Neuropsychiatric Disease and Treatment, vol. 12, p. 2605-2616. https://doi.org/10.2147/NDT.S84852.
Damaslo, A., "Alzheimer's Disease and Related Dementias," Cecil Textbook of Medicine, Eds. J. Claude Bennett, MD and Fred Plum, 20th edition (1996), vol. 2, pp. 1992-1996.
Dansie, E.J. & Turk, D.C. (2013) Assessment of patients with chronic pain. Br J Anaesth. 111(1):19-25.
Darveaux, J., & Busse, W. W. (2015). Biologics in Asthma—The Next Step Toward Personalized Treatment. J Allergy Clin Immunol Pract, 3(2), 152-160. https://doi.org/10.1016/j.jaip.2014.09.014.
Dash, S. (2019). The impact of genetic and cultural factors on anorexia and bulimia. Life Research, 2(2), 71-79. https://doi.org/10.12032/life2019-0425-004.
Dauer, W., & Przedborski, S. (2003). Parkinson's Disease: Mechanisms and Models. Neuron, 39(6), 889-909. https://doi.org/10.1016/S0896-6273(03)00568-3.
Dauvilliers, Y. & Barateau, L. (2017). Narcolepsy and Other Central Hypersomnias. Continyyn (Minneap Minn), 23(4):989-1004. https://doi.org/10.1212/CON.0000000000000492.
Dauvilliers, Y. et al. (2007). Narcolepsy with cataplexy. Lancet 369, 499-511. https://doi.org/10.1016/S0140-6736(07)60237-2.
Dauvilliers, Y. et al (2009). Psychological health in central hypersomnias: The French Harmony study. J. Neurol. Neurosurg. Psychiatry, 80, 636-641. https://doi.org/10.1136/jnnp.2008.161588.
Davila Gonzalez, I. et al. (2019). Benralizumab: A New Approach for the Treatment of Severe Eosinophilic Asthma. Journal of Investigational Allergology and Clinical Immunology, 29(2), 84-93. https://doi.org/10.18176/jiaci.0385.
Davis, C. (2015). The epidemiology and genetics of binge eating disorder (BED). CNS Spectrums, 20(6), pp. 522-529.
Davis, H., & Attia, E. (2017). Pharmacotherapy of eating disorders. Current Opinion in Psychiatry, 30(6), 452-457. https://doi.org/10.1097/YCO.0000000000000358.
De Veen, B.T.H. et al. (2017) "Psilocybin for treating substance use disorders?" Exp Rev Neurotherapeutics, 17(2):203-212; DOI: 10.1080/14737175.2016.1220834.
Deacon, R.M.J. & Rawlins, J.N.P. (2006) T-maze alternation in the rodent. Nat Protoc, 1(1):7-12. Available from: http://www.ncbi.nlm.nih.gov/pubmed/17406205.
Debacker, W.A. et al. (1995). Central apnea index decreases after prolonged treatment with acetazolamide. Am. J. Respir. Crit. Care Med., 151:87-91, https://doi.org/10.1164/ajrccm.151.1.7812578.
Debotton, N. and A. Dahan (2017) Applications of Polymers as Pharmaceutical Excipients in Solid Oral Dosage Forms. Med Res Rev, 37(1):52-97.
Decaluwe, V. and Braet, C. (2003). Prevalence of binge-eating disorder in obese children and adolescents seeking weight-loss treatment. International Journal of Obesity, 27(3), pp. 404-409.
Dejong, H. et al. (2013). Quality of life in anorexia nervosa, bulimia nervosa and eating disorder not-otherwise-specified. Journal of Eating Disorders, 1:43, http://www.jeatdisord.com/content/1/1/43, 8 pages.
Delisi, M. et al. (Jul. 2019) The etiology of antisocial personality disorder: The differential roles of adverse childhood experiences and childhood psychopathology. Compr Psychiatry, 92:1-6.
Dell'Osso, B. et al. (2018). Prevalence of suicide attempt and clinical characteristics of suicide attempters with obsessive-compulsive disorder: A report from the International College of Obsessive-Compulsive Spectrum Disorders (ICOCS). CNS Spectrums, 23(1), 59-66. https://doi.org/10.1017/S1092852917000177.
Depboylu, C. et al. (2015). Systemically administered neuregulin-1β1 rescues nigral dopaminergic neurons via the ErbB4 receptor tyrosine kinase in MPTP mouse models of Parkinson's disease. Journal of Neurochemistry, 133(4), 590-597. https://doi.org/10.1111/jnc.13026.
Di Lodovico, L., & Gorwood, P. (2020). The relationship between moderate to vigorous physical activity and cognitive rigidity in anorexia nervosa. Psychiatry Research, 284:112703, https://doi.org/10.1016/j.psychres.2019.112703, 9 pages.

(56) References Cited

OTHER PUBLICATIONS

Dijkstra, P.U. et al. (2002) Phantom pain and risk factors: A multivariate analysis. J Pain Symptom Manage. 24(6):578-585.
Diniz, J.B. et al. (2010) "Quetiapine versus clomipramine in the augmentation of selective serotonin reuptake inhibitors for the treatment of obsessive-compulsive disorder: A randomized, open-label trial" Journal of Psychopharmacology, 24(3):297-307.
Dold, M. et al. (2015). Antipsychotic Augmentation of Serotonin Reuptake Inhibitors in Treatment-Resistant Obsessive-Compulsive Disorder: An Update Meta-Analysis of Double-Blind, Randomized, Placebo-Controlled Trials. The International Journal of Neuropsychopharmacology, 1-11, https://doi.org/10.1093/ijnp/pyv047.
Dold, M. et al. (2015) "Second-Generation Antipsychotic Drugs in Anorexia Nervosa: A Meta-Analysis of Randomized Controlled Trials" Psychotherapy and Psychosomatics, 84(2):110-116. https://doi.org/10.1159/000369978.
Dotterer, H.L. et al. (2017) Amygdala reactivity predicts adolescent antisocial behavior but not callous-unemotional traits. Dev Cogn Neurosci, 24:84-92.
Drakatos, P. et al (2017). Safety and efficacy of long-term use of sodium oxybate for narcolepsy with cataplexy in routine clinical practice. Sleep Med, 35:80-84. https://doi.org/10.1016/j.sleep.2017.03.028.
Droogleever Fortuyn, H.A. et al. (2011). Narcolepsy and psychiatry: An evolving association of increasing interest. Sleep Med. 12, 714-719. https://doi.org/10.1016/j.sleep.2011.01.013.
Drover, D.R., 2004. Comparative pharmacokinetics and pharmacodynamics of short-acting hypnosedatives: Zaleplon, zolpidem and zopiclone. Clin. Pharmacokinet. 423(4):227-238. https://doi.org/10.2165/00003088-200443040-00002.
drugs.com (2014) Venlafaxine. Drugs.com, Web Archives [online]. Retrieved from: https://web.archive.org/web/20140502180823/https://www.drugs.com/venlafaxine.html; on May 2, 2014; 5 pages.
Dunning, C.J.R. et al. (2016). Multisite tyrosine phosphorylation of the N-terminus of Mint1/X11α by Src kinase regulates the trafficking of amyloid precursor protein. Journal of Neurochemistry, 137(4), 518-527. https://doi.org/10.1111/jnc.13571.
Durk, T. et al. (2005). 5-Hydroxytryptamine modulates cytokine and chemokine production in LPS-primed human monocytes via stimulation of different 5-HTR subtypes. International Immunology, 17(5), 599-606. https://doi.org/10.1093/intimm/dxh242.
Earle, W. J. (2014) "DSM-5" The Philosophical Forum [online]. Retrieved from: https://doi.org/10.1111/phil.12034; pp. 179-196.
Eckert, D.J. et al. (Feb. 2007). Central sleep apnea: Pathophysiology and treatment. Chest, 131:595-607. NIH Public Access Author Manuscript, available Apr. 3, 2008, 22 pages.
Edfawy, M. et al. (2019). Abnormal mGluR-mediated synaptic plasticity and autism-like behaviours in Gprasp2 mutant mice. Nature Communications. 10:1431, https://doi.org/10.1038/s41467-019-09382-9, 15 pages.
Edwards, A. (Jun. 2010) Book Review: Handbook of Depression (2nd ed.). Gotlib, I.H., Hammen, C.L. (Eds.), The Guilford Press: New York, 2009. Psychology Medicine, 40:1051-1052.
Eijk, S. et al. (2018). Autism Spectrum Disorder in an Unselected Cohort of Children with Neurofibromatosis Type 1 (NF1). Journal of Autism and Developmental Disorders, 15:2278-2285. https://doi.org/10.1007/s10803-018-3478-0.
Ekbom, K. et al. (Mar. 2002) Age at onset and sex ratio in cluster headache: Observations over three decades. Cephalalgia, 22(2):94-100.
Elbassuoni, E. A., & Ahmed, R. F. (2019). Mechanism of the neuroprotective effect of GLP-1 in a rat model of Parkinson's with pre-existing diabetes. Neurochemistry International, 131, 104583. https://doi.org/10.1016/j.neuint.2019.104583, 8 pages.
El-Emshaty, H. M., Nasif, W. A., & Mohamed, I. E. (2015). Serum Cytokine of IL-10 and IL-12 in Chronic Liver Disease: The Immune and Inflammatory Response. Disease Markers, https://doi.org/10.1155/2015/707254, 7 pages.
El-Gabalawy, H., Guenther, L. C., & Bernstein, C. N. (2010). Epidemiology of Immune-Mediated Inflammatory Diseases: Incidence, Prevalence, Natural History, and Comorbidities. The Journal of Rheumatology Supplement, 85, 2-10. https://doi.org/10.3899/jrheum.091461.
Epstein JN, Loren Rea. (2013) Changes in the definition of ADHD in DSM-5: Subtle but important. Neuropsychiatry, 3(5):455-8.
Erdur, L. et al. (2012). Somatic comorbidity in anorexia nervosa: First results of a 21-year follow-up study on female inpatients. BioPsychoSocial Medicine, 6:4, https://doi.org/10.1186/1751-0759-6-4, 6 pages.
Erskine, H. and Whiteford, H.(Nov. 2018). Epidemiology of binge eating disorder. Current Opinion in Psychiatry, 31(6), pp. 462-470.
Essau, C.A. et al. (2014). Anxiety disorders in adolescents and psychosocial outcomes at age 30. J. Affect. Disord. 163, 125-132. https://doi.org/10.1016/j.jad.2013.12.033. NIH Public Access Author Manuscript, 19 pages.
Evans, M.M. et al. (2016) Ego-dissolution and psychedelics: Validation of the Ego-Dissolution Inventory (EDI). Front Human Neurosci, 10:269, doi: 10.3389/fnhum.2016.00269, 13 pages.
Everitt, H. et al. (2018). Antidepressants for insomnia in adults (Review). Cochrane Database Syst. Rev., Issue 5, Art. No. CD010753, https://doi.org/10.1002/14651858.CD010753.pub2, 117 pages.
Fadiman, J. & Korb, S. (2019) Might Microdosing Psychedelics Be Safe and Beneficial? An Initial Exploration. J Psychoactive Drugs, 51(2):118-22. Available from: https://doi.org/10.1080/02791072.20191593561.
Fan, L.Y. et al. (Oct. 2018) Visual processing as a potential endophenotype in youths with attention-deficit/hyperactivity disorder: A sibling study design using the counting Stroop functional MRI. Hum Brain Mapp, 39(10):3827-35. Available from: http://www.ncbi.nlm.nih.gov/pubmed/29749060.
Fayaz, A. et al. (2016) Prevalence of chronic pain in the UK: a systematic review and meta-analysis of population studies. BMJ Open [Internet]. 6:e010364, doi:10.1136/bmjopen-2015-010364, 12 pages.
FDA mulls drug to slow late-stage Alzheimer's [online], [retrieved on Sep. 23, 2003]. Retrieved from the internet, http://www.cnn.com/2003/HEALTH/conditions/09/24/alzheimers.drug.ap/index.html. pp. 1-3, http://www.cnn.com/2003/HEALTH/conditions/09/24/alzheimers.drug.ap/index.html.
Feinstein, A.R. (1970). The pre-therapeutic classification of co-morbidity in chronic disease. Journal of Chronic Diseases, 23(7), 455-468. https://doi.org/10.1016/0021-9681(70)90054-8.
Ferguson, S.A. et al. (2010). Melatonin agonists and insomnia. Expert Rev. Neurother., 10(2):305-318. https://doi.org/10.1586/ern.10.1.
Fernandez, B. A., & Scherer, S.W. (2017). Syndromic autism spectrum disorders: Moving from a clinically defined to a molecularly defined approach. Dialogues in Clinical Neuroscience, 19:353-371.
Feyder, M. et al. (2010). Association of mouse Dlg4 (PSD-95) gene deletion and human DLG4 gene variation with phenotypes relevant to autism spectrum disorders and Williams' syndrome. American Journal of Psychiatry, 167:1508-1517. https://doi.org/10.1176/appi.ajp.2010.10040484.
Fiebich, B.L. et al. (2004). Antiinflammatory effects of 5-HT3 receptor antagonists in lipopolysaccharide-stimulated primary human monocytes. Scandinavian Journal of Rheumatology. 33:28-32. https://doi.org/15515409.
Fisher, G. (1970). The psycholytic treatment of a childhood schizophrenic girl. International Journal of Social Psychiatry. 16(2):112-130. https://doi.org/10.1177/002076407001600204.
Fisher, K.A. & Hany, M. (Jun. 24, 2020) Antisocial Personality Disorder. StatPearls [Internet]. NCBI Bookshelf. Retrieved from: http://www.ncbi.nlm.nih.gov/pubmed/31536279, 6 printed pages.
Fisher, R.S. et al. (2005). Epileptic Seizures and Epilepsy: Definitions Proposed by the International League Against Epilepsy (ILAE) and the International Bureau for Epilepsy (IBE). Epilepsia, 46(4), 470-472. https://doi.org/10.1111/j.0013-9580.2005.66104.x.
Flament, M.F. et al. (2012) Evidence-based pharmacotherapy of eating disorders. The International Journal of Neuropsychopharmacology, 15(02), 189-207. https://doi.org/10.1017/S1461145711000381.

(56) References Cited

OTHER PUBLICATIONS

Flanagan, T.W. et al. (2019). 5-HT2 receptor activation alleviates airway inflammation and structural remodeling in a chronic mouse asthma model. Life Sciences, 236:116790, https://doi.org/10.1016/j.lfs.2019.116790, 9 pages.
FMC Product Overview (2017) Avicel® SMCC HD 50 Silicified Microcrystalline cellulose NF. Product Specifications, 2 pages.
FMC Product Overview (2017) Avicel® SMCC HD 90 Silicified Microcrystalline cellulose NF. Product Specifications, 2 pages.
Folen, V. (1975) X-ray powder diffraction data for some drugs, excipients, and adulterants in illicit samples. Journal of Forensic Science. 1975, 20, 348-372.
Fond, G. et al. (2014). Anxiety and depression comorbidities in irritable bowel syndrome (IBS): a systematic review and meta-analysis. Eur. Arch. Psychiatry Clin. Neurosci. 264, 651-660. https://doi.org/10.1007/s00406-014-0502-z.
Fornasari, D. (2017) Pharmacotherapy for Neuropathic Pain: A Review. Pain Ther, 6(Suppl 1):S25-S33.
Fortuyn, H.A.D. et al. (2008). High Prevalence of Eating Disorders in Narcolepsy with Cataplexy: A Case-Control Study. Sleep 31, 335-341. https://doi.org/10.1093/sleep/31.3.335.
Fortuyn, H.A.D. et al. (2010). Anxiety and mood disorders in narcolepsy: a case-control study. Gen. Hosp. Psychiatry, 32:49-56. https://doi.org/10.1016/j.genhosppsych.2009.08.007.
*Freedom To Operate, Inc. v. Compass Pathways Limited*. Case PGR2022-00012, U.S. Pat. No. 10,947,257: Petitioner's Request for Rehearing Under 37 C.F.R. § 42.71 (PTAB Jul. 22, 2022); 17 pages.
*Freedom To Operate, Inc. v. Compass Pathways Limited*. Case PGR2022-00018, U.S. Pat. No. 10,954,259: Petitioner's Request for Rehearing Under 37 C.F.R. § 42.71 (PTAB Jul. 22, 2022); 17 pages.
*Freedom To Operate, Inc. v. Compass Pathways Limited*. Case PGR2022-00012, U.S. Pat. No. 10,947,257. and *Freedom to Operate, Inc. v. Compass Pathways Limited*. Case PGR2022-00018, U.S. Pat. No. 10,954,259; Order that the requests for POP review are denied and hat the original panel maintains authority over all matters, including considering the submitted rehearing requests, dated Feb. 10, 2023, 3 pages.
*Freedom To Operate, Inc. v. Compass Pathways Limited*. Case PGR2022-00012, U.S. Pat. No. 10,947,257. Exhibit 1006: Declaration of Sven Lidin, Ph.D. (PTAB Dec. 15, 2021), 68 pages.
*Freedom To Operate, Inc. v. Compass Pathways Limited*. Case PGR2022-00012, U.S. Pat. No. 10,947,257. Exhibit 1007: Curriculum Vitae—Sven Lidin, Ph.D. (PTAB Dec. 15, 2021), 2 pages.
*Freedom To Operate, Inc. v. Compass Pathways Limited*. Case PGR2022-00012, U.S. Pat. No. 10,947,257. Exhibit 1008: Declaration of James A. Kaduk, Ph.D. (PTAB Dec. 15, 2021), 25 pages.
*Freedom To Operate, Inc. v. Compass Pathways Limited*. Case PGR2022-00012, U.S. Pat. No. 10,947,257. Exhibit 1009: Curriculum Vitae—James A. Kaduk, Ph.D. (PTAB Dec. 15, 2021), 3 pages.
*Freedom To Operate, Inc. v. Compass Pathways Limited*. Case PGR2022-00012, U.S. Pat. No. 10,947,257. Exhibit 1010: Declaration of Raj Suryanarayanan, Ph.D. (PTAB Dec. 15, 2021), 23 pages.
*Freedom To Operate, Inc. v. Compass Pathways Limited*. Case PGR2022-00012, U.S. Pat. No. 10,947,257. Exhibit 1011: Curriculum Vitae—Raj Suryanarayanan, Ph.D. (PTAB Dec. 15, 2021), 53 pages.
*Freedom To Operate, Inc. v. Compass Pathways Limited*. Case PGR2022-00012, U.S. Pat. No. 10,947,257. Exhibit 1012: Declaration of Charles L. Raison, M.D. (PTAB Dec. 15, 2021), 6 pages.
*Freedom To Operate, Inc. v. Compass Pathways Limited*. Case PGR2022-00012, U.S. Pat. No. 10,947,257. Exhibit 1013: Hancock, B.C. and G. Zografi. Characteristics and Significance of the Amorphous State in Pharmaceutical Systems. Journal of Pharmaceutical Sciences, vol. 86, No. 1. (PTAB Dec. 15, 2021), 12 pages.
*Freedom To Operate, Inc. v. Compass Pathways Limited*. Case PGR2022-00012, U.S. Pat. No. 10,947,257. Exhibit 1014: Arlin, J.B. et al. Experimental Crystal Structure Determination, pp. 1-3, 2021 (PTAB Dec. 15, 2021).
*Freedom To Operate, Inc. v. Compass Pathways Limited*. Case PGR2022-00012, U.S. Pat. No. 10,947,257. Exhibit 1015: Bernstein J. Polymorphism in Molecular Crystals, International Union of Crystallography, Oxford, 2002 (PTAB Dec. 15, 2021), 429 pages.
*Freedom To Operate, Inc. v. Compass Pathways Limited*. Case PGR2022-00012, U.S. Pat. No. 10,947,257. Exhibit 1016: Boratto, M. H. Semiconducting and Insulating Oxides Applied to Electronic Devices. Thesis Ph.D. UNESP, School of Science, Bauru, 2018. (PTAB Dec. 15, 2021), 117 pages.
*Freedom To Operate, Inc. v. Compass Pathways Limited*. Case PGR2022-00012, U.S. Pat. No. 10,947,257. Exhibit 1017: D.E. Nichols, Synthesis of High Purity Psilocybin: Lot 10415-25, Nov. 1, 2009. (PTAB Dec. 15, 2021), 43 pages.
*Freedom To Operate, Inc. v. Compass Pathways Limited*. Case PGR2022-00012, U.S. Pat. No. 10,947,257. Exhibit 1018: Jun. 6, 2012 Letter from D. Nichols to R. Griffiths. (PTAB Dec. 15, 2021), 7 pages.
*Freedom To Operate, Inc. v. Compass Pathways Limited*. Case PGR2022-00012, U.S. Pat. No. 10,947,257. Exhibit 1019: Apr. 15, 2014 Letter from C. Kim to E. Elder. (PTAB Dec. 15, 2021), 4 pages.
*Freedom To Operate, Inc. v. Compass Pathways Limited*. Case PGR2022-00012, U.S. Pat. No. 10,947,257. Exhibit 1020: Declaration of Brett D. Bobzien. (PTAB Dec. 15, 2021), 5 pages.
*Freedom To Operate, Inc. v. Compass Pathways Limited*. Case PGR2022-00012, U.S. Pat. No. 10,947,257. Exhibit 1021: Triclinic Labs Report, Characterization of Psilocybin, Dec. 2, 2021. (PTAB Dec. 15, 2021), 11 pages.
*Freedom To Operate, Inc. v. Compass Pathways Limited*. Case PGR2022-00012, U.S. Pat. No. 10,947,257. Exhibit 1023: USP35-(941) Physical Tests/X-Ray Powder Diffraction. (PTAB Dec. 15, 2021), 7 pages.
*Freedom To Operate, Inc. v. Compass Pathways Limited*. Case PGR2022-00012, U.S. Pat. No. 10,947,257. Exhibit 1024: Ottoboni S. et al. Understanding API Static Drying with Hot Gas Flow: Design and Test of a Drying Rig Prototype and Drying Modeling Development. Org. Process Res. Dev. 2020, 24, 2505-2520. (PTAB Dec. 15, 2021).
*Freedom To Operate, Inc. v. Compass Pathways Limited*. Case PGR2022-00012, U.S. Pat. No. 10,947,257. Exhibit 1025: Airaksinen S. et al. Comparison of the effects of two drying methods on polymorphism of theophylline. International Journal of Pharmaceutics 276: 129-141 (2004). (PTAB Dec. 15, 2021).
*Freedom To Operate, Inc. v. Compass Pathways Limited*. Case PGR2022-00012, U.S. Pat. No. 10,947,257. Exhibit 1026: Lim, H.L. et al., Understanding and preventing agglomeration in a filter drying process. Powder Technology, 300 (2016) 146-156. (PTAB Dec. 15, 2021).
*Freedom To Operate, Inc. v. Compass Pathways Limited*. Case PGR2022-00012, U.S. Pat. No. 10,947,257. Exhibit 1028: Curriculum Vitae—Charles L. Raison, M.D. (PTAB Dec. 15, 2021), 59 pages.
*Freedom To Operate, Inc. v. Compass Pathways Limited*. Case PGR2022-00012, U.S. Pat. No. 10,947,257. Exhibit 1029: Excerpt from Diagnostic and Statistical Manual of Mental Disorders, Fifth Edition, DSM-5. Am. Psychiatric Assn., 2013; pp. 160-168. (PTAB Dec. 15, 2021).
*Freedom To Operate, Inc. v. Compass Pathways Limited*. Case PGR2022-00012, U.S. Pat. No. 10,947,257. Exhibit 1030: Declaration of Roland R. Griffiths, Ph.D. (PTAB Dec. 15, 2021), 6 pages.
*Freedom To Operate, Inc. v. Compass Pathways Limited*. Case PGR2022-00012, U.S. Pat. No. 10,947,257. Exhibit 1031: Excerpt from A. Dictionary of Chemistry, 6th Edition. John Daintith (Ed.) Oxford University Press; p. 428 (PTAB Dec. 15, 2021).
*Freedom To Operate, Inc. v. Compass Pathways Limited*. Case PGR2022-00012, U.S. Pat. No. 10,947,257. Exhibit 1032: *Astrazeneca AB v. Reddy's Laboratories, Inc.*, Civil Action No. 11-2317 (May 1, 2013). 2013 U.S. Dist. Lexis 62149; Dec. 13, 2021. (PTAB Dec. 15, 2021), 17 pages.
*Freedom To Operate, Inc. v. Compass Pathways Limited*. Case PGR2022-00012, U.S. Pat. No. 10,947,257. Exhibit 1033: Baker R.W. et al. Molecular Structures of Hallucinogenic Substances:

(56) References Cited

OTHER PUBLICATIONS

Lysergic Acid Diethylamide, Psilocybin, and 2,4,5-Trimethoxyamphetamine. Molecular Pharmacology, 9, 1973, 23-32. (PTAB Dec. 15, 2021).

*Freedom To Operate, Inc. v. Compass Pathways Limited.* Case PGR2022-00012, U.S. Pat. No. 10,947,257. Exhibit 1034: Petcher, T.J. and Weber, H.P. Crystal Structures of the Teonanácatl Hallucinogens. J. Chem Soc. Perkins Trans., 2, 8, 946-948, 1974.

*Freedom To Operate, Inc. v. Compass Pathways Limited.* Case PGR2022-00012, U.S. Pat. No. 10,947,257. Exhibit 1035: Kuhnert-Brandstätter, M. and Heindl, W. Polymorphe Modifikationen und Solvate von Psilocin und Psilocybin. Arch. Pharm, 1976, 309, 625-631 (German, English abstract on p. 626) (PTAB Dec. 15, 2021).

*Freedom To Operate, Inc. v. Compass Pathways Limited.* Case PGR2022-00012, U.S. Pat. No. 10,947,257. Exhibit 1036: Hofmann, A. et al. (1959) Psylocybin and Psilocin, zwei psychotrope Wirkstoffe aus mexikanischen Rauschpilzen. Helvetica Chimica Acta, vol. XLII (v), 1557-1572. (PTAB Dec. 15, 2021).

*Freedom To Operate, Inc. v. Compass Pathways Limited.* Case PGR2022-00012, U.S. Pat. No. 10,947,257. Exhibit 1041: Sherwood A.M. et al. An Improved, Practical, and Scalable Five-Step Synthesis of Psilocybin. Synthesis 2020, 52, 688-694 (PTAB Dec. 15, 2021).

*Freedom To Operate, Inc. v. Compass Pathways Limited.* Case PGR2022-00012, U.S. Pat. No. 10,947,257. Exhibit 1042: dos Santos, R.G. et al. Antidepressive, anxiolytic, and antiaddictive effects of ayahuasca, psilocybin and lysergic acid diethylamide (LSD): a systematic review of clinical trials published in the last 25 years. Ther Adv Psychopharmacol, 2016, vol. 6(3), 193-213. (PTAB Dec. 15, 2021).

*Freedom To Operate, Inc. v. Compass Pathways Limited.* Case PGR2022-00012, U.S. Pat. No. 10,947,257. Exhibit 1043: Hill, R.J. Expanded Use of the Rietveld Method in Studies of Phase Abundance in Multiphase Mixtures. Powder Diffraction, Jun. 1991, vol. 6, No. 2, pp. 74-77. (PTAB Dec. 15, 2021).

*Freedom To Operate, Inc. v. Compass Pathways Limited.* Case PGR2022-00012, U.S. Pat. No. 10,947,257. Exhibit 1044: Groom, C.R. et al. The Cambridge Structural Database. Acta Cryst. (2016). B72, 171-179. (PTAB Dec. 15, 2021).

*Freedom To Operate, Inc. v. Compass Pathways Limited.* Case PGR2022-00012, U.S. Pat. No. 10,947,257. Exhibit 1045: Lee, P.L. et al. A twelve-analyzer detector system for high-resolution powder diffraction. J Synchrotron Rad. (2008). 15, 427-432. (PTAB Dec. 15, 2021).

*Freedom To Operate, Inc. v. Compass Pathways Limited.* Case PGR2022-00012, U.S. Pat. No. 10,947,257. Exhibit 1046: Wang, J. et al. A dedicated powder diffraction beamline at the Advanced Photon Source: Commissioning and early operational results. Review of Scientific Instruments, 79, 085105 (2008). (PTAB Dec. 15, 2021).

*Freedom To Operate, Inc. v. Compass Pathways Limited.* Case PGR2022-00012, U.S. Pat. No. 10,947,257. Exhibit 1047: Antao, S.M. et al. State-of-the-Art High-Resolution Powder X-Ray Diffraction (HRPXRD) Illustrated With Rietveld Structure Refinement of Quartz, Sodalite, Tremolite, and Meionite. The Canadian Mineralogist, vol. 46, pp. 1501-1509 (2008). (PTAB Dec. 15, 2021).

*Freedom To Operate, Inc. v. Compass Pathways Limited.* Case PGR2022-00012, U.S. Pat. No. 10,947,257. Exhibit 1048: Toby B.H. and Von Dreele, B. GSAS-II: The genesis of a modern open-source all purpose crystallography software package. J Appl Cryst, (2013) 46, 544-549. (PTAB Dec. 15, 2021).

*Freedom To Operate, Inc. v. Compass Pathways Limited.* Case PGR2022-00012, U.S. Pat. No. 10,947,257. Exhibit 1049: Sykes, R.A. et al. New software for statistical analysis of Cambridge Structural Database data. J Appl Cryst, (2011) vol. 44, pp. 882-886. (PTAB Dec. 15, 2021).

*Freedom To Operate, Inc. v. Compass Pathways Limited.* Case PGR2022-00012, U.S. Pat. No. 10,947,257. Exhibit 1050: Bruno, I.J. et al. Retrieval of Crystallographically-Derived Molecular Geometry Information, J Chem Inf Comput Sci (2004) vol. 44, pp. 2133-2144. (PTAB Dec. 15, 2021).

*Freedom To Operate, Inc. v. Compass Pathways Limited.* Case PGR2022-00012, U.S. Pat. No. 10,947,257. Exhibit 1051: Kresse, G. and Furthmüller, J. Efficiency of ab-initio total energy calculations for metals and semiconductors using a plane-wave basis set. Computational Materials Science (1996) vol. 6, pp. 15-50. (PTAB Dec. 15, 2021).

*Freedom To Operate, Inc. v. Compass Pathways Limited.* Case PGR2022-00012, U.S. Pat. No. 10,947,257. Exhibit 1052: Dovesi, R. et al. Quantum-mechanical condensed matter simulations with Crystal. WIREs Comput Mol Sci (2018) e1360, pp. 1-36. (PTAB Dec. 15, 2021).

*Freedom To Operate, Inc. v. Compass Pathways Limited.* Case PGR2022-00012, U.S. Pat. No. 10,947,257. Exhibit 1053: Gatti, C. et al. Crystal field effects on the topological properties of the electron density in molecular crystals: The case of urea. J Chem Phys (1994) vol. 101, 10686. (PTAB Dec. 15, 2021), 12 pages.

*Freedom To Operate, Inc. v. Compass Pathways Limited.* Case PGR2022-00012, U.S. Pat. No. 10,947,257. Exhibit 1054: Peintinger, M.F. et al. Consistent Gaussian Basis Sets of Triple-Zeta Valence with Polarization Quality for Solid-State Calculations. Journal of Computational Chemistry (2012) 1-9. (PTAB Dec. 15, 2021).

*Freedom To Operate, Inc. v. Compass Pathways Limited.* Case PGR2022-00012, U.S. Pat. No. 10,947,257. Exhibit 1055: Louër, D. and Boultif, A. Some further considerations in powder diffraction pattern indexing with the dichotomy method. Powder Diffraction, 29(S2), S7-S12, Dec. 2014. (PTAB Dec. 15, 2021).

*Freedom To Operate, Inc. v. Compass Pathways Limited.* Case PGR2022-00012, U.S. Pat. No. 10,947,257. Exhibit 1056: Kourkoumelis, K. Powdl: a Reusable .net Component for Interconverting Powder Diffraction Data. Recent Developments. Powder Diffr., vol. 28, No. 2, Jun. 2013, pp. 137-148. (PTAB Dec. 15, 2021).

*Freedom To Operate, Inc. v. Compass Pathways Limited.* Case PGR2022-00012, U.S. Pat. No. 10,947,257. Exhibit 1057: Curriculum Vitae—Roland R. Griffiths. (PTAB Dec. 15, 2021), 64 pages.

*Freedom To Operate, Inc. v. Compass Pathways Limited.* Case PGR2022-00012, U.S. Pat. No. 10,947,257. Exhibit 1058: Zeeh Pharmaceutical Experiment Station, University of Wisconsin—Madison School of Pharmacy. Certificate of Analysis for Lot No. 10415-25. (PTAB Dec. 15, 2021), 1 page.

*Freedom To Operate, Inc. v. Compass Pathways Limited.* Case PGR2022-00012, U.S. Pat. No. 10,947,257. Exhibit 1059: Barrett, F.S. et al. Double-blind comparison of the two hallucinogens psilocybin and dextromethorphan: Effects on cognition. Psychopharmacology (Berl), Oct. 2018; 235(10): 2915-2927. HHS Public Access Author Manuscript. (PTAB Dec. 15, 2021).

*Freedom To Operate, Inc. v. Compass Pathways Limited.* Case PGR2022-00012, U.S. Pat. No. 10,947,257. Exhibit 1060: Non-Final Office Action, Aug. 13, 2020 (PTAB Dec. 15, 2021), 9 pages.

*Freedom To Operate, Inc. v. Compass Pathways Limited.* Case PGR2022-00012, U.S. Pat. No. 10,947,257. Exhibit 1061: Applicant-Initiated Interview Summary, filed Oct. 14, 2020 (PTAB Dec. 15, 2021), 3 pages.

*Freedom To Operate, Inc. v. Compass Pathways Limited.* Case PGR2022-00012, U.S. Pat. No. 10,947,257. Exhibit 1062: Amendment/Response to Non-Final Office Action, filed Nov. 13, 2020 (PTAB Dec. 15, 2021), 8 pages.

*Freedom To Operate, Inc. v. Compass Pathways Limited.* Case PGR2022-00012, U.S. Pat. No. 10,947,257. Exhibit 1063: Lakshmana Prabhu, S. and Suriyaprakash, T.N.K. Impurities and Its Importance in Pharmacy. Int Journal of Pharmaceutical Sciences Review and Research, vol. 3, Issue 2, Jul.-Aug. 2010, Article 012, pp. 66-71. (PTAB Dec. 15, 2021).

*Freedom To Operate, Inc. v. Compass Pathways Limited.* Case PGR2022-00012, U.S. Pat. No. 10,947,257. Exhibit 1064: ICH Topic Q 3 A (R2) Impurities In New Drug Substances, 2006. (PTAB Dec. 15, 2021), 15 pages.

*Freedom To Operate, Inc. v. Compass Pathways Limited.* Case PGR2022-00012, U.S. Pat. No. 10,947,257. Exhibit 1065: Excerpts of Handbook of Pharma Excipients, Sixth Edition. Rowe, R.C. et al. (Eds.) London, UK: Pharmaceutical Press, 2011; pp. 129-133, 139-141 (PTAB Dec. 15, 2021).

(56) References Cited

OTHER PUBLICATIONS

*Freedom To Operate, Inc. v. Compass Pathways Limited.* Case PGR2022-00012, U.S. Pat. No. 10,947,257. Exhibit 1066: Martin's Physical Pharmacy and Pharmaceutical Sciences, Sixth Edition. P.J. Sinko (Ed.) Lippincott Williams & Wilkins, 2011; p. 564 (PTAB Dec. 15, 2021).
*Freedom To Operate, Inc. v. Compass Pathways Limited.* Case PGR2022-00012, U.S. Pat. No. 10,947,257. Exhibit 1067: Supplemental Amendment, filed Nov. 19, 2020 (PTAB Dec. 15, 2021), 7 pages.
*Freedom To Operate, Inc. v. Compass Pathways Limited.* Case PGR2022-00012, U.S. Pat. No. 10,947,257. Exhibit 1068: The Manufacturing Process. Solid Dose Experts Techceuticals, vol. 15. (2015). (PTAB Dec. 15, 2021), 12 pages.
*Freedom To Operate, Inc. v. Compass Pathways Limited.* Case PGR2022-00012, U.S. Pat. No. 10,947,257. Exhibit 1069: Documentation of shipment of sample from Johns Hopkins University Batch to Triclinic Labs, Jul. 21, 2021. (PTAB Dec. 15, 2021), 3 pages.
*Freedom To Operate, Inc. v. Compass Pathways Limited.* Case PGR2022-00012, U.S. Pat. No. 10,947,257. Exhibit 1070: USP 24|NF 19. The Official Compendia of Standards, U.S. Pharmacopeia, 2000; pp. 738-739, 865-866. (PTAB Dec. 15, 2021).
*Freedom To Operate, Inc. v. Compass Pathways Limited.* Case PGR2022-00012, U.S. Pat. No. 10,947,257. Exhibit 1071: Sixsmith, D. The effect of compression on some physical properties of microcrystalline cellulose powders. J Pharm Pharmac, 1977, 29, 33-36. (PTAB Dec. 15, 2021).
*Freedom To Operate, Inc. v. Compass Pathways Limited.* Case PGR2022-00012, U.S. Pat. No. 10,947,257. Exhibit 1072: Curriculum Vitae—Brett D. Bobzien. (PTAB Dec. 15, 2021), 2 pages.
*Freedom To Operate, Inc. v. Compass Pathways Limited.* Case PGR2022-00012, U.S. Pat. No. 10,947,257. Exhibit 1073: Documentation of shipment of sample from Johns Hopkins University Batch to Triclinic Labs, Jul. 21, 2021. (PTAB Dec. 15, 2021), 3 pages.
*Freedom To Operate, Inc. v. Compass Pathways Limited.* Case PGR2022-00012, U.S. Pat. No. 10,947,257. Exhibit 1074: Altomare, A. et al. Expo2013: A kit of tools for phasing crystal structures from powder data. Journal of Applied Crystallography (2013) 46, 1231-1235. (PTAB Dec. 15, 2021).
*Freedom To Operate, Inc. v. Compass Pathways Limited.* Case PGR2022-00012, U.S. Pat. No. 10,947,257. Exhibit 1078: Petzoldt, C. et al. An example of how to handle amorphous fractions in API during early pharmaceutical development: SAR114137—A successful approach. European Journal of Pharmaceutics and Biopharmaceutics, 86 (2014) 337-350. (PTAB Dec. 15, 2021).
*Freedom To Operate, Inc. v. Compass Pathways Limited.* Case PGR2022-00012, U.S. Pat. No. 10,947,257. Exhibit 1079: Sivén, M. et al. Challenge of paediatric compounding to solid dosage forms sachets and hard capsules—Finnish perspective. Journal of Pharmacy and Pharmacol (2017) vol. 69, pp. 593-602 (PTAB Dec. 15, 2021).
*Freedom To Operate, Inc. v. Compass Pathways Limited.* Case PGR2022-00012, U.S. Pat. No. 10,947,257. Exhibit 1080: Tobyn, M. et al. (1998) Physicochemical comparison between microcrystalline cellulose and silicified microcrystalline cellulose. International Journal of Pharmaceutics, 169 (1998) 183-194. (PTAB Dec. 15, 2021).
*Freedom To Operate, Inc. v. Compass Pathways Limited.* Case PGR2022-00012, U.S. Pat. No. 10,947,257. Exhibit 1081: Packing Slip, Johns Hopkins BPRU Pharmacy to Triclinic Laboratories, Inc., Jul. 21, 2021. (PTAB Dec. 15, 2021), 2 pages.
*Freedom To Operate, Inc. v. Compass Pathways Limited.* Case PGR2022-00012, U.S. Pat. No. 10,947,257. Exhibit 1082: Triclinic Labs Inc., Standard Operating Procedure. Controlled Substances, No. G026.10 (PTAB Dec. 15, 2021), 11 pages.
*Freedom To Operate, Inc. v. Compass Pathways Limited.* Case PGR2022-00012, U.S. Pat. No. 10,947,257. Exhibit 1085: Sherwood, A.M. et al. Psilocybin: crystal structure solutions enable phase analysis of prior art and recently patented examples. Acta Cryst. (2022) C78, pp. 1-20. (PTAB Dec. 15, 2021).
*Freedom To Operate, Inc. v. Compass Pathways Limited.* Case PGR2022-00012, U.S. Pat. No. 10,947,257. Paper No. 18: Decision Denying Institution of Post-Grant Review (PTAB Jun. 22, 2022); 25 pages.
*Freedom To Operate, Inc. v. Compass Pathways Limited.* Case PGR2022-00012, U.S. Pat. No. 10,947,257. Paper No. 2: Petition for Post-Grant Review (PTAB Dec. 15, 2021), ), 68 pages.
*Freedom To Operate, Inc. v. Compass Pathways Limited.* Case PGR2022-00018, U.S. Pat. No. 10,954,259. Exhibit 1106: Declaration of Sven Lidin, Ph.D. (PTAB Dec. 22, 2021), 69 pages.
*Freedom To Operate, Inc. v. Compass Pathways Limited.* Case PGR2022-00018, U.S. Pat. No. 10,954,259. Exhibit 1108: Declaration of James A. Kaduk, Ph.D. (PTAB Dec. 22, 2021), 25 pages.
*Freedom To Operate, Inc. v. Compass Pathways Limited.* Case PGR2022-00018, U.S. Pat. No. 10,954,259. Exhibit 1110: Declaration of Raj Suryanarayanan, Ph.D. (PTAB Dec. 22, 2021), 23 pages.
*Freedom To Operate, Inc. v. Compass Pathways Limited.* Case PGR2022-00018, U.S. Pat. No. 10,954,259. Exhibit 1112: Declaration of Charles L. Raison, M.D. (PTAB Dec. 22, 2021), 6 pages.
*Freedom To Operate, Inc. v. Compass Pathways Limited.* Case PGR2022-00018, U.S. Pat. No. 10,954,259. Exhibit 1113: Roy, J. An Introduction to Pharmaceutical Sciences, Biohealthcare, UK (2011) (PTAB Dec. 22, 2021), 37 pages.
*Freedom To Operate, Inc. v. Compass Pathways Limited.* Case PGR2022-00018, U.S. Pat. No. 10,954,259. Exhibit 1120: Declaration of Brett D. Bobzien. (PTAB Dec. 22, 2021), 5 pages.
*Freedom To Operate, Inc. v. Compass Pathways Limited.* Case PGR2022-00018, U.S. Pat. No. 10,954,259. Exhibit 1130: Declaration of Roland R. Griffiths, Ph.D. (PTAB Dec. 22, 2021), 6 pages.
*Freedom To Operate, Inc. v. Compass Pathways Limited.* Case PGR2022-00018, U.S. Pat. No. 10,954,259. Exhibit 1160: Claims of '739 Application as Filed and Preliminary Amendment filed Dec. 9, 2020. (PTAB Dec. 22, 2021), 10 pages.
*Freedom To Operate, Inc. v. Compass Pathways Limited.* Case PGR2022-00018, U.S. Pat. No. 10,954,259. Exhibit 1161: Terminal Disclaimer. (PTAB Dec. 22, 2021), 3 pages.
*Freedom To Operate, Inc. v. Compass Pathways Limited.* Case PGR2022-00018, U.S. Pat. No. 10,954,259. Paper No. 16: Decision Denying Institution of Post-Grant Review (PTAB Jun. 22, 2022); 25 pages.
*Freedom To Operate, Inc. v. Compass Pathways Limited.* Case PGR2022-00018, U.S. Pat. No. 10,954,259. Paper No. 2: Petition for Post-Grant Review (PTAB Dec. 22, 2021), 67 pages.
Freudenberg, F., Alttoa, A., & Reif, A. (2015). Neuronal nitric oxide synthase (NOS1) and its adaptor, NOS1AP, as a genetic risk factors for psychiatric disorders. Genes, Brain and Behavior, 14(1), 46-63. https://doi.org/10.1111/gbb.12193.
Fuchs, X. et al. (2018) Psychological factors associated with phantom limb pain: A review of recent findings. Pain Res Manag, 2018:5080123, http://doi.org/10.1155/2018/5080123, 12 pages.
Funk, C. D., & Fitzgerald, G. A. (2007). COX-2 Inhibitors and Cardiovascular Risk. Journal of Cardiovascular Pharmacology, 50(5), 470-479. https://doi.org/10.1097/FJC.0b013e318157f72d.
Galbiati, A. et al. (2019). The risk of neurodegeneration in REM sleep behavior disorder: A systematic review and meta-analysis of longitudinal studies. Sleep Medicine Reviews, 43, 37-46. https://doi.org/10.1016/j.smrv.2018.09.008.
Galimberti, D. et al. (2008). Association of a NOS1 promoter repeat with Alzheimer's disease. Neurobiology of Aging, 29(9), 1359-1365. https://doi.org/10.1016/j.neurobiolaging.2007.03.003.
Galmiche, M. et al. (2019). Prevalence of eating disorders over the 2000-2018 period: a systematic literature review. The American Journal of Clinical Nutrition, 109(5), pp. 1402-1413.
Gamez, W. et al. (2014) The Brief Experiential Avoidance Questionnaire: Development and Initial Validation. Psychological Assessment. 26:35-45.
Gan, W., Mohamad, N. and Law, L. (2018). Factors Associated with Binge Eating Behavior among Malaysian Adolescents. Nutrients, 10:66, doi:10.3390/nu10010066, 12 pages.

(56) References Cited

OTHER PUBLICATIONS

Gandal, M. J. et al. (Feb. 2018). Shared molecular neuropathology across major psychiatric disorders parallels polygenic overlap. Science, 359:693-697. https://doi.org/10.1126/science.aad6469.

Gandy, M. et al. (2013). Rates of DSM-IV mood, anxiety disorders, and suicidality in Australian adult epilepsy outpatients: A comparison of well-controlled versus refractory epilepsy. Epilepsy Behav. 26, 29-35. https://doi.org/10.1016/j.yebeh.2012.10.023.

Ganesan, H. et al. (2019). mTOR signalling pathway—a root cause for idiopathic autism? BMB Reports, 52(7):424-433.

Garcia-Rayado, G., Navarro, M., & Lanas, A. (2018). NSAID induced gastrointestinal damage and designing GI-sparing NSAIDs. Expert Review of Clinical Pharmacology, 11(10), 1031-1043. https://doi.org/10.1080/17512433.2018.1516143.

Garcia-Romeu, A., Griffiths, R. and Johnson, M. (2015). Psilocybin-Occasioned Mystical Experiences in the Treatment of Tobacco Addiction. Current Drug Abuse Reviews, 7(3), pp. 157-164.

Gasior, M. et al (2017). A Phase 3, Multicenter, Open-Label, 12-Month Extension Safety and Tolerability Trial of Lisdexamfetamine Dimesylate in Adults With Binge Eating Disorder. Journal of Clinical Psychopharmacology, 37(3), pp. 315-322.

Gau, S.S.-F. & Huang, W.L. (2014) Rapid visual information processing as a cognitive endophenotype of attention deficit hyperactivity disorder. Psychol Med, 44(2):435-446.

Gaul, C. et al. (2011) Cluster Headache—Clinical Features and Therapeutic Options. Deutsches Arzteblatt International, 108(33):543-549.

GBD 2016 Parkinson's Disease Collaborators. (2018). Global, regional, and national burden of Parkinson's disease, 1990-2016: a systematic analysis for the Global Burden of Disease Study 2016. The Lancet. Neurology, 17(11), 939-953. https://doi.org/10.1016/S1474-4422(18)30295-3.

Gessner, P.K. et al. (1960) The relationship between the metabolic fate and pharmacological actions of serotonin, bufotenine and psilocybin. J. Pharmacol. Exp. Ther., 130:126-133.

Ghanizadeh, A. (2015) A systematic review of reboxetine for treating patients with attention deficit hyperactivity disorder. Nord J Psychiatry. 69(4):241-8.

Gibb, A. & Deeks, E.D.(2014). Vortioxetine: First global approval. Drugs 74:135-145, https://doi.org/10.1007/s40265-013-0161-9, 11 pages.

Gilon Mann, T. et al. (2018). Different attention bias patterns in anorexia nervosa restricting and binge/purge types. European Eating Disorders Review, 26(4):293-301. https://doi.org/10.1002/erv.2593.

Giovinazzo, S. et al. (2019). Anorexia nervosa and heart disease: a systematic review. Eating and Weight Disorders—Studies on Anorexia, Bulimia and Obesity, vol. 24, Issue 2, pp. 199-207. https://doi.org/10.1007/s40519-018-0567-1.

Glaesmer, H. et al. (2012) Psychometric properties and population-based norms of the Life Orientation Test Revised (LOT-R). British Journal of Health Psychology, 17:432-445.

Glashouwer, K. A., Van Der Veer, R. M. L., Adipatria, F., De Jong, P. J., & Vocks, S. (2019). The role of body image disturbance in the onset, maintenance, and relapse of anorexia nervosa: A systematic review. Clinical Psychology Review, 74:101771; DOI:10.1016/j.cpr.2019.101771, 21 pages.

Glenn, A.L. et al. (2013) Antisocial personality disorder: A current review. Current Psychiatry Reports, 15:427, DOI: 10.1007/s11920-013-0427-7, 9 pages.

Global Burden of Disease Study 2013 Collaborators. (2015). Global, regional, and national incidence, prevalence, and years lived with disability for 301 acute and chronic diseases and injuries in 188 countries, 1990-2013: a systematic analysis for the Global Burden of Disease Study 2013. Lancet (London, England), 386(9995), 743-800. https://doi.org/10.1016/S0140-6736(15)60692-4.

Golden, E.C. & Lipford, M.C. (2018). Narcolepsy: Diagnosis and management. Cleveland Clin. J. Med., 85(12):959-969. https://doi.org/10.3949/ccjm.85a.17086.

Goldstein-Piekarski, A.N. et al. (2016). A trans-diagnostic review of anxiety disorder comorbidity and the impact of multiple exclusion criteria on studying clinical outcomes in anxiety disorders. Transl. Psychiatry, 6:e847, doi.org/10.1038/tp.2016.108, 9 pages.

Golyala, A., & Kwan, P. (2017). Drug development for refractory epilepsy: The past 25 years and beyond. Seizure, 44, 147-156. https://doi.org/10.1016/j.seizure.2016.11.022.

Golzari, S.E.J. et al. Lidocaine and pain management in the emergency department: A review article. Anesthesiol Pain Med. 2014;4(1):1-6.

Gong, D. et al. (2012). TGFβ signaling plays a critical role in promoting alternative macrophage activation. BMC Immunology, 13:31, https://doi.org/10.1186/1471-2172-13-31, 10 pages.

Gonzalez-Maeso, J. et al. (2007) "Hallucinogens Recruit Specific Cortical 5-HT$_{2\alpha}$ Receptor-Mediated Signaling Pathways to Affect Behavior" Neuron, 53(3):439-452.

Gonzalez-Maeso J. et al. (Mar. 24, 2008) "Identification of a serotonin/glutamate receptor complex implicated in psychosis" Nature, 452(7183):93-7. Available from: http://www.nature.com/articles/nature06612.

Gooriah, R. et al. (2015) Evidence-based treatments for cluster headache. Ther Clin Risk Manag, 11:1687-1696. Available from: http://dx.doi.org/10.2147/TCRM.S94193.

Gorla, K., & Mathews, M. (2005). Pharmacological treatment of eating disorders. Psychiatry, 2(6), 43-48. http://www.ncbi.nlm.nih.gov/pubmed/21152155.

Gouzoulis-Mayfrank, E. et al (2002). Effects of the hallucinogen psilocybin on covert orienting of visual attention in humans. Neuropsychobiology, 45(4):205-212. Available from: http://www.ncbi.nlm.nih.gov/pubmed/12097810.

Grant, A.M. et al. (2002) The Self-Reflection and Insight Scale: A New Measure of Private Self-Consciousness. Social Behavior and Personality, 30(8), 821-836.

Grant, J. et al. (Jul. 2019). A double-blind, placebo-controlled study of vortioxetine in the treatment of binge-eating disorder. International Journal of Eating Disorders, 52(7), pp. 786-794.

Greenan, C. et al (Feb. 13, 2020) "Preparation and Characterization of Novel Crystalline Solvates and Polymorphs of Psilocybin and Identification of Solid Forms Suitable for Clinical Development" Preprint [online]. Retrieved from ResearchGate: https://www.researchgate.net/publication/339238710, 29 printed pages.

Greten, F.R. et al. (Sep. 2007). NF-κB Is a Negative Regulator of IL-1β Secretion as Revealed by Genetic and Pharmacological Inhibition of IKKβ. Cell, 130(5), 918-931. https://doi.org/10.1016/j.cell.2007.07.009.

Greyson, B. (19893) The Near-Death Experience Scale. The Journal of Nervous and Mental Disease, 171:369-375.

Grieco, M et al. (Oct. 2019). Glucagon-Like Peptide-1: A Focus on Neurodegenerative Diseases. Frontiers in Neuroscience, 13, Article 1112, 7 pages. https://doi.org/10.3389/fnins.2019.01112.

Grieshaber, A. F., Moore, K. A., & Levine, B. (2001). The detection of psilocin in human urine. Journal of Forensic Sciences, 46(3), 627-630. http://www.ncbi.nlm.nih.gov/pubmed/11373000.

Griffin, C.E. et al. (2013). Benzodiazepine pharmacology and central nervous system-mediated effects. Ochsner J. 13, 214-223.

Griffiths, K. (2019). Understanding the neural mechanisms of lisdexamfetamine dimesylate (LDX) pharmacotherapy in Binge Eating Disorder (BED): a study protocol. Journal of Eating Disorders, 7:23, https://doi.org/10.1186/s40337-019-0253-3, 10 pages.

Griffiths, K.R. et al. (2017). "Sustained attention and heart rate variability in children and adolescents with ADHD." Biol Psychol [Internet]. 124:11-20. Available from: http://www.ncbi.nlm.nih.gov/pubmed/28099875.

Griffiths, R.R. (Dec. 2011) Psilocybin occasioned mystical-type experiences: Immediate and persisting dose-related effects. Psychopharmacol, 218(4):649-665. NIH Public Access Author Manuscript, 27 pages.

Griffiths, R.R. et al. (Aug. 2006) Psilocybin can occasion mystical-type experiences having substantial and sustained meaning and spiritual significance. Psychopharmacol (Berl), 187(3):268-283.

Griffiths, R.R. et al. (2016) Psilocybin produces substantial and sustained decreases in depression and anxiety in patients with

(56) References Cited

OTHER PUBLICATIONS life-threatening cancer: A randomized double-blind trial. Journal of Psychopharmacology, 30(12):1181-1197.
Griffiths, S. (2019). "The Vulnerability Experiences Quotient (VEQ): A Study of Vulnerability, Mental Health and Life Satisfaction in Autistic Adults." Autism Research. (10):1516-28. https://doi.org/10.1002/aur.2162.
Grilo, C. et al. (2012). 12-month follow-up of fluoxetine and cognitive behavioral therapy for binge eating disorder. Journal of Consulting and Clinical Psychology, 80(6), pp. 1108-1113.
Grilo, C., Reas, D. and Mitchell, J. (2016). Combining Pharmacological and Psychological Treatments for Binge Eating Disorder: Current Status, Limitations, and Future Directions. Current Psychiatry Reports, 18:55, doi:10.1007/s11920-016-0696-z, 11 pages.
Grob, C.S. et al. (Jan. 2011) Pilot Study of Psilocybin Treatment for Anxiety in Patients with Advanced-Stage Cancer. Arch Gen Psychiatry, 68(1):71-78.
Grob, C.S. et al. (2013) Chapter 17: Use of the Classic Hallucinogen Psilocybin for Treatment of Existential Distress Associated with Cancer. In B.I. Carr and J. Steel (Eds.) Psychological Aspsects of Cancer. Springer Science + Business Media; p. 291-308.
Guerdjikova, A. et al. (2016). Novel pharmacologic treatment in acute binge eating disorder—role of lisdexamfetamine. Neuropsychiatric Disease and Treatment, 12:833-841.
Guerreiro, R. et al. (2015). "The age factor in Alzheimer's disease." Genome Medicine, 7:106, https://doi.org/10.1186/s13073-015-0232-5, 3 pages.
Guo, M. et al. (2003) "Potential Application of Silicified Microcrystalline Cellulose in Direct-Fill Formulations for Automatic Capsule-Filling Machines," Pharmaceutical Development and Technology, vol. 8, No. 1, pp. 47-59.
Gupta, S. P. et al. (2016). "Association of Polymorphism of Neuronal Nitric Oxide Synthase Gene with Risk to Parkinson's Disease." Molecular Neurobiology, 53(5), 3309-3314. https://doi.org/10.1007/s12035-015-9274-3.
Guze, S.B. (1995) Diagnostic and Statistical Manual of Mental Disorders, 4th ed. (DSM-IV). Am. J. Psychiatry, 152, 1228. https://doi.org/10.1176/ajp.152.8.1228.
Hajihosseini, A. et al. (2012). "The role of beta-gamma oscillations in unexpected rewards processing." Neuroimage. 60(3):1678-85. https://doi.org/10.1016/j.neuroimage.2012.01.125.
Halberstadt, A. L. et al. (2011). "Multiple receptors contribute to the behavioral effects of indoleamine hallucinogens." Neuropharmacology, 61(3):364-381, https://doi.org/10.1016/j.neuropharm.2011.01.017.
Hall N. et al. (2018). "Phantom limb pain: a review of pharmacological management." Br J Pain [Internet]. 12(4):202-7. Available from: https://doi.org/10.1177/2049463717747307.
Halpern, J.H. (2003) Hallucinogens: An Update. Current Psychiatry Reports, 5:347-354.
Hama, Y. et al. (2015). "Level of plasma neuregulin-1 SMDF is reduced in patients with idiopathic Parkinson's disease." Neuroscience Letters, 587, 17-21. https://doi.org/10.1016/j.neulet.2014.12.024.
Hamadjida, A. et al. (2020). "The highly selective mGlu2 receptor positive allosteric modulator LY-487,379 alleviates I-DOPA-induced dyskinesia in the 6-OHDA-lesioned rat model of Parkinson's disease." The European Journal of Neuroscience. 51(12):2412-2422. https://doi.org/10.1111/ejn.14679.
Hamilton, M. (1960) A Rating Scale for Depression. Journal of Neurology, Neurosurgery & Psychiatry. 23:56-62.
Hanes, K.R. (1996). "Serotonin, Psilocybin, and Body Dysmorphic Disorder." Journal of Clinical Psychopharmacology, 16(2), pp. 188-189.
Hanyu-Deutmeyer, A.A. et al. (2020) Phantom Limb Pain. StatPearls. StatPearls Publishing. [online]. Available from NCBI Bookshelf: http://www.ncbi.nlm.nih.gov/pubmed/28846343, 6 pages.
Haroon, E. et al. (2018). Antidepressant treatment resistance is associated with increased inflammatory markers in patients with major depressive disorder. Psychoneuroendocrinology, 95:43-49. https://doi.org/10.1016/j.psyneuen.2018.05.026.
Hasler, F. et al. (1997). "Determination of psilocin and 4-hydroxyindole-3-acetic acid in plasma by HPLC-ECD and pharmacokinetic profiles of oral and intravenous psilocybin in man." Pharmaceutica Acta Helvetiae, 72(3), 175-184. https://doi.org/10.1016/S0031-6865(97)00014-9.
Hasler, F. et al. (2002). "Renal excretion profiles of psilocin following oral administration of psilocybin: A controlled study in man." Journal of Pharmaceutical and Biomedical Analysis, 30(2), 331-339. https://doi.org/10.1016/S0731-7085(02)00278-9.
Hasler, F. et al. (2004) Acute psychological and physiological affects of psilocybin in healthy humans: A double-blind, placebo-controlled dose-effect study. Psychopharmacology, 172(2):145-156.
Heal, D. et al. (2017). Dopamine and μ-opioid receptor dysregulation in the brains of binge-eating female rats—possible relevance in the psychopathology and treatment of binge-eating disorder. Journal of Psychopharmacology, 31(6), pp. 770-783.
Hebert, L.E. et al. (2013). "Alzheimer disease in the United States (2010-2050) estimated using the 2010 census." Neurology, 80(19), 1778-1783. https://doi.org/10.1212/WNL.0b013e31828726f5.
Heim, R. et al. (Mar. 3, 1958) "Mycologie—Determinisme de la formation des carpophores et des sclerotes dans la culture du Psilocybe mexicana Heim, Agaric hallucinogene du Mexique, et mise en evidence de la psilocybine et de la psilocine [Mycology—Determinism in the formation of carpophores and sclerotia in the cultivation of Psilocybe mexicana Heim, an hallucinogenic Agaric of Mexico, and isolation of psilocybin and psilocyn]" Comptes Rendus Hebdomadaires des Seances de L'Academie des Sciences [Weekly Reports of the Sessions of the Academy of Sciences], 246(9):1346-1351.
Herr, N. et al. (Jul. 2017). "The Effects of Serotonin in Immune Cells." Frontiers in Cardiovascular Medicine, 4, Article 48, 11 pages. https://doi.org/10.3389/fcvm.2017.00048.
Herring, W.J. et al. (2012). "Orexin receptor antagonism for treatment of insomnia: A randomized clinical trial of suvorexant." Neurology 79, 2265-2274. https://doi.org/10.1212/WNL.0b013e31827688ee.
Hibicke, M. et al. (Apr. 1, 2019). "Psychedelics Improve the Mental Health of Rats." Faseb J., 33(S1):666.1; https://doi.org/10.1096/fasebj.2019.33.1_supplement.666.1, 3 pages.
Hilbert, A. et al. (2019). Meta-analysis of the efficacy of psychological and medical treatments for binge-eating disorder. Journal of Consulting and Clinical Psychology, 87(1), pp. 91-105.
Hill, L.S. et al. (2010) Scoff, the development of an eating disorder screening questionnaire. International Journal of Eating Disorders, 43(4):344-351. https://doi.org/10.1002/eat.20679.
Himmerich, H. et al. (2019). "Psychiatric comorbidity as a risk factor for mortality in people with anorexia nervosa." European Archives of Psychiatry and Clinical Neuroscience, 269(3), 351-359. https://doi.org/10.1007/s00406-018-0937-8.
Hoek, H. et al. (2003). "Review of the Prevalence and Incidence of Eating Disorders." International Journal of Eating Disorders, vol. 34, Issue 4, pp. 383-396. https://doi.org/10.1002/eat.10222.
Hofmann, A. et al. (1958) "Konstitutionsaufklärung und Synthese von Psilocybin [Constitutional elucidation and synthesis of psilocybin]" Experientia, 14(11):397-399, with English translation (3 pages).
Hofmann, A. et al. (Mar. 15, 1958) "Psilocybin, ein psychotroper Wirkstoff aus dem mexikanischen Rauschpilz Psilocybe mexicana Heim [Psilocybin, a psychotropic substance from Mexican magic mushrooms *Psilocybe mexicana Heim*]" Experientia, 14(3):107-109, with English translation (3 pages).
Hofmann, A. et al. (1959) "Psilocybin und Psilocin, zwei psychotrope Wirkstoffe aus mexikanischen Rauschpilzen [Psilocybin and Psilocin, two psychotropic active substances from Mexican magic mushrooms" Helvetica Chimica Acta, vol. XLII, Issue v, No. 168, pp. 1557-1572, with English translation (17 pages).
Holtkamp, K. et al. (2005). "A retrospective study of SSRI treatment in adolescent anorexia nervosa: Insufficient evidence for efficacy." Journal of Psychiatric Research, 39(3), 303-310. https://doi.org/10.1016/j.jpsychires.2004.08.001.

(56) References Cited

OTHER PUBLICATIONS

Hood, S.D. et al. (2014). "Benzodiazepine dependence and its treatment with low dose flumazenil." Br. J. Clin. Pharmacol. 77, 285-294. https://doi.org/10.1111/bcp.12023.
Howell, M. J. et al. (2015). "Rapid Eye Movement Sleep Behavior Disorder and Neurodegenerative Disease." JAMA Neurology, 72(6), 707-712. https://doi.org/10.1001/jamaneurol.2014.4563.
Hoyer, D. et al. (1985). "Molecular pharmacology of 5-HT1 and 5-HT2 recognition sites in rat and pig brain membranes: Radioligand binding studies with [3H]5-HT, [3H]8-OH-DPAT, (-)[125I]iodocyanopindolol, [3H]mesulergine and [3H]Ketanserin." Eur J Pharmacol. 118(1-2):13-23.
Hsu, E. et al. (2013). "Postamputation pain: Epidemiology, mechanisms, and treatment." J Pain Res, 6:121-136. http://dx.doi.org/10.2147/JPR.S32299.
Huang, H. et al. (2016). "Genetic association of NOS1 exon18, NOS1 exon29, ABCB1 1236C/T, and ABCB1 3435C/T polymorphisms with the risk of Parkinson's disease: A meta-analysis." Medicine, 95(40), e4982. https://doi.org/10.1097/MD.0000000000004982.
Hudson, C.C. et al. (2019). "Prevalence of Depressive Disorders in Individuals with Autism Spectrum Disorder: a Meta-Analysis." Journal of Abnormal Child Psychology. 47(1):165-75. https://doi.org/10.1007/s10802-018-0402-1.
Hudson, J.I. et al. (1992). "Polysomnographic Characteristics of Young Manic Patients: Comparison with Unipolar Depressed Patients and Normal Control Subjects." Arch. Gen. Psychiatry 49, 378-383. https://doi.org/10.1001/archpsyc.1992.01820050042006.
Hudson, J.I. et al. (2007). "The Prevalence and Correlates of Eating Disorders in the National Comorbidity Survey Replication." Biological Psychiatry, 61(3), 348-358. https://doi.org/10.1016/j.biopsych.2006.03.040.
Huecker, M. et al. (2020). Bupropion. StatPearls. NCBI Bookshelf [online]. Retrieved from: https://www.ncbi.nlm.nih.gov/books/NBK470212/; retrieved on Jul. 30, 2020, 4 pages.
Huedo-Medina, T.B. et al. (2012). "Effectiveness of non-benzodiazepine hypnotics in treatment of adult insomnia: Meta-analysis of data submitted to the Food and Drug Administration." BMJ, 345:e8343,. https://doi.org/10.1136/bmj.e8343, 13 pages.
Huff, T. and Daly, D.T. (2020) Neuroanatomy, Cranial Nerve 5 (Trigeminal). StatPearls. StatPearls Publishing; Available from NCBI Bookshelf: http://www.ncbi.nlm.nih.gov/pubmed/29489263.
Hughes, J.R. (2008). "Gamma, fast, and ultrafast waves of the brain: Their relationships with epilepsy and behavior." Epilepsy Behav. 13(1):25-31. https://doi.org/10.1016/j.yebeh.2008.01.011.
Hussman, J.P. et al. (2011). "A noise-reduction GWAS analysis implicates altered regulation of neurite outgrowth and guidance in autism." Molecular Autism. 2, 1. https://doi.org/10.1186/2040-2392-2-1.
Hutson, P., Balodis, I. and Potenza, M. (2018). Binge-eating disorder: Clinical and therapeutic Advances. Pharmacology & Therapeutics, 182:15-27.
Hutten, N.R.P.W. et al. (2019). "Self-Rated Effectiveness of Microdosing With Psychedelics for Mental and Physical Health Problems Among Microdosers." Front Psychiatry [Internet]. 10:672. Available from: http://www.ncbi.nlm.nih.gov/pubmed/31572246.
Huysmans, S. et al. (2019). "Melatonin and sleep disorders: Overview of literature and testing in psychiatric practice." Tijdschr. Psychiatr. 61, 854-861.
Hvolby, A. (2015). "Associations of sleep disturbance with ADHD: implications for treatment." ADHD Atten. Deficit Hyperact. Disord. 7(1):1-8. https://doi.org/10.1007/s12402-014-0151-0.
Hwang, J.Y. et al. (2008) The development of the Santa Clara brief compassion scale: An abbreviation of Sprecher and Fehr's compassionate love scale. Pastoral Psychology, 56(4):421-428.
ICH (Jun. 2017) Q3C—Tables and List Guidance for Industry. U.S. Department of Health and Human Services, Food and Drug Administration, Center for Drug Evaluation and Research (CDER), Center for Biologics Evaluation and Research (CBER) Revision 3, 10 pages.

Infliximab Side Effects. (2019). Drugs.Com [online]. Retrieved from: https://www.drugs.com/sfx/infliximab-side-effects.html, 11 pages.
Institute for Quality and Efficiency in Health Care (IQWiG) (Oct. 2017). Treatment options for generalized anxiety disorder [online]. InformedHealth.org. Retrieved from: https://www.ncbi.nlm.nih.gov/books/NBK279594/?report=printable; retrieved on Jul. 30, 2020, 3 pages.
Institute for Quality and Efficiency in Health Care (IQWiG) (Feb. 2018). What is an inflammation? [online]. Retrieved from: https://www.ncbi.nlm.nih.gov/books/NBK279298/; retrieved on Jul. 30, 2020, 1 page.
International Search Report and Written Opinion for PCT/IB2018/057811 mailed on Mar. 11, 2019, 10 pages.
International Search Report and Written Opinion issued in International Patent Application No. PCT/EP2022/058483, mailed Aug. 4, 2022, with Notification of Transmittal; 17 pages.
International Search Report and Written Opinion issued in International Patent Application No. PCT/IB2020/053684, mailed Aug. 26, 2020, with Notification of Transmittal; 24 total pages.
International Search Report and Written Opinion issued in International Patent Application No. PCT/IB2020/053687, mailed Aug. 26, 2020, with Notification of Transmittal; 22 total pages.
International Search Report and Written Opinion issued in International Patent Application No. PCT/IB2020/053688, mailed Aug. 26, 2020, with Notification of Transmittal; 30 total pages.
Isaacson, R.S. et al. (2018). "The clinical practice of risk reduction for Alzheimer's disease: A precision medicine approach." Alzheimer's & Dementia : The Journal of the Alzheimer's Association, 14(12), 1663-1673. https://doi.org/10.1016/j.jalz.2018.08.004.
Isooka, N. et al. (2020) "Dopaminergic neuroprotective effects of rotigotine via 5-HT1A receptors: Possibly involvement of metallothionein expression in astrocytes." Neurochemistry International, 132:104608, https://doi.org/10.1016/j.neuint.2019.104608, 13 pages.
Ivarsson, M. et al. (2005). "Antidepressants and REM sleep in Wistar-Kyoto and Sprague-Dawley rats" Eur. J. Pharmacol., 522(1-3):63-71. https://doi.org/10.1016/j.ejphar.2005.08.050.
Jack, C. R. et al. (2018). "NIA-AA Research Framework: Toward a biological definition of Alzheimer's disease." Alzheimer's & Dementia : The Journal of the Alzheimer's Association, 14(4), 535-562. https://doi.org/10.1016/j.jalz.2018.02.018.
Jaeger, J. and Domingo, S.Z. (2016) The Digit Symbol Substitution Test (DSST): Psychometric properties and clinical utility in major depressive disorder. Poster presented at the 29th ECNP Congress, Sep. 17-20, 2016, Vienna, Austria. Retrieved from ResearchGate [online], http://www.researchgate.net/publication/309602300.
Jafarian, S. et al. (2008). "High-altitude sleep disturbance: Results of the Groningen Sleep Quality Questionnaire survey." Sleep Med. 9, 446-449. https://doi.org/10.1016/j.sleep.2007.06.017.
Jagielska et al. (2017). "Outcome, comorbidity and prognosis in anorexia nervosa." Psychiatr. Pol, 51(2), 205-218. https://doi.org/10.12740/PP/64580.
Jagmag, S.A. et al. (2016). "Evaluation of Models of Parkinson's Disease." Frontiers in Neuroscience, 9: 503. https://doi.org/10.3389/fnins.2015.00503.
Jankovic, J. (2008). "Parkinson's disease: clinical features and diagnosis." Journal of Neurology, Neurosurgery & Psychiatry, 79(4), 368-376. https://doi.org/10.1136/jnnp.2007.131045.
Jansen, C. et al. (2019). "Interictal psychiatric comorbidities of drug-resistant focal epilepsy: Prevalence and influence of the localization of the epilepsy." Epilepsy Behav. 94, 288-296. https://doi.org/10.1016/j.yebeh.2018.06.046.
Javaheri, S. (2006). "Acetazolamide improves central sleep apnea in heart failure: a double-blind, prospective study." Am. J. Respir. Crit. Care Med. 173, 234-237.
Javaheri, S. et al. (1996). "Effect of theophylline on sleep-disordered breathing in heart failure." N. Engl. J. Med. 335, 562-567. https://doi.org/10.1056/NEJM199608223350805.
Jayakumar, A.R. & Norenberg, M.D. (2016). Glutamine Synthetase: Role in Neurological Disorders. The Glutamate/GABA-Glutamine Cycle. A. Schousboe, R. Sonnewald (eds.), Springer International Publishing. Advances in Neurobiology, vol. 13, https://doi.org/10.1007/978-3-319-45096-4_13; pp. 327-350.

(56) References Cited

OTHER PUBLICATIONS

Jennings, K. M. et al. (2017). "Eating Disorder Examination-Questionnaire (EDE-Q): Norms for Clinical Sample of Female Adolescents with Anorexia Nervosa." Archives of Psychiatric Nursing, 31(6), 578-581. https://doi.org/10.1016/j.apnu.2017.08.002.
Jiang, H.-R. et al. (2002). "Secretion of interleukin-10 or interleukin-12 by LPS-activated dendritic cells is critically dependent on time of stimulus relative to initiation of purified DC culture" Journal of Leukocyte Biology, 72(5):978-985.
Jiao, J.-J. et al. (2017). "GLP-1/GIP/Gcg receptor Triagonist improves the cognitive behaviors in triple-transgenic mice of Alzheimer's disease." Sheng Li Xue Bao : [Acta Physiologica Sinica], 69(2), 135-145. Retrieved from http://www.ncbi.nlm.nih.gov/pubmed/28435972.
Jin, L. et al. (2019). "Antidepressants for the treatment of narcolepsy: A prospective study of 148 patients in northern China." J. Clin. Neurosci. 63, 27-31. https://doi.org/10.1016/j.jocn.2019.02.014.
Johanson, M. et al. (Feb. 2020) A Systematic Literature Review of Neuroimaging of Psychopathic Traits. Front Psychiatry. 10:1027, doi: 10.3389/fpsyt.2019.01027, 20 pages.
John, O. P., & Srivastava, S. (1999). The Big-Five trait taxonomy: History, measurement, and theoretical perspectives. In L. A. Pervin & O. P. John (Eds.), Handbook of personality: Theory and Research (vol. 2, pp. 102-138). New York: Guilford Press.
Johns, M. (1991). "New Method for Measuring Daytime Sleepiness: The Epworth Sleepiness Scale." Sleep. 14(6):540-5 [online]. Retrieved from:https://academic.oup.com/sleep/article/14/6/540/2742871 (accessed Mar. 26, 2020).
Johnson et al., "Potential Therapeutic Effects of Psilocybin," Neurotherapeutics (2017) 14:734-740 (published Jun. 5, 2017).
Johnson, M.W. (2008) Human hallucinogen research: guidelines for safety. J Psychopharmacol, 22(6):603-620.
Johnson, M.W. et al. (Nov. 2014) Pilot Study of the 5-HT2AR Agonist Psilocybin in the Treatment of Tobacco Addiction. J Psychopharmacol. 28(11):983-992. doi:10.1177/0269881114548296.
Johnson, M.W. et al. (Jan. 2017) Long-term follow-up of psilocybin-facilitated smoking cessation. Am J Drug Alcohol Abuse. 2017;43(1):55-60. doi:10.3109/00952990.2016.1170135 [published correction appears in Am J Drug Alcohol Abuse. Jan. 2017;43(1):127]. HHS Public Access Author Manuscript, 10 pages.
Johnstad, P.G. (2018). "Powerful substances in tiny amounts: An interview study of psychedelic microdosing" Nord Stud Alcohol Drugs, 35(1):39-51.
Jyonouchi, H. (2013). "Immunological abnormalities in autism spectrum disorders." Advances in Neuroimmune Biology. vol. 4, No. 3, pp. 141-159. https://doi.org/10.3233/NIB-130061.
Kaelen, M. et al. (2015) LSD enhances emotional response to music. Psychopharmacology, 232(19):3607-3614.
Kaelen, M. et al. (2018) "The hidden therapist: evidence for a central role of music in psychedelic therapy" Psycopharmacology, 235:505-519.
Kaladjian, A. et al. (2014). "Troubles affectifs et comorbidités anxieuses." Encephale 40, S18-S22. https://doi.org/10.1016/S0013-7006(14)70126-5.
Kalliolias, G. D. et al. (2016). "TNF biology, pathogenic mechanisms and emerging therapeutic strategies." Nature Reviews Rheumatology, 12(1), 49-62. https://doi.org/10.1038/nrrheum.2015.169.
Kandel, S.A. and Mandiga P. (2020) Cluster Headache. StatPearls. StatPearls Publishing [Internet]. Available from NCI Bookshelf: http://www.ncbi.nlm.nih.gov/pubmed/31334961, 6 pages.
Kandil, E. et al. (2017). "Lidocaine Infusion: A Promising Therapeutic Approach for Chronic Pain." J Anesth Clin Res. 08(01): 697.
Kandratavicius, L. et al. (2014). Animal models of epilepsy: use and limitations. Neuropsychiatric Disease and Treatment, 1693. https://doi.org/10.2147/NDT.S50371.
Kang, D. W. et al. (2019). "Long-term benefit of Microbiota Transfer Therapy on autism symptoms and gut microbiota." Scientific Reports. 9(1):1-9. https://doi.org/10.1038/s41598-019-42183-0.
Kang Y. et al. (2018). "Self-report pain assessment tools for cognitively intact older adults: Integrative review." International journal of older people nursing. 13(2):e12170.
Kanner, A.M. (2011). "Anxiety disorders in epilepsy: The forgotten psychiatric comorbidity." Epilepsy Curr. 11(3):90-1. https://doi.org/10.5698/1535-7511-11.3.90.
Kantojarvi, K. et al. (2011). "Fine mapping of Xq11.1-q21.33 and mutation screening of RPS6KA6, ZNF711, ACSL4, DLG3, and IL1RAPL2 for autism spectrum disorders (ASD)." Autism Research. 4(3):228-33. https://doi.org/10.1002/aur.187.
Kargbo, R.B. et al. (2020) "Direct Phosphorylation of Psilocin Enables Optimized cGMP Kilogram-Scale Manufacture of Psilocybin" ACS Omega, 5:16959-16966.
Karimi, P. et al. (2017). Environmental factors influencing the risk of autism. J Res Med Sci. 22:27, https://doi.org/10.4103/1735-1995.200272, 12 pages.
Kasper LJ et al. (2012). "Moderators of working memory deficits in children with attention-deficit/hyperactivity disorder (ADHD): A meta-analytic review." Clinical Psychology Review. vol. 32, p. 605-17.
Kasper, S. et al. (2009). "Efficacy of pregabalin and venlafaxine-XR in generalized anxiety disorder: Results of a double-blind, placebo-controlled 8-week trial." Int. Clin. Psychopharmacol. 24, 87-96. https://doi.org/10.1097/YIC.0b013e32831d7980.
Katzman, M.A. et al. (2017). "Adult ADHD and comorbid disorders: Clinical implications of a dimensional approach." BMC Psychiatry. 17(1):1-15.
Kaur A et al. (2018). "Phantom limb pain: A literature review." Chinese Journal of Tramatology, 21(6):366-8. https://doi.org/10.1016/j.cjtee.2018.04.006.
Kaur, H. et al. (2018). Chronic Insomnia. StatPearls. NLM Bookshelf [online]. Retrieved from: https://www.ncbi.nih.gov/books/NBK526136/?report=reader; retrieved on Jul. 30, 2002; 5 pages.
Keezer, M. R. et al. (2016). "Comorbidities of epilepsy: current concepts and future perspectives." The Lancet Neurology, 15(1), 106-115. https://doi.org/10.1016/S1474-4422(15)00225-2.
Kelly, W.E. et al. (2019). "A brief self-report measure for frequent distressing nightmares: The Nightmare Experience Scale (NExS)." Dreaming 29, 180-195. https://doi.org/10.1037/drm0000106.
Kelton, M.C. et al. (Jun.-Aug. 2000). The effects of nicotine on Parkinson's disease. Brain and Cognition, 43(1-3):274-282 (abstract). Retrieved from http://www.ncbi.nlm.nih.gov/pubmed/10857708, 1 page.
Kessler, R. et al. (2016). The neurobiological basis of binge-eating disorder. Neuroscience & Biobehavioral Reviews, 63, pp. 223-238.
Kessler, R.C. et al. (2013). The prevalence and correlates of binge eating disorder in the World Health Organization World Mental Health Surveys. Biological Psychiatry, 73(9):904-914.
Khajehpour, H. et al. (2019). "Disrupted resting-state brain functional network in methamphetamine abusers: A brain source space study by EEG." PLoS One 14, e0226249. https://doi.org/10.1371/journal.pone.0226249.
Khalifa, N. et al. (2010) Pharmacological interventions for antisocial personality disorder. Cochrane Database Syst Rev. (8):CD007667, doi: 10.1002/14651858.CD007667.pub2. Europe PMC Funders Group Author Manuscript, 83 pages.
Khemka, S. et al. (2017). "Dissecting the function of hippocampal oscillations in a human anxiety model." J. Neurosci. 37, 6869-6876.
Khurshid KA. (2018). "Comorbid insomnia and psychiatric disorders: an update." Innovations in Clinical Neuroscience. 15(3-4):28.
Kim, J.W. et al. (2014). "Subchronic treatment of donepezil rescues impaired social, hyperactive, and stereotypic behavior in valproic acid-induced animal model of autism." PLoS One. 9(8):e104927.
Kim, Y. E., & Jeon, B. S. (2014). Clinical Implication of REM Sleep Behavior Disorder in Parkinson's Disease. Journal of Parkinson's Disease, 4(2), 237-244. https://doi.org/10.3233/JPD-130293.
Kinnaird, E. et al. (2019). Same behaviours, different reasons: what do patients with co-occurring anorexia and autism want from treatment? International Review of Psychiatry, 31(4), 308-317. https://doi.org/10.1080/09540261.2018.1531831.
Kirsh, K.L. (2010). "Differentiating and Managing Common Psychiatric Comorbidities Seen in Chronic Pain Patients." J Pain Palliat

(56) References Cited

OTHER PUBLICATIONS

Care Pharmacother, 24(1):39-47. Available from: https://www.tandfonline.com/action/journalInformation?journalCode=ippc20.

Kishi, T. et al. (Jun. 2012). Are Antipsychotics Effective for Anorexia Nervosa? Are Antipsychotics Effective for the Treatment of Anorexia Nervosa? Results From a Systematic Review and Meta-Analysis. J Clin Psychiatry, 73(6), 757-766. https://doi.org/10.4088/JCP.12r07691.

Kishi, T. et al. (2015). "Suvorexant for primary insomnia: A systematic review and meta-analysis of randomized placebo-controlled trials." PLoS One. 10(8):e0136910. https://doi.org/10.1371/journal.pone.0136910.

Klinkenberg I et al. (2010). "The validity of scopolamine as a pharmacological model for cognitive impairment: A review of animal behavioral studies." Neuroscience and Biobehavioral Reviews. vol. 34, p. 1307-50.

Knotkova, H. et al. (2012). "Current and future options for the management of phantom-limb pain." J Pain Res [Internet]. 5:39-49. Available from: http://dx.doi.org/10.2147/JPR.S16733.

Knyazev, G.G. et al. (2005). "Uncertainty, anxiety, and brain oscillations." Neurosci. Lett. 387, 121-125. https://doi.org/10.1016/j.neulet.2005.06.016.

*Kohn & Associates PLLC v. Compass Pathways Limited*, Case PGR2020-00030, U.S. Pat. No. 10,519,175, Exhibit 1005: The United States Pharmacopeial Convention (USP). 941 Characterization of Crystalline and Partially Crystalline Solids by X-Ray Powder Diffraction (XRPD). The United States Pharmacopeia. 35th Revision: The National Formulary. 30th ed (USP 35). 2011 (Official from May 1, 2012); pp. 427-433 (Exhibit E) (PTAB Feb. 21, 2020).

*Kohn & Associates PLLC v. Compass Pathways Limited*, Case PGR2020-00030, U.S. Pat. No. 10,519,175, Exhibit 2017: Clinical Trials.gov, "A Study of Psilocybin for Major Depressive Disorder (MDD)" Identifier: NCT03866174, Apr. 22, 2020, 12 pages (PTAB Jul. 22, 2020).

*Kohn & Associates PLLC v. Compass Pathways Limited*, Case PGR2020-00030, U.S. Pat. No. 10,519,175, Exhibit 2018: Sloshower, J. (May 6, 2020) "Psychedelics in the Treatment of Mood and Substance Use Disorders" Presentation, 31 pages (PTAB Jul. 22, 2020).

*Kohn & Associates PLLC v. Compass Pathways Limited*, Case PGR2020-00030, U.S. Pat. No. 10,519,175, Paper 23: Patent Owner's Sur-Reply to Petitioner's Reply (PTAB Jul. 22, 2020).

*Kohn & Associates PLLC v. Compass Pathways Limited*, Case PGR2020-00030, U.S. Pat. No. 10,519,175, Paper 25: Decision Denying Institution of Post-Grant Review (PTAB Aug. 20, 2020).

*Kohn & Associates PLLC v. Compass Pathways Limited*, Case PGR2020-00030, U.S. Pat. No. 10,519,175, Exhibit 1008: Declaration of Poncho Meisenheimer and Alex Sherwood (Exhibit H), (PTAB Feb. 21, 2020), pp. 1-4.

*Kohn & Associates PLLC v. Compass Pathways Limited*, Case PGR2020-00030, U.S. Pat. No. 10,519,175, Exhibit 1016: Abstracts of articles resulting from search of psilocybin treating depression and treatment resistant depression (Exhibit P) (PTAB Feb. 21, 2020), pp. 1-8.

*Kohn & Associates PLLC v. Compass Pathways Limited*, Case PGR2020-00030, U.S. Pat. No. 10,519,175, Exhibit 1017: Declaration of Jordan Sloshower, MD (Exhibit Q) (PTAB Feb. 21, 2020), 1 Page.

*Kohn & Associates PLLC v. Compass Pathways Limited*, Case PGR2020-00030, U.S. Pat. No. 10,519,175, Exhibit 1018: Declaration of Charles L. Raison, MD (Exhibit R) (PTAB Feb. 21, 2020), pp. 1-2.

*Kohn & Associates PLLC v. Compass Pathways Limited*, Case PGR2020-00030, U.S. Pat. No. 10,519,175, Exhibit 2004: Email Correspondence Between Petitioner and Patent Owner, dated Mar. 19-Apr. 1, 2020 (PTAB May 26, 2020), pp. 1-5.

*Kohn & Associates PLLC v. Compass Pathways Limited*, Case PGR2020-00030, U.S. Pat. No. 10,519,175, Exhibit 2005: Delaware Division of Corporations Details for Freedom to Operate, Inc., dated Apr. 1, 2020 (PTAB May 26, 2020), 1 Page.

*Kohn & Associates PLLC v. Compass Pathways Limited*, Case PGR2020-00030, U.S. Pat. No. 10,519,175, Exhibit 2006: A. Harrison, "Challenges to a Company's Psilocybin Patent Highlight Contrasting Business Strategies for Developers of Psychedelic Therapies," https://www.lucid.news/challenges-to-a-companyspsilocybin-patent-highlight-contrasting-business-strategies-fordevelopers-of-psychedelic-therapies/ (Apr. 7, 2020) (PTAB May 26, 2020), pp. 1-11.

*Kohn & Associates PLLC v. Compass Pathways Limited*, Case PGR2020-00030, U.S. Pat. No. 10,519,175, Exhibit 2007: Biography of Alexander Sherwood, Ph.D. (PTAB May 26, 2020), pp. 1-4.

*Kohn & Associates PLLC v. Compass Pathways Limited*, Case PGR2020-00030, U.S. Pat. No. 10,519,175, Exhibit 2008: Biography of Poncho Meisenheimer, Ph.D. (PTAB May 26, 2020), pp. 1-4.

*Kohn & Associates PLLC v. Compass Pathways Limited*, Case PGR2020-00030, U.S. Pat. No. 10,519,175, Exhibit 2009: Biography of Chuck Raison, M.D. (PTAB May 26, 2020), pp. 1-4.

*Kohn & Associates PLLC v. Compass Pathways Limited*, Case PGR2020-00030, U.S. Pat. No. 10,519,175, Exhibit 2010: Biography of Jordon Sloshower, M.D., MSc (PTAB May 26, 2020), pp. 1-4.

*Kohn & Associates PLLC v. Compass Pathways Limited*, Case PGR2020-00030, U.S. Pat. No. 10,519,175, Exhibit 2011: Biography of Bill Linton (PTAB May 26, 2020), pp. 1-3.

*Kohn & Associates PLLC v. Compass Pathways Limited*, Case PGR2020-00030, U.S. Pat. No. 10,519,175, Paper 1: Petition for Post Grant Review of U.S. Pat. No. 10,519,175 under 35 U.S.C. 321 (PTAB Feb. 21, 2020), pp. 1-30.

*Kohn & Associates PLLC v. Compass Pathways Limited*, Case PGR2020-00030, U.S. Pat. No. 10,519,175, Paper 11: Patent Owner's Exhibit List (PTAB Mar. 13, 2020), pp. 1-4.

*Kohn & Associates PLLC v. Compass Pathways Limited*, Case PGR2020-00030, U.S. Pat. No. 10,519,175, Paper 12: Notice Accepting Corrected Petition (PTAB Mar. 17, 2020), pp. 1-3.

*Kohn & Associates PLLC v. Compass Pathways Limited*, Case PGR2020-00030, U.S. Pat. No. 10,519,175, Paper 13: Corrected Petition for Post Grant Review of U.S. Pat. No. 10,519,175 Under 35 U.S.C. 321 (PTAB Mar. 20, 2020), pp. 1-48.

*Kohn & Associates PLLC v. Compass Pathways Limited*, Case PGR2020-00030, U.S. Pat. No. 10,519,175, Paper 15: Patent Owner's Preliminary Response (PTAB May 26, 2020), pp. 1-24.

*Kohn & Associates PLLC v. Compass Pathways Limited*, Case PGR2020-00030, U.S. Pat. No. 10,519,175, Paper 17: Reply to Patent Owner's Preliminary Response (PTAB Jul. 7, 2020), pp. 1-11.

*Kohn & Associates PLLC v. Compass Pathways Limited*, Case PGR2020-00030, U.S. Pat. No. 10,519,175, Paper 2: Petition for Post Grant Review of U.S. Pat. No. 10,519,175 Under 35 U.S.C. 321 Petitioner's List of Exhibits (PTAB Feb. 21, 2020), pp. 1-30.

*Kohn & Associates PLLC v. Compass Pathways Limited*, Case PGR2020-00030, U.S. Pat. No. 10,519,175, Paper 5: Notice of Filing Date Accorded to Petition and Time for Filing Patent Owner Preliminary Response (PTAB Feb. 26, 2020), pp. 1-5.

*Kohn & Associates PLLC v. Compass Pathways Limited*, Case PGR2020-00030, U.S. Pat. No. 10,519,175, Paper 6: Corrected Petition for Post Grant Review of U.S. Pat. No. 10,519,175 Under 35 U.S.C. 321 (PTAB Mar. 6, 2020), pp. 1-33.

*Kohn & Associates PLLC v. Compass Pathways Limited*, Case PGR2020-00030, U.S. Pat. No. 10,519,175, Paper 8: Patent Owner's Mandatory Notices (PTAB Mar. 13, 2020), pp. 1-5.

Kolar, D. et al. (2008) Treatment of adults with attention-deficit/hyperactivity disorder. Neuropsychiatric Dis Treat, 4(2):389-403.

Kolarik, J. (1967). Eeg-Veranderungen nach Psilocybin bei Epilepsien. Acta Univ. Palackianae Olomucensis, 47:253-263. (English Summary on p. 262).

Kolden, G.G. et al. (2000) The Therapeutic Realizations Scale-Revised (TRS-R): Psychometric Characteristics and Relationship to Treatment Process and Outcome. Journal of Clinical Psychology. 56(9):1207-1220.

Kolla, B. et al. (2017). "The prevalence of hypersomnolence, its correlates and associated role impairment in the National Comorbidity Survey Replication (NCS-R)." Sleep. 40(suppl_1), pp. A239-A239. https://doi.org/10.1093/sleepj/zsx050.645.

(56) References Cited

OTHER PUBLICATIONS

Kometer, M. et al. (2013). "Activation of Serotonin 2A Receptors Underlies the Psilocybin-Induced Effects on Oscillations, N170 Visual-Evoked Potentials, and Visual Hallucinations." Journal of Neuroscience, 33(25), 10544-10551. https://doi.org/10.1523/JNEUROSCI.3007-12.2013.

Korecka, J.A. et al. (2017). "Repulsive Guidance Molecule a (RGMa) Induces Neuropathological and Behavioral Changes That Closely Resemble Parkinson's Disease." The Journal of Neuroscience : The Official Journal of the Society for Neuroscience, 37(39), 9361-9379. https://doi.org/10.1523/JNEUROSCI.0084-17.2017.

Kornum, B.R. et al. (2017). "Narcolepsy." Nat. Rev. Dis. Prim. 3(1):1-9. https://doi.org/10.1038/nrdp.2016.100.

Kothare, S.V. et al. (2008) "Zonisamide: review of pharmacology, clinical efficacy, tolerability, and safety." Expert Opinion on Drug Metabolism & Toxicology, 4(4), 493-506. https://doi.org/10.1517/17425255.4.4.493.

Kotov, S.B. Bellman, and D.B. Watson (2004) Multidimensional Iowa Suggestibility Scale (MISS) Brief Manual. [online] Retrieved from: https://renaissance.stonybrookmedicine.edu/sites/default/files/MISSBriefManual.pdf, 16 pages.

Kouli, A. et al. (2018). Parkinson's Disease: Etiology, Neuropathology, and Pathogenesis. In Parkinson's Disease: Pathogenesis and Clinical Aspects. Thomas B. Stoker & Julia C. Greenland (Eds.) Codon Publications, pp. 3-26. Retrieved from http://www.ncbi.nlm.nih.gov/pubmed/30702842.

Kountza, M. et al. (2018). "La comorbidité psychiatrique de l'anorexie mentale : une étude comparative chez une population de patients anorexiques français et grecs." L'Encéphale, 44(5), 429-434. https://doi.org/10.1016/j.encep.2017.07.005. English abstract on p. 429.

Kryzhanovskii, G.N. et al. (1992). [The antiepileptic effects of sodium valproate and the calcium antagonist riodipine when used jointly in a model of generalized korazol-induced epileptic activity]. Biulleten' Eksperimental'noi Biologii i Meditsiny, 114(10), 376-378 [Abstract]. Retrieved from http://www.ncbi.nlm.nih.gov/pubmed/1288691, 1 page.

Krzyszkowiak, W. et al. (2019) "Treatment of obsessive-compulsive disorders (OCD) and obsessive-compulsive-related disorders (OCRD)" Psychiatr Pol, 53(4):825-843; DOI: https://doi.org/10.12740/PP/105130.

Kubera, M. et al. (2005). Effects of serotonin and serotonergic agonists and antagonists on the production of tumor necrosis factor α and interleukin-6. Psychiatry Research, 134(3), 251-258. https://doi.org/10.1016/j.psychres.2004.01.014.

Kuhnert, M. et al. (1976) "Polymorphe Modifikationen und Solvate von Psilocin und Psilocybin [Polymorphic Modifications and Solvates of Psilocin and Psilocybin]" Archiv der Pharmazie, 309:625-631, with English translation from Google Translate (14 total pages).

Kurrasch-Orbaugh, D.M. et al. (2003). Serotonin 5-Hydroxytryptamine$_{2a}$ Receptor-Coupled Phospholipase C and Phospholipase A$_2$ Signaling Pathways Have Different Receptor Reserves. J Pharmacol Exp Ther., 304(1), 229-237.

Kwan, P., & Brodie, M. J. (2001). Neuropsychological effects of epilepsy and antiepileptic drugs. The Lancet, 357(9251), 216-222. https://doi.org/10.1016/S0140-6736(00)03600-X.

Kwan, P. et al. (2009). Definition of drug resistant epilepsy: Consensus proposal by the ad hoc Task Force of the ILAE Commission on Therapeutic Strategies. Epilepsia, 51(6), 1069-1077. https://doi.org/10.1111/j.1528-1167.2009.02397.x.

Lader, M., 2015. Generalized Anxiety Disorder BT—Encyclopedia of Psychopharmacology, in: Stolerman, I.P., Price, L.H. (Eds.). Springer Berlin Heidelberg, pp. 699-702. https://doi.org/10.1007/978-3-642-36172-2_317.

Lahdenpaa et al., "Direct compression with silicified and non-silicified microcrystalline cellulose: study of some properties of powders and tablets," S.T.P. Pharma Sciences, 2001; 11(2):129-135. Supplied by the British Library Oct. 12, 2019, 8 pages.

Lahey, B.B. et al. (2005) Predicting Future Antisocial Personality Disorder in Males From a Clinical Assessment in Childhood. J Consult Clin Psychol, 73(3):389-399.

Lahmame, A. et al. (1997). "Are Wistar-Kyoto rats a genetic animal model of depression resistant to antidepressants?" Eur. J. Pharmacol. 337(2-3):115-23. https://doi.org/10.1016/S0014-2999(97)01276-4.

Lai, M.C. et al. (2019). "Prevalence of co-occurring mental health diagnoses in the autism population: a systematic review and meta-analysis." The Lancet Psychiatry. 6(10):819-29. https://doi.org/10.1016/S2215-0366(19)30289-5.

Landau, A.M. et al. (2005). "Defective Fas expression exacerbates neurotoxicity in a model of Parkinson's disease." The Journal of Experimental Medicine, 202(5), 575-581. https://doi.org/10.1084/jem.20050163.

Larrosa, O. et al. (2001). "Stimulant and Anticataplectic Effects of Reboxetine in Patients with Narcolepsy: A Pilot Study." Sleep. 24(3):282-5.

Layzer, R., "Section 5—Degenerative Diseases of the Nervous System," Cecil Textbook of Medicine, , Eds. J. Claude Bennett, MD and Fred Plum, 20th edition (1996), vol. 2, pp. 2050-2057.

Lecavalier, L. (2006). "Behavioral and emotional problems in young people with pervasive developmental disorders: Relative prevalence, effects of subject characteristics, and empirical classification." Journal of Autism and Developmental Disorders. 36(8):1101-14. https://doi.org/10.1007/s10803-006-0147-5.

Lecendreux, M. et al. (2015). Attention-Deficit/Hyperactivity Disorder (ADHD) Symptoms in Pediatric Narcolepsy: A Cross-Sectional Study. Sleep 38, 1285-1295. https://doi.org/10.5665/sleep.4910.

Leclerc, S. et al. (Jun. 2015). "Pharmacological therapies for autism spectrum disorder: A review." Pharmacy and Therapeutics. 40(6):389-397.

Ledonne, A., & Mercuri, N. B. (2020). On the modulatory roles of neuregulins/ErbB signaling on synaptic plasticity. International Journal of Molecular Sciences, 21:275, 23 pages. https://doi.org/10.3390/ijms21010275.

Lee, P. H. et al. (2019). "Genomic Relationships, Novel Loci, and Pleiotropic Mechanisms across Eight Psychiatric Disorders." Cell. 179(1469-1482):e11. https://doi.org/10.1016/j.cell.2019.11.020.

Lee, R.M. and Robbins, S.B. (1995) Measuring belongingness: the social connectedness and the social assurance scales Journal of Counseling Psychology. 42:232-241.

Lee, T. J. et al. (2017). "Repeated adolescent activity-based anorexia influences central estrogen signaling and adulthood anxiety-like behaviors in rats." Physiology and Behavior, 171, 199-206. https://doi.org/10.1016/j.physbeh.2016.12.039.

Lee, Y.C. et al. (2010). "A review of SSRIs and SNRIs in neuropathic pain." Expert Opin Pharmacother. 11(17):2813-25.

Leigh, J. P. et al. (2015). "Brief Report: Forecasting the Economic Burden of Autism in 2015 and 2025 in the United States." Journal of Autism and Developmental Disorders. 45(12):4135-9. https://doi.org/10.1007/s10803-015-2521-7.

Leonard, H.L., & Rapoport, J.L. (Sep. 1987) "Letter to the Editor: Relief of obsessive-compulsive symptoms by LSD and psilocin" American Journal of Psychiatry, 144(9):1239-1240.

Leroux, E. and Ducros, A. (2008) Cluster headache. Orphanet J Rare Dis, 3:20, doi: 10.1186/1750-1172-3-20, 11 pages.

Levin, E. D., & Rezvani, A. H. (2000). Development of nicotinic drug therapy for cognitive disorders. European Journal of Pharmacology, 393(1-3), 141-146. https://doi.org/10.1016/s0014-2999(99)00885-7.

Leysen, J.E. et al. (1982). [$^3$H]Ketanserin (R 41 468), a selective $^3$H-ligand for serotonin$_2$ receptor binding sites. Binding properties, brain distribution, and functional role. Molecular Pharmacology, 21(2), 301-314.

Li, T. et al. (2017). A scored human protein-protein interaction network to catalyze genomic interpretation. Nature Methods, 14(1), 61-64. https://doi.org/10.1038/nmeth.4083.

Li, Y. et al. (2011) "Quantification of polymorphic impurity in an enantiotropic polymorph system using differential scanning calorimetry, X-ray powder diffraction and Raman spectroscopy" Intl J Pharma, 415:110-118.

Liang, H. et al. (2019). Mammalian Target of Rapamycin at the Crossroad Between Alzheimer's Disease and Diabetes. In Diabetes

(56) References Cited

OTHER PUBLICATIONS

Mellitus. A Risk Factor for Alzheimer's Disease. Advances in Experimental Medicine and Biology, 1128, 185-225. https://doi.org/10.1007/978-981-13-3540-2_10.

Limakatso K et al. (2019). "The prevalence of phantom limb pain and associated risk factors in people with amputations: A systematic review protocol." Syst Rev. 8:17, 5 pages. https://doi.org/10.1186/s13643-018-0938-8.

Lindenblatt, H et al. (1998). "Quantitation of psilocin in human plasma by high-performance liquid chromatography and electrochemical detection: Comparison of liquid—liquid extraction with automated on-line solid-phase extraction." J Chromatogr B Biomed Appl. 709(2):255-63.

Liu, L. et al. (2018). "Deficiency of Sustained Attention in ADHD and Its Potential Genetic Contributor MAOA" J Atten Disord, 22(9):878-885.

Liu, P.-P. et al. (2019). "History and progress of hypotheses and clinical trials for Alzheimer's disease." Signal Transduction and Targeted Therapy, 4:29, https://doi.org/10.1038/s41392-019-0063-8, 22 pages.

Lopez-Castejon, G. et al. (2011). "Understanding the mechanism of IL-1β secretion." Cytokine & Growth Factor Reviews, 22(4), 189-195. https://doi.org/10.1016/j.cytogfr.2011.10.001.

Loth, E. et al. (2018). "Facial expression recognition as a candidate marker for autism spectrum disorder: how frequent and severe are deficits?" Molecular Autism, 9:7, https://doi.org/10.1186/s13229-018-0187-7, 11 pages.

Lu, T.-T., Wan, C., Yang, W., & Cai, Z. (2019). Role of Cdk5 in Amyloid-beta Pathology of Alzheimer's Disease. Current Alzheimer Research, 16(13), 1206-1215. https://doi.org/10.2174/1567205016666191210094435.

Lucchina, L. et al. (2014). "Altered Peripheral and Central Inflammatory Responses in a Mouse Model of Autism." Autism Research. 7(2):273-89. https://doi.org/10.1002/aur.1338.

Lucza, T. et al. (2015). "Screening Mild and Major Neurocognitive Disorders in Parkinson's Disease." Behavioural Neurology, 2015, Article ID 983606, 10 pages. https://doi.org/10.1155/2015/983606.

Lugli, S.M. et al. (1997). "Tumor Necrosis Factor α Enhances the Expression of the Interleukin (IL)-4 Receptor α-Chain on Endothelial Cells Increasing IL-4 or IL-13-induced Stat6 Activation." Journal of Biological Chemistry, 272(9), 5487-5494. https://doi.org/10.1074/jbc.272.9.5487.

Lynch ME et al. (2006). "The pharmacotherapy of chronic pain: A review." Pain Res Manag. 11(1):11-38.

Lyons, T and R.L. Carhart-Harris (2018) Increased nature relatedness and decreased authoritarian political views after psilocybin for treatment-resistant depression. Journal of Psychopharmacology, 32(7):811-819.

Mabunga, D.F.N. et al. (2015). "Exploring the Validity of Valproic Acid Animal Model of Autism." Experimental Neurobiology. 24(4):285-300. https://doi.org/10.5607/en.2015.24.4.285.

Macy, A.S. et al. (2013) "Quality of life in obsessive compulsive disorder" CNS Spectrums, 18(1):21-33.

Mahapatra et al., "Role of psilocybin in the treatment of depression," Ther Adv Psychopharmacol, Jan. 2017; 7(1): 54-56.

Mahfoud, Y. et al. (Sep. 2009). Sleep disorders in substance abusers: How common are they? Psychiatry, 6(9):38-42.

Mahone EM et al. (2017). "Attention-Deficit/Hyperactivity Disorder: A Historical Neuropsychological Perspective." J Int Neuropsychol Soc [Internet]. 23:916-29. Available from: http://www.rmtcnet.com/resources/Phenylbutazone_Review-Dr._Lawrence_R._Soma.pdf.

Maiano, C. et al. (2019). Psychometric Properties of the Body Checking Questionnaire (BCQ) and of the Body Checking Cognitions Scale (BCCS): A Bifactor-Exploratory Structural Equation Modeling Approach. Assessment, 1-15, https://doi.org/10.1177/1073191119858411.

Maimoun, L. et al. (2018). Effects of the two types of anorexia nervosa (binge eating/purging and restrictive) on bone metabolism in female patients. Clinical Endocrinology, 88(6):863-872. https://doi.org/10.1111/cen.13610.

Maina, G. et al. (2003) "Antipsychotic augmentation for treatment resistant obsessive-compulsive disorder: What if antipsychotic is discontinued?" International Clinical Psychopharmacology, 18(1):23-28; DOI: 10.1097/01.yic.0000047784.24295.2b.

Manavalan, A. et al. (2013). Brain site-specific proteome changes in aging-related dementia. Experimental & Molecular Medicine. 45:e39, 17 pages. https://doi.org/10.1038/emm.2013.76.

Marras, C. et al. (2018). Prevalence of Parkinson's disease across North America. npjParkinson's Disease. 4:21, https://doi.org/10.1038/s41531-018-0058-0, 7 pages.

Martin, W., Vaupel, D., Nozaki, M. and Bright, L. (1978). The identification of LSD-like hallucinogens using the chronic spinal dog. Drug and Alcohol Dependence, 3(2), pp. 113-123.

Martins, G.R. et al. (2016). Proinflammatory and Anti-Inflammatory Cytokines Mediated by NF-κ B Factor as Prognostic Markers in Mammary Tumors. Mediators of Inflammation, 2016:1-10. https://doi.org/10.1155/2016/9512743.

Martinussen R. et al. (2005). A meta-analysis of working memory impairments in children with attention-deficit/hyperactivity disorder. J Am Acad Child Adolesc Psychiatry, 44(4):377-84.

Marvanova, M. & Gramith, K. (2018). Role of antidepressants in the treatment of adults with anorexia nervosa. Ment Health Clin [Internet] 8(3):127-37. DOI: 10.9740/mhc.2018.05.127.

Mason, N.L. et al. (2019). Sub-Acute Effects of Psilocybin on Empathy, Creative Thinking, and Subjective Well-Being. Journal of Psychoactive Drugs, https://doi.org/10.1080/02791072.2019.1580804, 13 pages.

Mathes, B.M. et al. (2019). Epidemiological and Clinical Gender Differences in OCD. In Current Psychiatry Reports (vol. 21, Issue 5, pp. 1-7). Curr Psychiatry Rep, 21:36, 7 pages, https://doi.org/10.1007/s11920-019-1015-2.

Matheson, E. & Hainer, B.L. (2017) Insomnia: Pharmacologic Therapy—American Family Physician. Am Fam Physician, 96(1):29-35.

Matsushima, Y. et al. (2009). Effects of Psilocybe argentipes on Marble-Burying Behavior in Mice. Bioscience Biotechnology and Biochemistry, 73(8):1866-1868. https://doi.org/10.1271/bbb.90095.

Mattingly, G. et al. (2012). Attention deficit hyperactivity disorder subtypes and symptom response in adults treated with lisdexamfetamine dimesylate. Innov Clin Neurosci, 9(5-6):22-30.

Maxwell, C.R. et al. (2013). Atypical Laterality of Resting Gamma Oscillations in Autism Spectrum Disorders, 45(2):292-297, doi:10.1007/s10803-013-1842-7.

Mayhew A. & Argaez, C. (2018). Intravenous lidocaine for chronic pain: a review of the clinical effectiveness and guidelines. Ottawa: CADTH; Jan. 2018 (CADTH rapid response report: summary with critical appraisal), 22 pages.

Mazza M, Marano G, Janiri L. (2016) An update on pharmacotherapy for personality disorders. Expert Opinion on Pharmacotherapy. 17:(15):1977-1979.

McCarberg, B. & Billington, R. (2006). Consequences of neuropathic pain: Quality-of-life issues and associated costs. Am J Manag Care, 12(Suppl. 9):S263-8.

McCuen-Wurst, C. et al. (Jan. 2018). Disordered eating and obesity: associations between binge-eating disorder, night-eating syndrome, and weight-related comorbidities. Annals of the New York Academy of Sciences, 1411(1), pp. 96-105.

McCullough, M.E. et al. (2002) The grateful disposition: A conceptual and empiracal topography. Journal of Personality and Social Psychology, 82:112-127.

McElroy, S. et al. (2012). Pharmacological management of binge eating disorder: current and emerging treatment options. Therapeutics and Clinical Risk Management, 8:219-241.

McElroy, S. et al. (2013). A placebo-controlled pilot study of the novel opioid receptor antagonist ALKS-33 in binge eating disorder. International Journal of Eating Disorders, 46(3), pp. 239-245.

McElroy, S. et al. (2015). Efficacy and Safety of Lisdexamfetamine for Treatment of Adults With Moderate to Severe Binge-Eating Disorder. JAMA Psychiatry, 72(3), p. 235-246.

McGuire-Snieckus, R. et al. (2007) A new scale to assess the therapeutic relationship in community mental health care: STAR. Psychological Medicine. 37:85-95.

(56) References Cited

OTHER PUBLICATIONS

Medical News Today, M. (2020). What to know about Parkinson's dementia. Retrieved from https://www.medicalnewstoday.com/articles/314486, 14 pages.

Medzhitov, R. (2008). Origin and physiological roles of inflammation. Nature, 454(7203):428-435. https://doi.org/10.1038/nature07201.

Mei, L., & Nave, K.-A. (2014). Neuregulin-ERBB signaling in the nervous system and neuropsychiatric diseases. In Neuron, 83:27-49, https://doi.org/10.1016/j.neuron.2014.06.007.

Meier, S.M. et al. (2016). Mortality among persons with obsessive-compulsive disorder in Denmark. JAMA Psychiatry, 73(3):268-274. https://doi.org/10.1001/jamapsychiatry.2015.3105.

Meldrum, B.S. & Naquet, R. (1970). Effects of psilocybin, dimethyltryptamine and various lysergic acid derivatives on photically-induced epilepsy in the baboon (Papio papio). British Journal of Pharmacology, 40(1):144P-145P. Retrieved from http://www.ncbi.nlm.nih.gov/pubmed/4992165.

Meyer, A.-C. et al. (2010). Global disparities in the epilepsy treatment gap: a systematic review. Bulletin of the World Health Organization, 88(4):260-266. https://doi.org/10.2471/BLT.09.064147.

Miller, A.H., & Raison, C. L. (2016). Role of inflammation in depression from evolutionary imperative to modern treatment target. Nat Rev Immunol, 16(1):22-34. https://doi.org/10.1038/nri.2015.5.

Mills, S.E.E. et al. (2019). Chronic pain: a review of its epidemiology and associated factors in population-based studies. Br J Anaesth. 123(2):273-83.

Milos, G. et al. (2002). Comorbidity of obsessive-compulsive disorders and duration of eating disorders. International Journal of Eating Disorders, 31(3):284-289. https://doi.org/10.1002/eat.10013.

Min, S.S. et al. (2011). Neuregulin-1 prevents amyloid β-induced impairment of long-term potentiation in hippocampal slices via ErbB4. Neuroscience Letters, 505(1):6-9. https://doi.org/10.1016/j.neulet.2011.05.246.

Minen, M.T. et al. (2016). Migraine and its psychiatric comorbidities. J. Neurol. Neurosurg. Psychiatry, 87:741-749. https://doi.org/10.1136/jnnp-2015-312233.

Miniati, M. et al. (2016). Psychopharmacological options for adult patients with anorexia nervosa. CNS Spectrums, 21:134-142. https://doi.org/10.1017/S1092852914000790.

Mitsuyama, F. et al. (2009). Amyloid beta: a putative intra-spinal microtubule-depolymerizer to induce synapse-loss or dentritic spine shortening in Alzheimer's disease. Italian Journal of Anatomy and Embryology, 114(2-3), 109-120. [Abstract]. Retrieved from http://www.ncbi.nlm.nih.gov/pubmed/20198823, 1 page.

Molero, P. et al. (2018). Antidepressant Efficacy and Tolerability of Ketamine and Esketamine: A Critical Review. CNS Drugs 32:411-420). https://doi.org/10.1007/s40263-018-0519-3.

Montejo, A.L. et al. (2008) Psychometric Properties of the Psychotropic-Related Sexual Dysfunction Questionnaire (PRSexDQ-SALSEX) in Patients with Schizophrenia and Other Psychotic Disorders. Journal of Sex Marital Therapy. 34(3):227-39.

Montigny, C. (1989). Cholecystokinin Tetrapeptide Induces Panic-like Attacks in Healthy Volunteers: Preliminary Findings. Archives of General Psychiatry, 46:511-517. https://doi.org/10.1001/archpsyc.1989.01810060031006.

Moran, P. et al. (2003) Standardised Assessment of Personality—Abbreviated Scale (SAPAS): preliminary validation of a brief screen for personality disorder. The British Journal of Psychiatry, 183(3):228-232.

Moreno, F. A., & Delgado, P. L. (1997). Hallucinogen-induced relief of obsessions and compulsions. American Journal of Psychiatry, vol. 154, Issue 7, pp. 1037-1038. https://doi.org/10.1176/ajp.154.7.1037b.

Moreno, F.A. et al. (Nov. 2006). Safety, tolerability, and efficacy of psilocybin in 9 patients with obsessive-compulsive disorder. Journal of Clinical Psychiatry, 67(11), 1735-1740. https://doi.org/10.4088/JCP.v67n1110.

Morgan, C. et al. (2017). Tripping up addiction: the use of psychedelic drugs in the treatment of problematic drug and alcohol use. Current Opinion in Behavioral Sciences, 13, pp. 71-76.

Morilak, D.A. et al. (2005). Role of brain norepinephrine in the behavioral response to stress. Prog. Neuro-Psychopharmacology Biol. Psychiatry, 29:1214-1224. https://doi.org/10.1016/j.pnpbp.2005.08.007.

Moscovich, M. et al. (2017). Death certificate data and causes of death in patients with parkinsonism. Parkinsonism & Related Disorders, 41:99-103. https://doi.org/10.1016/j.parkreldis.2017.05.022.

Moser, P.C. et al. (Jul. 7, 1988) "The effect of benzodiazepines on the 5-HT agonist-induced head-twitch response in mice", Eur J. Pharmacol, 151(2): 223-231.

Mukherjee, S. et al. (2009). Lipopolysaccharide-driven Th2 Cytokine Production in Macrophages Is Regulated by Both MyD88 and TRAM. Journal of Biological Chemistry, 284(43):29391-29398. https://doi.org/10.1074/jbc.M109.005272.

Mula, M. et al. (2006). Psychopharmacology of topiramate: From epilepsy to bipolar disorder. Neuropsychiatric Disease and Treatment, 2(4):475-488. https://doi.org/10.2147/nedt.2006.2.4.475.

Mulvey, M.R. (2017) Neuropathic pain in cancer: systematic review, performance of screening tools and analysis of symptom profiles. British Journal of Anaesthesia, 119(4):765-774.

Municio, C. et al. (2018). Methotrexate limits inflammation through an A20-dependent cross-tolerance mechanism. Annals of the Rheumatic Diseases, 77(5):752-759. https://doi.org/10.1136/annrheumdis-2017-212537.

Murphy-Beiner, A. & Soar, K. (2020). Ayahuasca's 'afterglow': improved mindfulness and cognitive flexibility in ayahuasca drinkers. Psychopharmacology, published online, https://doi.org/10.1007/s00213-019-05445-3, 9 pages.

Murrough, J.W. et al. (2015). Emerging drugs for the treatment of anxiety. Expert Opin. Emerg. Drugs, 20(3):393-406. https://doi.org/10.1517/14728214.2015.1049996.

Nam, H. et al. (2014). Learned helplessness and social avoidance in the Wistar-Kyoto rat. Front. Behav. Neurosci., 8(109), https://doi.org/10.3389/fnbeh.2014.00109, 18 pages.

National Institute for Health and Care Excellence (NICE) (Jan. 28, 2019) Antisocial Personality Disorder: Prevention and Management. Clinical guidance CG77 [online]. Available from www.nice.org.uk/guidance/cg77, 35 pages.

National Institute of Mental Health (NIMH) (Nov. 2017) Eating Disorders. Mental Health Information—Statistics (online). Retrieved Mar. 5, 2020, from https://www.nimh.nih.gov/health/statistics/eating-disorders.shtml#part_155063, 14 pages.

Nau, F. et al. (2015). Serotonin 5-HT$_2$ receptor activation prevents allergic asthma in a mouse model. American Journal of Physiology. Lung Cellular and Molecular Physiology, 308(2), L191-8. https://doi.org/10.1152/ajplung.00138.2013.

Nau, F., Yu, B., Martin, D., & Nichols, C. D. (2013). Serotonin 5-HT$_{2a}$ Receptor Activation Blocks TNF-α Mediated Inflammation In Vivo. PLoS One, 8(10):2-9. https://doi.org/10.1371/journal.pone.0075426.

Naviaux, J.C. et al. (2014). Reversal of autism-like behaviors and metabolism in adult mice with single-dose antipurinergic therapy. Translational Psychiatry, 4:e400, 11 pages. https://doi.org/10.1038/tp.2014.33.

Nechita, D. et al. (2018). A review of the influence the anxiety exerts on human life. Rom. J. Morphol. Embryol., 59(4):1045-1051.

Nelis, S.M. et al. (2019). The impact of co-morbidity on the quality of life of people with dementia: findings from the IDEAL study. Age and Ageing, 48(3):361-367. https://doi.org/10.1093/ageing/afy155.

Nelson, R. J. et al. (2006). Pleiotropic contributions of nitric oxide to aggressive behavior. Neuroscience and Biobehavioral Reviews, 30(3):346-355. https://doi.org/10.1016/j.neubiorev.2005.02.002.

Newman-Tancredi, A. et al. (2018). Effects of the Serotonin 5-HT1A Receptor Biased Agonists, F13714 and F15599, on Striatal Neurotransmitter Levels Following L-DOPA Administration in Hemi-Parkinsonian Rats. Neurochemical Research, 43(5):1035-1046. https://doi.org/10.1007/s11064-018-2514-y.

Ngugi, A.K. et al. (2010). Estimation of the burden of active and life-time epilepsy: A meta-analytic approach. Epilepsia, 51(5): 883-890. https://doi.org/10.1111/j.1528-1167.2009.02481.x.

(56) References Cited

OTHER PUBLICATIONS

Ni, H.C. et al. (Oct. 2013) A head-to-head randomized clinical trial of methylphenidate and atomoxetine treatment for executive function in adults with attention-deficit hyperactivity disorder. Int J Neuropsychopharmacol, 16(9):1959-1973.
Nichols, D.E. (2004) Hallucinogens. Pharmacology & Therapeutics, 101:131-181.
Nichols, D.E. (Apr. 2016) Psychedelics. Pharmacol Reviews, 68:264-355.
Nichols et al., "Improvements to the Synthesis of Psilocybin and a Facile Method for Preparing the 0-Acetyl Prodrug of Psilocin," Synthesis. 1999; 6:935-938.
Nicholson, B. & Verma S. (2004). Comorbidities in chronic neuropathic pain. Pain Medicine. 5(S1):S9-25. Retrieved from: https://academic.oup.com/painmedicine/article-abstract/5/suppl_1/S9/1884243, on Jul. 30, 2020.
Nicolini, C. et al. (2015). Decreased mTOR signaling pathway in human idiopathic autism and in rats exposed to valproic acid. Acta Neuropathologica Communications, 3:3, 13 pages, https://doi.org/10.1186/s40478-015-0184-4.
Niederhofer, H. (2005). Atomoxetine Also Effective in Patients Suffering From Narcolepsy? Sleep, 28(9):1189, 1 page. https://www.researchgate.net/publication/7500498_Atomoxetine_Also_Effective_in_Patients_Suffering_From_Narcolepsy (accessed Mar. 26, 2020).
Nielsen, S. (2017). Benzodiazepines. Curr. Top. Behav. Neurosci. 34:141-159. https://doi.org/10.1007/7854_2015_425.
Nimmo-Smith, V. et al. (2020). Anxiety Disorders in Adults with Autism Spectrum Disorder: A Population-Based Study. Journal of Autism and Developmental Disorders, 50:308-318. https://doi.org/10.1007/s10803-019-04234-3.
Nisbet, E. et al. (Sep. 2009) The nature relatedness scale. Linking individuals' connection with nature to environmental concern and behavior. Environment and Behavior 41(5):715-740.
Norris, M.L. et al. (2011). Olanzapine Use for the Adjunctive Treatment of Adolescents with Anorexia Nervosa. Journal of Child and Adolescent Psychopharmacology, 21(3):213-220. https://doi.org/10.1089/cap.2010.0131.
Nour, M.M. et al. (Jun. 2016) Ego-Dissolution and Psychedelics: Validation of the Ego-Dissolution Inventory (EDI) Frontiers in Human Neuroscience, 10:269, doi: 10.3389/fnhum.2016.00269, 13 pages.
Nour, M.M. et al. (2017) Psychedelics, Personality and Political Perspectives. Journal of Psychoactive Drugs, 49(3):182-191.
Nowacka, A. & Borczyk, M. (2019). Ketamine applications beyond anesthesia—A literature review. European Journal of Pharmacology, 860, 172547, 14 pages. https://doi.org/10.1016/j.ejphar.2019.172547.
Nutt, D. et al. (Apr. 2, 2020) "Psychedelic Psychiatry's Brave New World", Cell, 181(1,2):24-28.
Oerbeck, B. et al. (2017) ADHD, comorbid disorders and psychosocial functioning: How representative is a child cohort study? Findings from a national patient registry. BMC Psychiatry, 17:23, 9 pages. Available from: http://dx.doi.org/10.1186/s12888-017-1204-7.
Olguin, P. et al. (2017). Medical comorbidity of binge eating disorder. Eat Weight Disord 22, 13-26.
Onakpoya, I.J. et al. (2019). Benefits and harms of pregabalin in the management of neuropathic pain: A rapid review and meta-analysis of randomised clinical trials. BMJ Open 9, e023600, 19 pages. https://doi.org/10.1136/bmjopen-2018-023600.
Opbroek, A. et al. (2002) Emotional blunting associated with SSRI-induced sexual dysfunction. Do SSRIs inhibit emotional responses? International Journal of Neuropsychopharmacology, 5:147-151.
Orekhova, E.V. et al. (2008). Sensory gating in young children with autism: Relation to age, IQ, and EEG gamma oscillations. Neurosci. Lett., 434:218-223. https://doi.org/10.1016/j.neulet.2008.01.066.
Osland, S. et al. (2018). The prevalence of diagnosed obsessive compulsive disorder and associated comorbidities: A population-based Canadian study. Psychiatry Research, 268:137-142. https://doi.org/10.1016/j.psychres.2018.07.018.
Ottman, R. et al.(2011). Comorbidities of epilepsy: results from the Epilepsy Comorbidities and Health (EPIC) survey. Epilepsia, 52(2):308-315. https://doi.org/10.1111/j.1528-1167.2010.02927.x.
Otto, M.W. et al. (2001). An effect-size analysis of the relative efficacy and tolerability of serotonin selective reuptake inhibitors for panic disorder. Am. J. Psychiatry 158:1989-1992. https://doi.org/10.1176/appi.ajp.158.12.1989.
Page, J. & Henry, D. (Mar. 2000). Consumption of NSAIDs and the Development of Congestive Heart Failure in Elderly Patients. Archives of Internal Medicine, 160(6):777-784. https://doi.org/10.1001/archinte.160.6.777.
Pahwa, R. et al. (2020). Chronic Inflammation. Statpearls [Internet]. NCBI Bookshelf. Retrieved from: https://www.ncbi.nlm.nih.gov/books/NBK493173/, 9 printed pages.
Palsson-McDermott, E. M. & O'Neill, L. A. J. (2004). Signal transduction by the lipopolysaccharide receptor, Toll-like receptor-4. Immunology, 113(2):153-162. https://doi.org/10.1111/j.1365-2567.2004.01976.x.
Papakostas, G.I. et al. (2006) "The combination of duloxetine and bupropion for treatment-resistant major depressive disorder" Depression and Anxiety, 23:178-181.
Parameswaran, N. & Patial, S. (2010). Tumor necrosis factor-α signaling in macrophages. Critical Reviews in Eukaryotic Gene Expression, 20(2):87-103. https://doi.org/10.1615/critreveukargeneexpr.v20.i2.10.
Park, A. (Dec. 2021) Characterization of Psilocybin. Freedom to Operate, LLC. Triclinic Labs Report No. R2021638.01, 11 pages.
Park, J.H. & Park, H.J. (2017) Botulinum toxin for the treatment of neuropathic pain. Toxins. 9:290, doi:10.3390/toxins9090260, 15 pages.
Parkinson's Foundation (2020). Prescription Medications for Parkinson Disease. Retrieved from https://www.parkinson.org/Understanding-Parkinsons/Treatment/Prescription-Medications; retrieved on Jul. 30, 2020; 6 pages.
Parkinson's Foundation, P. (2020). Stages of Parkinson's disease. Retrieved from https://www.parkinson.org/Understanding-Parkinsons/What-is-Parkinsons/Stages-of-Parkinsons, 8 pages.
Parnas, J. et al. (2005) EASE: Examination of Anomalous Self-Experience. Psychopathology. 38:236-258.
Passie, T. et al. (2002) The pharmacology of psilocybin. Addiction Biology, 7:357-364.
Patra, S. (Dec. 2016) "Return of the psychedelics: Psilocybin for treatment resistant depression," Asian Journal of Psychiatry, vol. 24, p. 51-52.
Patton, J.H. (Nov. 1995) Factor structure of the Barratt Impulsiveness Scale. Journal of Clinical Psychology. 51:768-774.
Pauli, D. et al. (2017). Motivation to change, coping, and self-esteem in adolescent anorexia nervosa: A validation study of the Anorexia Nervosa Stages of Change Questionnaire (ANSOCQ). Journal of Eating Disorders, 5(1):11, 11 pages. https://doi.org/10.1186/s40337-016-0125-z.
Pecina, S., & Berridge, K.C. (Dec. 2005). Hedonic hot spot in nucleus accumbens shell: Where do μ opioids cause increased hedonic impact of sweetness? The Journal of Neuroscience, 25(50):11777-11786.
Pelletier, M. & Siegel, R. M. (2009). Wishing away inflammation? New links between serotonin and TNF signaling. Molecular Interventions, 9(6):299-301. https://doi.org/10.1124/mi.9.6.5.
Pennington, S. et al. (2010). The cause of death in idiopathic Parkinson's disease. Parkinsonism & Related Disorders, 16(7): 434-437. https://doi.org/10.1016/j.parkreldis.2010.04.010.
Perez-Carbonell, L. et al. (2020). Adherence to wakefulness promoting medication in patients with narcolepsy. Sleep Med. 70:50-54. https://doi.org/10.1016/j.sleep.2020.02.013.
Perini, G. I. et al. (1996). Interictal mood and personality disorders in temporal lobe epilepsy and juvenile myoclonic epilepsy. Journal of Neurology, Neurosurgery & Psychiatry, 61(6):601-605. https://doi.org/10.1136/jnnp.61.6.601.
Perlis, M.L. et al. (2001). Beta/Gamma EEG Activity in Patients with Primary and Secondary Insomnia and Good Sleeper Controls. Sleep, 24(1):110-117.

(56) References Cited

OTHER PUBLICATIONS

Persson, S. A. (1978). LSD and related drugs as DA antagonists: receptor-mediated effects on the synthesis and turnover of DA. Life Sciences, 23(5):523-526. https://doi.org/10.1016/0024-3205(78)90165-0.

Peters, E. et al. (2004) Measuring Delusional Ideation: the 21-item Peters et al. Delusions Inventory (PDI). Schizophrenia Bulletin, 30(4):1005-1022.

Piedmont, R.L. (1999) Does spirituality represent the sixth factor of personality? Spiritual transcendence and the five-factor model. Journal of Personality. 67:985-1013.

Piton, A. et al. (2011). Systematic resequencing of X-chromosome synaptic genes in autism spectrum disorder and schizophrenia. Molecular Psychiatry, 16(8):867-880. https://doi.org/10.1038/mp.2010.54.

Pittenger, C. et al. (2014). Pharmacological treatment of obsessive-compulsive disorder. In Psychiatric Clinics of North America, 37(3):375-391. https://doi.org/10.1016/j.psc.2014.05.006.

Polat, G. et al. (2017). Sepsis and Septic Shock: Current Treatment Strategies and New Approaches. Eurasian Journal of Medicine, 49(1):53-58. https://doi.org/10.5152/eurasianjmed.2017.17062.

Polito, V. & Stevenson, R.J. (2019) A systematic study of microdosing psychedelics. PLoS One. 14(2):e0211023, https://doi.org/10.1371/journal.pone.0211023, 26 pages.

Postal, M. et al. (2016). Depressive symptoms are associated with tumor necrosis factor alpha in systemic lupus erythematosus. Journal of Neuroinflammation, 13(1):5. https://doi.org/10.1186/s12974-015-0471-9, 7 pages.

Price, J. et al. (2012) The Oxford Questionnaire on the Emotional Side-effects of Antidepressants (OQuESA): Development, validity, reliability and sensitivity to change. Journal of Affective Disorders. 140:66-74.

Prince J. (2008) Catecholamine dysfunction in attention-deficit/hyperactivity disorder. An update. Journal of Clinical Psychopharmacology. 48(3 Suppl 2):39-45.

Prochazkova, L. et al. (2018). Exploring the effect of microdosing psychedelics on creativity in an open-label natural setting. Psychopharmacology, 235(12):3401-3413. https://doi.org/10.1007/s00213-018-5049-7.

Prosolv® SMCC. Retrieved from Web Archive, Reset https://web.archive.org/web/20160318071326/http://www.jrspharma.com/pharmaen/products-services/excipients/hfe/prosolvs-mcc.php Retrieved Mar. 18, 2016.

Pryor, T. et al. (1996). Clinical correlates of anorexia nervosa subtypes. The International Journal of Eating Disorders, 19(4):371-379. http://www.ncbi.nlm.nih.gov/pubmed/9156690.

Psilocybin for the Treatment of Cluster Headache. ClinicalTrials.gov [Internet]. Identifier: NCT02981173. Retrieved from: https://clinicaltrials.gov/ct2/show/NCT02981173, 8 pages.

Psilocybin Patent Tracker. Psilocybin Alpha, 2020 [online]. Retrieved from: https://psilocybinalpha.com/data/psilocybin-patent-tracker; retrieved on Oct. 1, 2020, 2 printed pages.

Pugazhenthi, S. et al. (2013). Induction of an Inflammatory Loop by Interleukin-1β and Tumor Necrosis Factor-α Involves NF-κB and STAT-1 in Differentiated Human Neuroprogenitor Cells. PLOS ONE, 8(7):1-12. https://doi.org/10.1371/journal.pone.0069585.

Pulikkan, J. et al. (2019). Role of the Gut Microbiome in Autism Spectrum Disorders. In Advances in Experimental Medicine and Biology, 1118:253-269. https://doi.org/10.1007/978-3-030-05542-4_13.

Quadri, S. et al. (2009). Improvement of idiopathic central sleep apnea with zolpidem. J. Clin. Sleep Med. 5:122-129. https://doi.org/10.5664/jcsm.27439.

Quan, Q. et al. (2019). CDK5 Participates in Amyloid-β Production by Regulating PPARγ Phosphorylation in Primary Rat Hippocampal Neurons. Journal of Alzheimer's Disease : JAD, 71(2):443-460. https://doi.org/10.3233/JAD-190026.

Quan, X. et al. (2020). Related Network and Differential Expression Analyses Identify Nuclear Genes and Pathways in the Hippocampus of Alzheimer Disease. Medical Science Monitor : International Medical Journal of Experimental and Clinical Research, 26:e919311, 11 pages. https://doi.org/10.12659/MSM.919311.

Quintero J. et al. (2010). Reboxetine for ADHD in children non-responders or with poor tolerance to methylphenidate: A prospective long-term open-label study. ADHD Atten Deficit Hyperact Disord., 2(3):107-113.

Raffaeli, W. & Arnaudo, E. (2017). Pain as a disease: An overview. J Pain Res., 10:2003-2008.

Rai, D. et al. (2012). Epilepsy and psychiatric comorbidity: A nationally representative population-based study. Epilepsia 53:1095-1103. https://doi.org/10.1111/j.1528-1167.2012.03500.x.

Ramachandran, V. et al. (2018). Relief from intractable phantom pain by combining psilocybin and mirror visual-feedback (MVF). Neurocase, 24(2):105-110. Available from: https://doi.org/10.1080/13554794.2018.1468469.

Ramadan, M.I. et al. (2006). Protect against drug-drug interactions with anxiolytics. Current Psychiatry, 5(5):16-28.

Ramos, A.A. et al. (2019). A meta-analysis on verbal working memory in children and adolescents with ADHD. Clinical Neuropsychologist, 34(5):873-898.

Rastam, M., et al. (2003). Outcome of teenage-onset anorexia nervosa in a Swedish community-based sample. European Child and Adolescent Psychiatry, 12(Suppl. 1):78-90. https://doi.org/10.1007/s00787-003-1111-y.

Rautiainen, M-R. et al. (2016) Genome-wide association study of antisocial personality disorder. Transl Psychiatry. 6:e883, doi:10.1038/tp.2016.155, 10 pages.

Raval et al., "Silicified Microcrystalline Cellulose as a Multifunctional Pharmaceutical Excipient," Drug Delivery Technology, 2009;9(4):28 and 30-32. Supplied by the British Library Oct. 12, 2019, 6 pages.

Ravindran, L.N. & Stein, M.B. (2010). The pharmacologic treatment of anxiety disorders: A review of progress. J. Clin. Psychiatry. 71(7):839-854. https://doi.org/10.4088/JCP.10r06218blu.

Reas, D. and Grilo, C. (Mar. 2014). Current and emerging drug treatments for binge eating disorder. Expert Opinion on Emerging Drugs, 19(1), pp. 99-142.

Reimherr, F.W. et al. (2017). ADHD and Anxiety: Clinical Significance and Treatment Implications. Curr. Psychiatry Rep., 19:109, 10 pages. https://doi.org/10.1007/s11920-017-0859-6.

Reitz, C. & Mayeux, R. (2014). Alzheimer disease: Epidemiology, diagnostic criteria, risk factors and biomarkers. Biochemical Pharmacology, 88(4):640-651. https://doi.org/10.1016/j.bcp.2013.12.024.

Remes, O. et al. (2016). A systematic review of reviews on the prevalence of anxiety disorders in adult populations. Brain Behav. https://doi.org/10.1002/brb3.497, 33 pages.

Repke et al., Psilocin Analogs. 1. Synthesis of 3-[2-(Dialkylamino)ethyl]- and 3-[2-(Cycloalkylamino)ethyl] indol-4-ols, J. Heterocyclic Chem., 14, 71 (1977), 4 pages.

Rickels, K. et al. (Sep. 2005). Pregabalin for treatment of generalized anxiety disorder: A 4-week, multicenter, double-blind, placebo-controlled trial of pregabalin and alprazolam. Arch. Gen. Psychiatry 62, 1022-1030. https://doi.org/10.1001/archpsyc.62.9.1022.

Riediger C. et al. (2017). Adverse effects of antidepressants for chronic pain: A systematic review and meta-analysis. Front. Neurol. 8:307, 23 pages. doi: 10.3389/fneur.2017.00307.

Rintala, H. et al. (2017). Register-based study of the incidence, comorbidities and demographics of obsessive-compulsive disorder in specialist healthcare. BMC Psychiatry, 17(1):64, 8 pages. https://doi.org/10.1186/s12888-017-1224-3.

Ripoll, L.H. et al. (2011) Evidence-based pharmacotherapy for personality disorders. 14:1257-1288.

Robbins, M.S. (2013) The psychiatric comorbidities of cluster headache. Curr Pain Headache Rep, 17(2):313, DOI:10.1007/s11916-012-0313-8, 8 pages.

Robner, A. et al. (2017). Cognitive Flexibility in Juvenile Anorexia Nervosa in Relation to Comorbid Symptoms of Depression, Obsessive Compulsive Symptoms and Duration of Illness. Zeitschrift für Kinder- und Jugendpsychiatrie und Psychotherapie, 45 (5):371-380. https://doi.org/10.1024/1422-4917/a000493.

(56) References Cited

OTHER PUBLICATIONS

Rodriguez, C. et al. (2016). Attention deficit/hyperactivity disorder (ADHD) diagnosis: An activation-executive model. Front. Psychol. 7:1406, 13 pages. doi: 10.3389/fpsyg.2016.01406.

Rojas, D.C. & Wilson, L.B. (2014). γ-band abnormalities as markers of autism spectrum disorders. Biomark Med. Mar. 2014; 8(3):353-368. doi:10.2217/bmm.14.15.

Rosen, E. et al. (2017). Hepatic Complications of Anorexia Nervosa. Dig Dis Sci, 62:2977-2981. doi:10.1007/s10620-017-4766-9.

Rosenberg, M. (1965) Society and the adolescent self-image. Science, 148(3671):804, DOI:10.1126/science.148.3671.804.

Rosenblat, J.D. et al. (2014). Inflamed moods: A review of the interactions between inflammation and mood disorders. Progress in Neuro-Psychopharmacology and Biological Psychiatry, 53:23-34. https://doi.org/10.1016/j.pnpbp.2014.01.013.

Ross, S. et al. (2016). Rapid and sustained symptom reduction following psilocybin treatment for anxiety and depression in patients with life-threatening cancer: A randomized controlled trial. J. Psychopharmacol. 30:1165-1180. https://doi.org/10.1177/0269881116675512.

Rossi, P. and Whelan, J. (2016) What is cluster headache? Fact sheet for patients and their families. A publication to mark Cluster Headache Day 2016. Functional Neurology. 31(3):181-183.

Roth, T. et al. (2007). Efficacy and safety of doxepin 1 mg, 3 mg, and 6 mg in adults with primary insomnia. Sleep 30, 1555-61. https://doi.org/10.1093/sleep/30.11.1555.

Roth, T. et al. (2007). Insomnia: Definition, prevalence, etiology, and consequences. J. Clin. Sleep Med. Supplement to vol. 3, No. 5, https://doi.org/10.5664/jcsm.26929.

Rucker, J. et al. (Dec. 25, 2017) "Psychiatry & the psychedelic drugs. Past, present & future", Neuropharmacol, 142:200-218.

Rucker, J. et al. (Dec. 2019) Psilocybin administration to healthy participants: safety and feasibility in a placebo-controlled study. Poster # W111, presented at the 58th Annual Meeting of the American College of Neuropsychopharmacology, Orlando, FL, USA, Dec. 8-11, 2019.

Ruffolo, S. et al. (2006). Comorbidity of body dysmorphic disorder and eating disorders: Severity of psychopathology and body image disturbance. International Journal of Eating Disorders, 39(1), pp. 11-19.

Rupprecht, R. et al. (2009). Translocator protein (18 kD) as target for anxiolytics without benzodiazepine-like side effects. Science, New Series, vol. 325, No. 5939, pp. 490-493. https://doi.org/10.1126/science.1175055.

Ruscio, A. M. et al. (2010). The epidemiology of obsessive-compulsive disorder in the National Comorbidity Survey Replication. Molecular Psychiatry, 15(1), 53-63. https://doi.org/10.1038/mp.2008.94.

Rush, A.J. et al. (2003) The 16-Item Quick Inventory of Depressive Symptomatology (QIDS), Clinician Rating (QIDS-C), and Self-Report (QIDS-SR): A Psychometric Evaluation in Patients with Chronic Major Depression. Biol Psy, 54(5):573-583.

Russell, E.J. et al. (2013). Risk of obsessive-compulsive disorder in pregnant and postpartum women: A meta-analysis. Journal of Clinical Psychiatry, 74(4), 377-385. https://doi.org/10.4088/JCP.12r07917.

Russo, A.J. (2014). Increased Epidermal Growth Factor Receptor (EGFR) Associated with Hepatocyte Growth Factor (HGF) and Symptom Severity in Children with Autism Spectrum Disorders (ASDs). Journal of Central Nervous System Disease. 6:79-83. https://doi.org/10.4137/jcnsd.s13767.

Ryder, S. & A, Stannard C.F. (2005). Treatment of chronic pain: Antidepressant, antiepileptic and antiarrhythmic drugs. Contin Educ Anaesthesia, Crit Care Pain. 5(1):18-21.

Rylander, M. et al. (2017). A comparison of the metabolic complications and hospital course of severe anorexia nervosa by binge-purge and restricting subtypes. Eating Disorders, 25(4), 345-357. https://doi.org/10.1080/10640266.2016.1269555.

Sagata, N. et al. (2017). Dysregulated gene expressions of MEX3D, FOS and BCL2 in human induced-neuronal (iN) cells from NF1 patients: A pilot study. Scientific Reports. https://doi.org/10.1038/s41598-017-14440-7.

Sahu, A. & Gupta, R. (2017). A study of psychiatric comorbidity after traumatic limb amputation: A neglected entity. Ind Psychiatry J. 26(6):228-32.

Sakashita, Y. et al. (2015). Effect of Psilocin on Extracellular Dopamine and Serotonin Levels in the Mesoaccumbens and Mesocortical Pathway in Awake Rats. Biol. Pharm. Bull. 38, 134-138 (2015).

Salama, R. M. et al. (2020). Neuroprotective effect of crocin against rotenone-induced Parkinson's disease in rats: Interplay between PI3K/Akt/mTOR signaling pathway and enhanced expression of miRNA-7 and miRNA-221. Neuropharmacology, 164, 107900., 12 pages. https://doi.org/10.1016/j.neuropharm.2019.107900.

Salisbury-Afshar, E. (2018). Management of Insomnia Disorder in Adults—Implementing AHRQ Effective Health Care Reviews. Am Fam Physician. 98(5), 5 pages. https://www.aafp.org/afp/2018/0901/p319.html#afp20180901p319-b4.

Sandbank, M. et al. (2020). Project AIM: Autism intervention meta-analysis for studies of young children. Psychological Bulletin. 146(1):1-29. https://doi.org/10.1037/bul0000215.

Sandiego, C.M. et al. (2015). Imaging robust microglial activation after lipopolysaccharide administration in humans with PET. Proceedings of the National Academy of Sciences, 112(40), 12468-12473. https://doi.org/10.1073/pnas.1511003112.

Santiago, J.A. et al. (2017). Biological and Clinical Implications of Comorbidities in Parkinson's Disease. Frontiers in Aging Neuroscience, 9, 16 pages. https://doi.org/10.3389/fnagi.2017.00394.

Santini, E. et al. (2013). Exaggerated translation causes synaptic and behavioural aberrations associated with autism. Nature, 493, https://doi.org/10.1038/nature11782, 6 pages.

Saraf, G. et al. (2017). Bipolar disorder comorbidity in patients with a primary diagnosis of OCD, International Journal of Psychiatry in Clinical Practice, 21:1, 70-74, doi: 10.1080/13651501.2016.1233344.

Saraiva, M., & O'Garra, A. (2010). The regulation of IL-10 production by immune cells. Nature Reviews Immunology, 10(3), 170-181. https://doi.org/10.1038/nri2711.

Sard, H. et al. (2005). SAR of psilocybin analogs: Discovery of a selective 5-HT2C agonist. Bioorganic and Medicinal Chemistry Letters, 15(20), 4555-4559. https://doi.org/10.1016/j.bmcl.2005.06.104.

Saunders, A.M. et al. (1993). Association of apolipoprotein E allele ε4 with late-onset familial and sporadic Alzheimer's disease. Neurology, 43(8):1467-1467. https://doi.org/10.1212/WNL.43.8.1467.

Savage, C. (1952) Lysergic Acid Diethylamide (LSD-25). A Clinical-Psychological Study. The American Journal of Psychiatry, 108:896-900.

Savioz, A., Leuba, G., & Vallet, P. G. (2014). A framework to understand the variations of PSD-95 expression in brain aging and in Alzheimer's disease. Ageing Research Reviews, 18, 86-94. https://doi.org/10.1016/j.arr.2014.09.004.

Saxton, R. A. & Sabatini, D.M. (Mar. 2017). mTOR Signaling in Growth, Metabolism, and Disease. Cell, 168(6):960-976. https://doi.org/10.1016/j.cell.2017.02.004.

Sayal, K. et al. (2018) ADHD in children and young people: prevalence, care pathways, and service provision. The Lancet Psychiatry, 5(2):175-186. Available from: http://dx.doi.org/10.1016/S2215-0366(17)30167-0cdc.gov.

Scammell, T.E. (2015) Narcolepsy. N. Engl. J. Med., 373:4654-2662. https://doi.org/10.1056/NEJMra1500587.

Schachter, M. & Parkes, J.D. (1980). Fluvoxamine and clomipramine in the treatment of cataplexy. Journal of Neurology, Neurosurgery, and Psychiatry, 43:171-174.

Scheller, J. et al. (2011). The pro- and anti-inflammatory properties of the cytokine interleukin-6. Biochimica et Biophysica Acta, 1813(5):878-888. https://doi.org/10.1016/j.bbamcr.2011.01.034.

Schneider, T. et al. (2008). Gender-specific behavioral and immunological alterations in an animal model of autism induced by prenatal exposure to valproic acid. Psychoneuroendocrinology, 33:728-740. https://doi.org/10.1016/j.psyneuen.2008.02.011.

(56) References Cited

OTHER PUBLICATIONS

Schulke, S. (2018). Induction of Interleukin-10 Producing Dendritic Cells as a Tool to Suppress Allergen-Specific T Helper 2 Responses. Frontiers in Immunology, 9:455, https://doi.org/10.3389/fimmu.2018.00455, 18 pages.

Schwalberg, M.D. et al. (1992). Comparison of Bulimics, Obese Binge Eaters, Social Phobics, and Individuals With Panic Disorder on Comorbidity Across DSM-III-R Anxiety Disorders. J. Abnorm. Psychol., 101:675-681. https://doi.org/10.1037/0021-843X.101.4.675.

Sedgwick, O. et al. (2017) Neuropsychology and emotion processing in violent individuals with antisocial personality disorder or schizophrenia: The same or different? A systematic review and meta-analysis. Australian and New Zealand Journal of Psychiatry, 51(12):1178-1197.

Sedley, W. & Cunningham, M.O. (2013). Do cortical gamma oscillations promote or suppress perception? An under-asked question with an over-assumed answer. Front. Hum. Neurosci., 7:595, https://doi.org/10.3389/fnhum.2013.00595, 17 pages.

Serrano-Pozo, A. et al. (2011). Neuropathological Alterations in Alzheimer Disease. Cold Spring Harbor Perspectives in Medicine, 1(1):a006189, https://doi.org/10.1101/cshperspect.a006189, 23 pages.

Sewell, R.A. et al. (Jun. 2006) "Response of cluster headache to psilocybin and LSD" Neurology, 66(12):1920-1922.

Shah, K., & Lahiri, D.K. (2014). Cdk5 activity in the brain—multiple paths of regulation. Journal of Cell Science, 127(11):2391-2400. https://doi.org/10.1242/jcs.147553.

Shannon, P. et al. (2003). Cytoscape: a software environment for integrated models of biomolecular interaction networks. Genome Research, 13(11):2498-2504. https://doi.org/10.1101/gr.1239303.

Sharma, S.R. et al. (2018). Autism Spectrum Disorder: Classification, diagnosis and therapy. Pharmacology and Therapeutics, 190:91-104. https://doi.org/10.1016/j.pharmthera.2018.05.007.

Sherman, E.M.S. et al. (2011). Neuropsychological outcomes after epilepsy surgery: Systematic review and pooled estimates. Epilepsia, 52(5):857-869. https://doi.org/10.1111/j.1528-1167.2011.03022.x.

Sherwood, A.M. et al. (2021) Psilocybin: crystal structure solutions enable phase analysis of prior art and recently patented examples. Acta Crystallographica, 78(1):1-20.

Shier, A.C. et al. (2013) Pharmacological Treatment of Attention Deficit Hyperactivity Disorder in Children and Adolescents: Clinical Strategies. J Cent Nerv Syst Dis, 5, doi: 10.4137/JCNSD.S6691, 17 pages.

Shirota et al. (Jun. 2003) "Concise large-scale synthesis of psilocin and psilocybin, principal hallucinogenic constituents of 'magic mushroom' " J Nat Prod, 66(6):885-887.

Shofty, B. et al. (Apr. 26, 2019). Loss of function in the autism and learning disabilities associated gene Nf1 disrupts corticocortical and corticostriatal functional connectivity in human and mouse. BioRxiv, preprint, https://doi.org/10.1101/618223, 35 pages.

Shoja Shafti, S., & Kaviani, H. (2015). Aripiprazole versus quetiapine in treatment-resistant obsessive-compulsive disorder: A double-blind clinical trial. Therapeutic Advances in Psychopharmacology, 5(1):32-37. https://doi.org/10.1177/2045125314560739.

Shulgin et al., "Tihkal: The Continuation," Transform Press, 1997, pp. 468-473.

Sid-Otmane, L. et al. (2020). Selective metabotropic glutamate receptor 2 positive allosteric modulation alleviates L-DOPA-induced psychosis-like behaviours and dyskinesia in the MPTP-lesioned marmoset. European Journal of Pharmacology, 873:172957, https://doi.org/10.1016/j.ejphar.2020.172957, 6 pages.

Siervo, M. et al. (Jun. 2005). Application of the SCOFF, Eating Attitude Test 26 (EAT 26) and Eating Inventory (TFEQ) questionnaires in young women seeking diet-therapy. Eating and Weight Disorders, 10(2):76-82. https://doi.org/10.1007/BF03327528.

Silber, M.H. et al. (2002) The epidemiology of narcolepsy in Olmsted County, Minnesota: A population-based study. Sleep, 25(2):197-202. https://doi.org/10.1093/sleep/25.2.197.

Silva, N. et al. (2014) Searching for a neurobiological basis for self-medication theory in ADHD comorbid with substance use disorders: An in vivo study of dopamine transporters using $^{99m}$Tc-TRODAT-1 SPECT. Clin Nucl Med, 39(2):e129-e134.

Simon, N.M. (2009) Generalized Anxiety Disorder and Psychiatric Comorbidities Such as Depression, Bipolar Disorder, and Substance Abuse. J Clin Psychiatry, 70(suppl 2):10-14.

Singh, A., & Trevick, S. (2016). The Epidemiology of Global Epilepsy. Neurologic Clinics, 34(4):837-847. https://doi.org/10.1016/j.ncl.2016.06.015.

Siniscalco, D. et al. (Jun. 2018). Inflammation and neuro-immune dysregulations in autism spectrum disorders. Pharmaceuticals, 11:56, https://doi.org/10.3390/ph11020056, 14 pages.

Skapinakis, P. et al. (2016) "Pharmacological and psychotherapeutic interventions for management of obsessive-compulsive disorder in adults: a systematic review and network meta-analysis" The Lancet Psychiatry, 3(8):730-739. https://doi.org/10.1016/S2215-0366(16)30069-4.

Smith, B.W. et al. (2008) The Brief Resilience Scale: Assessing the Ability to Bounce Back. International Journal of Behavioral Medicine. 15:194-200.

Smith, K.N. et al. (2019). Changes in meal-related anxiety predict treatment outcomes in an intensive family-based treatment program for adolescents with anorexia nervosa. Eating Disorders, DOI: 10.1080/10640266.2019.1688008, 13 pages.

Snaith, R.P. et al. (1995) A scale for the assessment of hedonic tone. The Snaith-Hamilton Pleasure Scale. The British Journal of Psychiatry, 167:99-103.

Soler, J. et al. (2018). Genetic variability in scaffolding proteins and risk for schizophrenia and autism-spectrum disorders: A systematic review. Journal of Psychiatry and Neuroscience, 43(4):223-244. https://doi.org/10.1503/jpn.170066.

Souery, D. et al. (2007). Clinical Factors Associated With Treatment Resistance in Major Depressive Disorder: Results From a European Multicenter Study. The Journal of Clinical Psychiatry, 68(07):1062-1070. https://doi.org/10.4088/JCP.v68n0713.

Spangler, E.L., Rigby, P., & Ingram, D.K. (1986). Scopolamine impairs learning performance of rats in a 14-unit T-maze. Pharmacology, Biochemistry and Behavior, 25:673-679. https://doi.org/10.1016/0091-3057(86)90158-9.

Spielberger, C.D. (2020) State-Trait Anxiety Inventory for AdultsTM. STAI—Adult Manual. Mind Garden Inc., www.mindgarden.com, 87 pages.

Spowart-Manning L. et al. (May 2004) The T-maze continuous alternation task for assessing the effects of putative cognition enhancers in the mouse. Behav Brain Res, 151(1-2):37-46.

Srinivas, H.V. & Shah, U. (2017). Comorbidities of epilepsy. Neurology India, 65(Supplement):S18-S24. https://doi.org/10.4103/neuroindia.NI_922_16, 15 pages.

Srivastava, R.K. et al. (2011). Role of Donepezil in Autism: Its Conduciveness in Psychopharmacotherapy. Case Reports in Psychiatry, 2011:563204, https://doi.org/10.1155/2011/563204, 2 pages.

Stahl, S.M. (1998) Mechanism of action of serotonin selective reuptake inhibitors. Serotonin receptors and pathways mediate therapeutic effects and side effects. J. Affect. Disord., 51:215-235. https://doi.org/10.1016/S0165-0327(98)00221-3.

Stancil, S. et al. (2019). Naltrexone Reduces Binge Eating and Purging in Adolescents in an Eating Disorder Program. Journal of Child and Adolescent Psychopharmacology, 29(9):721-724.

Stancu, C., & Sima, A. (2001). Statins: mechanism of action and effects. Journal of Cellular and Molecular Medicine, 5(4), 378-387. https://doi.org/10.1111/j.1582-4934.2001.tb00172.x.

Starr, M.S. (1996). The role of dopamine in epilepsy. Synapse. 22:159-194.

Stefano, S. et al. (2008). Antidepressants in short-term treatment of binge eating disorder: Systematic review and meta-analysis. Eating Behaviors, 9(2), pp. 129-136.

Steger, M.F. et al. (2008) Understanding the search for meaning in life: Personality, cognitive style, and the dynamic between seeking and experiencing meaning. Journal of Personality, 76:199-228.

Stein, D.J. et al. (2017). Epidemiology of anxiety disorders: From surveys to nosology and back. Dialogues Clin Neurosci, 19:127-135.

(56) References Cited

OTHER PUBLICATIONS

Stein, D.J. et al. (2019) "Obsessive-compulsive disorder" Nature Reviews Disease Primers, 5(1):52; doi: 10.1038/s41572-019-0102-3, 21 pages.
Stein, M.B. & Sareen, J. (2015). Generalized anxiety disorder. N. Engl. J. Med., 373:2059-2068. https://doi.org/10.1056/NEJMcp1502514.
Steinhausen, H-C. (2009). Outcome of Eating Disorders. Child and Adolescent Psychiatric Clinics of North America, 18(Issue 1):225-242. https://doi.org/10.1016/j.chc.2008.07.013.
Stevenson, R.A. et al. (2019). Conjunctive visual processing appears abnormal in Autism. Frontiers in Psychology, 9:2668, https://doi.org/10.3389/fpsyg.2018.02668, 7 pages.
Stice, L. V., & Lavner, J. A. (2019). Social Connectedness and Loneliness Mediate the Association Between Autistic Traits and Internalizing Symptoms Among Young Adults. Journal of Autism and Developmental Disorders, 49(3), 1096-1110. https://doi.org/10.1007/s10803-018-3812-6.
Sticht, G., & Kaferstein, H. (2000). Detection of psilocin in body fluids. Forensic Science International, 113(1-3):403-407. https://doi.org/10.1016/S0379-0738(00)00213-9.
Stojanovic, A. et al. (2014). Increased serum interleukin-6 levels in early stages of psychosis: Associations with at-risk mental states and the severity of psychotic symptoms. Psychoneuroendocrinology, 41, 23-32. https://doi.org/10.1016/j.psyneuen.2013.12.005.
Strawbridge, R. et al. (2019). Inflammatory profiles of severe treatment-resistant depression. Journal of Affective Disorders, 246:42-51. https://doi.org/10.1016/j.jad.2018.12.037.
Strunk, D.R. et al. (2006) Depressive symptoms are associated with unrealistic negative predictions of future life events. Behavior Research and Therapy, 44:861-882.
Studerus, E. et al. (2010) Psychometric evaluation of the altered states of consciousness rating scale (OAV). PLoS One, 5:e12412, 19 pages.
Studerus, E. et al. (2011) "Acute, subacute and long-term subjective effects of psilocybin in healthy humans: a pooled analysis of experimental studies" J Psychopharmacol, 25(11):1434-1452.
Su, H., Lei, C.-T., & Zhang, C. (Apr. 2017). Interleukin-6 Signaling Pathway and Its Role in Kidney Disease: An Update. Frontiers in Immunology, 8:405, https://doi.org/10.3389/fimmu.2017.00405, 10 pages.
Subedi, B. & Grossberg, G.T. (2011) Phantom limb pain: Mechanisms and treatment approaches. Pain Res Treat, 2011:864605, doi:10.155/2011/864605, 8 pages.
Substance Abuse and Mental Health Services Administration. (Jun. 2016) Table 3.35, DSM-IV to DSM-5 Hypersomnolence Disorder Comparison. In: Impact of the DSM-IV to DSM-5 Changes on the National Survey on Drug Use and Health [Internet]. Rockville (MD): Substance Abuse and Mental Health Services Administration (US). Retrieved from NCBI Bookshelf, https://www.ncbi.nlm.nih.gov/books/NBK519704/table/ch3 .t35/, on Jul. 30, 2020, 3 printed pages.
Suda, S. et al. (2011). Decreased expression of axon-guidance receptors in the anterior cingulate cortex in autism. Molecular Autism, 2:14, https://doi.org/10.1186/2040-2392-2-14, 5 pages.
Suto, F. et al. (2005). Plexin-A4 mediates axon-repulsive activities of both secreted and transmembrane semaphorins and plays roles in nerve fiber guidance. Journal of Neuroscience, 25(14):3628-3637. https://doi.org/10.1523/JNEUROSCI.4480-04.2005.
Swieboda, P. et al. (2013) Assessment of pain: types, mechanism and treatment. Ann Agric Environ Med, 1(1):2-7.
Sztainberg, Y. & Zoghbi, H. Y. (2016). Lessons learned from studying syndromic autism spectrum disorders. Nature Neuroscience, 19(11):1408-1418. https://doi.org/10.1038/nn.4420.
Tai, J. et al. (2018). Neuroprotective effects of a triple GLP-1/GIP/glucagon receptor agonist in the APP/PS1 transgenic mouse model of Alzheimer's disease. Brain Research, 1678:64-74. https://doi.org/10.1016/j.brainres.2017.10.012.
Takamori, S. (Feb. 2016). Presynaptic Molecular Determinants of Quantal Size. Frontiers in Synaptic Neuroscience, 8:2, https://doi.org/10.3389/fnsyn.2016.00002, 9 pages.
Tan, L.L. et al. (2019). Gamma oscillations in somatosensory cortex recruit prefrontal and descending serotonergic pathways in aversion and nociception. Nat. Commun. 10:983, https://doi.org/10.1038/s41467-019-08873-z, 17 pages.
Tan, T. et al. (2018). Low-frequency rTMS ameliorates autistic-like behaviors in rats induced by neonatal isolation through regulating the synaptic GABA transmission. Frontiers in Cellular Neuroscience, 12:Article 46, https://doi.org/10.3389/fncel.2018.00046, 12 pages.
Tanaka, T. et al. (2014). IL-6 in Inflammation, Immunity, and Disease. Cold Spring Harbor Perspectives in Biology, 6(10):a016295, https://doi.org/10.1101/cshperspect.a016295, 16 pages.
Tarpey, P. et al. (2004). Mutations in the DLG3 gene cause nonsyndromic X-linked mental retardation. American Journal of Human Genetics, 75:318-324. https://doi.org/10.1086/422703.
Tatsumi, M. et al. (1997). Pharmacological profile of antidepressants and related compounds at human monoamine transporters. Eur. J. Pharmacol., 340, 249-258. https://doi.org/10.1016/S0014-2999(97)01393-9.
Taylor, J.F. et al. (1994) Self-Report Assessment of Female Sexual Function: Psychometrie Evaluation of the Brief Index of Sexual Functioning for Women. Archives of Sexual Behavior. 23(6):627-643.
Tecott, L. et al. (1995). Eating disorder and epilepsy in mice lacking 5-HT2C serotonin receptors. Nature, 374(6522), pp. 542-546.
Tellegen, A. and Atkinson, G. (1974) Openness To Absorbing and Self-Altering Experiences ("Absorption"), a Trait Relatedto Hypnotic Susceptibility. Journal of Abnormal Psychology, 83:268-277.
Tennant, R. et al. (2007) The Warrwick-Edinburgh Mental Well-being Scale (WEMWBS): development and the UK validation. Health and Quality of Life Outcomes, 5:63 doi:10.1186/1477-7525-5-63, 14 pages.
Terrando, N. et al. (2010). Tumor necrosis factor-a triggers a cytokine cascade yielding postoperative cognitive decline. Proceedings of the National Academy of Sciences, 107(47):20518-20522. https://doi.org/10.1073/pnas.1014557107.
Thamby, A., & Jaisoorya, T. S. (2019) "Antipsychotic augmentation in the treatment of obsessive-compulsive disorder" Indian Journal of Psychiatry, 61(7):S51-S57. https://doi.org/10.4103/psychiatry.IndianJPsychiatry_519_18.
Thapar, A. et al. (2005). Do depression symptoms predict seizure frequency—or vice versa? Journal of Psychosomatic Research, 59(5):269-274. https://doi.org/10.1016/j.jpsychores.2005.04.001.
Thase, M.E. (1999). Antidepressant treatment of the depressed patient with insomnia. Journal of Clinical Psychiatry, 60(suppl. 17):28-31.
Thomas, A. et al. (2009) "Marble burying reflects a repetitive and perseverative behavior more than novelty-induced anxiety" Psychopharmacology, 204(2):361-373. NIH Public Access Author Manuscript, available in PMC Jul. 8, 2010, 22 pages.
Tokudome, K. et al. (2016). Synaptic vesicle glycoprotein 2A (SV2A) regulates kindling epileptogenesis via GABAergic neurotransmission. Scientific Reports, 6(1):27420. https://doi.org/10.1038/srep27420, 12 pages.
Tolba, R. et al. (2018) The opioid epidemic and pain medicine specialists: Where to begin and what is next? Ochsner J, 18(1):20-22.
Toronto Research Chemicals; Certificate of Analysis; Product available for sale (Catalog No. P839650); Test Date: Apr. 5, 2013.
Torres, A.R. et al. (2006) "Obsessive-compulsive disorder: Prevalence, Comorbidity, impact, and help-seeking in the British National Psychiatric Morbidity Survey of 2000" American Journal of Psychiatry, 163(11):1978-1985. https://doi.org/10.1176/ajp.2006.163.11.1978.
Tramutola, A. et al. (2015). Alteration of mTOR signaling occurs early in the progression of Alzheimer disease (AD): analysis of brain from subjects with pre-clinical AD, amnestic mild cognitive impairment and late-stage AD. Journal of Neurochemistry, 133(5), 739-749. https://doi.org/10.1111/jnc.13037.

(56) References Cited

OTHER PUBLICATIONS

Treynor, W. et al. (Jun. 2003) Rumination Reconsidered: A Psychometric Analysis. Cognitive Therapy and Research, 27:247-259.
Trulson, M. E., Stark, A. D., & Jacobs, B. L. (1977). Comparative effects of hallucinogenic drugs on rotational behavior in rats with unilateral 6-hydroxydopamine lesions. European Journal of Pharmacology, 44(2), 113-119. https://doi.org/10.1016/0014-2999(77)90097-8.
Trunko, M.E. et al. (2011). Aripiprazole in anorexia nervosa and low-weight bulimia nervosa: Case reports. International Journal of Eating Disorders, 44(3):269-275. https://doi.org/10.1002/eat.20807.
Tsai, S.-J. (2017). Effects of interleukin-1beta polymorphisms on brain function and behavior in healthy and psychiatric disease conditions. Cytokine & Growth Factor Reviews, 37:89-97. https://doi.org/10.1016/j.cytogfr.2017.06.001.
Tucha, L. et al. (2017) Sustained attention in adult ADHD: time-on-task effects of various measures of attention. J Neural Transm, 124(Suppl. 1):S39-S53.
Tully, P.J. et al. (2014). The anxious heart in whose mind? A systematic review and meta-regression of factors associated with anxiety disorder diagnosis, treatment and morbidity risk in coronary heart disease. J. Psychosom. Res., 77:439-448. https://doi.org/10.1016/j.jpsychores.2014.10.001.
Tully, P.J. et al. (2016). Anxiety and Cardiovascular Disease Risk: a Review. Curr. Cardiol. Rep., 18:120, https://doi.org/10.1007/s11886-016-0800-3, 8 pages.
Tumolo, J. (Sep. 2018) "Uncovering the Therapeutic Potential of Psychedelics" Retrieved from Psychiatry & Behavioral Health Learning Network [online]. Retrieved from: https://www.hmpgloballearningnetwork.com/site/pcn/article/uncovering-therapeutic-potential-psychedelics, 8 pages.
Tyrer, P. and Baldwin, D. (2006). Generalised anxiety disorder. Lancet, 368:2156-2166. https://doi.org/10.1016/S0140-6736(06)69865-6.
Ulfvebrand, S. et al. (2015). Psychiatric comorbidity in women and men with eating disorders results from a large clinical database. Psychiatry Research, 230(2), 294-299. https://doi.org/10.1016/j.psychres.2015.09.008.
United Kingdom Office Action for Application GB2012911.0, dated Jan. 11, 2022, 3 pages.
United Kingdom Patent Application GB1816438.4: Examination Report, dated Jan. 10, 2022, 1 page.
United Kingdom Patent Application GB1816438.4: Search Report, dated Dec. 2, 2019, 7 pages.
United Kingdom Patent Application GB2012911.0: Search and Examination Report, dated Feb. 18, 2021, 4 pages.
United Kingdom Patent Application GB2012914.4: Search and Examination Report, dated Feb. 18, 2021, 6 pages.
United Kingdom Patent Application GB2012914.4: Examination Report, dated Jan. 11, 2022, 1 page.
United Kingdom Patent GB 2527023 (GB1810588.2): Examination Report, dated Nov. 18, 2019, 2 pages.
United Kingdom Patent GB 2527023 (GB1810588.2): Request for Opinion—Statement in Reply with Supplemental Statement of Truth, dated Jun. 24, 2021, 9 pages.
United Kingdom Patent GB 2527023 (GB1810588.2): Search Report, dated Aug. 21, 2018, 9 pages.
United Kingdom Patent GB 2527023 (GB1810588.2): Third Party Observations, dated Jan. 23, 2020, 13 pages.
United Kingdom Patent GB 2527023 (GB1810588.2): Opinion Under Section 74A, dated Jul. 28, 2021, including Letters to Proprietor and Requester; 17 pages.
United Kingdom Patent GB 2527023 (GB1810588.2): Third Party Request for Opinion dated Aug. 27, 2020, with Statement of Truth; 12 pages.
United Kingdom Patent GB 2571696 (GB1716505.1): Decision on Request for Opinion filed Jun. 11, 2020, by Kohn & Associates; Apr. 27, 2021, 14 pages.
United Kingdom Patent GB2571696 (GB1716505.1): Examination Report, dated Nov. 18, 2019, 2 pages.
United Kingdom Patent GB2571696 (GB1716505.1): Search Report, dated Dec. 19, 2017, 10 pages.
United Kingdom Patent GB2571696 (GB1716505.1): Search Report, dated Jan. 25, 2018, 2 pages.
United Kingdom Patent GB2571696 (GB1716505.1): Third Party Observations, Jan. 24, 2020, 10 pages.
Unruh, K. E., Bodfish, J. W., & Gotham, K. O. (2018). Adults with Autism and Adults with Depression Show Similar Attentional Biases to Social-Affective Images. Journal of Autism and Developmental Disorders, 50:2336-2347. https://doi.org/10.1007/s10803-018-3627-5.
U.S. Appl. No. 16/155,386: Third Party Observations with Concise Description of Relevance, filed Jul. 26, 2019, 22 pages.
U.S. Appl. No. 16/155,386: Third Party Observations with Concise Description of Relevance, filed May 23, 2019, 27 pages.
U.S. Appl. No. 16/155,386: Third Party Observations with Concise Description of Relevance, filed May 28, 2019, 31 pages.
U.S. Appl. No. 17/604,610: Third Party Pre-Issuance Submission Under 37 C.F.R. 1.290 with Concise Description of Relevance, filed Mar. 9, 2022, 128 pages.
Uyeno, E.T. (1967). Effects of mescaline and psilocybin on dominance behavior of the rat. Archives Internationales de Pharmacodynamie et de Therapie, 166(1), 60-64. http://www.ncbi.nlm.nih.gov/pubmed/6034329.
Valbrun, L. and Zvonarev, V. (2020). The Opioid System and Food Intake: Use of Opiate Antagonists in Treatment of Binge Eating Disorder and Abnormal Eating Behavior. Journal of Clinical Medicine Research, 12(2), pp. 41-63.
Van Ameringen, M. et al. (2014) "DSM-5 obsessive-compulsive and related disorders: Clinical implications of new criteria" Depression and Anxiety, 31(6):487-493. https://doi.org/10.1002/da.22259.
Van Den Beuken-Van Everdingen, M.H.J. et al. (Jun. 2006) Update on Prevalence of Pain in Patients with Cancer: Systematic Review and Meta-Analysis. Journal of Pain and Symptom Management. 51(6):1070-1090, with Appendix I, 1090:e1-e9.
Van Hecke, A.V. et al. (2013). Measuring the Plasticity of Social Approach: A Randomized Controlled Trial of the Effects of the PEERS Intervention on EEG Asymmetry in Adolescents with Autism Spectrum Disorders. J. Autism Dev. Disord., 45(2):316-335. https://doi.org/10.1007/s10803-013-1883-y.
Van Spijker, B.A.J. et al. (2014) The Suicidal Ideation Attributes Scale (SIDAS): Community-Based Validation Study of a New Scale for the Measurement of Suicidal Ideation. Suicide and Life-Threatening Behavior, 44(4):408-419.
Varga, Z. et al. (2017). Cardiovascular Risk of Nonsteroidal Anti-Inflammatory Drugs: An Under-Recognized Public Health Issue. Cureus, 9(4):e1144, https://doi.org/10.7759/cureus.1144, 12 pages.
Vaupel, D. et al. (1979). The inhibition of food intake in the dog by LSD, mescaline, psilocin, -amphetamine and phenylisopropylamine derivatives. Life Sciences, 24(26), pp. 2427-2431.
Veale, D. et al. (2014) "Atypical antipsychotic augmentation in SSRI treatment refractory obsessive-compulsive disorder: A systematic review and meta-analysis" BMC Psychiatry, 14(1):317, https://doi.org/10.1186/s12888-014-0317-5, 13 pages.
Velikonja, T., Fett, A. K., & Velthorst, E. (2019). Patterns of Nonsocial and Social Cognitive Functioning in Adults with Autism Spectrum Disorder: A Systematic Review and Meta-analysis. JAMA Psychiatry, 76(2):135-151. https://doi.org/10.1001/jamapsychiatry.2018.3645.
Venlafaxine Hydrochloride (Sep. 23, 2020). Drugs.com (online). Retrieved from: https://www.drugs.com/monograph/venlafaxine-hydrochloride.html, 19 printed pages.
Verbeeck, W. et al. (2017). Bupropion for attention deficit hyperactivity disorder (ADHD) in adults. Cochrane Database of Systematic Reviews, 2017, Issue 10, Art. No. CD009504, DOI: 10.1002/14651858.CD009504.pub2, 58 pages.
Vinik, A. et al. Diabetic Neuropathies. Table 7, Drugs Approved by the FDA for Treatment of Neuropathic Pain Syndromes. [Updated Feb. 5, 2018]. In: Feingold, K.R., Anawalt, B., Boyce, A. et al., editors. Endotext [Internet]. South Dartmouth (MA): MDText.com, Inc.; 2000-. Retrieved from: https://www.ncbi.nlm.nih.gov/books/NBK279175/table/diab-neuropathies.medication/, retrieved on Jul. 30, 2020, 2 printed pages.

(56) References Cited

OTHER PUBLICATIONS

Volkow, N.D. et al. (Aug. 2007) Depressed dopamine activity in caudate and preliminary evidence of limbic involvement in adults with attention-deficit/hyperactivity disorder. Arch Gen Psychiatry, 64(8):932-940.
Volkow, N.D. et al. (Feb. 1, 2007) Brain dopamine transporter levels in treatment and drug naïve adults with ADHD. Neuroimage [Internet]. 34(3):1182-90. Available from: http://www.ncbi.nlm.nih.gov/pubmed/17126039.
Vollenweider, F. (1998) Advances and Pathophysiological Models of Hallucinogenic Drug Actions in Humans: A Preamble to Schizophrenia Research. Pharmacopsychiatry, 31(Suppl):92-103. https://doi.org/10.1055/s-2007-979353.
Vollenweider, F.X. et al. (1999). 5-HT modulation of dopamine release in basal ganglia in psilocybin-induced psychosis in man—a PET study with [$^{11}$C]raclopride. Neuropsychopharmacology, 20(5):424-433. https://doi.org/10.1016/S0893-133X(98)00108-0.
Vollenweider, F.X. et al. (Sep. 2007) The effects of the preferential 5-HT2A agonist psilocybin on prepulse inhibition of startle in healthy human volunteers depend on interstimulus interval. Neuropsychopharmacology, 32(9):1876-1887.
Von Bernhardi, R. et al. (Oct. 28, 2015). Role of TGFβ signaling in the pathogenesis of Alzheimer's disease. Frontiers in Cellular Neuroscience, 9:426, https://doi.org/10.3389/fncel.2015.00426, 21 pages.
Voon, P. et al. (2017). Chronic pain and opioid misuse: a review of reviews. Substance Abuse Treatment, Prevention and Policy, 12:36, DOI 10.1186/s13011-017-0120-7, 9 pages.
Vossler, D.G. (2016). Antiepileptic drugs. Are generics as effective as brand name? Neurology, 87(17):e211-e214. https://doi.org/10.1212/WNL.0000000000003323.
Wade, A.G. et al. (2011). Prolonged release melatonin in the treatment of primary insomnia: Evaluation of the age cut-off for short- and long-term response. Curr. Med. Res. Opin., 27:87-98. https://doi.org/10.1185/03007995.2010.537317.
Wagner, J. and Wagner, M.L. (2000). Non-benzodiazepines for the treatment of insomnia. Sleep Med. Rev., 4(6):551-581. https://doi.org/10.1053/smrv.2000.0126.
Wahlberg (2015) "UW-Madison tunes in to 'magic mushroom' medicine" Oct. 11, 2015; retrieved from Web Archive, https://web.archive.org/web/20181214181711/https://madison.com/wsi/news/local/health-med-fit/uw-madison-tunes-in-to-magic-mushroom-medicine/article5c229322-1 132-5328-90cl-017e917f0696.html, retrieved Dec. 14, 2018.
Walia, K.S. et al. (2004) Side Effects of Antiepileptics—A Review. Pain Pract, (3):194-203.
Walsh, B.T. et al. (2006). Fluoxetine after weight restoration in anorexia nervosa: A randomized controlled trial. Journal of the American Medical Association, 295(22):2605-2612. https://doi.org/10.1001/jama.295.22.2605.
Wang, G. et al. (2017). Resveratrol mitigates lipopolysaccharide-mediated acute inflammation in rats by inhibiting the TLR4/NF-KBp65/MAPKs signaling cascade. Scientific Reports, 7:45006, https://doi.org/10.1038/srep45006, 13 pages.
Wang, J. et al. (2016). Enhanced Gamma oscillatory activity in rats with chronic inflammatory pain. Front. Neurosci. 10:489, https://doi.org/10.3389/fnins.2016.00489, 8 pages.
Wang, L. et al. (2003). IL-6 Induces NF-κB Activation in the Intestinal Epithelia. The Journal of Immunology, 171(6):3194-3201. https://doi.org/10.4049/jimmunol.171.6.3194.
Wang, Q. et al. (2018). CDK5-Mediated Phosphorylation-Dependent Ubiquitination and Degradation of E3 Ubiquitin Ligases GP78 Accelerates Neuronal Death in Parkinson's Disease. Molecular Neurobiology, 55(5):3709-3717. https://doi.org/10.1007/s12035-017-0579-2.
Wang, X. et al. (2018). Gastrodin Rescues Autistic-Like Phenotypes in Valproic Acid-Induced Animal Model. Frontiers in Neurology, 9:1052, https://doi.org/10.3389/fneur.2018.01052, 10 pages.
Wang, Z.-J. et al. (2020). A dual GLP-1 and Gcg receptor agonist rescues spatial memory and synaptic plasticity in APP/PS1 transgenic mice. Hormones and Behavior, 118:104640. https://doi.org/10.1016/j.yhbeh.2019.104640, 9 pages.
Washburn, J.J. et al. (Apr. 2007) Development of Antisocial Personality Disorder in Detained Youth: The Predictive Value of Mental Disorders. J Consult Clin Psychol, 75(2):221-231. NIH Public Access Author Manuscript, 20 pages.
Watson, J. et al. (Jul. 2019). Use of multiple inflammatory marker tests in primary care: using Clinical Practice Research Datalink to evaluate accuracy. British Journal of General Practice, 69(684), e462-e469. https://doi.org/10.3399/bjgp19X704309.
Weber, A. et al. (2010). Interleukin-1 (IL-1) Pathway. Science Signaling, 3(105):cm1, https://doi.org/10.1126/scisignal.3105cm1, 7 pages.
Weber et al. (1974) "Crystal structures of the teonanacatl hallucinogens. Part 1. Psilocybin C12HI7N204P" J Chem Soc, Perkin Trans, 2:942-946.
Wegner, D.M. and Zanakos, S. (1994) Chronic Thought Suppression. Journal of Personality, 62:615-640.
Wei, D. Y-T. et al. (2018) Cluster headache: Epidemiology, pathophysiology, clinical features, and diagnosis. Annals of Indian Academy of Neurology, 21(5):3-8.
Weissman, A.N. (1979) The Dysfunctional Attitude Scale: A validation study. [Dissertation in Education, Doctor of Philosophy]. University of Pennsylvania. Publicly Accessible Penn Dissertations. 1182. https://repository.upenn.edu/edissertations/1185, 209 pages.
Welch, E. et al. (2016). Treatment-seeking patients with binge-eating disorder in the Swedish national registers: clinical course and psychiatric comorbidity. BMC Psychiatry, 16:163, doi:10.1186/s12888-016-0840-7, 8 pages.
Werner, K.B. et al. (Apr. 2015) Epidemiology, comorbidity, and behavioral genetics of antisocial personality disorder and psychopathy. Psychiatr Ann. 45(4):195-199. HHS Public Access Author Manuscript, 8 pages.
Westmoreland, P. et al. (2016). Medical Complications of Anorexia Nervosa and Bulimia. The American Journal of Medicine, 129:30-37.
White, H. K., & Levin, E. D. (1999). Four-week nicotine skin patch treatment effects on cognitive performance in Alzheimer's disease. Psychopharmacology, 143(2):158-165. https://doi.org/10.1007/s002130050931.
Whitfield, D.R. et al. (2014). Assessment of ZnT3 and PSD95 protein levels in Lewy body dementias and Alzheimer's disease: association with cognitive impairment. Neurobiology of Aging, 35(12):2836-2844. https://doi.org/10.1016/j.neurobiolaging.2014.06.015.
Whyatt, C., & Craig, C. (Jul. 18, 2013). Sensory-motor problems in autism. Frontiers in Integrative Neuroscience. 7:51, https://doi.org/10.3389/fnint.2013.00051, 12 pages.
Wiedemann, K. et al. (2001). Anxiolyticlike effects of atrial natriuretic peptide on cholecystokinin tetrapeptide-induced panic attacks. Preliminary findings. Archives of General Psychiatry, 58:371-377. https://doi.org/10.1001/archpsyc.58.4.371.
Wilcox, J.A. (2014) "Psilocybin and obsessive compulsive disorder" Journal of Psychoactive Drugs, 46(5):393-395: DOI: 10.1080/02791072.2014.963754.
Wilens, T.E. et al. (Oct. 2011) An update on the pharmacotherapy of attention-deficit/hyperactivity disorder in adults. Expert Rev Neurother, 11(10):1443-1465. NIH Public Access Author Manuscript; available in PMC Aug. 1, 2012, 34 pages.
Williams, J.M.G. et al. (1986) Autobiographical Memory in Suicide Attempters. Journal of Abnormal Psychology, 95:144-149.
Williams, K. et al. (2013). Selective serotonin reuptake inhibitors (SSRIs) for autism spectrum disorders (ASD). Cochrane Database of Systematic Reviews, 8:CD004677, https://doi.org/10.1002/14651858.CD004677.pub3, 46 pages.
Willoughby, J.O. et al. (2003). Persistent abnormality detected in the non-ictal electroencephalogram in primary generalised epilepsy. J. Neurol. Neurosurg. Psychiatry, 74:51-55. https://doi.org/10.1136/jnnp.74.1.51.
Wilson, S. et al. (Jul. 2017) Interpersonal dysfunction in personality disorders: A meta-analytic review. Psychol Bull, 143(7):677-734. HHS Public Access Author Manuscript, 120 pages.

(56) References Cited

OTHER PUBLICATIONS

Wingo A, Ghaemi S. (2007) A systematic review of rates and diagnostic validity of comorbid adult attention-deficit/hyperactivity disorder and bipolar disorder. J Clin Psychiatry, 68(11):1775-1784.
Winkelman, J.W. et al. (2011). Randomized polysomnography study of gabapentin enacarbil in subjects with restless legs syndrome. Mov. Disord., 26:2065-2072. https://doi.org/10.1002/mds.23771.
Winter, J.C. et al. (2007). Psilocybin-induced stimulus control in the rat. Pharmacology Biochemistry and Behavior, 87(4):472-480. NIH Public Access Author Manuscript; available in PMC Oct. 3, 2007, 18 pages.
Witkin, J.M. (2008) "Animal models of obsessive-compulsive disorder" Current Protocols in Neuroscience. 45:9.30.1-9.30.9. DOI: 10.1002/0471142301.ns0930s45.
Wong, M. et al. (2008). TNFα blockade in human diseases: Mechanisms and future directions. Clinical Immunology, 126(2):121-136. https://doi.org/10.1016/j.clim.2007.08.013.
World Health Organization (WHO) (2015). International statistical classification of diseases and related health problems (ICD-10), 10th revision, Fifth edition. vol. 1, Tabular List. Geneva, Switzerland: WHO Press, www.who.int; 1076 pages.
World Health Organization (WHO) (2019). Risk reduction of cognitive decline and dementia—WHO Guidelines. Foreward and Executive Summary, pp. 3-11.
World Health Organization (WHO) (Sep. 19, 2019). Dementia. Retrieved from https://www.who.int/news-room/fact-sheets/detail/dementia, 5 pages.
Worrell, G.A. et al. (2004). High-frequency oscillations and seizure generation in neocortical epilepsy. Brain 127, 1496-1506. https://doi.org/10.1093/brain/awh149.
Wu, H. et al. (Sep. 2016). Field potential oscillations in the bed nucleus of the Stria terminalis correlate with compulsion in a rat model of obsessive-compulsive disorder. J. Neurosci. 36, 10050-10059.
Wultsch, T. et al. (2007) "Behavioural and expressional phenotyping of nitric oxide synthase-I knockdown animals" Journal of Neural Transmission, (Suppl 72):69-85. https://doi.org/10.1007/978-3-211-73574-9_10.
Xie, Z. et al. (2017). A review of sleep disorders and melatonin. Neurol. Res., 39:559-565. https://doi.org/10.1080/01616412.2017.1315864.
Xu, C. et al. (2019). Integrative analysis of shared genetic pathogenesis by obsessive-compulsive and eating disorders. Molecular Medicine Reports, 19(3):1761-1766. https://doi.org/10.3892/mmr.2018.9772.
Xu, P. et al. (2016). Activation of serotonin 2C receptors in dopamine neurons inhibits binge-like eating in mice. Biological Psychiatry, 81, 737-747.
Yang, S. et al. (Apr. 19, 2018). Role of TNF-TNF Receptor 2 Signal in Regulatory T Cells and Its Therapeutic Implications. Frontiers in Immunology, 9:784, https://doi.org/10.3389/fimmu.2018.00784, 11 pages.
Yilmaz, Z. et al. (2015). Genetics and epigenetics of eating disorders. Advances in Genomics and Genetics, 5:131-150. HHS Public Access Author Manuscript, 36 pages.
Ypsilantis, E. and Tang, T.Y. (2010) Pre-emptive analgesia for chronic limb pain after amputation for peripheral vascular disease: A systematic review. Annals of Vascular Surgery, 24:1139-1146.
Yu, B. et al. (2008). Serotonin 5-hydroxytryptamine$_{2a}$ receptor activation suppresses tumor necrosis factor-alpha-induced inflammation with extraordinary potency. The Journal of Pharmacology and Experimental Therapeutics, 327(2):316-323.
Zammit, G. et al. (2007). Evaluation of the efficacy and safety of ramelteon in subjects with chronic insomnia. J. Clin. Sleep Med., 3:495-504. https://doi.org/10.5664/jcsm.26914.
Zetner, M. et al. (2008) Emotions evoked by the sound of music: Characterization, classification, and measurement. Emotion. 8:494-521.
Zhai, H. et al. (2019). Baicalin attenuated substantia nigra neuronal apoptosis in Parkinson's disease rats via the mTOR/AKT/GSK-3β pathway. Journal of Integrative Neuroscience, 18(4), 423-429. https://doi.org/10.31083/j.jin.2019.04.192.
Zhang, J.-M., & An, J. (2007). Cytokines, Inflammation and Pain. Int Anesthesiol Clin., 69(2):482-489. NIH Public Access Author Manuscript, available in PMC Nov. 30, 2009, 10 pages.
Zhou, R. et al. (2018). Elevated Resting State Gamma Oscillatory Activities in Electroencephalogram of Patients With Post-herpetic Neuralgia. Front. Neurosci. 12, 750, 10 pages. https://doi.org/10.3389/fnins.2018.00750.
Zhou, Y. et al. (2017). Comorbid generalized anxiety disorder and its association with quality of life in patients with major depressive disorder. Sci. Rep. 7:40511, https://doi.org/10.1038/srep40511, 8 pages.
Zipfel, S. et al. (2015). Anorexia nervosa: Aetiology, assessment, and treatment. The Lancet Psychiatry, vol. 2, Issue 12, pp. 1099-1111. https://doi.org/10.1016/S2215-0366(15)00356-9.
Zulauf, C.A. et al. (Mar. 2014). The complicated relationship between attention deficit/hyperactivity disorder and substance use disorders. Curr Psychiatry Rep, 16(3):436; doi:10.1007/s11920-013-0436-6. HHS Public Access Author Manuscript; available in PMC Apr. 29, 2015, 17 pages.
Co-pending U.S. Appl. No. 18/032,320, inventor Hickey; Molly Tabitha, filed Apr. 17, 2023.
Co-pending U.S. Appl. No. 18/285,109, inventors Elder; David Philip et al., filed Sep. 29, 2023.
Gotvaldova et al., "Stability of psilocybin and its four analogs in the biomass of the psychotropic mushroom *Psilocybe cubensis*," Drug Test Anal. Feb. 2021;13(2):439-446. Epub Nov. 4, 2020.
Sifferlin A., "What You Need to Know About Magic Mushrooms and Depression," Time, 4 pages (Dec. 1, 2016).
Co-pending U.S. Appl. No. 18/703,950, inventor Mill; Trevor Anthony, filed Apr. 23, 2024.
Co-pending U.S. Appl. No. 18/718,103, inventors Londesbrough; Derek John et al., filed Jun. 10, 2024.
Hilfiker, Polymorhism: In the Pharmaceutical Industry. Wiley-VCH Vrlag GmbH & Co. KGaA, Weinheim. (2.7 Crystallization of Polymorphs; 8.3 Statistical Aspects and Frequency of Solvates, 18 pages (2016). retrieved at https://onlinelibrary.wiley.com/doi/epdf/10.1002/3527607889.fmatter.
Saigal N., et al., "Microcrystalline Cellulose as a Versatile Excipient in Drug Research," Journal of Young Pharmacists, 2009, vol. 1, pp. 6-12.

\* cited by examiner

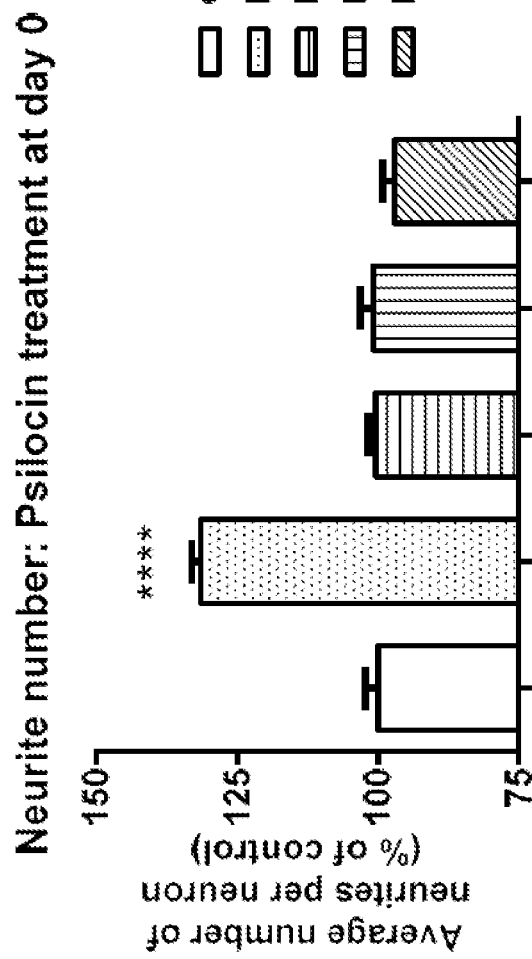
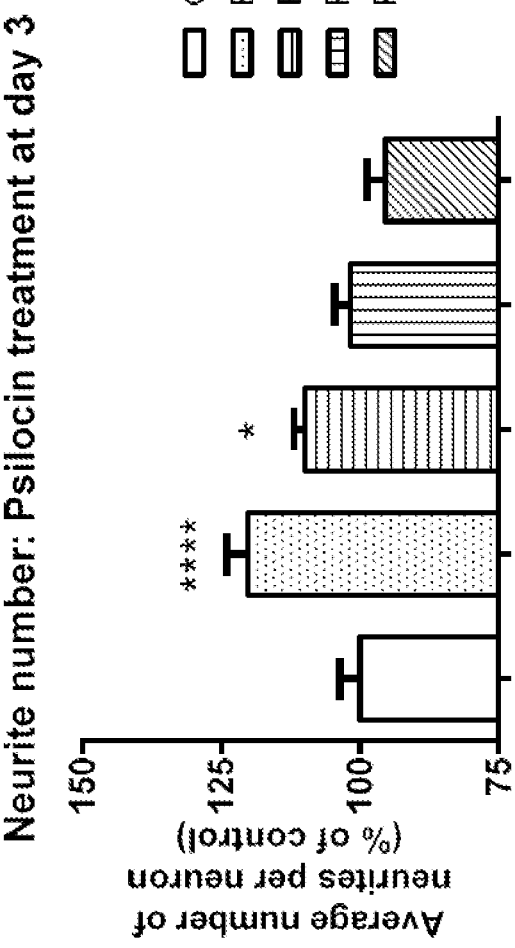
FIG. 60A
FIG. 60B

METHODS OF TREATING NEUROCOGNITIVE DISORDERS, CHRONIC PAIN AND REDUCING INFLAMMATION

RELATED APPLICATIONS

This application is a U.S. National Stage Application under 35 U.S.C. § 371 of International Application No. PCT/IB2020/053684, filed Apr. 17, 2020, which claims priority to and benefit of U.S. Application Ser. Nos. 62/835,449; 62/835,450; 62/835,458; 62/835,460; 62/835,464; 62/835,465; 62/835,472; 62/835,474; 62/835,476; 62/835,477; 62/835,478; 62/835,479; 62/835,480; 62/835,481; 62/835,482; 62/835,484; and 62/835,485, all filed Apr. 17, 2019; U.S. Application Ser. No. 62/893,110, filed Aug. 28, 2019, U.S. Application Ser. No. 62/893,611, filed Aug. 29, 2019, and U.S. Application Ser. No. 62/946,159, filed Dec. 10, 2019, each of which is incorporated herein by reference in its entirety.

BACKGROUND

Psilocybin belongs to a class of drugs referred to as psychedelics ("mind-manifesting" drugs). Specifically, psilocybin is considered a 5-hydroxytryptaminergic (serotonergic) psychedelic, as distinguished from other tryptamines such as dimethyltryptamine (DMT), ergolines such as lysergic acid diethylamide (LSD), and phenethylamines such as mescaline. Psilocybin was first isolated from psilocybe mushrooms and later synthesized in a laboratory.

There are several common diseases, disorders, and conditions for which no adequate treatments and/or therapies exist, including:

Alzheimer's disease (AD)—AD is a neurodegenerative brain disorder characterized by both cognitive and non-cognitive behavioral changes, particularly progressive memory deficits, depression, anxiety, dementia, irritability, mood swings, inattention, aggressive and/or apathetic behavior, confusion, gradual physical deterioration, and ultimately death.

Parkinson's disease (PD)—PD is the most common type of Parkinsonian syndrome, a term reflecting a group of neurological disorders with Parkinson's disease-like movements problems such as rigidity, slowness, and tremor. The clinical presentation of Parkinson's disease includes motor and non-motor symptoms.

Attention-deficit hyperactivity disorder (ADHD)—ADHD is a neurodevelopmental disorder characterized by one or more of inattention, hyperactivity, and impulsivity, which are otherwise not appropriate for a person's age. It is commonly diagnosed in childhood and is one of the most frequent conditions affecting school-aged children.

Epilepsy—Epilepsy is a neurological disorder marked by sudden recurrent episodes of sensory disturbance, loss of consciousness, or convulsions, associated with abnormal electrical activity in the brain. During a seizure, an individual with epilepsy experiences abnormal behavior, symptoms, and sensations, sometimes including loss of consciousness. There are few symptoms between seizures.

Autism spectrum disorder (ASD)—ASD is a neurodevelopmental syndrome characterized by core deficits in social interaction and communication, presence of repetitive and restricted patterns of behavior and interests, and/or unusual reactivity to sensory input.

Sleep-wake disorders—Sleep-wake disorders are a class of diseases or disorders including insomnia disorder, hypersomnolence disorder, narcolepsy, breathing-related sleep disorders (such as central sleep apnea), circadian rhythm sleep-wake disorders, non-rapid eye movement sleep arousal disorders, nightmare disorder, rapid eye movement sleep behavior disorder, restless leg syndrome, and substance/medication-induced sleep disorder. Individuals with these disorders typically present with sleep-wake complaints of dissatisfaction regarding the quality, timing, and amount of sleep, which often results in daytime distress.

Chronic pain—Pain is the most common symptom of disease and provides protection from dangerous and noxious stimuli. Chronic pain is pain that lasts longer than the usual course of an acute injury or disease, such as pain that recurs for months or years.

Inflammatory disorders—Inflammation underlies the generation and maintenance of some of the leading causes for morbidity and mortality around the world. Inflammatory disorders are often chronic and may be the result of immune signaling dysfunction.

Inflammatory bowel disease (IBD)—IBD is a term used to describe various diseases and disorders, including Crohn's Disease and Ulcerative Colitis, which are characterized by chronic inflammation of the gastrointestinal (GI) tract.

Stroke—A stroke is a sudden interruption in the blood supply of the brain. Brain cells begin to die within minutes of being deprived of oxygen and nutrients.

Amyotrophic lateral sclerosis (ALS)—ALS is a progressive neurodegenerative disease, also known as Motor Neuron Disease (MND), Lou Gehrig's Disease, and Charcot's disease. ALS attacks motor neurons in the brain and spinal cord, resulting in the wasting away of muscle and loss of movement.

There remains a need in the art for improved compositions and methods for treating these diseases, disorders, and conditions.

SUMMARY

Psilocybin may provide numerous clinical benefits, such as benefits in neural plasticity and cognitive function (as measured using e.g., Cambridge Neuropsychological Test Automated Battery (CANTAB) tests) with improvements in, for example, working memory and executive function, sustained attention, and episodic memory. These benefits have implications for psilocybin's use in the treatment of various diseases, disorders, and conditions, including both psychiatric and neurological aspects thereof.

Provided herein is a method for treating one or more neurocognitive disorders in a subject in need thereof, the method comprising administering to the subject a therapeutically effective amount of psilocybin or an active metabolite thereof.

Also provided herein is a method for treating a Parkinsonian syndrome or symptom thereof in a subject in need thereof, the method comprising administering to the subject a therapeutically effective amount of psilocybin or an active metabolite thereof.

Also provided herein is a method for treating attention-deficit hyperactivity disorder (ADHD) in a subject in need thereof, the method comprising administering to the subject a therapeutically effective amount of psilocybin or an active metabolite thereof.

Also provided herein is a method for treating epilepsy in a subject in need thereof, the method comprising administering to the subject a therapeutically effective amount of psilocybin or an active metabolite thereof.

Also provided herein is a method for treating an autism spectrum disorder (ASD) or a symptom thereof in a subject in need thereof, the method comprising administering to the subject a therapeutically effective amount of psilocybin or an active metabolite thereof.

Also provided herein is a method of treating one or more sleep-wake disorders in a subject in need thereof, the method comprising administering to the subject a therapeutically effective amount of psilocybin or an active metabolite thereof.

Also provided herein is a method of treating chronic pain in a subject in need thereof, the method comprising administering to the subject a therapeutically effective amount of psilocybin or an active metabolite thereof.

Also provided herein is a method of reducing inflammation in a subject in need thereof, the method comprising administering to the subject a therapeutically effective amount of psilocybin or an active metabolite thereof.

Also provided herein is a method of treating Inflammatory Bowel Disease (IBD) in a subject in need thereof, the method comprising administering to the subject a therapeutically effective amount of psilocybin or an active metabolite thereof.

Also provided herein is a method for treating stroke in a subject in need thereof, the method comprising administering to the subject a therapeutically effective amount of psilocybin or an active metabolite thereof.

Also provided herein is a method for treating a subject in need thereof, the method comprising administering to the subject a therapeutically effective amount of psilocybin or an active metabolite thereof; wherein the subject is recovering from a stroke.

Also provided herein is a method for treating amyotrophic lateral sclerosis (ALS) in a subject in need thereof, the method comprising administering to the subject a therapeutically effective amount of psilocybin or an active metabolite thereof.

In some embodiments, the psilocybin is administered in a dosage form comprising a therapeutically effective amount of highly pure crystalline psilocybin in the form of Polymorph A, wherein the crystalline psilocybin comprises at least 90% by weight of Polymorph A. In some embodiments, the crystalline psilocybin comprises at least 95% by weight of Polymorph A. In some embodiments, the crystalline psilocybin has a chemical purity of greater than 97% by high performance liquid chromatography (HPLC), and no single impurity of greater than 1%.

In some embodiments, the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%. In some embodiments, the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%, further comprising a mixture of two silicified microcrystalline cellulose variants wherein the first variant has a particle size from about 45 to 80 microns and the second variant has a particle size of about 90 to 150 microns. In some embodiments, 30% or less of the microcrystalline cellulose is the first variant having a particle size from about 45 to 80 microns and about 70% or more of the microcrystalline cellulose is the second variant having a particle size of about 90 to 150 microns. In some embodiments, the psilocybin is administered in an oral dosage form. In some embodiments, the psilocybin is administered in a capsule. In some embodiments the psilocybin is administered in a tablet.

In some embodiments, at least one dose of psilocybin is administered to the subject. In some embodiments, the dose of psilocybin is in the range of about 0.1 mg to about 100 mg. In some embodiments, the dose of psilocybin is about 25 mg.

In some embodiments, the subject participates in at least one psychological support session before administration of the psilocybin. In some embodiments, the subject participates in at least one psychological support session after administration of the psilocybin. In some embodiments, a therapist provides psychological support to the subject for approximately 4-8 hours after administration of the psilocybin.

Statistical significance was determined using one-way repeated measures ANOVA followed by Dunnett post-hoc test. *$p<0.05$. Data are expressed as mean±s.e.m.

Figure 41:
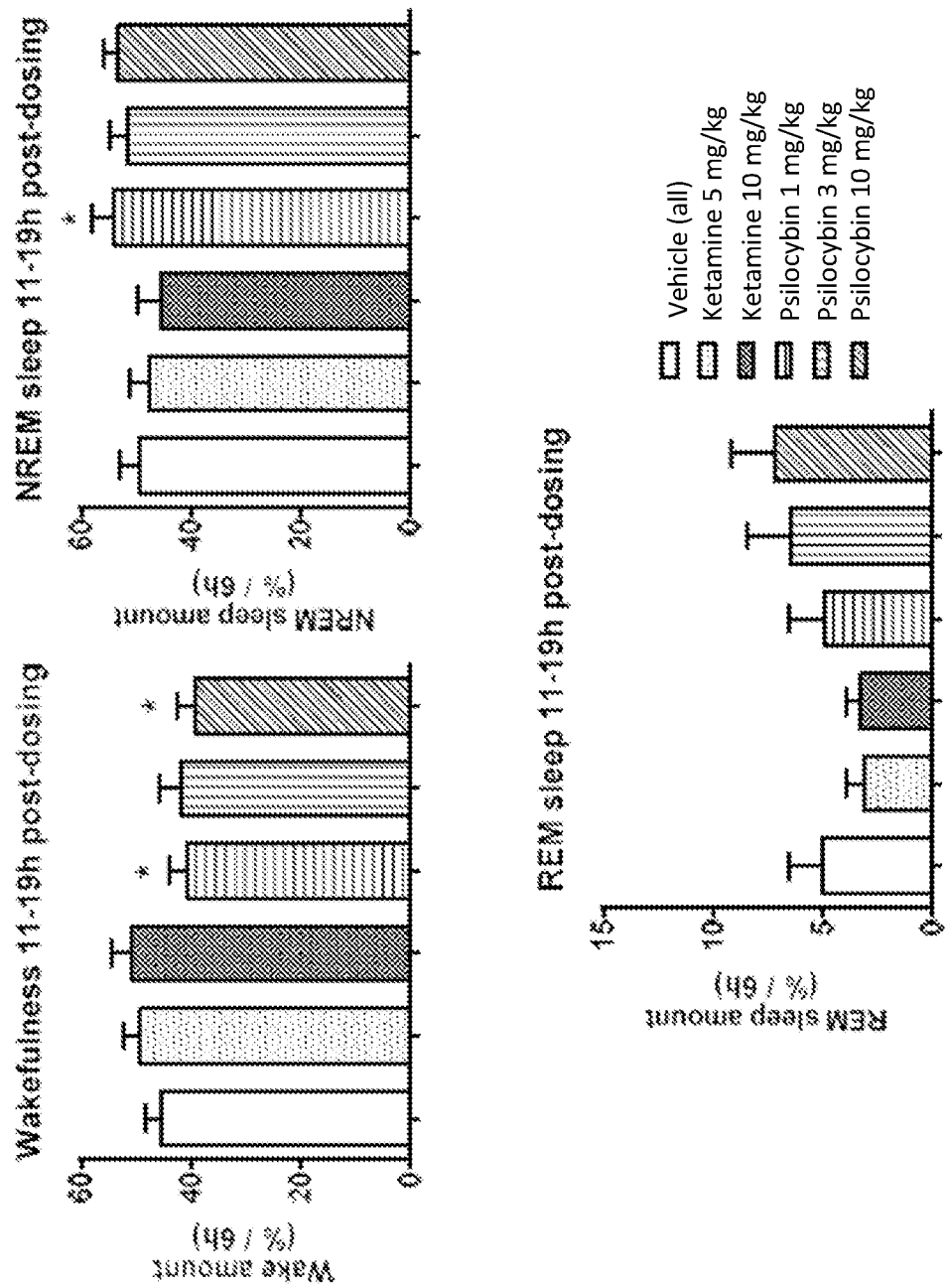

FIG. 41 is a series of graphs showing the amount of wakefulness, NREM sleep and REM sleep 11-19 hours (dark phase) post-dosing with psilocybin. Statistical significance was determined using repeated measures one-way ANOVA followed by Dunnett post-hoc test. *$p<0.05$. Data are expressed as mean±s.e.m.

Figure 42:
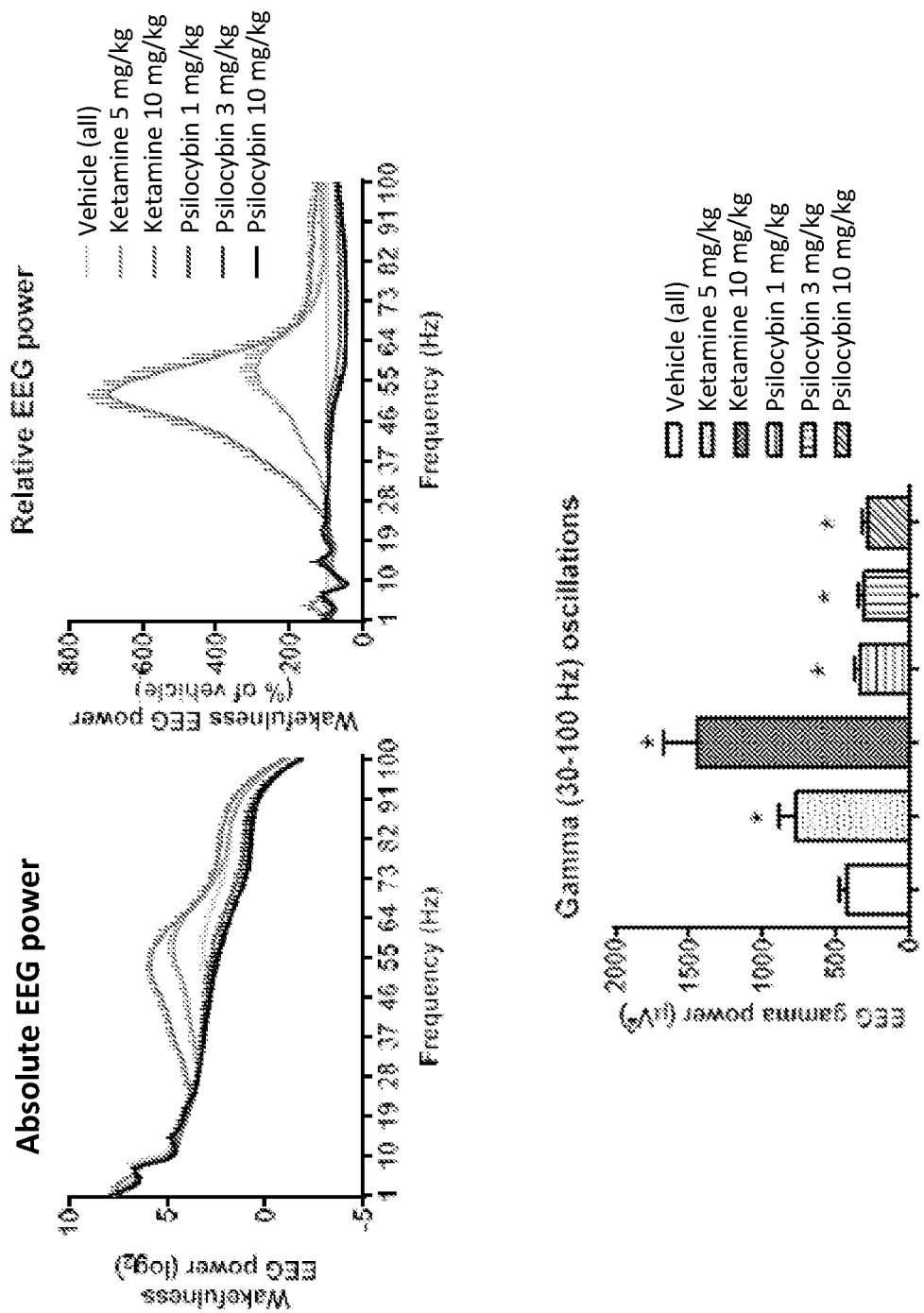

FIG. 42 is a series of graphs showing the changes in the absolute and relative wakefulness electroencephalogram (EEG) power with frequency, and the amount of gamma oscillations. Statistical significance was determined using one-way repeated measures ANOVA followed by Dunnett post-hoc test. *$p<0.05$. Data are expressed as mean±s.e.m.

Figure 43:
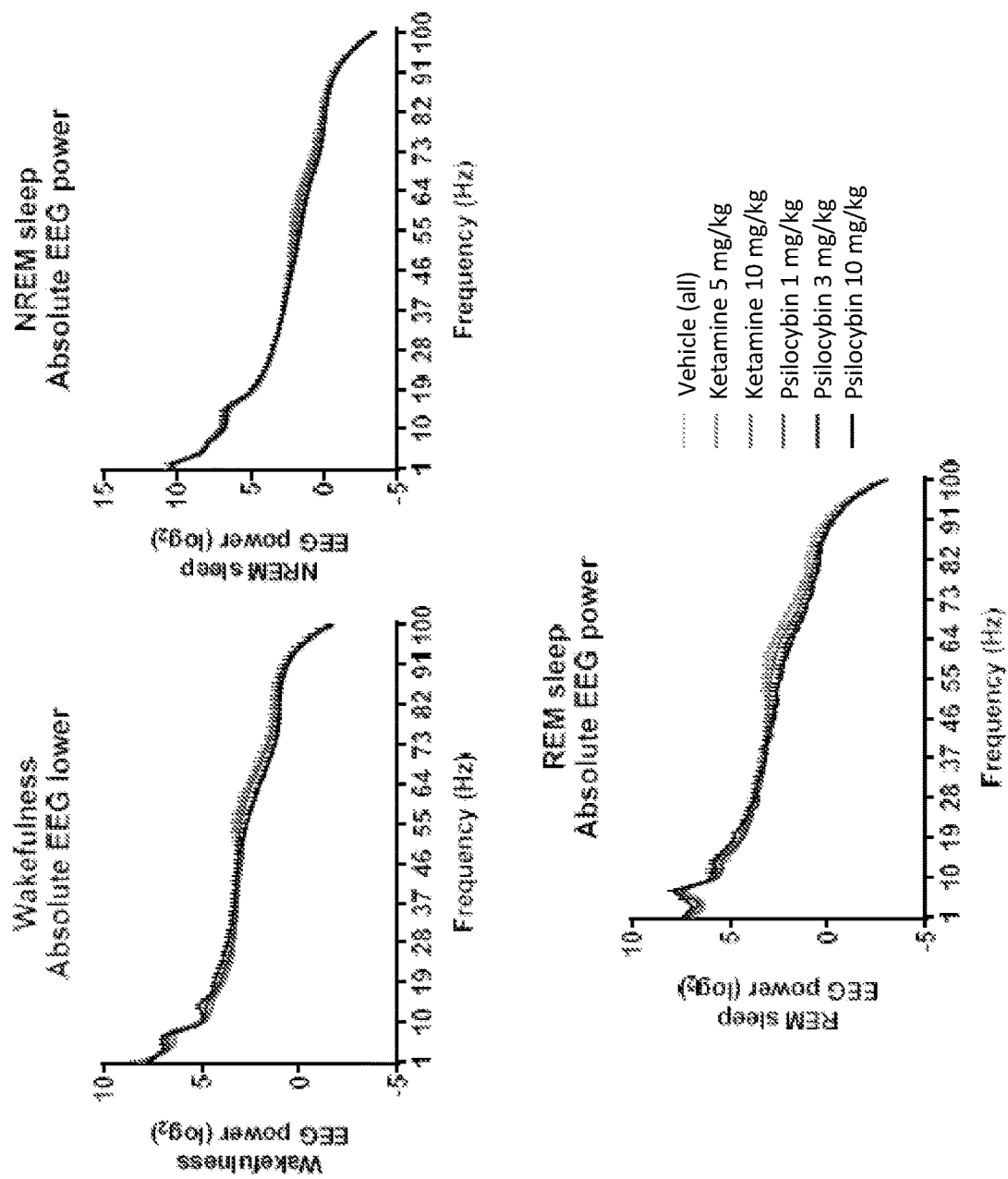
Figure 43:
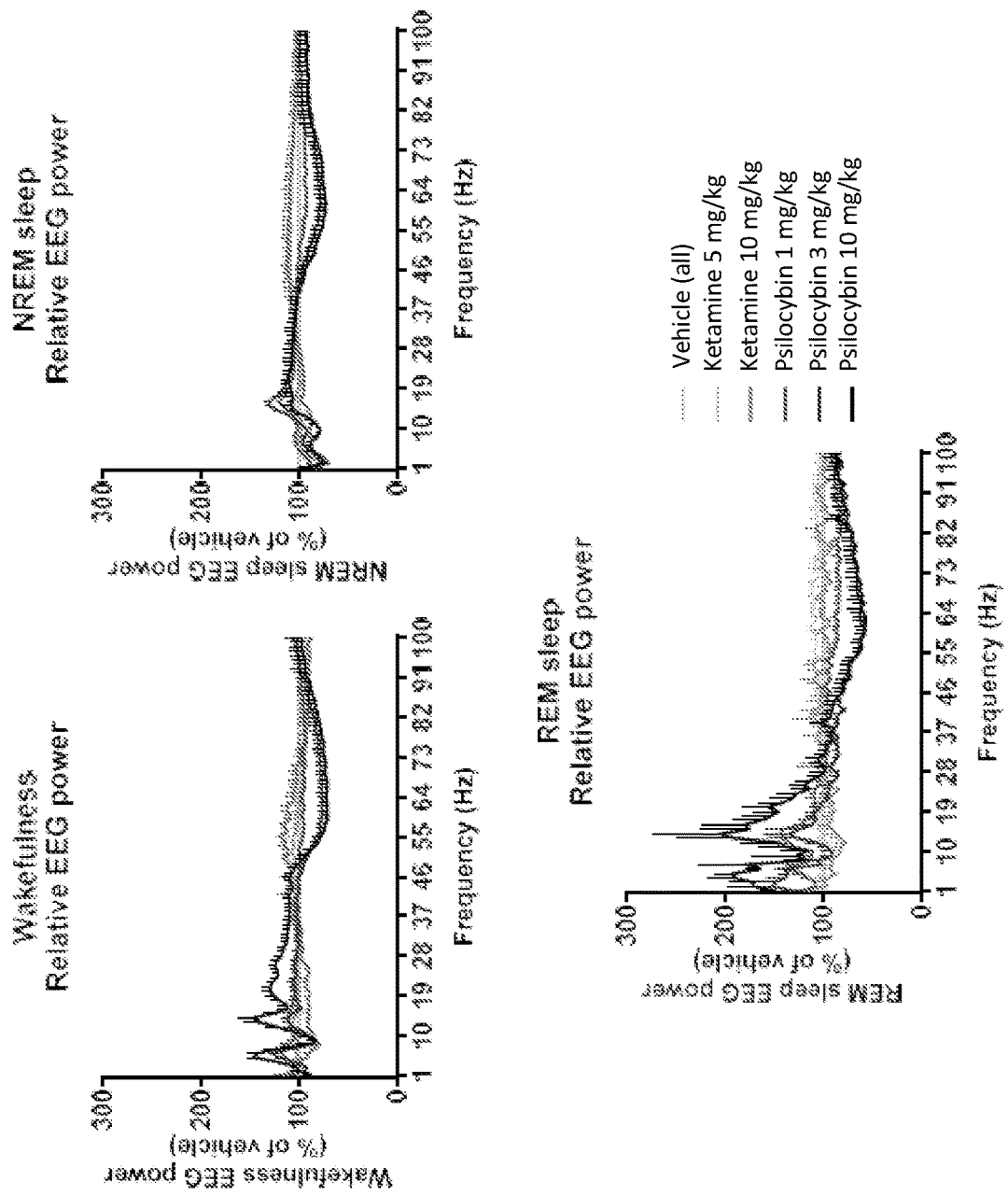

FIG. 43 is a series of graphs showing the changes in the absolute and relative wakefulness, NREM and REM sleep EEG power with frequency.

Figure 44:
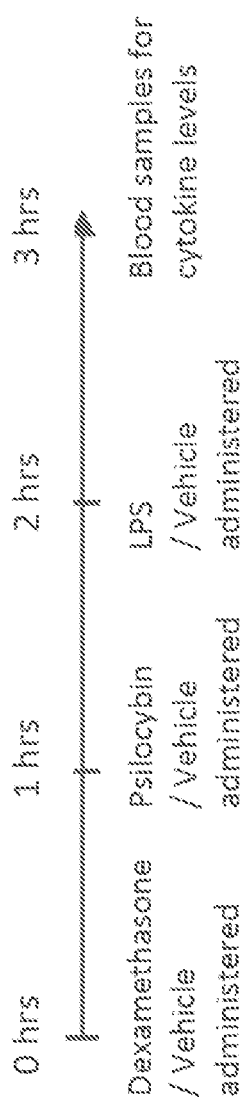

FIG. 44 is a schematic illustrating the dosing and sample collection protocol described in Example 26.

Figure 45:
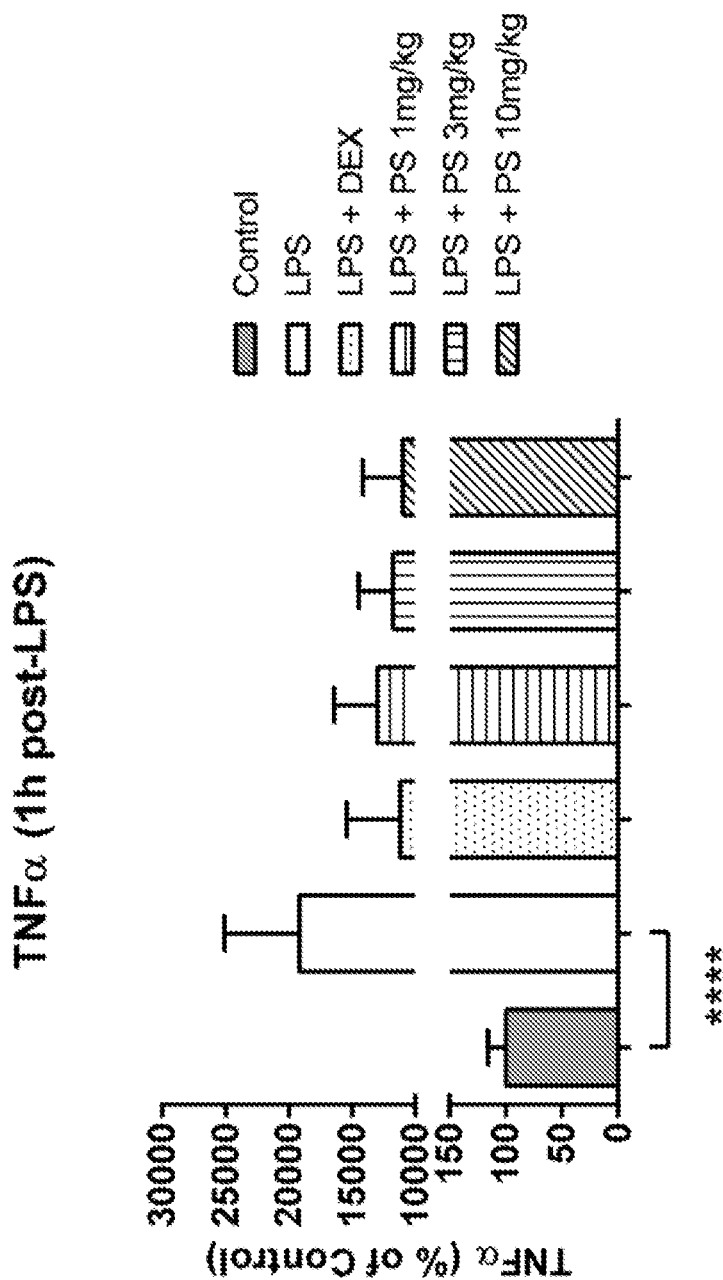

FIG. 45 is a graph showing tumor necrosis factor alpha (TNF-α) blood plasma level 1 hour post-lipopolysaccharide (LPS) administration in rats after pre-treatment with various doses (1, 3, and 10 mg/kg) of psilocybin or dexamethasone. Statistical significance was determined using a one-way ANOVA followed by Fisher's Least Significant Difference (LSD) for pairwise comparison test. DEX=dexamethasone, PS=psilocybin, *$p<0.05$, $p<0.01$, *$p<0.001$, ****$p<0.0001$. Data are expressed as mean±s.e.m. Significance determined by one-way ANOVA and post-hoc LSD vs control is represented by *. Significance determined by one-way ANOVA and post-hoc LSD vs LPS is represented by #.

Figure 46:
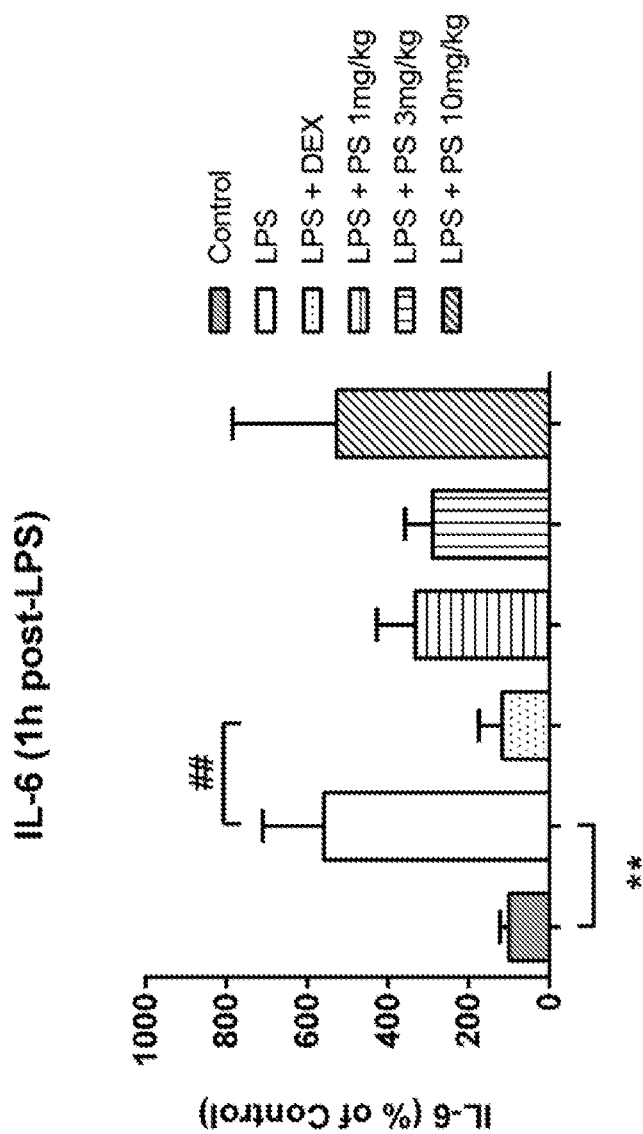

FIG. 46 is a graph showing interleukin-6 (IL-6) blood plasma level in rats 1 hour after (i) treatment with LPS alone, (ii) pre-treatment with LPS and dexamethasone, or (iii) pre-treatment with various doses (1, 3, and 10 mg/kg) of psilocybin. Statistical significance was determined using a one-way ANOVA followed by Fisher's Least Significant Difference (LSD) for pairwise comparison test. DEX=dexamethasone, PS=psilocybin, *$p<0.05$, $p<0.01$, *$p<0.001$, ****$p<0.0001$. Data are expressed as mean±s.e.m. Significance determined by one-way ANOVA and post-hoc LSD vs control is represented by *. Significance determined by one-way ANOVA and post-hoc LSD vs LPS is represented by #.

Figure 47:
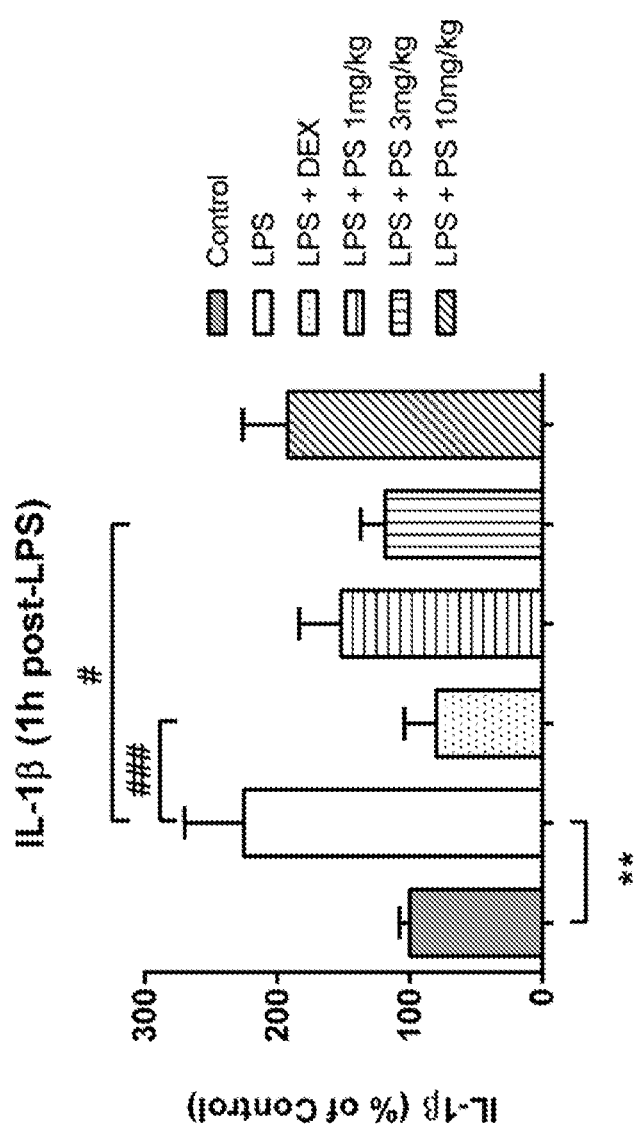

FIG. 47 is a graph showing interleukin-1β (IL-1β) blood plasma level 1 hour post-LPS administration in rats after pre-treatment with various doses (1, 3, and 10 mg/kg) of psilocybin. Statistical significance was determined using a one-way ANOVA followed by Fisher's Least Significant Difference (LSD) for pairwise comparison test. DEX=dexamethasone, PS=psilocybin, *$p<0.05$, $p<0.01$, *$p<0.001$, ****$p<0.0001$. Data are expressed as mean±s.e.m. Significance produced by one-way ANOVA and post-hoc LSD vs control is represented by *. Significance produced by one-way ANOVA and post-hoc LSD vs LPS is represented by #.

Figure 48:
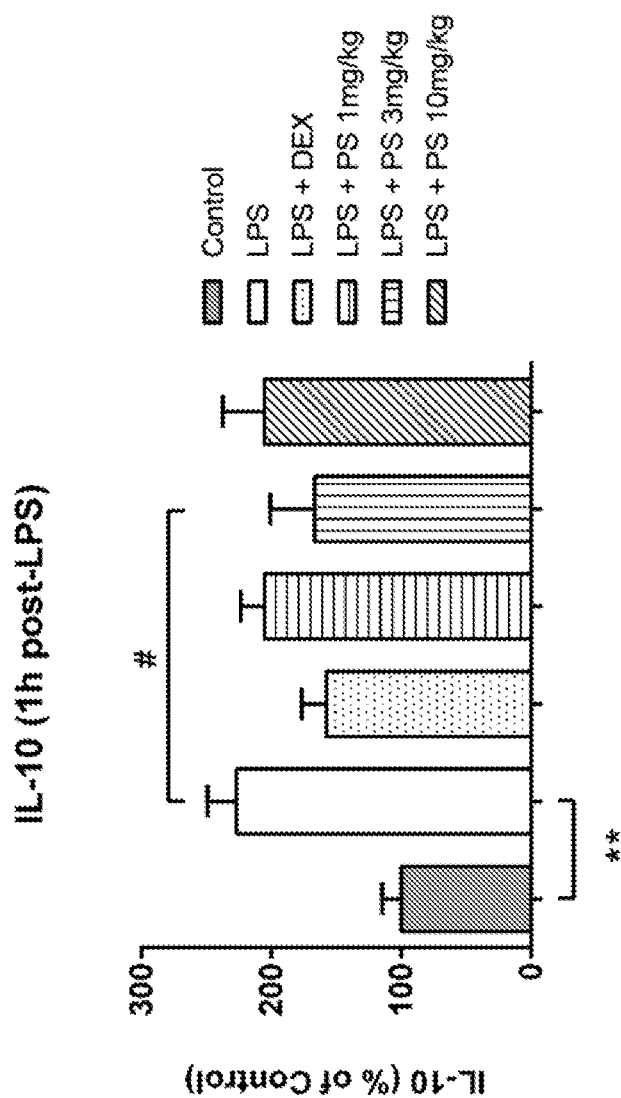

FIG. 48 is a graph showing interleukin-10 (IL-10) blood plasma level 1 hour post-LPS administration in rats after pre-treatment with various doses (1, 3, and 10 mg) of psilocybin.

Statistical significance was determined using a one-way ANOVA followed by Fisher's Least Significant Difference (LSD) for pairwise comparison test. DEX=dexamethasone, PS=psilocybin, *$p<0.05$, $p<0.01$, *$p<0.001$, ****$p<0.0001$. Data are expressed as mean±s.e.m. Significance produced by one-way ANOVA and post-hoc LSD vs control is represented by *. Significance produced by one-way ANOVA and post-hoc LSD vs LPS is represented by #.

Figure 49:
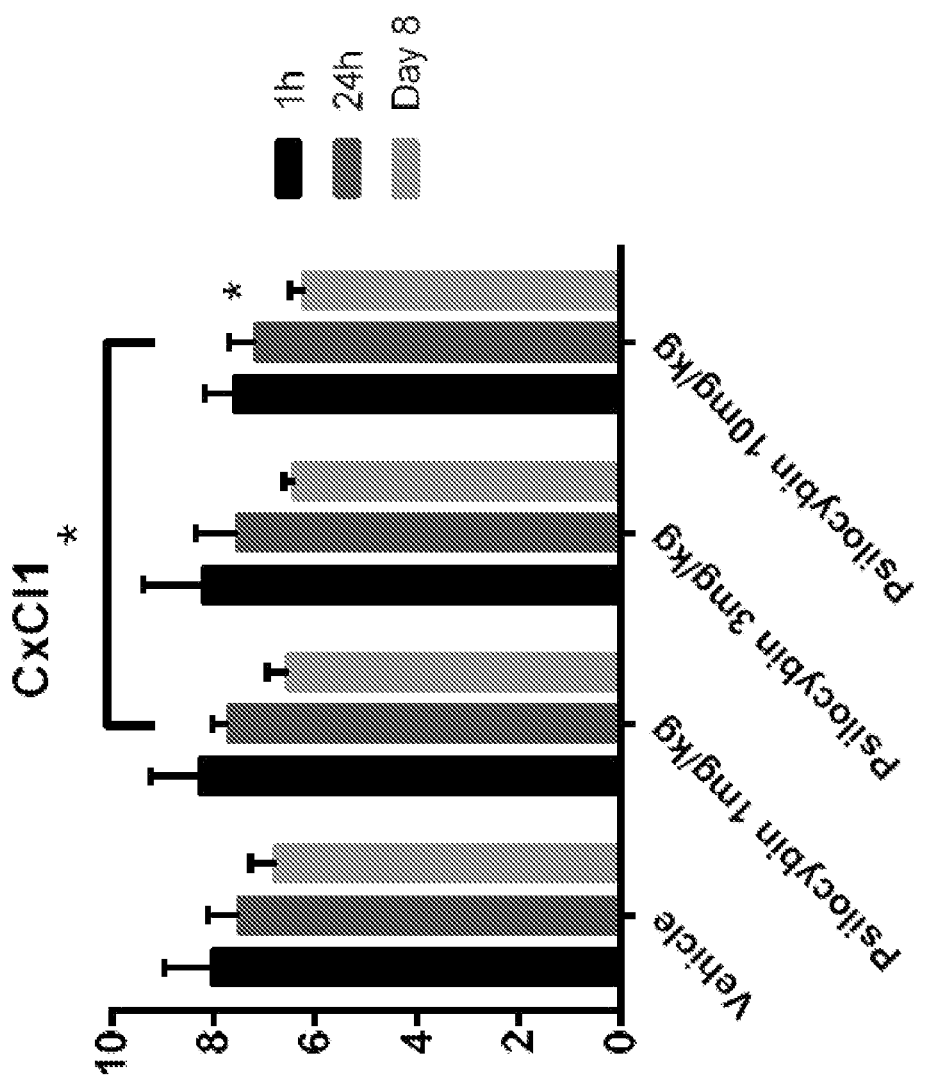

FIG. 49 is a graph showing C—X—C Chemokine Ligand 1 (CXCL1) expression levels at 1 hour, 24 hours, and on day 8 following a single administration of psilocybin in naïve mice compared to vehicle-treated animals (indicated by *) and compared to other psilocybin doses (indicated by brackets and *). Statistical significance was determined using two-way ANOVA repeated measures followed by Bonferroni multiple comparison test. *$p<0.05$, $p<0.01$, *$p<0.001$, ****$p<0.0001$. Data are expressed as mean±standard deviation (sd).

Figure 50:
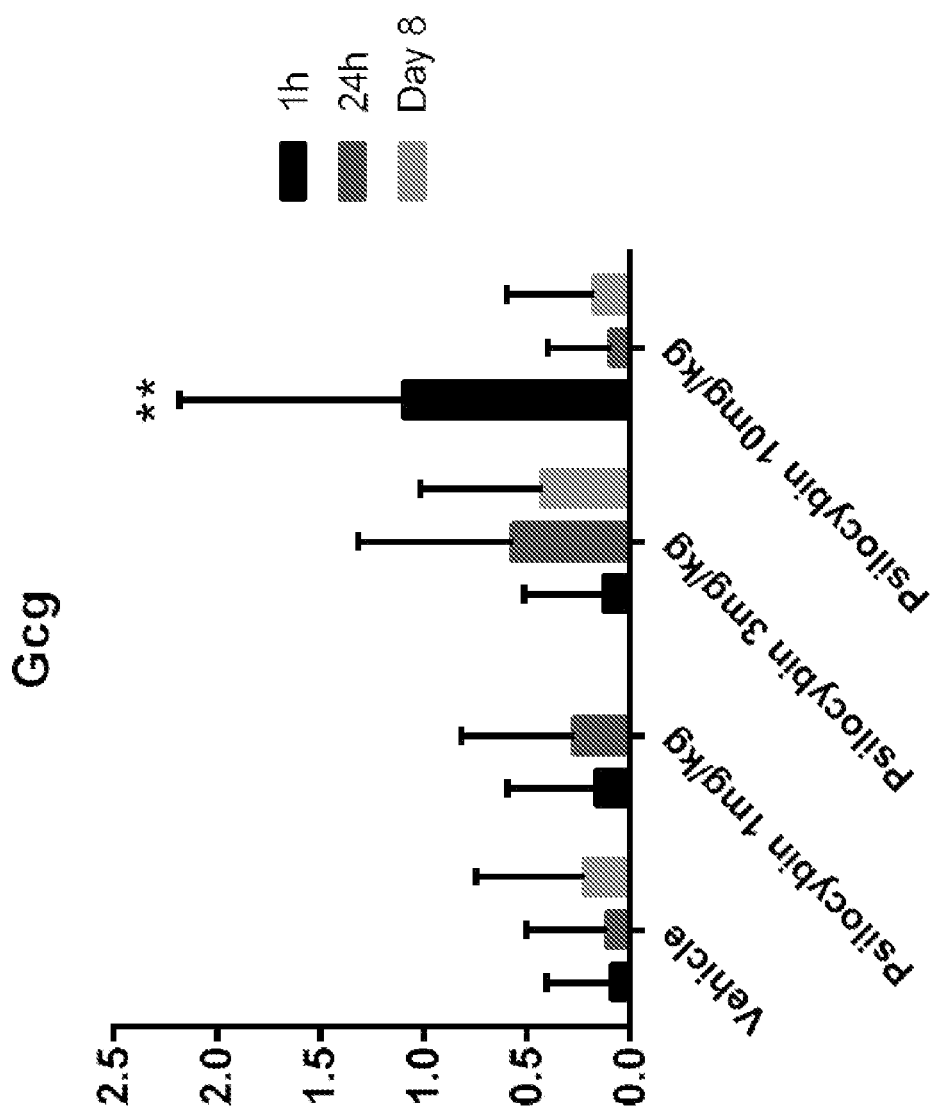

FIG. 50 is a graph showing glucagon (Gcg) expression levels at 1 hour, 24 hours, and on Day 8 following a single administration of psilocybin in naïve mice compared to vehicle treated animals. Statistical significance was determined using two-way ANOVA repeated measures followed by Bonferroni multiple comparison test, *$p<0.05$, $p<0.01$, *$p<0.001$, 0.0001. Data are expressed as mean±standard deviation (sd).

Figure 51:
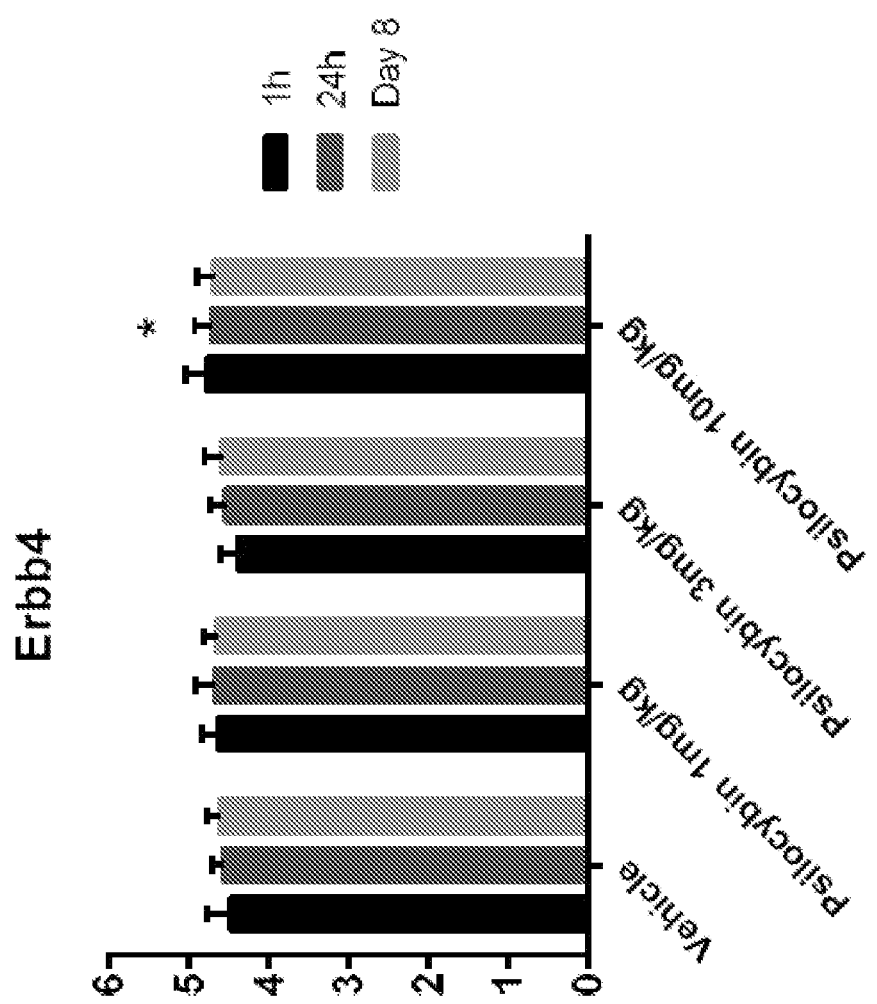

FIG. 51 is a graph showing receptor tyrosine-protein kinase Erbb4 expression levels at 1 hour, 24 hours, and on Day 8 following a single administration of psilocybin in naïve mice compared to vehicle treated animals. Statistical significance was determined using two-way ANOVA repeated measures followed by Bonferroni multiple comparison test, *$p<0.05$, $p<0.01$, *$p<0.001$, ****$p<0.0001$. Data are expressed as mean±standard deviation (sd).

Figure 52:
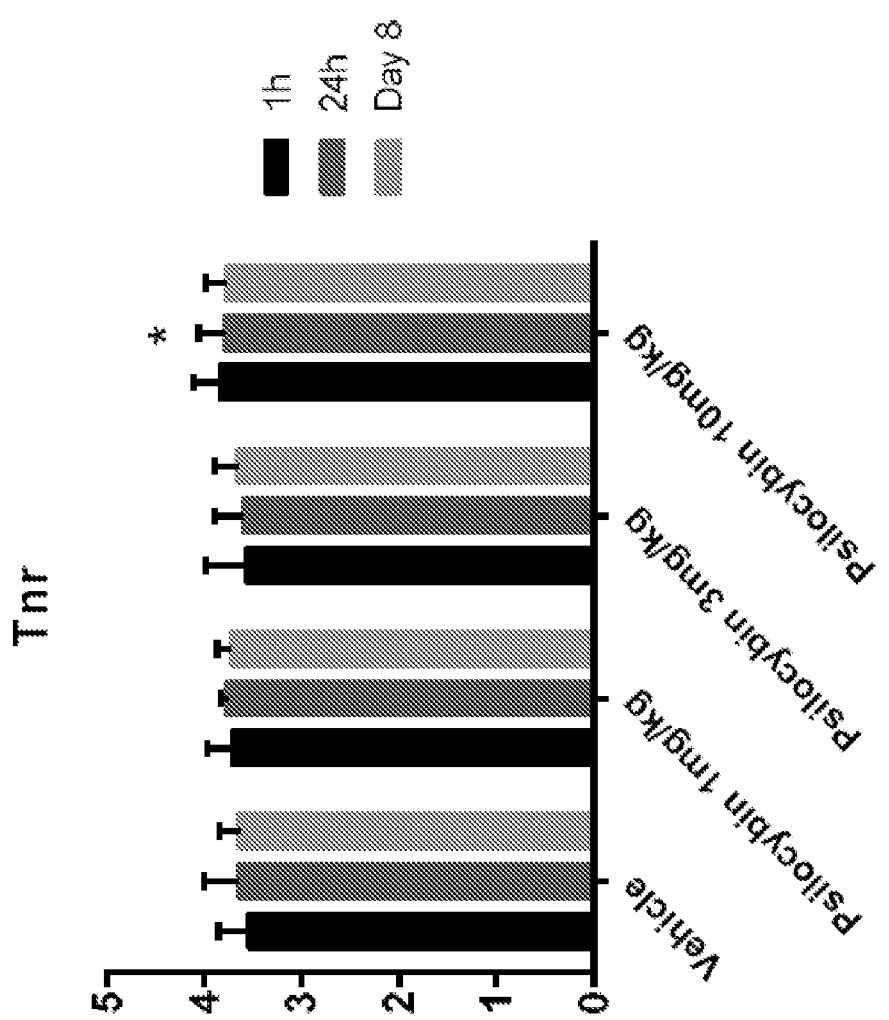

FIG. 52 is a graph showing tenascin-R (Tnr) expression levels at 1 hour, 24 hours, and on Day 8 following a single administration of psilocybin in naïve mice compared to vehicle treated animals. Statistical significance was determined using two-way ANOVA repeated measures followed by Bonferroni multiple comparison test, *$p<0.05$, $p<0.01$, *$p<0.001$, ****$p<0.0001$. Data are expressed as mean±standard deviation (sd).

Figure 53:
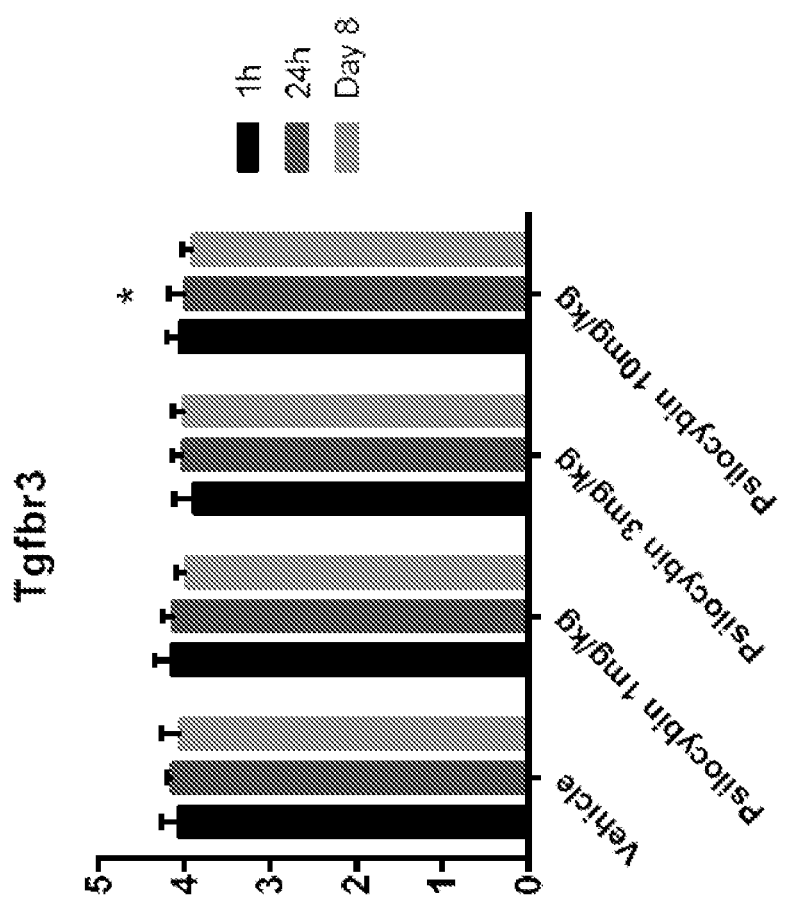

FIG. 53 is a graph showing transforming growth factor beta receptor 3 (Tgfbr3) expression levels at 1 hour, 24 hours, and on Day 8 following a single administration of psilocybin in naïve mice compared to vehicle treated animals. Statistical significance was determined using two-way ANOVA repeated measures followed by Bonferroni multiple comparison test, *$p<0.05$, $p<0.01$, *$p<0.001$, ****$p<0.0001$. Data are expressed as mean±standard deviation (sd).

Figure 54:
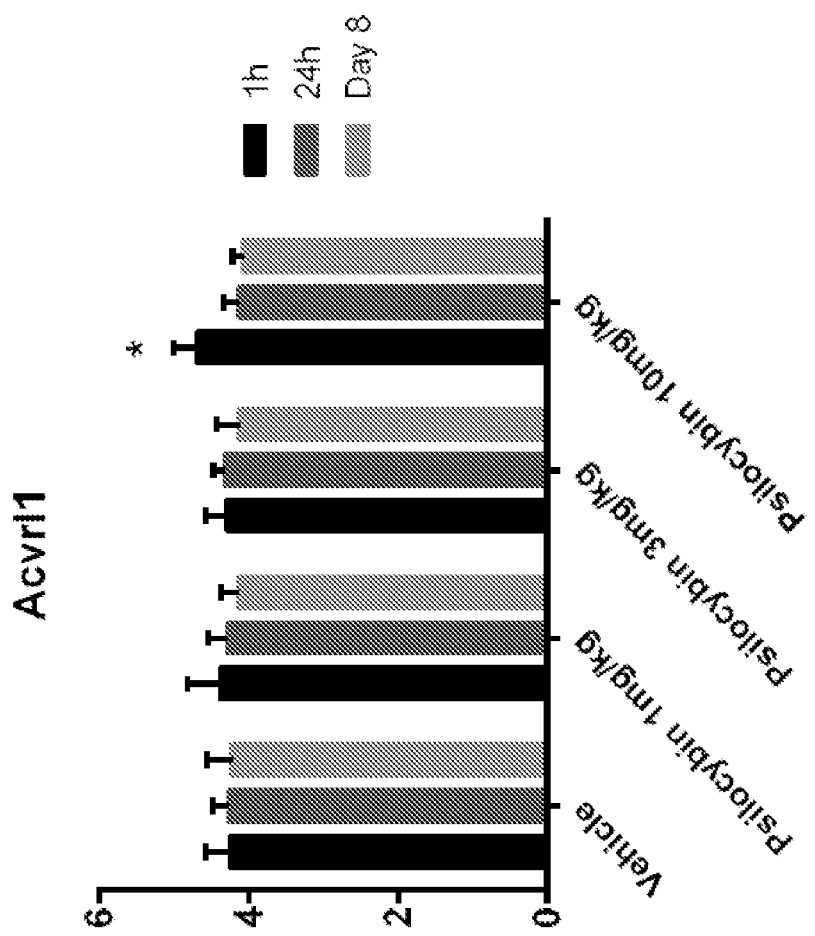

FIG. 54 is a graph showing activing A receptor, type II-like kinase 1 (Acvrl1) expression levels at 1 hour, 24 hours, and on Day 8 following a single administration of psilocybin in naïve mice compared to vehicle treated animals. Statistical significance was determined using two-way ANOVA repeated measures followed by Bonferroni multiple comparison test, *$p<0.05$, $p<0.01$, *$p<0.001$, ****$p<0.0001$. Data are expressed as mean±standard deviation (sd).

Figure 55:
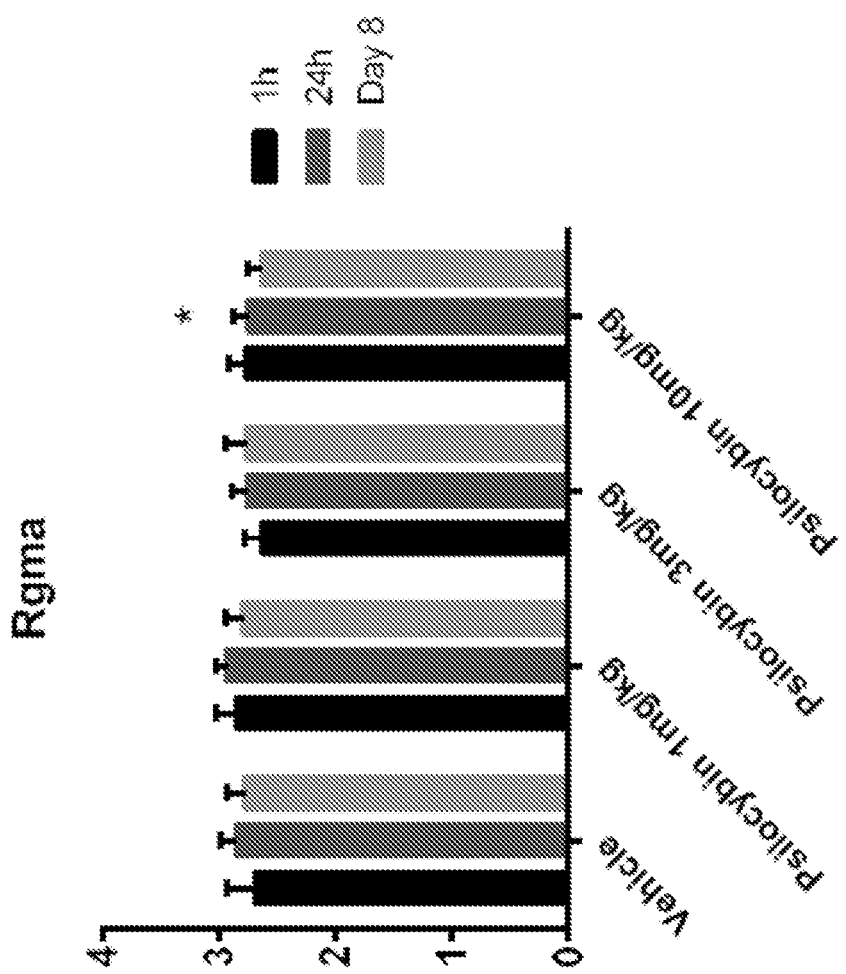

FIG. 55 shows the repulsive guidance molecule A (Rgma) expression levels at 1 hour, 24 hours, and on Day 8 following a single administration of psilocybin in naïve mice compared to vehicle treated animals in an in vivo model. Two-way ANOVA repeated measures followed by Bonferroni multiple comparison test, *$p<0.05$, **$p<0.01$,

*p<0.001, **p<0.0001. Data are expressed as mean±standard deviation (sd).

Figure 56:
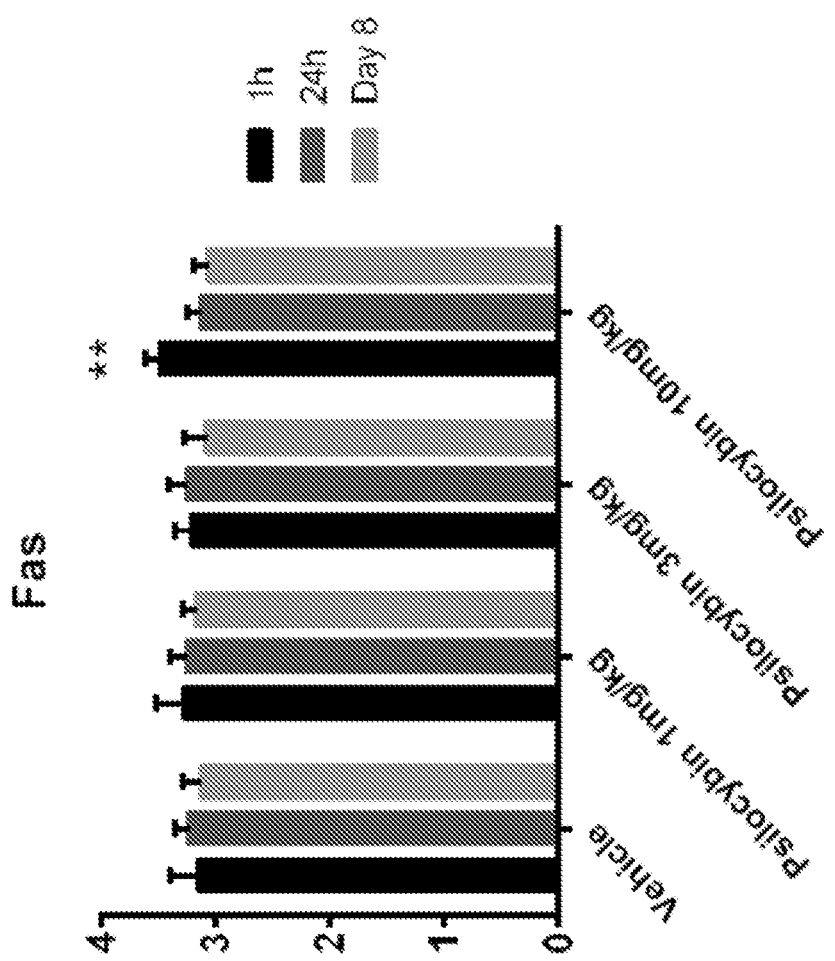

FIG. 56 shows the levels of tumor necrosis factor superfamily member 6 (Fas) expression levels at 1 hour, 24 hours, and on Day 8 following a single administration of psilocybin in naïve mice compared to vehicle treated animals in an in vivo model. Two-way ANOVA repeated measures followed by Bonferroni multiple comparison test, *p<0.05, p<0.01, *p<0.001, ****p<0.0001. Data are expressed as mean±standard deviation (sd).

Figure 57:
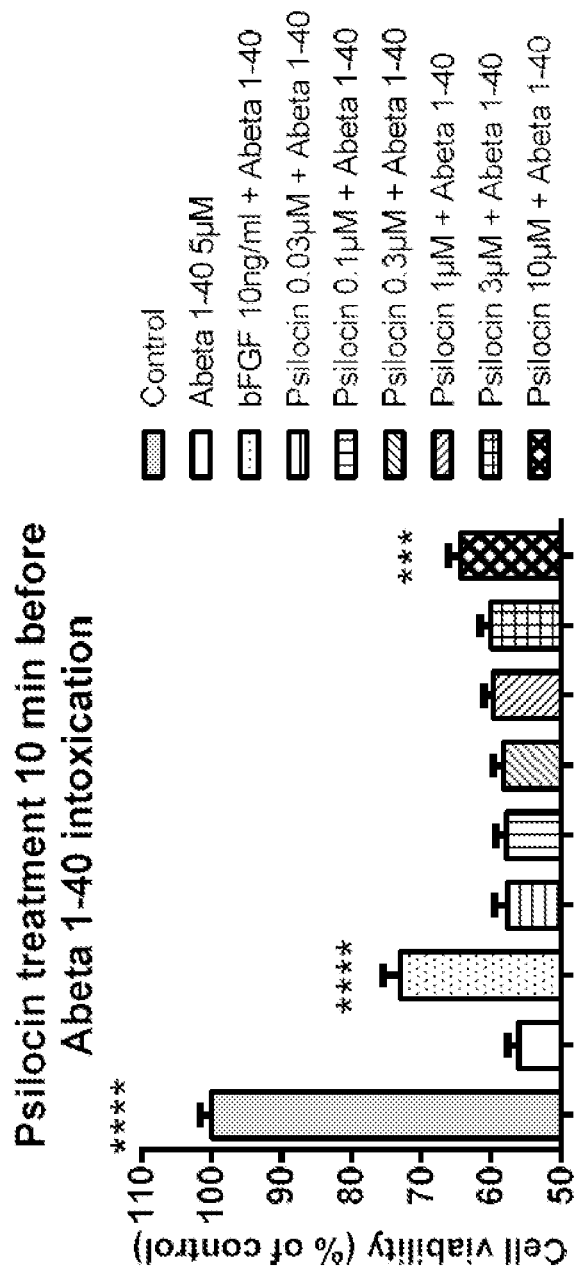

FIG. 57 is a graph showing percentage of cell viability with psilocin treatment 10 minutes before amyloid-beta (Abeta) 1-40 intoxication compared to Abeta 1-40 5 µM treated group. Statistical significance was determined using one-way ANOVA followed by Fishers LSD for pairwise comparison test, *p<0.05, p<0.01, *p<0.001, ****p<0.0001. Data are expressed as mean±standard error of the mean (sem).

Figure 58:
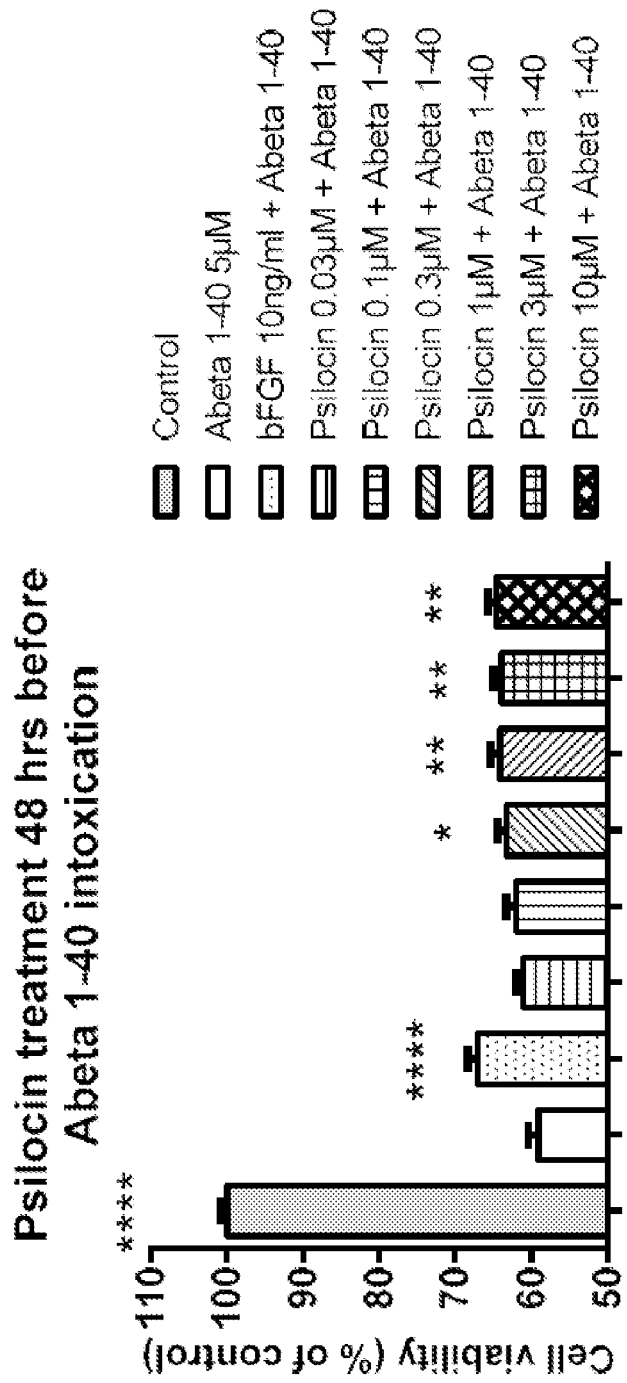

FIG. 58 is a graph showing percentage of cell viability with psilocin treatment 48 hours before Abeta 1-40 intoxication compared to Abeta 1-40 5 µM treated group. Statistical significance was determined using one-way ANOVA followed by Fishers LSD for pairwise comparison test, *p<0.05, p<0.01, *p<0.001, ****p<0.0001. Data are expressed as mean±sem.

Figure 59A:
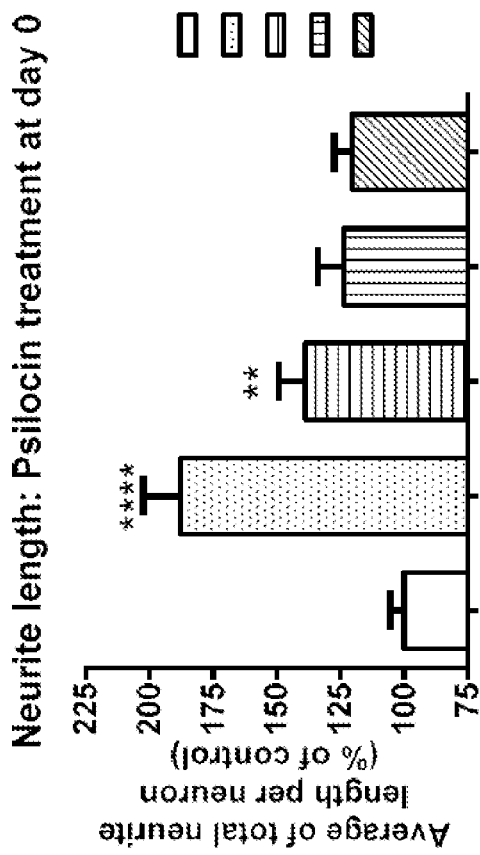

FIG. 59A is a graph showing percentage change of total neurite length after psilocin treatment at day 0 compared to the control group in human iPSC cells (induced pluripotent stem cells). Statistical significance was determined using one-way ANOVA followed by Fishers LSD for pairwise comparison test, *p<0.05, p<0.01, *p<0.001, ****p<0.0001. Data are expressed as mean±sem.

Figure 59B:
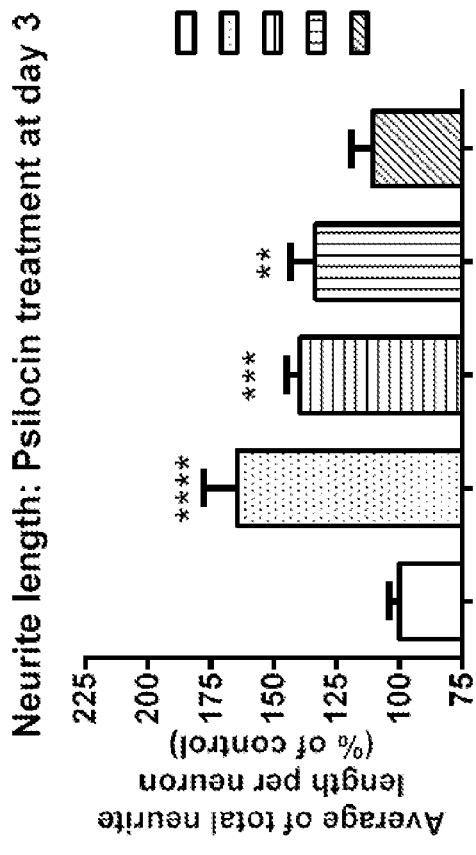

FIG. 59B is a graph showing percentage change of total neurite length after psilocin treatment at day 3 compared to the control group in human iPSC cells (induced pluripotent stem cells). Statistical significance was determined using one-way ANOVA followed by Fishers LSD for pairwise comparison test, *p<0.05, p<0.01, *p<0.001, ****p<0.0001. Data are expressed as mean±sem.

FIG. 60A is a graph showing percentage change of the number of neurites per neuron after psilocin treatment at day 0 compared to the control group in human iPSC cells (induced pluripotent stem cells). Statistical significance was determined using one-way ANOVA followed by Fishers LSD for pairwise comparison test, *p<0.05, p<0.01, *p<0.001, ****p<0.0001. Data are expressed as mean±sem.

FIG. 60B is a graph showing percentage change of the number of neurites per neuron after psilocin treatment at day 3 compared to the control group in human iPSC cells (induced pluripotent stem cells). Statistical significance was determined using one-way ANOVA followed by Fishers LSD for pairwise comparison test, *p<0.05, p<0.01, *p<0.001, ****p<0.0001. Data are expressed as mean±sem.

Figure 61:
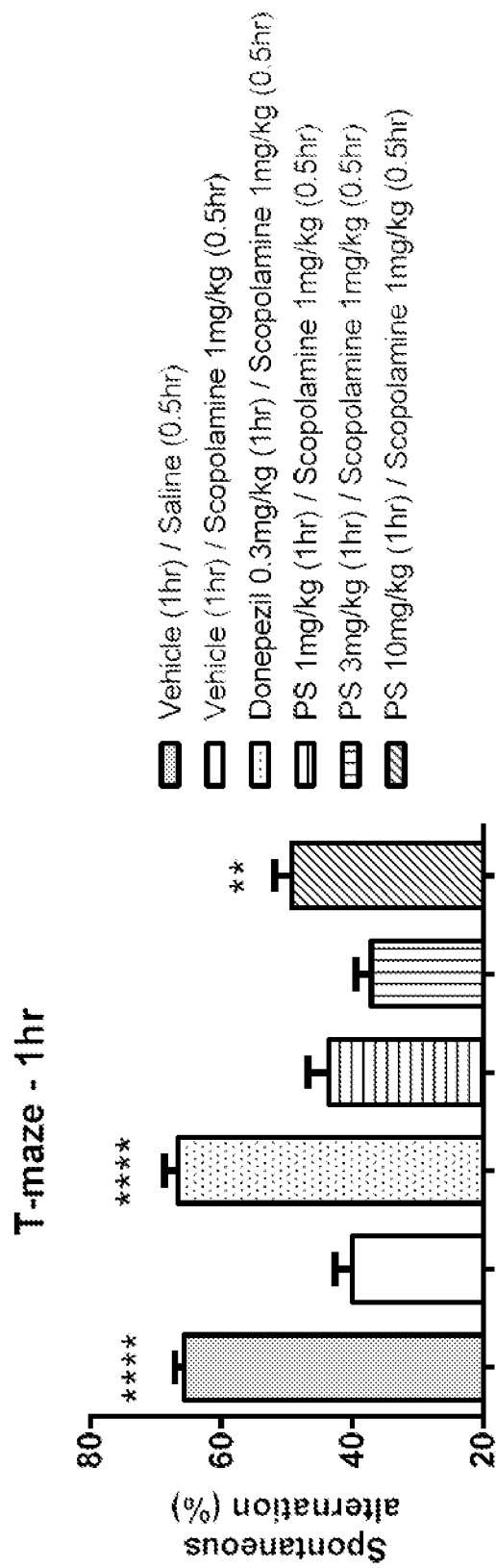

FIG. 61 is a graph showing percentage change of spontaneous alternations taken by mice in a T-maze 1 hour after psilocybin treatment compared to the Vehicle/Scopolamine treated group. Statistical significance was determined using one-way ANOVA followed by Fishers LSD for pairwise comparison test, *p<0.05, p<0.01, *p<0.001, ****p<0.0001. Data are expressed as mean±sem.

Figure 62:
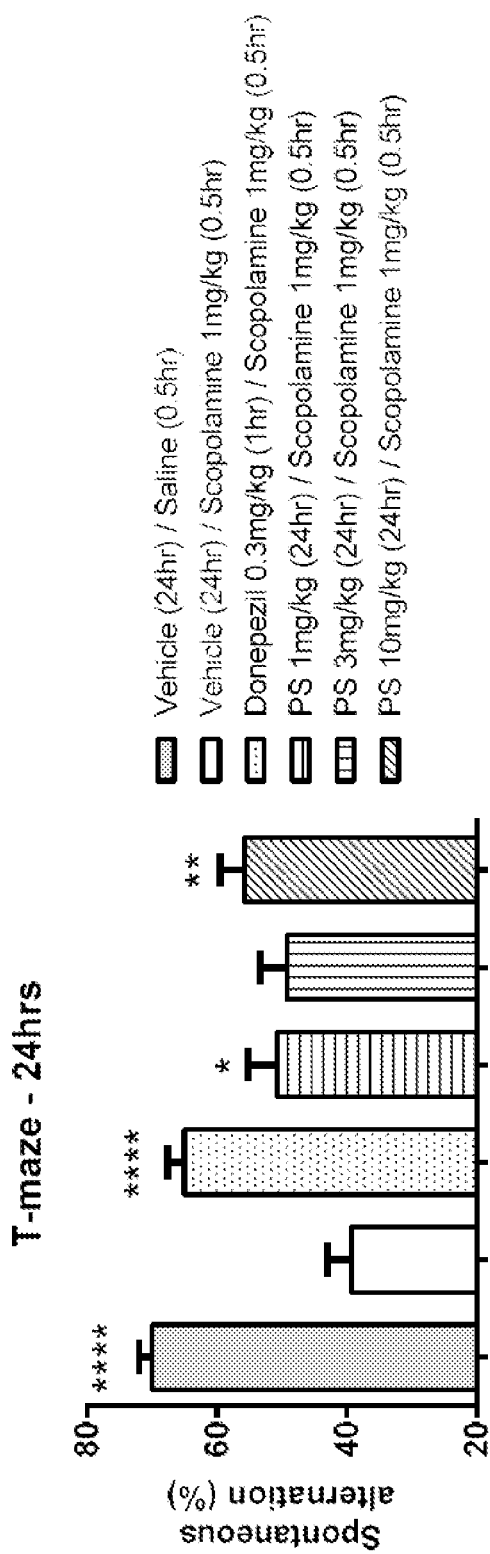

FIG. 62 is a graph showing percentage change of spontaneous alternations taken by mice in a T-maze 24 hours after psilocybin treatment compared to the Vehicle/Scopolamine treated group. Statistical significance was determined using one-way ANOVA followed by Fishers LSD for pairwise comparison test, *p<0.05, p<0.01, *p<0.001, ****p<0.0001. Data are expressed as mean±sem.

Figure 63:
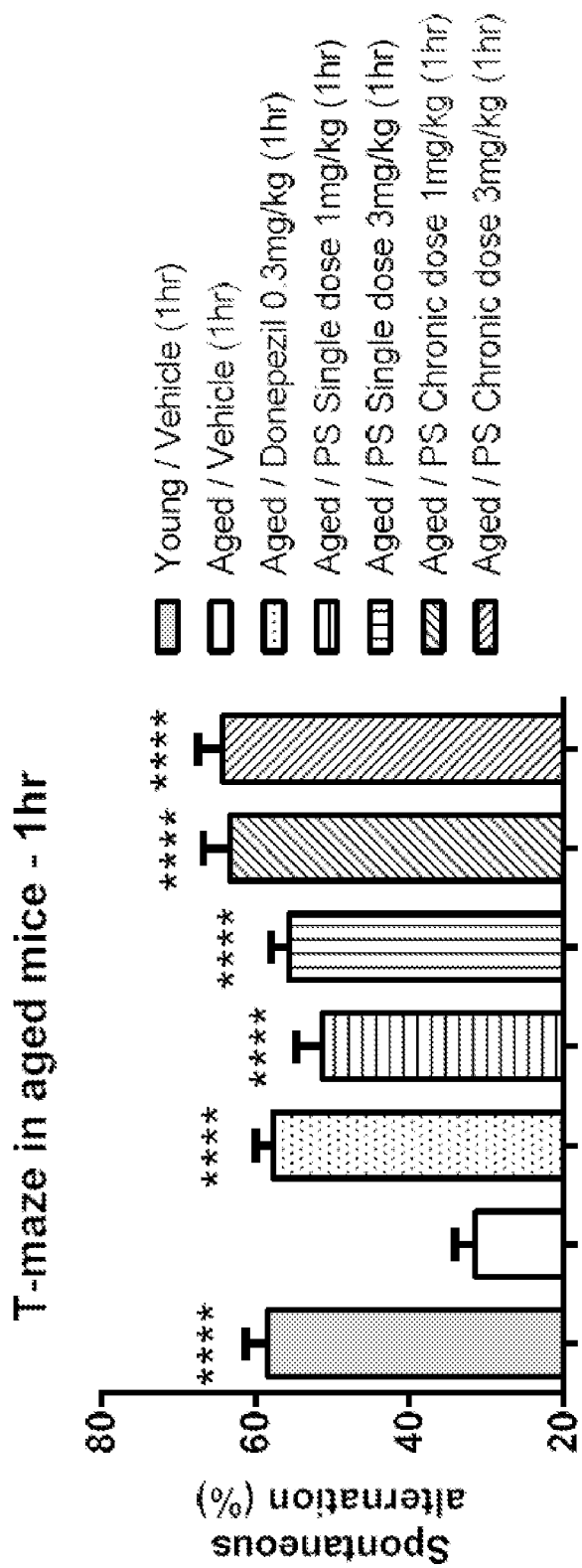

FIG. 63 is a graph showing percentage change of spontaneous alternations taken by aged mice in a T-maze 1 hour after a single or chronic dose psilocybin treatment compared to the Vehicle/Scopolamine treated group. Statistical significance was determined using one-way ANOVA followed by Fishers LSD for pairwise comparison test, *p<0.05, p<0.01, *p<0.001, ****p<0.0001. Data are expressed as mean±sem.

Figure 64:
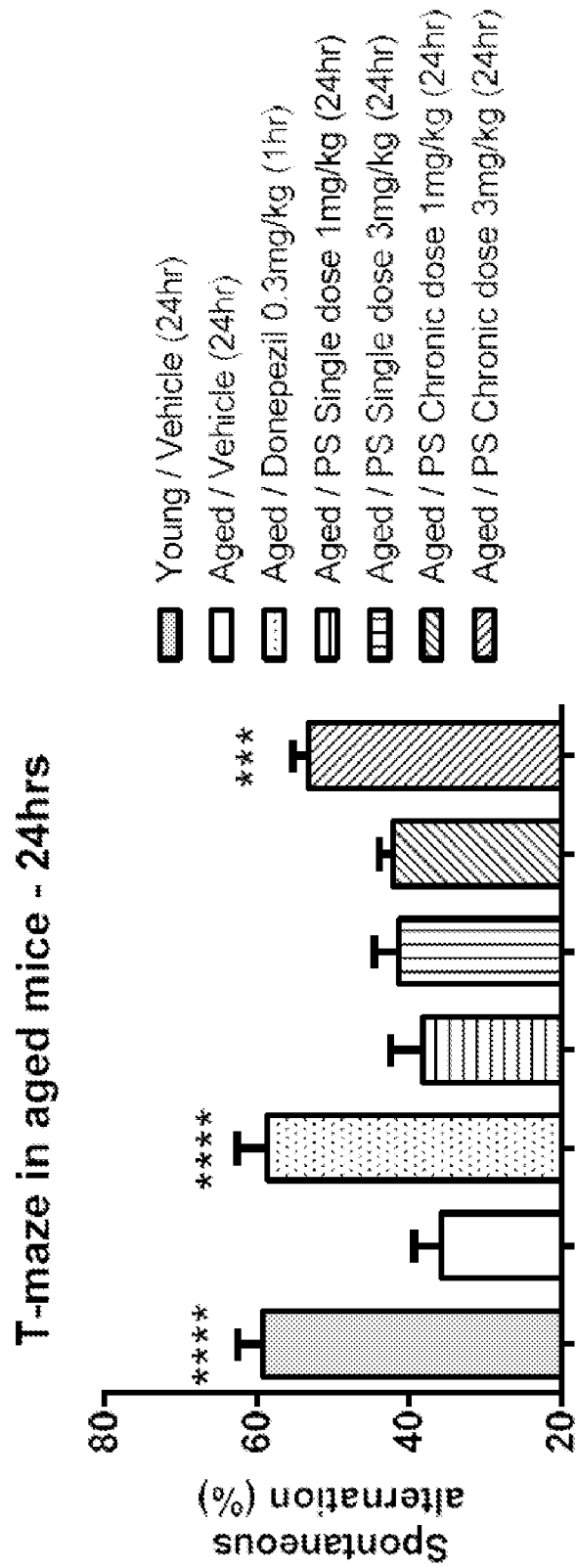

FIG. 64 is a graph showing percentage change of spontaneous alternations taken by aged mice in a T-maze 24 hours after a single or chronic dose psilocybin treatment compared to the Vehicle/Scopolamine treated group. Statistical significance was determined using one-way ANOVA followed by Fishers LSD for pairwise comparison test, *p<0.05, p<0.01, *p<0.001, ****p<0.0001. Data are expressed as mean±sem.

Figure 65:
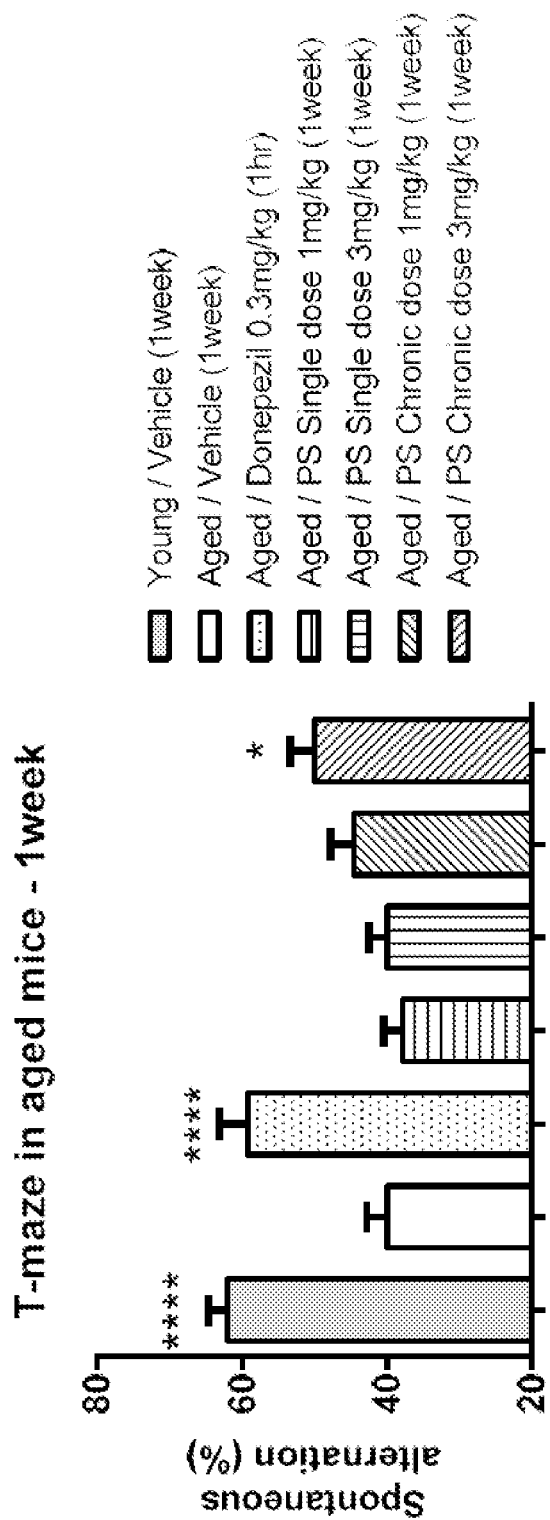

FIG. 65 is a graph showing percentage change of spontaneous alternations taken by aged mice in a T-maze 1 week after a single or chronic dose psilocybin treatment compared to the Vehicle/Scopolamine treated group. Statistical significance was determined using one-way ANOVA followed by Fishers LSD for pairwise comparison test, *p<0.05, p<0.01, *p<0.001, ****p<0.0001. Data are expressed as mean±sem.

DETAILED DESCRIPTION

Definitions

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

The singular forms "a," "an" and "the" are intended to include the plural forms as well, unless the context clearly indicates otherwise.

Furthermore, the term "about" as used herein when referring to a measurable value such as a dose, time, temperature, and the like, is meant to encompass variations of ±20%, ±10%, ±5%, ±1%, ±0.5%, or even ±0.1% of the specified amount.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless the context indicates otherwise, it is specifically intended that the various features described herein can be used in any combination.

As used herein, the terms "reduce," "decrease," "lessen" and similar terms mean a decrease of at least about 10%, about 15%, about 20%, about 25%, about 35%, about 50%, about 75%, about 80%, about 85%, about 90%, about 95%, about 97%, or more.

As used herein, the terms "improve," "increase," "enhance," and similar terms indicate an increase of at least about 10%, about 15%, about 20%, about 25%, about 50%, about 75%, about 100%, about 150%, about 200%, about 300%, about 400%, about 500%, or more.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

As used herein, "substantially absent" with reference to XRPD diffractogram peak means the peak has a relative intensity compared to a reference peak present in the diffractogram of less than about 5%, less than about 4%, less than about 3%, less than about 2%, or less than about 1% of the intensity of the reference peak, or that the peak is not detectable.

XRPD diffractograms and XRPD peak positions may be acquired using Cu Kα radiation.

DSC thermograms and TGA thermograms may be acquired using a heating rate of 20° C./min.

As used herein, the term "diffusion tensor imaging" or "DTI" refers to a technique that detects how water travels along the white matter tracts in the brain. In some embodiments, DTI is used to characterize microstructural changes associated with mental disorders (e.g., major depressive disorder) and/or the response to treatment in subjects with mental disorders.

All disease and disorders listed herein are defined as described in the Diagnostic and Statistical Manual of Mental Disorders (DSM-5), published by the American Psychiatric Association, or in International Classification of Diseases (ICD), published by the World Health Organization.

As used herein the term "subject" and "patient" are used interchangeably.

As used herein, "treating" and like terms refer to reducing the severity and/or frequency of one or more symptoms, eliminating one or more symptoms and/or the underlying cause of said symptoms, reducing the frequency or likelihood of one or more symptoms and/or their underlying cause, delaying, preventing and/or slowing the progression of diseases and/or disorders and improving or remediating damage caused, directly or indirectly, by the diseases and/or disorders.

As used herein, "therapeutically-effective dose" means a dose sufficient to achieve the intended therapeutic purpose, such as, to alleviate a sign or symptom of a disease or disorder in a subject.

As used herein a "precursor" and/or "derivative" of psilocybin includes, but is not limited to, prodrugs of psilocybin, prodrugs of an active metabolite of psilocybin, and an active metabolite of psilocybin.

As used herein, a subject that is "psilocybin-naïve" has not previously been exposed to psilocybin.

As used herein, the following Medical Dictionary for Regulatory Activities (MedDRA) terms are considered to be adverse events that are psychedelic in nature: altered mood, altered state of consciousness, autoscopy, delusional perception, disinhibition, dissociation, dissociative identity disorder, dreamy state, emotional disorder, euphoric mood, feeling abnormal, hallucination, hyperacusis, hyperaesthesia, hypoaesthesia, illusion, paranoia, parosmia, photophobia, sensory disturbance, time perception altered, thinking abnormal, synaesthesia, substance-induced psychotic distress, and somatic hallucination.

As used herein, a therapy or therapeutic that is administered "concurrently" with another drug is administered within 1 day of the other drug. In some embodiments, a therapy or therapeutic that is administered concurrently with another drug is administered at about the same time, within about 5 minutes, within about 10 minutes, within about 15 minutes, within about 20 minutes, within about 30 minutes, within about 45 minutes, within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours of administration of the other drug.

Psilocybin

In some embodiments, a method of treatment comprises the administration of a therapeutically effective amount of psilocybin, a prodrug of psilocybin, an active metabolite of psilocybin, or a prodrug of an active metabolite of psilocybin to a subject in need thereof as described herein. In some embodiments, a method of treatment comprises the administration of a therapeutically effective amount of psilocybin as described herein. In some embodiments, a method of treatment comprises the administration of a therapeutically effective amount of psilocin as described herein. Some embodiments comprise psilocybin, a prodrug of psilocybin, an active metabolite of psilocybin, or a prodrug of an active metabolite of psilocybin for use in the treatment of an indication as described herein. Some embodiments comprise psilocybin for use in the treatment of an indication as described herein. Some embodiments comprise psilocin for use in the treatment of an indication as described herein. Some embodiments comprise the use of psilocybin, a prodrug of psilocybin, an active metabolite of psilocybin, or a prodrug of an active metabolite of psilocybin in the manufacture of a medicament for the treatment of an indication as described herein.

Figure 1:
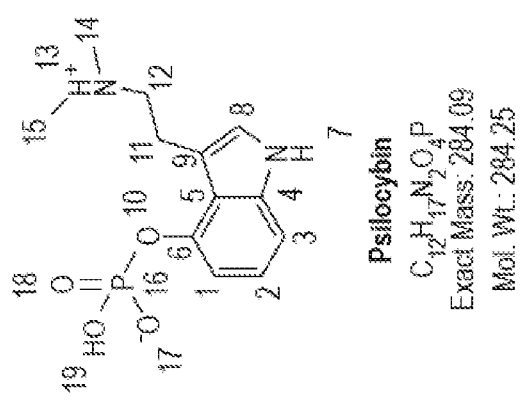
FIG. 1 is a numbered structural formula of psilocybin.

A numbered structural formula of psilocybin is shown in FIG. 1. Novel polymorphs and hydrates of psilocybin, along with the preparation and formulations thereof are disclosed in U.S. Application No. US2019/0119310 A1, which is incorporated by reference herein in its entirety. US2019/0119310 discloses a number of formulations and the challenges of formulating psilocybin due to e.g. its hygroscopicity and poor flow characteristics. US2019/0119310 also discloses the importance of a controlled aqueous crystallisation process.

In some embodiments, the psilocybin comprises crystalline psilocybin in the form Polymorph A or Polymorph A', as described herein, the crystalline psilocybin exhibits peaks in an X-ray powder diffraction (XRPD) diffractogram at 11.5, 12.0 and 14.5°2θ±0.1°2θ. In some embodiments, the crystalline psilocybin further exhibits at least one peak in the XRPD diffractogram at 19.7, 20.4, 22.2, 24.3 or 25.7°2θ±0.1°2θ. Illustrative XRPD diffractograms are provided as FIGS. 2A and 2B. In some embodiments, the crystalline psilocybin exhibits an endothermic event in a DSC thermogram having a first onset temperature of between 145° C. and 165° C. and a second onset temperature of between 205° C. and 220° C. Illustrative DSC thermograms are provided as FIGS. 3A and 3B.

Polymorph A

Figure 2A:
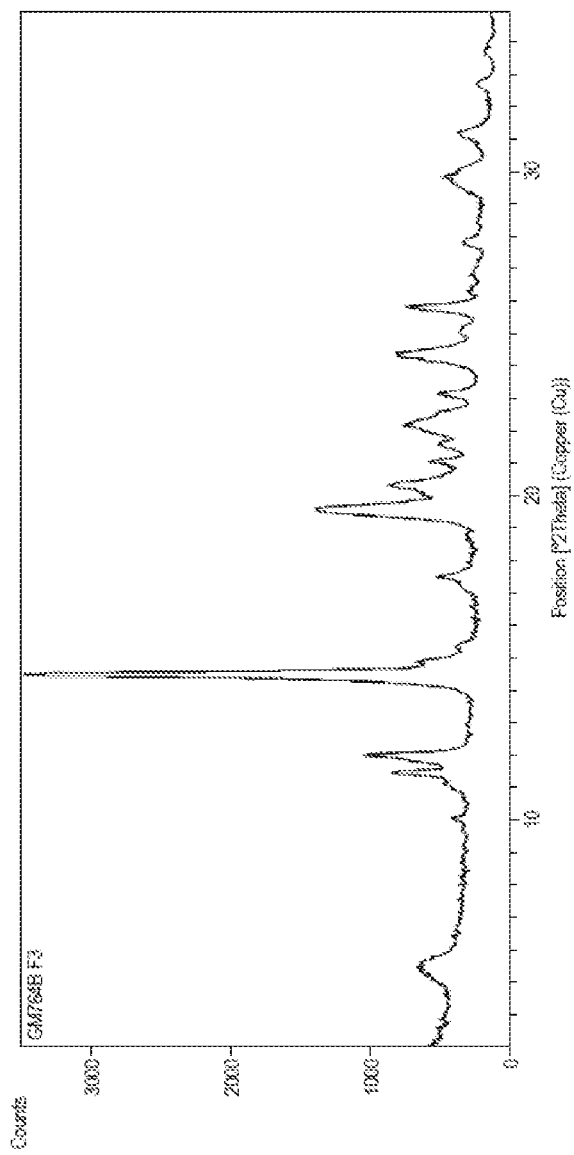
FIG. 2a is a XRPD diffractogram of Polymorph A (GM764B).
Figure 3A:
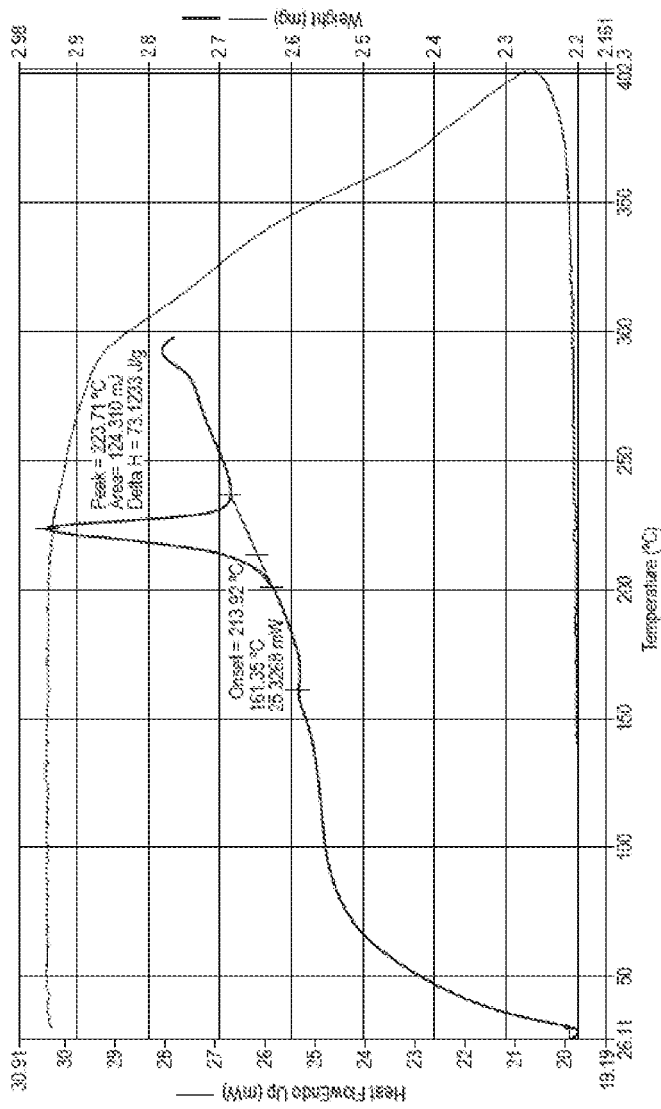
FIG. 3a is a DSC and TGA thermograph of Polymorph A (GM764B).

In some embodiments, the present disclosure provides crystalline psilocybin in the form Polymorph A, characterized by one or more of:
peaks in an XRPD diffractogram at 11.5, 12.0, 14.5, and 17.5, °2θ±0.1°2θ;
peaks in an XRPD diffractogram at 11.5, 12.0, 14.5 and 17.5, °2θ±0.1°2θ, further characterized by at least one further peak at 19.7, 20.4, 22.2, 24.3 or 25.7°2θ±0.1°2θ;
an XRPD diffractogram as substantially illustrated in FIG. 2a; or
an endothermic event in a DSC thermogram having an endothermic event in a DSC thermogram having a first onset temperature of between 145° C. and 165° C. and a second onset temperature of between 205° C. and 220° C. substantially as illustrated in FIG. 3a.

In some embodiments, the peak at 17.5°2θ±0.1°2θ has a relative intensity compared to the peak at 14.5°2θ±0.1°2θ of at least 5%, at least 6%, at least 7%, at least 8%, at least 9%, or at least 10%.

In some embodiments, the present disclosure provides crystalline psilocybin in the form Polymorph A, characterized by one or more of:
peaks in an XRPD diffractogram at 11.5, 12.0, 14.5, and 17.5, °2θ±0.2°2θ;
peaks in an XRPD diffractogram at 11.5, 12.0, 14.5 and 17.5, °2θ±0.2°2θ, further characterized by at least one further peak at 19.7, 20.4, 22.2, 24.3 or 25.7°2θ±0.2°2θ;
an XRPD diffractogram as substantially illustrated in FIG. 2a; or
an endothermic event in a DSC thermogram having an endothermic event in a DSC thermogram having a first onset temperature of between 145° C. and 165° C. and a second onset temperature of between 205° C. and 220° C. substantially as illustrated in FIG. 3a.

In some embodiments, the crystalline psilocybin of Polymorph A exhibits an XRPD diffractogram having at least 3, 4, 5, 6, 7, 8, 9, 10, 11, 12, 13, 14, 15, 16, or 17 of the peaks listed in Table 1, or equivalent peaks within about ±0.1°2θ of the peaks listed in Table 1. In some embodiments, the crystalline psilocybin of Polymorph A exhibits an XRPD diffractogram having at least 3, 4, 5, 6, 7, 8, 9, 10, 11, 12, 13, 14, 15, 16, or 17 of the peaks listed in Table 1, or equivalent peaks within about ±0.2°2θ of the peaks listed in Table 1. In some embodiments, Polymorph A exhibits a peak at 17.5°2θ±0.1°2θ that is substantially absent in Polymorph A'. In some embodiments, Polymorph A exhibits a peak at 17.5°2θ±0.2°2θ that is substantially absent in Polymorph A'.

TABLE 1

XRPD peak positions for Polymorph A

| Position [°2Th.] | Relative Intensity [%] |
|---|---|
| 5.6 | 8.42 |
| 11.5 | 13.05 |
| 12.0 | 26.45 |
| 14.5 | 100.00 |
| 17.5 | 10.71 |
| 19.7 | 37.29 |
| 20.4 | 20.06 |
| 22.2 | 17.83 |
| 23.2 | 6.99 |
| 24.3 | 17.93 |
| 25.7 | 16.40 |
| 26.8 | 3.15 |
| 27.8 | 4.54 |
| 29.7 | 9.53 |
| 31.2 | 6.51 |
| 32.6 | 2.45 |
| 33.7 | 1.75 |

In some embodiments, crystalline psilocybin Polymorph A exhibits XRPD diffractogram peaks at 11.5, 12.0, 14.5, and 17.5°2θ±0.1°2θ. In some embodiments, crystalline psilocybin Polymorph A exhibits at least one additional peak appearing at 19.7, 20.4, 22.2, 24.3 or 25.7°2θ±0.1°2θ. In some embodiments, crystalline psilocybin Polymorph A exhibits at least two additional peaks appearing at 19.7, 20.4, 22.2, 24.3 or 25.7°2θ±0.1°2θ. In some embodiments, crystalline psilocybin Polymorph A exhibits at least three additional peaks appearing at 19.7, 20.4, 22.2, 24.3 or 25.7°2θ±0.1°2θ. In some embodiments, crystalline psilocybin Polymorph A exhibits an XRPD diffractogram substantially the same as the XRPD diffractogram shown in FIG. 2A.

In some embodiments, crystalline psilocybin Polymorph A is characterized by XRPD diffractogram peaks at 14.5 and 17.5°2θ±0.1°2θ with the peak at 17.5°2θ having an intensity which is at least about 5%, at least about 6%, at least about 7%, at least about 8%, at least about 9%, or at least about 10% of the intensity of the peak at 14.5°2θ.

In some embodiments, the crystalline psilocybin Polymorph A exhibits no peak at 10.1—that is, the peak at 10.1 is absent or substantially absent.

In some embodiments, crystalline psilocybin Polymorph A is characterized by an endothermic event in a DSC thermogram having a first onset temperature of between 145° C. and 165° C. such as between 145 and 160° C., or such as between 145 and 155° C. and a second onset temperature of between 205 and 220° C., such as between 210 and 220° C., such as between 210 and 218° C., or such as between 210 and 216° C. In some embodiments, crystalline psilocybin Polymorph A exhibits an endothermic event in a DSC thermogram having an onset temperature of between about 205 and about 220° C., between about 210 and about 220° C., between about 210 and about 218° C., or between about 210 and about 216° C. In some embodiments, crystalline psilocybin Polymorph A further exhibits an endothermic event in the DSC thermogram having an onset temperature of between about 145 and about 165° C., between about 145 and about 160° C., or between about 145 and about 155° C. In some embodiments, crystalline psilocybin Polymorph A exhibits an endothermic event having an onset temperature of between about 205 and about 220° C., between about 210 and about 220° C., between about 210 and about 218° C., or between about 210 and about 216° C.; and an endothermic event having an onset temperature of between about 145 and about 165° C., between about 145 and about 160° C., between about 145 and about 155° C., in a DSC thermogram. In some embodiments, crystalline psilocybin Polymorph A exhibits a DSC thermogram substantially the same as the DSC thermogram in FIG. 3A.

In some embodiments, crystalline psilocybin Polymorph A exhibits a water content of <0.5% w/w, <0.4% w/w, <0.3% w/w, <0.2% w/w, or <0.1% w/w. The water content of a crystalline compound can be determined by known methods, for example Karl Fischer Titration. In some embodiments, crystalline psilocybin Polymorph A exhibits <0.5% w/w loss, <0.4% w/w, <0.3% w/w, <0.2% w/w, or <0.1% w/w in the TGA thermogram between ambient temperature, e.g., about 25° C., and 200° C. In some embodiments, crystalline psilocybin Polymorph A loses less than 2% by weight, less than 1% by weight, or than 0.5% by weight in a loss on drying test, e.g., a loss on drying test performed at 70° C.

In some embodiments, crystalline psilocybin Polymorph A is a highly pure crystalline form of Polymorph A, for example, the in a loss on drying test psilocybin comprises at least 90%, at least 95%, at least 99%, or at least 99.5% by weight crystalline psilocybin of Polymorph A.

In some embodiments, crystalline psilocybin Polymorph A is a white to off-white solid.

In some embodiments, crystalline psilocybin Polymorph A is chemically pure, for example the psilocybin has a chemical purity of greater than 97%, 98%, or 99% by HPLC. In some embodiments, crystalline psilocybin Polymorph A has no single impurity of greater than 1%, greater than 0.5%, greater than 0.4%, greater than 0.3%, or greater than 0.2% e.g., the impurity phosphoric acid as measured by $^{31}$P NMR, or the impurity psilocin measured by HPLC. In some embodiments, crystalline psilocybin Polymorph A has a chemical purity of greater than 97 area %, greater than 98 area %, or greater than 99 area % by HPLC. In some embodiments, crystalline psilocybin Polymorph A has no single impurity greater than 1 area %, greater than 0.5 area %, greater than 0.4%, greater than 0.3%, or greater than 0.2% as measured by HPLC. In some embodiments, crystalline psilocybin Polymorph A does not contain psilocin at a level greater than 1 area %, greater than 0.5 area %, greater than 0.4%, greater than 0.3%, or greater than 0.2% as measured by HPLC. In some embodiments, crystalline psilocybin Polymorph A does not contain phosphoric acid at a level greater than 1 weight %, greater than 0.5 weight %, greater than 0.4 weight %, 0.3 weight %, or greater than 0.2 weight %, as measured by $^{31}$P NMR. In some embodiments, crystalline psilocybin Polymorph A has a chemical assay of at least 95 weight %, at least 96 weight %, or at least 98 weight %.

Methods of Manufacturing Crystalline Psilocybin Polymorph A

In another embodiment, the disclosure provides a method for large scale manufacture of psilocybin characterized in that the method comprises subjecting psilocybin to a water crystallization step, with controlled drying, to produce crystalline psilocybin Polymorph A.

In another embodiment, the disclosure provides a method for large scale manufacture of psilocybin characterized in that the method comprises subjecting psilocybin to a water crystallization step, with controlled drying, to produced crystalline psilocybin Polymorph A with an XRPD diffractogram as illustrated in FIG. 2A and a DSC and TGA thermograph as illustrated in FIG. 3A. In another embodiment, the disclosure provides a method for large-scale manufacture of psilocybin characterized in that the method comprises subjecting psilocybin to a water crystallization step, with controlled drying, to produce a high purity crystalline psilocybin—Polymorph A with an XRPD diffractogram as illustrated in FIG. 2A and a DSC thermograph as illustrated in FIG. 3A.

In another embodiment of the disclosure, psilocybin is recrystallized in about 10-20 volumes of water, heated with agitation to a temperature of at least 70° C., polish filtered with a suitable cut off (typically, below 5 μm), seeded at a temperature of about 70° C., and cooled in a controlled manner to about 5° C. over a period of more than 2 hours.

In some embodiments, psilocybin recrystallization comprises controlled cooling which drops the temperature by about 5° C.-15° C. an hour, more preferably about 10° C. an hour. In certain embodiments, the polish filter step is done through an appropriately sized filter, such as, but not limited to, a 1.2 μm in line filter.

In some embodiments, agitation is by stirring at about 400-500 rpm, typically about 450 rpm.

In some embodiments, the psilocybin is dissolved in water heated to no more than 90° C. In some embodiments the psilocybin is dissolved in water heated to no more than 85° C. Without being bound by any particular mechanism, this dissolution step is intended to solubilize psilocybin whilst also minimizing the formation of hydrolysis products.

In some embodiments, the psilocybin solution is stirred to speed the solubilization and reduce the time that the solution is at a high temperature, namely one at or around 80° C., or higher.

In some embodiments, the seed is psilocybin Hydrate A. In one embodiment, 0.1% weight or less of seed is added to the process.

In some embodiments, the psilocybin the crystalline psilocybin is isolated by vacuum filtration.

In some embodiments, the isolated crystals are dried in vacuo at a temperature of at least 30° C., such as between 30 and 50° C., or such as between 40 and 50° C. In some embodiment, the isolated crystals are dried in vacuo for at least 10 hours, such as between 12 and 18 hours, or such as about 30 hours. In some embodiments, the isolated crystals are dried in vacuo at a temperature of at least 30° C., such as between 30 and 50° C., or such as between 40 and 50° C., for at least 10 hours, such as between 12 and 18 hours, or such as about 30 hours. In some embodiments, the isolated crystals are dried until the isolated crystals lose less than 2% weight in a loss on drying test, such as less than 0.5% weight.

In some embodiments, the isolated crystals are washed, several times, in water and dried in vacuo at about 50° C. for at least 12 hours.

In some embodiments, the crystals obtained are typically relatively large (range 50 to 200 microns) and uniform when viewed under the microscope×10.

In contrast, crystals obtained without controlled cooling which are much smaller in size (typically 5 to 50 microns) when viewed under the microscope×10.

In some embodiments, there is provided Psilocybin obtained by the method of crystallization described herein.

In some embodiments, there is provided a pharmaceutical formulation comprising psilocybin polymorph A obtained by the method of crystallization described herein.

In some embodiments, psilocybin manufactured prior to crystallization may be produced using one of the following methods: synthetic or biological, e.g. by fermentation or obtained by extraction from mushrooms. In some embodiments, psilocybin manufactured prior to crystallization is manufactured according to all or some of the methods described in U.S Application No. US2019/0119310 A1, which is incorporated by reference herein in its entirety.

Polymorph A'

Figure 2B:
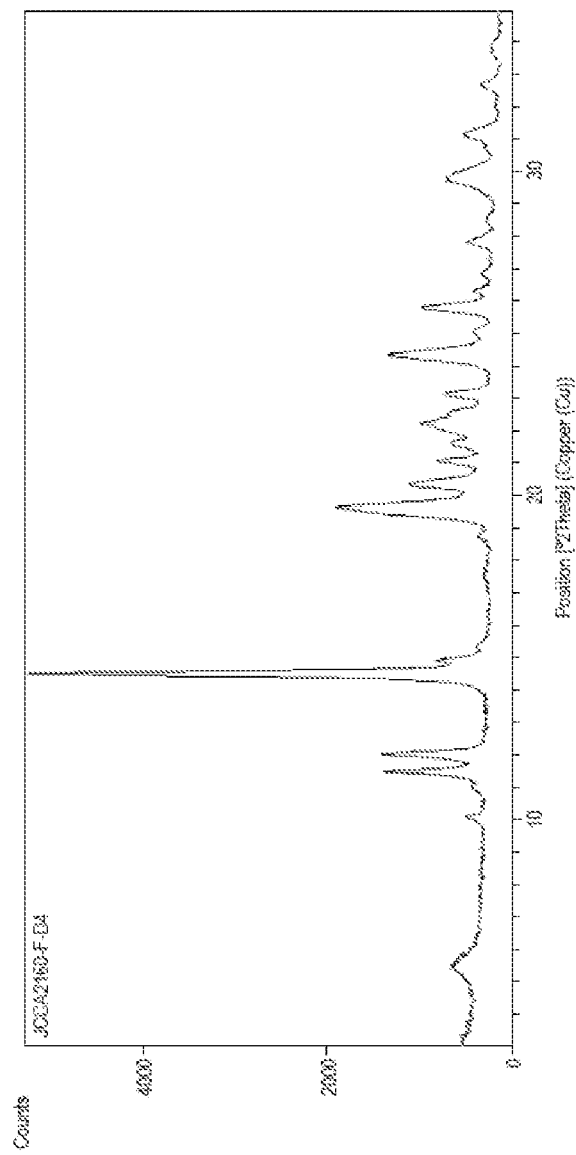
FIG. 2b is a XRPD diffractogram of Polymorph A' (JCCA2160F).
Figure 3B:
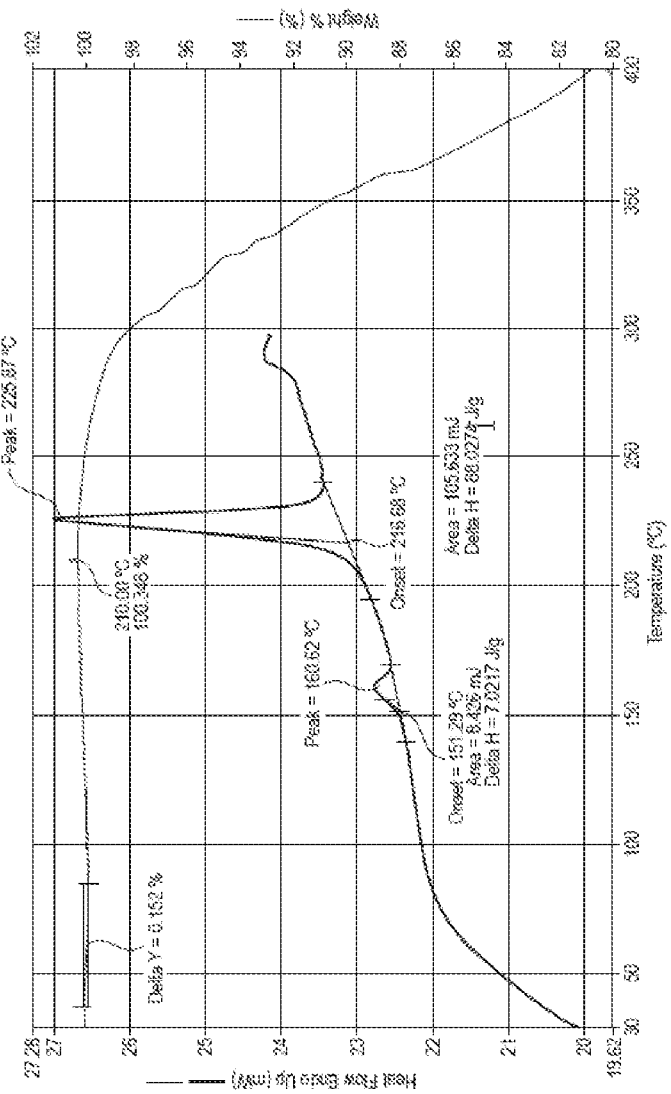
FIG. 3b is a DSC and TGA thermograph of Polymorph A' (JCCA2160F).

The present disclosure provides crystalline psilocybin in the form of Polymorph A', characterized by one or more of:

(i) peaks in an XRPD diffractogram at 11.5, 12.0 and 14.5°2θ±0.1°2θ, but absent or substantially absent of a peak at 17.5°2θ±0.1°2θ;

(ii) peaks in an XRPD diffractogram at 11.5, 12.0 and 14.5°2θ±0.1°2θ, but absent or substantially absent of a peak at 17.5°2θ±0.1°2θ, further characterized by at least one further peak at 19.7, 20.4, 22.2, 24.3 or 25.7°2θ±0.1°2θ;

(iii) an XRPD diffractogram as substantially illustrated in FIG. 2B; or (iv) an endothermic event in a DSC thermogram having a first onset temperature of between 145° C. and 165° C. and a second onset temperature of between 205° C. and 220° C. substantially as illustrated in FIG. 3B.

In some embodiments, the crystalline psilocybin comprises crystalline psilocybin Polymorph A'. Crystalline psilocybin Polymorph A' exhibits peaks in an XRPD diffractogram at 11.5, 12.0 and 14.5°2θ±0.1°2θ, but absent or substantially absent of a peak at 17.5°2θ±0.1°2θ.

In some embodiments, crystalline psilocybin Polymorph A' further exhibits 1, 2, 3, 4, or 5 peaks selected from 19.7, 20.4, 22.2, 24.3 or 25.7°2θ±0.1°2θ. An illustrative XRPD diffractogram for Polymorph A' is provided as FIG. 2B. An illustrative DSC thermogram having an onset temperature of between 205 and 220° C. for Polymorph A' is provided as FIG. 3B. In some embodiments, psilocybin Polymorph A' exhibits an XRPD diffractogram as summarized in Table 2. In some embodiments, crystalline psilocybin Polymorph A' exhibits at least 3, 4, 5, 6, 7, 8, 9, 10, 11, 12, 13, 14, 15, 16, 17, 18, 19, 20, 21, 22, 23, 24, or 25 peaks listed of Table 2 or equivalent peaks within about ±0.1°2θ, and absent or substantially absent peak at 17.5°2θ±0.1°2θ.

TABLE 2

XRPD peak positions for Polymorph A'

| Position [°2Th.] | Relative Intensity [%] |
|---|---|
| 5.5 | 4.89 |
| 10.1 | 4.09 |
| 11.5 | 22.05 |
| 12.0 | 22.77 |
| 14.5 | 100.00 |
| 14.9 | 11.29 |
| 17.5 | 1.08 |
| 18.7 | 2.44 |
| 19.4 | 23.02 |
| 19.6 | 33.70 |
| 20.3 | 17.01 |
| 21.1 | 12.08 |
| 21.6 | 8.51 |
| 22.2 | 15.54 |
| 22.6 | 8.78 |
| 23.1 | 10.11 |
| 24.3 | 21.83 |
| 25.1 | 4.36 |
| 25.8 | 15.40 |
| 26.3 | 4.28 |
| 26.8 | 2.86 |
| 27.8 | 5.96 |
| 28.6 | 1.91 |
| 29.7 | 10.56 |
| 31.1 | 7.35 |
| 32.6 | 3.72 |
| 33.8 | 1.54 |

In some embodiments, crystalline psilocybin Polymorph A' exhibits XRPD diffractogram peaks at 11.5, 12.0, and 14.5°2θ±0.1°2θ but substantially absent of a peak at 17.5°2θ±0.1°2θ. In some embodiments, crystalline psilocybin Polymorph A' further exhibits at least one additional peak appearing at 19.7, 20.4, 22.2, 24.3, or 25.7°2θ±0.1°2θ. In some embodiments, crystalline psilocybin Polymorph A' exhibits at least two additional peaks appearing at 19.7, 20.4, 22.2, 24.3, or 25.7°2θ±0.1°2θ. In some embodiments, crystalline psilocybin Polymorph A' exhibits and is distinguished from Polymorph A by the presence of a peak appearing at 10.1°2θ±0.1°2θ. In yet a further embodiment, crystalline psilocybin Polymorph A' exhibits an XRPD diffractogram substantially the same as the XRPD diffractogram shown in FIG. 2B.

In some embodiments, crystalline psilocybin Polymorph A' exhibits XRPD diffractogram peaks at 14.5 and 17.5°2θ±0.1°2θ, wherein the intensity of the peak at 17.5°2θ is less than 5%, less than 4%, less than 3%, less than 2%, or less than 1% of the intensity of the peak at 14.5°2θ.

In some embodiments, crystalline psilocybin Polymorph A' exhibits XRPD diffractogram peaks at 10.1 and 14.5°2θ±0.1°2θ, wherein the intensity of the peak at 10.1°2θ is at least 1%, at least 2%, at least 3%, or at least 4% of the intensity of the peak at 14.5°2θ.

In some embodiments, crystalline psilocybin Polymorph A' is characterized by an endothermic event in a DSC thermogram having a first onset temperature of between 145° C. and 165° C. such as between 145 and 160° C., or such as between 145 and 155° C. and a second onset temperature of between 205 and 220° C., such as between 210 and 220° C., such as between 210 and 218° C., or such as between 210 and 216° C. In some embodiments, crystalline psilocybin Polymorph A' is characterized by an endothermic event in a DSC thermogram having an onset temperature of between about 205 and about 220° C., between about 210 and about 220° C., between about 210 and about 218° C., or between about 210 and about 216° C.

In some embodiments, crystalline psilocybin Polymorph A' exhibits an endothermic event in the DSC thermogram having an onset temperature of between about 145 and about 165° C., between about 145 and about 160° C., or between about 145 and about 155° C. In some embodiments, crystalline psilocybin Polymorph A' exhibits an endothermic event having an onset temperature of between about 205 and about 220° C., between about 210 and about 220° C., between about 210 and about 218° C., or between about 210 and about 216° C., and an endothermic event having an onset temperature of between about 145 and about 165° C., between about 145 and about 160° C., or between about 145 and about 155° C., in a DSC thermogram. In some embodiments, crystalline psilocybin Polymorph A' exhibits a DSC thermogram substantially the same as the DSC thermogram in FIG. 3B.

In some embodiments, crystalline psilocybin Polymorph A' exhibits a water content of <0.5% w/w, <0.4% w/w, <0.3% w/w, <0.2% w/w, or <0.1% w/w. Methods to determine the water content of a crystalline compound are known, for example Karl Fischer Titration. In some embodiments, crystalline psilocybin Polymorph A' exhibits <0.5% w/w loss, <0.4% w/w, <0.3% w/w, <0.2% w/w, <0.1% w/w in the TGA thermogram between ambient temperature, e.g., 25° C., and 200° C. In some embodiments, crystalline psilocybin Polymorph A' loses less than 2% by weight, less than 1% by weight, or less than 0.5% by weight in a loss on drying test. In some embodiments, the loss on drying test is performed at 70° C.

In some embodiments, crystalline psilocybin Polymorph A' is a highly pure crystalline form of Polymorph A'. In some embodiments, the crystalline psilocybin comprises at least 90%, 95%, 99%, or 99.5% by weight of Polymorph A'.

In some embodiments, crystalline psilocybin Polymorph A's is a white to off white solid.

In some embodiments, crystalline psilocybin Polymorph A' is chemically pure, for example the psilocybin has a chemical purity of greater than 97%, greater than 98%, or than 99% by HPLC. In some embodiments, crystalline psilocybin Polymorph A' has no single impurity of greater than 1% or greater than 0.5%, e.g., the impurity phosphoric acid as measured by 31P NMR or the impurity psilocin as measured by HPLC. In some embodiments, crystalline psilocybin Polymorph A' has a chemical purity of greater than 97 area %, greater than 98 area %, or greater than 99 area % by HPLC. In some embodiments, crystalline psilocybin Polymorph A' has no single impurity greater than 1 area % or greater than 0.5 area %, e.g., as measured by HPLC. In some embodiments, crystalline psilocybin Polymorph A' does not contain psilocin at a level greater than 1 area % or greater than 0.5 area % as measured by HPLC. In some embodiments, crystalline psilocybin Polymorph A' does not contain phosphoric acid at a level greater than 1 weight % or greater than 0.5 weight % as measured by 31P NMR. In some embodiments, crystalline psilocybin Polymorph A' has a chemical assay of at least 95 weight %, at least 96 weight %, or at least 98 weight %.

In some embodiments, crystalline psilocybin Polymorph A' is chemically pure, for example the psilocybin has a chemical purity of greater than 97%, 98%, or 99% by HPLC. In some embodiments, crystalline psilocybin Polymorph A' has no single impurity of greater than 1%, greater than 0.5%, greater than 0.4%, greater than 0.3%, or greater than 0.2% e.g., the impurity phosphoric acid as measured by 31P NMR, or the impurity psilocin measured by HPLC. In some embodiments, crystalline psilocybin Polymorph A' has a chemical purity of greater than 97 area %, greater than 98 area %, or greater than 99 area % by HPLC. In some embodiments, crystalline psilocybin Polymorph A' has no single impurity greater than 1 area %, greater than 0.5 area %, greater than 0.4%, greater than 0.3%, or greater than 0.2% as measured by HPLC. In some embodiments, crystalline psilocybin Polymorph A' does not contain psilocin at a level greater than 1 area %, greater than 0.5 area %, greater than 0.4%, greater than 0.3%, or greater than 0.2% as measured by HPLC. In some embodiments, crystalline psilocybin Polymorph A' does not contain phosphoric acid at a level greater than 1 weight %, greater than 0.5 weight %, greater than 0.4 weight %, 0.3 weight %, or greater than 0.2 weight %, as measured by 31P NMR. In some embodiments, crystalline psilocybin Polymorph A' has a chemical assay of at least 95 weight %, at least 96 weight %, or at least 98 weight %.

Illustrative XRPD diffractograms for high purity crystalline psilocybin, Polymorph A or Polymorph A' are provided in FIGS. 2A and 2B. Illustrative DSC thermographs for high purity crystalline psilocybin, Polymorph A or Polymorph A' are provided in FIGS. 2A and 2B.

Figure 2C:
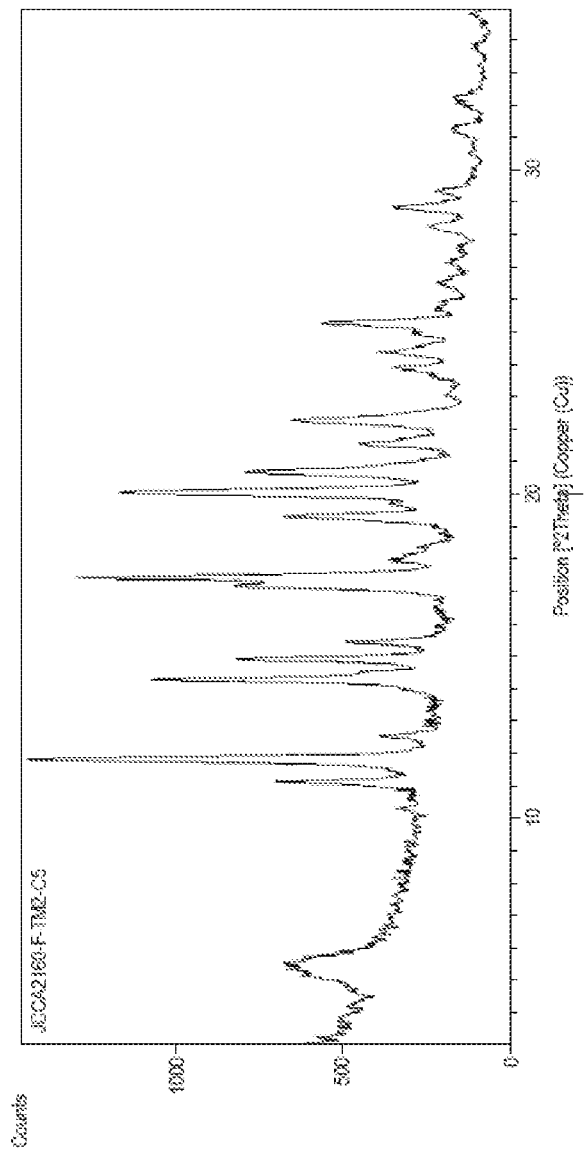
FIG. 2c is a XRPD diffractogram of Polymorph B (JCCA2160-F-TM2).
Figure 2D:
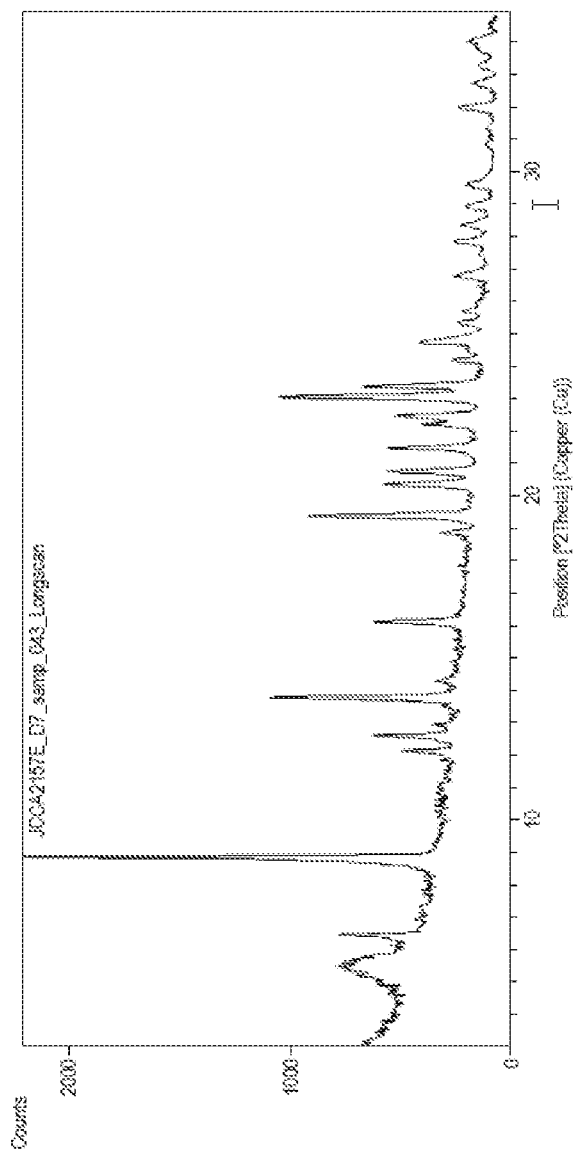
FIG. 2d is a XRPD diffractogram of a Hydrate A (JCCA2157E).
Figure 2E:
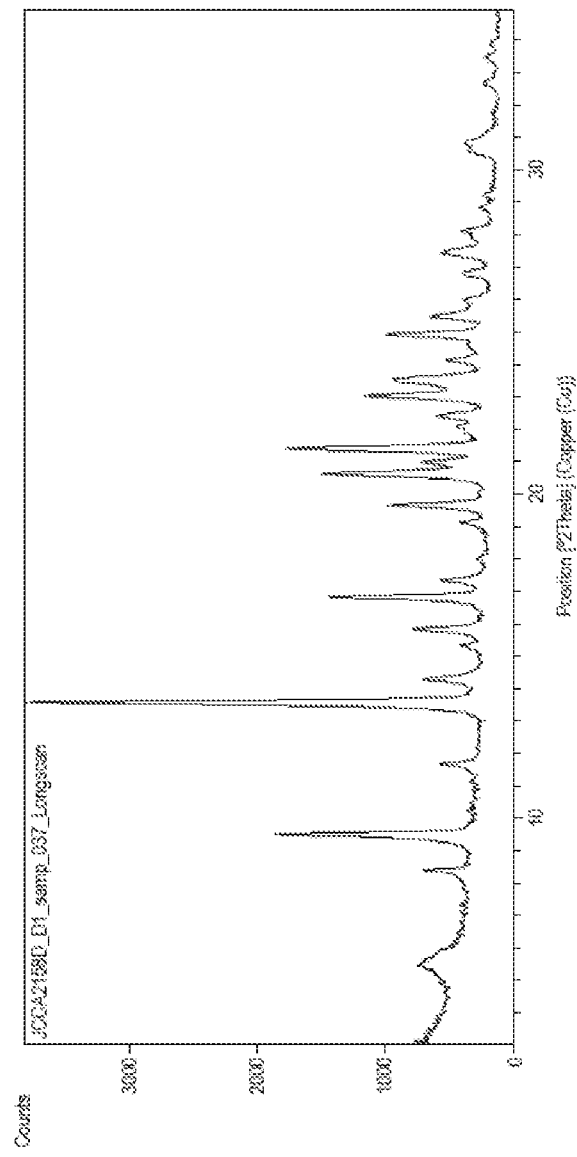
FIG. 2e is a XRPD diffractogram of an ethanol solvate (JCCA2158D).
Figure 2F:
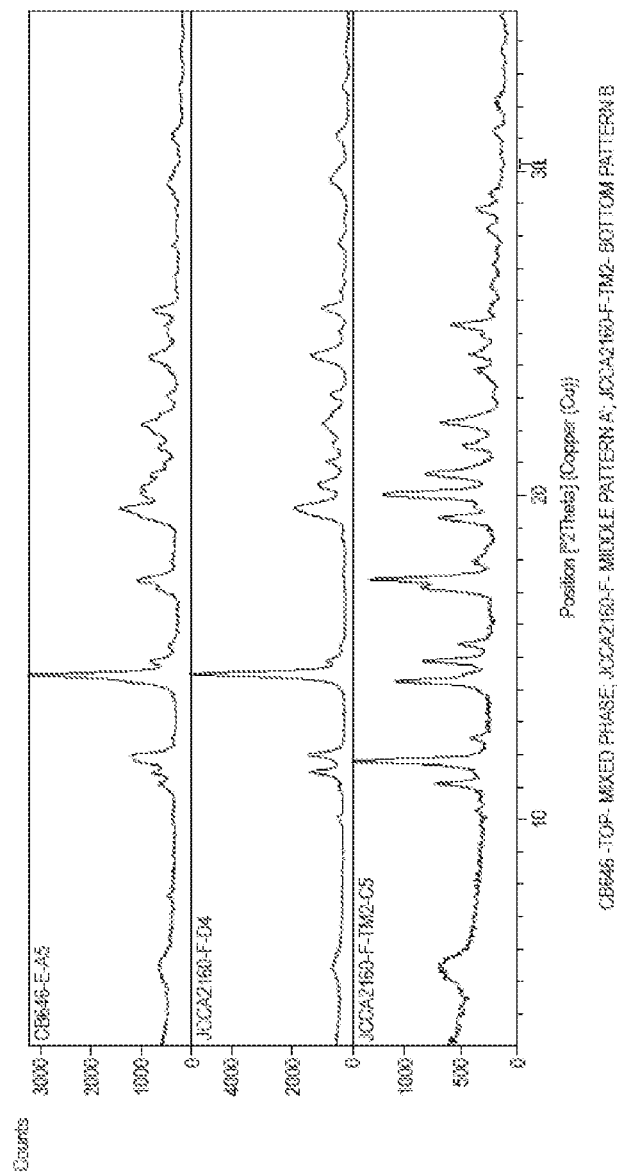
FIG. 2f is a XRPD diffractogram of product obtained during development of the process (CB646-E) (top)—compared to the diffractograms Polymorph A' (JCCA2160F) (middle) and Polymorph B (JCCA2160-TM2) (bottom).
Figure 4:
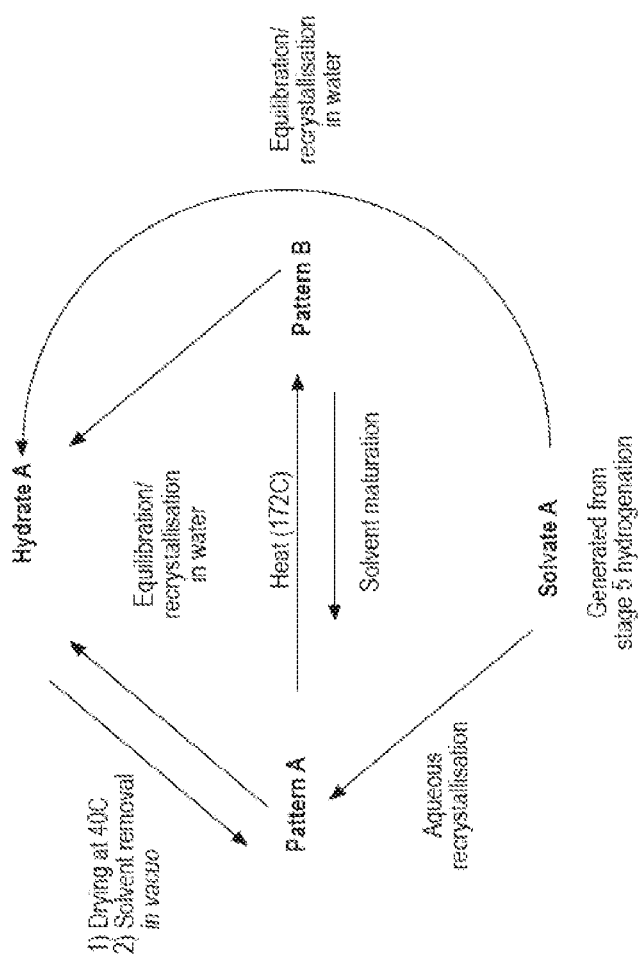
FIG. 4 is a form phase diagram showing the interrelationship of form in water-based systems.
Figure 5:
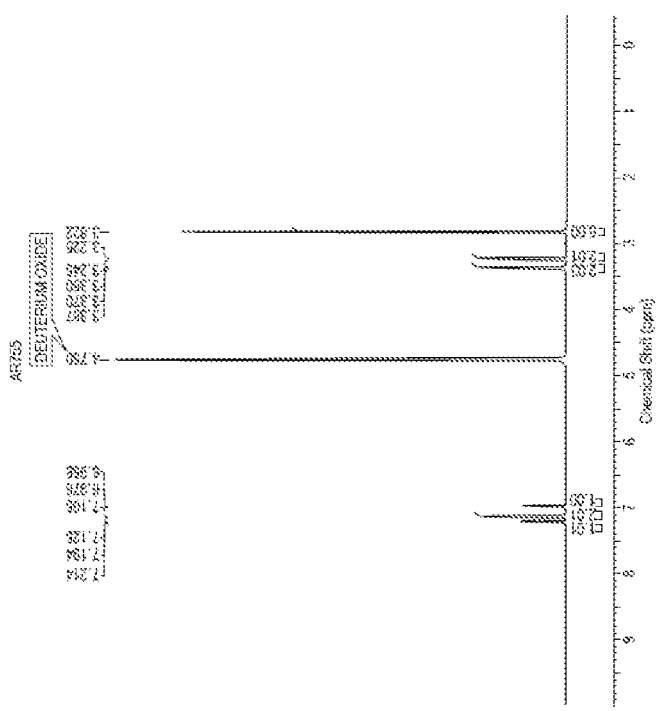
FIG. 5 is a 1H NMR (Nuclear Magnetic Resonance) spectrum of psilocybin.
Figure 6:
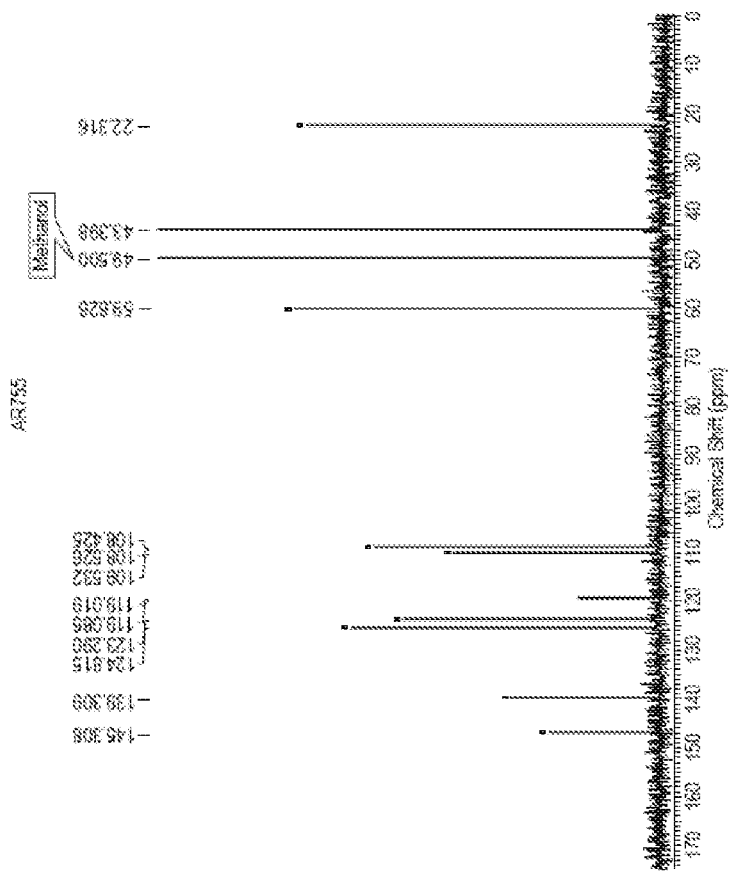
FIG. 6 is a 13C NMR spectrum of psilocybin.
Figure 7:
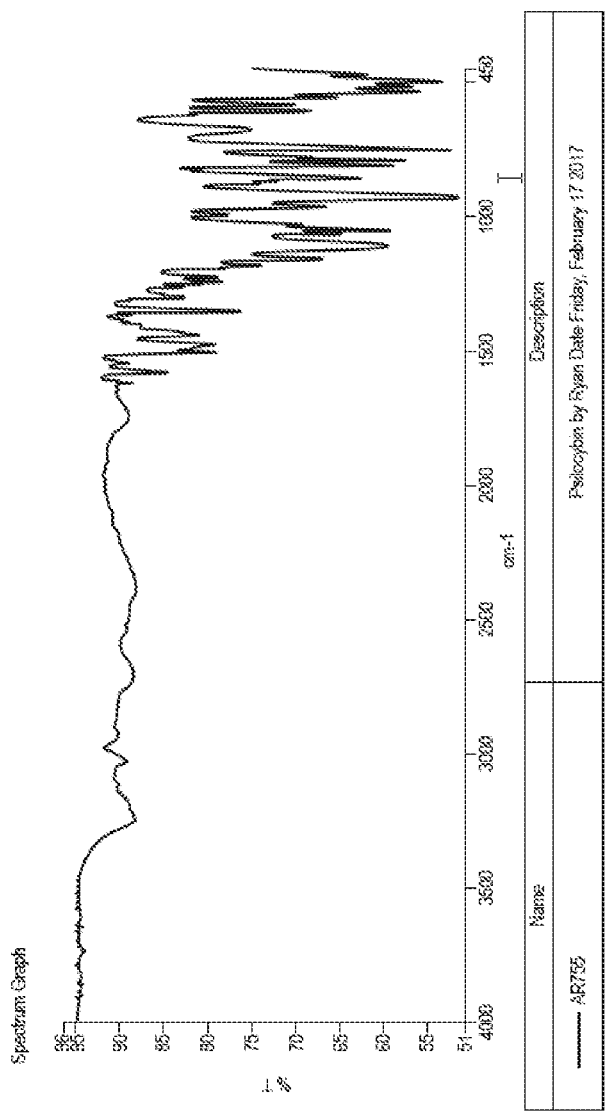
FIG. 7 is a FT-IR Spectrum of psilocybin.
Figure 8:
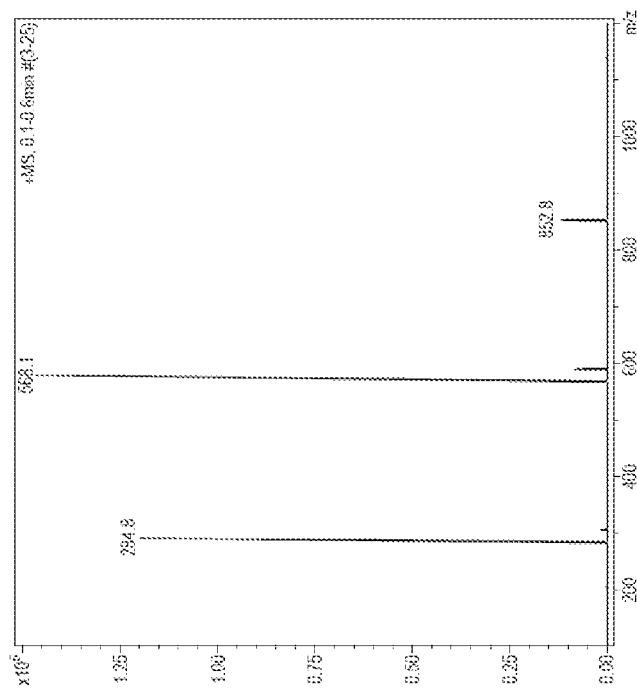
FIG. 8 is a Mass Spectrum of psilocybin.

Polymorph A (including its isostructural variant Polymorph A') (FIGS. 2A and 2B) differs from Polymorph B (FIG. 2C), the Hydrate A (FIG. 2D) and the ethanol solvate (FIG. 2E: Solvate A), and the relationship between some of the different forms is illustrated in FIG. 4.

In some embodiments, the crystalline psilocybin Polymorph A or Polymorph A' is a white to off white solid, and/or has a chemical purity of greater than 97%, 98%, or 99% by HPLC. In some embodiments, crystalline psilocybin Polymorph A or Polymorph A' has no single impurity of greater than 1%, greater than 0.5%, greater than 0.4%, greater than 0.3%, or greater than 0.2% e.g., the impurity phosphoric acid as measured by $^{31}P$ NMR, or the impurity psilocin measured by HPLC. In some embodiments, crystalline psilocybin Polymorph A or Polymorph A' has a chemical purity of greater than 97 area %, greater than 98 area %, or greater than 99 area % by HPLC. In some embodiments, crystalline psilocybin Polymorph A or Polymorph A' has no single impurity greater than 1 area %, greater than 0.5 area %, greater than 0.4%, greater than 0.3%, or greater than 0.2% as measured by HPLC. In some embodiments, crystalline psilocybin Polymorph A or Polymorph A' does not contain psilocin at a level greater than 1 area %, greater than 0.5 area %, greater than 0.4%, greater than 0.3%, or greater than 0.2% as measured by HPLC. In some embodiments, crystalline psilocybin Polymorph A or Polymorph A' does not contain phosphoric acid at a level greater than 1 weight %, greater than 0.5 weight %, greater than 0.4 weight %, 0.3 weight %, or greater than 0.2 weight %, as measured by $^{31}P$ NMR. In some embodiments, crystalline psilocybin Polymorph A or Polymorph A' has a chemical assay of at least 95 weight %, at least 96 weight %, or at least 98 weight %.

The heating of Polymorph A or A' results in an endothermic event having an onset temperature of circa 150° C. corresponding to solid-solid transition of Polymorph A or Polymorph A' to Polymorph B. Continued heating of the resulting solid, i.e., Polymorph B, results in a second endothermic event corresponding to a melting point having an onset temperature of between 205 and 220° C. (see FIGS. 3A and 3B).

Hydrate A

In some embodiments, the disclosure provides a crystalline form of psilocybin, Hydrate A. In some embodiments, crystalline psilocybin Hydrate A exhibits peaks in an XRPD diffractogram at 8.9, 12.6 and 13.8°2θ±0.1°2θ. In some embodiments, crystalline psilocybin Hydrate A further exhibits at least 1, 2, 3, 4, or 5 further peaks at 6.5, 12.2, 19.4, 20.4 or 20.8°2θ±0.1°2θ. An illustrative XRPD diffractogram is provided as FIG. 2D. In some embodiments, crystalline psilocybin Hydrate A further exhibits an endothermic event in a DSC thermogram having a first onset temperature of between 90° C. and 100° C., a second onset temperature of between 100° C. and 120° C. and a third onset temperature of between 210° C. and 220° C. An illustrative DSC thermogram is provided as FIG. 2D.

In some embodiments, psilocybin Hydrate A exhibits an XRPD diffractogram comprising at least 3, 4, 5, 6, 7, 8, 9, or 10 peaks listed in Table 3 or equivalent peaks within about ±0.1°2θ.

TABLE 3

XRPD peak positions for Hydrate A

| Position [°2Th.] | Relative Intensity [%] |
|---|---|
| 5.6 | 14.40 |
| 6.5 | 18.84 |
| 8.9 | 100.00 |
| 12.2 | 11.51 |
| 12.6 | 18.65 |
| 13.8 | 44.22 |
| 16.2 | 21.22 |
| 18.9 | 6.62 |
| 19.4 | 38.68 |
| 20.4 | 21.32 |
| 20.8 | 19.73 |
| 21.5 | 20.75 |
| 22.3 | 12.80 |
| 22.5 | 19.38 |
| 23.1 | 47.53 |
| 23.5 | 25.79 |
| 24.3 | 5.62 |
| 24.8 | 14.62 |
| 25.4 | 5.27 |
| 26.9 | 6.53 |
| 27.9 | 7.82 |
| 28.4 | 5.78 |
| 29.0 | 5.09 |
| 29.7 | 4.83 |
| 32.1 | 8.27 |
| 32.8 | 4.81 |
| 33.4 | 3.74 |
| 34.2 | 5.96 |

In some embodiments, crystalline psilocybin Hydrate A exhibits XRPD diffractogram peaks at 8.9, 12.6 and 13.8°2θ±0.1°2θ. In some embodiments, crystalline psilocybin Hydrate A exhibits at least one peak appearing at 6.5, 12.2, 19.4, 20.4 or 20.8°2θ±0.1°2θ. In some embodiments, crystalline psilocybin Hydrate A exhibits at least two peaks appearing at 6.5, 12.2, 19.4, 20.4 or 20.8°2θ±0.1°2θ. In some embodiments, crystalline psilocybin Hydrate A exhibits an XRPD diffractogram substantially the same as the XRPD diffractogram shown in FIG. 2D.

Figure 3C:
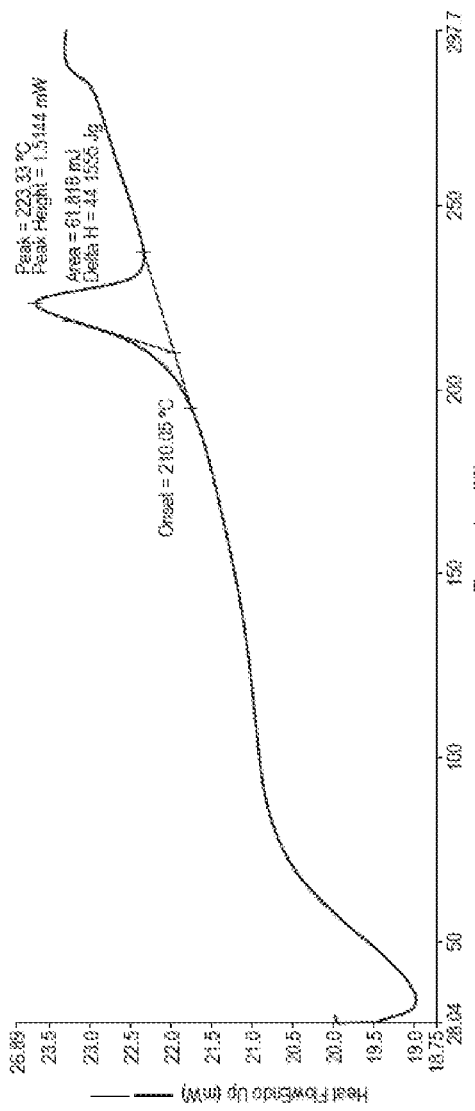
FIG. 3c is a DSC thermograph of Polymorph B (GM748A).
Figure 3D:
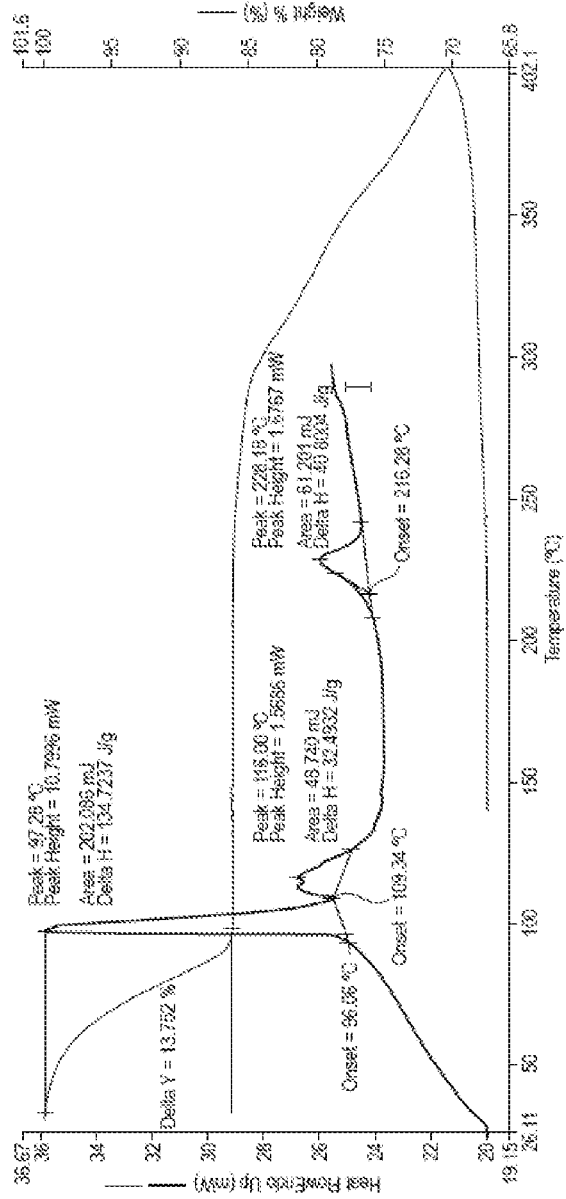
FIG. 3d is a DSC and TGA thermograph of Hydrate A (JCCA2157E).
Figure 3E:
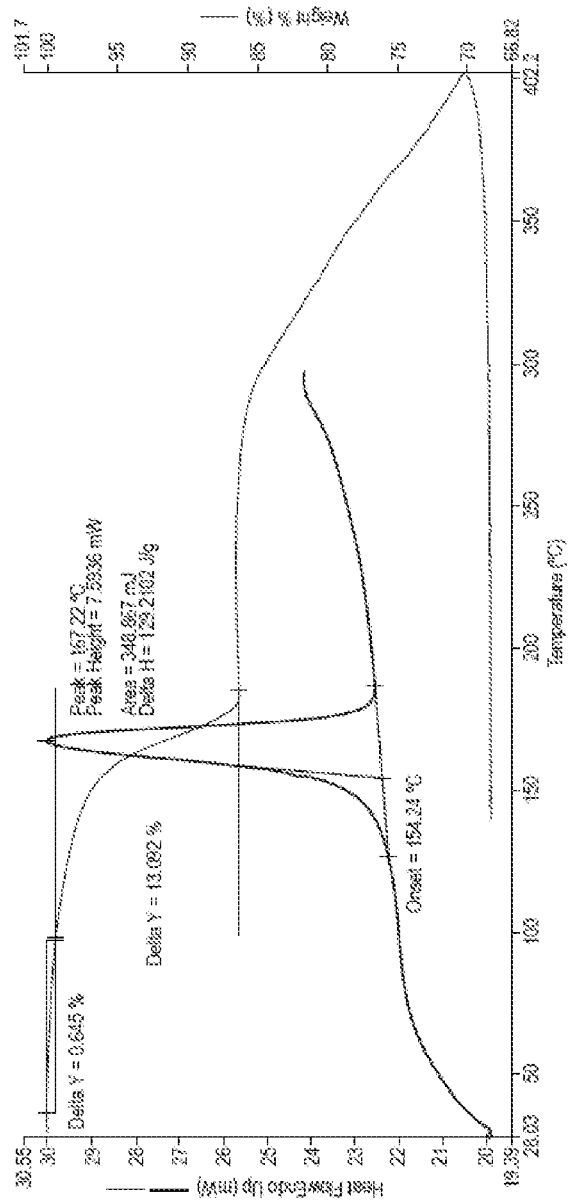
FIG. 3e is a DSC and TGA thermograph of ethanol solvate (JCCA2158D).

In certain embodiments, crystalline psilocybin Hydrate A is characterized by an endothermic event in a DSC thermogram having a first onset temperature of between 85° C. and 105° C., such as between 90° C. and 100° C. and most preferably at about 96° C., a second onset temperature of between 100° C. and 120° C. such as between 105° C. and 115° C., and most preferably at about 109° C. and a third onset temperature of between 205 and 220° C., such as between 210 and 220° C., such as between 210 and 218° C., or such as between 210 and 216° C., or about 216° C. In some embodiments, crystalline psilocybin Hydrate A exhibits an endothermic event in a DSC thermogram having an onset temperature of between about 205 and about 220° C., between about 210 and about 220° C., between about 210 and about 218° C., or between about 210 and about 216° C. In some embodiments, crystalline psilocybin Hydrate A exhibits an endothermic event in the DSC thermogram having an onset temperature of between about 85 and about 105° C., or between about 90 and about 100° C. In some embodiments, crystalline psilocybin Hydrate A exhibits an endothermic event having an onset temperature of between about 205 and about 220° C., between about 210 and about 220° C., between about 210 and about 218° C., or between about 210 and about 216° C., and an endothermic event having an onset temperature of between about 85 and about 105° C. or between about 90 and about 100° C., in a DSC thermogram. In some embodiments, crystalline psilocybin Hydrate A exhibits a DSC thermogram substantially the same as the DSC thermogram in FIG. 3D.

In some embodiments, crystalline psilocybin Hydrate A exhibits a water content of between about 10 and about 18%, between about 12 and about 16%, or about 13%. Methods to determine the water content of a crystalline compound are known, for example Karl Fischer Titration. In some embodiments, crystalline psilocybin Hydrate A exhibits a weight loss in the TGA thermogram of between about 10 and about 18%, between about 12 and about 16%, or about 13%, between ambient temperature, about 25° C., and 120° C.

In some embodiments, crystalline psilocybin Hydrate A is chemically pure, for example the psilocybin has a chemical purity of greater than 97%, 98%, or 99% by HPLC. In some embodiments, crystalline psilocybin Hydrate A has no single impurity of greater than 1%, greater than 0.5%, greater than 0.4%, greater than 0.3%, or greater than 0.2% e.g., the impurity phosphoric acid as measured by 31P NMR, or the impurity psilocin measured by HPLC. In some embodiments, crystalline psilocybin Hydrate A has a chemical purity of greater than 97 area %, greater than 98 area %, or greater than 99 area % by H PLC. In some embodiments, crystalline psilocybin Hydrate A has no single impurity greater than 1 area %, greater than 0.5 area %, greater than 0.4%, greater than 0.3%, or greater than 0.2% as measured by HPLC. In some embodiments, crystalline psilocybin Hydrate A does not contain psilocin at a level greater than 1 area %, greater than 0.5 area %, greater than 0.4%, greater than 0.3%, or greater than 0.2% as measured by HPLC. In some embodiments, crystalline psilocybin Hydrate A does not contain phosphoric acid at a level greater than 1 weight %, greater than 0.5 weight %, greater than 0.4 weight %, 0.3 weight %, or greater than 0.2 weight %, as measured by 31P NMR. In some embodiments, crystalline psilocybin Hydrate A has a chemical assay of at least 95 weight %, at least 96 weight %, or at least 98 weight %.

In some embodiments, crystalline psilocybin Hydrate A is a highly pure crystalline form of Hydrate A. In some embodiments, the crystalline psilocybin comprises at least 90%, at least 95%, at least 99%, or at least 99.5% by weight of Hydrate A.

Polymorph B

In some embodiments, the disclosure provides a crystalline form of psilocybin, Polymorph B. In some embodiments, crystalline psilocybin Polymorph B exhibits peaks in an XRPD diffractogram at 11.1, 11.8 and 14.3°2θ±0.1°2θ. In some embodiments, crystalline psilocybin Polymorph B exhibits at least 1, 2, 3, 4 or 5 peaks in an XRPD diffractogram at 14.9, 15.4, 19.3, 20.0 or 20.6°2θ±0.1°2θ. An illustrative XRPD diffractogram of crystalline psilocybin Polymorph B is provided as FIG. 2C. In some embodiments, crystalline psilocybin Polymorph B exhibits a single endothermic event in a DSC thermogram having an onset temperature of between about 205 and about 220° C. An illustrative DSC thermogram of crystalline psilocybin Polymorph B is provided as FIG. 3C.

In some embodiments, psilocybin Polymorph B exhibits an XRPD diffractogram comprising at least 3, 4, 5, 6, 7, 8, 9, or 10 peaks listed in Table 4 or equivalent peaks within about ±0.1°2θ.

TABLE 4

XRPD peak positions for Polymorph B

| Position [°2Th.] | Relative Intensity [%] |
|---|---|
| 5.5 | 21.33 |
| 11.1 | 36.91 |
| 11.8 | 100.00 |
| 12.5 | 12.73 |
| 14.3 | 70.23 |
| 14.9 | 50.01 |
| 15.4 | 23.67 |
| 17.1 | 51.58 |
| 17.4 | 91.25 |
| 18.0 | 12.61 |
| 19.3 | 39.33 |
| 20.0 | 76.61 |
| 20.6 | 50.26 |
| 21.5 | 20.77 |
| 22.3 | 40.19 |
| 23.9 | 13.32 |
| 24.3 | 16.03 |
| 25.3 | 32.94 |
| 28.3 | 7.60 |
| 28.9 | 17.89 |
| 29.3 | 8.96 |
| 31.3 | 6.57 |
| 32.2 | 6.90 |
| 33.8 | 2.37 |

In some embodiments, crystalline psilocybin Polymorph B exhibits XRPD diffractogram peaks at 11.1, 11.8 and 14.3°2θ±0.1°2θ. In some embodiments, crystalline psilocybin Polymorph B exhibits at least one peak at 14.9, 15.4, 19.3, 20.0 or 20.6°2θ±0.1°2θ. In some embodiments, crystalline psilocybin Polymorph B exhibits at least two peaks appearing at 14.9, 15.4, 19.3, 20.0 or 20.6°2θ±0.1°2θ. In some embodiments, crystalline psilocybin Polymorph B exhibits an XRPD diffractogram substantially the same as the XRPD diffractogram shown in FIG. 2C.

In some embodiments, crystalline psilocybin Polymorph B is characterized by a single endothermic event in a DSC thermogram having an onset temperature of between about 205 and about 220° C., between about 210 and about 220° C., between about 210 and about 218° C., or between about 210 and about 216° C. In some embodiments, crystalline psilocybin Polymorph B exhibits a DSC thermogram substantially the same as the DSC thermogram in FIG. 3C.

In some embodiments, crystalline psilocybin Polymorph B exhibits a water content of <0.5% w/w, <0.4% w/w, <0.3% w/w, <0.2% w/w, or <0.1% w/w. Methods to determine the water content of a crystalline compound are known, for example Karl Fischer Titration. In some embodiments, crystalline psilocybin Polymorph B exhibits <0.5% w/w, <0.4% w/w, <0.3% w/w, <0.2% w/w, or <0.1% w/w loss in the TGA thermogram between ambient temperature, about 25° C., and 200° C. In some embodiments, crystalline psilocybin Polymorph B exhibits a loss of less than 2% by weight, less than 1% by weight, or less than 0.5% by weight in a loss on drying test. In some embodiments, the loss on drying test is performed at 70° C.

In some embodiments, crystalline psilocybin Polymorph B is a highly pure crystalline form of Polymorph B, for example, psilocybin comprises at least 90%, at least 95%, at least 99%, or at least 99.5% by weight of Polymorph B.

In some embodiments, crystalline psilocybin Polymorph B is chemically pure, for example the psilocybin has a chemical purity of greater than 97%, 98%, or 99% by HPLC. In some embodiments, crystalline psilocybin Polymorph B has no single impurity of greater than 1%, greater than 0.5%, greater than 0.4%, greater than 0.3%, or greater than 0.2% e.g., the impurity phosphoric acid as measured by 31P NMR, or the impurity psilocin measured by HPLC. In some embodiments, crystalline psilocybin Polymorph B has a chemical purity of greater than 97 area %, greater than 98 area %, or greater than 99 area % by HPLC. In some embodiments, crystalline psilocybin Polymorph B has no single impurity greater than 1 area %, greater than 0.5 area %, greater than 0.4%, greater than 0.3%, or greater than 0.2% as measured by HPLC. In some embodiments, crystalline psilocybin Polymorph B does not contain psilocin at a level greater than 1 area %, greater than 0.5 area %, greater than 0.4%, greater than 0.3%, or greater than 0.2% as measured by HPLC. In some embodiments, crystalline psilocybin Polymorph B does not contain phosphoric acid at a level greater than 1 weight %, greater than 0.5 weight %, greater than 0.4 weight %, 0.3 weight %, or greater than 0.2 weight %, as measured by 31P NMR. In some embodiments, crystalline psilocybin Polymorph B has a chemical assay of at least 95 weight %, at least 96 weight %, or at least 98 weight %.

In some embodiments, the psilocybin of the disclosure in the form Polymorph A or A' has the general properties illustrated in Table 5.

TABLE 5

| Appearance: | White to off-white solid |
|---|---|
| Major endothermic event in DSC (onset temperature) (corresponding to a melt): | 210-215° C. |
| Hygroscopicity: | Psilocybin forms Hydrate A at high humidity and when added to water but the water of hydration is lost rapidly on drying. The anhydrous form is therefore being developed. |
| Crystalline form: | Anhydrous Polymorph A and/or A' |
| pKa (calculated): | 1.74, 6.71, 9.75 |
| Solubility | approx. 15 mg/ml in Water |

In some embodiments, the psilocybin conforms to the spectra as set out in Table 6 and illustrated in the spectra of FIGS. 5-8.

TABLE 6

| Technique | Conclusions |
|---|---|
| Proton ($^1$H) and Carbon ($^{13}$C) NMR | Assignment of the proton (FIG. 5) and carbon spectra (FIG. 6) are concordant with Psilocybin. |
| FT-Infrared Spectroscopy (FT-IR) | Assignment of the FT-IR spectrum (FIG. 7) is concordant with Psilocybin. |
| Mass Spectroscopy (MS) | Assignment of the mass spectrum (FIG. 8) is concordant with Psilocybin. |

Alternatively, and independently, the crystalline psilocybin may take the form of Hydrate A or Polymorph B.

In some embodiments, the disclosure provides the crystalline psilocybin in the form Polymorph A or Polymorph A' for use in medicine. In some embodiments, the disclosure provides crystalline psilocybin Polymorph A for use in medicine. In some embodiments, the disclosure provides crystalline psilocybin Polymorph A' for use in medicine. In some embodiments, the disclosure provides a high purity crystalline psilocybin Polymorph A for use in medicine. In some embodiments, the disclosure provides a high purity crystalline psilocybin Polymorph A' for use in medicine. Alternatively, and independently, the crystalline psilocybin may take the form of Hydrate A or Polymorph B.

In some embodiments, the disclosure provides crystalline psilocybin in the form Polymorph A or Polymorph A' for use in treating a subject in need thereof. Alternatively, and independently, the crystalline psilocybin may take the form of Hydrate A or Polymorph B.

In some embodiments, the disclosure provides crystalline psilocybin, Polymorph A or Polymorph A', for use in treating a subject in need thereof. In some embodiments, the disclosure provides crystalline psilocybin, Polymorph A or Polymorph A', for use in treating a subject in need thereof. In some embodiments, the disclosure provides crystalline psilocybin Polymorph A for use in treating a subject in need thereof. In some embodiments, the disclosure provides crystalline psilocybin Polymorph A' for use in treating a subject in need thereof. In some embodiments, the disclosure provides a high purity crystalline psilocybin Polymorph A for use in treating a subject in need thereof. In some embodiments, the disclosure provides a high purity crystalline psilocybin Polymorph A' for use in treating a subject in need thereof.

Pharmaceutical Compositions and Formulations

In some embodiments, the disclosure provides a pharmaceutical composition comprising crystalline psilocybin and one or more pharmaceutically acceptable carriers or excipients.

In some embodiments, the disclosure provides a pharmaceutical formulation comprising high purity psilocybin and one or more pharmaceutically acceptable carriers or excipients. In some embodiments, the disclosure provides a pharmaceutical formulation comprising crystalline psilocybin Polymorph A and one or more pharmaceutically acceptable carriers or excipients. In some embodiments, the disclosure provides a pharmaceutical formulation comprising crystalline psilocybin Polymorph A' and one or more pharmaceutically carriers or excipients. In some embodiments, the disclosure provides a pharmaceutical formulation comprising high purity crystalline psilocybin, Polymorph A or Polymorph A', and one or more pharmaceutically acceptable carriers or excipients. In some embodiments, the disclosure provides a pharmaceutical formulation comprising high purity crystalline psilocybin Polymorph A and one or more pharmaceutically acceptable carriers or excipients. In some embodiments, the disclosure provides a pharmaceutical formulation comprising high purity crystalline psilocybin Polymorph A' and one or more pharmaceutically acceptable carriers or excipients.

Preferred pharmaceutical excipients for an oral formulation include: diluents, such as microcrystalline cellulose, starch, mannitol, calcium hydrogen phosphate anhydrous or co-mixtures of silicon dioxide, calcium carbonate, microcrystalline cellulose and talc; disintegrants, such as sodium starch glycolate or croscarmellose sodium; binders, such as povidone, co-povidone or hydroxyl propyl cellulose; lubricants, such as magnesium stearate or sodium stearyl fumurate; glidants, such as colloidal silicon dioxide; and film coats, such as Opadry II white or PVA based brown Opadry II.

In some embodiments, the oral dosage form also comprises a disintegrant, such as, but not limited to: starch glycolate, croscarmellose sodium, and/or mixtures thereof. In some embodiments, the oral dosage form comprises 3% or less by wt disintegrant, less than 3% by wt disintegrant and greater than 0.001% by wt disintegrant, about 2.5% by wt or less disintegrant; 2% by wt or less disintegrant; 1.5% by wt or less disintegrant; 1% by wt or less disintegrant; 0.7% by wt or less disintegrant; 0.5% by wt or less disintegrant, or 0.3% by wt or less disintegrant.

In some embodiments, the disintegrant is sodium starch glycolate. In some embodiments, the sodium starch glycolate is present at less than 3% wt. In other embodiments, the sodium starch glycolate is present at about 2% by wt or less, about 2% by wt; about 1% by wt or less, about 1% by wt; about 0.7% by wt or less, about 0.7% by wt; about 0.5% by wt or less, or about 0.5% by wt. In still other embodiments, the sodium starch glycolate is present at about 0.5% to 1% by wt.

In some embodiments, the oral dosage form comprises 5 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 10 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 25 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5%.

In some embodiments, there is provided the crystalline psilocybin in the form Polymorph A or Polymorph A' for use in medicine. In some embodiments, there is provided crystalline psilocybin Polymorph A for use in medicine. In some embodiments, there is provided crystalline psilocybin Polymorph A' for use in medicine. In some embodiments, there is provided a high purity crystalline psilocybin Polymorph A for use in medicine. In some embodiments, there is provided a high purity crystalline psilocybin Polymorph A' for use in medicine.

Alternatively, and independently, the crystalline psilocybin may take the form of Hydrate A or Polymorph B.

In some embodiments, there is provided crystalline psilocybin, particularly but not essentially in the form Polymorph A or Polymorph A' for use in treating central nervous disorders.

Alternatively, and independently, the crystalline psilocybin may take the form of Hydrate A or Polymorph B.

In some embodiments, the pharmaceutical formulation is a parenteral dosage form. In some embodiments, the pharmaceutical formulation is an oral dosage form. In some embodiments, the pharmaceutical composition comprises a tablet. In some embodiments, the pharmaceutical composition comprises a capsule. In some embodiments, the pharmaceutical composition comprises a dry powder. In some embodiments, the pharmaceutical composition comprises a solution. In some embodiments, more than one dosage form is administered to the subject at substantially the same time. In some embodiments, the subject may be administered the entire therapeutic dose in one tablet or capsule. In some embodiments, the therapeutic dose may be split among multiple tablets or capsules. For example, for a dose of 25 mg, the subject may be administered 5 tablets or capsules each comprising 25 mg of psilocybin. Alternatively, for a dose of 10 mg, the subject may be administered 2 tablets or capsules each comprising 5 mg of psilocybin.

In some embodiments, the oral dosage form comprises a functional filler. The functional filler may be a silicified filler, such as, but not limited to silicified microcrystalline cellulose (SMCC). In some embodiments, the oral dosage form comprises high compactability grades of SMCC with a particle size range of from about 45 to 150 microns. A mixture of two functional fillers having different particle size ranges may be used with the weight percentages of the two favoring the larger sized particles.

In some embodiments, the silicified microcrystalline filler may comprise a first filler, having a particle size range of from about 45 to 80 microns in an amount of up to 30%, up to 20%, up to 15%, or less by weight of filler, and a second filler, having a particle size range of from about 90 to 150 microns, in an amount of up to 70%, up to 80%, up to 85%, or more, by weight of filler.

In some embodiments, the oral dosage form may comprise silicified microcrystalline cellulose with a particle size range of from about 45 to 80 microns (SMCC 50), such as Prosolv 50; silicified microcrystalline cellulose with a particle size range of from about 90 to 150 microns (SMCC 90), such as Prosolv 90; or mixtures thereof. In other embodiments, the oral dosage form may comprise SMCC 50 and SMCC 90. In other embodiments, the oral dosage form may comprise SMCC 50 and SMCC 90, wherein the ratio of SMCC 50 to SMCC 90 is 1:5 to 1:8 wt %. In still other embodiments, the ratio of SMCC 50 to SMCC 90 is 1:5-1:7; 1:6-1:7; 1:6-1:8; or 1.7-1.8. In still other embodiments, the ratio of SMCC 50 to SMCC 90 is 1:6; 1:6.1; 1:6.2; 1:6.3; 1:6.4; 1:6.5; 1:6.6; 1:6.7; 1:6.8; 1.6.9; or 1:7.

The formulation may further comprise or consist essentially of a disintegrant, including without limitation sodium starch glycolate; a glidant, including without limitation colloidal silicon dioxide; and a lubricant, including without limitation sodium stearyl fumarate.

In some embodiments, the oral dosage form may comprise a disintegrant such as sodium starch glycolate, at less than 3% (by wt), less than 2%, or 1% or less.

In some embodiments, the oral dosage form comprises 5 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 5 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 10 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 10 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 25 mg of psilocybin and SMCC 50 and SMCC 90, wherein the ratio of SMCC 50 to SMCC 90 is 1:6.4 and sodium starch glycolate at about 1%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5% to 1.0%. In some embodiments, the oral dosage form comprises 25 mg of psilocybin and SMCC 50 and SMCC 90, wherein the ratio of SMCC 50 to SMCC 90 is 1:6.4 and sodium starch glycolate at about 0.5%.

In some embodiments, the oral dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate. In some embodiments, the tablet or capsule comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

In some embodiments, the oral dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate. In some embodiments, the tablet or capsule comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

In some embodiments, the tablet or capsule comprises one or more excipients. Non-limiting exemplary excipients include microcrystalline cellulose and starch, including without limitation silicified microcrystalline cellulose.

It should be noted that the formulations may comprise psilocybin in any form, not only the polymorphic forms disclosed herein.

As used herein, oral doses of psilocybin are classified follows: "very low doses" (about 0.045 mg/kg or less); "low doses" (between about 0.115 and about 0.125 mg/kg), "medium doses" (between about 0.115 to about 0.260 mg/kg), and "high doses" (about 0.315 mg/kg or more). See Studerus et al (2011) *J Psychopharmacol* 25(11) 1434-1452.

In some embodiments, the formulated dose of psilocybin comprises from about 0.01 mg/kg to about 1 mg/kg. In some embodiments, a human dose (for an adult weighing 60-80 kg) comprises between about 0.60 mg and about 80 mg.

In some embodiments, a formulated dose comprises between about 2 and about 50 mg of crystalline psilocybin. In some embodiments, a formulated dose comprises between 2 and 40 mg, between 2 and 10 mg, between 5 and 30 mg, between 5 and 15 mg, or between 20 and 30 mg of crystalline psilocybin. In some embodiments, a formulated dose comprises about 1 mg, about 5 mg, about 10 mg, or about 25 mg of crystalline psilocybin.

In some embodiments, a formulated dose comprises between about 2 mg and about 50 mg of crystalline psilocybin Polymorph A or Polymorph A' or a mixture thereof. In some embodiments, a formulated dose comprises between 2 mg and 40 mg, between 2 mg and 10 mg, between 5 mg and 30 mg, between 5 mg and 15 mg, or between 20 and 30 mg of crystalline psilocybin Polymorph A or Polymorph A' or a mixture thereof. In some embodiments, a formulated dose comprises about 1 mg, about 5 mg, about 10 mg, or about 25 mg of crystalline psilocybin Polymorph A or Polymorph A' or a mixture thereof. In some embodiments, a formulated dose comprises about 5 mg of crystalline psilocybin Polymorph A or Polymorph A' or a mixture thereof.

In some embodiments, a formulated dose comprises between about 2 mg and about 50 mg of crystalline psilocybin Polymorph A. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Polymorph A. In some embodiments, a formulated dose comprises about 1 mg, about 5 mg, about 10 mg, or about 25 mg of crystalline psilocybin Polymorph A.

In some embodiments, a formulated dose comprises between about 2 mg and about 50 mg of crystalline psilocybin Polymorph A'. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Polymorph A'. In some embodiments, a formulated dose comprises about 1 mg, about 5 mg, about 10 mg, or about 25 mg of crystalline psilocybin Polymorph A'.

In some embodiments, a formulated dose comprises between about 2 mg and about 50 mg of crystalline psilocybin Polymorph B. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Polymorph B. In some embodiments, a formulated dose comprises about 1 mg, about 5 mg, about 10 mg, or about 25 mg of crystalline psilocybin Polymorph B.

In some embodiments, a formulated dose comprises between about 2 mg and about 50 mg of crystalline psilocybin Hydrate A. In some embodiments, a formulated dose comprises between 2 mg and 40 mg, between 2 mg and 10 mg, between 5 mg and 30 mg, between 5 mg and 15 mg, or between 20 mg and 30 mg of crystalline psilocybin Hydrate A. In some embodiments, a formulated dose comprises about 1 mg, about 5 mg, about 10 mg, or about 25 mg of crystalline psilocybin Hydrate A.

Dosing

In some embodiments, a therapeutically effective dose of psilocybin is administered to the subject. In some embodiments, each dose of psilocybin administered to the subject is a therapeutically effective dose.

In some embodiments, a dose of psilocybin may be in the range of about 1 mg to about 100 mg. For example, the dose may be about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. In some embodiments, the dose of psilocybin is between about 0.1 mg to about 100 mg, about 1 mg to about 50 mg, or about 5 mg to about 30 mg. In some embodiments, the dose of psilocybin is about 1 mg, about 10 mg, or about 25 mg. In some embodiments, the dose of psilocybin is in the range of about 0.001 mg to about 1 mg. In some embodiments, the dose of psilocybin is in the rage of about 100 mg to about 250 mg. In some embodiments, the dose of psilocybin is about 25 mg. In some embodiments, the psilocybin is in the form of polymorph A.

In some embodiments, an adult oral dose comprises about 1 mg to about 40 mg, about 2 to about 30 mg, or about 15 to about 30 mg of crystalline psilocybin, for example about 1 mg, about 5 mg, about 10 mg, or about 25 mg of crystalline psilocybin. In some embodiments, an adult oral dose comprises about 25 mg of crystalline psilocybin. In some embodiments, the crystalline psilocybin is in the form of polymorph A.

In some embodiments, a "micro-dose" of psilocybin is administered to a subject. A micro-dose may comprise, for example, about 0.05 mg to about 2.5 mg of crystalline psilocybin, such as about 1.0 mg. In the case of micro-dosing the regime may comprise a regular, continuous regime of, for example, daily administration, every other day administration, or weekly, administration. Such dosing may be absent of psychological support.

In some embodiments, one dose of psilocybin is administered to the subject. In some embodiments, multiple doses of psilocybin are administered to the subject. For example, at least 2, at least 3, at least 4, at least 5, at least 6, at least 7, at least 8, at least 9, at least 10, at least 15, at least 20, at least 25, at least 30, or at least 50 doses of psilocybin may be administered to the subject. In some embodiments, the same dose of psilocybin is administered to a subject during each administration. In some embodiments, a different dose of psilocybin is administered to a subject during each administration. In some embodiments, the dose of psilocybin administered to the subject is increased over time. In some embodiments, the dose of psilocybin administered to the subject is decreased over time.

In some embodiments, the psilocybin is administered at therapeutically effective intervals. In some embodiments, a therapeutically effective interval may be about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In some embodiments, a therapeutically effective interval may be about 1 month, about 3 months, about 6 months, or about 12 months. In some embodiments, the psilocybin is administered once per day. In some embodiments, the psilocybin is administered at least once per week or at least twice per week. In some embodiments, the psilocybin is administered at least once per month or at least twice per month. In some embodiments, the psilocybin is administered at least once every three months, at least once every six months, or at least once every 12 months.

In some embodiments, a first dose and a second dose of psilocybin are administered to the subject. In some embodiments, the first dose is about 1 mg and the second dose is about 1 mg. In some embodiments, the first dose is about 10 mg and the second dose is about 10 mg. In some embodiments, the first dose is about 25 mg and the second dose is about 25 mg. In some embodiments, the first dose is about 10 mg and the second dose is about 25 mg. In some embodiments, the first dose is about 25 mg and the second dose is about 10 mg. In some embodiments, the first dose is about 1 mg and the second dose is about 10 mg. In some embodiments, the first dose is about 1 mg and the second dose is about 25 mg. In some embodiments, the first dose is about 10 mg and the second dose is about 1 mg. In some embodiments, the first dose is about 25 mg and the second dose is about 1 mg.

In some embodiments a second dose of psilocybin is administered from about one week to about 12 weeks after a first dose. In some embodiments, a second dose of psilocybin is administered about one week after a first dose. In some embodiments, a second dose of psilocybin is administered about two weeks after a first dose. In some embodiments, a second dose of psilocybin is administered about three weeks after a first dose. In some embodiments, a second dose of psilocybin is administered about four weeks after a first dose. In some embodiments, a second dose of psilocybin is administered about five weeks after a first dose. In some embodiments, a second dose of psilocybin is administered about six weeks after a first dose.

Administration Routes

Exemplary modes for administration of psilocybin include oral, parenteral (e.g., intravenous, subcutaneous, intradermal, intramuscular [including administration to skeletal, diaphragm and/or cardiac muscle], intradermal, intrapleural, intracerebral, and intra-articular), topical (e.g., to both skin and mucosal surfaces, including airway surfaces, and transdermal administration), inhalation (e.g., via an aerosol), rectal (e.g., via a suppository), transmucosal, intranasal, buccal (e.g., sublingual), vaginal, intrathecal, intraocular, transdermal, in utero (or in ovo), intralymphatic, and direct tissue or organ injection (e.g., to liver, skeletal muscle, cardiac muscle, diaphragm muscle or brain). In some embodiments, psilocybin is administered orally to the subject.

Methods of Treatment

It is to be understood by one of skill in the art that the methods of treatment comprising administering psilocybin, a prodrug of psilocybin, a metabolite of psilocybin, and/or a prodrug of a metabolite of psilocybin for the treatment of one or more indications as described herein also include: the use of psilocybin, a prodrug of psilocybin, a metabolite of psilocybin, and/or a prodrug of a metabolite of psilocybin in the manufacture of a medicament for the treatment of one or more indications as described herein; and the use of psilocybin, a prodrug of psilocybin, a metabolite of psilocybin, and/or a prodrug of a metabolite of psilocybin for the treatment of one or more indications as described herein.

In some embodiments, a method for treating a subject in need thereof comprises administering to the subject a therapeutically effective dose of psilocybin. In some embodiments, a method for treating a subject in need thereof comprises administering to the subject a therapeutically effective dose of psilocybin in a controlled environment, wherein the subject is provided with psychological support.

In some embodiments, a method for treating a subject in need thereof comprises at least one of the following:

(i) administering to the subject a therapeutically effective dose of psilocybin in a controlled environment, wherein the subject is provided with psychological support;

(ii) having the subject participate in one or more pre-administration psychological support session(s); and/or (ii) having the subject participate in one or more post-administration psychological support session(s).

After administration of the psilocybin, the subject may not feel the effects of the drug for about 30 minutes to about 90 minutes. In some embodiments, the subject may not feel the effects of the drug for about 60 minutes. This period after administration and before the onset of effects will be referred to herein as the initial stage of the psilocybin session. The time marked by the onset of the drug's effects will be referred to herein as the early stage of the psilocybin session.

In some embodiments, the subject will experience the peak of the psilocybin's effects at about 1.5 hours to about 3.5 hours after administration thereof. The time period marked by the peak psilocybin experience will be referred to herein as the peak stage of the psilocybin session.

In some embodiments, the effects of the psilocybin may substantially wear off from about 4 hours to about 6 hours after administration. This time period will be referred to as the late stage of the psilocybin session.

In some embodiments, the subject's ability to reach a non-dual state (e.g., a mystical experience), or a sense of unity, boundlessness, ego-dissolution or transcendence correlates with positive clinical outcome. Each of these terms may be commonly defined as the breakdown of the usual relationship between self and other, whereby the subject might feel a oneness and increased sense of connectedness to the surrounding environment and/or the world at large.

In some embodiments, low levels of emotional arousal—which could indicate avoidance, lack of involvement or intellectualization—might, in some embodiments, be correlated with little or no improvement in treatment outcomes.

Factors that may influence the subjective experience of psilocybin include, for example, (i) dose, (ii) the mindset of the participant prior to the session, (iii) the setting of the session, (iv) the subject's ability to focus and stay with the experience, and/or (v) the subject's prior experience with psychedelics. These, and other factors, will be described in more detail below, along with ways to maximize therapeutic benefit of the psilocybin session.

Pre-Administration Psychological Support Sessions

In some embodiments, the subject participates in at least one psychological support session before administration of the psilocybin ("pre-administration psychological support session"). In some embodiments, a pre-administration psychological support session may be held about 1 month prior to the psilocybin administration. In some embodiments, a pre-administration psychological support session may be held about 2 weeks prior to the psilocybin administration. In some embodiments, a pre-administration psychological support session may be held about 1 week prior to the psilocybin administration. In some embodiments, a pre-administration psychological support session may be held about 3 days prior to the psilocybin administration. In some embodiments, a pre-administration psychological support session may be held about 1 day prior to the psilocybin administration. In some embodiments, a pre-administration psychological support session may be held on the same day as and prior to psilocybin administration.

In some embodiments, the subject may participate in one, two, three, four, five, six, seven, or eight pre-administration psychological support sessions. In some embodiments, the subject may participate in at least two pre-administration psychological support sessions. In some embodiments, the subject may participate in at least three pre-administration psychological support sessions. In some embodiments, the subject may participate in pre-administration psychological support sessions at least once per week, for at least two or three weeks prior to the psilocybin session. In some embodiments, the subject may additionally participate in a pre-administration psychological support session the day before the psilocybin session.

The pre-administration psychological support sessions may be individual sessions, wherein a subject meets one-on-one with a therapist. In some embodiments, the psychological support sessions may be group sessions, wherein more than one subject meets with a single therapist, or more than one therapist. In some embodiments, one or more of the subject's family members or friends may be present at the pre-administration psychological support session(s).

In some embodiments, the goals of the pre-administration session may include (i) establishing therapeutic alliance between subject and therapist; (ii) answering the subject's questions and addressing any concerns; and/or (iii) demonstrating and practicing the skills of self-directed inquiry and experiential processing. In some embodiments, the pre-administration psychological support sessions focus on discussion of possible psilocybin effects, and/or preparing subjects for the dosing session by practicing relevant therapeutic techniques to reduce avoidance and anxiety, eliciting relevant therapeutic goals, building rapport, and/or establishing therapeutic alliance. During the psychological support session, skills of self-directed inquiry and experiential processing may be demonstrated and/or practiced.

In some embodiments, breathing exercises meant to promote calm and/or ease anxiety may be demonstrated and/or practiced. In some embodiments, the breathing exercise comprise instructing the subject to focus on their breath and/or sensations associated with the breath throughout the body. For example the subject may be instructed to breathe in for a count of four, to hold their breath for a moment, and then to breathe out for a count of eight. In some embodiments, the therapist and subject may discuss the most helpful ways to support in case of emotional distress during the psilocybin session. In some embodiments, the subject is given access (e.g., online access) to materials concerning the safety and mechanism of action of psilocybin.

In some embodiments, the pre-administration psychological support sessions will serve to establish a therapeutic goal for the psilocybin session. In some embodiments, the subject suggests the therapeutic goal for herself or himself. In some embodiments, the therapist suggests the therapeutic goal to the subject. In some embodiments, the subject is reminded of the therapeutic goal during the pre-administration psychological support session.

In some embodiments, the therapists are trained to counsel the subject before, during, and/or after the psilocybin sessions. In some embodiments, the therapist will have mental health training. In some embodiments, the therapist will be a clinical psychologist, a psychiatrist, a social worker, a doctor or a nurse. In some embodiments, the therapist will meet the following criteria:

Demonstrate independent clinical experience with direct subject care in areas that require counselling and psychotherapeutic skills;

Current unrestricted professional license and/or good professional standing with no history of suspension, professional misconduct or disciplinary actions; and/or High level of openness to learning new approaches and receiving feedback.

Psychological Support During Psilocybin Sessions

During the treatment session, the subject may be supervised by one or more trained therapists. The therapist supervising the subject during the psilocybin session may be the same therapist from the subject's pre-administration psychological support session(s), or may be a different therapist. The therapist(s) may provide psychological support to the subject as necessary. As used herein, the term "psychological support" refers to any measure(s) taken by the therapist during the subject's psilocybin session to ensure the safety of the subject and maximize the clinical effectiveness of the psilocybin session. For example, the psychological support may be anything done by the therapist to (1) to ensure psychological safety of the subject; (2) to allow the subject's subjective experience to unfold naturally within the boundaries of the therapeutic intention set at the preparation; (3) to maintain participant's attention and awareness on the experience of the present moment thus allowing exposure and processing of the challenging emotional states and personal memories; and/or (4) to generate insights and solutions for the resolution of challenging personal situations, conflicts and traumatic experiences. In some embodiments, support can be in the form of therapeutic touch, verbal reassurance, guided imagery and/or relaxation or breathing exercises. In some embodiments, the support may comprise reminders, encouragement, or active guiding. Typically, only one technique is applied at a time to allow for minimal intervention and interference with the subject's unique process.

In some embodiments, the main therapeutic goals of the therapist during the psilocybin session are to (i) minimize extreme anxiety, and (ii) provide appropriate support that enables the skills and processes of self-directed inquiry and experiential processing. In some embodiments, the therapist demonstrates genuine presence, patience, curiosity, and/or openness during the psilocybin session. "Presence" refers to being totally available and present with the subject during all stages of the psilocybin session, and exuding calmness at all times. "Curiosity" refers to interest and willingness to understand the subject's experience, without making assumptions. "Patience" means that the therapist facilitates the participant taking as much time as needed to explore their experiences without controlling the natural urge to help or direct the experience. "Openness" is the ability of the therapist to remain cognitively and experientially open, including a capacity to be curious about how the subject's mind may uniquely choreograph the unfolding content of a session. This includes welcoming all emotions and expressions that might occur.

In some embodiments, the psychological support may comprise curious questioning. In this technique, brief, but detailed, questioning of subjects is used to help the subjects shift and sustain their attention towards different levels of cognition and emotions ("How does that make you feel?") Due to the applicability across a range of mental states and within various settings, the technique of curious questioning can typically be used safely and consistently during the psilocybin session, regardless of the quality or intensity of the experience of each subject.

In some embodiments, the level of psychological support will vary during the various stages of the subject's psilocybin experience (e.g., the initial stage, the early stage, the peak stage, and the late stage). In some embodiments, the type of psychological support will vary during the various stages of the subject's psilocybin experience (e.g., the initial stage, the early stage, the peak stage, and the late stage). Because non-dual, ego-dissolution or "unitive" experiences have been shown to positively correlate with the magnitude and durability of the clinical response, the therapist will, in some embodiments, attend to such states with particular care.

In some embodiments, a subject may experience of a compromised sense of self during the subject's psilocybin experience. In some embodiments, this is interpreted from a psychoanalytic perspective as a disruption of ego-boundaries, which results in a blurring of the distinction between self-representation and object-representation, and precludes the synthesis of self-representations into a coherent whole. In some embodiments, non-dual, ego-dissolution or "unitive" experiences refer to an altered state of consciousness in which there is a reduction in the self-referential awareness that defines normal waking consciousness, resulting in a compromised sense of "self" and instead only a undivided background awareness, often characterised by a sense of unity or "oneness" that exceeds sensory or cognitive apprehension. In some embodiments, a non-dual experience is state of consciousness in which the subject-object dichotomy in normal waking consciousness is substituted for a unified background awareness that is centreless and undivided. In some embodiments, an ego dissolution experience is a spontaneously occurring state of consciousness where there is a reduction in the self-referential awareness that defines normal waking consciousness, resulting in a compromised sense of "self". In some embodiments, a unitive experience is an experience characterised by a sense of unity or "oneness" that exceeds sensory or cognitive apprehension.

At the initial and early stage of the psilocybin session, psychological support may be used to reduce severe and/or prolonged anxiety. Anxiety prior to or during the onset of psilocybin effects is not uncommon, and the therapists may be specially trained to recognize and actively manage subjects through such periods of anxiety until the subject is comfortable enough to continue on their own. In some embodiments, therapists validate the subject's feelings of anxiety without providing interpretations of perceptual disturbances or guiding subjects towards a particular image or memory, other than encouraging them to stay relaxed and open to the emergent experiences. For example, in some embodiments, the therapist may help alleviate anxiety using a grounding exercise. In such an exercise, the subject may be encouraged to pay attention to the sounds around them or to sensations on their skin when touching the bed/couch, ground, or other objects.

At the initial and early stage of the psilocybin session, the therapist may encourage the subject to lie down, practice relaxation and breathing exercises, and/or listen to calming music. In some embodiments, the therapist may remind the subject of the intention for the treatment session. For example, the therapist may ask the subject "What does feeling better or recovery feel like?" or any number of similar questions. Such reminders prior to the onset of or at the onset of psilocybin effects provide an implicit direction for the subjective experience during the psilocybin session. In some embodiments, the therapist may remind the subject that their primary task during this session is to simply collect new and interesting experiences which can then be discussed with the therapist after the session. The therapist may remind the participant of the purpose of the psilocybin therapy and the role of experiential processing, namely allowing the participant to be open and curious to whatever arises and encountering thoughts and feelings previously unknown to them. In some embodiments, the therapist emphasizes that this process inherently requires letting go and a willing passivity to the psychedelic experience.

During the acute onset of action, the subject might experience perceptual changes in visual, auditory or olfactory modes, and a range of unusual physical sensations. These experiences could be anxiety-provoking. In some embodiments, the therapist may practice reassuring "arm holding". This is where, upon the subject's request, a therapist will place his or her hand on the subject's wrist, arm, hand, or shoulder, as a way of helping the subject feel secure during this phase. This exercise may have been previously practiced during the pre-administration psychological support session.

In some embodiments, the therapist may encourage the subject to put on an eye mask, such as a Mindfold eyeshade. In some embodiments, the therapist encourages the subject to put on the eye mask before, during, or after the onset of the psilocybin's effects.

In some embodiments, the therapist may encourage the subject to put on headphones and listen to music. In some embodiments, the headphones reduce outside noise (e.g., "noise-cancelling" headphones). In some embodiments, the music is calming music such as instrumental (e.g., classical) music. In some embodiments, the music comprises nature sounds and/or the sound of moving water (e.g., ocean sounds). In some embodiments, the music comprises isochronic tones. In some embodiments, the music comprises moments of silence. In some embodiments, the music is emotionally evocative. In some embodiments, the music comprises a playlist which mirrors the pharmacodynamics of a typical high-dose psilocybin session: the initial stage, the early stage, the peak stage, and the late stage. In some embodiments, listening to music helps the subject to focus on their internal experience.

In case of prolonged anxiety or distress, therapists may, in some embodiments, actively guide participants through such experiences without interpreting or judging the experiences or giving advice. Once participants are comfortable, the therapist may encourage them to again engage in introspection.

During the peak and late stages of the psilocybin session, the therapist may encourage subjects to face and explore their experience, including the challenging ones. Therapists may direct subjects to participate self-directed inquiry and experiential processing to develop a different perspective on their personal challenges and conflicts, and to generate their own solutions. Such self-generated insights are not only therapeutic because of the emotional resolution, but also empowering to subjects.

As used herein, the term "self-directed inquiry" refers to directing attention to internal states. Subjects are encouraged to be curious about experiences in the present moment, including foreground and background thoughts, emotions, and physical sensations. During the preparation and integration stages, this inquiry might mean asking specific and detailed questions to help direct attention to internal states. However, during the period of drug action, inquiry might simply mean an attitude of openness to inner experiences.

As used herein, "experiential processing" refers to a participant's ability to maintain full attention on the experiences that come into awareness through self-directed enquiry. This includes a willingness and ability to be with and/or move 'in and through' even uncomfortable or challenging thoughts, feelings, sensations or emotions, until discomfort is diminished or resolved.

In some embodiments, the therapist will employ a transdiagnostic therapy. In some embodiments, the transdiagnostic therapy is a Method of Levels (MOL) therapy. In still further embodiments, the MOL therapy comprises Self-Directed Enquiry and Experiential Processing. Typically, MOL uses brief, but detailed, curious questioning to help subjects shift and sustain their attention towards different levels of cognition and emotions (Carey, 2006; Carey, Mansell & Tai, 2015). The emphasis within MOL is on identifying and working with a subject's underlying distress as opposed to just their symptoms. Such MOL related methods and techniques can include: (1) Self-directed enquiry—directing attention to internal states. Participants are encouraged to be curious about experiences in the present moment, including foreground and background thoughts, emotions, and physical sensations; during the preparation and integration stages, such enquiry can mean asking specific and detailed questions to help direct attention to internal states, although for some embodiments, during the period of drug action, enquiry can refer to an attitude of openness to inner experiences; and (2) Experiential processing—sustained focus on the experience; refers to a participant's ability to maintain full attention on the experiences that come into awareness through self-directed enquiry. This includes a willingness and ability to be with and/or move 'in and through' even uncomfortable or challenging thoughts, feelings, sensations or emotions, until discomfort is diminished or resolved.

In some embodiments, the psychological support comprises mindfulness-based therapy or CBT cognitive behavioral therapy (CBT). In some embodiments, the psychological support is informed by a functional theory of human behavior called Perceptual Control Theory.

Occasionally, the subject will try to avoid emerging experiences or distract him/herself while trying to regain cognitive control over the unusual state of their mind. Such distractions may take different forms. For example, the subject might want to engage in a conversation or prematurely describe in detail their experience, visions or insights. When this occurs, the therapist may aim to remain as silent as possible, thereby enabling the subject and his/her inner experience to direct the course of the psilocybin session. In some embodiments, the therapist may use active listening skills paired with prompts to encourage the subject to continue focusing attention on present experiences, particularly if the participant engages the therapist in conversation. In another example, a subject might ask to go to the bathroom or have a drink of water. The sudden and urgent character of such requests might suggest that they are really trying to avoid emerging material. In such cases, the therapist may encourage the subject to stay with the experience by simply redirecting their attention. For example, the therapist may say something like, "We will take a bathroom break at the end of this piece of music" or "I will get you water in a little while. Why don't you put the eye shades back on and relax for a few minutes?" If the subject is trying to avoid a difficult experience, they might listen to the suggestion and relax.

In some embodiments, spontaneous movement such as shaking, stretching or dancing while engaging with the experience is accepted and often encouraged, unless the movement seems to be a way to distract oneself from the experience. In some embodiments, if the subject continues to move around a lot, reminders to periodically return to a lying down position and to actively focus inwards may be provided.

The therapist is not required to understand, support or even have an opinion about the nature or content of the subject's experiences, but the therapist may validate them and convey openness toward the subject's own view of them without dismissing or pathologizing any experience based on its unusual content. These experiences may provide the subject with a perspective that goes beyond identification with their personal narrative. In some embodiments, the therapist will validate one or more of the subject's experiences. In some embodiments, validation of the experiences simply means acknowledging the courage of opening up to the experience and the possibility that any experience will serve the intention of the session.

In some embodiments, a therapist provides psychological support for approximately 4-8 hours immediately after administration of the psilocybin. In some embodiments, the therapist uses guided imagery and/or breathing exercises to calm the subject and/or focus the subject's attention. In some embodiments, the therapist holds the hand, arm, or shoulder of the subject. In some embodiments, the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

In some embodiments, the therapist avoids initiating conversation with the subject, but responds if the subject initiates conversation. Typically, active intervention is kept to a minimum during the treatment experience. In some embodiments, the subject is encouraged to explore their own mental space, and simple guided imagery may be used to assist relaxation. "Guided imagery" refers to an exercise wherein the subject is asked to imagine a scene (e.g., "Invite a scene, perhaps a landscape, and tell me where you find yourself"; "Imagine a place that feels safe to you.")

Post-Administration Psychological Support Session

In some embodiments, subjects may be encouraged to engage in post-administration integration sessions with their therapist. Integration is a process that involves processing, or embodying, a psychedelic experience within a therapeutic context. The process initially begins by the subject verbalizing and reflecting upon any experience from the psilocybin session, and discussing it openly with their therapist. Successful integration of a psilocybin experience accommodates for emotional changes and comprises of translating experiences into new insights, perspectives, and subsequently new behaviors that can be used to benefit the subject's quality of life. New perspectives might in turn influence the participant's current knowledge or values and lead to new ways of relating to cognitions, emotions, behaviors and physical experiences.

In some embodiments, the goals and supportive methods used by the therapist throughout integration sessions should remain consistent, regardless of the intensity or content of the subjective experience explored by the subject. That said, the methods of support used by the therapist should accommodate for the full range of experiences a subject might have faced.

The integration process is not one that should be limited to the sessions with the therapist, and is a process that will likely continue to unfold beyond the visits in clinic. The therapist might encourage the participant to use methods such as spending time in nature, exercise, or creative expression to help facilitate the process further. The subject might also be encouraged to discuss experiences with their friends, family, and/or support network. The role of the integration sessions is not to cover and work on every experience, but to empower the participant by building their capacity to experientially process information safely. This enables the subject to continue self-directed integration, even outside of study visits.

In some embodiments, the subject participates in at least one psychological support session after administration of the psilocybin ("post-administration psychological support session"). In some embodiments, a post-administration psychological support session may be held on the same day as the psilocybin session, after the effects of the psilocybin have substantially worn off. In some embodiments, a post-administration psychological support session may be held the day after the psilocybin session. In some embodiments, a post-administration psychological support session may be held two days after the psilocybin session. In some embodiments, a post-administration psychological support session may be held three days after the psilocybin session. In some embodiments, a post-administration psychological support session may be held about one week after the psilocybin session. In some embodiments, a post-administration psychological support session may be held about two weeks after the psilocybin session. In some embodiments, a post-administration psychological support session may be held about one month after the psilocybin session. In some embodiments, a post-administration psychological support session may be held about three months after the psilocybin session. In some embodiments, a post-administration psychological support session may be held about six months after the psilocybin session. In some embodiments, a post-administration psychological support session may be held about twelve months after the psilocybin session.

In some embodiments, the subject may participate in one, two, three, four, five, six, seven, or eight post-administration psychological support sessions. In some embodiments, the subject may participate in at least two, or at least three post-administration psychological support sessions.

The post-administration psychological support sessions may be individual sessions, wherein a subject meets one-on-one with a therapist. In some embodiments, the psychological support sessions may be group sessions, wherein more than one subject meets with a single therapist, or more than one therapist. In some embodiments, one or more of the subject's family members or friends may be present at the post-administration psychological support session(s).

In some embodiments, the post-administration psychological support session may focus on integration of the psilocybin experience. Integration may involve processing a psychedelic experience in a therapeutic context. Integration may comprise psychological and somatic processing of the experience and a successful assimilation of insights into the subject's life for the purpose of growth, healing and/or well-being. During an integration session, a subject may be encouraged to talk about and reflect upon their experiences during the psilocybin session. In some embodiments, integration may comprise an external expression of the psilocybin experience, such as choice of words, tone of voice, gestures, and/or particular physical activities (yoga, exercise, bodywork, etc.) In some embodiments, integration comprises creatively expressing any insights or experiences gained during a psilocybin experience, for example through poetry, art, music/singing, dance, writing or drawing.

In some embodiments, the subject may be encouraged to reflect on both the thoughts and the feelings that he or she underwent during the psilocybin session, as well as to express those ideas and emotions into a concrete form that can serve as a tool for continuing to remember and integrate those lessons into the future. In some embodiments, the subject may be encouraged to acknowledge and connect with the range of the emotional cognitive and physical experiences of the psilocybin session, and relate them to current experiences in their life situation. This may be accomplished, for example, by discussing them initially with their therapist, and perhaps later with their family, friends, and support circle. Integration helps accommodate changes in emotional states as new insights are generated and integrated. When further explored through oscillating attention between foreground and background thoughts and emotions, such insights may lead to natural and effortless changes in perspectives or behaviors. In some embodiments, the integration process is not limited to initial integration meetings with the therapist, but continues to unfold spontaneously through a participant's own processing and actions in everyday life.

In the case of a low-intensity experience, the integration process might focus on the mental content that emerged during the hours of relaxation and introspection. This might also include reactions to what might have been an unremarkable experience, such as feeling of disappointment, anger, relief etc.

Psychological Support Provided Remotely

In some embodiments, psychological support may be provided remotely to a subject. For example, a therapist providing psychological support may not be in the same room, the same building, or in the same facility as a subject. Remote psychological support may be provided, for example by telephone (i.e., by voice call), by video call or video conference, by text, or by email.

In some embodiments, a pre-administration therapy session is conducted remotely. In some embodiments, a post-administration therapy session (e.g., an integration session) is conducted remotely.

In some embodiments, psychological support is provided remotely during the subject's psilocybin session. For example, in some embodiments, the subject takes the psilocybin in his or her own home, and a therapist provides psychological support by voice call, video call, text, email, etc., for at least 4-8 hours after the subject has taken the drug. In some embodiments, the subject takes the psilocybin in an administration facility as described herein, and the therapist provides psychological support to the subject a therapist provides psychological support by voice call, video call, text, email, etc., for at least 4-8 hours after the subject has taken the drug In some embodiments, remote psychological support is provided to the subject using a digital or electronic system. In some embodiments, the digital or electronic system may comprise one or more of the following features:

The digital or electronic system securely connects subjects with one or more therapists or physicians for "virtual visits." These virtual visits may be introductory or routine.

The digital or electronic system allows a subject to qualify, prequalify, or register for a psilocybin-based clinical trial, or a psilocybin-based psychological support session.

The digital or electronic system is configured to help therapists and/or physicians manage and interact with subjects. For example, the electronic system may allow the therapist to share documents with subjects, keep notes about sessions, or schedule future sessions.

The digital or electronic system is configured to provide alerts for crisis intervention. For example, the digital or electronic system may allow the subject to contact the therapist if they are feeling anxiety or otherwise urgently need to talk to the therapist.

The digital or electronic system is configured to help prepare the subject for a visit with their therapist and/or physician. For example, the digital or electronic system may contain information regarding psilocybin, the therapeutic protocol, etc.

The digital or electronic system is configured to allow the therapist to provide psychological support during the subject's psilocybin session. For example, the system may comprise a video calling or chat feature.

The digital or electronic system is configured to allow the therapist to provide psychological support during a post-administration session (e.g., an integration session).

The digital or electronic system is configured to track the subject's adherence to the treatment regimen or goals.

The digital or electronic system is configured to assess one or more clinical endpoints in the subject. For example, the system may comprise one or more questionnaires or exercises for the subject to complete. Results may be made available to the subject's physician and/or therapist.

In some embodiments, the digital or electronic system is an "app" for use on a mobile phone or a computer. In some embodiments, the digital or electronic system is a website. In some embodiments, the digital or electronic system comprises a "chat" feature which allows communication between the subject and the therapist in real time. In some embodiments, the website comprises a video calling feature, which allows for the therapist to communicate with the subject using video communication. In some embodiments, the digital or electronic system is configured to allow a single therapist to provide psychological support to one or more subjects at or around the same time.

In some embodiments, psychological support sessions may be pre-recorded (e.g., audio or video recording) and provided to the subject for use at the subject's convenience via the digital or electronic system.

Administration Facility, "Set and Setting"

As used herein, the term "set and setting" refers to the subject's mindset ("set") and the physical and social environment ("setting") in which the user has the psilocybin session. In some embodiments, the psilocybin may be administered in a particular set and setting. In some embodiments, the set and setting is controlled, to the extent possible, to maximize therapeutic benefit of the psilocybin session.

In some embodiments, the psilocybin is administered by in a facility specifically designed for psilocybin administration. Administration of the psilocybin to the subject in a facility where the subject feels safe and comfortable may help ease anxiety in the subject, and may facilitate maximum clinical benefit. Psilocybin may be administered to a subject, for example, in the subject's home or at a clinical facility.

In some embodiments, the psilocybin is administered to the subject in a facility (e.g., a room) with a substantially non-clinical appearance. For example, the psilocybin can be administered in a room that comprises soft furniture (e.g., plush couches, chairs, or pillows) and/or plants. In some embodiments, the room may be decorated using muted colors (e.g., greyed, dulled, or desaturated colors). In some embodiments, the light in the room is dimmed and/or light levels are kept or adjust to be relatively low. In some embodiments, the room lighting is adjusted for intensity and/or color. In some embodiments, a virtual reality or augmented reality system (e.g., computer with visual/graphical and auditory outputs) is used. In some embodiments, the room comprises a sound system, for example a high-resolution sound system. In some embodiments, the sound system can allow for simultaneous ambient and earphone listening. In some embodiments, the subject may bring meaningful photographs or objects into the administration room.

In some embodiments, the room comprises a couch. In some embodiments, the room comprises a bed. In some embodiments the room comprises more than one couch or bed, such as 2, 3, 4, 5, 6, 7, 8, 9, or 10 couches or beds. In some embodiments, the subject sits on or lies in the couch or bed for approximately 4-8 hours, or a substantial fraction thereof, immediately after administration of the psilocybin. In some embodiments, the subject listens to music for approximately 4-8 hours, or a substantial fraction thereof, immediately after administration of the psilocybin. In some embodiments, the subject wears an eye mask for approximately 4-8 hours, or a substantial fraction thereof, immediately after administration of the psilocybin. In some embodiments, the subject is provided with a weighted blanket.

In some embodiments, each subject is supervised by one therapist during the psilocybin session. In some embodiments, each subject is supervised by more than one therapist during the psilocybin session, such as two therapists, three therapists, four therapists, or five therapists. In some embodiments, one therapist multiple subjects, wherein each subject is participating in a psilocybin session. For example, one therapist may supervise two, three, four, five, six, seven, eight, nine, or ten subjects.

Embodiments of the disclosure include use of additional tools and/or technique(s) with dosage/administration, including various transcranial magnetic stimulation (TMS) methods and protocols, for example, prior or subsequent to one or more dosing(s), biofeedback devices, etc.

Some embodiments can be used with a digital health product or digital solution. Teachings of the disclosure include utilization of such digital health products and/or related digital biomarkers as diagnostic and/or prognostic tools for patient monitoring and management pre-treatment, during treatment, and/or post treatment. Digital biomarkers can include, by way of non-limiting example: Number of and/or time of phone calls/e-mails/texts; word length in text communication; Gestures used (taps, swipes, or other); Gyroscope derived information e.g. orientation of the phone; Acceleration of the phone; Keystroke patterns; Location derived information from GPS; facial expressions and/or microexpressions; voice or vocal markers; natural language processing; social media use; sleep patterns; specific words or emojis used or not used; and/or the like. For example, in one embodiment, a digital health product can be utilized to determine dosing amount and/or dosing frequency, indicator of a need for re-dosing, re-dosing amount, a warning or alert, as tracking of compliance, etc.

In some embodiments, methods of treatment can include providing a clearance time for a subject or patient, such one or more medications is not present or substantially cleared from the system of the subject/patient. For example, methods of treatment can be configured such that, upon administration, the subject is not taking other serotonergic medications such as: selective-serotonin reuptake inhibitors, selective norepinephrine reuptake inhibitors, tricyclic antidepressants, monoamine oxidase inhibitors and/or antipsychotics. In some embodiment, the method of treatment include treatment concurrently with one or more medications, including but not limited to selective-serotonin reuptake inhibitors, selective norepinephrine reuptake inhibitors, tricyclic antidepressants, and/or monoamine oxidase inhibitors. In some embodiments, the method include treatment such that subjects or patients take concomitant compounds or medications, including but not limited to benzodiazepines, cannabidiol (CBD) and/or other cannabinoids (e.g., THC (tetrahydrocannabinol); THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin); CBCV (cannabichromevarin); CBGV (cannabigerovarin); CBGM (cannabigerol monomethyl ether); CBE (cannabielsoin); CBT (cannabicitran); and/or the like) magnesium, Levomefolic acid, e.g., for a period of time prior to, just prior to, and/or at the same time as receiving psilocybin.

In some embodiments, the method includes treatment such that a subject has not taken one or more medications, particularly has not taken one or more serotonergic medications for at least 2 days, at least, 3 days, at least 4 days, at least 5 days, at least six days, at least 1 week, at least 2, 3, or 4 weeks before administration of the disclosed psilocybin compound.

In some embodiments, the method and/or treatment can comprise subperceptual-dosing (e.g., a dose of less than 3 mg, 2.5 mg, 2 mg, 1.5 mg, 1 mg, 0.9 mg, 0.8 mg, 0.7 mg, 0.6 mg, 0.5 mg, 0.4 mg, 0.3 mg, 0.2 mg, or 0.1 mg) prior to and/or following the administration of a relatively larger single dose or multiple doses (given a few days to a few weeks apart), where the relatively larger single dose or multiple doses is one or more of 5 mg or more, 10 mg or more, 15 mg or more, 20 mg or more, 25 mg or more, 30 mg or more, 35 mg or more, 40 mg or more, 45 mg or more, 50 mg or more.

Embodiments of the disclosure include method utilizing a digital biomarker, for example, as a diagnostic and/or prognostic tool for patient management pre-, during and/or post treatment with psilocybin wherein the digital biomarker is one or more biomarkers associated with executive function, cognitive control, working memory, processing speed, and/ or emotional valence.

In some embodiments the digital biomarker is identified from patterns in smartphone use such as swipes, taps, and other touchscreen activities, and can be scientifically validated to provide measurements of subject status, such as cognition and mood, including, by way of non-limiting example, as disclosed in one or more of the following, each of which is herein expressly incorporated by reference for all purposes: US20170086727, US20170258382, US20170258383, US20170287348, U.S. Ser. No. 10/148, 534, U.S. Pat. No. 9,737,759, and/or U.S. Ser. No. 10/231, 651.

Biomarkers which may serve as a diagnostic and/or prognostic tool for patient management pre, during and/or post treatment may be identified using one or more of: Number of and/or time of phone calls/e-mails/texts; word length in text communication; Gestures used (taps, swipes, or other); Gyroscope derived information e.g. orientation of the phone; Acceleration of the phone; Keystroke patterns; Location derived information from GPS; facial expressions and/or microexpressions; voice or vocal markers; natural language processing; social media use; sleep patterns; specific words or emojis used or not used; and/or the like. In some embodiments, health components and/or connected biomonitors and/or smart devices/wearables can be utilized to collect information to be used in diagnostic and/or prognostic outputs. For example, in some embodiments, a heart rate monitor or similar device can collect a subject's data and heart rate variability (for example only, as disclosed in U.S. Ser. No. 10/058,253, the entirety of which is herein incorporated by reference) can be used to assess/determine a metric relating to the subject's current emotional state, relative change in emotional state, etc., which can be used in determining a new or follow-on treatment plan, adjusting a treatment plan, etc.

In accordance with a further aspect of the disclosure, there is provided a method of assessing a subject pre, during and/or post treatment of a central nervous system disorder to determine whether to provide a psilocybin treatment or a further psilocybin treatment comprising monitoring one or more biomarkers associated with executive function, cognitive control, working memory, processing speed, and emotional valence, and determining the treatment based on an outcome. The method can further comprise the step of administering psilocybin for a first or a subsequent time.

In some embodiments, the biomarker is identified from patterns in smartphone use such as swipes, taps, and other touchscreen activities, and are scientifically validated to provide measurements of cognition and mood. For example, in some instances, the pattern is identified using one or more of: Number of and/or time of phone calls/e-mails/texts; word length in text communication; Gestures used (taps, swipes, or other); Gyroscope derived information e.g. orientation of the phone; Acceleration of the phone; Keystroke patterns; Location derived information from GPS; facial expressions and/or microexpressions; voice or vocal markers; natural language processing; social media use; sleep patterns; specific words or emojis used or not used; and/or the like.

Embodiments include a method of assessing a subject pre, during and/or post treatment of a central nervous system disorder to determine whether to provide a psilocybin treatment or a further psilocybin treatment comprising monitoring one or more biomarkers associated with executive function, cognitive control, working memory, processing speed, and emotional valence, and determining the treatment based on an outcome; the method can further comprise administering psilocybin for a first or a subsequent time.

In some embodiments, the disclosure provides for treating 2 or more subjects, the method comprising administering to each subject a therapeutically-effective dose of psilocybin at the same time or substantially the same time (e.g., dosed within several minutes of each other, within 5, 10, 15, 20, 25, or 30 min of each other), wherein each subject is aware of the other subject also receiving treatment. In some embodiments, the subjects are in the same room. In some embodiments, the subjects are in different rooms.

In some embodiments, the disclosure provides a method of treating a subject, the method comprising administering to the subject a therapeutically-effective dose of psilocybin, and providing a virtual reality/immersive reality digital tool. In some embodiments, the light in the room is dimmed and/or light levels are kept or adjusted to be relatively low. In some embodiments, darkened glasses or eye shades are provided. In some embodiments, the room lighting is adjusted for intensity and/or color. In some embodiments, a virtual reality or augmented reality system (e.g., computer with visual/graphical and auditory outputs) is used.

Subjects

In some embodiments, the subject is a male. In some embodiments, the subject is a female. In some embodiments, the female subject is pregnant or post-partum. In some embodiments, the subject is attempting to reduce or eliminate their use of a pharmaceutical agent, such as an antidepressant or an anti-epileptic drug. In some embodiments, the subject is attempting to reduce or eliminate their use of the pharmaceutical agent before becoming pregnant, having surgery or other medical procedure, or starting to use different pharmaceutical agent.

The subject may be a geriatric subject, a pediatric subject, a teenage subject, a young adult subject, or a middle aged subject. In some embodiments, the subject is less than about 18 years of age. In some embodiments, the subject is at least about 18 years of age. In some embodiments, the subject is about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 85-90, about 90-95, or about 95-100 years of age.

The subject may have a chronic disease or a terminal disease. In some embodiments, the subject may have a life-altering disease or condition (such as the loss of a limb or onset of blindness).

The subject may have recently been diagnosed with a disease, disorder, or condition. For example, the subject may have been diagnosed within 1 month, within 3 months, within 6 months, or within 1 year. In some embodiments, the subject may have been living with a disease, disorder, or condition for an extended period time, such as at least 6 months, at least 1 year, at least 3 years, at least 5 years, or at least 10 years.

In some embodiments, the subject may be a cancer patient, such as a Stage 4 or terminal cancer patient. In some embodiments, the subject may have been determined to have a limited time to live, such as less than 1 year, less than 6 months, or less than 3 months.

The subject may have previously taken a psychedelic drug, or may have never previously taken a psychedelic drug. For example, the subject may or may not have previously taken psilocybin, a psilocybin mushroom ("magic mushroom"), LSD (lysergic acid diethylamide or acid), mescaline, or DMT (N,N-Dimethyltryptamine).

In some embodiments, the subject may have previously taken one or more serotonergic antidepressants (e.g., selective serotonin reuptake inhibitors (SSRIs)). In some embodiments, the subject has never previously taken a serotonergic antidepressant. In some embodiments, the subject has not taken any serotonergic antidepressants for at least 2 weeks, at least 4 weeks, or at least 6 weeks prior to receiving psilocybin.

In some embodiments, the subject may have previously received electroconvulsive therapy (ECT). In some embodiments, the subject has not received any ECT for at least 2 weeks, at least 4 weeks, or at least 6 weeks prior to receiving psilocybin.

The subject may have a medical condition that prevents the subject from receiving a particular medical therapy (such as an SSRI or ECT). In some embodiments, the subject may have previously had an adverse reaction to a particular medical therapy (such as an SSRI or ECT). In some embodiments, a prior medical therapy (such as an SSRI or ECT) was not effective in treating a disease, disorder, or condition in the subject.

Diseases, Disorders, and/or Conditions to be Treated

Provided herein are methods of treating a subject in need thereof, the method comprising administering to the subject a therapeutically-effective dose of a therapeutically effective amount of psilocybin, a prodrug of psilocybin, an active metabolite of psilocybin, or a prodrug of an active metabolite of psilocybin.

Neurocognitive Disorders (e.g., Alzheimer's Disease/Parkinson's Disease)

In some embodiments, a method for treating one or more neurocognitive disorders in a subject in need thereof comprises administering to the subject an effective amount of psilocybin or an active metabolite thereof. In some embodiments, the active metabolite is psilocin.

In some embodiments, psilocybin treatment causes a demonstrated improvement in one or more of the following: the Mini-Mental State Exam (MMSE), the Mini-Cog test, a CANTAB test, a Cognigram test, a Cognivue test, a Cognition test, or an Automated Neuropsychological Assessment Metrics test.

In some embodiments, one or more additional therapeutics are administered in combination with the psilocybin (or active metabolite thereof). For example, the one or more additional therapeutics may be an antidepressant, cholinesterase inhibitors, AChE (acetylcholinesterase) inhibitor, BChE (Butyrylcholinesterase) inhibitor, NMDA (N-methyl-D-aspartate) antagonist, or combinations thereof. A non-limiting list of exemplary types of antidepressants includes: SSRIs (selective serotonin reuptake inhibitors), MAOIs (monoamine oxidase inhibitors), SNRIs (serotonin and norepinephrine reuptake inhibitors), and TCAs (tricyclic antidepressants). For example, the antidepressant may be citalopram, escitalopram, fluoxetine, fluvoxamine, paroxetine, sertraline, vortioxetine, vilazodone, duloxetine, venlafaxine, desvenlafazine, levomilnacipran, amitriptyline, amoxapine, clomipramine, desipramine, desipramine, doxepin, imipramine, nortriptyline, protriptyline, trimipramine, mirtazapine, bupropion, trazodone, vortioxetine, or vilazodone.

Exemplary Neurocognitive Disorders

As used herein, the term "neurocognitive disorder" refers to a wide range of disorders that affect the brain, and are often associated with decreased or altered mental function.

In some embodiments, the neurocognitive disorder is a major neurocognitive disorder. In some embodiments, the neurocognitive disorder is mild neurocognitive disorder.

In some embodiments, the neurocognitive disorder is dementia. In some embodiments, the dementia is late onset dementia (with or without hallucinations), hallucinations co-occurrent and due to late onset dementia; mild dementia; mixed dementia; moderate dementia; organic dementia; presbyophenia; presbyophrenic psychosis; presenile dementia; presenile dementia with delirium; presenile dementia with depression, presenile dementia with delusions; primary degenerative dementia; senile dementia; senile dementia with delusions; senile dementia with delirium, depression, paranoia, or psychosis; or severe dementia.

In some embodiments, the neurocognitive disorder is caused by traumatic brain injury, such as bleeding into the brain (intracerebral hemorrhage), bleeding into the space around the brain (subarachnoid hemorrhage), blood clot inside the skull causing pressure on brain (subdural or epidural hematoma), or concussion.

In some embodiments, the neurocognitive disorder is caused by a breathing condition, such as low oxygen in the body (hypoxia) or high carbon dioxide level in the body (hypercapnia).

In some embodiments, the neurocognitive disorder is caused by a cardiovascular disorder, such as dementia due to many strokes (multi-infarct dementia), heart infections (endocarditis, myocarditis), stroke, or transient ischemic attack (TIA).

In some embodiments, the neurocognitive disorder is caused by a degenerative disorder, such as Alzheimer's disease (also called senile dementia, Alzheimer type), Creutzfeldt-Jakob disease, Diffuse Lewy body disease, Huntington's disease, Multiple sclerosis, Normal pressure hydrocephalus, Parkinson's disease, or Pick disease. In some embodiments, the neurocognitive disorder is due to one or more of Alzheimer's disease, Lewy Body Dementia, Traumatic Brain Injury, Prion Disease, HIV Infection, Parkinson's disease, or Huntington's disease.

In some embodiments, the neurocognitive disorder is dementia due to metabolic causes, such as kidney disease, liver disease, thyroid disease (hyperthyroidism or hypothyroidism), or vitamin deficiency (B1, B12, or folate).

In some embodiments, the neurocognitive disorder is caused by a drug or alcohol-related condition, such as alcohol withdrawal state, intoxication from drug or alcohol use, Wernicke-Korsakoff syndrome (a long-term effect of excessive alcohol consumption or malnutrition), or withdrawal from drugs (such as sedative-hypnotics and corticosteroids).

In some embodiments, the neurocognitive disorder is caused by an infection, such has any sudden onset (acute) or long-term (chronic) infection. For example, the infection may be blood poisoning (septicaemia), brain infection (encephalitis), meningitis (infection of the lining of the brain and spinal cord), prion infections (e.g., mad cow disease), or late-stage syphilis.

In some embodiments, the neurocognitive disorder is caused by complications from cancer and/or cancer treatment with chemotherapy.

In some embodiments, the neurocognitive disorder is caused by depression, neurosis, or psychosis.

In some embodiments, the neurocognitive disorder is Mild Cognitive Impairment

Diseases, Disorders, or Conditions Comorbid with a Neurocognitive Disorder

In some embodiments, the subject has one or more diseases, disorders, or conditions that are comorbid with the neurocognitive disorder. For example, the one or more comorbidities may be hypertension, connective tissue disease, depression, diabetes, or chronic pulmonary disease.

Alzheimer's Disease

In some embodiments, the neurocognitive disorder is due to Alzheimer's disease (AD), such as sporadic Alzheimer's Disease or Familial Alzheimer's Disease.

Alzheimer's disease (AD) is a neurodegenerative brain disorder characterized by both cognitive and non-cognitive behavioral changes, particularly progressive memory deficits, depression, anxiety, dementia, irritability, mood swings, inattention, aggressive and/or apathetic behavior, confusion, gradual physical deterioration, and ultimately death. It is divided into sporadic AD and familial AD, where familial AD accounts for 1-5% of all cases of AD.

At the molecular and cellular levels, the pathological manifestation includes diffuse and extracellular amyloid plaques and intracellular neurofibrillary tangles accompanied by reactive microgliosis, dystrophic neurites, and loss of neurons and synapses.

There are various genetic risk factors for familial AD, of which the strongest genetic risk factor for familial AD is the epsilon 4 allele of APOE (apolipoprotein E). There is a greater likelihood of progression in those individuals with more than one of these risk factors.

The pathophysiology of sporadic AD is currently poorly understood, but it is believed to be multifactorial. Factors leading to the development and progression of AD can include:

dysregulation of the cholinergic system, aggregation of the amyloid beta (Aβ), propagation of hyperphosphorylated tau proteins, as well as inflammatory processes.

Amyloid deposits and neurofibrillary degeneration appear 20 and 10 years before the onset of memory decline, respectively. In 2018, a biomarker-based biological classification, the A/T/N (Amyloid/tau/neurodegeneration) system was proposed, in which, "A" refers to the presence of Aβ biomarkers detected on amyloid PET (positron emission tomography) or assaying CSF (cerebrospinal fluid) levels; "T" refers to the value of a tau biomarker measured in CSF phosphor-tau assay or on tau PET & "N" refers to biomarkers of neurodegeneration or neuronal injury evaluated on [$^{18}$F]-fluorodeoxyglucose-PET, structural MRI (magnetic resonance imaging), or measuring total tau in CSF. It allows the detection of very early stages of AD in patients, and consequently provides the clinical opportunity to give patients treatments early-on in order to limit and slow down the progression of the disease, and to delay the appearance of cognitive troubles. Even though the use of biomarkers is not yet common in clinical practice and there is need for further development to ease their use, they provide the unique opportunity to detect the onset of the disease and act quickly.

There are five drugs currently approved by the U.S. Food and Drug Administration that help manage symptoms of Alzheimer's disease (Table 7). However, there are currently no pharmacological interventions that slow disease progression or prevent the disease, including the damage and subsequent neuronal death that leads to AD symptoms and make the disease fatal.

TABLE 7

Drugs approved by FDA to manage symptoms of Alzheimer's disease

| Drug | Date of FDA approval | Action | Indication | Status |
| --- | --- | --- | --- | --- |
| Tacrine | 1995 | AChE inhibitor | N/A | Withdrawn for poor safety profile |
| Donepezil | 1996 | AChE inhibitor | Mild to moderate AD | Approved |
| Rivastigmine | 1997 | AChE and BChE inhibitor | Mild to moderate AD | Approved |
| Galantamine | 2001 | AChE inhibitor | Mild to moderate AD | Approved |
| Memantine | 2003 | NMDA antagonist | Moderate to severe AD | Approved |
| Memantine + Donepezil | 2014 | AChE inhibitor + NMDA antagonist | Moderate to severe AD For patient taking Donepezil | Approved |

AchE = acetylcholinesterase; BChE = Butyrylcholinesterase; NMDA = N-methyl-D-aspartate Cholinesterase inhibitors (e.g., Donepezil, Rivastigmine, and Galantamine) work by increasing levels of acetylcholine, a neurotransmitter messenger involved in memory, judgment and other thought processes. Certain brain cells release acetylcholine, which helps deliver messages to other cells. After a message reaches the receiving cell, various other chemicals, including an enzyme called acetylcholinesterase, break acetylcholine down so it can be recycled. Alzheimer's disease damages or destroys cells that produce and use acetylcholine, thereby reducing the amount available to carry messages. A cholinesterase inhibitor slows the breakdown of acetylcholine by blocking the activity of acetylcholinesterase. By maintaining acetylcholine levels, the drug helps compensate for the loss of functioning brain cells.

Memantine appears to work by regulating the activity of glutamate, a neurotransmitter involved in information processing, storage and retrieval. Glutamate plays an essential role in learning and memory by triggering NMDA receptors to let a controlled amount of calcium into a neuronal cell. The calcium helps create the chemical environment required for information storage. Excess glutamate, on the other hand, overstimulates NMDA receptors so that they allow too much calcium into neuronal cells which can result in the disruption and death of cells. Memantine may protect cells against excess glutamate by partially blocking NMDA receptors.

The efficacies of current Alzheimer's drugs vary by individual and are limited in their durations of effects. Moreover, none of the current medications can reverse Alzheimer's disease, thus do not stop the underlying destruction of nerve cells. Consequently, their ability to improve symptoms eventually declines as brain cell damage progresses.

Parkinson's Disease

Parkinson's disease is the most common type of parkinsonian syndrome, a term reflecting a group of neurological disorders with Parkinson's disease-like movements problems such as rigidity, slowness, and tremor. Atypical parkinsonism syndromes (illnesses with parkinsonism features plus other features) include multiple system atrophy, progressive supranuclear palsy, corticobasal degeneration and dementia with Lewi bodies.

The clinical presentation of Parkinson's disease includes motor and nonmotor symptoms (See Table 8, below). Motor symptoms consist of movement and physical tasks: tremor, stiffness, slowness and imbalance, and are the core feature of the pathology. Nonmotor symptoms affect many organs systems, such as gastrointestinal and genitourinary systems, and are heterogenous. Among the nonmotor features of Parkinson's disease, cognitive impairment is one of the most troublesome problems, as it diminishes the quality of life of patients.

TABLE 8

Clinical presentation of Parkinson's disease

| Symptom or Sign | Description |
| --- | --- |
| Motor symptoms | |
| Bradykinesia[a] | Slowness and progressively smaller movements as an individual repeats a task (eg, tapping index finger and thumb, opening and closing fist) multiple times in a row |
| Rigidity[a] | Involuntary, velocity-independent resistance to passive movement of a joint (eg, elbow or wrist) by an examiner, with or without a cogwheel phenomenon |
| Rest tremor[a] | A 4- to 6-Hz tremor in a fully resting limb, which temporarily disappears when the limb is held outstretched and then returns (reemergent tremor) and is not present during movement |
| Postural instability | Balance impairment affecting a person's ability to change or maintain postures such as walking or standing; typically a late Parkinson's disease feature |
| Nonmotor symptoms | |
| Olfactory loss | Decreased or absent sense of smell |
| Sleep dysfunction | Symptoms or rapid eye movement sleep behavior disorder, daytime sleepiness, sleep-maintenance insomnia |
| Autonomic dysfunction | Constipation, delayed gastric emptying, urinary urgency and frequency, erectile dysfunction, orthostatic hypotension, blood pressure variability |
| Psychiatric disturbances | Depression, anxiety, apathy, psychosis |
| Cognitive impairment | Mild cognitive impairment or dementia, often initially affecting attention, executive and visuospatial functions |
| Other | Fatigue, softening of the voice, sialorrhea, trouble swallowing |

[a]indicates a primary feature of Parkinson's disease

The pathophysiology of Parkinson's disease is characterized by death of dopaminergic neurons in the substantia nigra. The pathological hallmark of Parkinson's disease is the Lewy body, a neuronal inclusion consisting largely of α-synuclein protein aggregations. The most widely cited model to explain neuropathological progression of Parkinson's disease is the Braak hypothesis. This model suggests that Parkinson's disease starts (stage 1 and 2) in the medulla and the olfactory bulb. This early pathology is associated with symptoms occurring prior to the movement disorder onset, such as rapid eye movement sleep behavior disorder and decreased smell. In stages 3 and 4, pathology progresses to the substantia nigra pars *compacta* and other midbrain and basal forebrain structures. Pathology in these areas is associated with classic Parkinson's disease motor symptoms. It is typically diagnosed at this stage. In advanced Parkinson's disease, the pathology progresses to the cerebral cortices with onset of cognitive impairment and hallucinations.

Parkinson's disease involves progressive neurodegeneration and increasing symptom burden. Parkinson's disease-related deaths increase with age. Causes of death of individuals with Parkinson's disease are similar to causes in non-Parkinson cohorts, with death often occurring before advanced disease stage. When individuals die of Parkinson's disease-related symptoms, aspiration pneumonia is the most common cause.

Parkinson's disease is uncommon among individuals younger than 50 years and increases prevalence with age, peaking between ages 85 and 89 years and it is more common in men (1.4:1 male-to-female ratio). Most cases of Parkinson's disease are idiopathic, but there are known genetic and environmental contributions. Pesticides, herbicide and heavy metal exposures are linked to an increased risk of Parkinson's disease.

In some embodiments, a method for treating a Parkinsonian syndrome or symptom thereof in a subject in need thereof, the method comprising administering to the subject a therapeutically effective amount of psilocybin or an active metabolite thereof. In some embodiments, the Parkinsonian syndrome is Parkinson's disease. In some embodiments, the Parkinsonian syndrome is drug-induced.

In some embodiments, the Parkinsonian syndrome is an atypical Parkinsonian disorder. In some embodiments, the atypical parkinsonian disorder is multiple system atrophy progressive supranuclear palsy, corticobasal degeneration, or dementia with Lewy bodies.

In some embodiments, the subject suffers from a motor symptom or a nonmotor symptom, or combinations thereof. In some embodiments, the motor symptom is bradykinesia, rigidity, tremor, rest tremor, postural instability, stiffness, slowness, imbalance, or combinations thereof. In some embodiments, the nonmotor symptom is cognitive impairment, olfactory loss, sleep dysfunction, autonomic dysfunction, psychiatric disturbance, fatigue, softening of the voice, sialorrhea, trouble swallowing, or combinations thereof.

In some embodiments, the subject has one or more diseases, disorders, or conditions that are comorbid with a Parkinsonian syndrome. In some embodiments, the comorbidity results from a symptom of a Parkinsonian syndrome. In some embodiments, the comorbidity is selected from a neuropsychiatric disturbance, a sleep disorder, melanoma, neurogenic orthostatic hypotension, pseudobulbar affect, anemia, hypertension, type 2 diabetes, restless leg syndrome, cancer, or combinations thereof. In some embodiments, the comorbidity is a neuropsychiatric disturbance, and wherein the neuropsychiatric disturbance is dementia, depression, psychosis, apathy, anxiety, hallucinations, or combinations thereof. In some embodiments, comorbidity is a sleep disorder (e.g., rapid eye movement sleep behavior disorder), and wherein the sleep disorder is daytime drowsiness and sleepiness, sleep attacks, insomnia, or rapid eye movement sleep behavior disorder.

In some embodiments, the method for treating a Parkinsonian syndrome or symptom thereof in a subject in need thereof further comprises administering to the subject at least one additional therapy. In some embodiments, the additional therapy is exercise, physical, occupational, or speech therapy. In some embodiments, the additional therapy is a dopaminergic medication. In some embodiments, the additional therapy is carbidopa-levodopa, entacopone, tolcapone, carbidopa, levodopa entacopone, pramipexole, ropinirol, apomorphine, rotigotine, selegiline, rasagiline, safinamide, amantadine, istradefylline, trihexyphenidyl, benztropine, or combinations thereof.

In some embodiments, the methods for treating a Parkinsonian syndrome or symptom thereof described herein ameliorate the Parkinsonian syndrome, or at least one symptom thereof, in the subject. In some embodiments, one or more of the following scales are used to assess the efficacy of treating Parkinson's disease according to the methods of the disclosure: the Hoehn and Yahr staging scale, the Unified Parkinson's Disease Rating Scale (UPDRS), the Clinical Impression of Severity Index (CISI-PD), the Movement Disorders Society Sponsored Revision of the Unified Parkinson's Disease Rating Scale (MDS-UPDRS), Scales for Outcomes in Parkinson's Disease-motor (SCOPA-Motor), the Schwab & England Activities of Daily Living Scales (SES), the Self-assessment Parkinson's Disease Disability Scale (SPDDS), the Postural Instability and Gait Difficulty score (PIGD), Freezing of Gait Questionnaire (FOGQ), the Nonmotor Symptoms Questionnaire (NMSQuest), the Nonmotor Symptoms Scale (NMSS), Unified Dyskinesia Rating Scale (UDysRS), the Wearing-off Questionnaires (WOQ), self-reported total sleep time on the Pittsburgh Sleep quality index, the Beck Depression inventory, the Insomnia Severity Index, or combinations thereof.

In some embodiments, the Hoehn and Yahr staging scale is used to assess the efficacy of treating Parkinson's disease according to the methods of the disclosure. In some embodiments, after treating according to the methods of the disclosure, a subject's stage on the Hoehn and Yahr staging scale decreases compared to prior to treatment. In some embodiments, after treating according to the methods of the disclosure, a subject's stage on the Hoehn and Yahr staging scale decreases by about 1 stage, about 2 stages, about 3 stages, or about 4 stages, compared to prior to treatment.

In some embodiments, the Unified Parkinson's Disease Rating Scale (UPDRS) is used to assess the efficacy of treating Parkinson's disease according to the methods of the disclosure. In some embodiments, after treating according to the methods of the disclosure, a subject's stage on the UPDRS decreases compared to prior to treatment. In some embodiments, the decrease is about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, the UPDRS score is decreased by at least about 10%, at least about 20%, at least about 30%, at least about 40%, or at least about 50%. In some embodiments, the decreased UPDRS score is observed within about one week about one month, about 3 months, or about 6 months after psilocybin administration.

ADHD

As used herein, "Attention-deficit hyperactivity disorder" (ADHD) is a mental disorder of the neurodevelopmental type characterized by one or more of inattention, hyperactivity, and impulsivity, which are otherwise not appropriate for a person's age. It is commonly diagnosed in childhood, and is one of the most frequent condition affecting school-aged children. In children, the primary symptoms of inattention, hyperactivity, and impulsivity can lead to disruptive behavior at home and in school, which is a typical precursor to clinical referral for diagnosis and treatment. Hyperactivity often decreases in adulthood, however inattention, disorganization, and impulsivity typically persist, causing functional challenges to the patient on a day-to-day basis.

There are three subtypes of ADHD: predominantly inattentive, predominantly hyperactive/impulsive and combined presentation. These are characterized by the presence of excessive symptoms of inattention or hyperactivity-impulsivity, or equal predominance of the two symptom categories. In addition to these core features, multiple reports have indicated the presence of working memory deficits in children with ADHD that persist into adulthood. Phonological, verbal and visuospatial working memory may all be affected in ADHD patients and some studies have suggested that such deficits may be related to the primary symptoms of the disorder, especially inattention.

Individuals with ADHD may also have one or more comorbid diseases, disorders, or conditions. The presence of comorbidities is higher among adults with ADHD. A non-limiting list of comorbidities known to occur with ADHD includes: oppositional defiant disorder, learning difficulties, depression, anxiety, bipolar disorder, substance use disorders (SUD) (particularly alcohol, nicotine, cannabis, and cocaine in adults), personality disorders, obsessive compulsive disorder (OCD). These mental health problems can lead to broader negative outcomes such as underachievement in education, exclusion from schools, employment difficulties, difficulty forming relationships, and criminal activity.

Current pharmacotherapies for treating ADHD target the dysregulation in norepinephrine and dopamine neurotransmitter systems in ADHD. Specifically, ADHD pharmacotherapies increase norepinephrine and dopamine levels in subjects. Current pharmacotherapies target this dysregulation through various actions. Stimulants such as methylphenidate hydrochloride block dopamine transporters to increase extracellular dopamine and the rate of dopamine release. Dextroamphetamine, another stimulant, blocks the catabolism of norepinephrine and dopamine via interaction with the enzyme catechol-o-methyltransferase. Atomoxetine increases extracellular levels of dopamine in the prefrontal cortex, and alpha-adrenergic receptor agonists improve working memory by stimulating post synaptic alpha adrenoceptors. Furthermore, tricyclic antidepressants such as desipramine selectively inhibit norepinephrine reuptake, thereby increasing norepinephrine concentrations. In some embodiments, one or more of the medications listed below is administered to a subject in need thereof to treat ADHD, in combination with psilocybin or an activate metabolite thereof.

Stimulant medication is the most common treatment of ADHD, with 70-80% of patients at least partially responding to these treatments. Stimulants include methylphenidates (e.g. Ritalin), and amphetamines (e.g. Adderall). They have been shown to increase intrasynaptic dopamine and norepinephrine concentrations. Stimulants have been approved by the Food and Drug Administration to treat ADHD in children and adolescents and are typically the first-line pharmacological agents used in ADHD treatment. However, many caregivers are reluctant to consider stimulant therapy for their children or adolescents due to the abuse and addiction potential of stimulants, despite some evidence suggesting that this is not a common issue.

Methylphenidate improves attention and has been shown to cause increased dopamine levels in the ventral striatum, prefrontal cortex, and temporal cortex. Specifically, it is able to bind to the dopamine transporter and block dopamine reuptake from the synaptic cleft. The improvements in working memory caused by methylphenidate have been associated with normalizing underactive frontocingulate networks and striatal areas. Whilst stimulants have been shown to reduce emotional reactions to frustration and increase effortful behavior, they have also been found to promote risky behavior and increase susceptibility to environmental distraction.

Amphetamines block the action of catechol-o-methyltransferase, the enzyme that degrades norepinephrine and dopamine, increasing the availability of these neurotransmitters in the synaptic cleft. Dextroamphetamine is a commonly used stimulant comprising of three different formulations in regard to its duration of action: 1. Immediate-release dextroamphetamine, 2. Sustained-release dextroamphetamine, and 3. Extended-release mixed amphetamine salts (Adderall XR). All preparations are safe and effective in treating ADHD symptoms in children, adolescents and adults. Mixed amphetamine salts have good cardiovascular tolerability and can be used in patients with mild hypertension. However, common side effects include insomnia, decreased appetite and weight loss, headache, dry mouth, and nervousness.

Atomoxetine is a selective norepinephrine reuptake inhibitor used in the treatment of ADHD. It can be used alone or alongside stimulants. It has a slower onset than stimulants and may take several weeks for maximum treatment effect to be reached. It does not have an abuse potential, so can be used in adults with ADHD who may be at risk for substance abuse. Atomoxetine is metabolized by CYP2D6 isoenzyme and therefore is not suitable for depressive patients who take medications such as fluoxetine or paroxetine, which inhibit CYP2D6. Common side effects include nausea, decreased appetite (in 15-20% of patients), insomnia, fatigue, dizziness, abdominal pain and slightly increased diastolic blood pressure and heart rate. Weight loss and decrease in expected height has been observed in children treated with atomoxetine for 15 to 18 months but no significant growth impairments were reported at the end of a different study that lasted five years. Atomoxetine is not suitable for use in children or adolescents with serious structural cardiac abnormalities, heart rhythm abnormalities or cardiomyopathy. It has a similar molecular structure to fluoxetine and has been associated with suicidal ideation, leading to its FDA "black box" warning in 2005.

Reboxetine is a selective noradrenaline reuptake inhibitor that is used as an antidepressant. It increases norepinephrine and dopamine levels in the prefrontal cortex and causes the release of dopamine in subcortical structures through inhibition of dopamine D1 receptors. It is efficacious in reducing ADHD symptoms and is generally well tolerated with the most common adverse effects including drowsiness, decreased appetite, pallor, headaches, dizziness and sleep disturbance.

Antihypertensive agents such as guanfacine and clonidine act on presynaptic alpha-2 adrenoreceptors in the prefrontal cortex to inhibit norepinephrine release and downregulate the noradrenergic system. Immediate release guanfacine and clonidine are not approved by the FDA for children and adolescents with ADHD but are efficacious in ADHD children with comorbid tic disorder and in children with pervasive developmental disorders accompanied with hyperactivity and impulsivity. Extended release formulations of guanfacine and clonidine are FDA-approved for ADHD in children and adolescents as once daily monotherapy and as an adjunctive therapy to stimulants. Adverse effects include sedation, fatigue, headache, dry mouth, constipation, upper abdominal pain, irritability, dizziness, bradycardia, orthostatic hypotension, and withdrawal hypertension. Alpha-2 agonists are antihypertensive agents and therefore blood pressure and heart rate should be monitored throughout treatment, with cardiac consultation typically taking place prior to the start of treatment.

While tricyclic antidepressants improve mood and decrease hyperactivity, they do not improve cognitive performance and concentration. Desipramine is the most studied tricyclic antidepressant in the treatment of ADHD and has fewer side effects compared to other tricyclics. It selectively inhibits norepinephrine reuptake at the presynaptic transporter, thus increasing norepinephrine availability. Desipramine is effective in treating ADHD in adults but is considered less effective than stimulants. Side effects include dry mouth, constipation, sweating, insomnia, tachycardia, increased blood pressure, EKG changes, and orthostatic hypotension. These adverse effects suggest possible cardiotoxic effects, thereby limiting the use of desipramine to patients with no co-existing cardiovascular conditions.

Bupropion is an antidepressant and dopamine and norepinephrine reuptake inhibitor that has shown efficacy in improving ADHD symptoms. It has not been approved by the FDA as a pharmacotherapy for the treatment of ADHD. Side effects include tachycardia, insomnia, headache, dry mouth, nausea, and weight loss. Serious adverse effects include potential worsening of suicidal ideation and risk of seizures.

Modafinil is not approved for the treatment of ADHD but studies have investigated its efficacy in ADHD in children and adolescents. It appears to alter the balance of gamma-aminobutyric acid and glutamate, casing hypothalamus activation. A 6-week placebo-controlled trial in children aged 7 to 14 years old with ADHD reported a 78% response rate with modafinil compared to placebo. Adverse effects include insomnia, headache and decreased appetite. In 2006, the US Food and Drug Administration (FDA) rejected Modafinil for the treatment of ADHD as they claimed the drug was not safe enough to give to children.

In some embodiments, a method for treating attention-deficit hyperactivity disorder (ADHD) in a subject in need thereof, the method comprising administering to the subject a therapeutically effective amount of psilocybin or an active metabolite thereof. In some embodiments, the subject is a child. In some embodiments, the subject is an adult. In some embodiments, the subject is an adolescent.

In some embodiments, the subject in need thereof has an attention-deficit hyperactivity disorder subtype selected from predominantly inattentive, predominantly hyperactive/impulsive, or combined presentation. In some embodiments, the attention-deficit hyperactivity disorder subtype is predominantly inattentive. In some embodiments, the attention-deficit hyperactivity disorder subtype is predominantly hyperactive/impulsive. In some embodiments, the attention-deficit hyperactivity subtype disorder is combined presentation.

In some embodiments, the subject has at least one disease, disorder, or condition that is comorbid with ADHD. In some embodiments, the comorbidity is selected from oppositional defiant disorder, learning difficulties, depression, anxiety, bipolar disorder, substance use disorders, autism spectrum disorders, personality disorder, obsessive compulsive disorder, or combinations thereof. In some embodiments, the comorbidity is oppositional defiant disorder. In some embodiments, the comorbidity is anxiety.

In some embodiments, the subject is administered an additional therapy in addition to psilocybin (or active metabolite thereof). In some embodiments, the additional therapy is a stimulant, a norepinephrine reuptake inhibitor, an α-adrenergic agonist, a tricyclic antidepressant, modafinil, or combinations thereof. In some embodiments, the additional therapy is a stimulant (e.g., an amphetamine or methylphenidate). In some embodiments, the additional therapy is a norepinephrine reuptake inhibitor (e.g., atomoxetine or reboxetine).

In some embodiments, administration of psilocybin (or active metabolite thereof) to a subject alleviates at least one sign or symptom of ADHD.

In some embodiments, the ADHD Rating Scale V (ADHD-RS-V) is used to rate the symptoms of attention-deficit disorder, such as attention-deficit hyperactivity disorder. In some embodiments, after treating according to the methods of the disclosure, a subject's ADHD Rating Scale V score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Adult Self Report Scale is used to evaluate the symptoms of attention deficit disorder, such as attention-deficit hyperactivity disorder. In some embodiments, prior to treatment according to the methods of the disclosure, the subject has a score on the Adult Self Report Scale of greater than 24. In some embodiments, prior to treatment according to the methods of the disclosure, the subject has a score on the Adult Self Report Scale of between about 17 and 23. In some embodiments, after treating according to the methods of the disclosure, a subject's Adult Self Report Scale decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, the Diagnostic Interview for ADHD in Adults is used to diagnose ADHD.

In some embodiments, the ADHD Investigator Symptom Rating Scale (AISRS) is used to evaluate the symptoms of attention deficit disorder, such as attention-deficit hyperactivity disorder. In some embodiments, after treating according to the methods of the disclosure, a subject experiences an improvement in at least one, at least two, at least 3, at least 4, at least 5, at least 6, at least 7, at least 8, at least 9, at least 10, at least 11, at least 12, at least 13, at least 14, at least 15, at least 16, at least 17, or at least 18 symptoms of ADHD according to the AISRS. In some embodiments, after treating according to the methods of the disclosure, a subject's AISRS decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, the Conners' Adult Attention-Deficit/Hyperactivity Disorder Rating Scale is used to evaluate the symptoms of attention deficit disorder, such as attention-deficit hyperactivity disorder. In some embodiments, after treating according to the methods of the disclosure, a subject experiences an improvement in at least one, at least two, at least 3, at least 4, at least 5, at least 6, at least 7, at least 8, at least 9, at least 10, at least 11, at least 12, at least 13, at least 14, at least 15, at least 16, at least 17, or at least 18 symptoms of ADHD according to the Conners' Adult Attention-Deficit/Hyperactivity Disorder Rating Scale. In some embodiments, after treating according to the methods of the disclosure, a subject's Conners' Adult Attention-Deficit/Hyperactivity Disorder Rating Scale total score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, the Test of Variables of Attention (TOVA) score is used to evaluate the symptoms of attention deficit disorder, such as attention-deficit hyperactivity disorder. In some embodiments, prior to treating according to the methods of the disclosure, a subject's TOVA score (which is reported as a Z-score) is −1.80 or lower. In some embodiments, after treating according to the methods of the disclosure, a subject's TOVA score (which is reported as a Z-score) increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, or more compared to prior to said treating.

In some embodiments, the Brown Attention-Deficit Disorder (BADD) Scales are used to evaluate the symptoms of attention deficit disorder, such as attention-deficit hyperactivity disorder. In some embodiments, after treating according to the methods of the disclosure, a subject's BADD total score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, the National Institute for Children's Health Quality (NICHQ) Vanderbilt Assessment Scale is used to evaluate the symptoms of attention deficit disorder, such as attention-deficit hyperactivity disorder. In some embodiments, after treating according to the methods of the disclosure the NICHQ Vanderbilt Assessment scale score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the SNAP-IV Teacher and Parent Rating Scale is used to evaluate the symptoms of attention deficit disorder, such as attention-deficit hyperactivity disorder. In some embodiments, after treating according to the methods of the disclosure the SNAP-IV Teacher and Parent Rating Scale score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, prior to the treating, a subject with ADHD inattentive type has a teacher score of 2.56 or higher or a parent score of 1.78 or higher. In some embodiments, prior to the treating, a subject with ADHD hyperactive-impulsive type has a teacher score of 1.78 or higher or a parent score of 1.44 or higher. In some embodiments, prior to the treating, a subject with ADHD combined type has a teacher score of 2.00 or higher or a parent score of 1.67 or higher.

In some embodiments, the Conners-Wells' Adolescent Self-Report Scale is used to evaluate the symptoms of attention deficit disorder, such as attention-deficit hyperactivity disorder. In some embodiments, after treating according to the methods of the disclosure the Conners-Wells' Adolescent Self-Report Scale decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Child Behavior Checklist is used to evaluate the symptoms of attention deficit disorder, such as attention-deficit hyperactivity disorder. In some embodiments, after treating according to the methods of the disclosure the Child Behavior Checklist score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Conners' Comprehensive Behavior Rating Scale is used to evaluate the symptoms of attention deficit disorder, such as attention-deficit hyperactivity disorder. In some embodiments, after treating according to the methods of the disclosure the Conners' Comprehensive Behavior Rating Scale score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Adult ADHD Quality of Life is used to evaluate the symptoms of attention deficit disorder, such as attention-deficit hyperactivity disorder. In some embodiments, the Adult ADHD Quality of Life is used to evaluate how ADHD symptoms impact a subject's quality of life. In some embodiments, after treating according to the methods of the disclosure, a subject's Adult ADHD Quality of Life score increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, or more compared to prior to said treating.

In some embodiments, the Clinical Global Impression is used to evaluate the symptoms of attention deficit disorder, such as attention-deficit hyperactivity disorder. In some embodiments, the Clinical Global Impression is used to evaluate how ill or dysfunctional a subject is. In some embodiments, the CGI-Severity (CGI-S) subscale is used to measure the severity of a subject's illness or dysfunction. In some embodiments, the CGI-Improvement (CGI-I) subscale is used to measure an improvement in a subject's illness or dysfunction. In some embodiments, the CGI-Efficacy (CGI-E) subscale is used to measure the efficacy of treating according to the methods of the disclosure. In some embodiments, after treating according to the methods of the disclosure, a CGI score of subscore decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treating.

In some embodiments, the Global Assessment of Functioning Scale (GAF) is used to evaluate the symptoms of attention deficit disorder, such as attention-deficit hyperactivity disorder. In some embodiments, the GAF is used to assess a subject's everyday functioning. In some embodiments, after treating according to the methods of the disclosure, a subject's GAF score increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, or more compared to prior to said treating.

In some embodiments, the subject in need thereof has a decreased ADHD Rating Scale V score after treatment with psilocybin. In some embodiments, the decreased ADHD Rating Scale V score is observed within about one hour after psilocybin administration to about one year after psilocybin administration. In some embodiments, the ADHD Rating Scale V score is decreased by between about 20% and about 100%.

Epilepsy

Epilepsy is a neurological disorder marked by sudden recurrent episodes of sensory disturbance, loss of consciousness, or convulsions, associated with abnormal electrical activity in the brain. Epilepsy may occur as a result of a genetic disorder or an acquired brain injury, such as a trauma or stroke. During a seizure, an individual with epilepsy experiences abnormal behavior, symptoms, and sensations, sometimes including loss of consciousness. There are few symptoms between seizures. Common treatments for epilepsy include various medications (e.g., nerve pain medications, sedatives, anticonvulsants), and in some cases surgery, devices, or dietary changes.

In some embodiments, a method for treating epilepsy in a subject in need thereof comprises administering to the subject a therapeutically effective amount of psilocybin or an active metabolite thereof. In some embodiments, the epilepsy is generalized epilepsy, epilepsy with myoclonic absence seizures, focal epilepsy, generalized and focal epilepsy, unknown if generalized or focal epilepsy, autosomal dominant nocturnal frontal lobe epilepsy, childhood absence epilepsy, benign rolandic epilepsy, Doose syndrome, Dravet syndrome, early myoclonic encephalopathy, Jeavons syndrome, epilepsy in infancy with migrating focal seizures, epileptic encephalopathy with continuous spike and wave during sleep, febrile illness-related epilepsy syndrome, frontal lobe epilepsy, west syndrome, juvenile absence epilepsy, juvenile myoclonic epilepsy, Landau-Kleffner syndrome, Lennox-Gastaut syndrome, Ohtahara syndrome, Panayiotopoulos syndrome, progressive myoclonic epilepsy, reflex epilepsy, or temporal lobe epilepsy. In some embodiments, the subject in need thereof has generalized tonic-clonic, convulsive, absence, myoclonic, clonic, tonic, or atonic seizures.

In some embodiments, the subject has one or more diseases, disorders, or conditions that are comorbid with epilepsy. In some embodiments, the comorbidity is a psychiatric comorbidity, a neurological comorbidity, or a somatic condition. In some embodiments, the psychiatric comorbidity is bipolar disorder, ADHD, depression, anxiety, or combinations thereof. In some embodiments, the neurological comorbidity is migraine, cognitive impairment, stroke, cerebrovascular disease, or combinations thereof. In some embodiments, the neurological comorbidity is migraine. In some embodiments, the somatic condition is a cardiac, inflammatory, or pulmonary condition. In some embodiments, the cardiac condition is heart disease. In some embodiments, the inflammatory condition is an autoimmune disease, and the autoimmune disease is arthritis, diabetes mellitus, asthma, or combinations thereof. In some embodiments, the pulmonary condition is chronic obstructive pulmonary disease (COPD), chronic bronchitis, emphysema, or combinations thereof.

In some embodiments, a method for treating epilepsy in a subject in need thereof further comprises administering to the subject an additional therapy. In some embodiments, the additional therapy is a sodium channel blocker, calcium current inhibitor, gamma-aminobutyric (GABA) enhancer, glutamate receptor antagonists, carbonic anhydrase inhibitor, hormone, an N-methyl-D-aspartate (NMDA) receptor antagonist, synaptic vesicle glycoprotein 2A (SV2A) ligand, α-amino-3-hydroxy-5-methyl-4-isoxazolepropionic acid (AMPA)/Kainate receptor antagonist, or combinations thereof. In some embodiments, the additional therapy is a sodium channel blocker, and the sodium channel blocker is phenytoin, fosphenytoin, carbamazepine, lamotrigine, or valproate. In some embodiments, the additional therapy is a calcium channel antagonist, and wherein the calcium current inhibitor is ethosuximide or valproate. In some embodiments, the additional therapy is a GABA enhancer, and wherein the GABA enhancer is a benzodiazepine, barbiturate, progabide, progesterone, ganaxolone, vigabatrin, tiagabine, gabapentin, or valproate. In some embodiments, the additional therapy is an NMDA receptor antagonist, and the NMDA receptor antagonist is felbamate or levetiracetam. In some embodiments, the additional therapy is an AMPA/Kainate receptor antagonist, and wherein the AMPA/Kainate receptor antagonist is topiramate.

In some embodiments, the subject experiences a reduction in seizures per month of between about 15% and about 100% after treatment. In some embodiments, the subject experiences a reduction in seizure duration of between about 15% and about 100% after treatment.

In some embodiments, the efficacy of treating epilepsy according to the methods of the disclosure is assessed using diary assessment, assessment by clinician or caregiver, electroencephalogram, or clinical seizure rating scales. Non-limiting examples of clinical seizure rating scales include the VA Seizure Frequency and Severity Scale (VA Scale), the Chalfont-National Hospital Seizure Severity Scale, Liverpool Seizure Severity Scale, Hague Seizure Severity Scale, or Occupational Hazard scale.

In some embodiments, after a subject is treated according to the methods of the disclosure, the subject's Chalfont-National Hospital Seizure Severity Scale score is decreased by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treatment.

In some embodiments, after a subject is treated according to the methods of the disclosure, the subject's Liverpool Seizure Severity Scale score is decreased by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treatment.

In some embodiments, after a subject is treated according to the methods of the disclosure, the subject's Hague Seizure Severity Scale score is increased by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, or more, compared to prior to said treatment.

In some embodiments, after a subject is treated according to the methods of the disclosure, the subject's Occupational Hazard scale score is decreased by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to said treatment.

Autism

Autism spectrum disorder (ASD) is a neurodevelopmental syndrome characterized by core deficits in social interaction and communication, presence of repetitive and restricted patterns of behavior and interests, and/or unusual reactivity to sensory input. The DSM-5 redefined the autism spectrum disorders to include the previous diagnoses of autistic disorder, Asperger's syndrome, pervasive developmental disorder not otherwise specified (PDD-NOS) and childhood disintegrative disorder. Approximately 31% of individuals with ASD have intellectual disability defined as an intelligence quotient (IQ) below 70 with a further 25% being in the borderline range (IQ, 71-85), and approximately one-third are non-verbal.

At present, the etiology and pathophysiology of ASD are largely unknown and considered multi-factorial, given the heterogeneity of the population. Recent studies have suggested the cause of ASD is primarily genetic (heritability being approximately 80%), with the relative contribution of environmental factors being lesser than previously thought. Approximately 85% of ASD cases are idiopathic, without known etiological cause. By contrast, syndromic autism has defined somatic abnormalities and a neurobehavioral phenotype that often includes ASD, examples include fragile X syndrome, Rett syndrome and Tuberous Sclerosis Complex, and have around a 30-50% chance of also having ASD; these syndromic causes of ASD can be confirmed by genetic testing to confirm underlying abnormalities in risk genes, in FMR1 in fragile X syndrome, for example. Many ASD risk genes are related to processes of synaptic transmission such as neurite outgrowth, synaptic plasticity and synaptogenesis, suggesting their involvement in ASD pathophysiology.

In addition to the core symptomology of ASD described, another significant source of impaired functioning and reduced quality of life in this heterogenous population are the associated symptoms as well as comorbid psychiatric disorders. ASD-associated symptoms and challenging behaviors include irritability, aggression, self-injurious behavior, motor impairment and cognitive deficits such as those of cognitive flexibility, sustained attention, working memory, episodic memory and executive function. Psychiatric disorders are considered to be more prevalent in ASD than in the general population, although reported prevalence and diagnoses of co-occurring psychiatric disorders vary considerably. A recent systematic review and meta-analysis suggests that attention-deficit hyperactivity disorder (ADHD) and anxiety disorders are the most common comorbid conditions in ASD. Other psychiatric disorders prevalent in ASD include sleep-wake disorders; disruptive, impulse-control, and conduct disorders; depressive disorders; obsessive-compulsive disorder (OCD); bipolar disorder and schizophrenia spectrum disorders. Depression is also more prevalent in individuals with ASD.

Currently, no pharmacological treatments are approved for the core symptomology of ASD. The only FDA-approved pharmacotherapies in an ASD population are risperidone and aripiprazole for the associated irritability; risperidone is a second-generation antipsychotic and was the first drug approved by the FDA to treat ASD-related irritability in 2006 for children aged 5 or older and aripiprazole, a psychotropic drug, was approved by the FDA in 2009 for the same indication in children aged 6 to 17 years old. Other "off-label" pharmacological interventions used for ASD-associated symptom management, again, that aren't approved for treatment of core symptomology, include typical antipsychotic, haloperidol for irritability and aggression; selective-serotonin reuptake inhibitor (SSRI), sertraline for anxiety disorders; neuropeptide oxytocin, currently in development for social deficits; stimulant methylphenidate, an ADHD medication and venlafaxine, a serotonin and norepinephrine reuptake inhibitor (SNRI) for hyperactivity and inattention; SSRIs fluoxetine and citalopram for repetitive behaviors and N-methyl-D-aspartate (NMDA) receptor antagonist, memantine and acetylcholinesterase inhibitor, rivastigmine for cognitive dysfunction. Non-pharmacological treatments for ASD include psychosocial interventions such as applied behavior analysis (ABA), early intensive interventions, social skills training and cognitive behavioral therapy.

In some embodiments, a method for treating an autism spectrum disorder (ASD) or a symptom thereof in a subject in need thereof comprises administering to the subject a therapeutically effective amount of psilocybin or an active metabolite thereof. In some embodiments, the ASD is autistic disorder, Asperger's syndrome, pervasive developmental disorder not otherwise specified (PDD-NOS), childhood disintegrative disorder, or combinations thereof. In some embodiments, the sign or symptom of ASD is irritability, repetitive behavior, restricted behaviors, unusual reactivity to sensory stimuli, social communication deficits, aggression, self-injurious behavior, motor impairment, cognitive deficits, or combinations thereof.

In some embodiments, the subject is nonverbal.

In some embodiments, the subject has an intelligence quotient (IQ) of between about 71 and about 85. In some embodiments, the subject has an IQ of less than or equal to about 70. In some embodiments the subject has an IQ in the range of about 70 to about 79. In some embodiments the subject has an IQ in the range of about 80 to about 89. In some embodiments the subject has an IQ in the range of about 90 to about 109. In some embodiments the subject has an IQ in the range of about 110 to about 119. In some embodiments the subject has an IQ in the range of about 120 to about 129. In some embodiments the subject has an IQ greater than or equal to about 130.

In some embodiments, the subject suffers from cognitive deficits in cognitive flexibility, sustained attention, working memory, episodic memory, executive function, or combinations thereof.

In some embodiments, the subject has one or more diseases, disorders, or conditions which are comorbid with ASD. In some embodiments, the comorbidity is a psychiatric disorder such as attention-deficit hyperactivity disorder, anxiety disorders, sleep-wake disorder, impulse-control, disruptive behavior, conduct disorder, depressive disorders, obsessive-compulsive and related disorders, bipolar disorder, schizophrenia, or combinations thereof. In some embodiments, the comorbidity is an inflammatory disorder, gastrointestinal disorder, epilepsy, or a combination thereof.

In some embodiments, the method for treating an ASD or a symptom thereof further comprises administering to the subject one additional therapeutic agent. In some embodiments, the least one additional therapeutic agent is risperidione or aripiprazole. In some embodiments, the at least one additional therapeutic agent is an antidepressant, such as SSRIs (selective serotonin reuptake inhibitors), MAOIs (monoamine oxidase inhibitors), SNRIs (serotonin and norepinephrine reuptake inhibitors), and TCAs (tricyclic antidepressants). For example, the antidepressant may be citalopram, escitalopram, fluoxetine, fluvoxamine, paroxetine, sertraline, vortioxetine, vilazodone, duloxetine, venlafaxine, desvenlafazine, levomilnacipran, amitriptyline, amoxapine, clomipramine, desipramine, desipramine, doxepin, imipramine, nortriptyline, protriptyline, trimipramine, mirtazapine, bupropion, trazodone, vortioxetine, or vilazodone, In some embodiments, the Autism Diagnostic Observation Schedule, Second Edition (ADOS-2), Autism Diagnostic Interview-Revised (ADI-R), Childhood Autism Rating Scale, Second Edition (CARS2), Vineland-II Adaptive Behavior Scales (VABS-2), Aberrant Behavior Checklist (ABC), Child Behavior Checklist (CBCL), Autism Behavior Inventory (ABI), Social Responsiveness Scale, Second Edition (SRS-2), Repetitive Behavior Scale-Revised (RBS-R), the Ohio Autism Clinical Impressions Scale-Improvement (OACIS-I), Ohio Autism Clinical Impressions Scale-Severity (OACIS-S), the Gilliam Autism Rating Scale-Third Edition (GARS-3), Social Communication Questionnaire (SCQ), Autism Spectrum Quotient (AQ), Adult Repetitive Behavior Questionnaire-2 (RBQ-2A), or combinations thereof, are used to assess the efficacy of treating according to the methods of the disclosure.

In some embodiments, the Autism Diagnostic Observation Schedule, Second Edition (ADOS-2) is used to diagnose autism spectrum disorder and/or assess the efficacy of treating according to the methods of the disclosure. In some embodiments, after treating according to the methods of the disclosure, a subject's composite score on the ADOS-2 decreases compared to prior to said treatment by at least about 5%, for example, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, or more.

In some embodiments, the Autism Diagnostic Interview-Revised (ADI-R) is used to diagnose autism spectrum disorder and/or assess the efficacy of treating according to the methods of the disclosure. In some embodiments, after treating according to the methods of the disclosure, a subject's score on the ADI-R decreases compared to prior to said treatment by at least about 5%, for example, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, or more. In some embodiments, the Childhood Autism Rating Scale, Second Edition (CARS-2) is used to assess the efficacy of treating according to the methods of the disclosure. In some embodiments, after treating according to the methods of the disclosure, a subjects CARS-2 score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Vineland-II Adaptive Behavior Scales (VABS-2) is used to assess the efficacy of treating according to the methods of the disclosure. In some embodiments, after treating according to the methods of the disclosure, a subject's composite score on the VABS-2 decreases compared to prior to said treating by at least about 5%, for example, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, or more.

In some embodiments, the Aberrant Behavior Checklist—Second Edition (ABC) is used to assess the efficacy of treating according to the methods of the disclosure. In some embodiments, after treating according to the methods of the disclosure, a subjects ABC score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Child Behavior Checklist (CBCL) is used to assess the efficacy of treating according to the methods of the disclosure. In some embodiments, after treating according to the methods of the disclosure, a subject's CBCL percentile decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Autism Behavior Inventory (ABI) is used to assess the efficacy of treating according to the methods of the disclosure. In some embodiments, after treating according to the methods of the disclosure, a subject's ABI score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Social Responsiveness Scale, Second Edition (SRS-2) is used to assess the efficacy of treating according to the methods of the disclosure. In some embodiments, after treating according to the methods of the disclosure, a subject's SRS-2 proxy version t-score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Repetitive Behavior Scale-Revised (RBS-R) is used to assess the efficacy of treating according to the methods of the disclosure. In some embodiments, after treating according to the methods of the disclosure, a subject's RBS-R score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Ohio Autism Clinical Impressions Scale-Improvement/Severity (OACIS-I/S) are used to assess the efficacy of treating according to the methods of the disclosure. In some embodiments, after treating according to the methods of the disclosure, a subject's OACIS-I and/or OACIS-S score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Gilliam Autism Rating Scale-Third Edition (GARS-3) is used to assess the efficacy of treating according to the methods of the disclosure. In some embodiments, after treating according to the methods of the disclosure, a subject's GARS-3 score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Autism Spectrum Quotient (AQ) is used to assess the efficacy of treating according to the methods of the disclosure. In some embodiments, after treating according to the methods of the disclosure, a subject's AQ score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Adult Repetitive Behavior Questionnaire-2 (RBQ-2A) is used to assess the efficacy of treating according to the methods of the disclosure. In some embodiments, after treating according to the methods of the disclosure, a subject's RBQ-2A score decreases compared to prior to said treatment by about 5% to about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the method decreases the subject's Vineland-II Adaptive Behavior (VABS-2) score. In some embodiments, the increased VABS-2 score is observed within one month after psilocybin administration. In some embodiments, the VABS-2 score is decreased by at least about 5%, about 10%, about 15%, or by at least about 20%.

In some embodiments, the method decreases the subject's proxy version-t score on the Social Responsiveness Scale, Second Edition (SRS-2). In some embodiments, the decreased proxy version-t score is observed within one month after psilocybin administration. In some embodiments, the proxy version-t score is decreased by at least about 5%, about 10%, about 15%, or by at least about 20%.

Sleep-Wake Disorders

Sleep-wake disorders are a class of a diseases or disorders including insomnia disorder, hypersomnolence disorder, narcolepsy, breathing-related sleep disorders (such as central sleep apnea), circadian rhythm sleep-wake disorders, non-rapid eye movement sleep arousal disorders, nightmare disorder, rapid eye movement sleep behavior disorder, restless leg syndrome, and substance/medication-induced sleep disorder. Individuals with these disorders typically present with sleep-wake complaints of dissatisfaction regarding the quality, timing, and amount of sleep, which often results in daytime distress.

As used herein, the term insomnia refers to an individual's difficulty with sleep. It is diagnosed using the following criteria: (1) difficulty falling asleep, staying asleep or non-restorative sleep; (2) this difficulty is present despite adequate opportunity and circumstance to sleep; (3) this impairment in sleep is associated with daytime impairment or distress; and (4) this sleep difficulty occurs at least 3 times per week and has been a problem for at least 1 month. Insomnia disorder can be classified as chronic (sleep disturbances occur at least three times a week and have been present for the last 3 months), short-term (sleep disturbances have been present for over a period of up to 3 months) and other (difficulty in initiating or maintaining sleep that does not meet the criteria of chronic insomnia or short-term insomnia disorder). Primary insomnia occurs independently of other factors and may be related to a general psycho-physiological hyperarousal.

Hypersomnolence disorder is a condition where a person experiences significant episodes of sleepiness, even after having 7 hours or more of quality sleep with one of the 3 following symptoms; recurrent periods of sleep or lapses into sleep within the same day, a prolonged main sleep episode of more than 9 hours per day that is nonrestorative, or difficulty being fully awake after abrupt awakening. This disorder may also be characterized by excessive daytime sleepiness, excessive daytime somnolence, and hypersomnia. The exact cause of hypersomnia is unknown, but risk factors include stress, drug use, previous history of head trauma and family history of hypersomnolence.

Clinically, narcolepsy manifests with excessive daytime sleepiness that can be personally and socially disabling. Cataplexy, sleep paralysis, and hypnagogic or hypnopompic hallucinations can also be present. There are two types of narcolepsy; type 1 (with cataplexy; transient muscle weakness triggered by emotion thought to represent intrusion of REM sleep during wakefulness) and type 2 (without cataplexy). Narcolepsy type 1, 2 and idiopathic hypersomnia are subtypes of hypersomnolence.

The term "breathing-related sleep disorder" refers to a spectrum of breathing anomalies ranging from chronic or habitual snoring to upper airway resistance syndrome, to central sleep apnea or, in some cases, obesity hypoventilation syndrome. Central sleep apnea (CSA) is characterized by a lack of drive to breathe during sleep, resulting in insufficient or absent ventilation and compromised gas exchange, and is defined by a lack of respiratory effort during cessations of airflow. The term primary CSA, also known as idiopathic CSA (ICSA), describes an uncommon type of CSA wherein the cause is unknown. ICSA is characterized by periodic episodes of apnea or hypopnea resulting from decreased neural input to the respiratory motor neurons. ICSA patients usually present with complaints of snoring, witnessed apneas, restless sleep, insomnia and/or excessive daytime sleepiness.

Sleep-wake disorders may be diagnosed and/or evaluated using one or more clinical measurements such as Mean sleep latency (MSL), Multiple sleep latency test, Hypocretin (orexin) levels, Sleep onset rapid eye movement periods (SOREMPs) in Epworth Sleepiness Scale (ESS), Maintenance of Wakefulness Test (MVVT) scores, Cataplexy and cataplexy-like episodes, Objective and subjective sleep latency, Total Sleep Time (TST), Polysomnography, Insomnia severity index (ISI) questionnaire, Narcolepsy severity scale, Pittsburgh Sleep Quality Index score, Epworth Sleepiness Scale, Groningen Sleep Quality Questionnaire, Apnoea Hypopnea Index, The Nightmare Experience Scale.

Sleep-wake disorders may occur in association with one or more comorbidities. These comorbid conditions may be a cause or a consequence of the sleep-wake disorder, thus may precede, co-occur, or follow the diagnosis. Therefore, comorbid conditions and sleep-wake disorders can have a bidirectional relationship and share common underlying pathogenesis.

The same pathophysiological mechanisms that are implicated in psychiatric disorders, such as depression, anxiety, and psychosis, can also cause insomnia or hypersomnia. Medications that increase serotonergic activity (e.g., selective serotonin reuptake-inhibitors [SSRIs]) can cause insomnia. Increased dopaminergic states that are implicated in causation of psychosis can cause insomnia. This can also be true for drug-induced psychosis—the prototypical example is cocaine-induced psychosis and insomnia.

Insomnia is found to be highly comorbid with mood and affective disorders, such as major depressive disorder (MDD), mania, and anxiety. Insomnia is also common among subjects with substance abuse disorder and autism spectrum disorder.

Patients with central nervous system hypersomnia may have a spectrum of comorbid medical, neurologic, and psychiatric conditions. Hypersomnolence is comorbid with multiple psychiatric and substance abuse disorders, particularly insomnia, anxiety and depression, as well as antidepressant and benzodiazepine use. Other comorbid conditions may include eating disorders and obesity, diabetes, schizophrenia, fibromyalgia, migraine headaches, cognitive dysfunction, and psychosocial impairment.

Narcolepsy may be comorbid with attention deficit hyperactivity disorder (ADHD). Individuals with ADHD have an higher degree of association with restless legs syndrome/periodic limb movements in sleep, obstructive sleep apnea or snoring, rhythmic movement disorder (body rocking and head banging), and parasomnias.

Narcolepsy is also highly comorbid with psychiatric disorders. Depressed mood is the most commonly described psychiatric symptom. Many narcoleptic patients also suffer from depression. Anxiety disorders, such as panic attacks and social phobias, have been reported in many patients with narcolepsy. Schizophrenia and narcolepsy also have significant overlap in symptoms including hallucinations, sleep fragmentation, and psychosis. Comorbid schizophrenia and narcolepsy have been reported, but is thought to be relatively rare.

Some narcoleptic patients report irresistible and persistent craving for food, specifically binge eating with lack of control and restrictive actions to correct binging.

In some embodiments, a method of treating one or more sleep-wake disorders in a subject in need thereof comprises administering to the subject an effective amount of psilocybin or an active metabolite thereof. In some embodiments, the sleep-wake disorder is insomnia, hypersomnolence, narcolepsy, cataplexy, idiopathic hypersomnia, sleep paralysis, hypnagogic hallucinations, hypnopompic hallucinations, a breathing-related sleep disorder, a circadian rhythm sleep-wake disorder, a non-24 hour sleep wake disorder, a non-rapid eye movement sleep arousal disorder, a nightmare disorder, a rapid eye movement sleep behavior disorder, restless leg syndrome, a medication-induced sleep disorder, or a substance-induced sleep disorder.

In some embodiments, the sleep-wake disorder is insomnia. In some embodiments, the insomnia is chronic. In some embodiments, the insomnia is short term.

In some embodiments, the sleep-wake disorder is hypersomnolence. In some embodiments, the hypersomnolence is characterized by one or more of excessive daytime sleepiness, excessive daytime somnolence, and/or hypersomnia.

In some embodiments, the sleep wake disorder is narcolepsy, such as type 1 or type 2 narcolepsy.

In some embodiments, the subject has excessive daytime sleepiness, cataplexy, sleep paralysis, hypnagogic hallucinations, hypnopompic hallucinations, or combinations thereof prior to treatment with psilocybin or an active metabolite thereof. In some embodiments, the subject experiences an improvement in excessive daytime sleepiness, cataplexy, sleep paralysis, hypnagogic hallucinations, hypnopompic hallucinations or combinations thereof during treatment with psilocybin or an active metabolite thereof In some embodiments, the subject experiences an improvement in excessive daytime sleepiness, cataplexy, sleep paralysis, hypnagogic hallucinations, hypnopompic hallucinations or combinations thereof after treatment with psilocybin or an active metabolite thereof In some embodiments, the sleep-wake disorder is one or more breathing-related sleep disorders. For example, the breathing-related sleep disorder may be chronic snoring, upper airway resistance syndrome, sleep apnea, or obesity hypoventilation syndrome. In some embodiments, the breathing-related sleep disorder is sleep apnea, such as central sleep apnea (CSA). In some embodiments, the central sleep apnea is primary CSA, Cheyne-Stokes Breathing (CSB), high-altitude periodic breathing, CSA due to a medical condition without CSB, central sleep apnea due to a medication or substance, Treatment Emergent Central Apnea, or a combination thereof. In some embodiments, the subject experiences 1-30 fewer sleep apneas per hour of sleep after treatment with psilocybin. For example, the subject may experience a reduction in sleep apneas per hour of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more.

In some embodiments, the subject shows improvement in one or more of the following after treatment with psilocybin: mean sleep latency (MSL); multiple sleep latency test (MSLT); hypocretin (orexin) levels; sleep onset rapid eye movement periods (SOREMPs) in Epworth Sleepiness Scale (ESS); Maintenance of Wakefulness Test (MVVT) scores; cataplexy and cataplexy-like episodes; objective and subjective sleep latency; Total Sleep Time (TST); polysomnography; insomnia severity index (ISI) questionnaire; narcolepsy severity scale; Pittsburgh Sleep Quality Index score; Epworth Sleepiness Scale; Groningen Sleep Quality Questionnaire; Apnoea Hypopnea Index; and the Nightmare Experience Scale.

In some embodiments, the subject demonstrates an improvement in their MSLT after treatment with psilocybin as described herein as compared to their MSLT score prior to treatment. In some embodiments, the subject demonstrates an improvement of 1-10 minutes MSLT after treatment with psilocybin as described herein as compared to their MSLT score prior to treatment. In some embodiments, the subject demonstrates an improvement of 1-5 minutes MSLT after treatment with psilocybin as described herein as compared to their MSLT score prior to treatment. In some embodiments, the subject demonstrates an improvement of 1-3 minutes MSLT after treatment with psilocybin as described herein as compared to their MSLT score prior to treatment.

In some embodiments, the subject has one or more diseases, disorders, or conditions that are comorbid with the sleep-wake disorder. For example, the subject may have one or more of mood disorders, affective disorders, neurodegenerative disorders, neurodevelopmental disorders, autism spectrum disorders, and substance abuse disorders. In some embodiments, the subject has major depressive disorder, mania, depression, anxiety, psychosis, attention deficit hyperactivity disorder (ADHD), Parkinson's disorder, autism spectrum disorder (ASD), panic attacks, one or more social phobias, one or more eating disorders, and/or schizophrenia.

In some embodiments, the method of treating one or more sleep-wake disorders in a subject in need thereof further comprises administering to the subject at least one additional therapeutic agent. In some embodiments, the therapeutic agent increases serotonergic activity. In some embodiments, the therapeutic agent is a selective serotonin reuptake-inhibitor.

In some embodiments, the method of treating one or more sleep-wake disorders in a subject in need thereof further comprises administering to the subject cognitive behavioral therapy.

Pain, Including Chronic Pain

Pain is the most common symptom of disease and provides protection from dangerous and noxious stimuli. It is a sensory and perceptual phenomenon that causes suffering and reduces quality of life. Furthermore, pain is a subjective sensation as its intensity is context-dependent and can vary in the presence of other somatic and psychiatric conditions. Therefore, the same stimulus can be experienced differently by different individuals.

As used herein, the term "chronic pain" refers to pain that lasts longer than the usual course of an acute injury or disease, such as pain that recurs for months or years. "Nociceptive pain" is a high-threshold pain activated in the presence of intense stimuli, such as touching something too hot, cold, or sharp. It minimizes contact with harmful stimuli and demands immediate action and attention. "Neuropathic pain" is a chronic pain caused by lesion or disease of the somatosensory system and can lead to altered transmission of sensory signals to the spinal cord and brain. Conditions associated with neuropathic pain include multiple sclerosis, diabetic neuropathy, post-herpetic neuralgia, brachial plexus injury, allodynia, human immunodeficiency virus (HIV) infection, amputation, nerve injury pain, stroke, cancer-related pain, trigeminal neuralgia, central neuropathic pain, post-traumatic neuropathy, postsurgical neuropathy, cervical and lumbar polyradiculopathies, leprosy, autoimmune disorders, inflammatory disorders, channelopathies and metabolic disorders. Additional examples of types of pain include visceral pain and bone pain.

Amputations cause changes in the peripheral and central nervous system and cause phantom limb sensations where the patient feels the amputated limb is still present. Phantom limb pain is pain that is perceived by the sufferer to occur in a region of the body that is no longer present. Its onset may be immediate, or it may present itself years later. Common sensations described by patients are tingling, throbbing, piercing, pins and needles.

There are several self-report tools used in the assessment of pain, such as verbal rating scale (pain rating scale), Behavioral Rating Scale (pain intensity based on behavioral effects), Bodily pain subscale from SF-36 Health Survey Questionnaire, Gracely Box Scale (pain intensity and unpleasantness), Colored Analogue Scale, EQ5D three-level pain subscale (pain and discomfort scale), FACES, Faces Pain Scale, Facial Affective Scale (scale using facial expressions to depict pain), Geriatric Painful Events Inventory (hypothetical painful situations), Numeric Rating Scale (pain rating scale), Pain thermometer (verbal descriptor positioned along with a picture of a thermometer), Verbal Descriptor Scale (pain described using verbal descriptors with/without a numeric scale), Rand Coop Chart (cartoon characterizations of bodies), Visual Analog Scale (pain intensity), Brief Pain Inventory (pain intensity, location, effect on mood, effect on daily activities), Geriatric Pain Measure (pain intensity, disengagement because of pain, pain with ambulation, pain with strenuous activities, and pain with other activities), McCaffery and Pasero's Initial Pain Assessment Tool (location of pain, what makes the pain better/worse), McGill Pain Questionnaire (pain quality, location, exacerbating and ameliorating factors), Total Pain Index (pain rating for each body location, frequency, severity and duration over the last three months using a scale of 0 to 10), Pain Behavior Checklist (assess patient's pain behaviors), West Haven-Yale Multidimensional Pain Inventory (pain severity, interference, mood, activities, sense of control, support, quality of life), Leeds Assessment of Neuropathic Symptoms and Signs (assess neuropathic pain), Douleur Neuropathique en 4 (indicate neuropathic pain), or pain DETECT (screen for neuropathic pain).

Chronic pain is often associated with one or more additional comorbidities. For example, chronic pain may be associated with depression, anxiety, sleep disturbances, fatigue, or substance use disorder. Amputation following trauma can lead to various psychiatric disorders such as major depressive disorder, post-traumatic stress disorder, suicidal ideation, and anxiety.

Drugs currently approved by the FDA to treat neuropathic pain syndrome include gabapentin, pregabalin, lamotrigine, carbamazepine, duloxetine, 5% lidocaine patch, opioid analgesics, tramadol hydrochloride, tricyclic antidepressants, fluoxetine and tapentadol extended release.

First-line treatments for neuropathic pain include antidepressants, which include tricyclic antidepressants and serotonin-noradrenaline reuptake inhibitors. It also includes anticonvulsants that act at calcium channels, such as pregabalin and gabapentin. Topical lidocaine and opioids are often used as second- and third-line treatments for neuropathic pain Other antiepileptic drugs and topical capsaicin are used as third- and fourth-line treatments used in patients who are unable to tolerate or fail to respond to first- and second-line medications. A non-limiting list of drugs used to treat neuropathic pain includes: Antidepressants (tricyclic antidepressants (amitriptyline), serotonin-noradrenaline reuptake inhibitors (venlafaxine, duloxetine)), Antiepileptics (pregabalin, gabapentin), Lidocaine, Capsaicin, Tramadol, Botulinum toxin A, Opioid agonists (oxycodone, morphine, fentanyl), Cannabinoids, Ketamine.

A non-limiting list of drugs and other therapies used to treat phantom limb pain includes pre-emptive analgesia and anaesthesia (i.e., during the preoperative period), Acetaminophen, Nonsteroidal Anti-Inflammatory Drugs (NSAIDS), Opioids, Antidepressants, Anticonvulsants, Botulinum toxin type B injections, Calcitonin, NMDA receptor antagonists.

In some embodiments, a method of treating chronic pain in a subject in need thereof comprises administering to the subject a therapeutically effective amount of psilocybin or an active metabolite thereof.

In some embodiments, the chronic pain is caused by a peripheral neuropathic pain condition. In some embodiments, the peripheral neuropathic pain condition is characterized by allodynia. In some embodiments, the peripheral neuropathic pain condition is characterized by post-herpetic neuralgia.

In some embodiments, the chronic pain is a phantom limb pain.

In some embodiments, the chronic pain is caused by a central neuropathic pain condition. In some embodiments, the central neuropathic pain condition is brachial plexus injury.

In some embodiments, the chronic pain is caused by cancer or cancer treatment.

In some embodiments, administering psilocybin reduces the frequency, duration, or severity of pain in the subject. In some embodiments, the reduction in frequency, duration, or severity of pain is measured according to one or more of the following scales: Verbal rating scale, Behavioral Rating Scale, Bodily pain subscale (SF-36 Health Survey Questionnaire), Gracely Box Scale, Colored Analogue Scale, EQ5D three-level pain subscale, FACES, Faces Pain Scale, Facial Affective Scale, Geriatric Painful Events Inventory, Numeric Rating Scale, Pain thermometer, Verbal Descriptor Scale, Rand Coop Chart, Visual Analog Scale, Brief Pain Inventory, Geriatric Pain Measure, McCaffery and Pasero's Initial Pain Assessment Tool, McGill Pain Questionnaire, Total Pain Index, Pain Behavior Checklist, West Haven-Yale Multidimensional Pain Inventory, Leeds Assessment of Neuropathic Symptoms and Signs, Douleur Neuropathique en 4, or painDETECT.

In some embodiments, the frequency, duration, or severity of pain in the subject is improved within 24 hours of administration of the psilocybin. In some embodiments, the frequency, duration, or severity of pain in the subject is improved within 1 week of administration of the psilocybin. In some embodiments, the frequency, duration, or severity of pain in the subject is improved for a period of at least 1 month after administration of the psilocybin.

In some embodiments, the frequency, duration, or severity of pain in the subject is improved for a period of at least 3 months after administration of the psilocybin. In some embodiments, the frequency, duration, or severity of pain in the subject is improved for a period of at least 12 months after administration of the psilocybin.

In some embodiments, no other treatment is administered to the subject to treat the chronic pain after administration of the psilocybin.

In some embodiments, the method for treating a subject in need thereof further comprises administering to the subject at least one additional therapeutic. In some embodiments, the at least one additional therapeutic is a tricyclic antidepressant or a serotonin-noradrenaline reuptake inhibitor (SSRI). In some embodiments, the at least one additional therapeutic is pregabalin or gabapentin. In some embodiments, the at least one additional therapeutic is lidocaine, capsaicin, tramadol, botulinum toxin A, oxycodone, morphine, fentanyl, a cannabinoid, ketamine, acetaminophen, a nonsteroidal anti-inflammatory drug, an opioid, calcitonin, or a NMDA receptor antagonist.

Inflammatory Disorders

Inflammation is an adaptive response triggered by stimuli perceived as noxious by immune cells, such as tissue injury and infection. These triggers can also be 'self' proteins that have arisen from an immune privileged site due to tissue damage, as in autoimmune conditions such as arthritis. Other, non-noxious triggers of inflammation include organ transplants, harmless allergenics, and rhesus protein in haemolytic disease of the new-born.

The five symptoms considered indicative of acute inflammation comprise of redness, heat, swelling, pain and loss of function, however, some inflammations occur 'silently', and don't cause outward symptoms.

Pro-inflammatory cytokines, released by immune cells upon activation by 'noxious' stimuli, mediate inflammation through signaling at target cells and inducing further immune cell recruitment. The concentration of cytokines in the body (e.g., in a biological sample such as a blood or CSF sample) is therefore considered as a marker of inflammation.

Tumour necrosis factor alpha (TNFα), IL-6 and IL-1b are examples of proinflammatory cytokines produced by activated macrophages (a white blood cell capable of detecting, engulfing and destroying noxious foreign material and dead cells). IL-6 and TNFα are elevated in most, if not all, inflammatory states. Other pro-inflammatory cytokines include, for example IL-1 (e.g., IL-1a, IL-1b), IL-2, IL-6, IL-8, IL-12, and further TNFα production. IL-10 can repress expression of pro-inflammatory signals.

Inflammation underlies the generation and maintenance of some of the leading causes for morbidity and mortality around the world. Inflammatory diseases are often chronic and may be the result of immune signaling dysfunction. Exemplary immune diseases include but are not limited to, asthma, hepatitis, allergy, arthritis, inflammatory bowel disease, dermatitis, and coeliac disease. Examples of chronic inflammatory diseases include stroke, chronic respiratory diseases, heart disorders, cancer, obesity and diabetes. Furthermore, cytokine signaling is implicated in the initiation and persistence of pathological pain, such as inflammatory and neuropathic pain.

Inflammatory diseases can be treated by anti-inflammatory therapies which aim to reduce cytokine signaling and subsequent immune activation. Inhibiting the development of acute inflammation may also reduce the prevalence of chronic inflammatory diseases.

The following illustrative anti-inflammatory therapies may be used to manage chronic and acute inflammation: Metformin, Non-steroidal anti-inflammatory drugs (NSAIDs), Statins, Corticosteroids, Antibodies, and Methotrexate.

Various clinical measurements can be used to assess severity of inflammation, such as:
  Serum biomarker assays: C-reactive protein, erythrocyte sedimentation rate, leukocyte level, platelet level, ferritin, haptoglobin, ceruloplasmin, a-1-antitrypsin, plasminogen, complement factors, and fibrinogen, orosomucoid, IL6, Sialic acid, serum amyloid A, TNFα, IL1b, IL18, IL12, IL1 receptor antagonist, TGFbeta.
  Fecal immunochemical assays: faecal calprotectin, lactoferrin, polymorphonuclear elastase, myeloperoxidase, metalloproteinase-9, and neopterin.
  Plasma viscosity.
  Disease activity scores and clinical disease activity index.

In some embodiments, a method of reducing inflammation in a subject in need thereof comprises administering to the subject a therapeutically effective amount of psilocybin or an active metabolite thereof.

In some embodiments, the inflammation is acute. In some embodiments, the inflammation is chronic. In some embodiments, the inflammation is systemic. In some embodiments, the inflammation is local. In some embodiments, administration of the psilocybin reduces the duration of the inflammation.

In some embodiments, administration of the psilocybin reduces the level of at least one inflammatory biomarker or indicator in a biological sample of the subject. In some embodiments, wherein the biological sample is a blood sample such as a serum sample or a plasma sample. In some embodiments, the biological sample is a cerebral spinal fluid (CSF) sample.

In some embodiments, the inflammatory biomarker is a pro-inflammatory cytokine. In some embodiments, the pro-inflammatory cytokine is interleukin-1 (IL-1), tumor necrosis factor (TNF), gamma-interferon (IFN-γ), IL-1β, IL-6, IL-10, IL-12, IL-18, granulocyte-macrophage colony stimulating factor (GMCSF), C—X—C chemokine ligand 1 (CXCL1) or CXCL9. In some embodiments, the pro-inflammatory cytokine is TNF-α, IL-6, IL-1β, or IL-10. In some embodiments, the pro-inflammatory cytokine is CXCL1 or CXCL9. In some embodiments, the inflammatory biomarker is C-Reactive Protein (CRP), homocysteine, or hemoglobin A1c (HbA1c). In some embodiments, the inflammatory indicator is plasma viscosity.

In some embodiments, the level of at least one inflammatory biomarker or indicator is reduced within 24 hours of administration of the psilocybin. In some embodiments, the level of at least one inflammatory biomarker or indicator is reduced within 1 week of administration of the psilocybin.

In some embodiments, the level of at least one inflammatory biomarker or indicator is reduced for a period of at least 1 month after administration of the psilocybin.

In some embodiments, the level of at least one inflammatory biomarker or indicator is reduced for a period of at least 3 months after administration of the psilocybin. In some embodiments, the level of at least one inflammatory biomarker or indicator is reduced for a period of at least 12 months after administration of the psilocybin In some embodiments, administration of the psilocybin reduces at least one of fever, pain, skin redness, or swelling, or increases functionality in the subject. In some embodiments, the fever, pain, skin redness, or swelling is reduced, or the functionality is increased within 24 hours of administration of the psilocybin. In some embodiments, the fever, pain, skin redness, or swelling is reduced, or the function is increased within 1 week of administration of the psilocybin. In some embodiments, the fever, pain, skin redness, or swelling is reduced, or functionality is increased for a period of at least 1 month after administration of the psilocybin.

In some embodiments, the fever, pain, skin redness, or swelling is reduced, or the functionality is increased for a period of at least 3 months after administration of the psilocybin. In some embodiments, the fever, pain, skin redness, or swelling is reduced, or the function is increased for a period of at least 12 months after administration of the psilocybin.

In some embodiments, no other treatment is administered to the subject to reduce inflammation after administration of the psilocybin.

In some embodiments, the method of reducing inflammation in a subject in need thereof further comprises administering to the subject at least one additional therapeutic to reduce inflammation. In some embodiments, the at least one additional therapeutic is a non-steroidal anti-inflammatory drug (NSAID), such as ibuprofen, aspirin, or naproxen. In some embodiments, the at least one additional therapeutic is a corticosteroid such as cortisone, prednisone, or methylprednisolone. In some embodiments, the at least one additional therapeutic is metformin, a statin, methotrexate, or an antibody.

In some embodiments, the subject has asthma, celiac disease, hepatitis, allergy, arthritis, irritable bowel syndrome (IBS), or dermatitis. In some embodiments, the subject has Alzheimer's Disease, Parkinson's Disease, Amyotrophic Lateral Sclerosis (ALS), Multiple Sclerosis (MS), or autism spectrum disorder.

In some embodiments, administration of psilocybin treats or prevents one or more of allergy, asthma, Alzheimer's disease, diabetes, cardiovascular disease, sepsis, arthritis, joint disease, inflammatory bowel disease, or dermatitis in the subject. In some embodiments, administration of psilocybin treats or prevents one or more of chronic pain, neuropathic pain, and inflammatory pain in the subject. In some embodiments, administration of psilocybin treats or prevents a mood disorder (e.g., depression) in the subject.

Inflammatory Bowel Disease (IBD)

IBD is a term used to describe various diseases and disorders, including Crohn's Disease and Ulcerative Colitis, which are characterized by chronic inflammation of the gastrointestinal (GI) tract. Prolonged inflammation results in damage to the GI tract.

Crohn's Disease can affect any part of the GI tract, from the mouth to the anus. Damaged areas appear in patches that are next to areas of healthy tissue. Typically, it affects the large portion of the small intestine before the large intestine/colon. Crohn's associated inflammation may reach through the multiple layers of the walls of the GI tract.

Ulcerative Colitis occurs in the large intestine (colon) and the rectum. Damaged areas are continuous (not patchy), and typically start at the rectum and spread further into the colon. Inflammation is present only in the innermost layer of the lining of the colon.

Common symptoms of IBD include persistent diarrhea, abdominal pain, rectal bleeding, bloody stools, weight loss, and fatigue. In IBD, the immune system responds incorrectly to environmental triggers, which causes inflammation in the GI tract. Other symptoms may include mouth sores, skin problems, arthritis, or eye problems that affect vision. IBD symptoms may be exacerbated by stress. Although the exact cause of IBD is unknown, there appears to be a genetic component—individuals with a family history of IBD are more likely to develop the disease.

In some embodiments, a method of treating Inflammatory Bowel Disease (IBD) in a subject in need thereof comprises administering to the subject a therapeutically effective amount of psilocybin or an active metabolite thereof. In some embodiments, the IBD is ulcerative colitis. In some embodiments, the IBD is Crohn's disease.

In some embodiments, at least one sign or symptom of IBD is improved following administration of the psilocybin or active metabolite thereof. In some embodiments, the sign or symptom of IBD is diarrhea, fever, fatigue, abdominal pain and/or cramping, bloody stool, reduced appetite, or unintended weight loss. In some embodiments, the improvement is verified by endoscopy. In some embodiments, the improvement is verified by biopsy.

In some embodiments, the subject subject also has colon cancer. In some embodiments, the subject is taking medication to treat the colon cancer.

In some embodiments, administering psilocybin to the subject leads to an improvement in the Mayo Score and/or the Ulcerative Colitis Activity Index (UCSAI). Both the Mayo Score and the UCSAI incorporate scoring of stool frequency, rectal bleeding, endoscopic findings, and the physician's assessment of disease activity.

In some embodiments, at least one sign or symptom of IBD is improved within 24 hours of administration of the psilocybin. In some embodiments, at least one sign or symptom of IBD is improved within 1 week of administration of the psilocybin.

In some embodiments, at least one sign or symptom of IBD is improved for a period of at least 1 month after administration of the psilocybin. In some embodiments, at least one sign or symptom of IBD is improved for a period of at least 3 months after administration of the psilocybin. In some embodiments, at least one sign or symptom of IBD is improved for a period of at least 12 months after administration of the psilocybin.

In some embodiments, no other treatment is administered to the subject to treat IBD after administration of the psilocybin.

In some embodiments, the method of treating Inflammatory Bowel Disease (IBD) in a subject in need thereof further comprises administering to the subject at least one additional therapeutic to treat IBD, in addition to the psilocybin. In some embodiments, the at least one additional therapeutic is an aminosalicylate, a corticosteroid (e.g., prednisone) an immunomodulator, or a biologic (e.g., a monoclonal antibody). In some embodiments, the subject has surgery prior to or following administration of the psilocybin to removed damaged portions of the GI tract.

Stroke

A stroke is a sudden interruption in the blood supply of the brain. Some strokes are caused by an abrupt blockage of arteries leading to the brain (ischemic stroke). Other strokes are caused by bleeding into brain tissue when a blood vessel bursts (hemorrhagic stroke). In a transient ischemic attack (TIA) or mini-stroke, symptoms of the stroke last only a short time (e.g., less than about an hour). Brain cells begin to die within minutes of being deprived of oxygen and nutrients. Early treatment can reduce brain damage and other complications.

Strokes may cause sudden weakness, loss of sensation, or difficult with speaking, seeing, or walking. Since different parts of the brain control different areas and function, it is usually the area immediately surrounding the stroke is affected. Sometimes people with stroke have a headache, but stroke can also be completely painless.

The effects of a stroke depend on which part of the brain is injured, and how severely it is injured. A stroke can sometimes cause temporary or permanent disabilities. Complications may include (i) paralysis or loss of muscle movement (particularly on one side of the body), (ii) difficulty talking or swallowing, (iii) memory or thinking difficulties, (iv) emotional problems, (v) pain, (vi) changes in behavior or self-care ability.

In some embodiments, psilocybin may be used to treat stroke in a subject in need thereof. In some embodiments, a method for treating stroke in a subject in need thereof comprises administering to the subject a therapeutically effective amount of psilocybin or an active metabolite thereof. In some embodiments, the stroke is an ischemic stroke. In some embodiments, the stroke is a hemorrhagic stroke.

In some embodiments, administering the psilocybin improves a sign or symptom of stroke. The sign or symptom of stroke may be, for example, paralysis, numbness or weakness in the arm, face, or leg, trouble speaking or understanding speech, confusion, slurring speech, vision problems, trouble walking, loss of balance or coordination, dizziness, or headache.

In some embodiments, the sign or symptom of stroke is improved within 1 hour of administration of the psilocybin.

In some embodiments, the sign or symptom of stroke is improved within 12 hours of administration of the psilocybin.

In some embodiments, the sign or symptom of stroke is improved for a period of at least 1 month after administration of the psilocybin. In some embodiments, the sign or symptom of stroke is improved for a period of at least 3 months after administration of the psilocybin. In some embodiments, the sign or symptom of stroke is improved for a period of at least 12 months after administration of the psilocybin.

In some embodiments, no other treatment is administered to the subject to treat stroke after administration of the psilocybin.

In some embodiments, the method for treating stroke in a subject in need thereof further comprises administering to the subject a therapeutically effective amount of at least one additional therapeutic, in addition to the psilocybin. The additional therapeutic drug may be, for example an anti-platelet drug (e.g., aspirin) or an anti-coagulant (e.g., warfarin, dabigatran, rivaroxaban, apizaban, edoxaban).

In some embodiments, psilocybin may be used to treat a subject who is recovering from stroke. In some embodiments, a method for treating a subject in need thereof comprises administering to the subject a therapeutically effective amount of psilocybin or an active metabolite thereof, wherein the subject is recovering from a stroke. In some embodiments, the subject is recovering from an ischemic stroke. In some embodiments, the subject is recovering from a hemorrhagic stroke.

In some embodiments, administering the psilocybin improves a condition caused by the stroke. In some embodiments, the condition caused by the stroke is paralysis, cognitive issues, difficulty understanding speech, difficulty speaking, difficulty controlling or expressing emptions, numbness, pain in the hands or feet, trouble chewing or swallowing, problems with bladder or bowel control.

In some embodiments, the condition caused by the stroke is improved within 24 hours of administration of the psilocybin. In some embodiments, the condition caused by the stroke is improved within 1 week of administration of the psilocybin.

In some embodiments, the condition caused by the stroke is improved for a period of at least 1 month after administration of the psilocybin. In some embodiments, the condition caused by the stroke is improved for a period of at least 3 months after administration of the psilocybin. In some embodiments, the condition caused by the stroke is improved for a period of at least 12 months after administration of the psilocybin.

In some embodiments, wherein no other treatment is administered to the subject to treat the condition caused by the stroke after administration of the psilocybin.

In some embodiments the method for treating a subject recovering from stroke further comprises administering to the subject at least one additional therapeutic to treat the condition caused by the stroke, in addition to the psilocybin.

In some embodiments, the subject has depression. In some embodiments, administration of psilocybin alleviates depression in the subject.

Amyotrophic Lateral Sclerosis (ALS)

ALS is a progressive neurodegenerative disease. ALS is also known as Motor Neuron Disease (MND), Lou Gehrig's Disease, and Charcot's disease. ALS attacks motor neurons in the brain and spinal cord, resulting in the wasting away of muscle and loss of movement.

ALS typically affects people between the ages of 40 and 70. Signs and symptoms of ALS may include muscle cramps, muscle twitching, weakness in hands, legs, feet or ankles, difficulty speaking or swallowing. The senses (hearing, sight, smell, taste, and touch) are not affected by ALS. In most cases, cognitive function is not affected. Most cases of ALS are sporadic, with no history of the disease in the subject's family. A small percentage of ALS occur in individuals who have inhered a genetic mutation from their parents.

In some embodiments, a method for treating amyotrophic lateral sclerosis (ALS) a subject in need thereof comprises administering to the subject a therapeutically effective amount of psilocybin or an active metabolite thereof.

In some embodiments, administering the psilocybin improves a sign or symptom of ALS. In some embodiments, the sign or symptom of ALS is muscle twitching, muscle weakness, muscle stiffness, difficulty speaking, difficulty swallowing, difficulty breathing, cognitive impairment, or pain.

In some embodiments, the sign or symptom of ALS is improved within 24 hours of administration of the psilocybin. In some embodiments, the sign or symptom of ALS is improved within 1 week of administration of the psilocybin.

In some embodiments, the sign or symptom of ALS is improved for a period of at least 1 month after administration of the psilocybin. In some embodiments, the sign or symptom of ALS is improved for a period of at least 3 months after administration of the psilocybin. In some embodiments, the sign or symptom of ALS is improved for a period of at least 12 months after administration of the psilocybin.

In some embodiments, no other treatment is administered to the subject to treat ALS after administration of the psilocybin.

In some embodiments, the method for treating ALS a subject in need thereof further comprises administering to the subject at least one additional therapeutic to treat ALS, in addition to the psilocybin. In some embodiments, the at least one additional therapeutic is riluzole or edaravone.

In some embodiments, the subject has depression. In some embodiments, the administration of psilocybin alleviates depression in the subject.

Multiple Sclerosis (MS)

Multiple sclerosis (MS) is a demyelinating disease in which the insulating covers of nerve cells in the brain and spinal cord are damaged. This damage disrupts the ability of parts of the nervous system to transmit signals, resulting in a range of signs and symptoms, including physical, mental, and sometimes psychiatric problems.

In some embodiments, a method of treating multiple sclerosis (MS) in a subject in need there of comprises administering an effective amount of psilocybin or an active metabolite thereof to the subject. In some embodiments, the MS is clinically isolated syndrome (CIS). In some embodiments, the MS is relapsing-remitting MS (RRMS).

In some embodiments, the MS is primary progressive MS (PPMS). In some embodiments, the MS is secondary progressive MS (SPMS)

In some embodiments, administering the psilocybin improves a sign or symptom of MS. In some embodiments, the improved sign or symptom of MS can include a neurological symptom or sign, such as an autonomic, visual, motor, or sensory problem. In some embodiments, the improved sign or symptom of MS can include double vision, blindness in one eye, muscle weakness, trouble with sensation, trouble with coordination, loss of sensitivity, changes in sensation such as tingling, pins and needles or numbness, muscle weakness, blurred vision, very pronounced reflexes, muscle spasms, or difficulty in moving; difficulties with coordination and balance (ataxia); problems with speech or swallowing, visual problems (nystagmus, optic neuritis or double vision), feeling tired, acute or chronic pain, and bladder and bowel difficulties (such as neurogenic bladder). In some embodiments, the improved sign or symptom of MS can include difficulties thinking and emotional problems such as depression or unstable mood. In some embodiments, the improved sign or symptom of MS can include a reduction or decrease in Uhthoff's phenomenon, a worsening of symptoms due to exposure to higher than usual temperatures, and Lhermitte's sign, an electrical sensation that runs down the back when bending the neck. In some embodiments, after administration of psilocybin a subject demonstrates an improvement in their expanded disability status scale (EDSS) and/or multiple sclerosis functional composite score.

In some embodiments, the sign or symptom of MS is improved within 24 hours of administration of the psilocybin. In some embodiments, the sign or symptom of MS is improved within 1 week of administration of the psilocybin.

In some embodiments, the sign or symptom of MS is improved for a period of at least 1 month after administration of the psilocybin. In some embodiments, the sign or symptom of MS is improved for a period of at least 3 months after administration of the psilocybin. In some embodiments, the sign or symptom of MS is improved for a period of at least 12 months after administration of the psilocybin.

In some embodiments, no other treatment is administered to the subject to treat MS after administration of the psilocybin.

In some embodiments, the method for treating MS a subject in need thereof further comprises administering to the subject at least one additional therapeutic to treat MS, in addition to the psilocybin. In some embodiments, the at least one additional therapeutic is interferon beta-1a, interferon beta-1b, glatiramer acetate, mitoxantrone, natalizumab, fingolimod, teriflunomide, dimethyl fumarate, alemtuzumab, ocrelizumab, siponimod, cladribine, and ozanimod.

In some embodiments, the subject has depression. In some embodiments, the administration of psilocybin alleviates depression in the subject.

Opioid Use Disorder

Opioid Use Disorder (OUD) is a pattern of opioid use that leads to serious impairment or distress. OUD may be characterized by one or more of the following symptoms: (i) opioid taken in larger amounts or for a longer time than intended, (ii) persistent desire or unsuccessful effort to cut down or control use of an opioid, (iii) great deal of time spent obtaining, using, or recovering from opioid use, (iv) craving (a strong desire or urge) to use opioids, (v) continued opioid use that causes failures to fulfill major obligations at work, school, or home, (vi) continued opioid use despite causing recurrent social or personal problems, (vii) important social, occupational, or recreational activities are reduced because of opioid use, (viii) recurrent opioid use in dangerous situations, (ix) continued opioid use despite related physical or psychological problems, (x) tolerance (the need to take higher doses of a drug to feel the same effects, or a reduced effect from the same amount), or (xi) withdrawal (the experience of pain or other uncomfortable symptoms in the absence of a drug). In some embodiments, a method of treating OUD in a subject in need thereof comprises administering an effective amount of psilocybin or an active metabolite thereof to the subject. In some embodiments, a method of preventing relapse of OUD in a subject in need thereof comprises administering an effective amount of psilocybin or an active metabolite thereof to the subject.

In some embodiments, the subject has taken one or more opioid substitution therapies (OSTs) before administration of the psilocybin. A non-limiting list of exemplary OSTs includes: methadone, buprenorphine or naltrexone. In some embodiments, the subject stops taking the OST before administration of the psilocybin, for example at least 1 day, at least 1 week, or at least 2 weeks before administration of the psilocybin. In some embodiments, the subject continues taking the OST after administration of the psilocybin, for example for at least 1 week, at least 1 month, at least 3 months or at least 6 months after administration of the psilocybin. In some embodiments, the subject discontinues taking the OST after administration of the psilocybin.

In some embodiments, treatment with psilocybin reduces the number of opioid use days per week in the subject by at least 1, at least 2, at least 3, at least 4, at least 5, at least 6, or at least 7 days. In some embodiments, treatment with psilocybin reduces the number of OST use days per week in the subject by at least 1, at least 2, at least 3, at least 4, at least 5, at least 6, or at least 7 days.

In some embodiments, treatment with psilocybin prevents or substantially prevents relapse in the subject for at least 1 week, at least 2 weeks, at least 1 month, at least 2 months, at least 3 months, at least 6 months, at least 9 months, at least 1 year, or at least 5 years after administration of the psilocybin.

In some embodiments, treatment with psilocybin improves the subject's score on one or more of the following tests/assessments: C-SSRS, TLFB, OCS, SDS, MADRS, EQ-5D-5L, GAD-7, Severity of Dependence Scale, BIS-11, TIPI and Pain VAS. These tests/assessments are described in Table 9, below. In some embodiments, the subject's score is increased by about 5%, about 10%, about 20%, about 30%, about 40%, about 50%, or more after administration of the psilocybin. In some embodiments, the subject's score is improved within about 1 day, about 3 days, about 5 days, about 7 days, about 10 days, about 2 weeks, about 1 month, about 3 months, about 6 months, about 9 months or about 12 months after administration of the psilocybin. In some embodiments, the subject's score remains increased for a period of at least 1 day, at least 3 days, at least 5 days, at least 7 days, at least 10 days, at least 2 weeks, at least 1 month, at least 3 months, at least 6 months, at least 9 months or at least 12 months after administration of the psilocybin.

TABLE 9

Clinical tests and assessments

| Test or assessment | Description |
|---|---|
| C-SSRS (Columbia-Suicide Severity Rating Scale) | A semi-structured interview designed to assess the severity and intensity of suicidal ideation, suicidal behavior, and non-suicidal self-injurious behavior over a specified time period. The measurement |

TABLE 9-continued

Clinical tests and assessments

| Test or assessment | Description |
| --- | --- |
|  | of suicidal ideation is based on five "yes" or "no" questions with accompanying descriptions arranged in order of increasing severity. If the subject answers "yes" to either questions 1 or 2, the intensity of ideation is assessed in five additional questions related to frequency, duration, controllability, deterrents, and reasons for the most severe suicidal ideation. Suicidal behavior is assessed by asking questions categorizing behaviors into actual, aborted, and interrupted attempts; preparatory behavior; and non-suicidal self-injurious behavior. |
| TLVB (Timeline Followback) | A method that can be used to obtain a quantitative estimate of drug use. |
| OCS (Opioid Craving Scale) | A brief, 3-item measure used to measure opioid craving. The scale consists of 3 items rated on a visual analogue scale from 0-10. |
| SDS (Sheehan Disability Scale) | The SDS is a brief, 5-item self-report inventory that assesses functional impairment in work/school, social life, and family life. The total score ranges from 0 to 30 with 0 representing no impairment and 30 representing severe impairment. The last two items of the scale (Days Lost and Days Unproductive) do not count toward the total score. Each domain is rated on a 10-point VAS. |
| MADRS (Montgomery-Asberg Depression Rating Scale) | A clinician-rated scale measuring depression severity, consisting of 10 items, each scored from 0 (normal) to 6 (severe), for a total possible score of 60; higher scores denote greater severity. |
| EQ-5D-5L (EuroQoL-5-dimension 5-level Scale) | Includes two sections: the EQ-5D-5L descriptive system and the EQ visual analogue scale (EQ VAS). The descriptive system comprises five dimensions: mobility, self-care, usual activities, pain/discomfort, and anxiety/depression. Each dimension has five levels: no problems, slight problems, moderate problems, severe problems and extreme problems. The subject is asked to indicate his/her health state by ticking the box next to the most appropriate statement in each of the five dimensions. This decision results in a 1-digit number that expresses the level selected for that dimension. The digits for the five dimensions can be combined into a 5-digit number that describes the subject's health state. |
| Severity of Dependence Scale | Contains five items (which are summed to give a total score), all of which are explicitly concerned with psychological components of dependence. These items are specifically concerned with impaired control over drug taking and with preoccupation and anxieties about drug use. |
| GAD-7 (Generalized Anxiety Disorder scale - 7 item) | A screening tool and symptom severity measure for the seven most common anxiety disorders. Subjects choose one of 4 severity scores associated problems related to the common anxiety disorders and then indicate the degree to which these problems caused functional and/or social difficulties. Scores are determined by calculating the values for each column. A total score is obtained by the sum of all total column values. |
| BIS-11 (Barrett Impulsiveness Scale) | A 30-item self-reported questionnaire which measures impulsiveness. Subjects are given a statement detailing a thought or action and must indicate whether they agree with that thought/action on a four-point scale (ranging from 'Rarely/Never' to 'Almost Always/Always'). The BIS-11 provides both a total score by summing all items and subscales for three factors: attentional, motor and nonplanning. |
| TIPI (Ten Item Personality Inventory) | Measures the Big-Five personality dimensions, through a brief, 10-item, self-reported questionnaire. Subjects are asked to say whether they agree with each item, through a 7-point Likert scale, ranging from 'Disagree strongly' to 'Agree strongly'. A score is then provided for each of the Big-Five personality traits: Extraversion, Agreeableness, Conscientiousness, Emotional Stability and Openness to Experiences. |
| Pain VAS | A measure of pain intensity widely used in diverse adult populations. It is a continuous scale comprised as a vertical or horizontal line, usually 100 mm in length and anchored to two verbal descriptors, one for each extreme of pain intensity: "no pain" to "worst imaginable pain". The scale is quick to administer and has been found to be acceptable to subjects. Additionally, test-retest reliability has been found to be good and the measure is sensitive to changes in pain. |

Anti-Social Personality Disorder

Antisocial personality disorder, sometimes called sociopathy, is a mental disorder in which a person consistently shows no regard for right and wrong and ignores the rights and feelings of others. People with antisocial personality disorder tend to antagonize, manipulate or treat others harshly or with callous indifference. They typically show no guilt or remorse for their behavior.

Individuals with antisocial personality disorder often violate the law, becoming criminals. They may lie, behave violently or impulsively, and have problems with drug and alcohol use. Because of these characteristics, people with this disorder typically can't fulfill responsibilities related to family, work or school.

Exemplary signs and symptoms of anti-social personality disorder include: disregard for right and wrong, persistent lying or deceit to exploit others, being callous, cynical and disrespectful of others, using charm or with to manipulate others for personal gain or personal pleasure, arrogance, a sense of superiority and being extremely opinionated, recurring problems with the law, including criminal behavior, repeatedly violating the rights of others through intimidation and dishonesty, impulsiveness or failure to plan ahead, hostility, significant irritability, agitation, aggression or violence, lack of empathy for others and lack of remorse about harming others, unnecessary risk-taking or dangerous behavior with no regard for the safety of self or others, poor or abusive relationships, failure to consider the negative consequences of behavior or learn from them, being consistently irresponsible and repeatedly failing to fulfill work or financial obligations In some embodiments, a method for treating anti-social personality disorder in a subject in need thereof, the method comprising administering to the subject an effective amount of psilocybin or an active metabolite thereof. In some embodiments, one or more signs or symptoms of anti-social personality disorder are improved in the subject after administration of psilocybin. In some embodiments, the subject is administered one or more additional therapeutics.

In some embodiments, the subject has one or more comorbidities. For example, the comorbidity may be conduct disorder, depression, or anxiety. In some embodiments, psilocybin ameliorates at least one sign or symptom of the comorbidity.

Pre-Treatments and Combination Therapies

In some embodiments, the methods of treatment comprising administering psilocybin to a subject in need thereof further comprise pretreating the subject with magnesium before administration of the psilocybin. Sometimes, magnesium is administered daily for a least 1 day, at least 2 days, at least 3 days, at least 4 days, at least 5 days, at least 6 days, at least 1 week, at least 2 weeks, at least 3 weeks, at least 4 weeks, at least 5 weeks, or at least 6 weeks before administration of the psilocybin. In some embodiments, about 10 mg to about 500 mg of magnesium are administered to the subject per day. In some embodiments, about 30 mg, about 75 mg, about 80 mg, about 130 mg, about 240 mg, about 310 mg, about 320 mg, about 360 mg, about 410 mg, about 400 mg, or about 420 mg are administered to the subject per day. In some embodiments the magnesium is administered to the subject on the same day as the psilocybin. In some embodiments, the magnesium is administered to the subject immediately before, concurrently with, or immediately after administration of the psilocybin. In some embodiments, magnesium supplements are administered to the subject until the subject's blood level for magnesium is about 1.5 to about 2.5 mEq/L. In some embodiments, psilocybin is not administered to the subject if the subject's blood level of magnesium is less than about 1.5 to about 2.5 mEq/L.

In some embodiments, the methods of treatment comprising administering psilocybin to a subject in need thereof further comprise pretreating the subject with niacin before administration of the psilocybin. Sometimes, niacin is administered daily for a least 1 day, at least 2 days, at least 3 days, at least 4 days, at least 5 days, at least 6 days, at least 1 week, at least 2 weeks, at least 3 weeks, at least 4 weeks, at least 5 weeks, or at least 6 weeks before administration of the psilocybin. In some embodiments, about 1 mg to about 5,000 mg of niacin are administered to the subject per day, for example about 1 mg to about 50 mg, about 10 mg to about 100 mg, about 100 mg to about 200 mg, about 1 mg to about 200 mg, about 100 mg to about 200 mg, about 10 mg to about 50 mg, about 10 to about 35 mg, about 100 mg to about 500 mg, or about 1,000 mg to about 3,000 mg. In some embodiments, about 10 mg, about 14 mg, about 15 mg, about 16 mg, about 20 mg, about 30 mg, about 35 mg, about 50 mg, about 60 mg, about 75 mg, about 100 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1500 mg, about 2000 mg, about 2500 mg, or about 3000 mg of niacin are administered to the subject per day (while avoiding any toxic exposure from excess niacin). In some embodiments, niacin is included as an ingredient/component, for example, to reduce risk of abuse and/or to improve efficacy. In some embodiments the niacin is administered to the subject on the same day as the psilocybin. In some embodiments, the niacin is administered to the subject immediately before, concurrently with, or immediately after administration of the psilocybin.

In some embodiments, psilocybin is administered to the subject in combination with one or more additional therapies. In some embodiments, psilocybin is administered to the subject in combination with one or more anti-depressant or anti-anxiety drugs, such as SSRIs, tricyclic antidepressants (TCAs), monoamine oxidase inhibitors (MAOIs), or serotonin norepinephrine reuptake inhibitors (SNRIs).

In some embodiments, the disclosure provides a method of reducing anxiety in a subject undergoing treatment with psilocybin, the method comprising administering to the subject: i) psilocybin or a precursor or derivative thereof, and ii) one or more benzodiazepines.

In some embodiments, the one or more benzodiazepines are administered to the subject at or around the same time as the psilocybin or precursor or derivative thereof. In some embodiments, the one or more benzodiazepines are administered to the subject prior to administration of the psilocybin or precursor or derivative thereof, such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof. In some embodiments, the one or more benzodiazepines are administered to the subject after the psilocybin or precursor or derivative thereof, such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

In some embodiments, the one or more benzodiazepines are administered at a dose that is lower than doses typically used to treat anxiety, such as about 10%, 20%, 25%, 30%, 40%, 50%, or 75% of a typical dose. In some embodiments, the one or more benzodiazepines are administered at a dose that is approximately equivalent to doses typically used to treat anxiety. In some embodiments, the one or more benzodiazepines are administered at a dose that is higher than doses typically used to treat anxiety, such as about 125%, 150%, 175%, 200%, 250%, or 300% of a typical dose. In some embodiments, the one or more benzodiazepine is administered orally to the subject.

In some embodiments, the benzodiazepine is selected from the group consisting of adinazolam, alprazolam, bentazepam, bretazenil, bromazepam, bromazolam, brotizolam, camazepam, chlordiazepoxide, cinazepam, cinolazepam, clobazam, clonazepam, clonazolam, clorazepate, clotiazepam, cloxazolam, delorazepam, deschloroetizolam, diazepam, diclazepam, estazolam, ethyl carfluzepate, ethyl loflazepate, etizolam, flualprazolam, flubromazepam, flubromazolam, fluclotizolam, flunitrazepam, flunitrazolam, flurazepam, flutazolam, flutoprazepam, halazepam, ketazolam, loprazolam, lorazepam, lormetazepam, meclonazepam, medazepam, metizolam, mexazolam, midazolam, nifoxipam, nimetazepam, nitemazepam, nitrazepam, nitrazolam, nordiazepam, norflurazepam, oxazepam, phenazepam, pinazepam, prazepam, premazepam, pyrazolam, quazepam, rilmazafone, temazepam, tetrazepam, and triazolam.

In certain embodiments, a subject is administered psilocybin or a precursor or derivative thereof as described herein along with one or more $5\text{-}HT_{2A}$ specific antagonists and/or inverse agonists. In some embodiments, the subject is administered psilocybin or a precursor or derivative thereof and the one or more $5\text{-}HT_{2A}$ specific antagonists and/or inverse agonists at the same time. In other embodiments, the subject is administered one or more $5\text{-}HT_{2A}$ specific antagonists and/or inverse agonists prior to psilocybin administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before psilocybin administration. In some embodiments, the subject is administered one or more $5\text{-}HT_{2A}$ specific antagonists and/or inverse agonists after psilocybin administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after psilocybin administration.

In certain embodiments, the one or more $5\text{-}HT_{2A}$ specific antagonists and/or inverse agonists are administered at doses that are lower than doses typically used, e.g., about 10%, about 20%, about 25%, about 30%, about 40%, about 50%, or about 75% of a typical dose. In other embodiments, the one or more $5\text{-}HT_{2A}$ specific antagonists and/or inverse agonists are administered at doses that are equivalent to doses typically used. In yet other embodiments, the one or more $5\text{-}HT_{2A}$ specific antagonists and/or inverse agonists are administered at doses that are higher than doses typically used, e.g., about 125%, about 150%, about 175%, about 200%, about 250%, or about 300% of a typical dose.

Suitable $5\text{-}HT_{2A}$ antagonists include but are not limited to, trazodone, mirtazapine, metergoline, ketanserin, ritanserin, nefazodone, clozapine, olanzapine, quetiapine, risperidone, asenapine, MDL-100907, cyproheptadine, pizotifen, LY-367,265, 2-alkyl-4-aryl-tetrahydro-pyrimido-azepine, 9-aminomethyl-9,10-dihydroanthracene (AMDA), haloperidol, chlorpromazine, hydroxyzine (atarax), 5-MeO-NBpBrT, niaprazine, altanserin, aripiprazole, etoperidone, setoperone, chlorprothixene, cinaserin, adatanserin, medifoxamine, rauwolscine, phenoxybenzamine, pruvanserin, deramciclane, nelotanserin, lubazodone, mepiprazole, xylamidine, R-H-alpha-(2,3-dimethoxyphenyl)-1-[2-(4-fluorophenethyl)]-4-piperidinemethanol (M100907), mianserin, AT 1015, DV 7028, eplivanserin, 4F 4PP, fanaserin, alpha-phenyl-1-(2-phenylethyl)-4-piperidinemethanol (MDL 11,939), melperone, mesulergine, paliperidone, 1-[2-(3,4-Dihydro-1H-2-benzopyran-1-yl)ethyl]-4-(4-fluorophenyl) piperazine dihydrochloride (PNU 96415E), (2R,4R)-5-[2-[2-[2-(3-methoxyphenyl)ethyl]phenoxy]ethyl]-1-methyl-3-pyrrolidinol (R-96544), sarpogrelate, spiperone, ziprasidone, zotepine, and 7-[[4-[2-(4-fluorophenyl)ethyl]-1-piperazinyl]carbonyl]-1H-indole-3-carbonitrile (EMD 281014).

Suitable $5\text{-}HT_{2A}$ reverse agonists include but are not limited to, AC-90179, nelotanserin (APD-125), eplivanserin, pimavanserin (ACP-103), and volinaserin.

In certain embodiments, the $5\text{-}HT_{2A}$ antagonist is selected from the compounds of Table 10:

TABLE 10

| 5-HT2A antagonists |
|---|
| Acepromazine |
| Agomelatine |
| Amitriptyline |
| Amoxapine |
| Amperozide |
| APD791 |
| Aripiprazole |
| Aripiprazole lauroxil |
| Blonanserin |
| Brexpiprazole |
| Butriptyline |
| Captodiame |
| Cariprazine |
| Chlorpromazine |
| Chlorprothixene |
| Cinitapride |
| Citalopram |
| Clomipramine |
| Clozapine |
| Cyclobenzaprine |
| Cyproheptadine |
| Deramciclane |
| Desipramine |
| Dosulepin |
| Doxepin |
| Epinastine |
| Esmirtazapine |
| Etoperidone |
| Flibanserin |
| Fluoxetine |
| Flupentixol |
| Fluspirilene |
| Iloperidone |
| Imipramine |
| Lisuride |
| Loxapine |
| Lurasidone |
| Mesoridazine |
| Methotrimeprazine |
| Methysergide |
| Mianserin |
| Mirtazapine |
| Nefazodone |
| Nortriptyline |
| Olanzapine |
| Paliperidone |
| Pimavanserin |
| Pizotifen |
| Promazine |
| Propiomazine |
| PRX-08066 |
| Quetiapine |
| Risperidone |
| Sertindole |
| Thioproperazine |
| Thioridazine |
| Tramadol |
| Trazodone |
| Triflupromazine |
| Trimipramine |
| YKP-1358 |
| Yohimbine |
| Ziprasidone |
| Zotepine |
| Zuclopenthixol |

In some embodiments, the disclosure provides a method of reducing the negative side effects associated with a traumatic psychedelic experience in a subject undergoing treatment with psilocybin, the method comprising administering to the subject: i) psilocybin or a precursor or derivative thereof, and ii) one or more cannabinoids or cannabinoid derivatives.

In some embodiments, the cannabinoid is selected from the group consisting of THC (tetrahydrocannabinol), THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin); CBCV (cannabichromevarin); CBGV (cannabigerovarin); CBGM (cannabigerol monomethyl ether); CBE (cannabielsoin); and CBT (cannabicitran). In particular embodiments, the cannabinoid is CBD (cannabidiol).

In some embodiments, at least one symptom of a disease, disorder, or condition described herein is alleviated within 24 hours of administering psilocybin. In some embodiments, at least one symptom of the disease, disorder, or condition is alleviated within 1 week of the administering. In some embodiments, at least one symptom of the disease, disorder, or condition is alleviated within 1 month of the administering. In some embodiments, at least one symptom of the disease, disorder, or condition is alleviated within 6 months of the administering. In some embodiments, at least one symptom of the disease, disorder, or condition is alleviated within 12 months of the administering.

In some embodiments, at least one symptom of the disease, disorder, or condition is alleviated for a period of at least 1 month after administering psilocybin. In some embodiments, at least one symptom of the disease, disorder, or condition is alleviated for a period of at least 3 months after the administering. In some embodiments, at least one symptom of the disease, disorder, or condition is alleviated for a period of at least 6 months after the administering. In some embodiments, at least one symptom of the disease, disorder, or condition is alleviated for a period of at least 12 months after the administering.

In some embodiments, no other treatment is administered to the subject to treat the disease, disorder, or condition before administration of the psilocybin. In some embodiments, no other treatment is administered to the subject to treat the disease, disorder, or condition after administration of the psilocybin.

Safety and Efficacy of Psilocybin

The present disclosure also relates to the safety and efficacy of the use of psilocybin as disclosed herein. The following is a non-exhaustive list of tests that can be used to determine the effects of psilocybin, and in particular the psilocybin formulations as disclosed herein administered as disclosed herein.

In some embodiments, the Spatial Working Memory (SWM) test is utilized to evaluate the safety and efficacy of psilocybin as disclosed herein. SWM requires retention and manipulation of visuospatial information. Study subjects are required to find the blue tokens in the on-screen 'boxes'. Boxes are searched by touching them to determine whether they contain a token. Once a token has been located it is 'stacked' in a column on the right of the screen. Study subjects then search for further tokens until they have all been located. The remaining tokens will thereafter only be found in boxes that have not so far yielded a token. Study subjects are explicitly told this is the case and it they revisit a box in which a token has been found they commit a 'between error', the usual primary metric for this test. Occasions on which the subject revisits a box in the same search are scored as a 'within' error. Many study subjects will adopt a search strategy via which they systematically search the array of boxes. This is also scored by the Cambridge Neuropsychological Test Automated Battery system and yields a 'strategy' score. SWM performance is impaired by damage to the prefrontal cortex, especially the dorsolateral prefrontal cortex. Similarly, in neuroimaging studies in healthy volunteers, SWM performance is associated with activations in the dorsolateral and mid-ventrolateral prefrontal cortex. This test takes approximately 4 min to complete.

In some embodiments, the efficacy of psilocybin is evaluated using the spatial working memory between errors (SWMBE) score. In some embodiments, after treating according to the methods of the disclosure, a subject's SWMBE score decreases by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the efficacy of psilocybin is evaluated using the spatial working memory strategy (SWMS) score. In some embodiments, after treating according to the methods of the disclosure, a subject's SWMS score decreases by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the Rapid Visual Information Processing (RVP) test is utilized to evaluate the safety and efficacy of psilocybin. The RVP is a measure of sustained attention outputting measures of response accuracy, target sensitivity and reaction times. In this test, the study subject is required to monitor a stream of digits from 2 to 9 for specific sequences (e.g., 3-5-7) and to acknowledge detection of the sequence by touching the on-screen response button as quickly as possible after presentation of the third digit. Digits are presented pseudorandomly to create the possibility of 'false alarm' responses in which the first 2 digits of a sequence are not followed by a true target, e.g., when 3 is followed by a 5, but not then by a 7. In order to complete the task successfully study subjects must sustain attention to the white box in which the digits appear. Performance on this task is measured by the speed of response to the presentation of the final digit of a target, as well as the study subject's ability to detect specified sequences. This test takes approximately 7 min to complete.

In some embodiments, performance on the Rapid Visual Information Processing test is reported using a RVP A Prime (RPVA) score. Higher RVPA scores indicated better performance. In some embodiments, after treating according to the methods of the disclosure, a subject's RVPA score increases by between about 5% and about 300%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Paired Associates Learning (PAL) test is utilized to evaluate safety and/or efficacy of psilocybin. The PAL task is a measure of visuo-spatial memory in which study subjects are required to remember locations at which visual stimuli are located. Boxes are displayed on the screen and are "opened" in a randomized order. One or more of them will contain a pattern. The patterns are then displayed in the middle of the screen, one at a time and the subject must select the box in which the pattern was originally located. If the subject makes an error, the boxes are opened in sequence again to remind the subject of the locations of the patterns. Increased difficulty levels can be used to test high-functioning, healthy individuals. The primary metric for this test is the number of errors made. This test takes approximately 8 min to complete. Successful performance of the PAL test is dependent on functional integrity of the temporal lobe, particularly the entorhinal cortex. In some embodiments, the Paired Associates Learning total errors adjusted (PALTEA) score is used to assess the efficacy of psilocybin. In some embodiments, after treating according to the methods of the disclosure, a subject's PALTEA score decreases by between about 5% and about 100%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the efficacy and/or safety of psilocybin is evaluated using the cognitive flexibility panel test.

In some embodiments, the Emotion Recognition Task (ERT) test is utilized to evaluate the safety and/or efficacy of psilocybin. The ERT measures the ability to identify 6 basic emotions in facial expressions along a continuum of expression magnitude. In some embodiments, the ERT is performed according to the following protocol: Subjects are shown computer morphed images derived from the facial features of real individuals each showing a specific emotion, on a screen, one at a time. Each face is displayed for 200 ms and then immediately covered up, and the subject must select which emotion the face displayed from the six options (happy, sad, anger, fear, surprise, disgust). The ERT percent correct (ERTPC) of correct responses (emotion selection) the subject made is assessed. A higher score indicates better performance. In some embodiments, after treating according to the methods of the disclosure, a subject's ERTPC increases by between about 5% and about 300%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Intra-Extra Dimensional Set Shift (IED) test is used to evaluate the safety and/or efficacy of psilocybin. The IED consists of four 7-item subscales, each of which taps a separate aspect of the global concept "empathy." In some embodiments, the Intra-Extra Dimensional Set Shift total errors (IEDYERT) score is used to assess the efficacy of psilocybin.

In some embodiments, after treating according to the methods of the disclosure, a subject's IEDYERT score decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or more, compared to prior to treatment.

In some embodiments, the One Touch Stockings (OTS) of Cambridge test is used to evaluate the safety and/or efficacy of psilocybin. The OTS is a test of executive function, based upon the Tower of Hanoi test. It assesses both the spatial planning and the working memory subdomains. This test takes approximately 10 min to perform. The OTS test reports an one touch stockings of Cambridge problems solved on first choice (OTSPSFC) score. A higher OTSPSFC score is associated with better executive function. In some embodiments, after treatment according to the methods of the disclosure, a subject's OTSPSFC score increases by between about 5% and about 300%, for example, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, as compared to prior to treatment.

In some embodiments, verbal fluency is used to evaluate the safety and/or efficacy of psilocybin. In the verbal fluency test, the study subject is asked to name as many different category exemplars (e.g., 'animals') as they can in 1 min, subject to certain scoring rules, such as repetition. Successful performance on this test is reliant on the integrity of a number of cognitive abilities and especially those traditionally viewed as executive functions, such as planning and working memory. The primary metric for this test is the total number of acceptable words generated. In some embodiments, after treatment with psilocybin, a subject's verbal fluency category score improves by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, as compared to prior to treatment.

In some embodiments, the Digit Span Forward (DSF) test is used to evaluate the safety and/or efficacy of psilocybin. DSF is used to measure number storage capacity. Subjects hear a sequence of digits and are tasked to recall the sequence correctly, with increasingly longer sequences being tested in each trial. The subject's span is the longest number of sequential digits that can accurately be remembered. Digit span tasks can be given forwards or backwards, meaning that once the sequence is presented, the subject is asked to either recall the sequence in normal or reverse order. For this study, subjects will be asked to recall the sequence in the order presented, i.e., Digit Span Forward. The primary metric for this test is the number of digit sequences successfully recalled. In some embodiments, after treatment with psilocybin, a subject's Digit Span Forward score improves by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, as compared to prior to treatment.

In some embodiments, the Five Dimension Altered States of Consciousness questionnaire (5D-ASC) is utilized to evaluate the safety and/or efficacy of psilocybin. The 5D-ASC measures the acute drug effects using 5 primary dimensions and 11 lower-order scales to assess alterations in mood, perception and experience of self in relation to environment and thought disorder. The 5 dimensions include oceanic boundlessness, anxious ego dissolution, visionary restructuralization, auditory alterations and reduction of vigilance. In some embodiments, after treatment according to the methods of the disclosure, a subject experiences an increase on a dimension or a subscale compared to prior to treatment. The lower-order scales include "experience of unity," "spiritual experience," "blissful state," "insightfulness," "disembodiment," "impaired control of cognition," "anxiety," "complex imagery," "elementary imagery," "audio-visual synesthesia," and "changed meaning of percepts." In some embodiments, the increase is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Positive and Negative Affect Schedule (PANAS) is used to evaluate the safety and/or efficacy of psilocybin. The PANAS measures the acute emotional drug effects and comprises 2 mood scales that measure positive and negative affect. Positive affect refers to the propensity to experience positive emotions and interact with others positively. Negative affect involves experiencing the world in a more negative way. Subjects respond to 10 questions associated with negative affect and 10 questions associated with positive affect. The questions are scaled using a 5-point scale that ranges from "slightly or not at all (1)" to "extremely (5)". A total higher score on the positive affect questions indicates more of a positive effect while a lower score on the negative affect questions indicates less of a negative affect. In some embodiments, after treating according to the methods of the disclosure, a subject experiences a decrease in negative affect score of the PANAS, between about 5% and about 100%, for example about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, compared to prior to treatment. In some embodiments, after treating according to the methods of the disclosure, a subject experiences an increase in positive affect score of the PANAS, between about 5% and about 100%, for example about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the NEO-Five Factor Inventory (NEO-FFI) test is used to evaluate the safety and/or efficacy of psilocybin. The NEO-FFI evaluates 5 broad domains of personality—Neuroticism, Extroversion, Openness, Agreeableness and Conscientiousness.

In some embodiments, the Symptom Checklist-90 item (SCL-90) questionnaire is used to evaluate the safety and/or efficacy of psilocybin. The SCL-90 is a relatively brief self-report psychometric instrument designed to evaluate a broad range of psychological problems and symptoms of psychopathology. In some embodiments, the SCL-90 is used to assess somatization, obsessive-compulsive behaviors, interpersonal sensitivity, depression, anxiety, hostility, phobic anxiety, paranoid ideation, and psychoticism of a subject treated according to the methods of the disclosure. The 90 items in the questionnaire are scored on a 5-point Likert scale, indicating the rate of occurrence of the symptom during the time reference. In some embodiments, after treating according to the methods of the disclosure, a subject's SCL-90 score decreases by about 5% to about 100%, for example, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some embodiments, the Life Changes Inventory (LCI) questionnaire is utilized to evaluate the safety and/or efficacy of psilocybin. The LCI is designed as a questionnaire to investigate those variables present in the day-to-day experience of adults that might relate either to stability or decline of intellectual ability.

In some embodiments, Social Cognition Panel scales are utilized to evaluate the safety and/or efficacy of psilocybin. The social cognition panel scales comprise the pictorial empathy test (PET), reading the mind in the eyes test (RMET), social value orientation (SVO) test, the Toronto Empathy Questionnaire (TEQ), and the scale of social responsibility (SSR).

In some embodiments, the Pictorial Empathy Test (PET) is utilized to evaluate the effect of psilocybin on affective empathy.

In some embodiments, Reading the Mind in the Eyes Test (RMET) is utilized to evaluate the safety and/or efficacy of psilocybin. The RMET has 36 items, in which subjects are presented with a photograph of the eyes region of the face and must choose 1 of 4 adjectives or phrases to describe the mental state of the person pictured. A definition handout is provided at the beginning of the task and a practice item precedes the first trial.

In some embodiments, the Social Value Orientation (SVO) test is utilized to evaluate the safety and/or efficacy of psilocybin. The SVO Slider Measure has 6 primary items with 9 secondary (and optional) items. All of the items have the same general form. Each item is a resource allocation choice over a well-defined continuum of joint payoffs.

In some embodiments, after treating according to the methods of the disclosure, one or more of the subject's Social Cognition Panel Scales Score, i.e., PET, RMET, SVO, TEQ, and/or SSR score), improves by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Toronto Empathy Questionnaire (TEQ) is utilized to evaluate the safety and/or efficacy of psilocybin. The TEQ represents empathy as a primarily emotional process. The TEQ has exhibited good internal consistency and high test-retest reliability. The TEQ is a brief, reliable and valid instrument for the assessment of empathy. In some embodiments, after treating according to the methods of the disclosure, a subject's TEQ score increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%, or more, compared to prior to treatment.

In some embodiments, the Scale of Social Responsibility (SSR) is utilized to evaluate the safety and/or efficacy of psilocybin. The SSR measures perceptions regarding the importance of ethics and social responsibility.

In some embodiments, the Sheehan Suicidality Tracking Scale (SSTS) is utilized to evaluate the safety and/or efficacy of psilocybin. The SSTS is a 16-item scale that assesses the seriousness of suicidality phenomena on a Likert-type scale (0-4) ranging from "not at all" (0) to "extremely". The SSTS assesses the frequency of key phenomena and the overall time spent in suicidality.

In some embodiments, the Mini International Neuropsychiatric Interview (MINI) (version 7.0.2) is utilized to evaluate the safety and efficacy of psilocybin. The MINI is a brief structured interview for the major Axis I psychiatric disorders in DSM-5 and International Classification of Diseases-10. In some embodiments, the MINI is used to diagnose a subject with a disorder.

In some embodiments, the McLean Screening Instrument for Borderline Personality Disorder (MSIBPD) is utilized for evaluating the safety and/or efficacy of psilocybin. The MSIBPD is a useful screening tool for identifying the presence of DMS-IV borderline personality disorder.

In some embodiments, the Tellegen Absorption Scale is utilized for evaluating the safety and/or efficacy of psilocybin. The Tellegen Absorption Scale is a 34-item multidimensional measure that assesses imaginative involvement and the tendency to become mentally absorbed in everyday activities.

In some embodiments, the safety and/or efficacy of psilocybin is evaluated by physical examination. A physical examination, includes, but is not limited to, an examination of the subject's general appearance, including an examination of the skin, neck, eyes, ears, nose, throat, heart, lungs, abdomen, lymph nodes, extremities and musculoskeletal system.

In some embodiments, body weight and height of a subject are assessed. In some embodiments, body mass index is used to assess the safety and/or efficacy of psilocybin.

In some embodiments, an electrocardiogram (ECG) is utilized to evaluate the safety and/or efficacy of psilocybin. In some embodiments, a Standard 12-lead ECG is obtained.

In some embodiments, vital signs of a subject are used to evaluate safety and/or efficacy of psilocybin. Vital signs include, but are not limited to, blood pressure (BP), respiratory rate, oral body temperature and pulse. In some embodiments, blood pressure is taken after a subject has been sitting down for at least three minutes.

In some embodiments, clinical laboratory tests are utilized to evaluate the safety and/or efficacy of psilocybin. In some embodiments, the clinical laboratory tests include blood samples and/or urine samples. In some embodiments, hemoglobin, hematocrit, red blood cell count, mean corpuscular hemoglobin, mean corpuscular volume, mean corpuscular hemoglobin concentration, white blood cell count (with differential) and platelet count are measured to evaluate safety and/or efficacy of psilocybin. In some embodiments, albumin, alkaline phosphatase, alanine aminotransferase (ALT), amylase, aspartate aminotransferase (AST), bicarbonate, bilirubin (direct, indirect and total), calcium, chloride, creatine kinase, creatinine, γ-glutamyl transferase, glucose, lactate dehydrogenase, lipase, magnesium, phosphate, potassium, protein-total, sodium, blood urea nitrogen and/or uric acid are measured to evaluate the safety and/or efficacy of psilocybin.

In some embodiments, urine is tested for pregnancy and/or illicit drugs.

In some embodiments, the safety and/or efficacy of psilocybin are evaluated by measuring adverse events. Adverse events are classified as mild, moderate, or severe. A mild adverse event does not interfere in a significant manner with the subject's normal level of functioning. A moderate adverse event produces some impairment of functioning, but is not hazardous to the subject's health. A serious adverse event produces significant impairment of functioning or incapacitation and is a definite hazard to the subject's health. Adverse events may include, for example, euphoric mood, dissociative disorder, hallucination, psychotic disorder, cognitive disorder, disturbances in attention, mood alterations, psychomotor skill impairments, inappropriate affects, overdoses, and intentional product misuse. In some embodiments, serious adverse events include death, life-threatening adverse events, inpatient hospitalization or prolongation of existing hospitalization, persistent or significant disability/incapacity, and congenital anomaly/birth defect in the offspring of a subject who received psilocybin. In some embodiments, serious adverse events include intensive treatment in an emergency room or at home for allergic bronchospasm, blood dyscrasias or convulsions that do not result in inpatient hospitalization, or the development of drug dependency or drug abuse.

Numbered Embodiments of the Disclosure

In addition to the disclosure above, the Examples below, and the appended claims, the disclosure sets forth the following numbered embodiments.

Neuroplasticity Effects: Major and Mild Neurocognitive Disorders

1. A method for treating one or more neurocognitive disorders in a subject in need thereof, the method comprising administering to the subject an effective amount of psilocybin or an active metabolite thereof.

2. The method of embodiment 1, wherein the active metabolite is psilocin.

3. The method of any one of embodiments 1-2, wherein the neurocognitive disorder is major neurocognitive disorder.

4. The method of embodiment 3, wherein the major neurocognitive disorder is dementia.

5. The method of any one of embodiments 1-2, wherein the neurocognitive disorder is Mild Cognitive Impairment (MCI).

6. The method of any one of embodiments 1-4, wherein the one or more neurocognitive disorders is due to, one or more of Alzheimer's disease, Lewy Body Dementia, Traumatic Brain Injury, Prion Disease, HIV Infection, Parkinson's disease, or Huntington's disease.

7. The method of embodiment 6, wherein the one or more neurocognitive disorders is due to Alzheimer's disease (AD).

8. The method of any one of embodiments 1-7, wherein the subject demonstrates an improvement in one or more of the following: the Mini-Mental State Exam (MMSE), the Mini-Cog test, a CANTAB test, a Cognigram test, a Cognivue test, a Cognition test, or an Automated Neuropsychological Assessment Metrics test, after administration with psilocybin.

9. The method of any one of embodiments 1-8, wherein the subject has one or more comorbidities.

10. The method of embodiment 9, wherein the one or more comorbidities is hypertension, connective tissue disease, depression, diabetes, or chronic pulmonary disease.

11. The method of any one of embodiments 1-10, wherein the subject is administered one or more additional therapeutics.

12. The method of embodiment 11, wherein the one or more additional therapeutics is an antidepressant, cholinesterase inhibitors, acetylcholinesterase inhibitors, butyrylcholinesterase inhibitors, N-methyl-D-aspartate (NMDA) receptor antagonists, or combinations thereof.

13. The method of any one of embodiments 1-12, wherein the subject has no prior psilocybin exposure.

14. The method of any one of embodiments 1-12, wherein the subject has prior psilocybin exposure.

15. The method of any one of embodiments 1-14 wherein the subject is a mammal.

16. The method of embodiment 15, wherein the subject is a human.

17. The method of any of embodiments 1-16, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

18. The method of embodiment 17, wherein the crystalline psilocybin comprises at least 95% by weight of Polymorph A.

19. The method of embodiment 17 or 18, wherein the crystalline psilocybin has a chemical purity of greater than 97% by HPLC, and no single impurity of greater than 1%.

20. The method of any of embodiments 1-16, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

21. The method of embodiment 20, wherein the highly pure crystalline psilocybin comprises at least 90% by weight of Polymorph A.

22. The method of embodiment 20, wherein the highly pure crystalline psilocybin comprises at least 95% by weight of Polymorph A.

23. The method of any one of embodiments 17-22, wherein the highly pure crystalline psilocybin is further characterized having either: (i) a water content of <0.5% w/w; or (ii) <0.5% w/w loss in the TGA thermogram between 25° C. and 200° C.

24. The method of any of embodiments 17-23, wherein the highly pure crystalline psilocybin is further characterized by an endothermic event in a DSC thermogram having a first onset temperature of between 145° C. and 155° C. and a second onset temperature of between 205 and 220° C.

25. The method of any one of embodiments 17-24, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

26. The method of any of embodiments 23-25, wherein the highly pure crystalline psilocybin has no single impurity of greater than 0.5%.

27. The method of any of embodiments 17-26, wherein the dosage form further comprises about 5 to 40 mg of the highly pure crystalline psilocybin.

28. The method of embodiment 27, wherein the dosage form comprises 5 mg of highly pure crystalline psilocybin.

29. The method of embodiment 27, wherein the dosage form comprises about 10 mg of highly pure crystalline psilocybin.

30. The method of embodiment 27, wherein the dosage form comprises about 35 mg of highly pure crystalline psilocybin.

31. The method of any of embodiments 17-30, wherein the dosage form comprises silicified microcrystalline cellulose.

32. The method of embodiment 31, wherein the silicified microcrystalline cellulose has a particle size range from about 45 to 150 microns.

33. The method of any of embodiments 17-32, further comprising a mixture of two silicified microcrystalline cellulose variants wherein the first variant has a particle size from about 45 to 80 microns and the second variant has a particle size of about 90 to 150 microns.

34. The method of embodiment 33, wherein about 30% or less of the microcrystalline cellulose is the first variant having a particle size from about 45 to 80 microns and about 70% or more of the microcrystalline cellulose is the second variant having a particle size of about 90 to 150 microns.

35. The method of embodiment 33, wherein about 20% or less of the microcrystalline cellulose is the first variant having a particle size from about 45 to 80 microns and about 80% or more of the microcrystalline cellulose is the second variant having a particle size of about 90 to 150 microns.

36. The method of embodiment 33, wherein about 15% or less of the microcrystalline cellulose is the first variant having a particle size from about 45 to 80 microns and about 85% or more of the microcrystalline cellulose is the second variant having a particle size of about 90 to 150 microns.

37. The method of embodiment 33, wherein about 15% or less of the microcrystalline cellulose is the first variant having a particle size from about 45 to 80 microns and about 85% or more of the microcrystalline cellulose is the second variant having a particle size of about 90 to 150 microns.

38. The method of embodiment 37, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

39. The method of embodiment 37, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

40. The method any one of embodiments 17-39, wherein the dosage form is an oral dosage form.

41. The method embodiment 40, wherein the dosage form is a capsule.

42. The method embodiment 40, wherein the dosage form is a tablet.

43. The method of any one of embodiments 1-42, wherein at least one dose of psilocybin is administered to the subject.

44. The method of embodiment 43, wherein the at least dose of psilocybin is in the range of about 0.1 mg to about 100 mg.

45. The method of embodiment 44, wherein the dose of psilocybin is about 1 mg.

46. The method of embodiment 44, wherein the dose of psilocybin is about 10 mg.

47. The method of embodiment 44, wherein the dose of psilocybin is about 25 mg.

48. The method of any one of embodiments 1-42, wherein more than one dose of psilocybin is administered to the subject.

49. The method of embodiment 48, wherein at least two doses of psilocybin are administered to the subject.

50. The method of any one of embodiments 48-49, wherein the psilocybin is administered once per day.

51. The method of any one of embodiments 48-49, wherein the psilocybin is administered at least once per week.

52. The method of any one of embodiments 48-49, wherein the psilocybin is administered at least twice per week.

53. The method of any one of embodiments 48-49, wherein the psilocybin is administered at least once per month.

54. The method of any one of embodiments 48-49, wherein the psilocybin is administered at least twice per month.

55. The method of any one of embodiments 48-49, wherein the psilocybin is administered at least once every three months.

56. The method of any one of embodiments 48-49, wherein the psilocybin is administered at least once every six months.

57. The method of any one of embodiments 48-49, wherein the psilocybin is administered at least once every 12 months.

58. The method of any one of embodiments 48-57, wherein each dose of psilocybin administered is in the range of about 0.1 mg to about 100 mg.

59. The method of embodiment 58, wherein each dose of psilocybin administered is about 1 mg.

60. The method of embodiment 58, wherein each dose of psilocybin administered is about 10 mg.

61. The method of embodiment 58, wherein each dose of psilocybin administered is about 25 mg.

62. The method of any one of embodiments 17-61, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

63. The method of embodiment 62, wherein the psilocybin is administered orally.

64. The method of any one of embodiments 1-63, wherein the subject participates in at least one psychological support session before administration of the psilocybin.

65. The method of embodiment 64, wherein the subject participates in at least three psychological support sessions before administration of the psilocybin.

66. The method of any one of embodiments 64-65, wherein the at least one therapeutic intention is discussed during the psychological support session.

67. The method of any one of embodiments 64-66, wherein self-directed inquiry and experiential processing are practiced during the psychological support session.

68. The method of any one of embodiments 1-63, wherein the subject participates in at least one psychological support session after administration of the psilocybin.

69. The method of embodiment 68, wherein the subject participates in at least three psychological support sessions after administration of the psilocybin.

70. The method of any one of embodiments 63-69, wherein the psilocybin is administered to the subject in a room with a substantially non-clinical appearance.

71. The method of embodiment 70, wherein the room comprises soft furniture.

72. The method of embodiment 70, wherein the room is decorated using muted colors. 73. The method of embodiment 70, wherein the room comprises a high-resolution sound system.

74. The method of any one of embodiments 70-73, wherein the room comprises a bed or a couch.

75. The method of embodiment 74, wherein the subject lies in the bed or on the couch for approximately 4-8 hours, or a substantial fraction thereof, after administration of the psilocybin.

76. The method of any one of embodiments 10-75, wherein the subject listens to music for approximately 4-8 hours, or a substantial fraction thereof, after administration of the psilocybin.

77. The method of any one of embodiments 70-76, wherein the subject wears an eye mask for approximately 4-8 hours, or a substantial fraction thereof, after administration of the psilocybin.

78. The method of any one of embodiments 70-77, wherein a therapist provides psychological support to the subject for approximately 4-8 hours after administration of the psilocybin.

79. The method of embodiment 78, wherein the therapist uses guided imagery to calm the subject and/or focus the subject's attention.

80. The method of embodiment 78, wherein the therapist provides reassuring physical contact with the subject.

81. The method of embodiment 80, wherein the therapist holds the hand, arm, or shoulder of the subject.

82. The method of embodiment 78, wherein the therapist encourages the subject to perform self-directed inquiry and experiential processing.

83. The method of embodiment 78, wherein the therapist reminds the subject of at least one therapeutic intention.

84. The method of embodiment 78, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

85. The method of embodiment 78, wherein the therapist does not initiate conversation with the subject.

86. The method of embodiment 78, wherein the therapist responds to the subject if the subject initiates conversation.

Parkinson's Disease

1. A method for treating a Parkinsonian syndrome or symptom thereof in a subject in need thereof, the method comprising administering to the subject a therapeutically effective amount of psilocybin or an active metabolite thereof.

2. The method of embodiment 1, wherein the active metabolite is psilocin.

3. The method of any one of embodiments 1-2, wherein the Parkinsonian syndrome is Parkinson's disease.

4. The method of any one of embodiments 1-2, wherein the Parkinsonian syndrome is an atypical Parkinsonian disorder.

5. The method of embodiment 1, wherein the Parkinsonian syndrome is drug-induced.

6. The method of embodiment 4, wherein the atypical parkinsonian disorder is multiple system atrophy progressive supranuclear palsy, corticobasal degeneration, or dementia with Lewy bodies.

7. The method of any one of embodiments 1-6, wherein the subject in need thereof suffers from a motor symptom, a nonmotor symptom, or combinations thereof.

8. The method of embodiment 7, wherein the subject in need thereof suffers from a motor symptom, and wherein the motor symptom is bradykinesia, rigidity, tremor, rest tremor, postural instability, stiffness, slowness, imbalance, or combinations thereof.

9. The method of embodiment 7, wherein the subject in need thereof suffers from a nonmotor symptom, and wherein the nonmotor symptom is cognitive impairment, olfactory loss, sleep dysfunction, autonomic dysfunction, psychiatric disturbance, fatigue, softening of the voice, sialorrhea, trouble swallowing, or combinations thereof.

10. The method of any one of embodiments 1-9, wherein the subject has a comorbidity.

11. The method of embodiment 10, wherein the comorbidity is a symptom of a Parkinsonian syndrome.

12. The method of embodiment 11, wherein the comorbidity is selected from a neuropsychiatric disturbance, a sleep disorder, melanoma, neurogenic orthostatic hypotension, pseudobulbar affect, anemia, hypertension, type 2 diabetes, restless leg syndrome, cancer, or combinations thereof.

13. The method of embodiment 11, wherein the comorbidity is a neuropsychiatric disturbance, and wherein the neuropsychiatric disturbance is dementia, depression, psychosis, apathy, anxiety, hallucinations, or combinations thereof.

14. The method of embodiment 11, wherein the comorbidity is a sleep disorder, and wherein the sleep disorder is daytime drowsiness and sleepiness, sleep attacks, insomnia, or rapid eye movement sleep behavior disorder.

15. The method of embodiment 14, wherein the sleep disorder is rapid eye movement sleep behavior disorder.

16. The method of any one of embodiments 1-15, wherein an additional therapy is administered to the subject.

17. The method of embodiment 16, wherein the additional therapy is exercise, physical, occupational, or speech therapy.

18. The method of embodiment 16, wherein the additional therapy is a dopaminergic medication.

19. The method of embodiment 16, wherein the additional therapy is carbidopa-levodopa, entacopone, tolcapone, carbidopa, levodopa entacopone, pramipexole, ropinirol, apomorphine, rotigotine, selegiline, rasagiline, safinamide, amantadine, istradefylline, trihexyphenidyl, benztropine, or combinations thereof.

20. The method of any one of embodiments 16-19, wherein the administering of an additional therapy is prior to administration of psilocybin.

21. The method of any one of embodiments 16-19, wherein the additional therapy is administered to the subject after administration of psilocybin.

22. The method of any one of embodiments 16-19, wherein the additional therapy is administered to the subject concurrent with administration of psilocybin.

23. The method of any one of embodiments 1-22, wherein after treating the subject in need thereof has a decreased Unified Parkinson's disease rating scale (UPDRS) score.

24. The method of embodiment 23, wherein the decreased UPDRS score is observed within one month after psilocybin administration.

25. The method of embodiment 23, wherein the UPDRS score is decreased by at least about 20%.

26. The method of any one of embodiments 1-25, wherein the subject has no prior psilocybin exposure.

27. The method of any one of embodiments 1-25, wherein the subject has prior psilocybin exposure.

28. The method of any one of embodiments 1-27 wherein the subject is a mammal.

29. The method of embodiment 28, wherein the subject is a human.

30. The method of any of embodiments 1-29, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

31. The method of embodiment 30, wherein the crystalline psilocybin comprises at least 95% by weight of Polymorph A.

32. The method of embodiment 30 or 31, wherein the crystalline psilocybin has a chemical purity of greater than 97% by HPLC, and no single impurity of greater than 1%.

33. The method of any of embodiments 1-29, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

34. The method of embodiment 33, wherein the highly pure crystalline psilocybin comprises at least 90% by weight of Polymorph A.

35. The method of embodiment 33, wherein the highly pure crystalline psilocybin comprises at least 95% by weight of Polymorph A.

36. The method of any one of embodiments 30-35, wherein the highly pure crystalline psilocybin is further characterized having either: (i) a water content of <0.5% w/w; or (ii) <0.5% w/w loss in the TGA thermogram between 25° C. and 200° C.

37. The method of any of embodiments 30-36, wherein the highly pure crystalline psilocybin is further characterized by an endothermic event in a DSC thermogram having a first onset temperature of between 145° C. and 155° C. and a second onset temperature of between 205 and 220° C.

38. The method of any one of embodiments 30-37, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

39. The method of any of embodiments 36-38, wherein the highly pure crystalline psilocybin has no single impurity of greater than 0.5%.

40. The method of any of embodiments 13-39, wherein the dosage form further comprises about 5 to 40 mg of the highly pure crystalline psilocybin. 41. The method of embodiment 40, wherein the dosage form comprises 5 mg of highly pure crystalline psilocybin.

42. The method of embodiment 40, wherein the dosage form comprises about 10 mg of highly pure crystalline psilocybin.

43. The method of embodiment 40, wherein the dosage form comprises about 35 mg of highly pure crystalline psilocybin.

44. The method of any of embodiments 30-43, wherein the dosage form comprises silicified microcrystalline cellulose.

45. The method of embodiment 44, wherein the silicified microcrystalline cellulose has a particle size range from about 45 to 150 microns.

46. The method of any of embodiments 30-43, further comprising a mixture of two silicified microcrystalline cellulose variants wherein the first variant has a particle size from about 45 to 80 microns and the second variant has a particle size of about 90 to 150 microns.

47. The method of embodiment 46, wherein about 30% or less of the microcrystalline cellulose is the first variant having a particle size from about 45 to 80 microns and about 70% or more of the microcrystalline cellulose is the second variant having a particle size of about 90 to 150 microns.

48. The method of embodiment 46, wherein about 20% or less of the microcrystalline cellulose is the first variant having a particle size from about 45 to 80 microns and about 80% or more of the microcrystalline cellulose is the second variant having a particle size of about 90 to 150 microns.

49. The method of embodiment 46, wherein about 15% or less of the microcrystalline cellulose is the first variant having a particle size from about 45 to 80 microns and about 85% or more of the microcrystalline cellulose is the second variant having a particle size of about 90 to 150 microns.

50. The method of embodiment 46, wherein about 15% or less of the microcrystalline cellulose is the first variant having a particle size from about 45 to 80 microns and about 85% or more of the microcrystalline cellulose is the second variant having a particle size of about 90 to 150 microns.

51. The method of embodiment 50, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

52. The method of embodiment 50, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

53. The method any one of embodiments 30-52, wherein the dosage form is an oral dosage form.

54. The method embodiment 53, wherein the dosage form is a capsule. 55. The method embodiment 53, wherein the dosage form is a tablet.

56. The method of any one of embodiments 1-55, wherein at least one dose of psilocybin is administered to the subject.

57. The method of embodiment 56, wherein the at least dose of psilocybin is in the range of about 0.1 mg to about 100 mg.

58. The method of embodiment 57, wherein the dose of psilocybin is about 1 mg.

59. The method of embodiment 57, wherein the dose of psilocybin is about 10 mg.

60. The method of embodiment 57, wherein the dose of psilocybin is about 25 mg.

61. The method of any one of embodiments 1-60, wherein more than one dose of psilocybin is administered to the subject.

62. The method of embodiment 61, wherein at least two doses of psilocybin are administered to the subject.

63. The method of any one of embodiments 61-62, wherein the psilocybin is administered once per day.

64. The method of any one of embodiments 61-62, wherein the psilocybin is administered at least once per week.

65. The method of any one of embodiments 61-62, wherein the psilocybin is administered at least twice per week.

66. The method of any one of embodiments 61-62, wherein the psilocybin is administered at least once per month.

67. The method of any one of embodiments 61-62, wherein the psilocybin is administered at least twice per month.

68. The method of any one of embodiments 61-62, wherein the psilocybin is administered at least once every three months.

69. The method of any one of embodiments 61-62, wherein the psilocybin is administered at least once every six months.

70. The method of any one of embodiments 61-62, wherein the psilocybin is administered at least once every 12 months.

71. The method of any one of embodiments 67-70, wherein each dose of psilocybin administered is in the range of about 0.1 mg to about 100 mg.

72. The method of embodiment 71, wherein each dose of psilocybin administered is about 1 mg.

73. The method of embodiment 71, wherein each dose of psilocybin administered is about 10 mg.

74. The method of embodiment 71, wherein each dose of psilocybin administered is about 25 mg.

75. The method of any one of embodiments 30-74, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

76. The method of embodiment 75, wherein the psilocybin is administered orally.

77. The method of any one of embodiments 1-75, wherein the subject participates in at least one psychological support session before administration of the psilocybin.

78. The method of embodiment 77, wherein the subject participates in at least three psychological support sessions before administration of the psilocybin.

79. The method of any one of embodiments 77-78, wherein the at least one therapeutic intention is discussed during the psychological support session.

80. The method of any one of embodiments 77-79, wherein self-directed inquiry and experiential processing are practiced during the psychological support session.

81. The method of any one of embodiments 1-80, wherein the subject participates in at least one psychological support session after administration of the psilocybin.

82. The method of embodiment 81, wherein the subject participates in at least three psychological support sessions after administration of the psilocybin.

83. The method of any one of embodiments 76-82, wherein the psilocybin is administered to the subject in a room with a substantially non-clinical appearance.

84. The method of embodiment 83, wherein the room comprises soft furniture.

85. The method of embodiment 83, wherein the room is decorated using muted colors.

86. The method of embodiment 83, wherein the room comprises a high-resolution sound system.

87. The method of any one of embodiments 83-86, wherein the room comprises a bed or a couch.

88. The method of embodiment 87, wherein the subject lies in the bed or on the couch for approximately 4-8 hours, or a substantial fraction thereof, after administration of the psilocybin.

89. The method of any one of embodiments 83-88, wherein the subject listens to music for approximately 4-8 hours, or a substantial fraction thereof, after administration of the psilocybin.

90. The method of any one of embodiments 83-89, wherein the subject wears an eye mask for approximately 4-8 hours, or a substantial fraction thereof, after administration of the psilocybin.

91. The method of any one of embodiments 1-90, wherein a therapist provides psychological support to the subject for approximately 4-8 hours after administration of the psilocybin.

92. The method of embodiment 91, wherein the therapist uses guided imagery to calm the subject and/or focus the subject's attention.

93. The method of embodiment 91, wherein the therapist provides reassuring physical contact with the subject.

94. The method of embodiment 93, wherein the therapist holds the hand, arm, or shoulder of the subject.

95. The method of embodiment 91, wherein the therapist encourages the subject to perform self-directed inquiry and experiential processing.

96. The method of embodiment 91, wherein the therapist reminds the subject of at least one therapeutic intention.

97. The method of embodiment 91, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

98. The method of embodiment 91, wherein the therapist does not initiate conversation with the subject.

99. The method of embodiment 91, wherein the therapist responds to the subject if the subject initiates conversation.

Autism

1. A method for treating an autism spectrum disorder (ASD) or a symptom thereof in a subject in need thereof, the method comprising administering to the subject a therapeutically effective amount of psilocybin or an active metabolite thereof.

2. The method of embodiment 1, wherein the active metabolite is psilocin.

3. The method of any one of embodiments 1-2, wherein the subject in need thereof is nonverbal.

4. The method of any one of embodiments 1-4, wherein the subject in need thereof has an intelligent quotient (IQ) of between about 70 to 129.

5. The method of embodiment 4, wherein the subject in need thereof has an intelligence quotient (IQ) of between about 71 and about 85.

6. The method of any one of embodiments 1-5, wherein the symptom thereof is irritability, repetitive behavior, restricted behaviors, social deficits, unusual reactivity to sensory stimuli, communication deficits, aggression, self-injurious behavior, motor impairment, cognitive deficits, or combinations thereof.

7. The method of embodiment 6, wherein the subject in need thereof suffers from cognitive deficits in cognitive flexibility, sustained attention, working memory, episodic memory, executive function, or combinations thereof.

8. The method of any one of embodiments 1-7, wherein the subject has a comorbidity.

9. The method of embodiment 8, wherein the comorbidity is a psychiatric disorder, and wherein the psychiatric disorder is selected from attention-deficit hyperactivity disorder, anxiety disorders, sleep-wake disorder, impulse-control, disruptive behavior, conduct disorder, depressive disorders, obsessive-compulsive and related disorders, bipolar disorder, schizophrenia, or combinations thereof.

10. The method of embodiment 8, wherein the comorbidity is an inflammatory disorder, gastrointestinal disorder, epilepsy, or a combination thereof.

11. The method of any one of embodiments 1-10, wherein the subject is administered at least one additional therapeutic agent.

12. The method of embodiment 11, wherein at least one additional therapeutic agent is risperidione or aripiprazole.

13. The method of embodiment 11 or 12, wherein the administering of an additional therapeutic agent is prior to administration of psilocybin.

14. The method of embodiment 11 or 12, wherein the administering of an additional therapeutic agent is after administration of psilocybin.

15. The method of embodiment 11 or 12, wherein the administering of an additional therapeutic agent is concurrent with administration of psilocybin.

16. The method of any one of embodiments 1-15, wherein after treating the subject in need thereof has a decreased Vineland-II Adaptive Behavior (VABS-2) score.

17. The method of embodiment 16, wherein the idecreased VABS-2 score is observed within one month after psilocybin administration.

18. The method of embodiment 16, wherein the VABS-2 score is decreased by at least about 5%, about 10%, about 15%, about 20%, or more.

19. The method of any one of embodiments 1-18, wherein after treating the subject in need thereof has a decreased proxy version-t score on the Social Responsiveness Scale, Second Edition (SRS-2).

20. The method of embodiment 19, wherein the decreased proxy version-t score is observed within one month after psilocybin administration.

21. The method of embodiment 19, wherein the proxy version-t score is decreased by at least about 5%, about 10%, about 15%, or by at least about 20%.

22. The method of any one of embodiments 1-21, wherein the subject has no prior psilocybin exposure.

23. The method of any one of embodiments 1-21, wherein the subject has prior psilocybin exposure.

24. The method of any one of embodiments 1-23 wherein the subject is a mammal.

25. The method of embodiment 24, wherein the subject is a human.

26. The method of any of embodiments 1-25, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

27. The method of embodiment 26, wherein the crystalline psilocybin comprises at least 95% by weight of Polymorph A.

28. The method of embodiment 26 or 27, wherein the crystalline psilocybin has a chemical purity of greater than 97% by HPLC, and no single impurity of greater than 1%.

29. The method of any of embodiments 1-25, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

30. The method of embodiment 29, wherein the highly pure crystalline psilocybin comprises at least 90% by weight of Polymorph A.

31. The method of embodiment 29, wherein the highly pure crystalline psilocybin comprises at least 95% by weight of Polymorph A.

32. The method of any one of embodiments 26-31, wherein the highly pure crystalline psilocybin is further characterized having either: (i) a water content of <0.5% w/w; or (ii) <0.5% w/w loss in the TGA thermogram between 25° C. and 200° C.

33. The method of any of embodiments 26-32, wherein the highly pure crystalline psilocybin is further characterized by an endothermic event in a DSC thermogram having a first onset temperature of between 145° C. and 155° C. and a second onset temperature of between 205 and 220° C.

34. The method of any one of embodiments 26-33, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}P$ NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

35. The method of any of embodiments 26-34, wherein the highly pure crystalline psilocybin has no single impurity of greater than 0.5%.

36. The method of any of embodiments 26-35, wherein the dosage form further comprises about 5 to 40 mg of the highly pure crystalline psilocybin.

37. The method of embodiment 36, wherein the dosage form comprises 5 mg of highly pure crystalline psilocybin.

38. The method of embodiment 36, wherein the dosage form comprises about 10 mg of highly pure crystalline psilocybin.

39. The method of embodiment 36, wherein the dosage form comprises about 35 mg of highly pure crystalline psilocybin.

40. The method of any of embodiments 26-39, wherein the dosage form comprises silicified microcrystalline cellulose.

41. The method of embodiment 40, wherein the silicified microcrystalline cellulose has a particle size range from about 45 to 150 microns.

42. The method of any of embodiments 26-41, further comprising a mixture of two silicified microcrystalline cellulose variants wherein the first variant has a particle size from about 45 to 80 microns and the second variant has a particle size of about 90 to 150 microns.

43. The method of embodiment 42, wherein about 30% or less of the microcrystalline cellulose is the first variant having a particle size from about 45 to 80 microns and about 70% or more of the microcrystalline cellulose is the second variant having a particle size of about 90 to 150 microns.

44. The method of embodiment 42, wherein about 20% or less of the microcrystalline cellulose is the first variant having a particle size from about 45 to 80 microns and about 80% or more of the microcrystalline cellulose is the second variant having a particle size of about 90 to 150 microns.

45. The method of embodiment 42, wherein about 15% or less of the microcrystalline cellulose is the first variant having a particle size from about 45 to 80 microns and about 85% or more of the microcrystalline cellulose is the second variant having a particle size of about 90 to 150 microns.

46. The method of embodiment 42, wherein about 15% or less of the microcrystalline cellulose is the first variant having a particle size from about 45 to 80 microns and about 85% or more of the microcrystalline cellulose is the second variant having a particle size of about 90 to 150 microns.

47. The method of embodiment 46, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

48. The method of embodiment 46, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

49. The method any one of embodiments 26-48, wherein the dosage form is an oral dosage form.

50. The method embodiment 49, wherein the dosage form is a capsule.

51. The method embodiment 49, wherein the dosage form is a tablet.

52. The method of any one of embodiments 1-51, wherein at least one dose of psilocybin is administered to the subject.

53. The method of embodiment 52, wherein the at least dose of psilocybin is in the range of about 0.1 mg to about 100 mg.

54. The method of embodiment 53, wherein the dose of psilocybin is about 1 mg.

55. The method of embodiment 53, wherein the dose of psilocybin is about 10 mg.

56. The method of embodiment 53, wherein the dose of psilocybin is about 25 mg.

57. The method of any one of embodiments 1-56, wherein more than one dose of psilocybin is administered to the subject.

58. The method of embodiment 57, wherein at least two doses of psilocybin are administered to the subject.

59. The method of any one of embodiments 57-58, wherein the psilocybin is administered once per day.

60. The method of any one of embodiments 57-58, wherein the psilocybin is administered at least once per week.

61. The method of any one of embodiments 57-58, wherein the psilocybin is administered at least twice per week.

62. The method of any one of embodiments 57-58, wherein the psilocybin is administered at least once per month.

63. The method of any one of embodiments 57-58, wherein the psilocybin is administered at least twice per month.

64. The method of any one of embodiments 57-58, wherein the psilocybin is administered at least once every three months.

65. The method of any one of embodiments 57-58, wherein the psilocybin is administered at least once every six months.

66. The method of any one of embodiments 57-58, wherein the psilocybin is administered at least once every 12 months.

67. The method of any one of embodiments 57-66, wherein each dose of psilocybin administered is in the range of about 0.1 mg to about 100 mg.

68. The method of embodiment 67, wherein each dose of psilocybin administered is about 1 mg.

69. The method of embodiment 67, wherein each dose of psilocybin administered is about 10 mg.

70. The method of embodiment 67, wherein each dose of psilocybin administered is about 25 mg.

71. The method of any one of embodiments 52-70, wherein the psilocybin is administered by one of the following routes: oral, intravenous, subcutaneous, intramuscular, intraperitoneal, parenteral, topical, inhalation, rectal, transmucosal, intranasal, buccal, vaginal, intrathecal, intraocular, transdermal, in utero, intralymphatic, or by direct tissue or organ injection.

72. The method of embodiment 71, wherein the psilocybin is administered orally.

73. The method of any one of embodiments 1-72, wherein the subject participates in at least one psychological support session before administration of the psilocybin.

74. The method of embodiment 73, wherein the subject participates in at least three psychological support sessions before administration of the psilocybin.

75. The method of any one of embodiments 73-74, wherein the at least one therapeutic intention is discussed during the psychological support session.

76. The method of any one of embodiments 73-75, wherein self-directed inquiry and experiential processing are practiced during the psychological support session.

77. The method of any one of embodiments 73-76, wherein the subject participates in at least one psychological support session after administration of the psilocybin.

78. The method of embodiment 77, wherein the subject participates in at least three psychological support sessions after administration of the psilocybin.

79. The method of any one of embodiments 72-79, wherein the psilocybin is administered to the subject in a room with a substantially non-clinical appearance.

80. The method of embodiment 79, wherein the room comprises soft furniture.

81. The method of embodiment 79, wherein the room is decorated using muted colors.

82. The method of embodiment 79, wherein the room comprises a high-resolution sound system.

83. The method of any one of embodiments 79-82, wherein the room comprises a bed or a couch.

84. The method of embodiment 83, wherein the subject lies in the bed or on the couch for approximately 4-8 hours, or a substantial fraction thereof, after administration of the psilocybin.

85. The method of any one of embodiments 72-84, wherein the subject listens to music for approximately 4-8 hours, or a substantial fraction thereof, after administration of the psilocybin.

86. The method of any one of embodiments 72-84, wherein the subject wears an eye mask for approximately 4-8 hours, or a substantial fraction thereof, after administration of the psilocybin.

87. The method of any one of embodiments 1-86, wherein a therapist provides psychological support to the subject for approximately 4-8 hours after administration of the psilocybin.

88. The method of embodiment 87, wherein the therapist uses guided imagery to calm the subject and/or focus the subject's attention.

89. The method of embodiment 87, wherein the therapist provides reassuring physical contact with the subject.

90. The method of embodiment 89, wherein the therapist holds the hand, arm, or shoulder of the subject.

91. The method of embodiment 87, wherein the therapist encourages the subject to perform self-directed inquiry and experiential processing.

92. The method of embodiment 87, wherein the therapist reminds the subject of at least one therapeutic intention.

93. The method of embodiment 87, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

94. The method of embodiment 87, wherein the therapist does not initiate conversation with the subject.

95. The method of embodiment 87, wherein the therapist responds to the subject if the subject initiates conversation.

Epilepsy

1. A method for treating epilepsy in a subject in need thereof, the method comprising administering to the subject a therapeutically effective amount of psilocybin or an active metabolite thereof.

2. The method of embodiment 1, wherein the active metabolite is psilocin.

3. The method of any one of embodiments 1-2, wherein the subject in need thereof has generalized tonic-clonic, convulsive, absence, myoclonic, clonic, tonic, or atonic seizures.

4. The method of embodiment 3, wherein the epilepsy is generalized epilepsy, epilepsy with myoclonic absence seizures, focal epilepsy, generalized and focal epilepsy, unknown if generalized or focal epilepsy, autosomal dominant nocturnal frontal lobe epilepsy, childhood absence epilepsy, benign rolandic epilepsy, Doose syndrome, Dravet syndrome, early myoclonic encephalopathy, Jeavons syndrome, epilepsy in infancy with migrating focal seizures, epileptic encephalopathy with continuous spike and wave during sleep, febrile illness-related epilepsy syndrome, frontal lobe epilepsy, west syndrome, juvenile absence epilepsy, juvenile myoclonic epilepsy, Landau-Kleffner syndrome, Lennox-Gastaut syndrome, Ohtahara syndrome, Panayiotopoulos syndrome, progressive myoclonic epilepsy, reflex epilepsy, or temporal lobe epilepsy.

5. The method of any one of embodiments 1-4, wherein the subject has a comorbidity.

6. The method of embodiment 5, wherein the comorbidity is a psychiatric comorbidity, a neurological comorbidity, or a somatic condition.

7. The method of embodiment 6, wherein the comorbidity is a psychiatric comorbidity, and wherein the psychiatric comorbidity is bipolar disorder, ADHD, depression, anxiety, or combinations thereof.

8. The method of embodiment 6, wherein the comorbidity is a neurological comorbidity, and wherein the neurological comorbidity is migraine, cognitive impairment, stroke, cerebrovascular disease, or combinations thereof.

9. The method of embodiment 8, wherein the neurological comorbidity is migraine.

10. The method of embodiment 6, wherein the comorbidity is a somatic condition, and the somatic condition is a cardiac, inflammatory, or pulmonary condition.

11. The method of embodiment 10, wherein the cardiac condition is heart disease.

12. The method of embodiment 10, wherein the inflammatory disease is an autoimmune disease, and the autoimmune disease is arthritis, diabetes mellitus, asthma, or combinations thereof.

13. The method of embodiment 10, wherein the pulmonary disease is chronic obstructive pulmonary disease (COPD), chronic bronchitis, emphysema, or combinations thereof.

14. The method of any one of embodiments 1-13, wherein the subject is administered an additional therapy.

15. The method of embodiment 14, wherein the additional therapy is a sodium channel blocker, calcium current inhibitor, gamma-aminobutyric (GABA) enhancer, glutamate receptor antagonists, carbonic anhydrase inhibitor, hormone, an N-methyl-D-aspartate (NMDA) receptor antagonist, synaptic vesicle glycoprotein 2A (SV2A) ligand, α-amino-3-hydroxy-5-methyl-4-isoxazolepropionic acid (AMPA)/Kainate receptor antagonist, or combinations thereof.

16. The method of embodiment 15, wherein the additional therapy is a sodium channel blocker, and the sodium channel blocker is phenytoin, fosphenytoin, carbamazepine, lamotrigine, or valproate.

17. The method of embodiment 15, wherein the additional therapy is a calcium channel antagonist, and wherein the calcium current inhibitor is ethosuximide or valproate.

18. The method of embodiment 15, wherein the additional therapy is a GABA enhancer, and wherein the GABA enhancer is a benzodiazepine, barbiturate, progabide, progesterone, ganaxolone, vigabatrin, tiagabine, gabapentin, or valproate.

19. The method of embodiment 15, wherein the additional therapy is an NMDA receptor antagonist, and the NMDA receptor antagonist is felbamate or levetiracetam.

20. The method of embodiment 15, wherein the additional therapy is an AMPA/Kainate receptor antagonist, and wherein the AMPA/Kainate receptor antagonist is topiramate.

21. The method of any one of embodiments 14-20, wherein the administering of an additional therapy is after administration of psilocybin.

22. The method of any one of embodiments 14-20, wherein the administering of an additional therapy is concurrent with administration of psilocybin.

23. The method of embodiment 14-20, wherein the administering of an additional therapy is prior to administration of psilocybin.

24. The method of any one of embodiments 1-23, wherein after treating the subject in need thereof experiences a reduction in seizures per month of between about 15% and about 100%.

25. The method of any one of embodiments 1-24, wherein after treating the subject in need thereof experiences a reduction in seizure duration of between about 15% and about 100%.

26. The method of any one of embodiments 1-25, wherein the subject has no prior psilocybin exposure.

27. The method of any one of embodiments 1-25, wherein the subject has prior psilocybin exposure.

28. The method of any one of embodiments 1-27 wherein the subject is a mammal.

29. The method of embodiment 28, wherein the subject is a human.

30. The method of any of embodiments 1-29, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

31. The method of embodiment 30, wherein the crystalline psilocybin comprises at least 95% by weight of Polymorph A.

32. The method of embodiment 30 or 31, wherein the crystalline psilocybin has a chemical purity of greater than 97% by HPLC, and no single impurity of greater than 1%.

33. The method of any of embodiments 1-29, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

34. The method of embodiment 33, wherein the highly pure crystalline psilocybin comprises at least 90% by weight of Polymorph A.

35. The method of embodiment 33, wherein the highly pure crystalline psilocybin comprises at least 95% by weight of Polymorph A.

36. The method of any one of embodiments 30-35, wherein the highly pure crystalline psilocybin is further characterized having either: (i) a water content of <0.5% w/w; or (ii) <0.5% w/w loss in the TGA thermogram between 25° C. and 200° C.

37. The method of any of embodiments 30-36, wherein the highly pure crystalline psilocybin is further characterized by an endothermic event in a DSC thermogram having a first onset temperature of between 145° C. and 155° C. and a second onset temperature of between 205 and 220° C.

38. The method of any one of embodiments 30-37, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

39. The method of any of embodiments 30-38, wherein the highly pure crystalline psilocybin has no single impurity of greater than 0.5%.

40. The method of any of embodiments 30-39, wherein the dosage form further comprises about 5 to 40 mg of the highly pure crystalline psilocybin.

41. The method of embodiment 40, wherein the dosage form comprises 5 mg of highly pure crystalline psilocybin.

42. The method of embodiment 40, wherein the dosage form comprises about 10 mg of highly pure crystalline psilocybin.

43. The method of embodiment 40, wherein the dosage form comprises about 35 mg of highly pure crystalline psilocybin.

44. The method of any of embodiments 30-43, wherein the dosage form comprises silicified microcrystalline cellulose.

45. The method of embodiment 44, wherein the silicified microcrystalline cellulose has a particle size range from about 45 to 150 microns.

46. The method of any of embodiments 30-45, further comprising a mixture of two silicified microcrystalline cellulose variants wherein the first variant has a particle size from about 45 to 80 microns and the second variant has a particle size of about 90 to 150 microns.

47. The method of embodiment 46, wherein about 30% or less of the microcrystalline cellulose is the first variant having a particle size from about 45 to 80 microns and about 70% or more of the microcrystalline cellulose is the second variant having a particle size of about 90 to 150 microns.

48. The method of embodiment 46, wherein about 20% or less of the microcrystalline cellulose is the first variant having a particle size from about 45 to 80 microns and about 80% or more of the microcrystalline cellulose is the second variant having a particle size of about 90 to 150 microns.

49. The method of embodiment 46, wherein about 15% or less of the microcrystalline cellulose is the first variant having a particle size from about 45 to 80 microns and about 85% or more of the microcrystalline cellulose is the second variant having a particle size of about 90 to 150 microns.

50. The method of embodiment 46, wherein about 15% or less of the microcrystalline cellulose is the first variant having a particle size from about 45 to 80 microns and about 85% or more of the microcrystalline cellulose is the second variant having a particle size of about 90 to 150 microns.

51. The method of embodiment 50, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

52. The method of embodiment 50, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

53. The method any one of embodiments 30-52, wherein the dosage form is an oral dosage form.

54. The method embodiment 53, wherein the dosage form is a capsule.

55. The method embodiment 53, wherein the dosage form is a tablet.

56. The method of any one of embodiments 1-55, wherein at least one dose of psilocybin is administered to the subject.

57. The method of embodiment 56, wherein the at least dose of psilocybin is in the range of about 0.1 mg to about 100 mg.

58. The method of embodiment 57, wherein the dose of psilocybin is about 1 mg. 59. The method of embodiment 57, wherein the dose of psilocybin is about 10 mg.

60. The method of embodiment 57, wherein the dose of psilocybin is about 25 mg.

61. The method of any one of embodiments 1-60, wherein more than one dose of psilocybin is administered to the subject.

62. The method of embodiment 61, wherein at least two doses of psilocybin are administered to the subject.

63. The method of any one of embodiments 61-62, wherein the psilocybin is administered once per day.

64. The method of any one of embodiments 61-62, wherein the psilocybin is administered at least once per week.

65. The method of any one of embodiments 61-62, wherein the psilocybin is administered at least twice per week.

66. The method of any one of embodiments 61-62, wherein the psilocybin is administered at least once per month.

67. The method of any one of embodiments 61-62, wherein the psilocybin is administered at least twice per month.

68. The method of any one of embodiments 61-62, wherein the psilocybin is administered at least once every three months.

69. The method of any one of embodiments 61-62, wherein the psilocybin is administered at least once every six months.

70. The method of any one of embodiments 61-62, wherein the psilocybin is administered at least once every 12 months.

71. The method of any one of embodiments 61-70, wherein each dose of psilocybin administered is in the range of about 0.1 mg to about 100 mg.

72. The method of embodiment 71, wherein each dose of psilocybin administered is about 1 mg.

73. The method of embodiment 71, wherein each dose of psilocybin administered is about 10 mg.

74. The method of embodiment 71, wherein each dose of psilocybin administered is about 25 mg.

75. The method of any one of embodiments 56-74, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

76. The method of embodiment 75, wherein the psilocybin is administered orally.

77. The method of any one of embodiments 1-76, wherein the subject participates in at least one psychological support session before administration of the psilocybin.

78. The method of embodiment 77, wherein the subject participates in at least three psychological support sessions before administration of the psilocybin.

79. The method of any one of embodiments 77-78, wherein the at least one therapeutic intention is discussed during the psychological support session.

80. The method of any one of embodiments 77-79, wherein self-directed inquiry and experiential processing are practiced during the psychological support session.

81. The method of any one of embodiments 77-80, wherein the subject participates in at least one psychological support session after administration of the psilocybin.

82. The method of embodiment 81, wherein the subject participates in at least three psychological support sessions after administration of the psilocybin.

83. The method of any one of embodiments 76-82, wherein the psilocybin is administered to the subject in a room with a substantially non-clinical appearance.

84. The method of embodiment 83, wherein the room comprises soft furniture.

85. The method of embodiment 83, wherein the room is decorated using muted colors.

86. The method of embodiment 83, wherein the room comprises a high-resolution sound system.

87. The method of any one of embodiments 83-86, wherein the room comprises a bed or a couch.

88. The method of embodiment 87, wherein the subject lies in the bed or on the couch for approximately 4-8 hours, or a substantial fraction thereof, after administration of the psilocybin.

89. The method of any one of embodiments 76-88, wherein the subject listens to music for approximately 4-8 hours, or a substantial fraction thereof, after administration of the psilocybin.

90. The method of any one of embodiments 76-88, wherein the subject wears an eye mask for approximately 4-8 hours, or a substantial fraction thereof, after administration of the psilocybin.

91. The method of any one of embodiments 1-90, wherein a therapist provides psychological support to the subject for approximately 4-8 hours after administration of the psilocybin.

92. The method of embodiment 91, wherein the therapist uses guided imagery to calm the subject and/or focus the subject's attention.

93. The method of embodiment 91, wherein the therapist provides reassuring physical contact with the subject.

94. The method of embodiment 93, wherein the therapist holds the hand, arm, or shoulder of the subject.

95. The method of embodiment 91, wherein the therapist encourages the subject to perform self-directed inquiry and experiential processing.

96. The method of embodiment 91, wherein the therapist reminds the subject of at least one therapeutic intention.

97. The method of embodiment 91, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

98. The method of embodiment 91, wherein the therapist does not initiate conversation with the subject.

99. The method of embodiment 91, wherein the therapist responds to the subject if the subject initiates conversation.

Inflammation

1. A method of reducing inflammation in a subject in need thereof, the method comprising administering to the subject a therapeutically effective amount of psilocybin or an active metabolite thereof.

2. The method of embodiment 1, wherein the inflammation is acute.

3. The method of embodiment 1, wherein the inflammation is chronic.

4. The method of embodiment 1, wherein the inflammation is systemic.

5. The method of embodiment 1, wherein the inflammation is local.

6. The method of any one of embodiments 1-5, wherein administration of the psilocybin reduces the duration of the inflammation.

7. The method of any one of embodiments 1-6, wherein administration of the psilocybin reduces the level of at least one inflammatory biomarker or indicator in a biological sample of the subject.

8. The method of embodiment 7, wherein the inflammatory biomarker is a pro-inflammatory cytokine.

9. The method of embodiment 8, wherein the pro-inflammatory cytokine is interleukin-1 (IL-1), tumor necrosis factor (TNF), gamma-interferon (IFN-γ), IL-1β, IL-6, IL-10, IL-12, IL-18, granulocyte-macrophage colony stimulating factor (GMCSF), C—X—C chemokine ligand 1 (CXCL1) or CXCL9.

10. The method of embodiment 8, wherein the pro-inflammatory cytokine is TNF-α, IL-6, IL-1β, or IL-10.

11. The method of embodiment 8, wherein the pro-inflammatory cytokine is CXCL1 or CXCL9.

12. The method of embodiment 7, wherein the inflammatory biomarker is C-Reactive Protein (CRP), homocysteine, or hemoglobin A1c (HbA1c).

13. The method of embodiment 7, wherein the inflammatory indicator is plasma viscosity.

14. The method of any one of embodiments 7-13, wherein the biological sample is a blood sample.

15. The method of embodiment 14, wherein the blood sample is a serum sample or a plasma sample.

16. The method of any one of embodiments 7-13, wherein the biological sample is a cerebral spinal fluid (CSF) sample.

17. The method of any one of embodiments 7-16, wherein the level of the at least one inflammatory biomarker or indicator is reduced within 24 hours of administration of the psilocybin.

18. The method of any one of embodiments 7-16, wherein the level of the at least one inflammatory biomarker or indicator is reduced within 1 week of administration of the psilocybin.

19. The method of any one of embodiments 7-18, wherein the level of the at least one inflammatory biomarker or indicator is reduced for a period of at least 1 month after administration of the psilocybin.

20. The method of any one of embodiments 7-18, wherein the level of the at least one inflammatory biomarker or indicator is reduced for a period of at least 3 months after administration of the psilocybin.

21. The method of any one of embodiments 7-18, wherein the level of the at least one inflammatory biomarker or indicator is reduced for a period of at least 12 months after administration of the psilocybin 22. The method of any one of embodiments 1-21, wherein administration of the psilocybin reduces at least one of fever, pain, skin redness, or swelling, or increases functionality in the subject.

23. The method of embodiment 22, wherein the fever, pain, skin redness, or swelling is reduced, or the functionality is increased within 24 hours of administration of the psilocybin.

24. The method of embodiment 22, wherein the fever, pain, skin redness, or swelling is reduced, or the function is increased within 1 week of administration of the psilocybin.

25. The method of embodiment 22, wherein the fever, pain, skin redness, or swelling is reduced, or functionality is increased for a period of at least 1 month after administration of the psilocybin.

26. The method of embodiment 22, wherein the fever, pain, skin redness, or swelling is reduced, or the functionality is increased for a period of at least 3 months after administration of the psilocybin.

27. The method of embodiment 22, wherein the fever, pain, skin redness, or swelling is reduced, or the function is increased for a period of at least 12 months after administration of the psilocybin.

28. The method of any one of embodiments 1-27, wherein no other treatment is administered to the subject to reduce inflammation after administration of the psilocybin.

29. The method of any one of embodiments 1-27, wherein the method further comprises administering to the subject at least one additional therapeutic to reduce inflammation.

30. The method of embodiment 29, wherein the at least one additional therapeutic is a non-steroidal anti-inflammatory drug (NSAID).

31. The method of embodiment 30, wherein the NSAID is ibuprofen, aspirin, or naproxen.

32. The method of embodiment 29, wherein the at least one additional therapeutic is a corticosteroid.

33. The method of embodiment 32, wherein the corticosteroid is cortisone, prednisone, or methylprednisolone.

34. The method of embodiment 29, wherein the at least one additional therapeutic is metformin, a statin, methotrexate, or an antibody.

35. The method of any one of embodiments 29-34, wherein the at least one additional therapeutic is administered prior to administration of psilocybin.

36. The method of any one of embodiments 29-34, wherein the at least one additional therapeutic is administered after administration of psilocybin.

37. The method of any one of embodiments 29-34, wherein the at least one additional therapeutic is administered on the same day as the psilocybin.

38. The method of any one of embodiments 1-37, wherein the subject has no prior psilocybin exposure.

39. The method of any one of embodiments 1-37, wherein the subject has prior psilocybin exposure.

40. The method of any one of embodiments 1-39, wherein the subject has asthma, celiac disease, hepatitis, allergy, arthritis, Inflammatory Bowel Disease (IBD), or dermatitis.

41. The method of any one of embodiments 1-40, wherein the subject has Alzheimer's Disease, Parkinson's Disease, Amyotrophic Lateral Sclerosis (ALS) or Multiple Sclerosis (MS).

42. The method of any one of embodiments 1-40, wherein reducing inflammation in the subject treats or prevents one or more of allergy, asthma, Alzheimer's disease, diabetes, cardiovascular disease, sepsis, arthritis, joint disease, inflammatory bowel disease, or dermatitis in the subject.

43. The method of any one of embodiments 1-40, wherein reducing inflammation in the subject treats or prevents one or more of chronic pain, neuropathic pain, and inflammatory pain in the subject.

44. The method of any one of embodiments 1-40, wherein reducing inflammation in the subject treats or prevents a mood disorder in the subject.

45. The method of embodiment 44, wherein the mood disorder is depression.

46. The method of any one of embodiments 1-45 wherein the subject is a mammal.

47. The method of embodiment 46, wherein the subject is a human.

48. The method of any of embodiments 1-47, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

49. The method of embodiment 48, wherein the crystalline psilocybin comprises at least 95% by weight of Polymorph A.

50. The method of embodiment 48 or 49, wherein the crystalline psilocybin has a chemical purity of greater than 97% by HPLC, and no single impurity of greater than 1%.

51. The method of any of embodiments 1-47, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

52. The method of embodiment 51, wherein the highly pure crystalline psilocybin comprises at least 90% by weight of Polymorph A.

53. The method of embodiment 52, wherein the highly pure crystalline psilocybin comprises at least 95% by weight of Polymorph A.

54. The method of any one of embodiments 48-53, wherein the highly pure crystalline psilocybin is further characterized having either: (i) a water content of <0.5% w/w; or (ii) <0.5% w/w loss in the TGA thermogram between 25° C. and 200° C.

55. The method of any of embodiments 48-54, wherein the highly pure crystalline psilocybin is further characterized by an endothermic event in a DSC thermogram having a first onset temperature of between 145° C. and 155° C. and a second onset temperature of between 205 and 220° C.

56. The method of any one of embodiments 48-55, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

57. The method of any of embodiments 58-56, wherein the highly pure crystalline psilocybin has no single impurity of greater than 0.5%.

58. The method of any of embodiments 48-57, wherein the dosage form further comprises about 5 to 40 mg of the highly pure crystalline psilocybin.

59. The method of embodiment 58, wherein the dosage form comprises 5 mg of highly pure crystalline psilocybin.

60. The method of embodiment 58, wherein the dosage form comprises about 10 mg of highly pure crystalline psilocybin.

61. The method of embodiment 58, wherein the dosage form comprises about 35 mg of highly pure crystalline psilocybin.

62. The method of any of embodiments 48-61, wherein the dosage form comprises silicified microcrystalline cellulose.

63. The method of embodiment 62, wherein the silicified microcrystalline cellulose has a particle size range from about 45 to 150 microns.

64. The method of any of embodiments 48-63, further comprising a mixture of two silicified microcrystalline cellulose variants wherein the first variant has a particle size from about 45 to 80 microns and the second variant has a particle size of about 90 to 150 microns.

65. The method of embodiment 64, wherein about 30% or less of the microcrystalline cellulose is the first variant having a particle size from about 45 to 80 microns and about 70% or more of the microcrystalline cellulose is the second variant having a particle size of about 90 to 150 microns.

66. The method of embodiment 64, wherein about 20% or less of the microcrystalline cellulose is the first variant having a particle size from about 45 to 80 microns and about 80% or more of the microcrystalline cellulose is the second variant having a particle size of about 90 to 150 microns.

67. The method of embodiment 64, wherein about 15% or less of the microcrystalline cellulose is the first variant having a particle size from about 45 to 80 microns and about 85% or more of the microcrystalline cellulose is the second variant having a particle size of about 90 to 150 microns.

68. The method of embodiment 64, wherein about 15% or less of the microcrystalline cellulose is the first variant having a particle size from about 45 to 80 microns and about 85% or more of the microcrystalline cellulose is the second variant having a particle size of about 90 to 150 microns.

69. The method of embodiment 68, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

70. The method of embodiment 68, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

71. The method any one of embodiments 48-70, wherein the dosage form is an oral dosage form.

72. The method embodiment 71, wherein the dosage form is a capsule.

73. The method embodiment 71, wherein the dosage form is a tablet.

74. The method of any one of embodiments 1-73, wherein at least one dose of psilocybin is administered to the subject.

75. The method of embodiment 74, wherein the at least dose of psilocybin is in the range of about 0.1 mg to about 100 mg.

76. The method of embodiment 75, wherein the dose of psilocybin is about 1 mg. 77. The method of embodiment 75, wherein the dose of psilocybin is about 10 mg.

78. The method of embodiment 75, wherein the dose of psilocybin is about 25 mg.

79. The method of any one of embodiments 1-73, wherein more than one dose of psilocybin is administered to the subject.

80. The method of embodiment 79, wherein at least two doses of psilocybin are administered to the subject.

81. The method of any one of embodiments 79-80, wherein the psilocybin is administered once per day.

82. The method of any one of embodiments 79-80, wherein the psilocybin is administered at least once per week.

83. The method of any one of embodiments 79-80, wherein the psilocybin is administered at least twice per week.

84. The method of any one of embodiments 79-80, wherein the psilocybin is administered at least once per month.

85. The method of any one of embodiments 79-80, wherein the psilocybin is administered at least twice per month.

86. The method of any one of embodiments 79-80, wherein the psilocybin is administered at least once every three months.

87. The method of any one of embodiments 79-80, wherein the psilocybin is administered at least once every six months.

88. The method of any one of embodiments 79-80, wherein the psilocybin is administered at least once every 12 months.

89. The method of any one of embodiments 79-88, wherein each dose of psilocybin administered is in the range of about 0.1 mg to about 100 mg.

90. The method of embodiment 89, wherein each dose of psilocybin administered is about 1 mg.

91. The method of embodiment 89, wherein each dose of psilocybin administered is about 10 mg.

92. The method of embodiment 89, wherein each dose of psilocybin administered is about 25 mg.

93. The method of any one of embodiments 74-93, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

94. The method of embodiment 93, wherein the psilocybin is administered orally.

95. The method of any one of embodiments 1-94, wherein the subject participates in at least one psychological support session before administration of the psilocybin.

96. The method of embodiment 95, wherein the subject participates in at least three psychological support sessions before administration of the psilocybin.

97. The method of any one of embodiments 95-96, wherein the at least one therapeutic intention is discussed during the psychological support session.

98. The method of any one of embodiments 95-97, wherein self-directed inquiry and experiential processing are practiced during the psychological support session.

99. The method of any one of embodiments 95-98, wherein the subject participates in at least one psychological support session after administration of the psilocybin.

100. The method of embodiment 99, wherein the subject participates in at least three psychological support sessions after administration of the psilocybin.

101. The method of any one of embodiments 95-100, wherein the psilocybin is administered to the subject in a room with a substantially non-clinical appearance.

102. The method of embodiment 101, wherein the room comprises soft furniture.

103. The method of embodiment 101, wherein the room is decorated using muted colors.

104. The method of embodiment 101, wherein the room comprises a high-resolution sound system.

105. The method of any one of embodiments 101-104, wherein the room comprises a bed or a couch.

106. The method of embodiment 105, wherein the subject lies in the bed or on the couch for approximately 4-8 hours, or a substantial fraction thereof, after administration of the psilocybin.

107. The method of any one of embodiments 101-106, wherein the subject listens to music for approximately 4-8 hours, or a substantial fraction thereof, after administration of the psilocybin.

108. The method of any one of embodiments 101-107, wherein the subject wears an eye mask for approximately 4-8 hours, or a substantial fraction thereof, after administration of the psilocybin.

109. The method of any one of embodiments 101-108, wherein a therapist provides psychological support to the subject for approximately 4-8 hours after administration of the psilocybin.

110. The method of embodiment 109, wherein the therapist uses guided imagery to calm the subject and/or focus the subject's attention.

111. The method of embodiment 109, wherein the therapist provides reassuring physical contact with the subject.

112. The method of embodiment 111, wherein the therapist holds the hand, arm, or shoulder of the subject.

113. The method of embodiment 109, wherein the therapist encourages the subject to perform self-directed inquiry and experiential processing.

114. The method of embodiment 109, wherein the therapist reminds the subject of at least one therapeutic intention.

115. The method of embodiment 109, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

116. The method of embodiment 109, wherein the therapist does not initiate conversation with the subject.

117. The method of embodiment 109, wherein the therapist responds to the subject if the subject initiates conversation.

Pain

1. A method of treating chronic pain in a subject in need thereof, the method comprising administering to the subject a therapeutically effective amount of psilocybin or an active metabolite thereof.

2. The method of embodiment 1, wherein chronic pain is caused by a peripheral neuropathic pain condition.

3. The method of embodiment 2, wherein the peripheral neuropathic pain condition is characterized by allodynia.

4. The method of embodiment 2, wherein the peripheral neuropathic pain condition is characterized by post-herpetic neuralgia.

5. The method of embodiment 1, wherein the chronic pain is a phantom limb pain.

6. The method of embodiment 1, wherein the chronic pain is caused by a central neuropathic pain condition.

7. The method of embodiment 6, wherein the central neuropathic pain condition is brachial plexus injury.

8. The method of embodiment 1, wherein the chronic pain is caused by cancer or cancer treatment.

9. The method of any one of embodiments 1-8, wherein administering psilocybin reduces the frequency, duration, or severity of pain in the subject.

10. The method of embodiment 9, wherein the reduction in frequency, duration, or severity of pain is measured according to one or more of the following scales: Verbal rating scale, Behavioral Rating Scale, Bodily pain subscale (SF-36 Health Survey Questionnaire), Gracely Box Scale, Colored Analogue Scale, EQSD three-level pain subscale, FACES, Faces Pain Scale, Facial Affective Scale, Geriatric Painful Events Inventory, Numeric Rating Scale, Pain thermometer, Verbal Descriptor Scale, Rand Coop Chart, Visual Analog Scale, Brief Pain Inventory, Geriatric Pain Measure, McCaffery and Pasero's Initial Pain Assessment Tool, McGill Pain Questionnaire, Total Pain Index, Pain Behavior Checklist, West Haven-Yale Multidimensional Pain Inventory, Leeds Assessment of Neuropathic Symptoms and Signs, Douleur Neuropathique en 4, or painDETECT.

11. The method of any one of embodiments 9-10, wherein the frequency, duration, or severity of pain in the subject is improved within 24 hours of administration of the psilocybin.

12. The method of any one of embodiments 9-10, wherein the frequency, duration, or severity of pain in the subject is improved within 1 week of administration of the psilocybin.

13. The method of any one of embodiments 9-12, wherein the frequency, duration, or severity of pain in the subject is improved for a period of at least 1 month after administration of the psilocybin.

14. The method of any one of embodiments 9-12, wherein the frequency, duration, or severity of pain in the subject is improved for a period of at least 3 months after administration of the psilocybin.

15. The method of any one of embodiments 9-12, wherein the frequency, duration, or severity of pain in the subject is improved for a period of at least 12 months after administration of the psilocybin.

16. The method of any one of embodiments 1-15, wherein no other treatment is administered to the subject to treat the chronic pain after administration of the psilocybin.

17. The method of any one of embodiments 1-15, wherein the method further comprises administering to the subject at least one additional therapeutic.

18. The method of embodiment 17, wherein the at least one additional therapeutic is administered prior to administration of psilocybin.

19. The method of embodiment 17, wherein the at least one additional therapeutic is administered after administration of psilocybin.

20. The method of embodiment 17, wherein the at least one additional therapeutic is administered on the same day as the psilocybin.

21. The method of any one of embodiments 17-20, wherein the at least one additional therapeutic is a tricyclic antidepressant or a serotonin-noradrenaline reuptake inhibitor (SSRI).

22. The method of any one of embodiments 17-20, wherein the at least one additional therapeutic is pregabalin or gabapentin.

23. The method of any one of embodiments 17-20, wherein the at least one additional therapeutic is lidocaine, capsaicin, tramadol, botulinum toxin A, oxycodone, morphine, fentanyl, a cannabinoid, ketamine, acetaminophen, a nonsteroidial anti-inflammatory drug, an opioid, calcitonin, or a NMDA receptor antagonist.

24. The method of any one of embodiments 1-23, wherein the subject has no prior psilocybin exposure.

25. The method of any one of embodiments 1-23, wherein the subject has prior psilocybin exposure.

26. The method of any one of embodiments 1-25, wherein administering the psilocybin also ameliorates one or more conditions comorbid with the chronic pain.

27. The method of embodiment 26, wherein the condition comorbid with the chronic pain is a mood disorder.

28. The method of embodiment 27, wherein the mood disorder is depression.

29. The method of embodiment 26, wherein the condition comorbid with the chronic pain is a substance use disorder.

30. The method of embodiment 26, wherein the condition comorbid with the chronic pain is anxiety, sleep disturbances, stress, or fatigue.

31. The method of any one of embodiments 1-30 wherein the subject is a mammal.

32. The method of embodiment 31, wherein the subject is a human.

33. The method of any of embodiments 1-32, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

34. The method of embodiment 33, wherein the crystalline psilocybin comprises at least 95% by weight of Polymorph A.

35. The method of embodiment 33 or 34, wherein the crystalline psilocybin has a chemical purity of greater than 97% by HPLC, and no single impurity of greater than 1%.

36. The method of any of embodiments 1-32, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

37. The method of embodiment 36, wherein the highly pure crystalline psilocybin comprises at least 90% by weight of Polymorph A.

38. The method of embodiment 36, wherein the highly pure crystalline psilocybin comprises at least 95% by weight of Polymorph A.

39. The method of any one of embodiments 33-38, wherein the highly pure crystalline psilocybin is further characterized having either: (i) a water content of <0.5% w/w; or (ii) <0.5% w/w loss in the TGA thermogram between 25° C. and 200° C.

40. The method of any of embodiments 33-38, wherein the highly pure crystalline psilocybin is further characterized by an endothermic event in a DSC thermogram having a first onset temperature of between 145° C. and 155° C. and a second onset temperature of between 205 and 220° C.

41. The method of any one of embodiments 33-38, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

42. The method of any of embodiments 33-41, wherein the highly pure crystalline psilocybin has no single impurity of greater than 0.5%.

43. The method of any of embodiments 33-42, wherein the dosage form further comprises about 5 to 40 mg of the highly pure crystalline psilocybin.

44. The method of embodiment 43, wherein the dosage form comprises 5 mg of highly pure crystalline psilocybin.

45. The method of embodiment 43, wherein the dosage form comprises about 10 mg of highly pure crystalline psilocybin.

46. The method of embodiment 43, wherein the dosage form comprises about 35 mg of highly pure crystalline psilocybin.

47. The method of any of embodiments 33-46, wherein the dosage form comprises silicified microcrystalline cellulose.

48. The method of embodiment 47, wherein the silicified microcrystalline cellulose has a particle size range from about 45 to 150 microns.

49. The method of any of embodiments 33-48, further comprising a mixture of two silicified microcrystalline cellulose variants wherein the first variant has a particle size from about 45 to 80 microns and the second variant has a particle size of about 90 to 150 microns.

50. The method of embodiment 49, wherein about 30% or less of the microcrystalline cellulose is the first variant having a particle size from about 45 to 80 microns and about 70% or more of the microcrystalline cellulose is the second variant having a particle size of about 90 to 150 microns.

51. The method of embodiment 49, wherein about 20% or less of the microcrystalline cellulose is the first variant having a particle size from about 45 to 80 microns and about 80% or more of the microcrystalline cellulose is the second variant having a particle size of about 90 to 150 microns.

52. The method of embodiment 49, wherein about 15% or less of the microcrystalline cellulose is the first variant having a particle size from about 45 to 80 microns and about 85% or more of the microcrystalline cellulose is the second variant having a particle size of about 90 to 150 microns.

53. The method of embodiment 49, wherein about 15% or less of the microcrystalline cellulose is the first variant having a particle size from about 45 to 80 microns and about 85% or more of the microcrystalline cellulose is the second variant having a particle size of about 90 to 150 microns.

54. The method of embodiment 53, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

55. The method of embodiment 53, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

56. The method any one of embodiments 33-55, wherein the dosage form is an oral dosage form.

57. The method embodiment 56, wherein the dosage form is a capsule.

58. The method embodiment 56, wherein the dosage form is a tablet.

59. The method of any one of embodiments 1-58, wherein at least one dose of psilocybin is administered to the subject.

60. The method of embodiment 59, wherein the at least dose of psilocybin is in the range of about 0.1 mg to about 100 mg.

61. The method of embodiment 75, wherein the dose of psilocybin is about 1 mg.

62. The method of embodiment 75, wherein the dose of psilocybin is about 10 mg.

63. The method of embodiment 75, wherein the dose of psilocybin is about 25 mg.

64. The method of any one of embodiments 1-58, wherein more than one dose of psilocybin is administered to the subject.

65. The method of embodiment 64, wherein at least two doses of psilocybin are administered to the subject.

66. The method of any one of embodiments 64-65, wherein the psilocybin is administered once per day.

67. The method of any one of embodiments 64-65, wherein the psilocybin is administered at least once per week.

68. The method of any one of embodiments 64-65, wherein the psilocybin is administered at least twice per week.

69. The method of any one of embodiments 64-65, wherein the psilocybin is administered at least once per month.

70. The method of any one of embodiments 64-65, wherein the psilocybin is administered at least twice per month.

71. The method of any one of embodiments 64-65, wherein the psilocybin is administered at least once every three months.

72. The method of any one of embodiments 64-65, wherein the psilocybin is administered at least once every six months.

73. The method of any one of embodiments 64-65, wherein the psilocybin is administered at least once every 12 months.

74. The method of any one of embodiments 64-73, wherein each dose of psilocybin administered is in the range of about 0.1 mg to about 100 mg.

75. The method of embodiment 74, wherein each dose of psilocybin administered is about 1 mg.

76. The method of embodiment 74, wherein each dose of psilocybin administered is about 10 mg.

77. The method of embodiment 74, wherein each dose of psilocybin administered is about 25 mg.

78. The method of any one of embodiments 1-77, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

79. The method of embodiment 78, wherein the psilocybin is administered orally.

80. The method of any one of embodiments 1-79, wherein the subject participates in at least one psychological support session before administration of the psilocybin.

81. The method of embodiment 80, wherein the subject participates in at least three psychological support sessions before administration of the psilocybin.

82. The method of any one of embodiments 80-81, wherein the at least one therapeutic intention is discussed during the psychological support session.

83. The method of any one of embodiments 80-82, wherein self-directed inquiry and experiential processing are practiced during the psychological support session.

84. The method of any one of embodiments 1-83, wherein the subject participates in at least one psychological support session after administration of the psilocybin.

85. The method of embodiment 84, wherein the subject participates in at least three psychological support sessions after administration of the psilocybin.

86. The method of any one of embodiments 80-85, wherein the psilocybin is administered to the subject in a room with a substantially non-clinical appearance.

87. The method of embodiment 86, wherein the room comprises soft furniture.

88. The method of embodiment 86, wherein the room is decorated using muted colors.

89. The method of embodiment 86, wherein the room comprises a high-resolution sound system.

90. The method of any one of embodiments 86-89, wherein the room comprises a bed or a couch.

91. The method of embodiment 90, wherein the subject lies in the bed or on the couch for approximately 4-8 hours, or a substantial fraction thereof, after administration of the psilocybin.

92. The method of any one of embodiments 86-91, wherein the subject listens to music for approximately 4-8 hours, or a substantial fraction thereof, after administration of the psilocybin.

93. The method of any one of embodiments 86-92, wherein the subject wears an eye mask for approximately 4-8 hours, or a substantial fraction thereof, after administration of the psilocybin.

94. The method of any one of embodiments 1-93, wherein a therapist provides psychological support to the subject for approximately 4-8 hours after administration of the psilocybin.

95. The method of embodiment 94, wherein the therapist uses guided imagery to calm the subject and/or focus the subject's attention.

96. The method of embodiment 94, wherein the therapist provides reassuring physical contact with the subject.

97. The method of embodiment 96, wherein the therapist holds the hand, arm, or shoulder of the subject.

98. The method of embodiment 94, wherein the therapist encourages the subject to perform self-directed inquiry and experiential processing.

99. The method of embodiment 94, wherein the therapist reminds the subject of at least one therapeutic intention.

100. The method of embodiment 94, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

101. The method of embodiment 94, wherein the therapist does not initiate conversation with the subject.

102. The method of embodiment 94, wherein the therapist responds to the subject if the subject initiates conversation.

ADHD

1. A method for treating attention-deficit hyperactivity disorder (ADHD) in a subject in need thereof, the method comprising administering to the subject a therapeutically effective amount of psilocybin or an active metabolite thereof.

2. The method of embodiment 1, wherein the active metabolite is psilocin.

3. The method of any one of embodiments 1-2, wherein the subject in need thereof has an attention-deficit hyperactivity disorder subtype selected from predominantly inattentive, predominantly hyperactive/impulsive, or combined presentation.

4. The method of embodiment 3, wherein the attention-deficit hyperactivity disorder subtype is predominantly inattentive.

5. The method of embodiment 3, wherein the attention-deficit hyperactivity disorder subtype is predominantly hyperactive/impulsive.

6. The method of embodiment 3, wherein the attention-deficit hyperactivity disorder subtype is combined presentation.

7. The method of any one of embodiments 1-6, wherein the subject has a comorbidity.

8. The method of embodiment 7, wherein the comorbidity is selected from oppositional defiant disorder, learning difficulties, depression, anxiety, bipolar disorder, substance use disorders, autism spectrum disorders, personality disorder, obsessive compulsive disorder, or combinations thereof.

9. The method of embodiment 8, wherein the comorbidity is oppositional defiant disorder.

10. The method of embodiment 8, wherein the comorbidity is anxiety.

11. The method of any one of embodiments 1-10, wherein the subject is administered an additional therapy.

12. The method of embodiment 11, wherein the additional therapy is a stimulant, a norepinephrine reuptake inhibitor, an α-adrenergic receptor agonist, a tricyclic antidepressant, modafinil, or combinations thereof.

13. The method of embodiment 12, wherein the additional therapy is a stimulant, and the stimulant is an amphetamine or methylphenidate.

14. The method of embodiment 11, wherein the additional therapy is a norepinephrine reuptake inhibitor, and the norepinephrine reuptake inhibitor is atomoxetine or reboxetine.

15. The method of any one of embodiments 11-14, wherein the administering of an additional therapy is prior to administration of psilocybin.

16. The method of any one of embodiments 11-14, wherein the administering of an additional therapy is after administration of psilocybin.

17. The method of any one of embodiments 11-14, wherein the administering of an additional therapy is concurrent with administration of psilocybin.

18. The method of embodiment 11-14, wherein the administering of an additional therapy is prior to administration of psilocybin.

19. The method of any one of embodiments 1-18, wherein after treating the subject in need thereof has a decreased ADHD Rating Scale V score.

20. The method of embodiment 19, wherein the decreased ADHD Rating Scale V score is observed within about one hour after psilocybin administration to about one year after psilocybin administration.

21. The method of embodiment 19, wherein the ADHD Rating Scale V score is decreased by between about 20% and about 100%.

22. The method of any one of embodiments 1-21, wherein the subject in need is a child.

23. The method of any one of embodiments 1-21, wherein the subject in need is an adult.

24. The method of any one of embodiments 1-21, wherein the subject in need is an adolescent.

25. The method of any one of embodiments 1-25, wherein the subject has no prior psilocybin exposure.

26. The method of any one of embodiments 1-25, wherein the subject has prior psilocybin exposure.

27. The method of any one of embodiments 1-26 wherein the subject is a mammal.

28. The method of embodiment 27, wherein the subject is a human.

29. The method of any of embodiments 1-28, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

30. The method of embodiment 29, wherein the crystalline psilocybin comprises at least 95% by weight of Polymorph A.

31. The method of embodiment 29 or 30, wherein the crystalline psilocybin has a chemical purity of greater than 97% by HPLC, and no single impurity of greater than 1%.

32. The method of any of embodiments 1-28, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

33. The method of embodiment 32, wherein the highly pure crystalline psilocybin comprises at least 90% by weight of Polymorph A.

34. The method of embodiment 32, wherein the highly pure crystalline psilocybin comprises at least 95% by weight of Polymorph A.

35. The method of any one of embodiments 29-34, wherein the highly pure crystalline psilocybin is further characterized having either: (i) a water content of <0.5% w/w; or (ii) <0.5% w/w loss in the TGA thermogram between 25° C. and 200° C.

36. The method of any of embodiments 29-35, wherein the highly pure crystalline psilocybin is further characterized by an endothermic event in a DSC thermogram having a first onset temperature of between 145° C. and 155° C. and a second onset temperature of between 205 and 220° C.

37. The method of any one of embodiments 29-36, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

38. The method of any of embodiments 29-37, wherein the highly pure crystalline psilocybin has no single impurity of greater than 0.5%.

39. The method of any of embodiments 29-38, wherein the dosage form further comprises about 5 to 40 mg of the highly pure crystalline psilocybin.

40. The method of embodiment 39, wherein the dosage form comprises 5 mg of highly pure crystalline psilocybin.

41. The method of embodiment 39, wherein the dosage form comprises about 10 mg of highly pure crystalline psilocybin.

42. The method of embodiment 39, wherein the dosage form comprises about 35 mg of highly pure crystalline psilocybin.

43. The method of any of embodiments 29-42, wherein the dosage form comprises silicified microcrystalline cellulose.

44. The method of embodiment 43, wherein the silicified microcrystalline cellulose has a particle size range from about 45 to 150 microns.

45. The method of any of embodiments 29-44, further comprising a mixture of two silicified microcrystalline cellulose variants wherein the first variant has a particle size from about 45 to 80 microns and the second variant has a particle size of about 90 to 150 microns.

46. The method of embodiment 45, wherein about 30% or less of the microcrystalline cellulose is the first variant having a particle size from about 45 to 80 microns and about 70% or more of the microcrystalline cellulose is the second variant having a particle size of about 90 to 150 microns.

47. The method of embodiment 45, wherein about 20% or less of the microcrystalline cellulose is the first variant having a particle size from about 45 to 80 microns and about 80% or more of the microcrystalline cellulose is the second variant having a particle size of about 90 to 150 microns.

48. The method of embodiment 45, wherein about 15% or less of the microcrystalline cellulose is the first variant having a particle size from about 45 to 80 microns and about 85% or more of the microcrystalline cellulose is the second variant having a particle size of about 90 to 150 microns.

49. The method of embodiment 45, wherein about 15% or less of the microcrystalline cellulose is the first variant having a particle size from about 45 to 80 microns and about 85% or more of the microcrystalline cellulose is the second variant having a particle size of about 90 to 150 microns.

50. The method of embodiment 49, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

51. The method of embodiment 49, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

52. The method any one of embodiments 29-51, wherein the dosage form is an oral dosage form.

53. The method embodiment 52, wherein the dosage form is a capsule.

54. The method embodiment 52, wherein the dosage form is a tablet.

55. The method of any one of embodiments 1-54, wherein at least one dose of psilocybin is administered to the subject.

56. The method of embodiment 55, wherein the at least dose of psilocybin is in the range of about 0.1 mg to about 100 mg.

57. The method of embodiment 56, wherein the dose of psilocybin is about 1 mg.

58. The method of embodiment 56, wherein the dose of psilocybin is about 10 mg.

59. The method of embodiment 56, wherein the dose of psilocybin is about 25 mg.

60. The method of any one of embodiments 1-59, wherein more than one dose of psilocybin is administered to the subject.

61. The method of embodiment 60, wherein at least two doses of psilocybin are administered to the subject.

62. The method of any one of embodiments 60-61, wherein the psilocybin is administered once per day.

63. The method of any one of embodiments 60-61, wherein the psilocybin is administered at least once per week.

64. The method of any one of embodiments 60-61, wherein the psilocybin is administered at least twice per week.

65. The method of any one of embodiments 60-61, wherein the psilocybin is administered at least once per month.

66. The method of any one of embodiments 60-61, wherein the psilocybin is administered at least twice per month.

67. The method of any one of embodiments 60-61, wherein the psilocybin is administered at least once every three months.

68. The method of any one of embodiments 60-61, wherein the psilocybin is administered at least once every six months.

69. The method of any one of embodiments 60-61, wherein the psilocybin is administered at least once every 12 months.

70. The method of any one of embodiments 60-69, wherein each dose of psilocybin administered is in the range of about 0.1 mg to about 100 mg.

71. The method of embodiment 70, wherein each dose of psilocybin administered is about 1 mg.

72. The method of embodiment 70, wherein each dose of psilocybin administered is about 10 mg.

73. The method of embodiment 70, wherein each dose of psilocybin administered is about 25 mg.

74. The method of any one of embodiments 55-73, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

75. The method of embodiment 74, wherein the psilocybin is administered orally.

76. The method of any one of embodiments 1-75, wherein the subject participates in at least one psychological support session before administration of the psilocybin.

77. The method of embodiment 76, wherein the subject participates in at least three psychological support sessions before administration of the psilocybin.

78. The method of any one of embodiments 76-77, wherein the at least one therapeutic intention is discussed during the psychological support session.

79. The method of any one of embodiments 76-78, wherein self-directed inquiry and experiential processing are practiced during the psychological support session.

80. The method of any one of embodiments 76-79, wherein the subject participates in at least one psychological support session after administration of the psilocybin.

81. The method of embodiment 80, wherein the subject participates in at least three psychological support sessions after administration of the psilocybin.

82. The method of any one of embodiments 75-81, wherein the psilocybin is administered to the subject in a room with a substantially non-clinical appearance.

83. The method of embodiment 82, wherein the room comprises soft furniture.

84. The method of embodiment 82, wherein the room is decorated using muted colors.

85. The method of embodiment 82, wherein the room comprises a high-resolution sound system.

86. The method of any one of embodiments 82-87, wherein the room comprises a bed or a couch.

87. The method of embodiment 86, wherein the subject lies in the bed or on the couch for approximately 4-8 hours, or a substantial fraction thereof, after administration of the psilocybin.

88. The method of any one of embodiments 75-87, wherein the subject listens to music for approximately 4-8 hours, or a substantial fraction thereof, after administration of the psilocybin.

89. The method of any one of embodiments 75-87, wherein the subject wears an eye mask for approximately 4-8 hours, or a substantial fraction thereof, after administration of the psilocybin.

90. The method of any one of embodiments 1-89, wherein a therapist provides psychological support to the subject for approximately 4-8 hours after administration of the psilocybin.

91. The method of embodiment 90, wherein the therapist uses guided imagery to calm the subject and/or focus the subject's attention.

92. The method of embodiment 90, wherein the therapist provides reassuring physical contact with the subject.

93. The method of embodiment 92, wherein the therapist holds the hand, arm, or shoulder of the subject.

94. The method of embodiment 90, wherein the therapist encourages the subject to perform self-directed inquiry and experiential processing.

95. The method of embodiment 90, wherein the therapist reminds the subject of at least one therapeutic intention.

96. The method of embodiment 90, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

97. The method of embodiment 90, wherein the therapist does not initiate conversation with the subject.

98. The method of embodiment 90, wherein the therapist responds to the subject if the subject initiates conversation.

Sleep-Wake Disorders

1. A method of treating one or more sleep-wake disorders in a subject in need thereof, the method comprising administering to the subject an effective amount of psilocybin or an active metabolite thereof.

2. The method of embodiment 1, wherein the sleep-wake disorder is insomnia, hypersomnolence, narcolepsy, cataplexy, idiopathic hypersomnia, sleep paralysis, hypnagogic hallucinations, hypnopompic hallucinations, a breathing-related sleep disorder, a circadian rhythm sleep-wake disorder, a non-24-hour sleep wake disorder, a non-rapid eye movement sleep arousal disorder, a nightmare disorder, a rapid eye movement sleep behavior disorder, restless leg syndrome, a medication-induced sleep disorder, or a substance-induced sleep disorder.

3. The method of embodiment 2, wherein the sleep-wake disorder is insomnia.

4. The method of embodiment 3, wherein the insomnia is chronic.

5. The method of embodiment 3, wherein the insomnia is short term.

6. The method of embodiment 2, wherein the sleep-wake disorder is hypersomnolence.

7. The method of embodiment 2, wherein the sleep wake disorder is narcolepsy.

8. The method of embodiment 7, wherein the narcolepsy is type 1 or type 2.

9. The method of embodiment 7, wherein the subject has excessive daytime sleepiness, cataplexy, sleep paralysis, hypnagogic hallucinations, hypnopompic hallucinations, or combinations thereof prior to treatment with psilocybin or an active metabolite thereof.

10. The method of embodiment 9, wherein the subject experiences an improvement in excessive daytime sleepiness, cataplexy, sleep paralysis, hypnagogic hallucinations, hypnopompic hallucinations or combinations thereof during treatment with psilocybin or an active metabolite thereof 11. The method of embodiment 9, wherein the subject experiences an improvement in excessive daytime sleepiness, cataplexy, sleep paralysis, hypnagogic hallucinations, hypnopompic hallucinations or combinations thereof after treatment with psilocybin or an active metabolite thereof 12. The method of embodiment 2, wherein the sleep-wake disorder is one or more breathing-related sleep disorders.

13. The method of embodiment 12, wherein the breathing-related sleep disorder is chronic snoring, upper airway resistance syndrome, sleep apnea, or obesity hypoventilation syndrome.

14. The method of embodiment 13, wherein the breathing-related sleep disorder is sleep apnea.

15. The method of embodiment 14, wherein the sleep apnea is central sleep apnea (CSA).

16. The method of embodiment 15, wherein the central sleep apnea is primary CSA, Cheyne-Stokes Breathing (CSB), high-altitude periodic breathing, CSA due to a medical condition without CSB, central sleep apnea due to a medication or substance, Treatment Emergent Central Apnea, or a combination thereof.

17. The method of any one of embodiments 12-16, wherein the subject experiences 1-30 fewer sleep apneas per hour of sleep after treatment with psilocybin.

18. The method of any one of embodiments 1-17, wherein the subject shows improvement in one or more of the following after treatment with psilocybin: mean sleep latency (MSL); multiple sleep latency test (MSLT); hypocretin (orexin) levels; sleep onset rapid eye movement periods (SOREMPs) in Epworth Sleepiness Scale (ESS); Maintenance of Wakefulness Test (MVVT) scores; cataplexy and cataplexy-like episodes; objective and subjective sleep latency; Total Sleep Time (TST); polysomnography; insomnia severity index (ISI) questionnaire; narcolepsy severity scale; Pittsburgh Sleep Quality Index score; Epworth Sleepiness Scale; Groningen Sleep Quality Questionnaire; Apnoea Hypopnea Index; and the Nightmare Experience Scale.

19. The method of embodiment 18, wherein the subject demonstrates an improvement in their MSLT after treatment with psilocybin as described herein as compared to their MSLT score prior to treatment.

20. The method of embodiment 19, wherein the subject demonstrates an improvement of 1-10 minutes MSLT after treatment with psilocybin as described herein as compared to their MSLT score prior to treatment.

21. The method of embodiment 19, wherein the subject demonstrates an improvement of 1-5 minutes MSLT after treatment with psilocybin as described herein as compared to their MSLT score prior to treatment.

22. The method of embodiment 19, wherein the subject demonstrates an improvement of 1-3 minutes MSLT after treatment with psilocybin as described herein as compared to their MSLT score prior to treatment.

23. The method of any one of embodiments 1-22, wherein the subject also suffers from one or more further indications, selected from mood disorders, affective disorders, neurodegenerative disorders, neurodevelopmental disorders, autism spectrum disorders, and substance abuse disorders.

24. The method of embodiment 23, wherein the further indication is major depressive disorder, mania, depression, anxiety, psychosis, attention deficit hyperactivity disorder (ADHD), Parkinson's disorder, autism, panic attacks, one or more social phobias, one or more eating disorders, and/or schizophrenia.

25. The method of any of embodiments 1-24, wherein the subject is administered at least one additional therapeutic agent.

26. The method of embodiment 25, wherein the therapeutic agent increases serotonergic activity.

27. The method of embodiment 26, wherein the therapeutic agent is a selective serotonin reuptake-inhibitor.

28. The method of any of embodiments 1-26, wherein the subject is receiving additional therapy.

29. The method of embodiment 29, wherein the additional therapy is cognitive behavioral therapy.

30. The method of any embodiments 1-29, wherein the active metabolite is psilocin.

31. The method of any one of embodiments 1-30 wherein the subject is a mammal.

32. The method of embodiment 31, wherein the subject is a human.

33. The method of any of embodiments 1-32, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

34. The method of embodiment 33, wherein the crystalline psilocybin comprises at least 95% by weight of Polymorph A.

35. The method of embodiment 33 or 34, wherein the crystalline psilocybin has a chemical purity of greater than 97% by HPLC, and no single impurity of greater than 1%.

36. The method of any of embodiments 1-32, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

37. The method of embodiment 36, wherein the highly pure crystalline psilocybin comprises at least 90% by weight of Polymorph A.

38. The method of embodiment 36, wherein the highly pure crystalline psilocybin comprises at least 95% by weight of Polymorph A.

39. The method of any one of embodiments 33-38, wherein the highly pure crystalline psilocybin is further characterized having either: (i) a water content of <0.5% w/w; or (ii) <0.5% w/w loss in the TGA thermogram between 25° C. and 200° C.

40. The method of any of embodiments 33-38, wherein the highly pure crystalline psilocybin is further characterized by an endothermic event in a DSC thermogram having a first onset temperature of between 145° C. and 155° C. and a second onset temperature of between 205 and 220° C.

41. The method of any one of embodiments 33-38, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

42. The method of any of embodiments 33-41, wherein the highly pure crystalline psilocybin has no single impurity of greater than 0.5%.

43. The method of any of embodiments 33-42, wherein the dosage form further comprises about 5 to 40 mg of the highly pure crystalline psilocybin.

44. The method of embodiment 43, wherein the dosage form comprises 5 mg of highly pure crystalline psilocybin.

45. The method of embodiment 43, wherein the dosage form comprises about 10 mg of highly pure crystalline psilocybin.

46. The method of embodiment 43, wherein the dosage form comprises about 35 mg of highly pure crystalline psilocybin.

47. The method of any of embodiments 33-46, wherein the dosage form comprises silicified microcrystalline cellulose.

48. The method of embodiment 47, wherein the silicified microcrystalline cellulose has a particle size range from about 45 to 150 microns.

49. The method of any of embodiments 33-48, further comprising a mixture of two silicified microcrystalline cellulose variants wherein the first variant has a particle size from about 45 to 80 microns and the second variant has a particle size of about 90 to 150 microns.

50. The method of embodiment 49, wherein about 30% or less of the microcrystalline cellulose is the first variant having a particle size from about 45 to 80 microns and about 70% or more of the microcrystalline cellulose is the second variant having a particle size of about 90 to 150 microns.

51. The method of embodiment 49, wherein about 20% or less of the microcrystalline cellulose is the first variant having a particle size from about 45 to 80 microns and about 80% or more of the microcrystalline cellulose is the second variant having a particle size of about 90 to 150 microns.

52. The method of embodiment 49, wherein about 15% or less of the microcrystalline cellulose is the first variant having a particle size from about 45 to 80 microns and about 85% or more of the microcrystalline cellulose is the second variant having a particle size of about 90 to 150 microns.

53. The method of embodiment 49, wherein about 15% or less of the microcrystalline cellulose is the first variant having a particle size from about 45 to 80 microns and about 85% or more of the microcrystalline cellulose is the second variant having a particle size of about 90 to 150 microns.

54. The method of embodiment 53, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

55. The method of embodiment 53, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

56. The method any one of embodiments 33-55, wherein the dosage form is an oral dosage form.

57. The method embodiment 56, wherein the dosage form is a capsule.

58. The method embodiment 56, wherein the dosage form is a tablet.

59. The method of any one of embodiments 1-58, wherein at least one dose of psilocybin is administered to the subject.

60. The method of embodiment 59, wherein the at least dose of psilocybin is in the range of about 0.1 mg to about 100 mg.

61. The method of embodiment 75, wherein the dose of psilocybin is about 1 mg.

62. The method of embodiment 75, wherein the dose of psilocybin is about 10 mg.

63. The method of embodiment 75, wherein the dose of psilocybin is about 25 mg.

64. The method of any one of embodiments 1-58, wherein more than one dose of psilocybin is administered to the subject.

65. The method of embodiment 64, wherein at least two doses of psilocybin are administered to the subject.

66. The method of any one of embodiments 64-65, wherein the psilocybin is administered once per day.

67. The method of any one of embodiments 64-65, wherein the psilocybin is administered at least once per week.

68. The method of any one of embodiments 64-65, wherein the psilocybin is administered at least twice per week.

69. The method of any one of embodiments 64-65, wherein the psilocybin is administered at least once per month.

70. The method of any one of embodiments 64-65, wherein the psilocybin is administered at least twice per month.

71. The method of any one of embodiments 64-65, wherein the psilocybin is administered at least once every three months.

72. The method of any one of embodiments 64-65, wherein the psilocybin is administered at least once every six months.

73. The method of any one of embodiments 64-65, wherein the psilocybin is administered at least once every 12 months.

74. The method of any one of embodiments 64-73, wherein each dose of psilocybin administered is in the range of about 0.1 mg to about 100 mg.

75. The method of embodiment 74, wherein each dose of psilocybin administered is about 1 mg.

76. The method of embodiment 74, wherein each dose of psilocybin administered is about 10 mg.

77. The method of embodiment 74, wherein each dose of psilocybin administered is about 25 mg. 78. The method of any one of embodiments 1-77, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

79. The method of embodiment 78, wherein the psilocybin is administered orally. 80. The method of any one of embodiments 1-79, wherein the subject participates in at least one psychological support session before administration of the psilocybin.

81. The method of embodiment 80, wherein the subject participates in at least three psychological support sessions before administration of the psilocybin.

82. The method of any one of embodiments 80-81, wherein the at least one therapeutic intention is discussed during the psychological support session.

83. The method of any one of embodiments 80-82, wherein self-directed inquiry and experiential processing are practiced during the psychological support session.

84. The method of any one of embodiments 1-83, wherein the subject participates in at least one psychological support session after administration of the psilocybin.

85. The method of embodiment 84, wherein the subject participates in at least three psychological support sessions after administration of the psilocybin.

86. The method of any one of embodiments 80-85, wherein the psilocybin is administered to the subject in a room with a substantially non-clinical appearance.

87. The method of embodiment 86, wherein the room comprises soft furniture.

88. The method of embodiment 86, wherein the room is decorated using muted colors.

89. The method of embodiment 86, wherein the room comprises a high-resolution sound system.

90. The method of any one of embodiments 86-89, wherein the room comprises a bed or a couch.

91. The method of embodiment 90, wherein the subject lies in the bed or on the couch for approximately 4-8 hours, or a substantial fraction thereof, after administration of the psilocybin.

92. The method of any one of embodiments 86-91, wherein the subject listens to music for approximately 4-8 hours, or a substantial fraction thereof, after administration of the psilocybin.

93. The method of any one of embodiments 86-92, wherein the subject wears an eye mask for approximately 4-8 hours, or a substantial fraction thereof, after administration of the psilocybin.

94. The method of any one of embodiments 1-93, wherein a therapist provides psychological support to the subject for approximately 4-8 hours after administration of the psilocybin.

95. The method of embodiment 94, wherein the therapist uses guided imagery to calm the subject and/or focus the subject's attention.

96. The method of embodiment 94, wherein the therapist provides reassuring physical contact with the subject.

97. The method of embodiment 96, wherein the therapist holds the hand, arm, or shoulder of the subject.

98. The method of embodiment 94, wherein the therapist encourages the subject to perform self-directed inquiry and experiential processing.

99. The method of embodiment 94, wherein the therapist reminds the subject of at least one therapeutic intention.

100. The method of embodiment 94, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

101. The method of embodiment 94, wherein the therapist does not initiate conversation with the subject.

102. The method of embodiment 94, wherein the therapist responds to the subject if the subject initiates conversation.
IBD 1. A method of treating Inflammatory Bowel Disease (IBD) in a subject in need thereof, the method comprising administering to the subject a therapeutically effective amount of psilocybin or an active metabolite thereof.

2. The method of embodiment 1, wherein the IBD is ulcerative colitis.

3. The method of embodiment 1, wherein the IBD is Crohn's disease.

4. The method of any one of embodiment 1-3, wherein at least one sign or symptom of IBD is improved following administration of the psilocybin or active metabolite thereof.

5. The method of embodiment 4, wherein the sign or symptom of IBD is diarrhea, fever, fatigue, abdominal pain and/or cramping, bloody stool, reduced appetite, or unintended weight loss.

6. The method of embodiment 4 or 5, wherein the improvement is verified by endoscopy.

7. The method of embodiment 4 or 5, wherein the improvement is verified by biopsy.

8. The method of any one of embodiments 1-7, wherein the administering causes the subject to have an improvement in the Mayo Score and/or the Ulcerative Colitis Activity Index (UCSAI).

9. The method of any one of embodiments 1-8, wherein the at least one sign or symptom of IBD is improved within 24 hours of administration of the psilocybin.

10. The method of any one of embodiments 1-8, wherein at least one sign or symptom of IBD is improved within 1 week of administration of the psilocybin.

11. The method of any one of embodiments 1-8, wherein the at least one sign or symptom of IBD is improved for a period of at least 1 month after administration of the psilocybin.

12. The method of any one of embodiments 1-8, wherein the at least one sign or symptom of IBD is improved for a period of at least 3 months after administration of the psilocybin.

13. The method of any one of embodiments 1-8, wherein the at least one sign or symptom of IBD is improved for a period of at least 12 months after administration of the psilocybin.

14. The method of any one of embodiments 1-13, wherein no other treatment is administered to the subject to treat IBD after administration of the psilocybin.

15. The method of any one of embodiments 1-13, wherein the method further comprises administering to the subject at least one additional therapeutic to treat IBD.

16. The method of embodiment 15, wherein the at least one additional therapeutic is administered prior to administration of psilocybin.

17. The method of embodiment 15, wherein the at least one additional therapeutic is administered after administration of psilocybin.

18. The method of embodiment 15, wherein the at least one additional therapeutic is administered on the same day as the psilocybin.

19. The method of any one of embodiments 1-18, wherein the subject has no prior psilocybin exposure.

20. The method of any one of embodiments 1-18, wherein the subject has prior psilocybin exposure.

21. The method of any one of embodiments 1-20, wherein the subject also has colon cancer.

22. The method of embodiment 21, wherein the subject is taking medication to treat the colon cancer.

23. The method of any one of embodiments 1-22 wherein the subject is a mammal.

24. The method of embodiment 23, wherein the subject is a human.

25. The method of any of embodiments 1-24, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

26. The method of embodiment 25, wherein the crystalline psilocybin comprises at least 95% by weight of Polymorph A.

27. The method of embodiment 25 or 26, wherein the crystalline psilocybin has a chemical purity of greater than 97% by HPLC, and no single impurity of greater than 1%.

28. The method of any of embodiments 1-24, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

29. The method of embodiment 28, wherein the highly pure crystalline psilocybin comprises at least 90% by weight of Polymorph A.

30. The method of embodiment 28, wherein the highly pure crystalline psilocybin comprises at least 95% by weight of Polymorph A.

31. The method of any one of embodiments 25-30, wherein the highly pure crystalline psilocybin is further characterized having either: (i) a water content of <0.5% w/w; or (ii) <0.5% w/w loss in the TGA thermogram between 25° C. and 200° C.

32. The method of any of embodiments 25-31, wherein the highly pure crystalline psilocybin is further characterized by an endothermic event in a DSC thermogram having a first onset temperature of between 145° C. and 155° C. and a second onset temperature of between 205 and 220° C.

33. The method of any one of embodiments 25-32, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

34. The method of any of embodiments 25-33, wherein the highly pure crystalline psilocybin has no single impurity of greater than 0.5%.

35. The method of any of embodiments 25-34, wherein the dosage form further comprises about 5 to 40 mg of the highly pure crystalline psilocybin.

36. The method of embodiment 35, wherein the dosage form comprises 5 mg of highly pure crystalline psilocybin.

37. The method of embodiment 36, wherein the dosage form comprises about 10 mg of highly pure crystalline psilocybin.

38. The method of embodiment 36, wherein the dosage form comprises about 35 mg of highly pure crystalline psilocybin.

39. The method of any of embodiments 25-38, wherein the dosage form comprises silicified microcrystalline cellulose.

40. The method of embodiment 39, wherein the silicified microcrystalline cellulose has a particle size range from about 45 to 150 microns.

41. The method of any of embodiments 25-40, further comprising a mixture of two silicified microcrystalline cellulose variants wherein the first variant has a particle size from about 45 to 80 microns and the second variant has a particle size of about 90 to 150 microns.

42. The method of embodiment 41, wherein about 30% or less of the microcrystalline cellulose is the first variant having a particle size from about 45 to 80 microns and about 70% or more of the microcrystalline cellulose is the second variant having a particle size of about 90 to 150 microns.

43. The method of embodiment 41, wherein about 20% or less of the microcrystalline cellulose is the first variant having a particle size from about 45 to 80 microns and about 80% or more of the microcrystalline cellulose is the second variant having a particle size of about 90 to 150 microns.

44. The method of embodiment 41, wherein about 15% or less of the microcrystalline cellulose is the first variant having a particle size from about 45 to 80 microns and about 85% or more of the microcrystalline cellulose is the second variant having a particle size of about 90 to 150 microns.

45. The method of embodiment 41, wherein about 15% or less of the microcrystalline cellulose is the first variant having a particle size from about 45 to 80 microns and about 85% or more of the microcrystalline cellulose is the second variant having a particle size of about 90 to 150 microns.

46. The method of embodiment 45, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

47. The method of embodiment 45, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

48. The method any one of embodiments 25-47, wherein the dosage form is an oral dosage form.

49. The method embodiment 48, wherein the dosage form is a capsule.

50. The method of embodiment 48, wherein the dosage form is a tablet.

51. The method of any one of embodiments 1-50, wherein at least one dose of psilocybin is administered to the subject.

52. The method of embodiment 51, wherein the at least dose of psilocybin is in the range of about 0.1 mg to about 100 mg.

53. The method of embodiment 52, wherein the dose of psilocybin is about 1 mg.

54. The method of embodiment 52, wherein the dose of psilocybin is about 10 mg.

55. The method of embodiment 52, wherein the dose of psilocybin is about 25 mg.

56. The method of any one of embodiments 1-54, wherein more than one dose of psilocybin is administered to the subject.

57. The method of embodiment 56, wherein at least two doses of psilocybin are administered to the subject.

58. The method of any one of embodiments 56-57, wherein the psilocybin is administered once per day.

59. The method of any one of embodiments 56-57, wherein the psilocybin is administered at least once per week.

60. The method of any one of embodiments 56-57, wherein the psilocybin is administered at least twice per week.

61. The method of any one of embodiments 56-57, wherein the psilocybin is administered at least once per month.

62. The method of any one of embodiments 56-57, wherein the psilocybin is administered at least twice per month.

63. The method of any one of embodiments 56-57, wherein the psilocybin is administered at least once every three months.

64. The method of any one of embodiments 56-57, wherein the psilocybin is administered at least once every six months.

65. The method of any one of embodiments 56-57, wherein the psilocybin is administered at least once every 12 months.

66. The method of any one of embodiments 56-65, wherein each dose of psilocybin administered is in the range of about 0.1 mg to about 100 mg.

67. The method of embodiment 66, wherein each dose of psilocybin administered is about 1 mg.

68. The method of embodiment 66, wherein each dose of psilocybin administered is about 10 mg.

69. The method of embodiment 66, wherein each dose of psilocybin administered is about 25 mg.

70. The method of any one of embodiments 51-69, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

71. The method of embodiment 70, wherein the psilocybin is administered orally.

72. The method of any one of embodiments 1-71, wherein the subject participates in at least one psychological support session before administration of the psilocybin.

73. The method of embodiment 72, wherein the subject participates in at least three psychological support sessions before administration of the psilocybin.

74. The method of any one of embodiments 72-73, wherein the at least one therapeutic intention is discussed during the psychological support session.

75. The method of any one of embodiments 72-74, wherein self-directed inquiry and experiential processing are practiced during the psychological support session.

76. The method of any one of embodiments 1-75, wherein the subject participates in at least one psychological support session after administration of the psilocybin.

77. The method of embodiment 76, wherein the subject participates in at least three psychological support sessions after administration of the psilocybin.

78. The method of any one of embodiments 71-77, wherein the psilocybin is administered to the subject in a room with a substantially non-clinical appearance.

79. The method of embodiment 78, wherein the room comprises soft furniture.

80. The method of embodiment 78, wherein the room is decorated using muted colors.

81. The method of embodiment 78, wherein the room comprises a high-resolution sound system.

82. The method of any one of embodiments 78-81, wherein the room comprises a bed or a couch.

83. The method of embodiment 82, wherein the subject lies in the bed or on the couch for approximately 4-8 hours, or a substantial fraction thereof, after administration of the psilocybin.

84. The method of any one of embodiments 78-83, wherein the subject listens to music for approximately 4-8 hours, or a substantial fraction thereof, after administration of the psilocybin.

85. The method of any one of embodiments 78-84, wherein the subject wears an eye mask for approximately 4-8 hours, or a substantial fraction thereof, after administration of the psilocybin.

86. The method of any one of embodiments 1-85, wherein a therapist provides psychological support to the subject for approximately 4-8 hours after administration of the psilocybin.

87. The method of embodiment 86, wherein the therapist uses guided imagery to calm the subject and/or focus the subject's attention.

88. The method of embodiment 86, wherein the therapist provides reassuring physical contact with the subject.

89. The method of embodiment 88, wherein the therapist holds the hand, arm, or shoulder of the subject.

90. The method of embodiment 86, wherein the therapist encourages the subject to perform self-directed inquiry and experiential processing.

91. The method of embodiment 86, wherein the therapist reminds the subject of at least one therapeutic intention.

92. The method of embodiment 86, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

93. The method of embodiment 86, wherein the therapist does not initiate conversation with the subject.

94. The method of embodiment 86, wherein the therapist responds to the subject if the subject initiates conversation.

Stroke

1. A method for treating stroke in a subject in need thereof, the method comprising administering to the subject a therapeutically effective amount of psilocybin or an active metabolite thereof.

2. The method of embodiment 1, wherein the stroke is an ischemic stroke.

3. The method of embodiment 1, wherein the stroke is a hemorrhagic stroke.

4. The method of any one of embodiments 1-3, wherein administering the psilocybin improves a sign or symptom of stroke.

5. The method of embodiment 4, wherein the sign or symptom of stroke is paralysis, numbness or weakness in the arm, face, or leg, trouble speaking or understanding speech, confusion, slurring speech, vision problems, trouble walking, loss of balance or coordination, dizziness, or headache.

6. The method of any one of embodiments 4-5, wherein the sign or symptom of stroke is improved within 1 hour of administration of the psilocybin.

7. The method of any one of embodiments 4-5, wherein the sign or symptom of stroke is improved within 12 hours of administration of the psilocybin.

8. The method of any one of embodiments 4-7, wherein the sign or symptom of stroke is improved for a period of at least 1 month after administration of the psilocybin.

9. The method of any one of embodiments 4-7, wherein the sign or symptom of stroke is improved for a period of at least 3 months after administration of the psilocybin.

10. The method of any one of embodiments 4-7, wherein the sign or symptom of stroke is improved for a period of at least 12 months after administration of the psilocybin.

11. The method of any one of embodiments 1-10, wherein no other treatment is administered to the subject to treat stroke after administration of the psilocybin.

12. The method of any one of embodiments 1-10, wherein the method further comprises administering to the subject at least one additional therapeutic.

13. The method of embodiment 12, wherein the at least one additional therapeutic is administered prior to administration of psilocybin.

14. The method of embodiment 12, wherein the at least one additional therapeutic is administered after administration of psilocybin.

15. The method of embodiment 12, wherein the at least one additional therapeutic is administered on the same day as the psilocybin.

16. A method for treating a subject in need thereof, the method comprising administering to the subject a therapeutically effective amount of psilocybin or an active metabolite thereof; wherein the subject is recovering from a stroke.

17. The method of embodiment 16, wherein the subject is recovering from an ischemic stroke.

18. The method of embodiment 16, wherein the subject is recovering from a hemorrhagic stroke.

19. The method of any one of embodiments 16-18, wherein administering the psilocybin improves a condition caused by the stroke.

20. The method of embodiment 19, wherein the condition caused by the stroke is paralysis, cognitive issues, difficulty understanding speech, difficulty speaking, difficulty controlling or expressing emptions, numbness, pain in the hands or feet, trouble chewing or swallowing, problems with bladder or bowel control.

21. The method of any one of embodiments 19-20, wherein the condition caused by the stroke is improved within 24 hours of administration of the psilocybin.

22. The method of any one of embodiments 19-20, wherein the condition caused by the stroke is improved within 1 week of administration of the psilocybin.

23. The method of any one of embodiments 19-22, wherein the condition caused by the stroke is improved for a period of at least 1 month after administration of the psilocybin.

24. The method of any one of embodiments 19-22, wherein the condition caused by the stroke is improved for a period of at least 3 months after administration of the psilocybin.

25. The method of any one of embodiments 19-22, wherein the condition caused by the stroke is improved for a period of at least 12 months after administration of the psilocybin.

26. The method of any one of embodiments 1-25, wherein no other treatment is administered to the subject to treat the condition caused by the stroke after administration of the psilocybin.

27. The method of any one of embodiments 1-25, wherein the method further comprises administering to the subject at least one additional therapeutic to treat the condition caused by the stroke.

28. The method of embodiment 27, wherein the at least one additional therapeutic is administered prior to administration of psilocybin.

29. The method of embodiment 27, wherein the at least one additional therapeutic is administered after administration of psilocybin.

30. The method of embodiment 27, wherein the at least one additional therapeutic is administered on the same day as the psilocybin.

31. The method of any one of embodiments 1-30, wherein the subject has depression.

32. The method of embodiment 31, wherein the administration of psilocybin alleviates depression in the subject.

33. The method of any one of embodiments 1-32, wherein the subject has no prior psilocybin exposure.

34. The method of any one of embodiments 1-32, wherein the subject has prior psilocybin exposure. 35. The method of any one of embodiments 1-34 wherein the subject is a mammal.

36. The method of embodiment 35, wherein the subject is a human.

37. The method of any of embodiments 1-36, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

38. The method of embodiment 37, wherein the crystalline psilocybin comprises at least 95% by weight of Polymorph A.

39. The method of embodiment 37 or 38, wherein the crystalline psilocybin has a chemical purity of greater than 97% by HPLC, and no single impurity of greater than 1%.

40. The method of any of embodiments 1-36, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

41. The method of embodiment 40, wherein the highly pure crystalline psilocybin comprises at least 90% by weight of Polymorph A.

42. The method of embodiment 40, wherein the highly pure crystalline psilocybin comprises at least 95% by weight of Polymorph A.

43. The method of any one of embodiments 37-42, wherein the highly pure crystalline psilocybin is further characterized having either: (i) a water content of <0.5% w/w; or (ii) <0.5% w/w loss in the TGA thermogram between 25° C. and 200° C.

44. The method of any of embodiments 37-43, wherein the highly pure crystalline psilocybin is further characterized by an endothermic event in a DSC thermogram having a first onset temperature of between 145° C. and 155° C. and a second onset temperature of between 205 and 220° C.

45. The method of any one of embodiments 37-44, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

46. The method of any of embodiments 37-45, wherein the highly pure crystalline psilocybin has no single impurity of greater than 0.5%.

47. The method of any of embodiments 37-46, wherein the dosage form further comprises about 5 to 40 mg of the highly pure crystalline psilocybin.

48. The method of embodiment 47, wherein the dosage form comprises 5 mg of highly pure crystalline psilocybin.

49. The method of embodiment 47, wherein the dosage form comprises about 10 mg of highly pure crystalline psilocybin.

50. The method of embodiment 47, wherein the dosage form comprises about 35 mg of highly pure crystalline psilocybin.

51. The method of any of embodiments 37-50, wherein the dosage form comprises silicified microcrystalline cellulose.

52. The method of embodiment 51, wherein the silicified microcrystalline cellulose has a particle size range from about 45 to 150 microns.

53. The method of any of embodiments 37-52, further comprising a mixture of two silicified microcrystalline cellulose variants wherein the first variant has a particle size from about 45 to 80 microns and the second variant has a particle size of about 90 to 150 microns.

54. The method of embodiment 53, wherein about 30% or less of the microcrystalline cellulose is the first variant having a particle size from about 45 to 80 microns and about 70% or more of the microcrystalline cellulose is the second variant having a particle size of about 90 to 150 microns.

55. The method of embodiment 53, wherein about 20% or less of the microcrystalline cellulose is the first variant having a particle size from about 45 to 80 microns and about 80% or more of the microcrystalline cellulose is the second variant having a particle size of about 90 to 150 microns.

56. The method of embodiment 53, wherein about 15% or less of the microcrystalline cellulose is the first variant having a particle size from about 45 to 80 microns and about 85% or more of the microcrystalline cellulose is the second variant having a particle size of about 90 to 150 microns.

57. The method of embodiment 53, wherein about 15% or less of the microcrystalline cellulose is the first variant having a particle size from about 45 to 80 microns and about 85% or more of the microcrystalline cellulose is the second variant having a particle size of about 90 to 150 microns.

58. The method of embodiment 57, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

59. The method of embodiment 57, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

60. The method any one of embodiments 37-59, wherein the dosage form is an oral dosage form.

61. The method embodiment 60, wherein the dosage form is a capsule.

62. The method embodiment 60, wherein the dosage form is a tablet.

63. The method of any one of embodiments 1-62, wherein at least one dose of psilocybin is administered to the subject.

64. The method of embodiment 63, wherein the at least dose of psilocybin is in the range of about 0.1 mg to about 100 mg.

65. The method of embodiment 63, wherein the dose of psilocybin is about 1 mg.

66. The method of embodiment 63, wherein the dose of psilocybin is about 10 mg.

67. The method of embodiment 63, wherein the dose of psilocybin is about 25 mg.

68. The method of any one of embodiments 1-62, wherein more than one dose of psilocybin is administered to the subject.

69. The method of embodiment 68, wherein at least two doses of psilocybin are administered to the subject.

70. The method of any one of embodiments 68-69, wherein the psilocybin is administered once per day.

71. The method of any one of embodiments 68-69, wherein the psilocybin is administered at least once per week.

72. The method of any one of embodiments 68-69, wherein the psilocybin is administered at least twice per week.

73. The method of any one of embodiments 68-69, wherein the psilocybin is administered at least once per month.

74. The method of any one of embodiments 68-69, wherein the psilocybin is administered at least twice per month.

75. The method of any one of embodiments 68-69, wherein the psilocybin is administered at least once every three months.

76. The method of any one of embodiments 68-69, wherein the psilocybin is administered at least once every six months.

77. The method of any one of embodiments 68-69, wherein the psilocybin is administered at least once every 12 months.

78. The method of any one of embodiments 68-77, wherein each dose of psilocybin administered is in the range of about 0.1 mg to about 100 mg.

79. The method of embodiment 78, wherein each dose of psilocybin administered is about 1 mg.

80. The method of embodiment 78, wherein each dose of psilocybin administered is about 10 mg.

81. The method of embodiment 78, wherein each dose of psilocybin administered is about 25 mg.

82. The method of any one of embodiments 63-81, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection. 83. The method of embodiment 82, wherein the psilocybin is administered orally.

84. The method of any one of embodiments 1-83, wherein the subject participates in at least one psychological support session before administration of the psilocybin.

85. The method of embodiment 84, wherein the subject participates in at least three psychological support sessions before administration of the psilocybin.

86. The method of any one of embodiments 84-85, wherein the at least one therapeutic intention is discussed during the psychological support session.

87. The method of any one of embodiments 84-86, wherein self-directed inquiry and experiential processing are practiced during the psychological support session.

88. The method of any one of embodiments 1-87, wherein the subject participates in at least one psychological support session after administration of the psilocybin.

89. The method of embodiment 88, wherein the subject participates in at least three psychological support sessions after administration of the psilocybin.

90. The method of any one of embodiments 83-89, wherein the psilocybin is administered to the subject in a room with a substantially non-clinical appearance.

91. The method of embodiment 90, wherein the room comprises soft furniture.

92. The method of embodiment 90, wherein the room is decorated using muted colors.

93. The method of embodiment 90, wherein the room comprises a high-resolution sound system.

94. The method of any one of embodiments 90-93, wherein the room comprises a bed or a couch.

95. The method of embodiment 94, wherein the subject lies in the bed or on the couch for approximately 4-8 hours, or a substantial fraction thereof, after administration of the psilocybin.

96. The method of any one of embodiments 90-95, wherein the subject listens to music for approximately 4-8 hours, or a substantial fraction thereof, after administration of the psilocybin.

97. The method of any one of embodiments 90-96, wherein the subject wears an eye mask for approximately 4-8 hours, or a substantial fraction thereof, after administration of the psilocybin.

98. The method of any one of embodiments 90-97, wherein a therapist provides psychological support to the subject for approximately 4-8 hours after administration of the psilocybin.

99. The method of embodiment 98, wherein the therapist uses guided imagery to calm the subject and/or focus the subject's attention.

100. The method of embodiment 98, wherein the therapist provides reassuring physical contact with the subject.

101. The method of embodiment 100, wherein the therapist holds the hand, arm, or shoulder of the subject.

102. The method of embodiment 98, wherein the therapist encourages the subject to perform self-directed inquiry and experiential processing.

103. The method of embodiment 98, wherein the therapist reminds the subject of at least one therapeutic intention.

104. The method of embodiment 98, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

105. The method of embodiment 98, wherein the therapist does not initiate conversation with the subject.

106. The method of embodiment 98, wherein the therapist responds to the subject if the subject initiates conversation.

Amyotrophic Lateral Sclerosis

1. A method for treating amyotrophic lateral sclerosis (ALS) a subject in need thereof, the method comprising administering to the subject a therapeutically effective amount of psilocybin or an active metabolite thereof.

2. The method of embodiment 1, wherein administering the psilocybin improves a sign or symptom of ALS.

3. The method of embodiment 2, wherein the sign or symptom of ALS is muscle twitching, muscle weakness, muscle stiffness, difficulty speaking, difficulty swallowing, difficulty breathing, cognitive impairment, or pain.

4. The method of any one of embodiments 2-3, wherein the sign or symptom of ALS is improved within 24 hours of administration of the psilocybin.

5. The method of any one of embodiments 2-3, wherein the sign or symptom of ALS is improved within 1 week of administration of the psilocybin.

6. The method of any one of embodiments 2-5, wherein the sign or symptom of ALS is improved for a period of at least 1 month after administration of the psilocybin.

7. The method of any one of embodiments 2-5, wherein the sign or symptom of ALS is improved for a period of at least 3 months after administration of the psilocybin.

8. The method of any one of embodiments 2-5, wherein the sign or symptom of ALS is improved for a period of at least 12 months after administration of the psilocybin.

9. The method of any one of embodiments 1-8, wherein no other treatment is administered to the subject to treat ALS after administration of the psilocybin.

10. The method of any one of embodiments 1-8, wherein the method further comprises administering to the subject at least one additional therapeutic to treat ALS.

11. The method of embodiment 10, wherein the at least one additional therapeutic is riluzole or edaravone.

12. The method of any one of embodiments 10-11, wherein the at least one additional therapeutic is administered prior to administration of psilocybin.

13. The method of any one of embodiments 10-11, wherein the at least one additional therapeutic is administered after administration of psilocybin.

14. The method of any one of embodiments 10-11, wherein the at least one additional therapeutic is administered on the same day as the psilocybin.

15. The method of any one of embodiments 1-14, wherein the subject has depression. 16. The method of embodiment 15, wherein the administration of psilocybin alleviates depression in the subject.

17. The method of any one of embodiments 1-16, wherein the subject has no prior psilocybin exposure.

18. The method of any one of embodiments 1-16, wherein the subject has prior psilocybin exposure.

19. The method of any one of embodiments 1-18 wherein the subject is a mammal.

20. The method of embodiment 19, wherein the subject is a human.

21. The method of any of embodiments 1-20, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

22. The method of embodiment 21, wherein the crystalline psilocybin comprises at least 95% by weight of Polymorph A.

23. The method of embodiment 21 or 22, wherein the crystalline psilocybin has a chemical purity of greater than 97% by HPLC, and no single impurity of greater than 1%.

24. The method of any of embodiments 1-20, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

25. The method of embodiment 24, wherein the highly pure crystalline psilocybin comprises at least 90% by weight of Polymorph A.

26. The method of embodiment 24, wherein the highly pure crystalline psilocybin comprises at least 95% by weight of Polymorph A.

27. The method of any one of embodiments 21-26, wherein the highly pure crystalline psilocybin is further characterized having either: (i) a water content of <0.5% w/w; or (ii) <0.5% w/w loss in the TGA thermogram between 25° C. and 200° C.

28. The method of any of embodiments 21-27, wherein the highly pure crystalline psilocybin is further characterized by an endothermic event in a DSC thermogram having a first onset temperature of between 145° C. and 155° C. and a second onset temperature of between 205 and 220° C.

29. The method of any one of embodiments 21-28, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

30. The method of any of embodiments 21-29, wherein the highly pure crystalline psilocybin has no single impurity of greater than 0.5%.

31. The method of any of embodiments 21-30, wherein the dosage form further comprises about 5 to 40 mg of the highly pure crystalline psilocybin.

32. The method of embodiment 31, wherein the dosage form comprises 5 mg of highly pure crystalline psilocybin.

33. The method of embodiment 31, wherein the dosage form comprises about 10 mg of highly pure crystalline psilocybin.

34. The method of embodiment 31, wherein the dosage form comprises about 35 mg of highly pure crystalline psilocybin.

35. The method of any of embodiments 31-34, wherein the dosage form comprises silicified microcrystalline cellulose.

36. The method of embodiment 35, wherein the silicified microcrystalline cellulose has a particle size range from about 45 to 150 microns.

37. The method of any of embodiments 21-36, further comprising a mixture of two silicified microcrystalline cellulose variants wherein the first variant has a particle size from about 45 to 80 microns and the second variant has a particle size of about 90 to 150 microns.

38. The method of embodiment 37, wherein about 30% or less of the microcrystalline cellulose is the first variant having a particle size from about 45 to 80 microns and about 70% or more of the microcrystalline cellulose is the second variant having a particle size of about 90 to 150 microns.

39. The method of embodiment 37, wherein about 20% or less of the microcrystalline cellulose is the first variant having a particle size from about 45 to 80 microns and about 80% or more of the microcrystalline cellulose is the second variant having a particle size of about 90 to 150 microns.

40. The method of embodiment 37, wherein about 15% or less of the microcrystalline cellulose is the first variant having a particle size from about 45 to 80 microns and about 85% or more of the microcrystalline cellulose is the second variant having a particle size of about 90 to 150 microns.

41. The method of embodiment 37, wherein about 15% or less of the microcrystalline cellulose is the first variant having a particle size from about 45 to 80 microns and about 85% or more of the microcrystalline cellulose is the second variant having a particle size of about 90 to 150 microns.

42. The method of embodiment 41, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

43. The method of embodiment 41, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

44. The method any one of embodiments 21-43, wherein the dosage form is an oral dosage form.

45. The method embodiment 44, wherein the dosage form is a capsule.

46. The method embodiment 44, wherein the dosage form is a tablet.

47. The method of any one of embodiments 1-46, wherein at least one dose of psilocybin is administered to the subject.

48. The method of embodiment 47, wherein the at least one dose of psilocybin is in the range of about 0.1 mg to about 100 mg.

49. The method of embodiment 48, wherein the dose of psilocybin is about 1 mg.

50. The method of embodiment 48, wherein the dose of psilocybin is about 10 mg.

51. The method of embodiment 48, wherein the dose of psilocybin is about 25 mg.

52. The method of any one of embodiments 1-46, wherein more than one dose of psilocybin is administered to the subject.

53. The method of embodiment 52, wherein at least two doses of psilocybin are administered to the subject.

54. The method of any one of embodiments 52-53, wherein the psilocybin is administered once per day.

55. The method of any one of embodiments 52-53, wherein the psilocybin is administered at least once per week.

56. The method of any one of embodiments 52-53, wherein the psilocybin is administered at least twice per week.

57. The method of any one of embodiments 52-53, wherein the psilocybin is administered at least once per month.

58. The method of any one of embodiments 52-53, wherein the psilocybin is administered at least twice per month.

59. The method of any one of embodiments 52-53, wherein the psilocybin is administered at least once every three months.

60. The method of any one of embodiments 52-53, wherein the psilocybin is administered at least once every six months.

61. The method of any one of embodiments 52-53, wherein the psilocybin is administered at least once every 12 months.

62. The method of any one of embodiments 52-61, wherein each dose of psilocybin administered is in the range of about 0.1 mg to about 100 mg.

63. The method of embodiment 62, wherein each dose of psilocybin administered is about 1 mg.

64. The method of embodiment 62, wherein each dose of psilocybin administered is about 10 mg.

65. The method of embodiment 62, wherein each dose of psilocybin administered is about 25 mg.

66. The method of any one of embodiments 47-65, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

67. The method of embodiment 66, wherein the psilocybin is administered orally.

68. The method of any one of embodiments 1-67, wherein the subject participates in at least one psychological support session before administration of the psilocybin.

69. The method of embodiment 68, wherein the subject participates in at least three psychological support sessions before administration of the psilocybin.

70. The method of any one of embodiments 68-69, wherein the at least one therapeutic intention is discussed during the psychological support session.

71. The method of any one of embodiments 68-70, wherein self-directed inquiry and experiential processing are practiced during the psychological support session.

72. The method of any one of embodiments 1-71, wherein the subject participates in at least one psychological support session after administration of the psilocybin.

73. The method of embodiment 72, wherein the subject participates in at least three psychological support sessions after administration of the psilocybin.

74. The method of any one of embodiments 67-73, wherein the psilocybin is administered to the subject in a room with a substantially non-clinical appearance.

75. The method of embodiment 74, wherein the room comprises soft furniture.

76. The method of embodiment 74, wherein the room is decorated using muted colors.

77. The method of embodiment 74, wherein the room comprises a high-resolution sound system.

78. The method of any one of embodiments 74-77, wherein the room comprises a bed or a couch.

79. The method of embodiment 78, wherein the subject lies in the bed or on the couch for approximately 4-8 hours, or a substantial fraction thereof, after administration of the psilocybin.

80. The method of any one of embodiments 74-79, wherein the subject listens to music for approximately 4-8 hours, or a substantial fraction thereof, after administration of the psilocybin.

81. The method of any one of embodiments 74-80, wherein the subject wears an eye mask for approximately 4-8 hours, or a substantial fraction thereof, after administration of the psilocybin.

82. The method of any one of embodiments 1-81, wherein a therapist provides psychological support to the subject for approximately 4-8 hours after administration of the psilocybin.

83. The method of embodiment 82, wherein the therapist uses guided imagery to calm the subject and/or focus the subject's attention.

84. The method of embodiment 82, wherein the therapist provides reassuring physical contact with the subject.

85. The method of embodiment 84, wherein the therapist holds the hand, arm, or shoulder of the subject.

86. The method of embodiment 84, wherein the therapist encourages the subject to perform self-directed inquiry and experiential processing.

87. The method of embodiment 84, wherein the therapist reminds the subject of at least one therapeutic intention.

88. The method of embodiment 84, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

89. The method of embodiment 84, wherein the therapist does not initiate conversation with the subject.

90. The method of embodiment 84, wherein the therapist responds to the subject if the subject initiates conversation.

Anti-Social Personality Disorder

1. A method for treating anti-social personality disorder in a subject in need thereof, the method comprising administering to the subject an effective amount of psilocybin or an active metabolite thereof.

2. The method of embodiment 1, wherein the active metabolite is psilocin.

3. The method of any one of embodiments 1-2, wherein one or more signs or symptoms of anti-social personality disorder are improved in the subject after administration of psilocybin.

4. The method of any one of embodiments 1-3, wherein the subject has one or more comorbidities.

5. The method of embodiment 4, wherein the comorbidity is conduct disorder, depression, or anxiety.

6. The method of claim 5, wherein administration of the psilocybin ameliorates at least one sign or symptom of the comorbidity.

7. The method of any one of embodiments 1-6, wherein the subject is administered one or more additional therapeutics.

8. The method of any one of embodiments 1-7, wherein the subject has no prior psilocybin exposure.

9. The method of any one of embodiments 1-7, wherein the subject has prior psilocybin exposure.

10. The method of any one of embodiments 1-9 wherein the subject is a mammal.

11. The method of embodiment 10, wherein the subject is a human.

12. The method of any of embodiments 1-11, wherein the psilocybin is administered in a dosage form comprising a therapeutically effective amount of highly pure crystalline psilocybin in the form of Polymorph A, wherein the crystalline psilocybin comprises at least 90% by weight of Polymorph A.

13. The method of embodiment 12, wherein the crystalline psilocybin comprises at least 95% by weight of Polymorph A.

14. The method of embodiment 12 or 13, wherein the crystalline psilocybin has a chemical purity of greater than 97% by HPLC, and no single impurity of greater than 1%.

15. The method of any of embodiments 1-11, wherein the psilocybin is administered in a dosage form comprising a therapeutically effective amount of highly pure crystalline psilocybin in the form of Polymorph A, wherein the crystalline psilocybin has a chemical purity of greater than 97% by HPLC, and no single impurity of greater than 1%.

16. The method of embodiment 15, wherein the highly pure crystalline psilocybin comprises at least 90% by weight of Polymorph A.

17. The method of embodiment 15, wherein the highly pure crystalline psilocybin comprises at least 95% by weight of Polymorph A.

18. The method of any one of embodiments 12-17, wherein the highly pure crystalline psilocybin is further characterized having either: (i) a water content of <0.5% w/w; or (ii) <0.5% w/w loss in the TGA thermogram between 25° C. and 200° C.

19. The method of any of embodiments 12-18, wherein the highly pure crystalline psilocybin is further characterized by an endothermic event in a DSC thermogram having a first onset temperature of between 145° C. and 155° C. and a second onset temperature of between 205 and 220° C.

20. The method of any one of embodiments 12-19, wherein the highly pure crystalline psilocybin is further characterized by one or more of the following: (a) a loss on drying of no more than 2% w/w; (b) residue on ignition of no more than 0.5% w/w; (c) assay (on a dry basis) of 95-103% by weight as measured by HPLC; (d) residual solvent content of no more than 3000 ppm methanol; 5000 ppm ethanol, 720 ppm THF, and 890 ppm toluene, as measured by HRGC; (e) phosphoric acid content of no more than 1% w/w as measured by $^{31}$P NMR; and (f) Inductively Coupled Plasma Mass Spectrometry (ICP-MS) elemental analysis of: (i) no more than 1.5 ppm Cd; (ii) no more than 1.5 ppm Pb; (iii) no more than 4.5 ppm As; (iv) no more than 9.0 ppm Hg; (v) no more than 15 ppm Co; (vi) no more than 30 ppm V; (vii) no more than 60 ppm Ni; (viii) no more than 165 ppm Li; and (ix) no more than 30 ppm Pd.

21. The method of any of embodiments 18-20, wherein the highly pure crystalline psilocybin has no single impurity of greater than 0.5%.

22. The method of any of embodiments 12-21, wherein the dosage form further comprises about 5 to 40 mg of the highly pure crystalline psilocybin.

23. The method of embodiment 22, wherein the dosage form comprises 5 mg of highly pure crystalline psilocybin.

24. The method of embodiment 22, wherein the dosage form comprises about 10 mg of highly pure crystalline psilocybin.

25. The method of embodiment 22, wherein the dosage form comprises about 35 mg of highly pure crystalline psilocybin.

26. The method of any of embodiments 12-25, wherein the dosage form comprises silicified microcrystalline cellulose.

27. The method of embodiment 26, wherein the silicified microcrystalline cellulose has a particle size range from about 45 to 150 microns.

28. The method of any of embodiments 12-27, further comprising a mixture of two silicified microcrystalline cellulose variants wherein the first variant has a particle size from about 45 to 80 microns and the second variant has a particle size of about 90 to 150 microns.

29. The method of embodiment 28, wherein about 30% or less of the microcrystalline cellulose is the first variant having a particle size from about 45 to 80 microns and about 70% or more of the microcrystalline cellulose is the second variant having a particle size of about 90 to 150 microns.

30. The method of embodiment 28, wherein about 20% or less of the microcrystalline cellulose is the first variant having a particle size from about 45 to 80 microns and about 80% or more of the microcrystalline cellulose is the second variant having a particle size of about 90 to 150 microns.

31. The method of embodiment 28, wherein about 15% or less of the microcrystalline cellulose is the first variant having a particle size from about 45 to 80 microns and about 85% or more of the microcrystalline cellulose is the second variant having a particle size of about 90 to 150 microns.

32. The method of embodiment 28, wherein about 15% or less of the microcrystalline cellulose is the first variant having a particle size from about 45 to 80 microns and about 85% or more of the microcrystalline cellulose is the second variant having a particle size of about 90 to 150 microns.

33. The method of embodiment 32, wherein the dosage form comprises 5 mg of crystalline psilocybin in the form of Polymorph A, 12.5 mg of SMCC 50, 79.5 mg of SMCC 90, 1 mg sodium starch glycolate, 1 mg colloidal silicon dioxide and 1 mg sodium stearyl fumarate.

34. The method of embodiment 32, wherein the dosage form comprises 1 mg of crystalline psilocybin in the form of Polymorph A, 20.5 mg of SMCC 50, 75.5 mg of SMCC 90, 1 mg sodium starch glycolate, 1 mg colloidal silicon dioxide, and 1 mg sodium stearyl fumarate.

35. The method any one of embodiments 12-34, wherein the dosage form is an oral dosage form. 36. The method embodiment 35, wherein the dosage form is a capsule.

37. The method embodiment 35, wherein the dosage form is a tablet.

38. The method of any one of embodiments 1-37, wherein at least one dose of psilocybin is administered to the subject.

39. The method of embodiment 38, wherein the at least dose of psilocybin is in the range of about 0.1 mg to about 100 mg.

40. The method of embodiment 39, wherein the dose of psilocybin is about 1 mg.

41. The method of embodiment 39, wherein the dose of psilocybin is about 10 mg.

42. The method of embodiment 39, wherein the dose of psilocybin is about 25 mg.

43. The method of any one of embodiments 1-37, wherein more than one dose of psilocybin is administered to the subject.

44. The method of embodiment 43, wherein at least two doses of psilocybin are administered to the subject.

45. The method of any one of embodiments 43-44, wherein the psilocybin is administered once per day.

46. The method of any one of embodiments 43-44, wherein the psilocybin is administered at least once per week.

47. The method of any one of embodiments 43-44, wherein the psilocybin is administered at least twice per week.

48. The method of any one of embodiments 43-44, wherein the psilocybin is administered at least once per month.

49. The method of any one of embodiments 43-44, wherein the psilocybin is administered at least twice per month.

50. The method of any one of embodiments 43-44, wherein the psilocybin is administered at least once every three months.

51. The method of any one of embodiments 43-44, wherein the psilocybin is administered at least once every six months.

52. The method of any one of embodiments 43-44, wherein the psilocybin is administered at least once every 12 months.

53. The method of any one of embodiments 43-52, wherein each dose of psilocybin administered is in the range of about 0.1 mg to about 100 mg.

54. The method of embodiment 53, wherein each dose of psilocybin administered is about 1 mg.

55. The method of embodiment 53, wherein each dose of psilocybin administered is about 10 mg.

56. The method of embodiment 53, wherein each dose of psilocybin administered is about 25 mg.

57. The method of any one of embodiments 12-56, wherein the psilocybin is administered by one of the following routes: oral, parenteral, topical, inhalation, rectal, transmucosal, intranasal, buccal, vaginal, intrathecal, intraocular, transdermal, in utero, intralymphatic, or by direct tissue or organ injection.

58. The method of embodiment 57, wherein the psilocybin is administered orally.

59. The method of any one of embodiments 1-58, wherein the subject participates in at least one psychological support session before administration of the psilocybin.

60. The method of embodiment 59, wherein the subject participates in at least three psychological support sessions before administration of the psilocybin.

61. The method of any one of embodiments 59-60, wherein the at least one therapeutic intention is discussed during the psychological support session.

62. The method of any one of embodiments 59-61, wherein self-directed inquiry and experiential processing are practiced during the psychological support session.

63. The method of any one of embodiments 1-58, wherein the subject participates in at least one psychological support session after administration of the psilocybin.

64. The method of embodiment 63, wherein the subject participates in at least three psychological support sessions after administration of the psilocybin.

65. The method of any one of embodiments 58-64, wherein the psilocybin is administered to the subject in a room with a substantially non-clinical appearance.

66. The method of embodiment 65, wherein the room comprises soft furniture.

67. The method of embodiment 65, wherein the room is decorated using muted colors.

68. The method of embodiment 65, wherein the room comprises a high-resolution sound system.

69. The method of any one of embodiments 65-68, wherein the room comprises a bed or a couch.

70. The method of embodiment 69, wherein the subject lies in the bed or on the couch for approximately 4-8 hours, or a substantial fraction thereof, after administration of the psilocybin.

71. The method of any one of embodiments 58-70, wherein the subject listens to music for approximately 4-8 hours, or a substantial fraction thereof, after administration of the psilocybin.

72. The method of any one of embodiments 58-70, wherein the subject wears an eye mask for approximately 4-8 hours, or a substantial fraction thereof, after administration of the psilocybin.

73. The method of any one of embodiments 58-72, wherein a therapist provides psychological support to the subject for approximately 4-8 hours after administration of the psilocybin.

74. The method of embodiment 73, wherein the therapist uses guided imagery to calm the subject and/or focus the subject's attention.

75. The method of embodiment 73, wherein the therapist provides reassuring physical contact with the subject.

76. The method of embodiment 75, wherein the therapist holds the hand, arm, or shoulder of the subject.

77. The method of embodiment 73, wherein the therapist encourages the subject to perform self-directed inquiry and experiential processing.

78. The method of embodiment 73, wherein the therapist reminds the subject of at least one therapeutic intention.

79. The method of embodiment 73, wherein the therapist counsels the subject to do one or more of the following: (1) to accept feelings of anxiety, (2) to allow the experience to unfold naturally, (3) to avoid psychologically resisting the experience, (4) to relax, and/or (5) to explore the subject's own mental space.

80. The method of embodiment 73, wherein the therapist does not initiate conversation with the subject.

81. The method of embodiment 73, wherein the therapist responds to the subject if the subject initiates conversation.

Co-Administration of Psilocybin and Benzodiazepines

1. A method of reducing anxiety in a subject undergoing treatment with psilocybin, the method comprising administering to the subject:
   i) psilocybin or a precursor or derivative thereof, and
   ii) one or more benzodiazepines.

2. The method of embodiment 1, wherein the subject suffers from a disease, disorder, or condition selected from Disruptive Mood Dysregulation Disorder, Major Depressive Disorder (MDD), Treatment Resistant Depression, Persistent Depressive Disorder (Dysthymia), Premenstrual Dysphoric Disorder, Substance/Medication-Induced Depressive Disorder, Post-Partum depression, or Depressive Disorder due to Another Medical Condition, Separation Anxiety Disorder, Selective Mutism, Specific Phobia, Social Anxiety Disorder (Social Phobia), Panic Disorder, Panic Attack, Agoraphobia, Generalized Anxiety Disorder, Substance-Medication-Induced Anxiety Disorder, Anxiety Disorder Due to Another Medical Condition, Somatic Symptom Disorder, Illness Anxiety Disorder (hypochondriac), Conversion Disorder (Functional Neurological Symptom Disorder), Factitious Disorder, Post-Traumatic Stress Disorder (PTSD), Adjustment Disorders, Acute Distress Disorder, Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, Obsessive-Compulsive and Related Disorder due to Another Medical Condition, Substance-Related Disorders, Alcohol-Related Disorders, Cannabis-Related Disorders, Hallucinogen-Related Disorders, Inhalant-Related Disorders, Cocaine-Related Disorders, Opioid-Related Disorders, Sedative-, Hypnotic-, or Anxiolytic-Related Disorders, Stimulant-Related Disorders, Tobacco-Related Disorders, Non-Substance-Related Disorders (Gambling or Gaming Disorder), Migraines, Cluster Headaches such as Chronic Cluster Headaches, Cyclical Vomiting, Tension-Type Headache, Dysphasia, Pica, Anorexia Nervosa, Bulimia Nervosa, Binge-Eating Disorder, Oppositional Defiant Disorder, Intermittent Explosive Disorder, Conduct Disorder, Antisocial Personality Disorder, Psychopathy, Pyromania, and Kleptomania.

3. The method of embodiment 1 or 2, wherein the one or more benzodiazepines are administered to the subject at or around the same time as the psilocybin or precursor or derivative thereof.

4. The method of embodiment 1 or 2, wherein the one or more benzodiazepines are administered to the subject prior to administration of the psilocybin or precursor or derivative thereof.

5. The method of embodiment 4, wherein the one or more benzodiazepines are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof.

6. The method of embodiment 1 or 2, wherein the one or more benzodiazepines are administered to the subject after the psilocybin or precursor or derivative thereof.

7. The method of embodiment 6, wherein the one or more benzodiazepines are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

8. The method of any one of embodiments 1-7, wherein the psilocybin or precursor or derivative thereof, is administered to the subject at a dose of between about 0.1 mg to about 100 mg.

9. The method of embodiment 8, wherein the psilocybin or precursor or derivative thereof is administered to the subject at a dose of between about 1 mg to about 50 mg.

10. The method of embodiment 9, wherein the psilocybin or precursor or derivative thereof is administered to the subject at a dose of about 1 mg, about 10 mg, or about 25 mg.

11. The method of any one of embodiments 1-10, wherein the one or more benzodiazepines are administered at a dose that is lower than doses typically used to treat anxiety.

12. The method of embodiment 11, wherein the dose is about 10%, 20%, 25%, 30%, 40%, 50%, or 75% of a typical dose.

13. The method of any one of embodiments 1-10, wherein the one or more benzodiazepines are administered at a dose that is approximately equivalent to doses typically used to treat anxiety.

14. The method of any one of embodiments 1-10, wherein the one or more benzodiazepines are administered at a dose that is higher than doses typically used to treat anxiety.

15. The method of embodiment 14, wherein the dose is about 125%, 150%, 175%, 200%, 250%, or 300% of a typical dose.

16. The method of any one of embodiments 1-15, wherein the benzodiazepine is selected from the group consisting of adinazolam, alprazolam, bentazepam, bretazenil, bromazepam, bromazolam, brotizolam, camazepam, chlordiazepoxide, cinazepam, cinolazepam, clobazam, clonazepam, clonazolam, clorazepate, clotiazepam, cloxazolam, delorazepam, deschloroetizolam, diazepam, diclazepam, estazolam, ethyl carfluzepate, ethyl loflazepate, etizolam, flualprazolam, flubromazepam, flubromazolam, fluclotizolam, flunitrazepam, flunitrazolam, flurazepam, flutazolam, flutoprazepam, halazepam, ketazolam, loprazolam, lorazepam, lormetazepam, meclonazepam, medazepam, metizolam, mexazolam, midazolam, nifoxipam, nimetazepam, nitemazepam, nitrazepam, nitrazolam, nordiazepam, norflurazepam, oxazepam, phenazepam, pinazepam, prazepam, premazepam, pyrazolam, quazepam, rilmazafone, temazepam, tetrazepam, and triazolam.

17. The method of embodiment 16, wherein the benzodiazepine is alprazolam.

18. The method of embodiment 16, wherein the benzodiazepine is diazepam.

19. The method of any one of embodiments 1-18, wherein the psilocybin is a crystalline psilocybin in the form of Polymorph A, Polymorph A', Polymorph B, or Hydrate A.

20. The method of embodiment 19, wherein the crystalline psilocybin is Polymorph A, characterised by one or more of:
  a. peaks in an XRPD diffractogram at 11.5, 12.0, 14.5, and 17.5, °2θ±0.1°2θ;
  b. peaks in an XRPD diffractogram at 11.5, 12.0, 14.5 and 17.5, °2θ±0.1°2θ, further characterised by at least one further peak at 19.7, 20.4, 22.2, 24.3 or 25.7°2θ±0.1°2θ;
  c. an XRPD diffractogram as substantially illustrated in FIG. 2a; and/or
  d. an endothermic event in a DSC thermogram having a first onset temperature of between 145° C. and 165° C. and a second onset temperature of between 205° C. and 220° C. substantially as illustrated in FIG. 3a.

21. The method of embodiment 19, wherein the crystalline psilocybin is Polymorph A', characterised by one or more of:
  a. peaks in an XRPD diffractogram at 11.5, 12.0 and 14.5°2θ±0.1°2θ, but absent or substantially absent of a peak at 17.5°2θ±0.1°2θ;
  b. peaks in an XRPD diffractogram at 11.5, 12.0 and 14.5°2θ±0.1°2θ, but absent or substantially absent of a peak at 17.5°2θ±0.1°2θ, further characterised by at least one further peak at 19.7, 20.4, 22.2, 24.3 or 25.7°2θ±0.1°2θ;
  c. an XRPD diffractogram as substantially illustrated in FIG. 2b; and/or
  d. an endothermic event in a DSC thermogram having a first onset temperature of between 145° C. and 165° C. and a second onset temperature of between 205° C. and 220° C. substantially as illustrated in FIG. 3b.

22. The method of any one of embodiments 1-21, wherein the psilocybin or precursor or derivative thereof is administered orally to the subject.

23. The method of any one of embodiments 1-22, wherein the one or more benzodiazepine is administered orally to the subject.
24. The method of any one of embodiments 1-23, wherein the psilocybin or precursor or derivative thereof is administered at least once to the subject.
25. The method of embodiment 24, wherein the psilocybin is administered at least twice to the subject, at therapeutically effective intervals.
26. The method of embodiment 25, wherein the therapeutically effective intervals are about 2 weeks, about 3 weeks, about 4 weeks, about 5 weeks, about 6 weeks, about 7 weeks, about 8 weeks, about 9 weeks, about 10 weeks, about 11 weeks, or about 12 weeks.
27. The method of any one of embodiments 1-16, wherein the subject has never taken psilocybin before.
28. The method of any one of embodiments 1-26, wherein the subject has taken psilocybin before.
29. The method of any one of embodiments 1-28, wherein the subject is supervised during the administration and for at least 4 to 12 hours thereafter.
30. The method of any one of embodiments 1-29, wherein the subject receives psychological support during the administration, and for at least 4 to 12 hours thereafter.
31. The method of any one of embodiments 1-30, wherein the subject has not taken any serotonergic antidepressant for at least 2 weeks, at least 4 weeks, or at least 6 weeks prior.
32. The method of any one of embodiments 1-31, wherein the subject receives counseling with regard to the expected effects of the psilocybin.
33. The method of any one of embodiments 1-32, wherein the subject is a male.
34. The method of any one of embodiments 1-32, wherein the subject is a female.
35. A combination therapy for treating or preventing a disease, disorder, or condition selected from Disruptive Mood Dysregulation Disorder, Major Depressive Disorder (MDD), Treatment Resistant Depression, Persistent Depressive Disorder (Dysthymia), Premenstrual Dysphoric Disorder, Substance/Medication-Induced Depressive Disorder, Post-Partum depression, or Depressive Disorder due to Another Medical Condition, Separation Anxiety Disorder, Selective Mutism, Specific Phobia, Social Anxiety Disorder (Social Phobia), Panic Disorder, Panic Attack, Agoraphobia, Generalized Anxiety Disorder, Substance-Medication-Induced Anxiety Disorder, Anxiety Disorder Due to Another Medical Condition, Somatic Symptom Disorder, Illness Anxiety Disorder (hypochondriac), Conversion Disorder (Functional Neurological Symptom Disorder), Factitious Disorder, Post-Traumatic Stress Disorder (PTSD), Adjustment Disorders, Acute Distress Disorder, Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, Obsessive-Compulsive and Related Disorder due to Another Medical Condition, Substance-Related Disorders, Alcohol-Related Disorders, Cannabis-Related Disorders, Hallucinogen-Related Disorders, Inhalant-Related Disorders, Cocaine-Related Disorders, Opioid-Related Disorders, Sedative-, Hypnotic-, or Anxiolytic-Related Disorders, Stimulant-Related Disorders, Tobacco-Related Disorders, Non-Substance-Related Disorders (Gambling or Gaming Disorder), Migraines, Cluster Headaches such as Chronic Cluster Headaches, Cyclical Vomiting, Tension-Type Headache, Dysphasia, Pica, Anorexia Nervosa, Bulimia Nervosa, Binge-Eating Disorder, Oppositional Defiant Disorder, Intermittent Explosive Disorder, Conduct Disorder, Antisocial Personality Disorder, Psychopathy, Pyromania, and Kleptomania, the combination therapy comprising administering to the subject:
  i) psilocybin or a precursor or derivative thereof, and
  ii) one or more benzodiazepines.
36. A kit for treating a subject in need thereof, the kit comprising:
  a first pharmaceutical composition comprising psilocybin, or a precursor or derivative thereof, and
  a second pharmaceutical composition comprising one or more benzodiazepines.
37. The kit of embodiment 36, wherein the kit further comprises instructions for administering the first and the second pharmaceutical composition to the subject.

Co-Administration of Psilocybin and 5-HT2A Specific Antagonists and/or Inverse Agonists.

1. A method of reducing the negative side effects associated with a traumatic psychedelic experience in a subject undergoing treatment with psilocybin, the method comprising administering to the subject:
  i) psilocybin or a precursor or derivative thereof, and
  ii) one or more 5-$HT_{2A}$ specific antagonists and/or inverse agonists.
2. The method of embodiment 1, wherein the subject suffers from a disease, disorder, or condition selected from Disruptive Mood Dysregulation Disorder, Major Depressive Disorder (MDD), Treatment Resistant Depression, Persistent Depressive Disorder (Dysthymia), Premenstrual Dysphoric Disorder, Substance/Medication-Induced Depressive Disorder, Post-Partum depression, or Depressive Disorder due to Another Medical Condition, Separation Anxiety Disorder, Selective Mutism, Specific Phobia, Social Anxiety Disorder (Social Phobia), Panic Disorder, Panic Attack, Agoraphobia, Generalized Anxiety Disorder, Substance-Medication-Induced Anxiety Disorder, Anxiety Disorder Due to Another Medical Condition, Somatic Symptom Disorder, Illness Anxiety Disorder (hypochondriac), Conversion Disorder (Functional Neurological Symptom Disorder), Factitious Disorder, Post-Traumatic Stress Disorder (PTSD), Adjustment Disorders, Acute Distress Disorder, Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, Obsessive-Compulsive and Related Disorder due to Another Medical Condition, Substance-Related Disorders, Alcohol-Related Disorders, Cannabis-Related Disorders, Hallucinogen-Related Disorders, Inhalant-Related Disorders, Cocaine-Related Disorders, Opioid-Related Disorders, Sedative-, Hypnotic-, or Anxiolytic-Related Disorders, Stimulant-Related Disorders, Tobacco-Related Disorders, Non-Substance-Related Disorders (Gambling or Gaming Disorder), Migraines, Cluster Headaches such as Chronic Cluster Headaches, Cyclical Vomiting, Tension-Type Headache, Dysphasia, Pica, Anorexia Nervosa, Bulimia Nervosa, Binge-Eating Disorder, Oppositional Defiant Disorder, Intermittent Explosive Disorder, Conduct Disorder, Antisocial Personality Disorder, Psychopathy, Pyromania, Kleptomania, and burnout, vegetative states, and asthma (and other inflammatory diseases).
3. The method of embodiment 1 or 2, wherein the one or more 5-$HT_{2A}$ specific antagonists and/or inverse agonists are administered to the subject at or around the same time as the psilocybin or precursor or derivative thereof.
4. The method of embodiment 1 or 2, wherein the one or more 5-$HT_{2A}$ specific antagonists and/or inverse agonists are administered to the subject prior to administration of the psilocybin or precursor or derivative thereof.

5. The method of embodiment 4, wherein the one or more 5-HT$_{2A}$ specific antagonists and/or inverse agonists are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof.

6. The method of embodiment 1 or 2, wherein the one or more 5-HT$_{2A}$ specific antagonists and/or inverse agonists are administered to the subject after the psilocybin or precursor or derivative thereof.

7. The method of embodiment 6, wherein the one or more 5-HT$_{2A}$ specific antagonists and/or inverse agonists are administered to the subject about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

8. The method of any one of embodiments 1-7, wherein the psilocybin or precursor or derivative thereof, is administered to the subject at a dose of between about 0.1 mg to about 100 mg.

9. The method of embodiment 8, wherein the psilocybin or precursor or derivative thereof is administered to the subject at a dose of between about 1 mg to about 50 mg.

10. The method of embodiment 9, wherein the psilocybin or precursor or derivative thereof is administered to the subject at a dose of about 1 mg, about 10 mg, or about 25 mg.

11. The method of any one of embodiments 1-10, wherein the one or more 5-HT$_{2A}$ specific antagonists and/or inverse agonists are administered at a dose that is lower than a typical dose.

12. The method of embodiment 11, wherein the dose is about 10%, 20%, 25%, 30%, 40%, 50%, or 75% of a typical dose.

13. The method of any one of embodiments 1-10, wherein the one or more 5-HT$_{2A}$ specific antagonists and/or inverse agonists are administered at a dose that is approximately equivalent to a typical dose.

14. The method of any one of embodiments 1-10, wherein the one or more 5-HT$_{2A}$ specific antagonists and/or inverse agonists are administered at a dose that is higher than a typical dose.

15. The method of embodiment 14, wherein the dose is about 125%, 150%, 175%, 200%, 250%, or 300% of a typical dose.

16. The method of any one of embodiments 1-15, wherein the 5-HT$_{2A}$ specific antagonist is trazodone, mirtazapine, metergoline, ketanserin, ritanserin, nefazodone, clozapine, olanzapine, quetiapine, risperidone, asenapine, MDL-100907, cyproheptadine, pizotifen, LY-367,265, 2-alkyl-4-aryl-tetrahydro-pyrimido-azepine, 9-aminomethyl-9,10-dihydroanthracene (AMDA), haloperidol, chlorpromazine, hydroxyzine (atarax), 5-MeO-NBpBrT, niaprazine, altanserin, aripiprazole, etoperidone, setoperone, chlorprothixene, cinaserin, adatanserin, medifoxamine, rauwolscine, phenoxybenzamine, pruvanserin, deramciclane, nelotanserin, lubazodone, mepiprazole, xylamidine, R-H-alpha-(2,3-dimethoxyphenyl)-1-[2-(4-fluorophenethyl)]-4-piperidinemethanol (M100907), mianserin, AT 1015, DV 7028, eplivanserin, 4F 4PP, fanaserin, alpha-phenyl-1-(2-phenylethyl)-4-piperidinemethanol (MDL 11,939), melperone, mesulergine, paliperidone, 1-[2-(3,4-Dihydro-1H-2-benzopyran-1-yl)ethyl]-4-(4-fluorophenyl)piperazine dihydrochloride (PNU 96415E), (2R,4R)-5-[2-[2-[2-(3-methoxyphenyl)ethyl]phenoxy]ethyl]-1-methyl-3-pyrrolidinol (R-96544), sarpogrelate, spiperone, ziprasidone, zotepine, or 7-[[4-[2-(4-fluorophenyl)ethyl]-1-piperazinyl]carbonyl]-1H-indole-3-carbonitrile (EMD 281014).

17. The method of embodiment 16, wherein the 5-HT$_{2A}$ specific antagonist is ketanserin.

18. The method of any one of embodiments 1-15, wherein the 5-HT$_{2A}$ inverse antagonist is AC-90179, nelotanserin (APD-125), eplivanserin, pimavanserin (ACP-103), or volinaserin.

19. The method of embodiment 18, wherein the 5-HT$_{2A}$ inverse antagonist is pimavanserin.

20. The method of any one of embodiments 1-19, wherein the psilocybin is a crystalline psilocybin in the form of Polymorph A, Polymorph A', Polymorph B, or Hydrate A.

21. The method of embodiment 20, wherein the crystalline psilocybin is Polymorph A, characterised by one or more of:
   e. peaks in an XRPD diffractogram at 11.5, 12.0, 14.5, and 17.5, °2θ±0.1°2θ;
   f. peaks in an XRPD diffractogram at 11.5, 12.0, 14.5 and 17.5, °2θ±0.1°2θ, further characterised by at least one further peak at 19.7, 20.4, 22.2, 24.3 or 25.7°2θ±0.1°2θ;
   g. an XRPD diffractogram as substantially illustrated in FIG. 2a; and/or
   h. an endothermic event in a DSC thermogram having a first onset temperature of between 145° C. and 165° C. and a second onset temperature of between 205° C. and 220° C. substantially as illustrated in FIG. 3a.

22. The method of embodiment 20, wherein the crystalline psilocybin is Polymorph A', characterised by one or more of:
   e. peaks in an XRPD diffractogram at 11.5, 12.0 and 14.5°2θ±0.1°2θ, but absent or substantially absent of a peak at 17.5°2θ±0.1°2θ;
   f. peaks in an XRPD diffractogram at 11.5, 12.0 and 14.5°2θ±0.1°2θ, but absent or substantially absent of a peak at 17.5°2θ±0.1°2θ, further characterised by at least one further peak at 19.7, 20.4, 22.2, 24.3 or 25.7°2θ±0.1°2θ;
   g. an XRPD diffractogram as substantially illustrated in FIG. 2b; and/or
   h. an endothermic event in a DSC thermogram having a first onset temperature of between 145° C. and 165° C. and a second onset temperature of between 205° C. and 220° C. substantially as illustrated in FIG. 3b.

23. The method of any one of embodiments 1-22, wherein the psilocybin or precursor or derivative thereof is administered orally to the subject.

24. The method of any one of embodiments 1-23, wherein the one or more 5-HT$_{2A}$ specific antagonists and/or inverse agonists is administered orally to the subject.

25. The method of any one of embodiments 1-24, wherein the psilocybin or precursor or derivative thereof is administered at least once to the subject.

26. The method of embodiment 25, wherein the psilocybin is administered at least twice to the subject, at therapeutically effective intervals.

27. The method of embodiment 26, wherein the therapeutically effective intervals are about 2 weeks, about 3 weeks, about 4 weeks, about 5 weeks, about 6 weeks, about 7 weeks, about 8 weeks, about 9 weeks, about 10 weeks, about 11 weeks, or about 12 weeks.

28. The method of any one of embodiments 1-27, wherein the subject has never taken psilocybin before.

29. The method of any one of embodiments 1-27, wherein the subject has taken psilocybin before.

30. The method of any one of embodiments 1-29, wherein the subject is supervised during the administration and for at least 4 to 12 hours thereafter.

31. The method of any one of embodiments 1-30, wherein the subject receives psychological support during the administration, and for at least 4 to 12 hours thereafter.

32. The method of any one of embodiments 1-31, wherein the subject has not taken any serotonergic antidepressant for at least 2 weeks, at least 4 weeks, or at least 6 weeks prior.

33. The method of any one of embodiments 1-32, wherein the subject receives counseling with regard to the expected effects of the psilocybin.

34. The method of any one of embodiments 1-33, wherein the subject is a male.

35. The method of any one of embodiments 1-33, wherein the subject is a female.

36. A combination therapy for treating or preventing a disease, disorder, or condition selected from Disruptive Mood Dysregulation Disorder, Major Depressive Disorder (MDD), Treatment Resistant Depression, Persistent Depressive Disorder (Dysthymia), Premenstrual Dysphoric Disorder, Substance/Medication-Induced Depressive Disorder, Post-Partum depression, or Depressive Disorder due to Another Medical Condition, Separation Anxiety Disorder, Selective Mutism, Specific Phobia, Social Anxiety Disorder (Social Phobia), Panic Disorder, Panic Attack, Agoraphobia, Generalized Anxiety Disorder, Substance-Medication-Induced Anxiety Disorder, Anxiety Disorder Due to Another Medical Condition, Somatic Symptom Disorder, Illness Anxiety Disorder (hypochondriac), Conversion Disorder (Functional Neurological Symptom Disorder), Factitious Disorder, Post-Traumatic Stress Disorder (PTSD), Adjustment Disorders, Acute Distress Disorder, Obsessive-Compulsive Disorder, Body Dysmorphic Disorder, Hoarding Disorder, Trichotillomania (Hair-Pulling Disorder), Excoriation (Skin-Picking) Disorder, Substance/Medication-Induced Obsessive-Compulsive and Related Disorder, Obsessive-Compulsive and Related Disorder due to Another Medical Condition, Substance-Related Disorders, Alcohol-Related Disorders, Cannabis-Related Disorders, Hallucinogen-Related Disorders, Inhalant-Related Disorders, Cocaine-Related Disorders, Opioid-Related Disorders, Sedative-, Hypnotic-, or Anxiolytic-Related Disorders, Stimulant-Related Disorders, Tobacco-Related Disorders, Non-Substance-Related Disorders (Gambling or Gaming Disorder), Migraines, Cluster Headaches such as Chronic Cluster Headaches, Cyclical Vomiting, Tension-Type Headache, Dysphasia, Pica, Anorexia Nervosa, Bulimia Nervosa, Binge-Eating Disorder, Oppositional Defiant Disorder, Intermittent Explosive Disorder, Conduct Disorder, Antisocial Personality Disorder, Psychopathy, Pyromania, Kleptomania, and burnout, vegetative states, and asthma (and other inflammatory diseases), the combination therapy comprising administering to the subject:
  i) psilocybin or a precursor or derivative thereof, and
  ii) one or more 5-HT$_{2A}$ specific antagonists and/or inverse agonists.

37. A kit for treating a subject in need thereof, the kit comprising:
  a first pharmaceutical composition comprising psilocybin, or a precursor or derivative thereof, and
  a second pharmaceutical composition comprising one or more 5-HT$_{2A}$ specific antagonists and/or inverse agonists.

38. The kit of embodiment 37, wherein the kit further comprises instructions for administering the first and the second pharmaceutical composition to the subject.

39. A method of reducing the negative side effects associated with a traumatic psychedelic experience in a subject undergoing treatment with psilocybin, the method comprising administering to the subject:
  i) psilocybin or a precursor or derivative thereof, and
  ii) one or more cannabinoids or cannabinoid derivatives.

Polymorph a and Use Thereof

1. Crystalline psilocybin Polymorph A or Polymorph A', characterised by one or more of:
  a) peaks in an XRPD diffractogram at 11.5, 12.0 and 14.5°2θ±0.1°2θ; and/or
  b) an endothermic event in a DSC thermogram having a first onset temperature of between 145° C. and 155° C. and a second onset temperature of between 210° C. and 220° C.
  for use in the treatment of: Alzheimer's, Autism spectrum disorder, Attention Deficit Hyperactivity Disorder (ADHD), Downs, Epilepsy (though not seizures), Multiple Sclerosis, Parkinson's disease, Schizophrenia, Huntington's, Stroke and other cerebrovascular conditions, Traumatic brain injury, Major depressive disorder, chronic cluster headaches, antisocial personality disorder and psychopathy.

2. A method for the treatment of Alzheimer's, Autism spectrum disorder, Attention deficit hyperactivity disorder (ADHD), Downs, Epilepsy (though not seizures), Multiple Sclerosis, Parkinson's disease, Schizophrenia, Huntington's, Stroke and other cerebrovascular conditions, Traumatic brain injury, Major depressive disorder, chronic cluster headaches, antisocial personality disorder and psychopathy comprising administering to a subject in need thereof an effective amount of crystalline psilocybin Polymorph A or Polymorph A', characterised by one or more of
  a) peaks in an XRPD diffractogram at 11.5, 12.0 and 14.5°2θ±0.1°2θ; and/or
  b) an endothermic event in a DSC thermogram having a first onset temperature of between 145° C. and 155° C. and a second onset temperature of between 210° C. and 220° C.

3. Crystalline psilocybin Polymorph A or Polymorph A', characterised by one or more of:
  a) peaks in an XRPD diffractogram at 11.5, 12.0 and 14.5°2θ±0.1°2θ; and/or
  b) an endothermic event in a DSC thermogram having a first onset temperature of between 145° C. and 155° C. and a second onset temperature of between 210° C. and 220° C.
  for use in the treatment of a central nervous disorder together with psychotherapy wherein the psychotherapy is a transdiagnostic therapy.

4. Crystalline psilocybin Polymorph A or Polymorph A' for use as claimed in claim 3 wherein the transdiagnostic therapy is a Method of Levels (MOL) therapy.

5. Crystalline psilocybin Polymorph A or Polymorph A' for use as claimed in claim 4 wherein the Method of Levels (MOL) therapy comprises Self-directed enquiry and Experiential processing.

6. A method for the treatment of a central nervous disorder together with psychotherapy wherein the psychotherapy is a transdiagnostic therapy.

7. A method as claimed in claim 6 wherein the transdiagnostic therapy is a Method of Levels (MOL) therapy.

8. A method as claimed in claim 7 wherein the Method of Levels (MOL) therapy comprises Self-directed enquiry and Experiential processing.

9. A digital biomarker, as a diagnostic and/or prognostic tool for patient management pre, during and/or post treatment of a central nervous system disorder with psilocybin wherein the digital biomarker is one or more biomarkers associated with executive function, cognitive control, working memory, processing speed, and emotional valence.

10. A digital biomarker as claimed in claim 9 wherein the biomarker is identified from patterns in smartphone use such as swipes, taps, and other touchscreen activities, and are scientifically validated to provide measurements of cognition and mood.

11. A digital biomarker as claimed in claim 10 wherein the pattern is identified using one or more:
   Number of and/or time of phone calls/e-mails/texts;
   Gestures used (taps, swipes, or other);
   Gyroscope derived information e.g. orientation of the phone;
   Acceleration of the phone;
   Keystroke patterns;
   Location derived information from GPS; and/or
   Specific words or emojis used or not used;
and the central nervous system disorder treated is treatment resistant depression.

12. A method of assessing a subject pre, during and/or post treatment of a central nervous system disorder to determine whether to provide a psilocybin treatment or a further psilocybin treatment comprising monitoring one or more biomarkers associated with executive function, cognitive control, working memory, processing speed, and emotional valence, and determining the treatment based on an outcome.

13. A method as claimed in claim 12 further comprising administering psilocybin for a first or a subsequent time.

14. A method as claimed in claim 13 wherein the psilocybin is administered together with psychotherapy.

Formulations of Psilocybin

1. A pharmaceutic formulation comprising psilocybin, one or more fillers, and one or more disintegrants.

2. The pharmaceutical formulation of embodiment 1 wherein one or more of the fillers is a silicified filler.

3. The pharmaceutical formulation of embodiment 2 wherein one or more silicified filler is silicified microcrystalline cellulose.

4. The pharmaceutical formulation of embodiment 3 comprising silicified microcrystalline cellulose with a particle size range of from about 45 to 80 microns (SMCC 50), silicified microcrystalline cellulose with a particle size range of from about 90 to 150 microns (SMCC 90), or mixtures thereof.

5. The pharmaceutical formulation of embodiment 4 comprising SMCC 50 and SMCC 90.

6. The pharmaceutical formulation of embodiment 5 wherein the ratio of SMCC 50 to SMCC 90 is 1:5 to 1:8 (SMCC 50:SMCC 90) wt %.

7. The pharmaceutical formulation of embodiment 6 wherein the ratio of SMCC 50 to SMCC 90 is 1:6 to 1:7 (SMCC 50:SMCC 90) wt %.

8. The pharmaceutical formulation of embodiment 7 wherein the ratio of SMCC 50 to SMCC 90 is 1:6.4 (SMCC 50:SMCC 90) wt %.

9. The pharmaceutical formulation of any of embodiment 1-8 wherein the disintegrant is present in an amount of less than 3% by weight.

10. The pharmaceutical formulation of embodiment 9 wherein the disintegrant is present in an amount of less than 2% by weight.

11. The pharmaceutical formulation of embodiment 10 wherein the disintegrant is present in an amount of 1% or less by weight.

12. The pharmaceutical formulation of any of embodiment 1-11 wherein the disintegrant is sodium starch glycolate, croscarmellose sodium, or mixtures thereof.

13. The pharmaceutical formulation of embodiment 12 wherein the disintegrant is sodium starch glycolate.

14. The pharmaceutical formulation of any of embodiment 1-13 wherein the psilocybin is crystalline psilocybin in the form of Polymorph A, Polymorph A', Polymorph B, or Hydrate A.

15. The pharmaceutical formulation of embodiment 14 wherein the psilocybin is crystalline psilocybin in the form of Polymorph A, characterized by one or more of:
   a. peaks in an XRPD diffractogram at 11.5, 12.0, 14.5, and 17.5, °2θ±0.1°2θ;
   b. peaks in an XRPD diffractogram at 11.5, 12.0, 14.5 and 17.5, °2θ±0.1°2θ, further characterized by at least one further peak at 19.7, 20.4, 22.2, 24.3 or 25.7°2θ±0.1°2θ;
   c. an XRPD diffractogram as substantially illustrated in FIG. 7*a*; and/or
   d. an endothermic event in a DSC thermogram having a first onset temperature of between 145° C. and 165° C. and a second onset temperature of between 205° C. and 220° C. substantially as illustrated in FIG. 8*a*.

16. The pharmaceutical formulation of embodiment 14 wherein the psilocybin is crystalline psilocybin in the form of Polymorph A', according to embodiment 1 or 2 characterized by one or more of:
   a. peaks in an XRPD diffractogram at 11.5, 12.0 and 14.5°2θ±0.1°2θ, but absent or substantially absent of a peak at 17.5°2θ±0.1°2θ;
   b. peaks in an XRPD diffractogram at 11.5, 12.0 and 14.5°2θ±0.1°2θ, but absent or substantially absent of a peak at 17.5°2θ±0.1°2θ, further characterized by at least one further peak at 19.7, 20.4, 22.2, 24.3 or 25.7°2θ±0.1°2θ;
   c. an XRPD diffractogram as substantially illustrated in FIG. 7*b*; and/or
   d. an endothermic event in a DSC thermogram having a first onset temperature of between 145° C. and 165° C. and a second onset temperature of between 205° C. and 220° C. substantially as illustrated in FIG. 8*b*.

17. The pharmaceutical formulation of any of embodiment 1-16 comprising about 1 mg to about 50 mg psilocybin.

18. The pharmaceutical formulation of embodiment 17 comprising about 1 mg, 5 mg, 10 mg, 15 mg, 20 mg, 25 mg, 30 mg, 35 mg, 40 mg, 45 mg, or 50 mg psilocybin.

19. A method for large scale manufacture of psilocybin in the form Polymorph A or Polymorph A', characterised by one or more of
   a) peaks in an XRPD diffractogram at 11.5, 12.0 and 14.5°2θ±0.1°2θ; and/or
   b) an endothermic event in a DSC thermogram having a first onset temperature of between 145° C. and 165° C. and a second onset temperature of between 205° C. and 220° C. wherein the method comprises water crystallization wherein psilocybin is solubilized in water at a temperature below 90° C. to provide an aqueous solution of psilocybin.

20. The method of embodiment 19 wherein psilocybin is solubilized in water at a temperature below 85° C. to provide an aqueous solution of psilocybin.

21. The method of embodiment 19 or 20 wherein the temperature of the aqueous solution of psilocybin is lowered at a rate of about 5° C.-15° C. an hour to provide crystalline psilocybin 22. The method of embodiment 21 wherein the temperature of the aqueous solution of psilocybin is lowered at a rate of about 10° C. an hour to provide crystalline psilocybin.

23. The method of any one of embodiments 19-22 further comprising stirring the solution during solubilization.

EXAMPLES

The following examples, which are included herein for illustration purposes only, are not intended to be limiting.

Example 1—Formulation Development

The five formulations (Ex 1A, 1B, 1C, 1D, and 1E) described in Table 11 were assessed for powder flow, blend uniformity, content uniformity and dissolution.

TABLE 11

| Material Name | Ex 1A | Ex 1B | Ex 1C | Ex 1D | Ex 1E |
|---|---|---|---|---|---|
| | % w/w | | | | |
| Psilocybin | 1.0 | 1.0 | 1.0 | 1.0 | 1.0 |
| Prosolv SMCC 50* | 15.5 | 20.5 | 10.5 | 20.5 | 10.5 |
| Prosolv SMCC 90* | 79.0 | 74.0 | 83.5 | 73.5 | 84.25 |
| Ratio | 1:5.1 | 1:3.6 | 1:8 | 1:3.6 | 1:8 |
| Sodium Starch glycolate | 3.0 | 3.0 | 3.0 | 3.0 | 3.0 |
| Colloidal Silicon Dioxide (Aerosil 200) | 0.5 | 0.25 | 1.0 | 1.0 | 0.25 |
| Sodium Stearyl Fumarate | 1.0 | 1.0 | 1.0 | 1.0 | 1.0 |
| TOTAL weight of tablet | 100.0 | 100.0 | 100.0 | 100.0 | 100.0 |
| Powder flow (Hausner ratio) | 22.4 | 26.5 | 21.8 | 21.3 | 19.5 |
| Blend Uniformity | | | | | |
| TOP | 107.6 | 103.0 | 96.0 | 97.0 | 96.0 |
| MIDDLE | 114.3 | 106.9 | 100.0 | 99.0 | 99.0 |
| BOTTOM | 125.6 | 109.3 | 108.0 | 104.0 | 103.0 |
| MEAN | 115.8 | 106.4 | 101.0 | 100.0 | 99.0 |
| % RSD | 7.8 | 3.7 | 5.5 | 3.3 | 3.1 |
| Content Uniformity | | | | | |
| % label Claim | 97.0 | 96.0 | 95.0 | 98.0 | 96.0 |
| AV | 4.3 | 4.5 | 5.5 | 2.0 | 4.8 |
| Dissolution Time (min) | % release | | | | |
| 5 | 94 | 93 | 92 | 94 | 94 |
| 10 | 96 | 96 | 95 | 97 | 96 |
| 15 | 96 | 96 | 95 | 97 | 95 |
| 30 | 95 | 96 | 95 | 96 | 95 |
| Infinity | 95 | 95 | 94 | 96 | 94 |
| Assay (%) | 97.0 | 95.0 | 95.0 | 98.0 | 96.0 |

*The quantity of fillers adjusted to account for glidant quantity and total tablet weight.

Ex. 1D was used as a base formulation for the optimization of an exemplary higher dose tablet (5 mg). Tablets tested for dissolution from all five examples were found be unaffected by change in the fillers ratio and quantity of glidant. Hence, it was decided to study the level of disintegrate in the final formulation. Two batches of Psilocybin tablet 5 mg were manufactured using high (3% w/w) and low (1% w/w) levels of a disintegrant in the formulation composition.

The additional studies were conducted to justify the amount of disintegrant in the formulation. These studies were performed on the higher strength product (5 mg). A quantity of filler was replaced with psilocybin, the active pharmaceutical ingredient (API) in order to accommodate the additional amount API. The formulation composition and results for powder flow, blend uniformity, content uniformity and dissolution for Ex. 1F and 1G are summarized in Table 12.

TABLE 12

| Material Name | Ex. 1F | Ex. 1G |
|---|---|---|
| | % w/w | |
| Psilocybin | 5.0 | 5.0 |
| Prosolv SMCC 50 | 14.5 | 12.5 |
| Prosolv SMCC 90 | 75.5 | 79.5 |
| Ratio | 1:5.2 | 1:6.4 |
| Sodium Starch glycolate | 3.0 | 1.0 |
| Colloidal Silicon Dioxide (Aerosil 200) | 1.0 | 1.0 |
| Sodium Stearyl Fumarate | 1.0 | 1.0 |
| TOTAL weight of tablet | 100.0 | 100.0 |
| Powder flow (Hausner ratio) | 22.6 | 20.9 |
| Blend Uniformity | | |
| TOP | 98.0 | 98.0 |
| MIDDLE | 99.0 | 99.0 |
| BOTTOM | 102.0 | 100.0 |
| MEAN | 100.0 | 99.0 |
| % RSD | 1.7 | 1.9 |
| Content Uniformity | | |
| % label Claim | 96.0 | 97.0 |
| AV | 9.2 | 3.7 |
| Dissolution Time (min) | % release | |
| 5 | 98.0 | 90.0 |
| 10 | 101.0 | 102.0 |
| 15 | 100.0 | 102.0 |
| 30 | 100.0 | 101.0 |
| Infinity | 99.0 | 101.0 |
| Assay (%) | 96.0 | 97.0 |

Both examples met pre-defined criteria for blend uniformity, content uniformity, assay and dissolution. The material flow property was measured using Hausner ratio and no significant difference was found between the two formulations. However, the content uniformity results for Ex. 1G (AV=3.7) was found better in comparison to Ex. 1F (AV=9.2).

Tablets from both batches (Ex. 1F and Ex. 1G) were tested for dissolution. The results showed no significant difference between two formulations.

Psilocybin tablet formulations comprising 1 mg and 5 mg of API are presented in Table 13.

TABLE 13

| Excipient/ material Name | Psilocybin 1 mg Tablet | | Psilocybin 5 mg Tablet | |
|---|---|---|---|---|
| | Percent Formula (% w/w) | Quantity (mg/ tablet) | Percent Formula (% w/w) | Quantity (mg/ tablet) |
| Psilocybin | 1.0 | 1.0 | 5.0 | 5.0 |
| Silicified Microcrystalline Cellulose SMCC 50 | 20.5 | 20.5 | 12.5 | 12.5 |
| Silicified Microcrystalline Cellulose SMCC 90 | 75.5 | 75.5 | 79.5 | 79.5 |
| Ratio | 1:3.7 | | 1:6.4 | |
| Sodium Starch Glycolate (disintegrant) | 1.0 | 1.0 | 1.0 | 1.0 |

TABLE 13-continued

| Excipient/ material Name | Psilocybin 1 mg Tablet | | Psilocybin 5 mg Tablet | |
|---|---|---|---|---|
| | Percent Formula (% w/w) | Quantity (mg/ tablet) | Percent Formula (% w/w) | Quantity (mg/ tablet) |
| Colloidal silicon Dioxide (Aerosil) (glidant) | 1.0 | 1.0 | 1.0 | 1.0 |
| Sodium Stearyl Fumarate (Pruv) (lubricant) | 1.0 | 1.0 | 1.0 | 1.0 |
| TOTAL | 100.0 | 100.0 | 100.0 | 100.0 |

It will be noted that alternative disintegrants, glidants and lubricants to those exemplified may be used.

Example 2: Treating a Subject with High Dose Psilocybin

Initially, a subject is counseled as to the expected effects of psilocybin by a professional who is trained to administer psilocybin therapy. One or more tablets or capsules comprising psilocybin are administered to the subject, in an environment where the subject is made to feel safe and comfortable. The total dose of psilocybin administered to the subject is between about 1 mg to about 25 mg.

The subject is supervised by the professional during administration of the psilocybin, and for a period of time thereafter (e.g., from about 4 hours to about 12 hours) until the psychoactive effects of the psilocybin have worn off. Optionally, the subject may receive psychological support during administration of the psilocybin, and for a period of time thereafter (e.g., from about 4 hours to about 12 hours).

Example 3: Safety and Efficacy of Psilocybin in Healthy Subjects

Aim of Study:

A Phase 1 randomized, double-blind, placebo-controlled study to evaluate the effect of psilocybin on cognitive and emotional processing as compared to placebo in healthy volunteers was conducted. The study investigated the short-term (Day 7) and long-term (Day 28) effects of moderate (10 mg) and high doses (25 mg) of psilocybin on key domains of cognition, such as episodic memory, attention, working and spatial memory, social cognition and elements of executive function, including cognitive flexibility.

Study Design:

Subjects 90 healthy subjects were studied. Approximately 50% of the subjects were psilocybin-naïve. For subjects with prior psilocybin experience, the last exposure was at least 1 year prior to the signing of the Informed Consent Form (ICF). Approximately 50% of the subjects were female. Subjects were stratified by sex and age (18-35 years old; >35 years old).

Dosing Procedure:

Each subject was assigned 1 treatment bottle containing 5 capsules packaged in a double-blind fashion, depending on the randomized treatment arm, the bottle contained one of the following:
a. Psilocybin 10 mg: 2×5-mg oral psilocybin capsules plus 3×placebo capsules
b. Psilocybin 25 mg: 5×5-mg oral psilocybin capsules
c. Placebo: 5×placebo capsules Each 5-mg oral psilocybin capsule comprised 5 mg crystalline psilocybin in the form of Polymorph A, 12.5 mg of SMCC 50, 79.5 mg of SMCC 90, 1 mg sodium starch glycolate, 1 mg colloidal silicon dioxide, and 1 mg sodium stearyl fumarate The dose was swallowed with at least a full glass of water.

Outcome Measures:

The following list of outcome measures are non-exhaustive:

a. The short-term change from Baseline (Day −1 [Visit 2]) to Day 7 (Visit 5) in cognitive measures of attention, spatial and working memory and executive function was measured by a composite score of the CANTAB Panel (Spatial Working Memory [SWM], Rapid Visual Information Processing [RVP], Paired Associates Learning [PAL]).
b. The short-term change from Baseline (Day −1 [Visit 2]) to Day 7 (Visit 5) in Social Cognition Panel scales (Pictorial Empathy Test [PET], Reading the Mind in the eyes Test [RMET], Toronto Empathy Questionnaire [TEQ], Social Value Orientation [SVO], Scale of Social Responsibility [SSR]).
c. The change from Baseline (Day −1 [Visit 2]) to Day 28 (Visit 6) in cognitive measures of attention, spatial and working memory and executive function as measured by a composite score of the CANTAB Panel (SWM, RVP, PAL).
d. The long-term change from Baseline (Day −1 [Visit 2]) to Day 84 (Visit 7) in Social Cognition Panel scales (PET, RMET, TEQ, SVO, SSR).
e. Dose-related differences between cognitive effects of psilocybin at Baseline (Day −1 [Visit 2]), Day 7 (Visit 5) and Day 28 (Visit 6), as measured by a composite score of the CANTAB Panel (SWM, RVP, PAL).
f. Dose-related differences between psychological effects of psilocybin at Baseline (Day −1 [Visit 2]), Day 7 (Visit 5) and Day 84 (Visit 7), as measured by Social Cognition Panel scales (PET, RMET, TEQ, SVO, SSR).
g. Differences in cognitive effects of psilocybin between psilocybin-naïve and experienced subjects at Baseline (Day −1 [Visit 2]), Day 7 (Visit 5) and Day 28 (Visit 6), as measured by a composite score of the CANTAB Panel (SWM, RVP, PAL).
h. Differences in Positive and Negative Affect Schedule (PANAS) after study drug administration on Day 0 (Visit 3).
i. Differences between psilocybin and placebo in the Emotion Recognition Test (ERT), Intra-Extra Dimensional Set Shift (IED), One Touch Stockings (OTS), Verbal Fluency and Digit Span Forward at Day 7 (Visit 5).
j. A composite score of the CANTAB Panel, including the following tests:
  i. Spatial Working Memory (SWM) (performed at Visit 2, Visit 5, and Visit 6).
  ii. Rapid Visual Information Processing (RVP) (performed at Visit 2, Visit 5, and Visit 6).
  iii. Paired Associates Learning (PAL) (performed at Visit 2, Visit 5, and Visit 6).
k. Cognitive Flexibility Panel
  i. Emotion Recognition Task (ERT) (performed at Visit 5).
  ii. Intra-Extra Dimensional Set Shift (IED) (performed at Visit 5).
  iii. One Touch Stockings (OTS) (performed at Visit 5).
  iv. Verbal Fluency (performed at Visit 5).
  v. Digit Span Forward (performed at Visit 5).

l. Five Dimension Altered States of Consciousness questionnaire (5D-ASC) (performed at Visit 3).
m. PANAS (performed at Visit 2 and Visit 3).
n. NEO-Five Factor Inventory (NEO-FFI) (performed at Visit 2, Visit 5, and Visit 7).
o. Symptom Checklist-90 item (SCL-90) (performed at Visit 2, Visit 5, and Visit 7).
p. Life Changes Inventory (LCI): The LCI measures changes in attitudes and values after near-death experiences often used to evaluate personal transformation following spiritually oriented experiences and practices. (performed at Visit 5 and Visit 7).
q. Social Cognition Panel scales
   i. Pictorial Empathy Test (PET) (performed at Visit 2, Visit 5, and Visit 7).
   ii. Reading the Mind in the Eyes Test (RMET) (performed at Visit 2, Visit 5, and Visit 7).
   iii. Social Value Orientation (SVO) (performed at Visit 2, Visit 5, and Visit 7).
   iv. Toronto Empathy Questionnaire (TEQ) (performed at Visit 2, Visit 5, and Visit 7).
   v. Scale of Social Responsibility (SSR) (performed at Visit 2, Visit 5, and Visit 7).
r. Sheehan Suicidality Tracking Scale (SSTS)
s. Mini International Neuropsychiatric Interview (MINI).
t. McLean Screening Instrument for Borderline Personality Disorder (MSIBPD) (performed at Visit 1).
u. Tellegen Absorption Scale (performed at Visit 2).
v. Physical Examination (performed at Visit 1).
w. Electrocardiogram (ECG) (performed at Visit 1, Visit 2, Visit 3 and Visit 4).

Clinical Laboratory Tests: Blood samples were obtained at Screening (Visit 1) and Day 1 (Visit 4) for the following:
   i. Hematology: hemoglobin, hematocrit, red blood cell count, mean corpuscular hemoglobin, mean corpuscular volume, mean corpuscular hemoglobin concentration, white blood cell count (with differential) and platelet count.
   ii. Chemistry: albumin, alkaline phosphatase, alanine aminotransferase (ALT), amylase, aspartate aminotransferase (AST), bicarbonate, bilirubin (direct, indirect and total), calcium, chloride, creatine kinase, creatinine, γ-glutamyl transferase, glucose, lactate dehydrogenase, lipase, magnesium, phosphate, potassium, protein-total, sodium, blood urea nitrogen and uric acid.

Urine samples were obtained at Screening (Visit 1) and Baseline (Visit 2) for the following:
   i. Urine Drug Screen: for illicit drugs or drugs of abuse at Screening (Visit 1) and Baseline (Visit 2). Results of a positive drug screen will be reviewed by the study clinician for pattern of use.
   ii. Urine Pregnancy Test: a dipstick test in females of childbearing potential at Screening (Visit 1) and Baseline (Visit 2).

Adverse events: Throughout the course of the study, all AEs were monitored and recorded. Each AE was classified according to the following criteria:
   i. Mild: The AE does not interfere in a significant manner with the subject's normal level of functioning.
   ii. Moderate: The AE produces some impairment of functioning, but is not hazardous to the subject's health.
   iii. Severe: The AE produces significant impairment of functioning or incapacitation and is a definite hazard to the subject's health.

Selected Adverse Events of included:
(a) Euphoric mood
(b) Dissociative disorder
(c) Hallucination
(d) Psychotic disorder
(e) Cognitive disorder
(f) Disturbance in attention
(g) Altered mood
(h) Impairment of psychomotor skills
(i) Inappropriate affect
(j) Overdose
(k) Intentional product misuse
(l) Illusion Serious adverse events included:
(a) Death.
(b) Life-threatening: An AE is life-threatening if the subject was at immediate risk of death from the event as it occurred; i.e., it did not include a reaction that if it had occurred in a more serious form might have caused death. For example, drug-induced hepatitis that resolved without evidence of hepatic failure would not be considered life threatening even though drug-induced hepatitis can be fatal.
(c) Inpatient hospitalization or prolongation of existing hospitalization.
(d) Persistent or significant disability/incapacity.
(e) Congenital anomaly/birth defect in the offspring of a subject who received psilocybin.
(f) Other: Important medical events that may not result in death, be life-threatening, or require hospitalization, may be considered an SAE when, based upon appropriate medical judgment, they may jeopardize the subject and may require medical or surgical intervention to prevent one of the outcomes listed in this definition. Examples of such events are:
   (i) Intensive treatment in an emergency room or at home for allergic bronchospasm.
   (ii) Blood dyscrasias or convulsions that do not result in inpatient hospitalization.
   (iii) Development of drug dependency or drug abuse.

Visits:
Visit 1 (V1): Eligibility Screening (Days −56 to Day −2): All subjects were screened for eligibility in the 8 weeks (i.e., Day −56 to Day −2) prior to Baseline: including medical and psychiatric history, the Mini International Neuropsychiatric Interview (MINI, English version, 7.0.2), McLean Screening Instrument for Borderline Personality Disorder (MSIBPD), SSTS, physical examination, vital signs, body weight, height, body mass index (BMI), 12-lead electrocardiogram (ECG), clinical laboratory tests, urine drug screen, urine pregnancy test, documentation of contraceptive method, review of prior and concomitant medications and recording of AEs.

Visit 2 (V2): Baseline Assessments (Day −1): Subjects completed the Baseline assessments (Day −1 [V2]) 1 day prior to study drug administration including: Tellegen Absorption Scale (TAS), NEO-FFI, SCL-90, PANAS, PET, RMET, SVO, TEQ, SSR, SWM, RVP, SSTS, Paired Associates Learning (PAL), vital signs, urine drug screen, review of prior and concomitant medications and recording of AEs. During this visit, subjects joined in a 2 hour group session with the study psychiatrist, lead therapist, chaperones, and all subjects to be dosed the following day. The subject was informed about what to expect during the session. All questions were answered. Subjects who had additional questions or concerns were able to have a 1:1 preparatory session with the assigned chaperone.

Visit 3 (V3): Drug Administration (Day 0): The subject was asked to eat a light breakfast at least two hours prior to coming to the clinic for study drug administration. On Day 0 (V3), the subject underwent the SSTS, had vital signs obtained, medications reviewed, AEs recorded and eligibility reviewed prior to being randomized to study drug. The study drug was administered to up to six subjects simultaneously in individual beds separated by a curtain. The subject was invited to put on eyeshades and headphones, lie down and listen to calming music for the rest of the session (six hours). The subject was supported 1:1 with a chaperone and supervised by the study psychiatrist and lead therapist.

The effects of psilocybin usually started about 20 to 30 min after administration, becoming most intense in the first 90 to 120 min and gradually subsiding in about 5 to 6 hours. The subjects were asked to remain in the room for the duration of the session regardless of the intensity of the effects, preferably lying down and mostly silent unless they have a concern or need to communicate a discomfort or seek reassurance from the therapist, or use the restroom. A light meal and fruit were available for the subject after the session. After the acute effects of study drug administration had subsided, all subjects were assessed for safety and asked to complete the following assessments: PANAS and 5D-ASC. Medications used, if any, during the study drug administration session, and adverse events were recorded. The subjects also discussed their psilocybin experience with their therapist. The subject was discharged 6 to 8 hours post dose when, in the opinion of the investigator, the acute effects of psilocybin were resolved. After the acute effects of study drug administration subsided, subjects returned home accompanied by a family member, friend, or chaperone. The therapists checked with the subjects by phone at the end of the day to ensure that the subject arrived home safely.

Visit 4 (V4): Safety Assessments (Day 1): Subjects returned to the clinic the next morning (Day 1 [V4]) for safety assessments, including but not limited to: SSTS, vital signs, clinical laboratory tests, review of concomitant medications and AEs and a one-on-one discussion about the subject's experience with the subject's assigned therapist.

Visit 5 (V5): Follow up visit (Day 7 or at Early Termination): Psychometric assessments were completed remotely on Day 7 (V5) or at Early Termination (ET): NEO-FFI, SCL-90, LCI, PET, RMET, SVO, TEQ, SSR, SSTS, SWM, RVP, PAL, review of concomitant medication and recording of AEs. Additionally, at Day 7 (V5) the ERT, IED, OTS, Verbal Fluency and Digit Span Forward tests were conducted.

Visit 6: Follow up visit (Day 28): The SSTS, SWM, RVP, PAL, review of concomitant medication and recording of AEs were obtained at Day 28 (V6).

Visit 7: Follow up Visit (Day 84): The NEO-FFI, SCL-90, LCI, PET, RMET, SVO, TEQ and SSR was obtained remotely at Day 84 (V7). If the subject discontinued the study early, this visit was performed early.

Recording of adverse events and prior/concomitant medication was performed at each visit.

Table 14 summarizes the assessments and procedures that were performed at each visit.

TABLE 14

Schedule of Visits

| | Screening | Baseline | Treatment Period Visit | | | | |
|---|---|---|---|---|---|---|---|
| | V1 | V2 | V3 | V4 | V5 | V6 | V7 (EDS/ET) |
| | | | | Day | | | |
| | −56 to −2 | −1 | 0 | 1 | 7 | 28 | 84 |
| | | | | Allowed Window | | | |
| | | | | | ±1 Day | ±3 Days | ±7 Days |
| | | | Place of Testing | | | | |
| | Clinic | Clinic | Clinic | Clinic | Remote[1] | Remote[1] | Remote[1] |
| Assessments and Procedures | | | | | | | |
| ICF | | | | | | | |
| Medical and Psychiatric History | X | | | | | | |
| MINI | X | | | | | | |
| MSIBPD | X | | | | | | |
| TAS[2] | | X | | | | | |
| NEO-FFI[2] | | X | | | | X | X |
| SCL-90[2] | | X | | | X | | X |
| LCI[2] | | | | | X | | X |
| Eligibility Review | X | X | X[3] | | | | |
| Randomization | | | X[3] | | | | |
| Preparatory Session[4] | | X | X | X[5] | | | |
| Study Drug Administration | | | X | | | | |
| PANAS[2] | | X | X[6] | | | | |
| 5D-ASC[2] | | | X[6] | | | | |
| Social Cognition Panel[2] | | | | | | | |
| PET | | X | | | X | | X |
| RMET | | X | | | X | | X |
| SVO | | X | | | X | | X |
| TEQ | | X | | | X | | X |
| SSR | | X | | | X | | X |

TABLE 14-continued

Schedule of Visits

| | Screening | Baseline | Treatment Period | | | | |
|---|---|---|---|---|---|---|---|
| Visit | V1 | V2 | V3 | V4 | V5 | V6 | V7 (EDS/ET) |
| Day | −56 to −2 | −1 | 0 | 1 | 7 | 28 | 84 |
| Allowed Window | | | | ±1 Day | ±3 Days | ±7 Days | |
| Place of Testing | Clinic | Clinic | Clinic | Clinic | Remote[1] | Remote[1] | Remote[1] |
| Exploratory Assessments | | | | | | | |
| ERT[7] | | | | | X | | |
| IED[7] | | | | | X | | |
| OTS[7] | | | | | X | | |
| Verbal Fluency[8] | | | | | X | | |
| Digit Span Forward[8] | | | | | X | | |
| Safety Assessments | | | | | | | |
| SSTS[2] | X | X | X[3] | X | X | X | |
| SWM[9] | | X | | | X | X | |
| RVP[9] | | X | | | X | X | |
| PAL[9] | | X | | | X | X | |
| Physical Examination | X | | | | | | |
| Vital Signs[10] | X | X | X[3] | X | | | |
| Body Weight, Height and BMI | X | | | | | | |
| 12-lead ECG | X | | | | | | |
| Clinical Laboratory Tests[11] | X | | | X | | | |
| Urine Drug Screen | X | X | | | | | |
| Urine Pregnancy Test[12] | X | X | | | | | |
| Documentation of Contraceptive Method[13] | X | | | | | | |
| Prior/Concomitant Medications[14] | X | X | X | X | X | X | X |
| AE[15] | X | X | X | X | X | X | X |

[1]This session may be done remotely by telephone or in the clinic.
[2]Paper and pencil test.
[3]Obtained prior to study drug administration.
[4]A preparatory session will be conducted in a group session at Baseline (Day −1, V2) and prior to dosing on Day 0 (V3). An individual session will also be conducted at Baseline (Day −1, V2).
[5]A group discussion will be held about the study drug administration experience.
[6]Obtained immediately after study drug administration.
[7]Part of the Cambridge Cognition Panel; to be recorded on the digital platform.
[8]Part of the Cambridge Cognition Panel; to be recorded during the telephone interview.
[9]To be done electronically. V1, subjects will carry out a practice session of the computerized tests, but the data will not be used.
[10]Vital signs (sitting BP, pulse, oral body temperature and respiratory rate) are to be obtained after the subject has been seated for at least 3 min.
[11]Chemistry: albumin, alkaline phosphatase, ALT, amylase, AST, bicarbonate, bilirubin (direct, indirect and total), calcium, chloride, creatine kinase, creatinine, GGT, glucose, LDH, lipase, magnesium, phosphate, potassium, protein-total, sodium, BUN and uric acid.
Haematology: haemoglobin, haematocrit, red blood cell count, mean corpuscular haemoglobin, mean corpuscular volume, mean corpuscular haemoglobin concentration, white blood cell count (with differential) and platelet count.
[12]All females.
[13]For females of childbearing potential and all males; site is to document method of contraception agreed to be used by each subject.
[14]Prior medications will be obtained until dosing of study drug, thereafter, concomitant medications will be recorded.
[15]All AEs occurring after the subject signs the ICF and up to the last study event will be recorded. Any AEs occurring before the start of treatment (i.e., before the administration of the study drug on Day 0 [V3]) will be recorded in the medical history.

Results

Figure 9A:
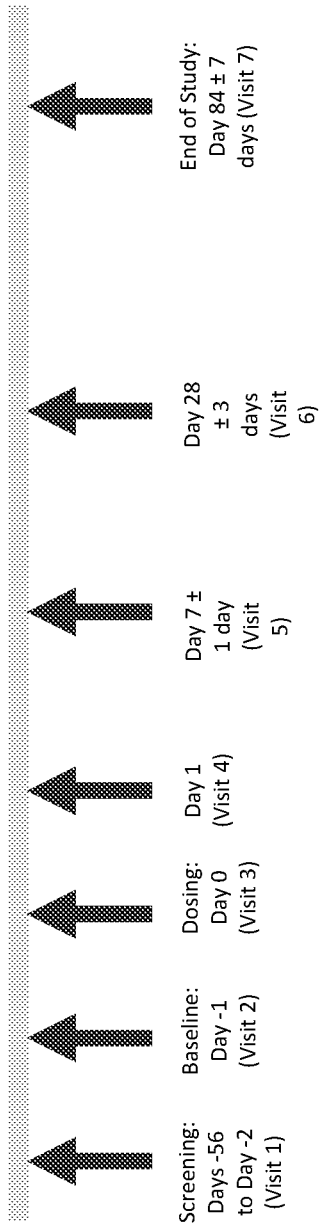
FIG. 9A shows a timeline of the Phase 1 exploratory study, which evaluated psilocybin treatment in healthy volunteer subjects.

The phase I, randomized, double-blind, placebo-controlled study to evaluate the effects of 10 mg and 25 mg COMP360 (psilocybin) compared with placebo in healthy subjects was performed. FIG. 9A shows a timeline of the study.

A total of 89 subjects were enrolled in the study. Of these, 30 participants were randomized to receive 25 mg psilocybin, 30 to 10 mg psilocybin, and 29 to placebo. All subjects randomized to both psilocybin arms completed the study; four (13.8%) placebo-treated subjects did not complete all study visits (three were lost to follow-up and one subject discontinued due to a protocol violation). Some subjects that completed the study did not complete certain cognition and/or emotional processing assessments at all timepoints. In these instances, analyses only included the available data and missing data were not imputed. Table 15 shows the number of subjects from each treatment arm that completed the study.

TABLE 15

Number of Subjects that Completed the Phase 1 Clinical Study

| Parameter | Statistic | Psilocybin (25 mg) (N = 30) | Psilocybin (10 mg) (N = 30) | Placebo (N = 29) | Overall (N = 89) |
|---|---|---|---|---|---|
| Number of randomized population | N | 30 | 30 | 29 | 89 |
| Number of completions | N (%) | 30 (100.0) | 30 (100.0) | 25 (86.2) | 85 (95.5) |
| Number of early terminations | N (%) | 0 | 0 | 4 (13.8) | 4 (4.5) |
| Reason for early terminations | | | | | |
| Lost to follow-up | N (%) | 0 | 0 | 3 (10.3) | 3 (3.4) |
| Protocol violation | N (%) | 0 | 0 | 1 (3.4) | 1 (1.1) |

Abbreviation: N = number of subjects.

During administration of psilocybin, each subject received one on one support from a trained assisting therapist and each dosing session was supervised by a study psychiatrist and a lead therapist. The study drug was administered simultaneously to up to six participants as a single 5-capsule oral dose (10 mg psilocybin: 2×5-mg psilocybin capsules plus 3×placebo capsules; 25 mg psilocybin: 5×5-mg psilocybin capsules; placebo: 5×placebo capsules). Twenty-five dosing sessions were completed, with up to six participants dosed simultaneously per session. Each session lasted approximately 6 to 8 hours with subjects encouraged to relax and engage in introspection for the duration. After the acute effects of the study drug had subsided, subjects were discharged.

Figure 9B:
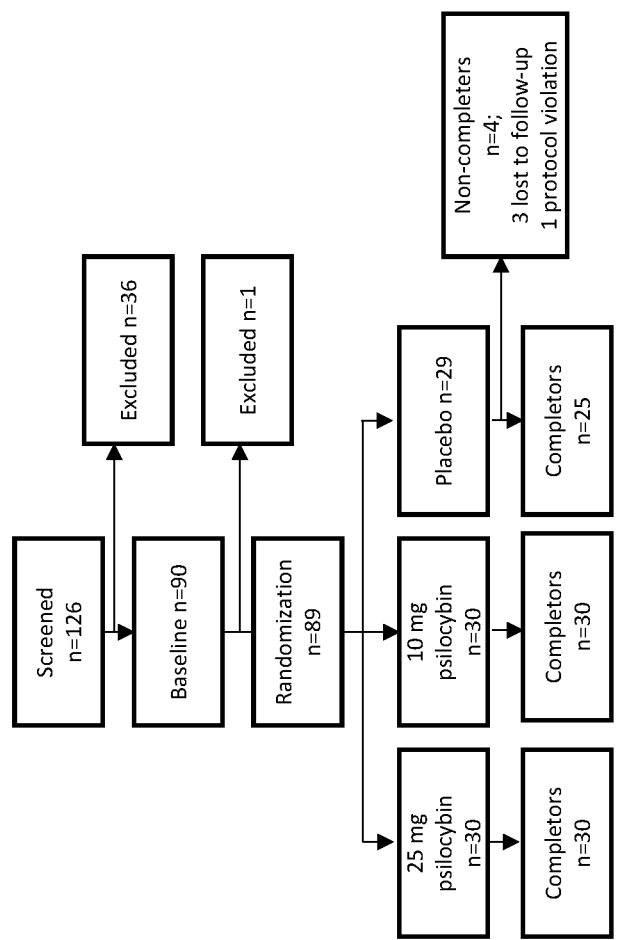
FIG. 9B shows the number of subjects that completed screening (Visit 1), baseline measurements (Visit 2), and drug administration (Visit 3) of the Phase 1 exploratory study.

A diagram of the study is presented in FIG. 9B, which shows the number of subjects that completed screening (Visit 1), baseline measurements (Visit 2), and drug administration (Visit 3).

The mean (SD) age of the subjects was 36.1 (9.06) years with the range of 20 to 59 years. The majority of the subjects were white (72 [80.9%]). Forty-eight (53.9%) of subjects were male and 41 (46.1%) were female. The mean (SD) BMI of the subjects was 23.2 (3.37) kg/m² with the range of 18 to 35 kg/m². Thirty-three (37.1%) subjects had prior psilocybin experience. For subjects with prior psilocybin experience, the last experience was at least one year prior to the signing of the informed consent form. The subjects were highly educated with approximately 97% having an education level over Undergraduate/Higher National Diploma. The average age and gender of the subjects was consistent across the treatment arms.

The demographics of the subjects are revealed in Table 16.

TABLE 16

Demographics of Subjects in Healthy Volunteer Study

| Parameter | 25 mg psilocybin (n = 30) | 10 mg psilocybin (n = 30) | Placebo (n = 29) | Overall (n = 89) |
|---|---|---|---|---|
| Sex, n (%) | | | | |
| Male | 16 (53.3) | 16 (53.3) | 16 (55.2) | 48 (53.9) |
| Female | 14 (46.7) | 14 (46.7) | 13 (44.8) | 41 (46.1) |
| Ethnicity, n (%) | | | | |
| White | 25 (83.3) | 27 (90.0) | 20 (69.0) | 72 (80.9) |
| Asian | 2 (6.7) | 1 (3.3) | 3 (10.3) | 6 (6.7) |
| Mixed | 2 (6.7) | 1 (3.3) | 1 (3.4) | 4 (4.5) |
| Black | — | — | 1 (3.4) | 1 (1.1) |
| Other | 1 (3.3) | 1 (3.3) | 4 (13.8) | 6 (6.7) |
| Age at screening, years | | | | |
| Mean (SD) | 36.6 (10.29) | 36.1 (9.25) | 35.6 (7.69) | 36.1 (9.06) |
| BMI, kg/m² | | | | |
| Mean (SD) | 23.0 (3.74) | 23.0 (2.89) | 23.7 (3.49) | 23.2 (3.37) |
| Prior psilocybin experience n (%) | | | | |
| Yes | 11 (36.7) | 15 (50.0) | 7 (24.1) | 33 (37.1) |
| No | 19 (63.3) | 15 (50.0) | 22 (75.9) | 56 (62.9) |
| Educational level n (%) | | | | |
| A level/NVQ | 2 (6.7) | 1 (3.3) | 0 | 3 (3.4) |
| Undergrad/Higher National Diploma | 9 (30.0) | 11 (36.7) | 10 (34.5) | 30 (33.7) |
| Masters or postgraduate diploma | 16 (53.3) | 16 (53.3) | 15 (51.7) | 47 (52.8) |
| PhD | 3 (10.0) | 2 (6.7) | 4 (13.8) | 9 (10.1) |

Figure 9C:
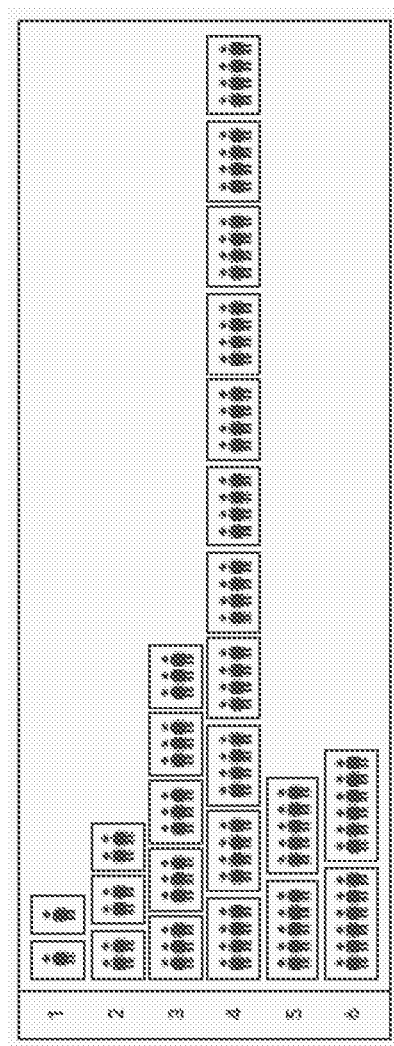
FIG. 9C shows the group sizes of the dosing sessions of the Phase 1 exploratory study.

89 subjects were administered psilocybin or placebo in a dosing session, which contained between 1 and 6 subjects. FIG. 9C shows the group size of the dosing sessions.

All subjects that were administered psilocybin (groups 1 and 2) completed the study.

511 adverse events (AEs) were reported throughout the 12-week duration of the study: 217 in the 25 mg psilocybin arm (reported by 96.7% of subjects); 203 in the 10 mg psilocybin arm (reported by 96.7% of subjects); and 91 in the placebo arm (reported by 89.7% of subjects). Of these, 473 (92.6%) AEs were deemed by the investigators to potentially be related to study treatment, including 208 (95.9%) in the 25 mg psilocybin arm, 188 (92.6%) in the 10 mg psilocybin arm, and 77 (84.6%) in the placebo arm. There were no serious adverse events or adverse events that led to withdrawal.

Overall, the most common treatment-emergent adverse events (TEAEs) by system organ class were Psychiatric disorders, Nervous system disorders, General disorders and administration site conditions, Gastrointestinal disorders and Infections and infestations. The most frequent TEAEs were (number of events in parentheses): Illusion (56), Mood altered (54), Hallucination visual (44), Headache (33), Fatigue (21), Somatic hallucination (19), Euphoric mood (14), Paraesthesia (12), Tension headache (12), Time perception altered (11), Hallucination, auditory (9), Affect lability (9), Feeling of relaxation (8), Emotional disorder (8), Hypoaesthesia (7).

Table 17 shows a summary of treatment-emergent adverse events.

TABLE 17

Summary of Treatment-Emergent Adverse Events

|  | Psilocybin 25 mg (N = 30) | | Psilocybin 10 mg (N = 30) | | Placebo (N = 29) | |
|---|---|---|---|---|---|---|
|  | N (%) | Events | N (%) | Events | N (%) | Events |
| Any TEAE | 29 (96.7) | 217 | 29 (96.7) | 203 | 26 (89.7) | 91 |
| Any serious TEAE | 0 | 0 | 0 | 0 | 0 | 0 |
| Any TEAE related to study treatment | 29 (96.7) | 208 | 29 (96.7) | 188 | 23 (79.3) | 77 |
| Any serious TEAE related to study treatment | 0 | 0 | 0 | 0 | 0 | 0 |
| Any severe TEAE | 10 (33.3) | 29 | 10 (33.3) | 22 | 1 (3.4) | 2 |
| Any Selected TEAE | 27 (90.0) | 106 | 27 (90.0) | 106 | 11 (37.9) | 24 |
| Any TEAE leading to study discontinuation | 0 | 0 | 0 | 0 | 0 | 0 |
| Any TEAE leading to death | 0 | 0 | 0 | 0 | 0 | 0 |

Percentages are based on the number of subjects in each treatment group.
Adverse events are coded using MedDRA.
N = Number of subjects; MedDRA = Medical Dictionary for Regulatory Activities; TEAE = Treatment-emergent adverse event.

Figure 9D:
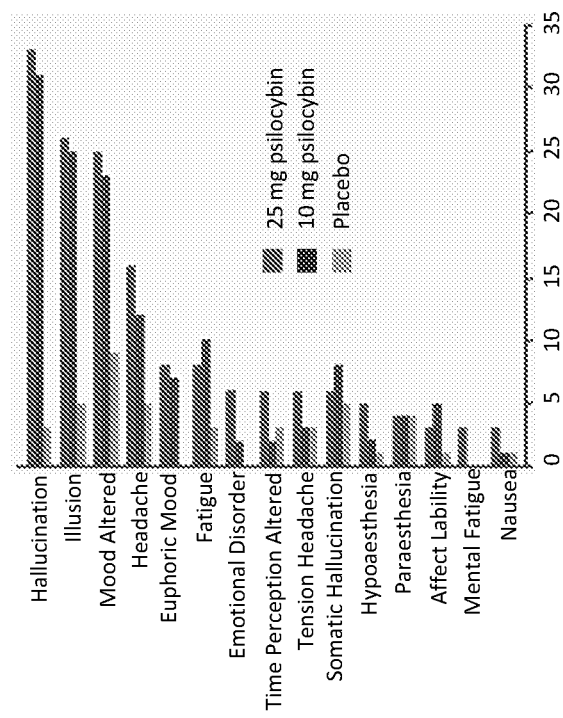
FIG. 9D shows the most frequently reported adverse events of the Phase 1 exploratory study.

A summary of TEAEs by Medical Dictionary for Regulatory Activities (MedDRA) SOC and PTs is presented in Table 18 and FIG. 9D.

TABLE 18

Summary of Treatment-Emergent Adverse Events by MedDRA Primary SOC and PT With ≥10% Subjects in Each Treatment Arm (Safety Population)

| System Organ Class Preferred Term | Psilocybin 25 mg (N = 30) | | Psilocybin 10 mg (N = 30) | | Placebo (N = 29) | |
|---|---|---|---|---|---|---|
|  | N (%) | Events | N (%) | Events | N (%) | Events |
| Any TEAE | 29 (96.7) | 217 | 29 (96.7) | 203 | 26 (89.7) | 91 |
| Gastrointestinal disorders | 5 (16.7) | 5 | 4 (13.3) | 4 | 5 (17.2) | 5 |
| Nausea | 3 (10.0) | 3 | 1 (3.3) | 1 | 1 (3.4) | 1 |
| General disorders and administration site conditions | 15 (50.0) | 18 | 17 (56.7) | 27 | 7 (24.1) | 7 |
| Fatigue | 8 (26.7) | 8 | 9 (30.0) | 10 | 3 (10.3) | 3 |
| Feeling abnormal | 0 | 0 | 4 (13.3) | 4 | 0 | 0 |
| Feeling of relaxation | 1 (3.3) | 1 | 3 (10.0) | 5 | 2 (6.9) | 2 |
| Infections and infestations | 4 (13.3) | 4 | 4 (13.3) | 4 | 5 (17.2) | 5 |
| Investigations | 1 (3.3) | 1 | 2 (6.7) | 2 | 4 (13.8) | 5 |
| Musculoskeletal and connective tissue disorders | 3 (10.0) | 4 | 1 (3.3) | 1 | 3 (10.3) | 3 |
| Nervous system disorders | 25 (83.3) | 43 | 21 (70.0) | 35 | 12 (41.4) | 16 |
| Headache | 15 (50.0) | 16 | 9 (30.0) | 12 | 5 (17.2) | 5 |
| Hypoaesthesia | 3 (10.0) | 4 | 2 (6.7) | 2 | 1 (3.4) | 1 |
| Paraesthesia | 4 (13.3) | 4 | 4 (13.3) | 4 | 4 (13.8) | 4 |
| Tension headache | 6 (20.0) | 6 | 3 (10.0) | 3 | 3 (10.3) | 3 |
| Psychiatric disorders | 29 (96.7) | 135 | 27 (90.0) | 121 | 16 (55.2) | 44 |
| Affect lability | 3 (10.0) | 3 | 5 (16.7) | 5 | 1 (3.4) | 1 |
| Emotional disorder | 5 (16.7) | 6 | 2 (6.7) | 2 | 0 | 0 |
| Euphoric mood | 7 (23.3) | 8 | 7 (23.3) | 7 | 0 | 0 |
| Hallucination | 2 (6.7) | 2 | 3 (10.0) | 3 | 0 | 0 |
| Hallucination, auditory | 4 (13.3) | 4 | 4 (13.3) | 4 | 1 (3.4) | 1 |
| Hallucination, tactile | 4 (13.3) | 4 | 2 (6.7) | 2 | 0 | 0 |
| Hallucination, visual | 21 (70.0) | 22 | 18 (60.0) | 20 | 2 (6.9) | 2 |
| Illusion | 18 (60.0) | 26 | 19 (63.3) | 25 | 4 (13.8) | 5 |
| Mental fatigue | 3 (10.0) | 3 | 0 | 0 | 0 | 0 |
| Mood altered | 15 (50.0) | 25 | 13 (43.3) | 23 | 6 (20.7) | 9 |
| Somatic hallucination | 5 (16.7) | 6 | 8 (26.7) | 8 | 4 (13.8) | 5 |
| Time perception altered | 6 (20.0) | 6 | 2 (6.7) | 2 | 3 (10.3) | 3 |
| Respiratory, thoracic and mediastinal disorders | 3 (10.0) | 3 | 0 | 0 | 2 (6.9) | 2 |

Percentages are based on the number of subjects in each treatment group.
Adverse events are coded using MedDRA.
N = Number of subjects; MedDRA = Medical Dictionary for Regulatory Activities; PT = Preferred term; SOC = System organ class; TEAE = Treatment-emergent adverse event.

The majority of TEAEs were of mild to moderate severity (Table 19). The incidence of severe TEAEs was higher in the subjects receiving psilocybin (both 10 mg and 25 mg) compared to placebo (29 in the psilocybin 25 mg arm, 22 in the psilocybin 10 mg arm, and two in the placebo arm).

The majority of the severe TEAEs were psychiatric disorders for both the psilocybin 10 mg and 25 mg arms. The incidence of Illusion, Hallucination (visual), Mood altered, Headache, Fatigue and Euphoric mood were higher in the subjects receiving psilocybin (both 10 and 25 mg) compared to placebo.

TABLE 19

Summary of TEAES by MedDRA Primary System Organ Class (SOC) and preferred term (PT) with ≥10% Subjects in Each Treatment Arm by Worst Severity (Safety Population)

| System Organ Class | Worst | Psilocybin 25 mg (N = 30) | | Psilocybin 10 mg (N = 30) | | Placebo (N = 29) | |
| --- | --- | --- | --- | --- | --- | --- | --- |
| Preferred Term | Severity | N (%) | Events | N (%) | Events | N (%) | Events |
| Any TEAE | Mild | 3 (10.0) | 14 | 6 (20.0) | 12 | 16 (55.2) | 40 |
|  | Moderate | 16 (53.3) | 52 | 13 (43.3) | 38 | 9 (31.0) | 23 |
|  | Severe | 10 (33.3) | 29 | 10 (33.3) | 22 | 1 (3.4) | 2 |
| Gastrointestinal disorders | Mild | 4 (13.3) | 4 | 3 (10.0) | 3 | 3 (10.3) | 3 |
|  | Moderate | 1 (3.3) | 1 | 1 (3.3) | 1 | 2 (6.9) | 2 |
|  | Severe | 0 | 0 | 0 | 0 | 0 | 0 |
| General disorders and administration site conditions | Mild | 8 (26.7) | 8 | 13 (43.3) | 17 | 3 (10.3) | 3 |
|  | Moderate | 6 (20.0) | 7 | 3 (10.0) | 6 | 3 (10.3) | 3 |
|  | Severe | 1 (3.3) | 1 | 1 (3.3) | 1 | 1 (3.4) | 1 |
| Fatigue | Mild | 3 (10.0) | 3 | 6 (20.0) | 6 | 2 (6.9) | 2 |
|  | Moderate | 5 (16.7) | 5 | 2 (6.7) | 3 | 1 (3.4) | 1 |
|  | Severe | 0 | 0 | 1 (3.3) | 1 | 0 | 0 |
| Feeling abnormal | Mild | 0 | 0 | 3 (10.0) | 3 | 0 | 0 |
|  | Moderate | 0 | 0 | 1 (3.3) | 1 | 0 | 0 |
|  | Severe | 0 | 0 | 0 | 0 | 0 | 0 |
| Infections and infestations | Mild | 4 (13.3) | 4 | 2 (6.7) | 2 | 4 (13.8) | 4 |
|  | Moderate | 0 | 0 | 2 (6.7) | 2 | 1 (3.4) | 1 |
|  | Severe | 0 | 0 | 0 | 0 | 0 | 0 |
| Investigations | Mild | 1 (3.3) | 1 | 2 (6.7) | 2 | 3 (10.3) | 4 |
|  | Moderate | 0 | 0 | 0 | 0 | 1 (3.4) | 1 |
|  | Severe | 0 | 0 | 0 | 0 | 0 | 0 |
| Musculoskeletal and connective tissue disorders | Mild | 2 (6.7) | 3 | 0 | 0 | 3 (10.3) | 3 |
|  | Moderate | 1 (3.3) | 1 | 1 (3.3) | 1 | 0 | 0 |
|  | Severe | 0 | 0 | 0 | 0 | 0 | 0 |
| Nervous system disorders | Mild | 16 (53.3) | 24 | 15 (50.0) | 23 | 11 (37.9) | 15 |
|  | Moderate | 8 (26.7) | 10 | 6 (20.0) | 8 | 1 (3.4) | 1 |
|  | Severe | 1 (3.3) | 1 | 0 | 0 | 0 | 0 |
| Headache | Mild | 10 (33.3) | 10 | 9 (30.0) | 12 | 4 (13.8) | 4 |
|  | Moderate | 5 (16.7) | 5 | 0 | 0 | 1 (3.4) | 1 |
|  | Severe | 0 | 0 | 0 | 0 | 0 | 0 |
| Hypoaesthesia | Mild | 3 (10.0) | 4 | 2 (6.7) | 2 | 1 (3.4) | 1 |
|  | Moderate | 0 | 0 | 0 | 0 | 0 | 0 |
|  | Severe | 0 | 0 | 0 | 0 | 0 | 0 |
| Paraesthesia | Mild | 3 (10.0) | 3 | 4 (13.3) | 4 | 4 (13.8) | 4 |
|  | Moderate | 1 (3.3) | 1 | 0 | 0 | 0 | 0 |
|  | Severe | 0 | 0 | 0 | 0 | 0 | 0 |
| Tension headache | Mild | 4 (13.3) | 4 | 1 (3.3) | 1 | 3 (10.3) | 3 |
|  | Moderate | 2 (6.7) | 2 | 2 (6.7) | 2 | 0 | 0 |
|  | Severe | 0 | 0 | 0 | 0 | 0 | 0 |
| Psychiatric disorders | Mild | 4 (13.3) | 5 | 4 (13.3) | 6 | 8 (27.6) | 13 |
|  | Moderate | 16 (53.3) | 45 | 13 (43.3) | 29 | 7 (24.1) | 15 |
|  | Severe | 9 (30.0) | 27 | 10 (33.3) | 21 | 1 (3.4) | 1 |
| Affect lability | Mild | 2 (6.7) | 2 | 3 (10.0) | 3 | 0 | 0 |
|  | Moderate | 1 (3.3) | 1 | 2 (6.7) | 2 | 1 (3.4) | 1 |
|  | Severe | 0 | 0 | 0 | 0 | 0 | 0 |
| Emotional disorder | Mild | 1 (3.3) | 1 | 1 (3.3) | 1 | 0 | 0 |
|  | Moderate | 4 (13.3) | 5 | 1 (3.3) | 1 | 0 | 0 |
|  | Severe | 0 | 0 | 0 | 0 | 0 | 0 |
| Euphoric mood | Mild | 3 (10.0) | 3 | 0 | 0 | 0 | 0 |
|  | Moderate | 4 (13.3) | 4 | 6 (20.0) | 6 | 0 | 0 |
|  | Severe | 0 | 0 | 1 (3.3) | 1 | 0 | 0 |
| Hallucination | Mild | 0 | 0 | 0 | 0 | 0 | 0 |
|  | Moderate | 2 (6.7) | 2 | 3 (10.0) | 3 | 0 | 0 |
|  | Severe | 0 | 0 | 0 | 0 | 0 | 0 |
| Hallucination, auditory | Mild | 1 (3.3) | 1 | 1 (3.3) | 1 | 0 | 0 |
|  | Moderate | 3 (10.0) | 3 | 1 (3.3) | 1 | 1 (3.4) | 1 |
|  | Severe | 0 | 0 | 2 (6.7) | 2 | 0 | 0 |
| Hallucination, visual | Mild | 3 (10.0) | 3 | 3 (10.0) | 3 | 1 (3.4) | 1 |
|  | Moderate | 13 (43.3) | 13 | 8 (26.7) | 8 | 1 (3.4) | 1 |
|  | Severe | 5 (16.7) | 5 | 7 (23.3) | 7 | 0 | 0 |
| Illusion | Mild | 3 (10.0) | 4 | 7 (23.3) | 7 | 3 (10.3) | 4 |
|  | Moderate | 10 (33.3) | 12 | 12 (40.0) | 16 | 0 | 0 |
|  | Severe | 5 (16.7) | 7 | 0 | 0 | 1 (3.4) | 1 |

TABLE 19-continued

Summary of TEAES by MedDRA Primary System Organ Class (SOC) and preferred term (PT) with ≥10% Subjects in Each Treatment Arm by Worst Severity (Safety Population)

| System Organ Class Preferred Term | Worst Severity | Psilocybin 25 mg (N = 30) N (%) | Events | Psilocybin 10 mg (N = 30) N (%) | Events | Placebo (N = 29) N (%) | Events |
|---|---|---|---|---|---|---|---|
| Mood altered | Mild | 2 (6.7) | 3 | 2 (6.7) | 2 | 0 | 0 |
| | Moderate | 6 (20.0) | 7 | 5 (16.7) | 8 | 6 (20.7) | 6 |
| | Severe | 7 (23.3) | 9 | 6 (20.0) | 9 | 0 | 0 |
| Somatic hallucination | Mild | 2 (6.7) | 2 | 1 (3.3) | 1 | 4 (13.8) | 5 |
| | Moderate | 2 (6.7) | 2 | 7 (23.3) | 7 | 0 | 0 |
| | Severe | 1 (3.3) | 2 | 0 | 0 | 0 | 0 |
| Time perception altered | Mild | 2 (6.7) | 2 | 1 (3.3) | 1 | 3 (10.3) | 3 |
| | Moderate | 4 (13.3) | 4 | 1 (3.3) | 1 | 0 | 0 |
| | Severe | 0 | 0 | 0 | 0 | 0 | 0 |

Percentages are based on the number of subjects in each treatment group.
Adverse events are coded using MedDRA.
Abbreviations: N = Number of subjects; MedDRA = Medical Dictionary for Regulatory Activities; PT = Preferred term; SOC = System organ class; TEAE = Treatment-emergent adverse event.

Selected adverse events are displayed in Table 20. The most frequent of these adverse events were Mood altered (n=57), Illusion (n=56), Hallucination visual (n=44), Somatic hallucination (n=19) and Euphoric mood (n=15).

TABLE 20

Summary of selected TEAEs of by MedDRA primary system organ class and preferred term

| System Organ Class Preferred Term | Psilocybin 25 mg (N = 30) N (%) | Events | Psilocybin 10 mg (N = 30) N (%) | Events | Placebo (N = 29) N (%) | Events |
|---|---|---|---|---|---|---|
| Selected TEAE | 27 (90.0) | 106 | 27 (90.0) | 106 | 11 (37.9) | 24 |
| Nervous system disorders | 0 | 0 | 2 (6.7) | 2 | 0 | 0 |
| Memory impairment | 0 | 0 | 1 (3.3) | 1 | 0 | 0 |
| Psychomotor skills impaired | 0 | 0 | 1 (3.3) | 1 | 0 | 0 |
| Psychiatric disorders | 27 (90.0) | 106 | 27 (90.0) | 104 | 11 (37.9) | 24 |
| Affect lability | 3 (10.0) | 3 | 5 (16.7) | 5 | 1 (3.4) | 1 |
| Change in sustained attention | 0 | 0 | 2 (6.7) | 2 | 0 | 0 |
| Depressed mood | 2 (6.7) | 2 | 1 (3.3) | 1 | 1 (3.4) | 1 |
| Dissociative identity disorder | 2 (6.7) | 2 | 1 (3.3) | 2 | 0 | 0 |
| Euphoric mood | 7 (23.3) | 8 | 7 (23.3) | 7 | 0 | 0 |
| Hallucination | 2 (6.7) | 2 | 3 (10.0) | 3 | 0 | 0 |
| Hallucination, auditory | 4 (13.3) | 4 | 4 (13.3) | 4 | 1 (3.4) | 1 |
| Hallucination, gustatory | 0 | 0 | 1 (3.3) | 1 | 0 | 0 |
| Hallucination, olfactory | 1 (3.3) | 1 | 1 (3.3) | 1 | 0 | 0 |
| Hallucination, tactile | 4 (13.3) | 4 | 2 (6.7) | 2 | 0 | 0 |
| Hallucination, visual | 21 (70.0) | 22 | 18 (60.0) | 20 | 2 (6.9) | 2 |
| Somatic hallucination | 5 (16.7) | 6 | 8 (26.7) | 8 | 4 (13.8) | 5 |
| Illusion[a] | 18 (60.0) | 26 | 19 (63.3) | 25 | 4 (13.8) | 5 |
| Mood altered | 15 (50.0) | 25 | 13 (43.3) | 23 | 6 (20.7) | 9 |
| Substance-induced psychotic disorder[b] | 1 (3.3) | 1 | 0 | 0 | 0 | 0 |

Percentages are based on the number of subjects in each treatment group.
Adverse events are coded using MedDRA.
Abbreviations: N = Number of subjects; MedDRA = Medical Dictionary for Regulatory Activities; PT = Preferred term; SOC = System organ class; TEAE = Treatment-emergent adverse event.
[b]This subject became behaviorally disinhibited during the acute drug experience. After a medical assessment, 2.5 mg oromucosal midazolam was administered. The subject recovered with no sequelae and was discharged 11 hours after receiving the study intervention. This event was not considered to be an SAE, and no clinically significant ongoing effects were noted at follow-up.

Mood alteration (MedDRA term is 'mood altered') was one of the most frequently reported adverse events. 57 AEs of mood alteration were reported (grouped according to regulatory requirements in MedDRA terms).

Table 21 shows the frequency of specific 'mood altered' AEs. Most 'mood altered' AEs were positive or neutral in nature (96%).

TABLE 21

Reported Mood Altered Events (ranked by incidence in the 25 mg psilocybin group)

| Description of 'Mood altered' Event | 25 mg psilocybin (n = 30) | 10 mg psilocybin (n = 30) | Placebo (n = 29) | Overall (n = 89) |
|---|---|---|---|---|
| Introspection | 8 | 5 | 2 | 15 |
| Reflections | 4 | 3 | 2 | 9 |
| Sense of oneness | 2 | 4 | 0 | 6 |
| Increased empathy | 2 | 2 | 0 | 4 |
| Contemplative state | 1 | 1 | 0 | 2 |
| Laughter | 1 | 1 | 0 | 2 |
| Clarity of thought | 1 | 0 | 0 | 1 |
| Increased compassion | 1 | 0 | 0 | 1 |
| Increased creativity | 1 | 0 | 0 | 1 |
| Increased sense of connectedness | 1 | 0 | 0 | 1 |
| More socially upbeat | 1 | 0 | 0 | 1 |
| Saw themselves from a new perspective | 1 | 0 | 0 | 1 |
| Being less judgmental | 0 | 1 | 0 | 1 |
| Feeling more moody/sensitive | 0 | 1 | 0 | 1 |
| Feeling rested | 0 | 1 | 0 | 1 |
| Increased wit | 0 | 1 | 0 | 1 |
| Sense of openness | 0 | 1 | 0 | 1 |
| Unusual appreciation of music | 0 | 0 | 1 | 1 |
| Calm | 0 | 0 | 1 | 1 |
| Feeling of adrenaline release | 0 | 0 | 1 | 1 |
| Negative mood | 0 | 0 | 1 | 1 |

Figure 9E:
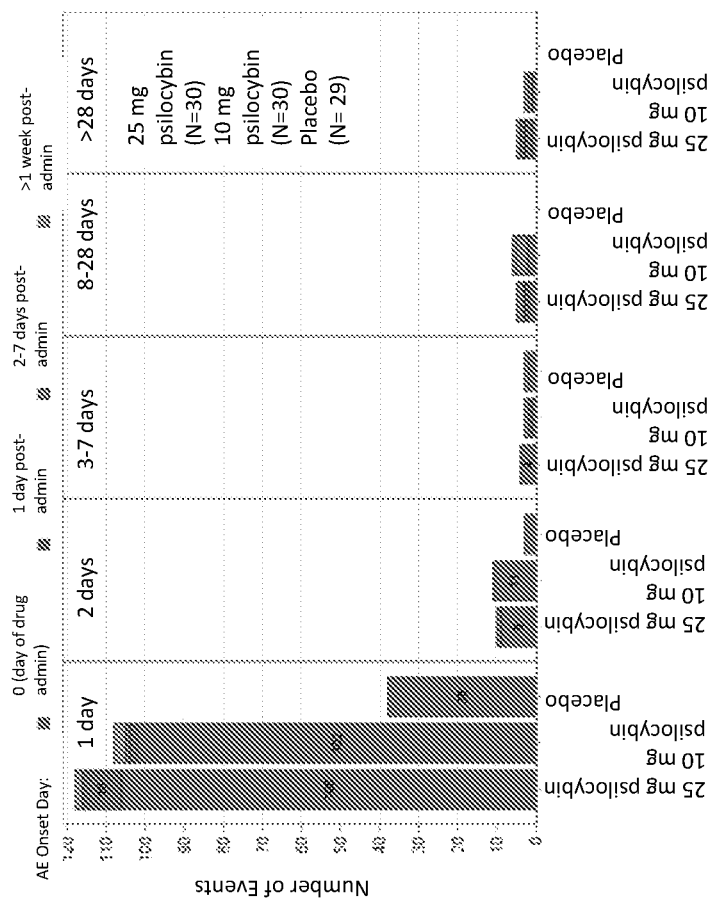
FIG. 9E shows the duration of adverse events of the Phase 1 exploratory study.

The median duration of adverse events in all treatment arms across the 12-week trial was one day, as shown in FIG. 9E. 67% of all adverse events appeared and resolved on day 0 (day of dosing). 92% of adverse events likely to be psychedelic in nature were resolved on the day of onset or within a day of onset The efficacy of psilocybin was assessed using the Cambridge Neuropsychological Test Automated Battery (CANTAB). The CANTAB variables analysed are shown in Table 22.

TABLE 22

CANTAB Variables Analyzed During Phase 1 Study

| Test | Domain Tested | Outcome Variable | Variable Code |
|---|---|---|---|
| Primary and secondary efficacy and safety | | | |
| PAL, SWM, RVP (Safety) | Global cognition | CANTAB global functioning composite | CANTAB composite (+ve) |
| PAL | Episodic memory | Total errors adjusted | PALTEA (−ve) |
| SWM | Working memory | Between errors | SWMBE (−ve) |
| SWM | Executive function | Strategy | SWMS (−ve) |
| RVP | Sustained attention | A' (A prime) | RVPA (+ve) |

TABLE 22-continued

CANTAB Variables Analyzed During Phase 1 Study

| Test | Domain Tested | Outcome Variable | Variable Code |
|---|---|---|---|
| Exploratory efficacy | | | |
| ERT | Emotion perception | Percent correct | ERTPC (+ve) |
| OTS | Planning | Problems solved on first choice | OTSPSFC (+ve) |
| IED | Cognitive flexibility | Total errors | IEDYERT (−ve) |

Figure 9F:
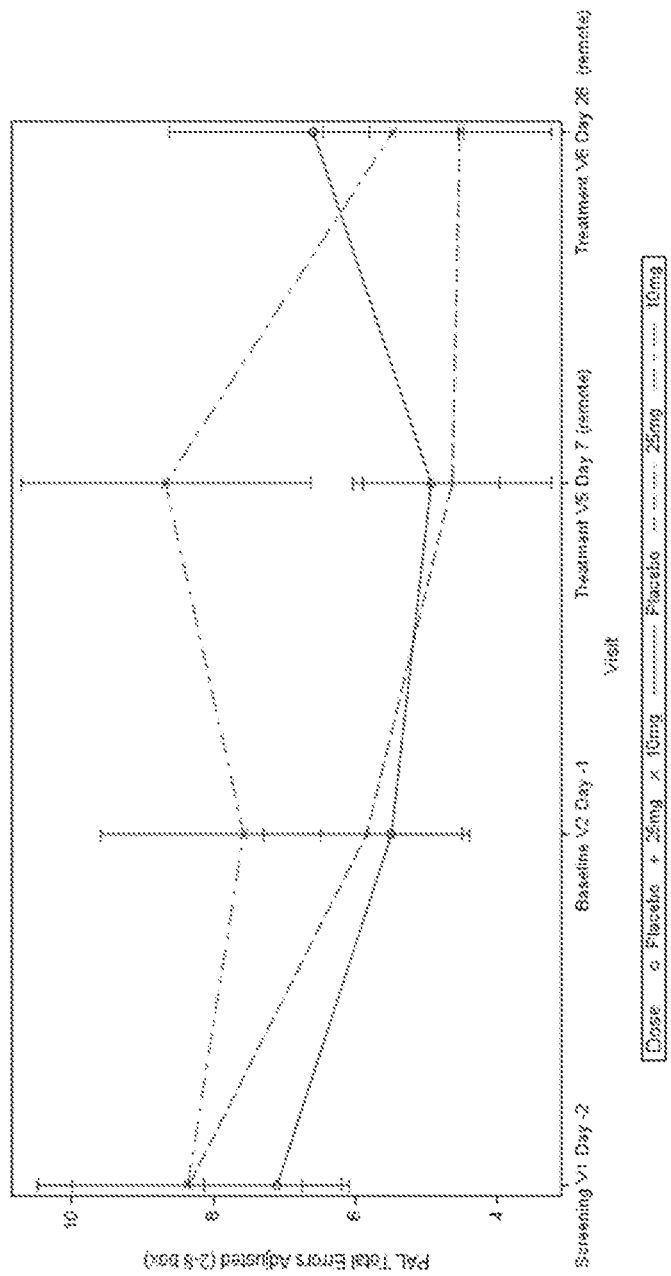
FIG. 9F shows a graph of the Paired Associates Learning Total Errors Adjusted (PALTEA) score of the Cambridge Neuropsychological Test Automated Battery (CANTAB) over time for the psilocybin-treated and placebo-treated subjects of the Phase 1 exploratory study.
Figure 9G:
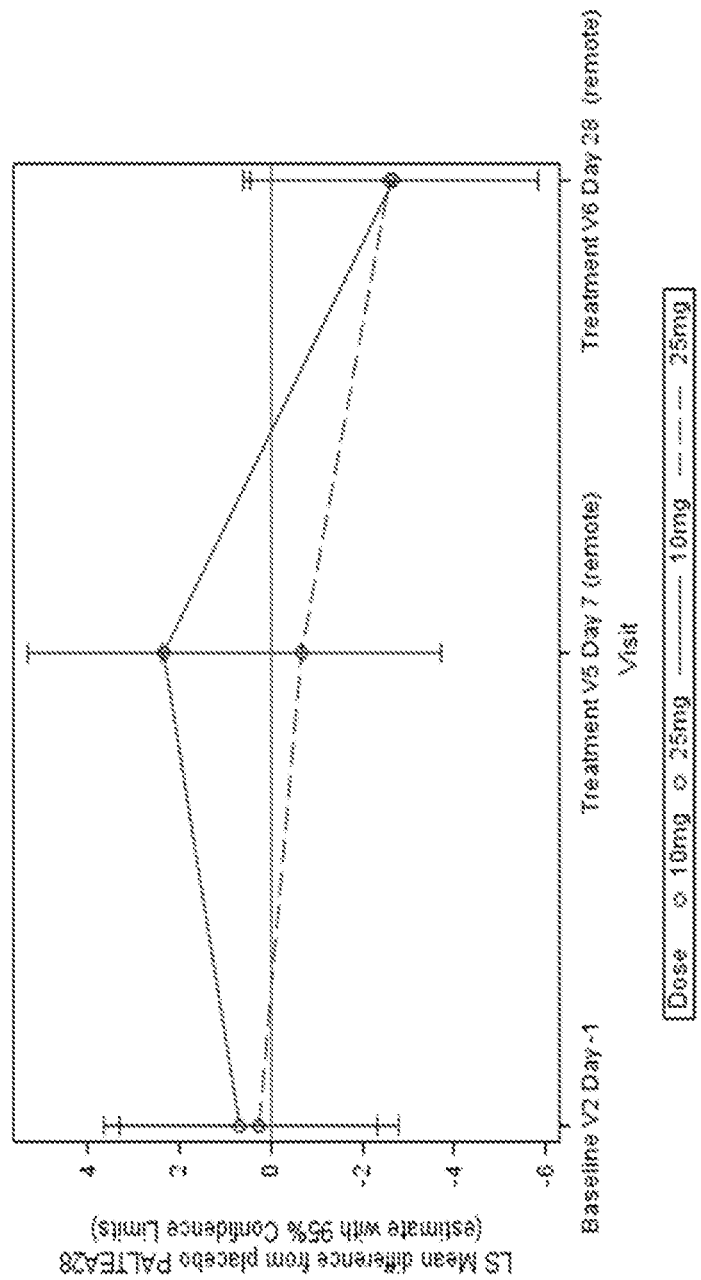
FIG. 9G shows a graph of the least squares mean difference from placebo for the PALTEA score of the CANTAB over time for the psilocybin-treated subjects of the Phase 1 exploratory study.

Abbreviations: CANTAB = Cambridge Neuropsychological Test Automated Battery; ERT = Emotion Recognition Test; ERTPC = Emotion Recognition Test percent correct; IED = Intra-Extra Dimensional Set Shift; IEDYERT = Intra-Extra Dimensional Set Shift total errors; OTS = One Touch Stockings of Cambridge; OTSPSFC = One Touch Stockings of Cambridge problems solved on first choice; PAL = Paired Associates Learning; PALTEA = Paired Associates Learning total errors adjusted; RVP = Rapid Visual Information Processing; RVPA = Rapid Visual Information Processing A prime; SWM = Spatial Working Memory; SWMBE = Spatial Working Memory between errors; SWMS = Spatial Working Memory strategy.
−ve lower scores indicate better performance
+ve higher scores indicate better performance The Paired Associates Learning (PAL) test of the CANTAB was used to assess the effect of psilocybin on memory. The result of the PAL was reported as PAL Total Errors Adjusted (PALTEA). A lower score on the PALTEA indicated better performance (lower error count) and a positive change from baseline indicated worse performance (higher error count). On average, there was a numeric improvement in performance for the 10 mg and 25 mg psilocybin groups from Baseline to Day 28 whereas the placebo group showed a decrease in performance from Baseline to Day 28 as shown in FIG. 9F. Both the 10 mg psilocybin and 25 mg psilocybin groups showed on average of about a 2-point improvement in performance compared to the placebo group (LS mean difference from placebo) at Day 28 as shown in FIG. 9G.

Figure 9H:
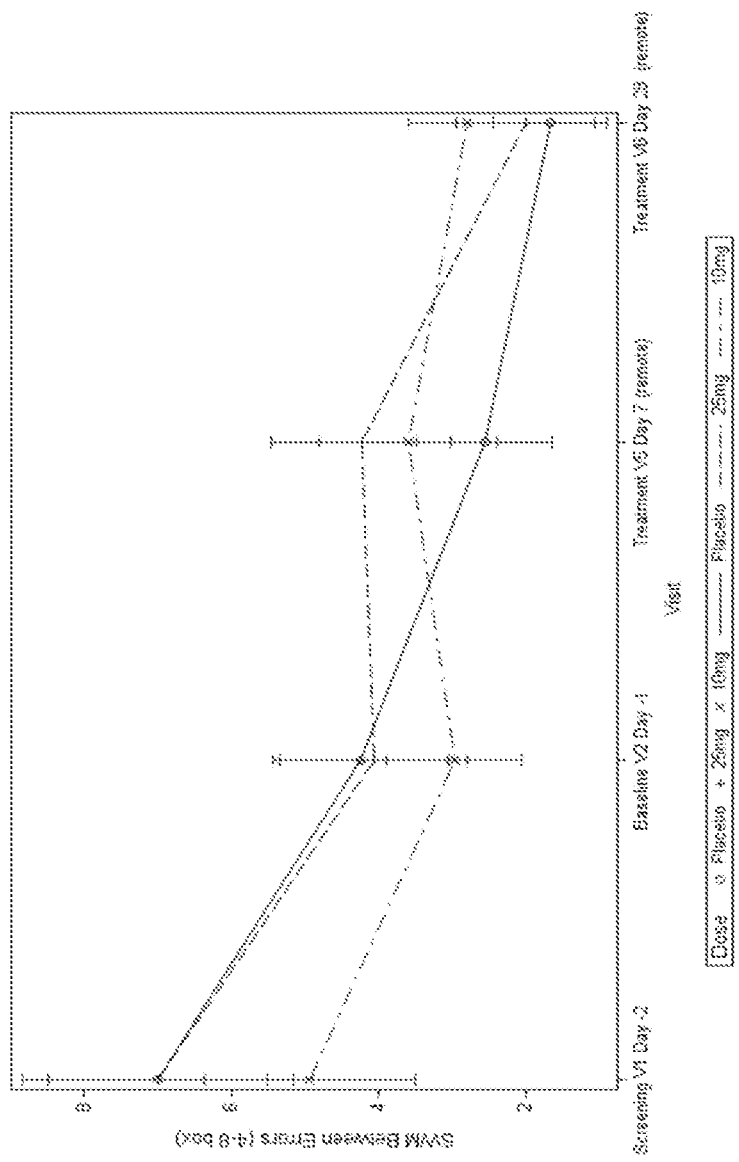
FIG. 9H shows a graph of the spatial working memory between errors (SWMBE) score of the CANTAB over time for the psilocybin-treated and placebo-treated subjects of the Phase 1 exploratory study.
Figure 9I:
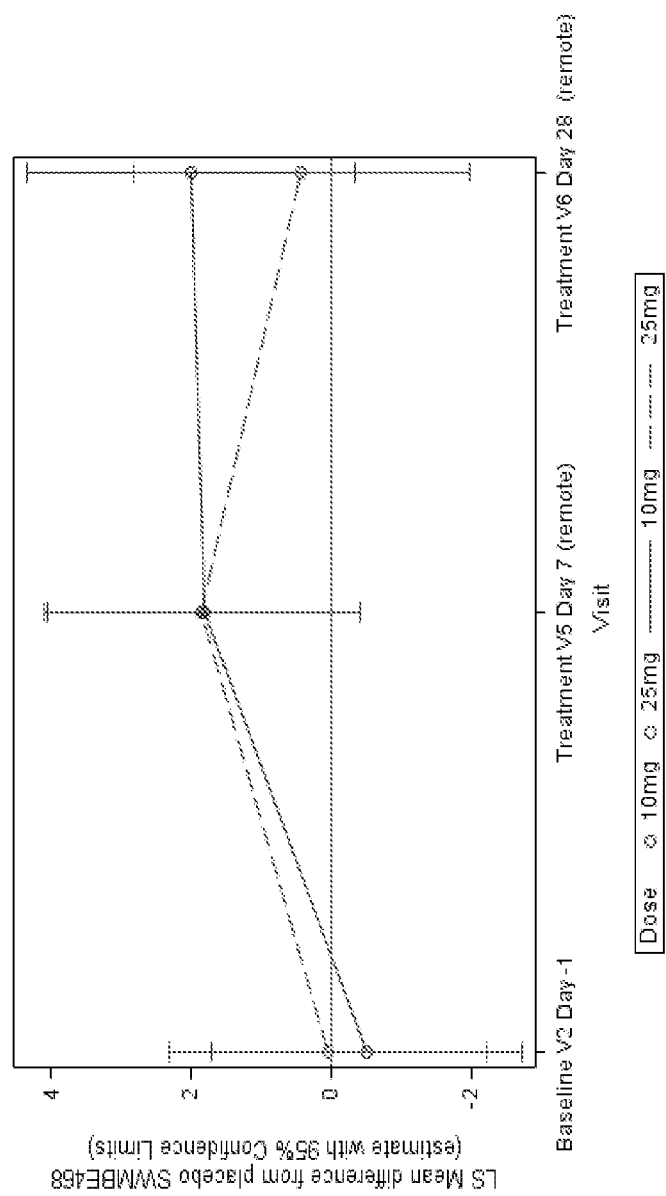
FIG. 9I shows a graph of the least squares mean difference from placebo for the SWMBE score of the CANTAB over time for the psilocybin-treated subjects of the Phase 1 exploratory study.

The Spatial Working Memory (SWM) of CANTAB was also used to assess the effect of psilocybin on memory. The result of the SWM was reported as Spatial Working Memory between errors (SWMBE). A lower SWMBE score indicated better performance. Therefore, a negative change from baseline indicates better performance (lower error count), and a positive change from baseline indicates worse performance (higher error count). On average, performance improved numerically across psilocybin-treated and placebo treated groups from Baseline to Day 28, with the 25 mg psilocybin group showing a similar performance to that of placebo. The 10 mg group improved less, on average, with a higher error score at Day 28 than placebo as shown in FIG. 9H. The least squares (LS) mean difference indicated the 10 mg group performed less well on average than the placebo group at both Day 7 and Day 28, whilst the 25 mg group performs similarly to the placebo group at Day 28 (FIG. 9I). However, for these effects there was insufficient evidence of change.

Figure 9J:
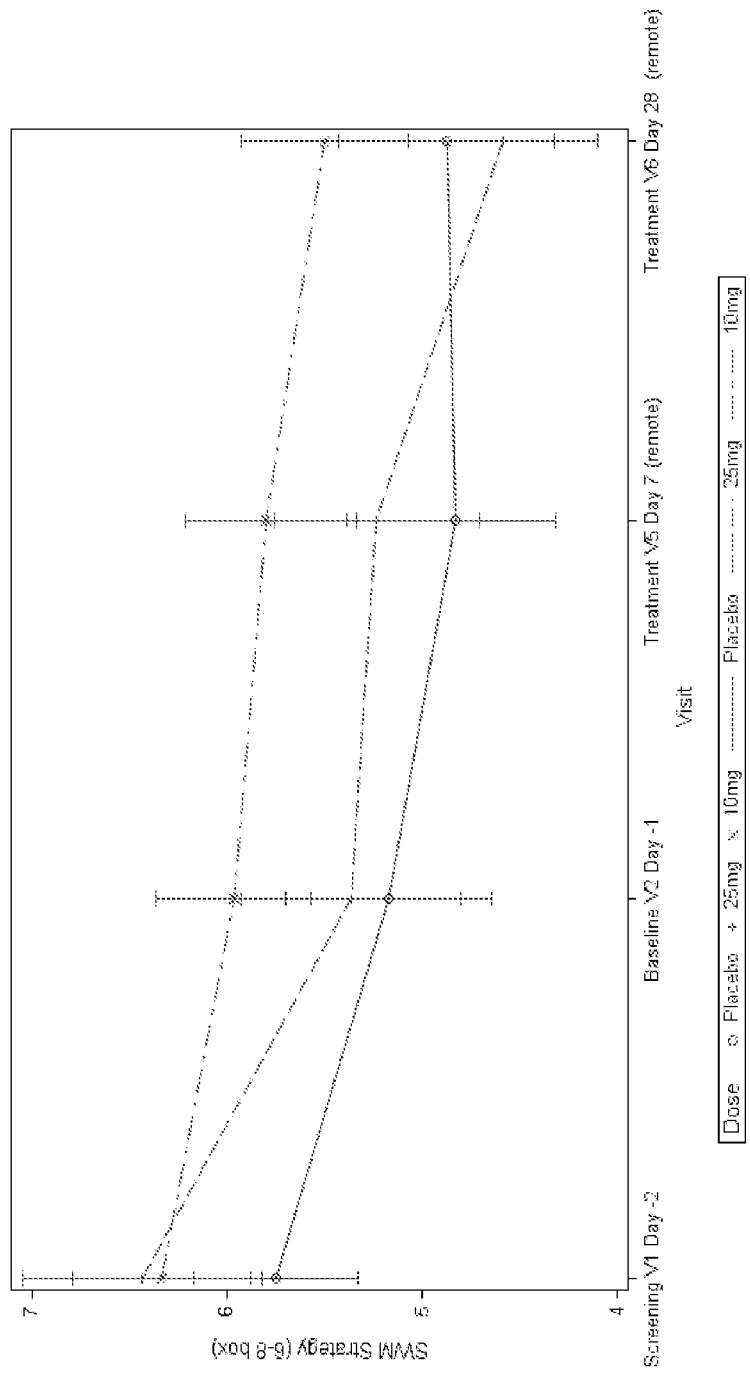
FIG. 9J shows a graph of the spatial working memory strategy (SWM strategy) score of the CANTAB over time for the psilocybin-treated and placebo-treated subjects of the Phase 1 exploratory study.
Figure 9K:
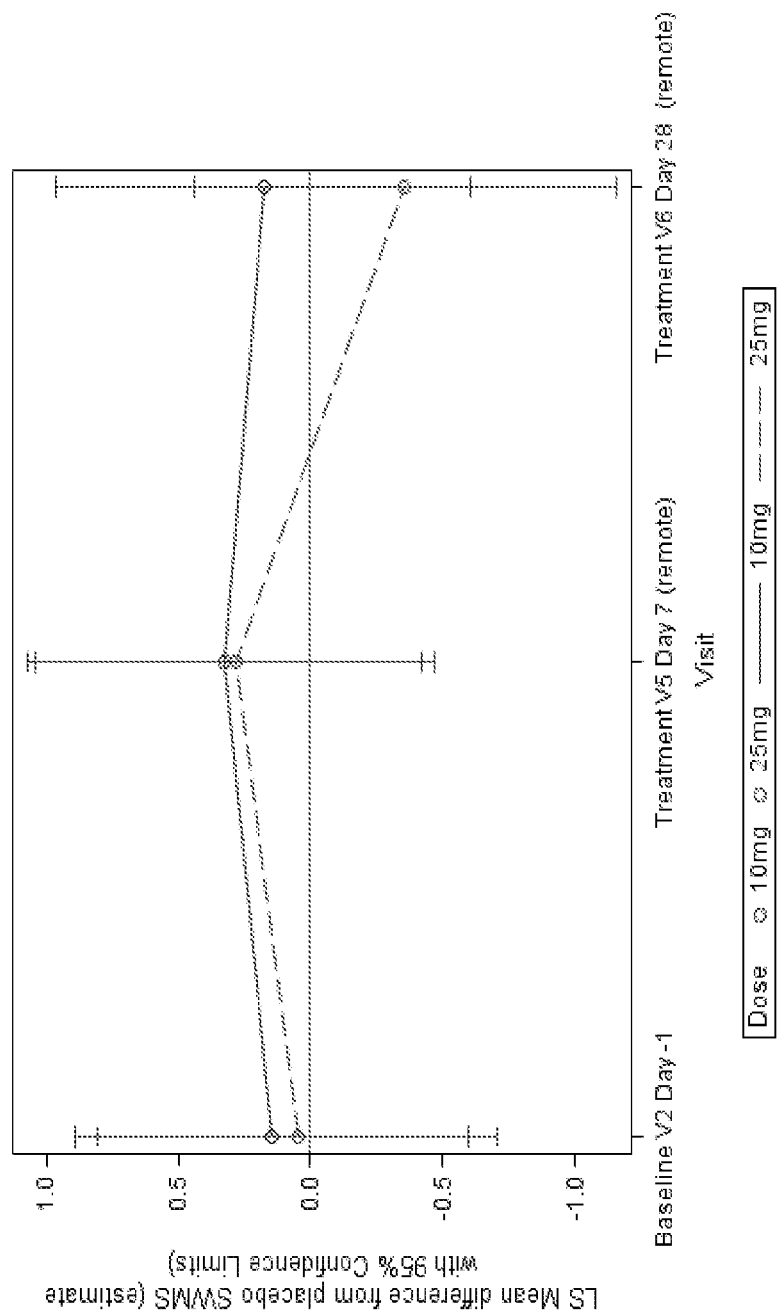
FIG. 9K shows a graph of the least squares mean difference from placebo for the SWM strategy score of the CANTAB over time for the psilocybin-treated subjects of the Phase 1 exploratory study.
Figure 9L:
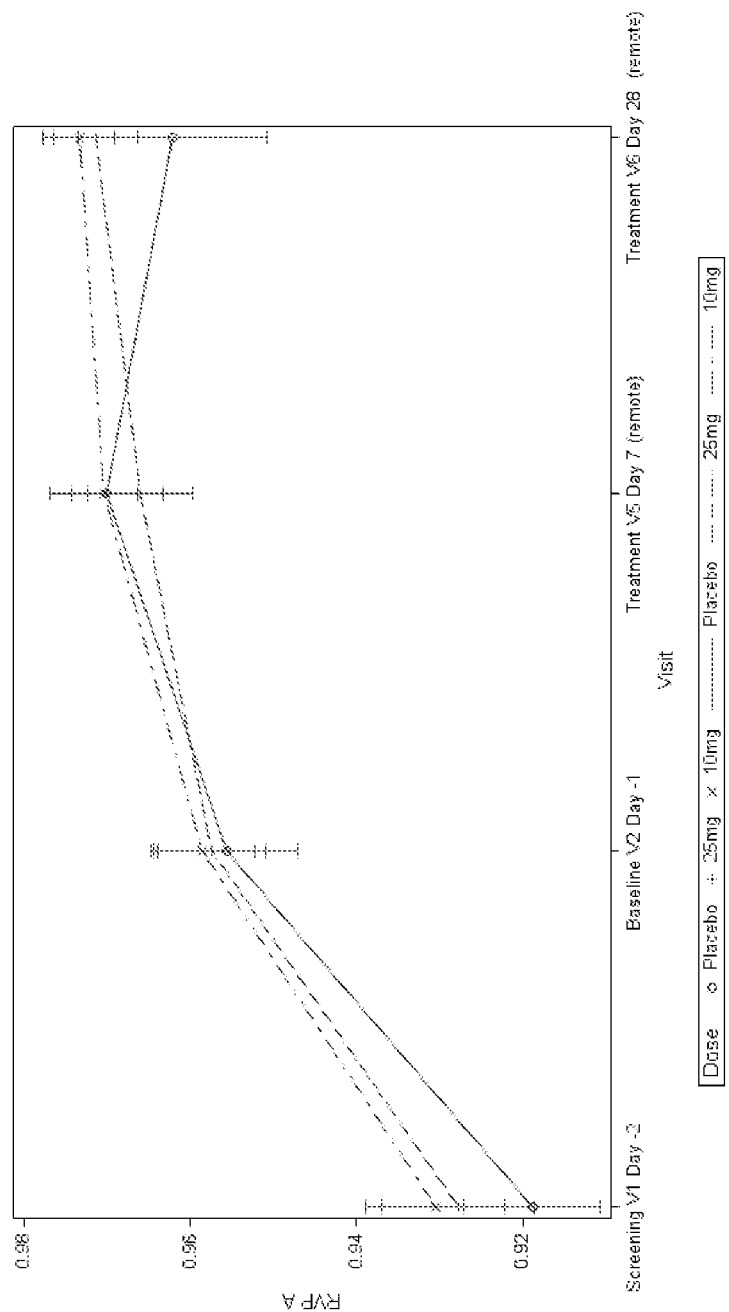
FIG. 9L shows a graph of the Rapid Visual Information Processing A Prime (RVPA) score of the CANTAB over time for the psilocybin-treated and placebo-treated subjects of the Phase 1 exploratory study.

The spatial working memory strategy score (SWMS) of CANTAB was also assessed. Lower SWMS scores indicated better performance. On average, there was a small numeric improvement in performance from Baseline to Day 28 across 10 mg and 25 mg psilocybin groups and placebo (FIG. 9J). The least squares mean difference indicated that the 25 mg psilocybin group and 10 mg psilocybin group performed similar to placebo at Day 7. However, the 25 mg group performed on average slightly better than the placebo, whilst the 10 mg group performed on average slightly worse than placebo at Day 28 (FIG. 9K).

No main effect for psilocybin status or interaction (psilocybin status by visit by dose) was observed for the CANTAB composite measure in the subjects who completed the assessments without a major protocol deviation as part of the analysis of covariance (ANCOVA) analysis (p-values>0.05), suggesting no consistent differential performance due to previous exposure to psilocybin.

Figure 9M:
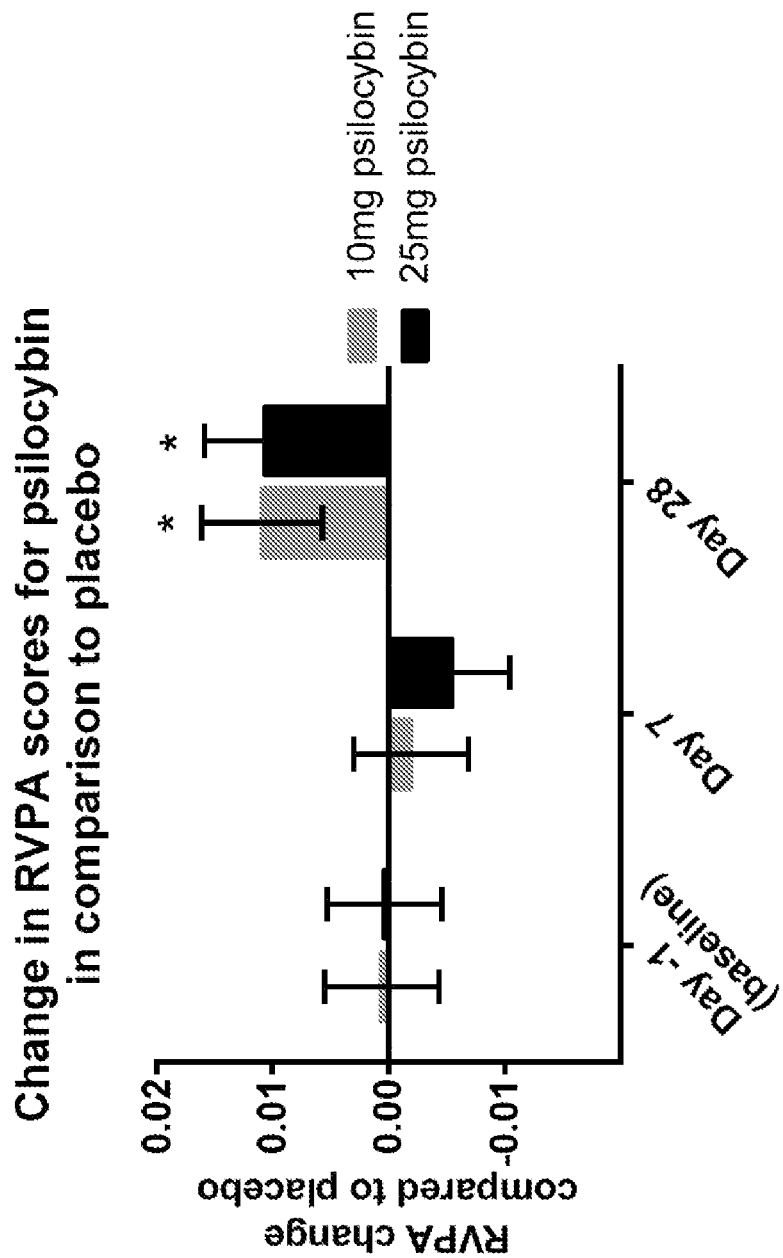
FIG. 9M shows a graph of the least squares (LS) mean difference of psilocybin groups (10 mg and 25 mg) compared to placebo groups over time. Psilocybin was administered on Day 0. Data on Days 7 and Day 28 were collected remotely. Positive scores indicate treatment performed better than placebo. Negative scores indicate placebo performed better than psilocybin. LS means were calculated using repeated-measures ANOVA and compared with placebo. $*p \leq 0.05$. Data are expressed as LS mean±sem.
Figure 9N:
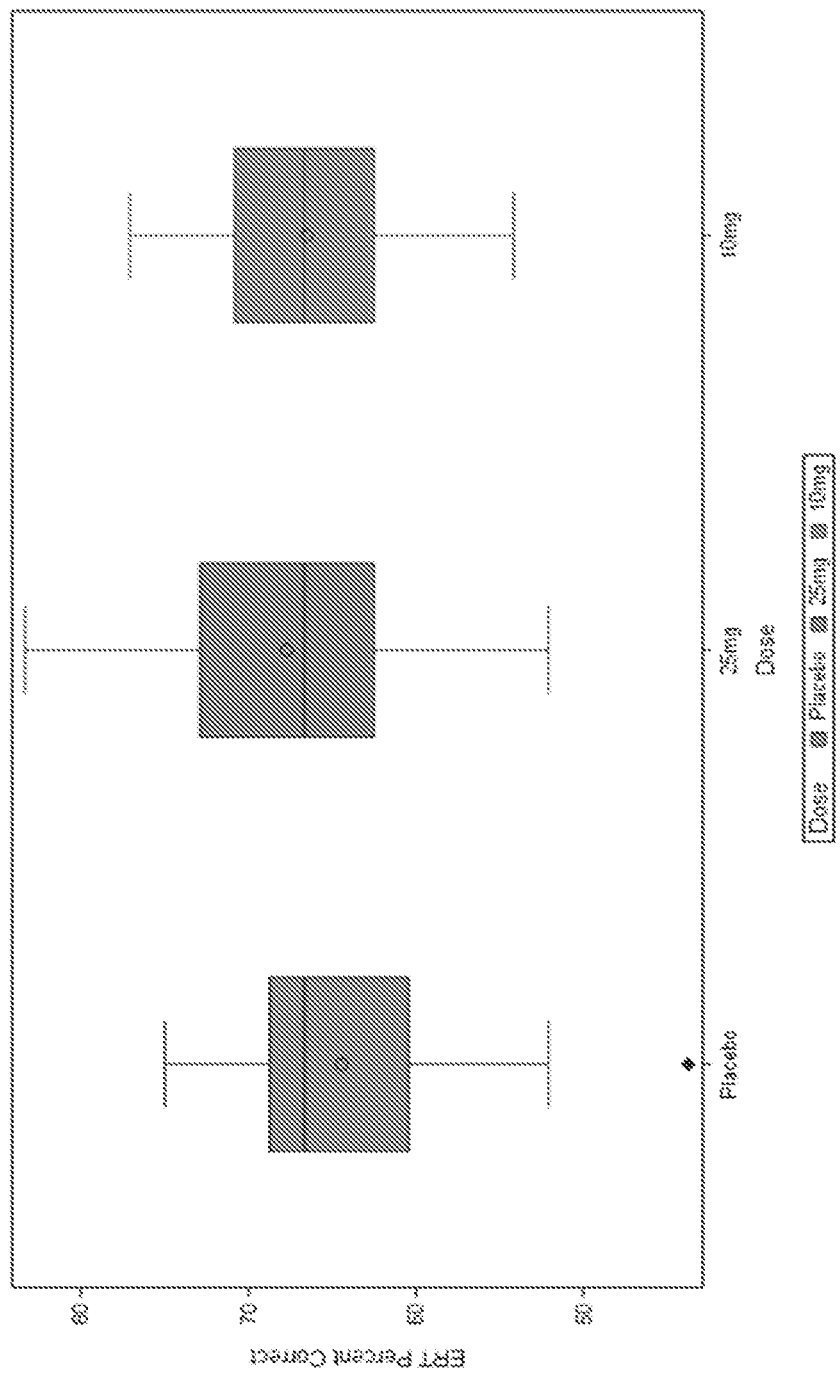
FIG. 9N shows a graph of the Emotional Recognition Task percent correct (ERTPC) of the CANTAB for the psilocybin-treated and placebo-treated subjects of the Phase 1 exploratory study.
Figure 9O:
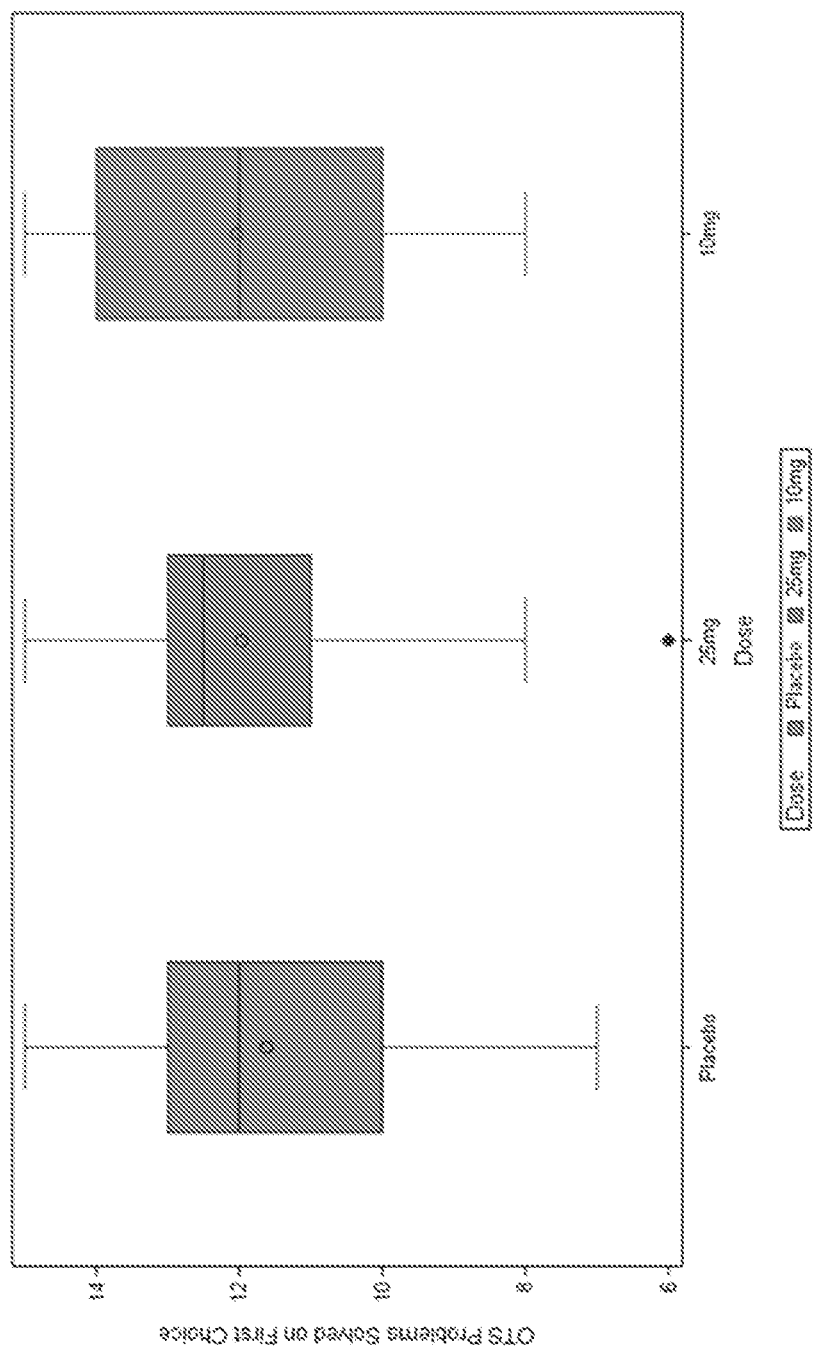
FIG. 9O shows a graph of the One Touch Stockings Problems Solved on First Choice (OTSPSFC) of the CANTAB for the psilocybin-treated and placebo-treated subjects of the Phase 1 exploratory study.
Figure 9P:
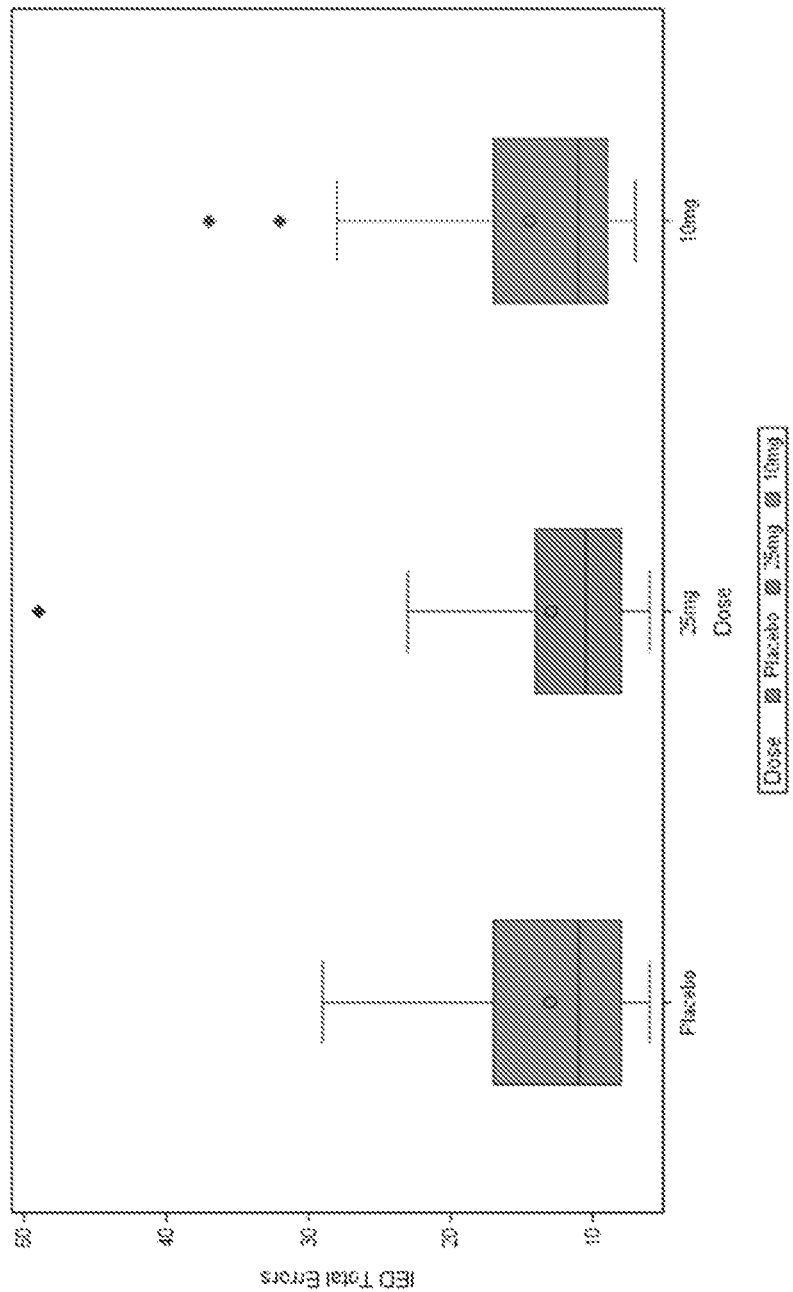
FIG. 9P shows a graph of the intra-extra dimensional set shift total errors (IEDYERT) of the CANTAB for the psilocybin-treated and placebo-treated subjects of the Phase 1 exploratory study.
Figure 9Q:
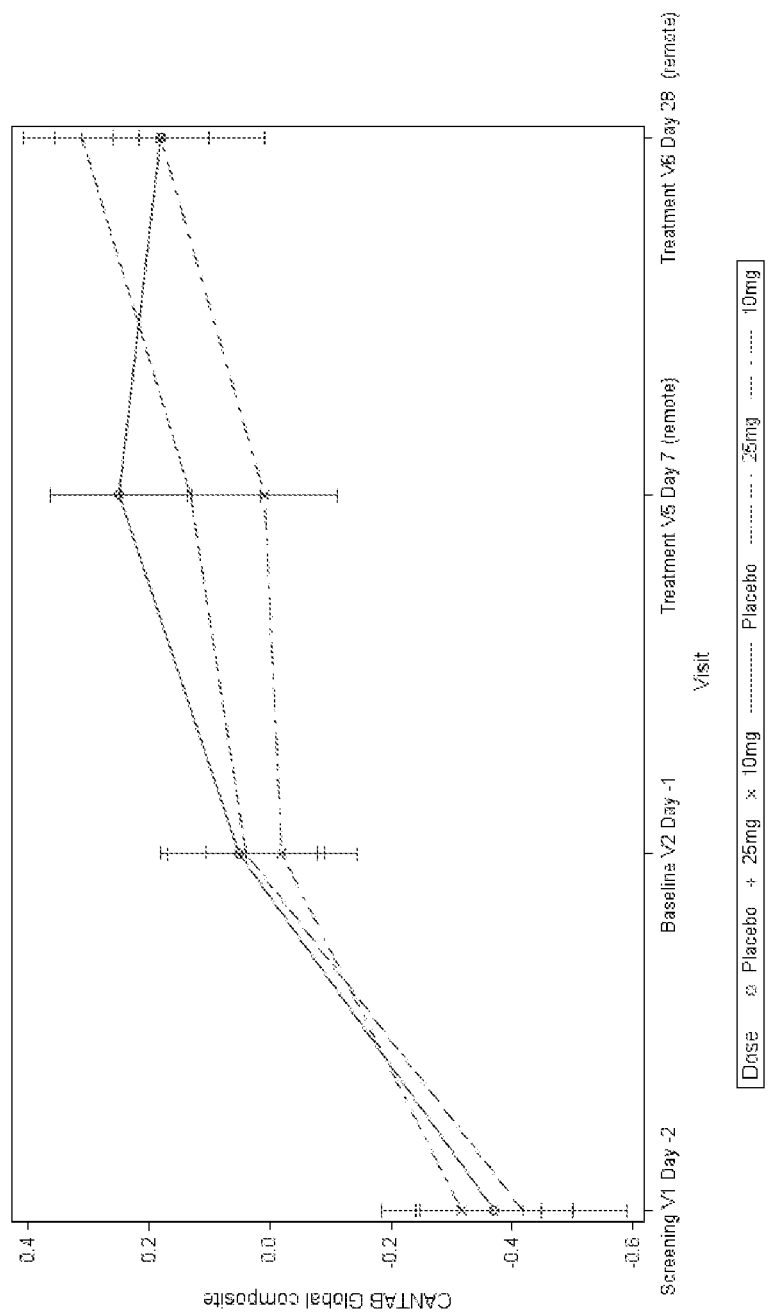
FIG. 9Q shows a graph of the CANTAB global composite score over time for the psilocybin-treated and placebo-treated subjects of the Phase 1 exploratory study.

Least square means estimates indicated an improvement from Baseline to Day 7 and Day 28 in those psilocybin-naïve subjects in the placebo group. Conversely, least square means estimates indicated improvement from Baseline to Day 28 for those from the 10 mg psilocybin dose group who were previously exposed to psilocybin only. This improvement from baseline to Day 28 in the psilocybin experienced subjects was also an improvement relative to placebo. FIG. 9V shows the CANTAB composite score for psilocybin-naïve subjects (0) and psilocybin-experienced subjects (1).

However, for the 25 mg group, an improvement to Day 28 was observed irrespective of previous psilocybin exposure. This improvement was also higher relative to placebo.

The Emotional Recognition Task (ERT) test of the CANTAB was used to assess the effect of psilocybin. The result of the ERT was reported as the ERT percent correct (ERTPC). Higher ERTPC scores indicated better performance. No evidence of a difference was observed between the 25 mg and 10 mg psilocybin groups and placebo nor between the 25 mg and 10 mg psilocybin groups at Day 7 (FIG. 9N).

The One Touch Stockings of CANTAB was used to assess the effect of psilocybin on executive function. A higher OTS Problems Solved on First Choice (OTSPSFC) indicated better performance. There was insufficient evidence of a difference observed between the 25 mg and 10 mg psilocybin groups or difference of these groups from placebo for performance on OTSPSFC at Day 7 (FIG. 9O).

The Intra-Extra Dimensional Set Shift of CANTAB was used to assess the effect of psilocybin on executive function. A lower IED Total Errors (IEDYERT) score indicated better performance. No difference in performance on IEDYERT was observed between psilocybin-treated groups or between placebo and psilocybin-treated groups at Day 7 (FIG. 9P).

The composite score of the CANTAB was assessed. The composite score was derived from Z scores for each CANTAB outcomes measure (PALTEA, SWMBE, SWMS, RVPA). A higher global composite score indicated a better performance. Both psilocybin-treated groups and placebo showed an improvement in performance over time from Baseline to Day 28 (FIG. 9Q).

Figure 9R:
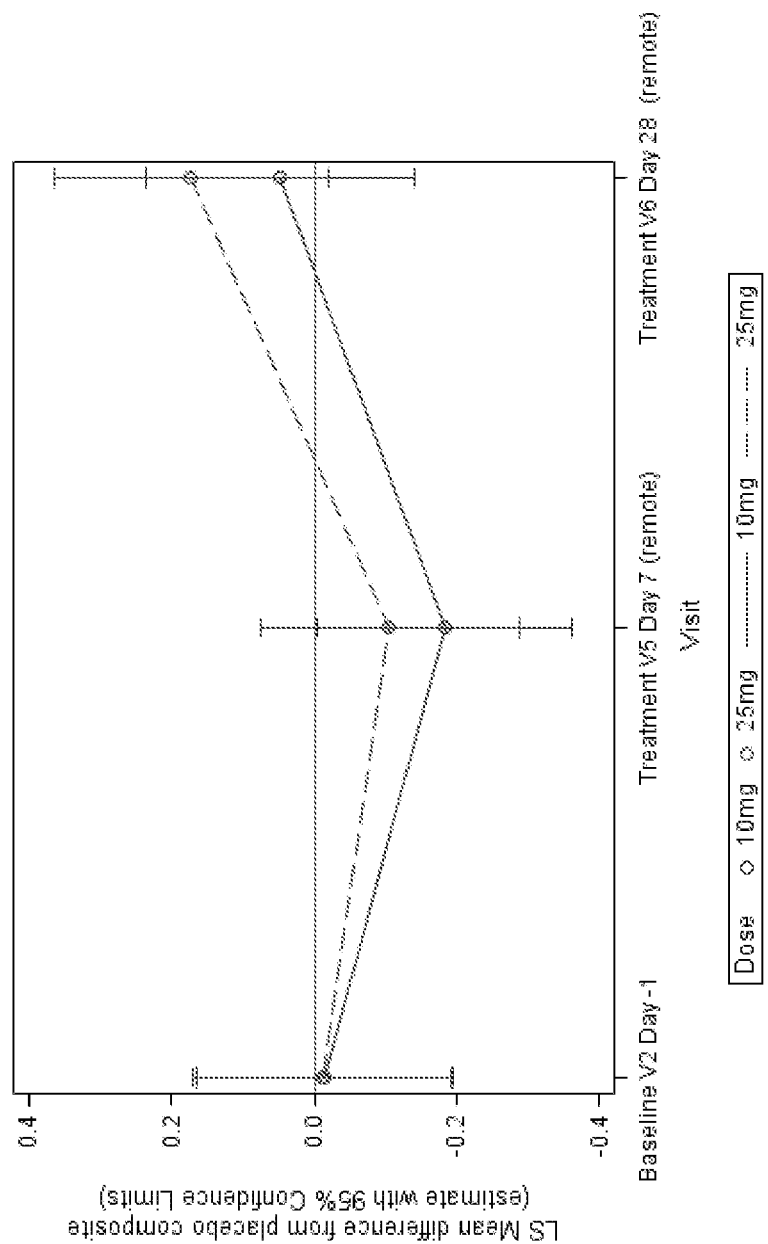
FIG. 9R shows a graph of the least squares mean difference from placebo for the CANTAB global composite score over time for the psilocybin-treated subjects of the Phase 1 exploratory study.

The LS mean difference from placebo was different from 0 for the 10 mg group at Day 7 (FIG. 9R, LS mean difference=−0.18320, p value~0.04460, effect size 0.53). For the 10 mg group, performance increased again at Day 28 suggesting no adverse effects of the 10 mg dose compared with placebo.

Figure 9S:
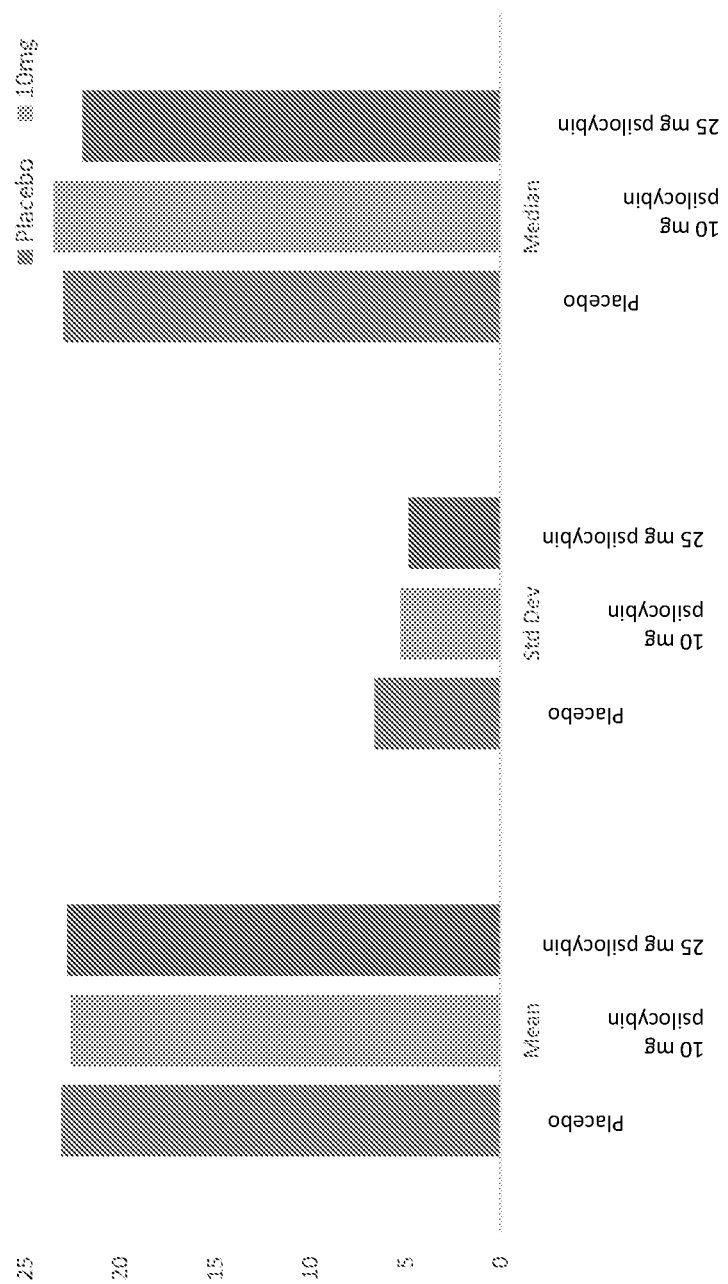
FIG. 9S shows a graph of the verbal fluency test for the psilocybin-treated and placebo-treated subjects of the Phase 1 exploratory study.

The verbal fluency test was completed at Visit 5 via phone. This task was reliant on the integrity of a range of cognitive abilities including executive functions such as planning and working memory. Subjects were asked to name different category exemplars (e.g. animals) in one minute. No statistically significant difference in the verbal fluency score was observed compared to placebo for both the psilocybin 10 mg (p-value 0.7635) and 25 mg arm (p-value 0.8412) (FIG. 9S).

Figure 9T:
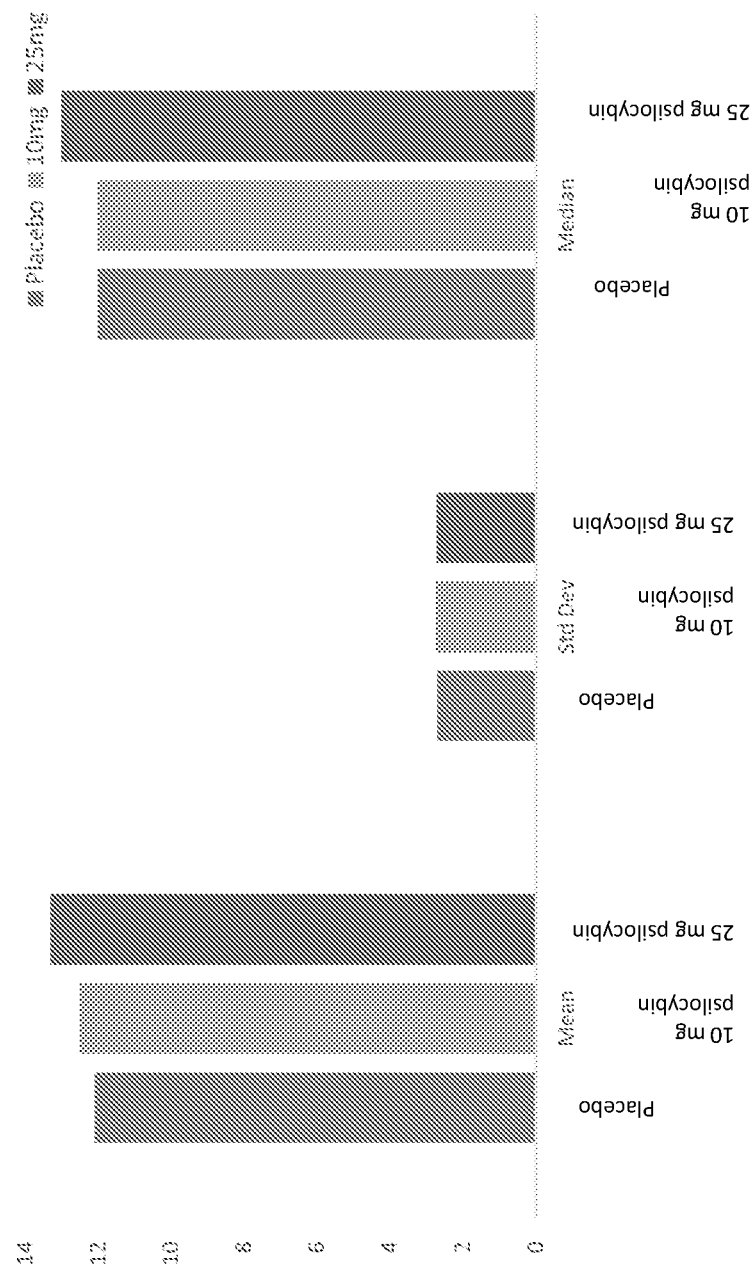
FIG. 9T shows a graph of the digit span forward test for the psilocybin-treated and placebo-treated subjects of the Phase 1 exploratory study.

The digit span forward test was completed at Visit 5 via phone. This task was a measure of number storage capacity, a common measure of short-term memory. No statistically significant difference in digit span scores was observed compared to placebo for both the psilocybin 10 mg (p value 0.6432) and 25 mg arm (p value 0.1147) (FIG. 9T).

Figure 9U:
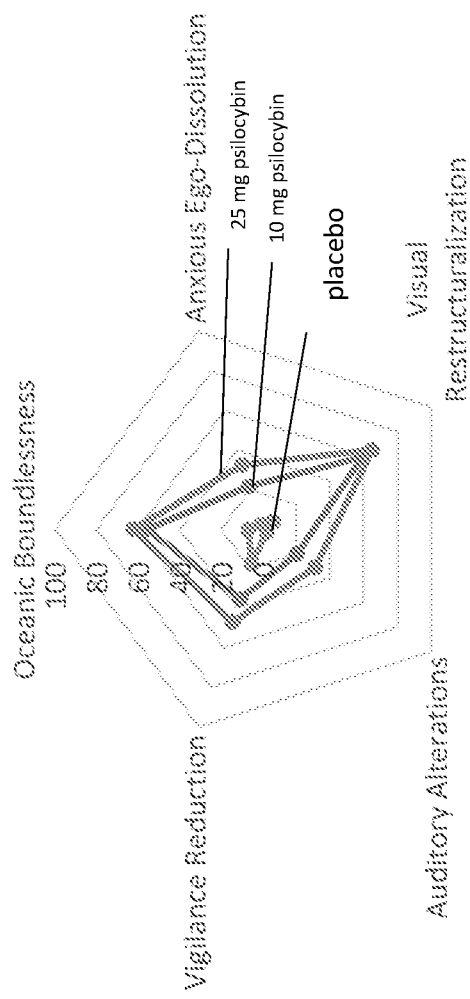
FIG. 9U shows a graph of the Five Dimensional-Altered States of Consciousness (5D-ASC), which measures alterations in mood, perception, and experience of self, after administration of psilocybin or placebo in the Phase 1 exploratory study.
Figure 9V:
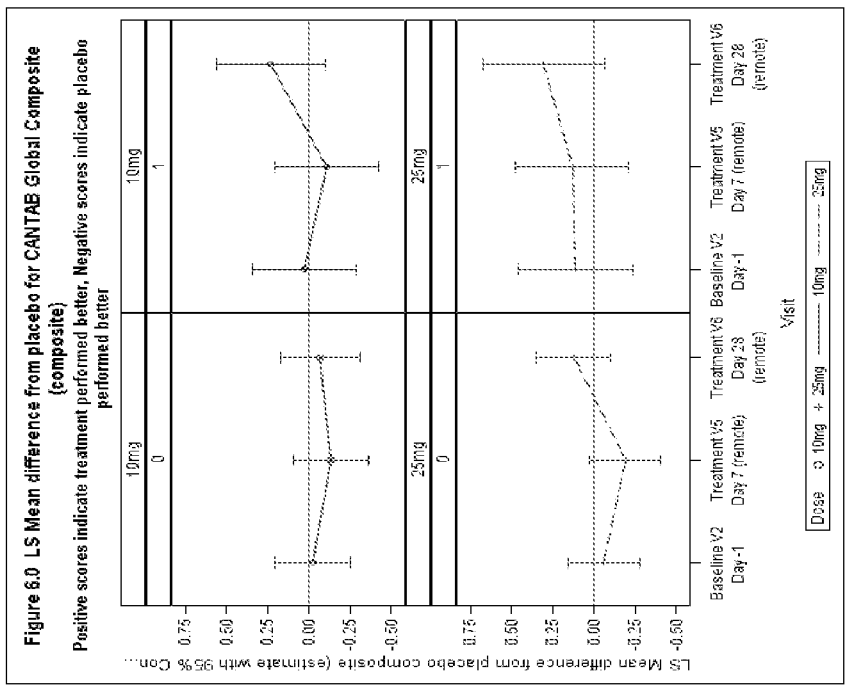
FIG. 9V shows the difference in CANTAB composite score between "psilocybin-naïve" (0, left-hand side) subjects and subjects with prior psilocybin experience (1, right-hand side).

The Five-Dimensional Altered States of Consciousness (5D-ASC) Questionnaire was administered, as summarized in Table 23. FIG. 9U summarizes the results of the Five Dimensional-Altered States of Consciousness (5D-ASC).

TABLE 23

Analysis of variance (ANOVA) Model F-Tests for the 5D-ASC

| Parameter | Source | DF | SS | MS | F-value | Pvalue |
|---|---|---|---|---|---|---|
| Oceanic | Treatment | 2 | 47562.11748 | 23781.05874 | 62.66 | <0.0001 |
| boundlessness | FPE | 1 | 406.80610 | 406.80610 | 1.07 | 0.3035 |
| Dread of ego | Treatment | 2 | 13243.54504 | 6621.77252 | 21.81 | <0.0001 |
| dissolution | FPE | 1 | 398.65320 | 398.65320 | 1.31 | 0.2552 |
| Visual | Treatment | 2 | 55584.85537 | 27792.42768 | 113.68 | <0.0001 |
| restructuralisation | FPE | 1 | 31.46543 | 31.46543 | 0.13 | 0.7207 |
| Auditory alteration | Treatment | 2 | 11807.54615 | 5903.77308 | 26.51 | <0.0001 |
|  | FPE | 1 | 171.64561 | 171.64561 | 0.77 | 0.3825 |
| Vigilance reduction | Treatment | 2 | 12983.11807 | 6491.55904 | 14.43 | <0.0001 |
|  | FPE | 1 | 1669.03601 | 1669.03601 | 3.71 | 0.0576 |
| Experience of unity | Treatment | 2 | 45746.16992 | 22873.08496 | 38.52 | <0.0001 |
|  | FPE | 1 | 419.21831 | 419.21831 | 0.71 | 0.4033 |
| Spiritual experience | Treatment | 2 | 44295.01759 | 22147.50880 | 33.47 | <0.0001 |
|  | FPE | 1 | 106.12236 | 106.12236 | 0.16 | 0.6899 |
| Blissful state | Treatment | 2 | 48144.44507 | 24072.22254 | 39.91 | <0.0001 |
|  | FPE | 1 | 21.22999 | 21.22999 | 0.04 | 0.8517 |
| Insightfulness | Treatment | 2 | 51518.58287 | 25759.29144 | 45.01 | <0.0001 |
|  | FPE | 1 | 82.51431 | 82.51431 | 0.14 | 0.7051 |
| Disembodiment | Treatment | 2 | 38024.97280 | 19012.48640 | 39.19 | <0.0001 |
|  | FPE | 1 | 432.56944 | 432.56944 | 0.89 | 0.3478 |
| Impaired control and | Treatment | 2 | 14847.05053 | 7423.52526 | 18.90 | <0.0001 |
| cognition | FPE | 1 | 367.97317 | 367.97317 | 0.94 | 0.3359 |
| Anxiety | Treatment | 2 | 13654.18304 | 6827.09152 | 19.43 | <0.0001 |
|  | FPE | 1 | 90.95683 | 90.95683 | 0.26 | 0.6122 |
| Complex imagery | Treatment | 2 | 55098.80129 | 27549.40064 | 103.59 | <0.0001 |
|  | FPE | 1 | 148.07986 | 148.07986 | 0.56 | 0.4577 |
| Elementary imagery | Treatment | 2 | 72036.48627 | 36018.24314 | 61.13 | <0.0001 |
|  | FPE | 1 | 411.61569 | 411.61569 | 0.70 | 0.4057 |

TABLE 23-continued

Analysis of variance (ANOVA) Model F-Tests for the 5D-ASC

| Parameter | Source | DF | SS | MS | F-value | Pvalue |
|---|---|---|---|---|---|---|
| Audio-visual synaesthesia | Treatment | 2 | 79483.55646 | 39741.77823 | 79.53 | <0.0001 |
| | FPE | 1 | 421.45066 | 421.45066 | 0.84 | 0.3611 |
| Changed meaning of percepts | Treatment | 2 | 34476.31342 | 17238.15671 | 24.58 | <0.0001 |
| | FPE | 1 | 319.13449 | 319.13449 | 0.46 | 0.5018 |

Note:
F-test from ANOVA model with fixed effect for treatment and FPE.

Abbreviations: 5D-ASC = Five-Dimensional Altered States of Consciousness questionnaire; ANOVA = Analysis of variance; DF = Degrees of freedom; FPE = Former psilocybin experience; MS = Mean sum of squares; SS = Sum of squares; TAS = Tellegen absorption scale.

There were differences detected among treatment groups for each domain of the 5D-ASC. Prior exposure to psilocybin had no apparent effect on this scale. Differences between the placebo and psilocybin groups in each of the primary domains of the 5D-ASC scale were observed. The Dread of Ego Dissolution and Auditory Alteration subscales also showed a difference between psilocybin doses (10 mg and 25 mg; p≤0.05), with the 25 mg psilocybin group showing higher scores than the 10 mg psilocybin group on both domains, as shown in Table 24.

TABLE 24

Differences between placebo and psilocybin-treated groups in the primary dimensions of the 5D-ASC

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25 mg-10 mg |
|---|---|---|---|---|---|---|---|
| Oceanic boundlessness | | | | | | | |
| Post-Treatment Day 0 | n | 30 | 30 | 29 | — | — | — |
| | Mean | 62.9 | 55.7 | 8.0 | 54.9 | 47.7 | 7.2 |
| | 95% CI | — | — | — | 44.48, 65.32 | 37.11, 58.26 | -2.86, 17.29 |
| | p value | — | — | — | <0.0001 | <0.0001 | 0.1581 |
| Dread of ego dissolution | | | | | | | |
| Post-Treatment Day 0 | n | 30 | 30 | 26 | — | — | — |
| | Mean | 31.9 | 21.7 | 1.2 | 30.6 | 20.5 | 10.1 |
| | 95% CI | — | — | — | 21.32, 39.95 | 11.03, 29.95 | 1.13, 19.16 |
| | p value | — | — | — | <0.0001 | <0.0001 | 0.0278 |
| Visual restructuralisation | | | | | | | |
| Post-Treatment Day 0 | n | 30 | 30 | 26 | — | — | — |
| | Mean | 65.2 | 59.1 | 6.5 | 58.7 | 52.6 | 6.1 |
| | 95% CI | — | — | — | 50.35, 67.07 | 44.11, 61.09 | -1.98, 14.20 |
| | p value | — | — | — | <0.0001 | <0.0001 | 0.1366 |
| Auditory alteration | | | | | | | |
| Post-Treatment Day 0 | n | 30 | 30 | 26 | — | — | — |
| | Mean | 30.7 | 20.3 | 1.7 | 29.1 | 18.6 | 10.5 |
| | 95% CI | — | — | — | 21.07, 37.03 | 10.46, 26.66 | 2.77, 18.21 |
| | p value | — | — | — | <0.0001 | <0.0001 | 0.0083 |
| Vigilance reduction | | | | | | | |
| Post-Treatment Day 0 | n | 30 | 30 | 26 | — | — | — |
| | Mean | 45.7 | 35.3 | 15.3 | 30.4 | 20.0 | 10.3 |
| | 95% CI | — | — | — | 19.03, 41.72 | 8.51, 31.55 | -0.62, 21.31 |
| | p value | — | — | — | <0.0001 | 0.0009 | 0.0642 |

Note:
LS means and p-values from ANOVA model with fixed effects for treatment and FPE.

Abbreviations: 5D-ASC = Five-Dimensional Altered States of Consciousness questionnaire; ANOVA = Analysis of variance; CI = Confidence interval; FPE = Former psilocybin experience; LS = Least squares; N = All subjects randomized; n = Subjects with post-treatment assessments.

As shown in Table 25 below, differences between each of the psilocybin dose groups and placebo were observed for the 11 sub-scores of the 5D-ASC (p 0.0001). There was insufficient evidence for differences between the psilocybin doses except for the anxiety and complex imagery subscales which showed a higher mean value in the psilocybin 25 mg dose group compared to psilocybin 10 mg (p≤0.001).

TABLE 25

Differences between placebo and psilocybin-treated groups in the 11 sub-dimensions of the 5D-ASC

| Parameter | | Psilocybin 25 mg (N = 30) | Psilocybin 10 mg (N = 30) | Placebo (N = 29) | Psilocybin 25 mg - Placebo | Psilocybin 10 mg - Placebo | Psilocybin 25 mg - 10 mg |
|---|---|---|---|---|---|---|---|
| \multicolumn{8}{c}{Experience of unity} |
| Post-Treatment Day 0 | N | 30 | 30 | 26 | — | — | — |
| | Mean | 60.9 | 54.4 | 7.2 | 53.6 | 47.1 | 6.5 |
| | 95% CI | — | — | — | 40.60, 66.66 | 33.89, 60.35 | −6.09, 19.11 |
| | p-value | — | — | — | <0.0001 | <0.0001 | 0.3070 |
| \multicolumn{8}{c}{Spiritual experience} |
| Post-Treatment Day 0 | n | 30 | 30 | 26 | — | — | — |
| | Mean | 57.9 | 48.7 | 4.2 | 53.7 | 44.6 | 9.2 |
| | 95% CI | — | — | — | 39.98, 67.50 | 30.61, 58.55 | −4.14, 22.46 |
| | p-value | — | — | — | <0.0001 | <0.0001 | 0.1745 |
| \multicolumn{8}{c}{Blissful state} |
| Post-Treatment Day 0 | n | 29 | 30 | 26 | — | — | — |
| | Mean | 61.9 | 59.1 | 8.2 | 53.6 | 50.9 | 2.8 |
| | 95% CI | — | — | — | 40.39, 66.90 | 37.54, 64.22 | −10.03, 15.56 |
| | p-value | — | — | — | <0.0001 | <0.0001 | 0.6683 |
| \multicolumn{8}{c}{Insightfulness} |
| Post-Treatment Day 0 | n | 30 | 30 | 26 | — | — | — |
| | Mean | 64.4 | 53.9 | 6.3 | 58.2 | 47.6 | 10.5 |
| | 95% CI | — | — | — | 45.38, 70.97 | 34.64, 60.62 | −1.83, 22.92 |
| | p-value | — | — | — | <0.0001 | <0.0001 | 0.0937 |
| \multicolumn{8}{c}{Disembodiment} |
| Post-Treatment Day 0 | n | 30 | 30 | 26 | — | — | — |
| | Mean | 53.8 | 52.7 | 6.9 | 46.9 | 45.8 | 1.1 |
| | 95% CI | — | — | — | 35.08, 58.64 | 33.81, 57.73 | −10.30, 12.48 |
| | p-value | — | — | — | <0.0001 | <0.0001 | 0.8490 |
| \multicolumn{8}{c}{Impaired control and cognition} |
| Post-Treatment Day 0 | n | 30 | 30 | 26 | — | — | — |
| | Mean | 32.7 | 27.9 | 1.8 | 30.9 | 26.2 | 4.7 |
| | 95% CI | — | — | — | 20.33, 41.53 | 15.42, 36.94 | −5.50, 15.00 |
| | p-value | — | — | — | <0.0001 | <0.0001 | 0.3593 |
| \multicolumn{8}{c}{Anxiety} |
| Post-Treatment Day 0 | n | 30 | 30 | 26 | — | — | — |
| | Mean | 32.4 | 15.7 | 1.1 | 31.3 | 14.6 | 16.7 |
| | 95% CI | — | — | — | 21.25, 41.30 | 4.39, 24.75 | 7.01, 26.39 |
| | p-value | — | — | — | <0.0001 | 0.0056 | 0.0010 |
| \multicolumn{8}{c}{Complex imagery} |
| Post-Treatment Day 0 | n | 30 | 30 | 26 | — | — | — |
| | Mean | 64.9 | 53.0 | 4.4 | 60.5 | 48.6 | 11.9 |
| | 95% CI | — | — | — | 51.76, 69.20 | 39.70, 57.41 | 3.49, 20.36 |
| | p-value | — | — | — | <0.0001 | <0.0001 | 0.0061 |
| \multicolumn{8}{c}{Elementary imagery} |
| Post-Treatment Day 0 | n | 30 | 30 | 26 | — | — | — |
| | Mean | 76.9 | 76.5 | 13.0 | 64.0 | 63.6 | 0.4 |
| | 95% CI | — | — | — | 51.00, 76.97 | 50.40, 76.76 | −12.15, 12.96 |
| | p-value | — | — | — | <0.0001 | <0.0001 | 0.9489 |
| \multicolumn{8}{c}{Audio-visual synaesthesia} |
| Post-Treatment Day 0 | n | 30 | 30 | 26 | — | — | — |
| | Mean | 75.4 | 74.7 | 8.1 | 67.3 | 66.6 | 0.7 |
| | 95% CI | — | — | — | 55.38, 79.29 | 54.51, 78.79 | −10.87, 12.24 |
| | p-value | — | — | — | <0.0001 | <0.0001 | 0.9064 |

TABLE 25-continued

| | | Psilocybin 25 mg (N = 30) | Psilocybin 10 mg (N = 30) | Placebo (N = 29) | Psilocybin 25 mg - Placebo | Psilocybin 10 mg - Placebo | Psilocybin 25 mg - 10 mg |
|---|---|---|---|---|---|---|---|
| Parameter | | | | | | | |

Differences between placebo and psilocybin-treated groups in the 11 sub-dimensions of the 5D-ASC

| | | | | | | | |
|---|---|---|---|---|---|---|---|
| | | Changed meaning of percepts | | | | | |
| Post-Treatment Day 0 | n | 30 | 30 | 26 | — | — | — |
| | Mean | 46.1 | 46.6 | 2.2 | 43.9 | 44.4 | -0.5 |
| | 95% CI | — | — | — | 29.73, 58.05 | 30.00, 58.76 | -14.19, 13.20 |
| | p-value | — | — | — | <0.0001 | <0.0001 | 0.9430 |

Note:
LS means and p-values from ANOVA model with fixed effects for treatment and FPE.
Abbreviations: 5D-ASC = Five-Dimensional Altered States of Consciousness questionnaire; ANOVA = Analysis of variance; CI = confidence interval; FPE = Former psilocybin experience; LS = least squares; N = All subjects randomized; n = Subjects with post-treatment assessments.

The Positive and Negative Affects Schedule (PANAS) score was also evaluated to measure the effect of psilocybin. For the change in PANAS score (from pre- to post-treatment), an effect of treatment was observed for positive affect (p=0.02) but not for negative affect (p=0.0604). The ANCOVA model components are shown in Table 26.

TABLE 26

F-tests from Analysis of Covariance Model: PANAS

| Parameter | Source | DF | SS | MS | F-value | P-value |
|---|---|---|---|---|---|---|
| PANAS-Negative | Treatment | 2 | 54.3731933 | 27.1865967 | 2.90 | 0.0604 |
| | FPE | 1 | 0.0197343 | 0.0197343 | 0.00 | 0.9635 |
| | Baseline score | 1 | 298.2929518 | 298.2929518 | 31.86 | <0.0001 |
| PANAS-Positive | Treatment | 2 | 507.1469094 | 253.5734547 | 4.10 | 0.0200 |
| | FPE | 1 | 174.4461646 | 174.4461646 | 2.82 | 0.0968 |
| | Baseline score | 1 | 710.6961764 | 710.6961764 | 11.49 | 0.0011 |

Source: Emotional Processing Table 14.8.1.12
Abbreviations: ANCOVA = Analysis of covariance; DF = Degrees of freedom; MS = Mean sum of squares; PANAS = Positive and Negative Affect Schedule; SS = Sum of squares.

Prior psilocybin experience did not have a significant impact on the change in PANAS score, but the baseline value was highly predictive, with higher pre-treatment scores predicting a greater increase after dosing.

As shown in Table 27 below, the placebo group showed a reduction in positive affect from baseline to the day of dosing which was not observed in the psilocybin groups (p<0.03). By contrast, the 25 mg psilocybin group had a mean increase in negative affect of 1.3, compared to a slight decrease observed in the 10 mg group (p=0.0218) and the placebo group (p=0.0989).

TABLE 27

Summary of PANAS-Change from Baseline After Treatment on Day 0

| Parameter | | Psilocybin 25 mg (N = 30) | Psilocybin 10 mg (N = 30) | Placebo (N = 29) | Psilocybin 25 mg- Placebo | Psilocybin 10 mg- Placebo | Psilocybin 25 mg- 10 mg |
|---|---|---|---|---|---|---|---|
| | | PANAS-Negative | | | | | |
| Post-Treatment Day 0 | n | 29 | 30 | 29 | — | — | — |
| | Mean | 1.3 | -0.6 | -0.1 | 1.4 | -0.5 | 1.9 |
| | 95% CI | — | — | — | -0.26, 2.99 | -2.16, 1.09 | 0.28, 3.51 |
| | P value | — | — | — | 0.0989 | 0.5164 | 0.0218 |
| | | PANAS-Positive | | | | | |
| Post-Treatment Day 0 | n | 29 | 30 | 29 | — | — | — |
| | Mean | -0.4 | 0.7 | -5.0 | 4.6 | 5.7 | -1.0 |
| | 95% CI | — | — | — | 0.48, 8.79 | 1.49, 9.87 | -5.14, 3.05 |
| | P value | — | — | — | 0.0293 | 0.0085 | 0.6126 |

Note:
LS means and p-values from ANCOVA model with fixed effects for treatment and FPE, and baseline score as covariate.
Abbreviations: ANCOVA = Analysis of covariance; CI = confidence interval; FPE = Former psilocybin experience; LS = least squares; N = All subjects randomized; n = Subjects with post-treatment assessments; PANAS = Positive and Negative Affect Schedule.

The Pictorial Empathy Test (PET), Reading the Mind in the Eyes Test (RMET), Scale of Social Responsibility (SSR), Social Value Orientation (SVO), and Toronto Empathy Questionnaire (TEQ) were performed. Table 28 summarizes the results of the mixed model for repeated measures (MMRM) analysis for each of the aforementioned social cognition panel scales measured on Day 7 and Day 84 after study drug administration.

TABLE 28

F-Tests from MMRM Model: PET, RMET, SSR, SVO, and TEQ

| Parameter | Source | DF | Denominator DF | F-value | Pvalue |
|---|---|---|---|---|---|
| PET | Baseline score | 1 | 82.753690 | 0.33 | 0.5690 |
| | FPE | 1 | 82.739811 | 1.64 | 0.2035 |
| | Treatment | 2 | 81.827569 | 2.66 | 0.0761 |
| | Visit | 1 | 80.165106 | 3.16 | 0.0794 |
| | Treatment × Visit | 2 | 80.123570 | 0.01 | 0.9889 |
| RMET | Baseline score | 1 | 79.642446 | 13.11 | 0.0005 |
| | FPE | 1 | 81.293995 | 0.30 | 0.5841 |
| | Treatment | 2 | 81.089435 | 0.09 | 0.9109 |
| | Visit | 1 | 78.718169 | 0.58 | 0.4502 |
| | Treatment × Visit | 2 | 78.697428 | 0.11 | 0.8983 |
| SSR global | Baseline score | 1 | 78.029198 | 1.76 | 0.1890 |
| | FPE | 1 | 77.981354 | 2.57 | 0.1130 |
| | Treatment | 2 | 77.535686 | 1.73 | 0.1846 |
| | Visit | 1 | 74.336261 | 0.69 | 0.4076 |
| | Treatment × Visit | 2 | 74.149063 | 0.17 | 0.8465 |
| SSR fulfilling expectation | Baseline score | 1 | 79.708607 | 7.43 | 0.0079 |
| | FPE | 1 | 80.530339 | 1.10 | 0.2965 |
| | Treatment | 2 | 79.898753 | 1.17 | 0.3164 |
| | Visit | 1 | 77.391208 | 0.16 | 0.6881 |
| | Treatment × Visit | 2 | 77.356175 | 1.82 | 0.1682 |
| SSR compliance social rules | Baseline score | 1 | 81.040786 | 15.30 | 0.0002 |
| | FPE | 1 | 79.293376 | 0.10 | 0.7527 |
| | Treatment | 2 | 78.731740 | 1.44 | 0.2440 |
| | Visit | 1 | 75.158892 | 0.00 | 0.9739 |
| | Treatment × Visit | 2 | 74.971352 | 0.02 | 0.9843 |

TABLE 28-continued

F-Tests from MMRM Model: PET, RMET, SSR, SVO, and TEQ

| Parameter | Source | DF | Denominator DF | F-value | Pvalue |
|---|---|---|---|---|---|
| SVO angle | Baseline score | 1 | 84.293719 | 2.33 | 0.1305 |
| | FPE | 1 | 81.152189 | 0.02 | 0.8978 |
| | Treatment | 2 | 80.655666 | 2.81 | 0.0661 |
| | Visit | 1 | 80.233253 | 3.68 | 0.0588 |
| | Treatment × Visit | 2 | 80.245032 | 0.02 | 0.9821 |
| SVO type | Baseline score | 1 | 83.474000 | 14.15 | 0.0003 |
| | FPE | 1 | 80.219127 | 0.05 | 0.8176 |
| | Treatment | 2 | 79.202003 | 0.99 | 0.3770 |
| | Visit | 1 | 78.469668 | 1.19 | 0.2783 |
| | Treatment × Visit | 2 | 78.517417 | 0.00 | 0.9975 |
| TEQ | Baseline score | 1 | 78.310229 | 10.05 | 0.0022 |
| | FPE | 1 | 80.793937 | 0.07 | 0.7882 |
| | Treatment | 2 | 79.633057 | 0.83 | 0.4381 |
| | Visit | 1 | 77.965918 | 0.08 | 0.7725 |
| | Treatment × Visit | 2 | 77.943131 | 0.13 | 0.8800 |

Note:
F-tests from a MMRM analysis with change from baseline score as the dependent variable. Model has fixed effects for treatment, visit, FPE, and treatment by visit interaction, visit as the repeating factor, subject as a random effect, and baseline score as a covariate. Abbreviations: DF = Degrees of freedom; FPE = Former psilocybin experience; MMRM = Mixed model for repeated measures; PET = Pictorial Empathy Test; RMET = Reading the Eyes in the Mind Test; SSR = Scale of Social Responsibility; SVO = Social Value Orientation; TEQ = Tellegen Absorption Questionnaire.

No differences among treatment groups for change from baseline values of RMET, SSR, SVO Type, or TEQ were found (p>0.05 in all cases). P-values were approaching the <0.05 level for PET and SVO Angle. In each statistical model, the baseline score was typically the best independent predictor of change, with higher pre-treatment scores predicting a greater increase after dosing.

Table 29 shows tests of pairwise differences between treatment groups in the MMRM model for each of the parameters at Day 7 and Day 84.

TABLE 29

Summary of PET, RMET, SSR, SVO, and TEQ Results-Change from Baseline on Day 7 and Day 84

| | Parameter | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25mg-10mg |
|---|---|---|---|---|---|---|---|
| | | | | PET | | | |
| Day 7 | n | 29 | 30 | 26 | — | — | — |
| | Mean | 0.0 | −0.3 | −0.1 | 0.2 | −0.1 | 0.3 |
| | 95% CI | — | — | — | 0.11, 0.42 | −0.39, 0.15 | 0.02, 0.54 |
| | p-value | — | — | — | 0.2429 | 0.3659 | 0.0360 |
| Day 84 | n | 27 | 30 | 23 | — | — | — |
| | Mean | −0.1 | −0.3 | −0.2 | 0.1 | −0.1 | 0.3 |
| | 95% CI | — | — | — | −0.12, 0.41 | −0.39, 0.15 | 0.00, 0.52 |
| | p-value | — | — | — | 0.2851 | 0.3807 | 0.0464 |
| | | | | RMET | | | |
| Day 7 | n | 29 | 30 | 26 | — | — | — |
| | Mean | 0.4 | 0.4 | 0.3 | 0.2 | 0.1 | 0.0 |
| | 95% CI | — | — | — | −1.44, 1.74 | −1.43, 1.69 | −1.50, 1.55 |
| | p-value | — | — | — | 0.8505 | 0.8719 | 0.9748 |
| Day 84 | n | 27 | 30 | 23 | — | — | — |
| | Mean | 0.4 | 0.1 | −0.1 | 0.5 | 0.2 | 0.3 |
| | 95% CI | — | — | — | −1.29, 2.28 | −1.53, 1.95 | −1.39, 1.97 |
| | p-value | — | — | — | 0.5806 | 0.8103 | 0.7339 |
| | | | | SSR global | | | |
| Day 7 | n | 26 | 29 | 25 | — | — | — |
| | Mean | −0.3 | −2.0 | −3.2 | 2.8 | 1.2 | 1.6 |
| | 95% CI | — | — | — | 0.50, 6.18 | −2.16, 4.56 | −1.58, 4.86 |
| | p-value | — | — | — | 0.0941 | 0.4783 | 0.3141 |

TABLE 29-continued

Summary of PET, RMET, SSR, SVO, and TEQ Results-Change from Baseline on Day 7 and Day 84

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin 25mg-10mg |
|---|---|---|---|---|---|---|---|
| Day 84 | n | 26 | 28 | 20 | — | — | — |
| | Mean | 0.1 | −1.8 | −2.1 | 2.2 | 0.3 | 1.8 |
| | 95% CI | — | — | — | −0.94, 5.29 | −2.83, 3.49 | −1.04, 4.71 |
| | p-value | — | — | — | 0.1687 | 0.8338 | 0.2068 |
| SSR fulfilling expectations | | | | | | | |
| Day 7 | n | 28 | 29 | 26 | — | — | — |
| | Mean | −0.0 | −0.1 | −0.2 | 0.2 | 0.1 | 0.1 |
| | 95% CI | — | — | — | −0.04, 0.35 | −0.14, 0.26 | −0.10, 0.28 |
| | p-value | — | — | — | 0.1233 | 0.5468 | 0.3461 |
| Day 84 | n | 26 | 29 | 22 | — | — | — |
| | Mean | −0.0 | −0.2 | −0.1 | 0.0 | −0.1 | 0.2 |
| | 95% CI | — | — | — | 0.16, 0.23 | −0.32, 0.08 | −0.04, 0.34 |
| | p-value | — | — | — | 0.7238 | 0.2461 | 0.1114 |
| SSR compliance social rules | | | | | | | |
| Day 7 | n | 27 | 30 | 25 | — | — | — |
| | Mean | 0.0 | −0.1 | −0.1 | 0.1 | 0.0 | 0.1 |
| | 95% CI | — | — | — | −0.07, 0.34 | −0.19, 0.22 | −0.08, 0.32 |
| | p-value | — | — | — | 0.1983 | 0.8831 | 0.2331 |
| Day 84 | n | 26 | 29 | 20 | — | — | — |
| | Mean | 0.0 | −0.1 | −0.1 | 0.1 | −0.0 | 0.1 |
| | 95% CI | — | — | — | −0.08, 0.35 | −0.22, 0.22 | −0.06, 0.33 |
| | p-value | — | — | — | 0.2242 | 0.9949 | 0.1827 |
| SVO angle | | | | | | | |
| Day 7 | n | 29 | 30 | 26 | — | — | — |
| | Mean | 0.5 | 1.8 | −1.6 | 2.1 | 3.4 | −1.3 |
| | 95% CI | — | — | — | −1.32, 5.58 | −0.05, 6.85 | −4.60, 2.04 |
| | p-value | — | — | — | 0.2233 | 0.0531 | 0.4466 |
| Day 84 | n | 27 | 30 | 23 | — | — | — |
| | Mean | −0.9 | 0.1 | −3.3 | 2.4 | 3.4 | −1.0 |
| | 95% CI | — | — | — | −1.16, 6.06 | −0.16, 6.97 | −4.34, 2.44 |
| | p-value | — | — | — | 0.1803 | 0.0613 | 0.5785 |
| SVO type | | | | | | | |
| Day 7 | n | 29 | 30 | 26 | — | — | — |
| | Mean | 0.1 | 0.1 | −0.0 | 0.1 | 0.1 | −0.0 |
| | 95% CI | — | — | — | −0.11, 0.24 | −0.07, 0.28 | −0.21, 0.13 |
| | p-value | — | — | — | 0.4551 | 0.2460 | 0.6630 |
| Day 84 | n | 27 | 30 | 23 | — | — | — |
| | Mean | 0.0 | 0.1 | −0.0 | 0.1 | 0.1 | −0.0 |
| | 95% CI | — | — | — | −0.10, 0.24 | −0.06, 0.28 | −0.20, 0.12 |
| | p-value | — | — | — | 0.4321 | 0.1993 | 0.5994 |
| TEQ | | | | | | | |
| Day 7 | n | 29 | 30 | 26 | — | — | — |
| | Mean | 0.0 | −0.1 | −0.1 | 0.2 | 0.1 | 0.1 |
| | 95% CI | — | — | — | −0.08, 0.38 | −0.16, 0.31 | −0.14, 0.30 |
| | p-value | — | — | — | 0.2004 | 0.5425 | 0.4846 |
| Day 84 | n | 26 | 30 | 23 | — | — | — |
| | Mean | −0.0 | −0.1 | −0.2 | 0.1 | 0.1 | 0.0 |
| | 95% CI | — | — | — | 0.13, 0.36 | −0.15, 0.34 | −0.21, 0.25 |
| | p-value | — | — | — | 0.3420 | 0.4403 | 0.8454 |

Note:
LS means and p-values from a MMRM analysis with change from baseline score as the dependent variable. Model has fixed effects for treatment, visit, FPE, and treatment by visit interaction, visit as the repeating factor, subject as a random effect, and baseline score as a covariate.
Abbreviations: CI = Confidence interval; FPE = Former psilocybin experience; LS = Least squares; MMRM = Mixed model for repeated measures; N = All subjects randomized; n = Subjects with post-treatment assessments; PET = Pictorial Empathy Test; RMET = Reading the Eyes in the Mind Test; SSR = Scale of Social Responsibility; SVO = Social Value Orientation; TEQ = Tellegen Absorption Questionnaire.

There was no difference between either psilocybin group and placebo on PET, RMET, SSR, SVO, or TEQ at either timepoint. The reduction in PET score was greater with 10 mg than 25 mg psilocybin at both Day 7 and Day 84, but no differences were detected between psilocybin groups and placebo (for all p>0.05).

The Neuroticism Extraversion Openness-Five Factor Inventory (NEO-FFI) and Symptom Checklist-90 Item (SCL-90) were administered. Details of the MMRM applied to the change from baseline scores for the NEO-FFI and SCL-90 are provided below in Table 30.

TABLE 30

F-Tests from MMRM Model: NEO-FFI and SCL-90

| Parameter | Source | DF | Denominator DF | F-value | P-value |
|---|---|---|---|---|---|
| NEO-neuroticism | Baseline score | 1 | 76.979208 | 5.74 | 0.0190 |
| | FPE | 1 | 77.840113 | 0.93 | 0.3383 |
| | Treatment | 2 | 77.617527 | 0.25 | 0.7790 |
| | Visit | 1 | 73.682482 | 7.74 | 0.0068 |
| | Treatment × Visit | 2 | 73.686883 | 0.68 | 0.5082 |
| NEO-extraversion | Baseline score | 1 | 78.374755 | 14.95 | 0.0002 |
| | FPE | 1 | 78.343718 | 0.96 | 0.3292 |
| | Treatment | 2 | 78.626820 | 0.02 | 0.9845 |
| | Visit | 1 | 73.855914 | 4.63 | 0.0348 |
| | Treatment × Visit | 2 | 73.862965 | 0.81 | 0.4477 |
| NEO-openness | Baseline score | 1 | 74.806595 | 6.32 | 0.0141 |
| | FPE | 1 | 77.275373 | 0.00 | 0.9549 |
| | Treatment | 2 | 76.498330 | 1.41 | 0.2503 |
| | Visit | 1 | 74.250319 | 0.24 | 0.6261 |
| | Treatment × Visit | 2 | 74.270107 | 0.61 | 0.5446 |
| NEO agreeableness | Baseline score | 1 | 78.147167 | 5.13 | 0.0263 |
| | FPE | 1 | 78.408944 | 0.40 | 0.5292 |
| | Treatment | 2 | 78.501462 | 0.37 | 0.6886 |
| | Visit | 1 | 73.826719 | 5.46 | 0.0221 |
| | Treatment × Visit | 2 | 73.845054 | 0.29 | 0.7497 |
| NEO conscientious-ness | Baseline score | 1 | 77.124423 | 4.82 | 0.0312 |
| | FPE | 1 | 77.786049 | 1.86 | 0.1764 |
| | Treatment | 2 | 76.183832 | 1.12 | 0.3301 |
| | Visit | 1 | 74.486641 | 4.14 | 0.0454 |
| | Treatment × Visit | 2 | 74.477293 | 0.56 | 0.5741 |
| SCL-90-somatisation | Baseline score | 1 | 79.868863 | 0.55 | 0.4613 |
| | FPE | 1 | 80.705569 | 1.49 | 0.2256 |
| | Treatment | 2 | 81.464446 | 0.34 | 0.7150 |
| | Visit | 1 | 78.071807 | 0.94 | 0.3357 |
| | Treatment × Visit | 2 | 78.070370 | 0.42 | 0.6559 |
| SCL-90 obsessive compulsive | Baseline score | 1 | 80.547228 | 14.11 | 0.0003 |
| | FPE | 1 | 82.484967 | 3.28 | 0.0736 |
| | Treatment | 2 | 81.559194 | 0.59 | 0.5556 |
| | Visit | 1 | 80.073966 | 0.33 | 0.5691 |
| | Treatment × Visit | 2 | 80.064909 | 0.42 | 0.6554 |
| SCL-90 interpersonal sensitivity | Baseline score | 1 | 80.121543 | 3.70 | 0.0580 |
| | FPE | 1 | 80.874433 | 3.13 | 0.0807 |
| | Treatment | 2 | 82.579702 | 0.30 | 0.7403 |
| | Visit | 1 | 77.993603 | 1.43 | 0.2350 |
| | Treatment × Visit | 2 | 77.991778 | 0.28 | 0.7566 |
| SCL-90 depression | Baseline score | 1 | 80.197894 | 2.91 | 0.0918 |
| | FPE | 1 | 80.342361 | 1.84 | 0.1784 |
| | Treatment | 2 | 81.303470 | 0.07 | 0.9345 |
| | Visit | 1 | 77.391519 | 0.31 | 0.5802 |
| | Treatment × Visit | 2 | 77.389587 | 0.06 | 0.9420 |
| SCL-90 anxiety | Baseline score | 1 | 80.428114 | 12.64 | 0.0006 |
| | FPE | 1 | 81.212552 | 0.15 | 0.7015 |
| | Treatment | 2 | 82.662941 | 0.18 | 0.8352 |
| | Visit | 1 | 78.366882 | 0.13 | 0.7161 |
| | Treatment × Visit | 2 | 78.359701 | 0.13 | 0.8758 |
| SCL-90 anger hostility | Baseline score | 1 | 79.979660 | 54.73 | <0.0001 |
| | FPE | 1 | 79.997333 | 0.83 | 0.3636 |
| | Treatment | 2 | 76.243037 | 0.22 | 0.8001 |
| | Visit | 1 | 76.998093 | 3.73 | 0.0571 |
| | Treatment × Visit | 2 | 76.998109 | 0.66 | 0.5194 |
| SCL-90 phobic anxiety | Baseline score | 1 | 80.002443 | 72.72 | <0.0001 |
| | FPE | 1 | 80.012526 | 1.66 | 0.2014 |
| | Treatment | 2 | 83.392134 | 0.25 | 0.7801 |
| | Visit | 1 | 77.011834 | 0.35 | 0.5541 |
| | Treatment × Visit | 2 | 77.011930 | 0.11 | 0.9001 |
| SCL-90 paranoid ideation | Baseline score | 1 | 82.462798 | 2.09 | 0.1525 |
| | FPE | 1 | 81.511417 | 3.38 | 0.0695 |
| | Treatment | 2 | 80.282457 | 1.35 | 0.2658 |
| | Visit | 1 | 79.911612 | 1.70 | 0.1954 |
| | Treatment × Visit | 2 | 79.848142 | 0.59 | 0.5550 |
| SCL-90 psychoticism | Baseline score | 1 | 79.993358 | 0.75 | 0.3887 |
| | FPE | 1 | 81.786131 | 0.93 | 0.3379 |
| | Treatment | 2 | 81.672000 | 0.18 | 0.8367 |
| | Visit | 1 | 79.185707 | 0.18 | 0.6729 |
| | Treatment × Visit | 2 | 79.178467 | 0.67 | 0.5153 |

Note:
F-tests from a MMRM analysis with change from baseline score as the dependent variable. Model has fixed effects for treatment, visit, FPE, and treatment by visit interaction, visit as the repeating factor, subject as a random effect, and baseline score as a covariate.
Abbreviations: DF = Degrees of freedom; FPE = Former psilocybin experience; MMRM = Mixed model for repeated measures; NEO-FFI = Neuroticism Extraversion Openness - Five Factor Inventory; SCL-90 = Symptom Checklist - 90 Item.

The strongest predictor of change in each scale was the baseline value itself, which was positively correlated with the change after dosing, whereas prior exposure to psilocybin had no detectable effect.

Table 31 presents the LS means and pairwise treatment comparisons based on the change from baseline scores for NEO-FFI and SCL-90.

TABLE 31

Summary of NEO-FFI and SCL-90 Results-Change from Baseline on Day 7 and Day 84

| | Parameter | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| | | | | NEO neuroticism | | | |
| Day 7 | n | 28 | 28 | 26 | — | — | — |
| | Mean | 0.2 | 0.2 | 0.4 | 0.2 | −0.2 | −0.0 |
| | 95% CI | — | — | — | −2.31, 1.96 | −2.28, 1.93 | −2.04, 2.04 |
| | p value | — | — | — | 0.8714 | 0.8701 | 0.9997 |
| Day 84 | n | 26 | 27 | 22 | — | — | — |
| | Mean | 0.8 | 2.1 | 1.8 | −1.0 | 0.3 | −1.3 |
| | 95% CI | — | — | — | −3.56, 1.60 | −2.24, 2.83 | −3.70, 1.14 |
| | p value | — | — | — | 0.4512 | 0.8152 | 0.2957 |

TABLE 31-continued

Summary of NEO-FFI and SCL-90 Results-Change from Baseline on Day 7 and Day 84

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| | | | | NEO extraversion | | | |
| Day 7 | n | 28 | 28 | 26 | — | — | — |
| | Mean | 0.3 | 0.3 | −0.1 | 0.5 | 0.4 | 0.1 |
| | 95% CI | — | — | — | −1.19, 2.10 | −1.28, 2.06 | −1.56, 1.68 |
| | p value | — | — | — | 0.5848 | 0.6411 | 0.9399 |
| Day 84 | n | 26 | 27 | 22 | — | — | — |
| | Mean | −0.7 | −0.9 | −0.2 | −0.5 | −0.7 | 0.2 |
| | 95% CI | — | — | — | −2.52, 1.55 | −2.70, 1.39 | −1.78, 2.13 |
| | p value | — | — | — | 0.6383 | 0.5255 | 0.8617 |
| | | | | NEO openness | | | |
| Day 7 | n | 28 | 28 | 26 | — | — | — |
| | Mean | 0.4 | 0.3 | −0.8 | 1.2 | 1.1 | 0.1 |
| | 95% CI | — | — | — | −0.25, 2.71 | −0.37, 2.59 | −1.34, 1.58 |
| | p value | — | — | — | 0.1030 | 0.1405 | 0.8717 |
| Day 84 | n | 26 | 27 | 22 | — | — | — |
| | Mean | 0.3 | 0.4 | −0.7 | 0.4 | 1.1 | −0.7 |
| | 95% CI | — | — | — | −1.28, 2.14 | −0.60, 2.79 | −2.31, 0.97 |
| | p value | — | — | — | 0.6190 | 0.2026 | 0.4202 |
| | | | | NEO agreeableness | | | |
| Day 7 | n | 28 | 30 | 26 | — | — | — |
| | Mean | 0.1 | −0.2 | 0.2 | −0.1 | −0.4 | 0.4 |
| | 95% CI | — | — | — | −1.50, 1.31 | −1.89, 0.99 | −1.04, 1.75 |
| | p value | — | — | — | 0.8963 | 0.5355 | 0.6115 |
| Day 84 | n | 26 | 27 | 22 | — | — | — |
| | Mean | −0.9 | −0.9 | −0.2 | −0.7 | −0.8 | 0.1 |
| | 95% CI | — | — | — | −2.37, 1.03 | −2.47, 0.97 | −1.56, 1.72 |
| | p value | — | — | — | 0.4339 | 0.3873 | 0.9242 |
| | | | | NEO conscientiousness | | | |
| Day 7 | n | 28 | 28 | 26 | — | — | — |
| | Mean | 0.1 | −0.1 | −0.6 | 0.7 | 0.4 | 0.3 |
| | 95% CI | — | — | — | −0.91, 2.34 | −1.20, 2.10 | −1.34, 1.86 |
| | p value | — | — | — | 0.3855 | 0.5892 | 0.7446 |
| Day 84 | n | 26 | 27 | 22 | — | — | — |
| | Mean | −0.1 | −1.3 | −1.5 | 1.4 | 0.2 | 1.2 |
| | 95% CI | — | — | — | −0.40, 3.20 | −1.56, 2.05 | −0.56, 2.88 |
| | p value | — | — | — | 0.1243 | 0.7873 | 0.1844 |
| | | | | SCL-90-somatisation | | | |
| Day 7 | n | 29 | 30 | 26 | — | — | — |
| | Mean | 0.1 | 0.1 | −0.0 | 0.1 | 0.1 | −0.0 |
| | 95% CI | — | — | — | −0.06, 0.17 | −0.06, 0.18 | −0.12, 0.11 |
| | p value | — | — | — | 0.3299 | 0.3277 | 0.9794 |
| Day 84 | n | 27 | 30 | 23 | — | — | — |
| | Mean | 0.0 | 0.0 | 0.0 | 0.0 | 0.0 | 0.0 |
| | 95% CI | — | — | — | −0.10, 0.18 | −0.13, 0.15 | −0.11, 0.16 |
| | p value | — | — | — | 0.6109 | 0.9229 | 0.6672 |
| | | | | SCL-90 obsessive compulsive | | | |
| Day 7 | n | 29 | 30 | 26 | — | — | — |
| | Mean | −0.1 | −0.1 | −0.2 | 0.1 | 0.1 | −0.0 |
| | 95% CI | — | — | — | −0.09, 0.28 | −0.09, 0.29 | −0.18, 0.18 |
| | p value | — | — | — | 0.3052 | 0.3049 | 0.9908 |
| Day 84 | n | 27 | 30 | 23 | — | — | — |
| | Mean | −0.1 | −0.0 | −0.1 | 0.0 | 0.1 | −0.1 |
| | 95% CI | — | — | — | −0.17, 0.21 | −0.11, 0.28 | −0.25, 0.12 |
| | p value | — | — | — | 0.8118 | 0.3756 | 0.4944 |
| | | | | SCL-90 interpersonal sensitivity | | | |
| Day 7 | n | 29 | 30 | 26 | — | — | — |
| | Mean | 0.0 | −0.0 | 0.0 | 0.0 | −0.0 | 0.1 |
| | 95% CI | — | — | — | −0.11, 0.15 | −0.17, 0.09 | −0.07, 0.18 |
| | p value | — | — | — | 0.8110 | 0.5479 | 0.3802 |
| Day 84 | n | 27 | 30 | 23 | — | — | — |
| | Mean | 0.0 | 0.0 | 0.1 | −0.0 | −0.1 | 0.0 |
| | 95% CI | — | — | — | −0.21, 0.13 | −0.23, 0.11 | −0.14, 0.18 |
| | p value | — | — | — | 0.6592 | 0.4992 | 0.8067 |

TABLE 31-continued

Summary of NEO-FFI and SCL-90 Results-Change from Baseline on Day 7 and Day 84

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| | | | | SCL-90 depression | | | |
| Day 7 | n | 29 | 30 | 26 | — | — | — |
| | Mean | 0.0 | 0.0 | 0.0 | 0.0 | 0.0 | −0.0 |
| | 95% CI | — | — | — | −0.17, 0.21 | −0.17, 0.22 | −0.19, 0.18 |
| | p value | — | — | — | 0.8566 | 0.7878 | 0.9259 |
| Day 84 | n | 27 | 30 | 23 | — | — | — |
| | Mean | 0.1 | 0.1 | 0.0 | 0.0 | 0.0 | 0.0 |
| | 95% CI | — | — | — | 0.18, 0.28 | −0.19, 0.27 | −0.21, 0.23 |
| | pvalue | — | — | — | 0.6964 | 0.7395 | 0.9501 |
| | | | | SCL-90 anxiety | | | |
| Day 7 | n | 29 | 30 | 26 | — | — | — |
| | Mean | −0.0 | −0.0 | −0.0 | 0.0 | −0.0 | 0.0 |
| | 95% CI | — | — | — | −0.12, 0.11 | −0.14, 0.10 | −0.10, 0.13 |
| | p value | — | — | — | 0.9312 | 0.7178 | 0.7739 |
| Day 84 | n | 27 | 30 | 23 | — | — | — |
| | Mean | −0.0 | −0.0 | 0.0 | −0.0 | −0.1 | 0.0 |
| | 95% CI | — | — | — | −0.23, 0.13 | −0.23, 0.13 | −0.17, 0.17 |
| | p value | — | — | — | 0.5904 | 0.5588 | 0.9674 |
| | | | | SCL-90 anger hostility | | | |
| Day 7 | n | 29 | 30 | 26 | — | — | — |
| | Mean | −0.0 | −0.0 | 0.0 | −0.0 | −0.0 | 0.0 |
| | 95% CI | — | — | — | −0.09, 0.07 | −0.13, 0.03 | −0.04, 0.11 |
| | p value | — | — | — | 0.7591 | 0.2564 | 0.3847 |
| Day 84 | n | 27 | 30 | 23 | — | — | — |
| | Mean | 0.0 | 0.0 | 0.0 | −0.0 | −0.0 | −0.0 |
| | 95% CI | — | — | — | −0.16, 0.09 | −0.14, 0.11 | −0.14, 0.10 |
| | p value | — | — | — | 0.5890 | 0.8112 | 0.7495 |
| | | | | SCL-90 phobic anxiety | | | |
| Day 7 | n | 29 | 30 | 26 | — | — | — |
| | Mean | 0.0 | −0.0 | 0.0 | 0.0 | −0.0 | 0.0 |
| | 95% CI | — | — | — | −0.03, 0.04 | −0.05, 0.03 | −0.02, 0.05 |
| | p value | — | — | — | 0.7815 | 0.5556 | 0.3647 |
| Day 84 | n | 27 | 30 | 23 | — | — | — |
| | Mean | 0.0 | 0.0 | 0.0 | 0.0 | −0.0 | 0.0 |
| | 95% CI | — | — | — | 0.04, 0.07 | −0.06, 0.05 | −0.04, 0.06 |
| | p value | — | — | — | 0.7081 | 0.9499 | 0.6450 |
| | | | | SCL-90 paranoid ideation | | | |
| Day 7 | n | 29 | 30 | 26 | — | — | — |
| | Mean | 0.1 | −0.0 | −0.0 | 0.1 | 0.0 | 0.1 |
| | 95% CI | — | — | — | −0.02, 0.23 | −0.09, 0.17 | −0.06, 0.19 |
| | p-value | — | — | — | 0.1016 | 0.5489 | 0.2800 |
| Day 84 | n | 27 | 30 | 23 | — | — | — |
| | Mean | 0.1 | 0.1 | −0.0 | 0.1 | 0.1 | 0.0 |
| | 95% CI | — | — | — | −0.05, 0.18 | −0.05, 0.18 | −0.11, 0.11 |
| | p-value | — | — | — | 0.2543 | 0.2863 | 0.9363 |
| | | | | SCL-90 psychoticism | | | |
| Day 7 | n | 29 | 30 | 26 | — | — | — |
| | Mean | 0.0 | 0.0 | 0.0 | 0.0 | 0.0 | 0.0 |
| | 95% CI | — | — | — | −0.07, 0.08 | −0.07, 0.07 | −0.06, 0.08 |
| | p-value | — | — | — | 0.8196 | 0.9812 | 0.8302 |
| Day 84 | n | 27 | 30 | 23 | — | — | — |
| | Mean | 0.0 | −0.0 | 0.0 | −0.0 | −0.0 | 0.0 |
| | 95% CI | — | — | — | −0.08, 0.07 | −0.11, 0.04 | −0.05, 0.10 |
| | p-value | — | — | — | 0.8823 | 0.3851 | 0.4476 |

Note:
LS means and p-values from a MMRM with fixed effects for treatment, visit, FPE, and treatment by visit interaction term, with visit as the repeating factor, subject as a random effect, and baseline score as a covariate.
Abbreviations: CI = Confidence interval; DF = Degrees of freedom; FPE = Former psilocybin experience; LS = Least squares; MMRM = Mixed model for repeated measures; N = All subjects randomized; n = Subjects with post-treatment assessments; NEO-FFI = Neuroticism Extraversion Openness-Five Factor Inventory; SCL-90 = Symptom Checklist-90 Item.

Table 32 summarizes the results of the MMRM model applied to LCI parameters measured on Day 7 and Day 84 after study drug administration.

TABLE 32

F-Tests from MMRM Model: LCI Measures

| Parameter | Source | DF | Denominator DF | F-value | P-value |
|---|---|---|---|---|---|
| LCI—absolute change | FPE | 1 | 82.799713 | 0.04 | 0.8352 |
|  | Treatment | 2 | 82.605786 | 12.69 | <0.0001 |
|  | Visit | 1 | 78.162909 | 0.31 | 0.5765 |
|  | Treatment × Visit | 2 | 78.054268 | 0.40 | 0.6740 |
| LCI appreciation for life | FPE | 1 | 82.909504 | 0.33 | 0.5661 |
|  | Treatment | 2 | 82.198916 | 12.35 | <0.0001 |
|  | Visit | 1 | 79.332039 | 0.02 | 0.8767 |
|  | Treatment × Visit | 2 | 79.170548 | 0.17 | 0.8464 |
| LCI self-acceptance | FPE | 1 | 83.843514 | 0.03 | 0.8521 |
|  | Treatment | 2 | 83.332333 | 23.73 | <0.0001 |
|  | Visit | 1 | 81.020342 | 0.66 | 0.4199 |
|  | Treatment × Visit | 2 | 80.834117 | 0.98 | 0.3791 |
| LCI concern for others | FPE | 1 | 83.730773 | 0.01 | 0.9302 |
|  | Treatment | 2 | 82.680005 | 7.95 | 0.0007 |
|  | Visit | 1 | 80.322544 | 0.33 | 0.5660 |
|  | Treatment × Visit | 2 | 80.155567 | 0.42 | 0.6578 |
| LCI concern for worldly achievement | FPE | 1 | 82.629869 | 1.17 | 0.2826 |
|  | Treatment | 2 | 83.456184 | 3.78 | 0.0269 |
|  | Visit | 1 | 77.542669 | 0.67 | 0.4161 |
|  | Treatment × Visit | 2 | 77.464305 | 0.75 | 0.4750 |
| LCI concern social | FPE | 1 | 82.874879 | 0.63 | 0.4297 |
|  | Treatment | 2 | 83.174991 | 2.06 | 0.1334 |
|  | Visit | 1 | 78.231885 | 1.02 | 0.3167 |
|  | Treatment × Visit | 2 | 78.123691 | 0.21 | 0.8137 |
| LCI quest for meaning | FPE | 1 | 81.846606 | 0.04 | 0.8448 |
|  | Treatment | 2 | 82.365281 | 6.71 | 0.0020 |
|  | Visit | 1 | 76.551800 | 0.36 | 0.5495 |
|  | Treatment × Visit | 2 | 76.488228 | 0.11 | 0.8952 |
| LCI spirituality | FPE | 1 | 83.145868 | 0.09 | 0.7617 |
|  | Treatment | 2 | 82.820446 | 5.08 | 0.0083 |
|  | Visit | 1 | 79.406353 | 0.03 | 0.8635 |
|  | Treatment × Visit | 2 | 79.252439 | 0.44 | 0.6459 |
| LCI religiousness | FPE | 1 | 83.221381 | 0.00 | 0.9560 |
|  | Treatment | 2 | 81.343523 | 0.71 | 0.4966 |
|  | Visit | 1 | 79.127237 | 0.01 | 0.9113 |
|  | Treatment × Visit | 2 | 78.990086 | 0.01 | 0.9922 |
| LCI appreciation of death | FPE | 1 | 83.009544 | 0.24 | 0.6288 |
|  | Treatment | 2 | 83.554368 | 2.48 | 0.0897 |
|  | Visit | 1 | 78.314013 | 3.04 | 0.0853 |
|  | Treatment × Visit | 2 | 78.209655 | 0.54 | 0.5853 |

Note:
F-tests from a MMRM with outcome score as the dependent variable. The model has fixed effects for treatment, visit, FPE, and treatment by visit interaction, visit as the repeating 0factor, and subject as a random effect.
Abbreviations: DF = Degrees of freedom; FPE = Former psilocybin experience; MMRM = Mixed model for repeated measures; LCI = Line Changes Inventory.

An overall effect of treatment was found for all LCI domains except Concern Social, Religiousness, and Appreciation of Death. No treatment by visit interaction was found in any case, indicating that the treatment effect was consistent over time. Time and prior psilocybin use had no apparent impact on this scale.

LS means and pairwise treatment comparisons for each domain of the LCI scale are summarized in Table 33 below.

TABLE 33

Summary of LCI Results on Day 7 and Day 84

| | Parameter | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| \multicolumn{8}{c}{LCI-absolute change} |
| Day 7 | n | 29 | 30 | 26 | — | — | — |
|  | Mean | 0.4 | 0.5 | 0.1 | 0.3 | 0.4 | −0.1 |
|  | 95% CI | — | — | — | 0.14, 0.48 | 0.20, 0.55 | −0.23, 0.11 |
|  | p-value | — | — | — | 0.0007 | <0.0001 | 0.4723 |
| Day 84 | n | 27 | 30 | 21 | — | — | — |
|  | Mean | 0.5 | 0.5 | 0.1 | 0.4 | 0.4 | −0.0 |
|  | 95% CI | — | — | — | 0.19, 0.55 | 0.21, 0.56 | −0.19, 0.15 |
|  | p-value | — | — | — | <0.0001 | <0.0001 | 0.8393 |
| \multicolumn{8}{c}{LCI appreciation for life} |
| Day 7 | n | 29 | 30 | 26 | — | — | — |
|  | Mean | 0.6 | 0.8 | 0.2 | 0.5 | 0.6 | −0.2 |
|  | 95% CI | — | — | — | 0.16, 0.74 | 0.31, 0.90 | −0.44, 0.13 |
|  | p-value | — | — | — | 0.0028 | <0.0001 | 0.2762 |
| Day 84 | N | 27 | 30 | 21 | — | — | — |
|  | Mean | 0.7 | 0.8 | 0.2 | 0.5 | 0.6 | −0.1 |
|  | 95% CI | — | — | — | 0.24, 0.79 | 0.35, 0.90 | −0.37, 0.15 |
|  | p-value | — | — | — | 0.0003 | <0.0001 | 0.4037 |
| \multicolumn{8}{c}{LCI self-acceptance} |
| Day 7 | N | 29 | 30 | 26 | — | — | — |
|  | Mean | 0.6 | 0.8 | 0.1 | 0.5 | 0.7 | −0.1 |
|  | 95% CI | — | — | — | 0.32, 0.75 | 0.45, 0.88 | −0.35, 0.07 |
|  | p-value | — | — | — | <0.0001 | <0.0001 | 0.1938 |

TABLE 33-continued

Summary of LCI Results on Day 7 and Day 84

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| Day 84 | N | 27 | 30 | 21 | — | — | — |
| | Mean | 0.6 | 0.6 | 0.1 | 0.5 | 0.5 | 0.0 |
| | 95% CI | — | — | — | 0.28, 0.76 | 0.26, 0.75 | −0.21, 0.24 |
| | p-value | — | — | — | <0.0001 | <0.0001 | 0.8961 |
| | | | | LCI concern for others | | | |
| Day 7 | n | 29 | 30 | 26 | — | — | — |
| | Mean | 0.6 | 0.5 | 0.1 | 0.4 | 0.4 | 0.0 |
| | 95% CI | — | — | — | 0.15, 0.71 | 0.11, 0.67 | −0.23, 0.31 |
| | p-value | — | — | — | 0.0034 | 0.0075 | 0.7864 |
| Day 84 | n | 27 | 30 | 21 | — | — | — |
| | Mean | 0.7 | 0.5 | 0.1 | 0.5 | 0.4 | 0.1 |
| | 95% CI | — | — | — | 0.25, 0.77 | 0.12, 0.64 | −0.12, 0.37 |
| | p-value | — | — | — | 0.0002 | 0.0046 | 0.3046 |
| | | | | LCI concern for worldly achievement | | | |
| Day 7 | n | 29 | 30 | 26 | — | — | — |
| | Mean | −0.2 | −0.2 | −0.0 | −0.1 | −0.2 | 0.1 |
| | 95% CI | — | — | — | −0.31, 0.02 | −0.37, −0.03 | −0.11, 0.22 |
| | p-value | — | — | — | 0.0908 | 0.0197 | 0.4818 |
| Day 84 | n | 27 | 30 | 21 | — | — | — |
| | Mean | −0.1 | −0.2 | 0.0 | −0.1 | −0.2 | 0.1 |
| | 95% CI | — | — | — | −0.29, 0.09 | −0.44, −0.06 | −0.03, 0.33 |
| | p-value | — | — | — | 0.3069 | 0.0118 | 0.1050 |
| | | | | LCI concern social | | | |
| Day 7 | n | 29 | 30 | 26 | — | — | — |
| | Mean | 0.2 | 0.2 | 0.1 | 0.2 | 0.1 | 0.1 |
| | 95% CI | — | — | — | 0.01, 0.33 | −0.05, 0.27 | −0.10, 0.22 |
| | p-value | — | — | — | 0.0412 | 0.1915 | 0.4428 |
| Day 84 | n | 27 | 30 | 21 | — | — | — |
| | Mean | 0.2 | 0.2 | 0.1 | 0.1 | 0.1 | 0.0 |
| | 95% CI | — | — | — | −0.06, 0.32 | −0.07, 0.32 | −0.17, 0.19 |
| | p-value | — | — | — | 0.1741 | 0.1952 | 0.9365 |
| | | | | LCI quest for meaning | | | |
| Day 7 | n | 29 | 30 | 26 | — | — | — |
| | Mean | 0.5 | 0.5 | 0.1 | 0.4 | 0.4 | 0.0 |
| | 95% CI | — | — | — | 0.16, 0.64 | 0.15, 0.64 | −0.23, 0.24 |
| | p-value | — | — | — | 0.0015 | 0.0018 | 0.9737 |
| Day 84 | n | 27 | 30 | 21 | — | — | — |
| | Mean | 0.5 | 0.5 | 0.1 | 0.4 | 0.4 | −0.0 |
| | 95% CI | — | — | — | 0.07, 0.63 | 0.11, 0.66 | −0.30, 0.23 |
| | p-value | — | — | — | 0.0139 | 0.0070 | 0.7956 |
| | | | | LCI spirituality | | | |
| Day 7 | n | 29 | 30 | 26 | — | — | — |
| | Mean | 0.4 | 0.5 | 0.2 | 0.2 | 0.3 | −0.1 |
| | 95% CI | — | — | — | −0.03, 0.51 | 0.05, 0.59 | −0.34, 0.18 |
| | p-value | — | — | — | 0.0789 | 0.0204 | 0.5318 |
| Day 84 | n | 27 | 30 | 21 | — | — | — |
| | Mean | 0.5 | 0.5 | 0.1 | 0.4 | 0.4 | −0.0 |
| | 95% CI | — | — | — | 0.09, 0.65 | 0.12, 0.68 | −0.29, 0.23 |
| | p-value | — | — | — | 0.0105 | 0.0052 | 0.7985 |
| | | | | LCI religiousness | | | |
| Day 7 | n | 29 | 30 | 26 | — | — | — |
| | Mean | 0.0 | −0.0 | 0.0 | 0.0 | −0.1 | 0.1 |
| | 95% CI | — | — | — | −0.09, 0.15 | −0.17, 0.07 | −0.04, 0.19 |
| | p-value | — | — | — | 0.6789 | 0.4061 | 0.1991 |
| Day 84 | n | 27 | 30 | 21 | — | — | — |
| | Mean | 0.0 | −0.0 | −0.0 | 0.0 | −0.0 | 0.1 |
| | 95% CI | — | — | — | −0.19, 0.24 | −0.25, 0.17 | −0.13, 0.26 |
| | p-value | — | — | — | 0.8056 | 0.7212 | 0.5143 |
| | | | | LCI appreciation of death | | | |
| Day 7 | n | 29 | 30 | 26 | — | — | — |
| | Mean | 0.1 | 0.2 | 0.0 | 0.1 | 0.1 | −0.0 |
| | 95% CI | — | — | — | −0.06, 0.25 | −0.03, 0.28 | −0.17, 0.13 |
| | p-value | — | — | — | 0.2163 | 0.1265 | 0.7511 |

TABLE 33-continued

Summary of LCI Results on Day 7 and Day 84

| Parameter | | Psilocybin 25 mg (N = 30) | Psilocybin 10 mg (N = 30) | Placebo (N = 29) | Psilocybin 25 mg-Placebo | Psilocybin 10 mg-Placebo | Psilocybin (25 mg-10 mg) |
|---|---|---|---|---|---|---|---|
| Day 84 | n | 27 | 30 | 21 | — | — | — |
| | Mean | 0.3 | 0.2 | 0.1 | 0.2 | 0.2 | 0.0 |
| | 95% CI | — | — | — | −0.01, 0.45 | −0.05, 0.40 | −0.17, 0.25 |
| | p-value | — | — | — | 0.0597 | 0.1190 | 0.7010 |

Note:
LS means and p-values from the MMRM with outcome score as the dependent variable. The model has fixed effects for treatment, visit, FPE, and treatment by visit interaction, visit as the repeating factor, and subject as a random effect.
Abbreviations: CI = Confidence interval; FPE = Former psilocybin experience; LCI = Line Changes Inventory; LS = least squares; MMRM = Mixed model for repeated measures; N = All subjects randomized; n = Subjects with post-treatment assessments.

Each psilocybin dose group showed a higher absolute change in LCI compared to the placebo group at both Day 7 and Day 84 after drug administration (p<0.05). The effect of each psilocybin dose compared to placebo was <0.05 for nearly all LCI domains at both timepoints, notably Appreciation for Life, Self-Acceptance, Concern for Others, and Quest for Meaning. Positive trends were also observed for Spirituality, Concern for Worldly Achievement, and Concern Social. However, Religiousness and Appreciation of Death appeared to be unaffected.

The differences between psilocybin dose effects (10 mg versus 25 mg) were not statistically significant for any LCI domain at either timepoint.

Psilocybin had an effect on each of the five primary dimensions of the 5D-ASC scale compared to placebo assessed immediately post-treatment (p≤0.0001). Differences between doses were observed (p≤0.05) in two cases (Dread of Ego Dissolution and Auditory Alteration), with the 25 mg psilocybin group showing higher scores than the 10 mg psilocybin group on each of these domains. The 11 sub-scores of the 5D-ASC scale also showed differences between each of the psilocybin dose groups and placebo (p≤0.0001). Only two of the subscales showed a dose relationship: the mean scores for Anxiety and Complex Imagery were higher in the 25 mg dose group than in the 10 mg dose group.

At both the 25 mg and 10 mg doses, subjects treated with psilocybin showed an increase in the LCI absolute change (p≤0.0007) and in LCI domain scores measuring Appreciation for Life (p≤0.0028), Self-Acceptance (p<0.0001), Concern for Others (P≤0.0075), and Quest for Meaning (p<0.0139). These effects were evident regardless of the psilocybin dose administered.

PANAS scores, measured immediately post-treatment, showed a reduction in Positive Affect for placebo-treated subjects, which was not observed in the psilocybin groups (p<0.03). PANAS Negative Affect was increased in the 25 mg psilocybin group, compared to a slight decrease in the 10 mg group (p=0.0218) and the placebo group (p=0.0989).

There were no consistent or noteworthy trends to suggest that either dose of psilocybin had a short- or long-term effect on PET, RMET, SSR, SVO, or TEQ. Likewise, psilocybin had no detectable effect on changes in NEO-FFI or SCL 90 scales at either Day 7 or Day 84.

There was no evidence of improvement or deterioration in performance on CANTAB tasks as a result of the psilocybin exposure over this 28-day study in this study population of healthy volunteers (inclusion criteria ranging from 20 to 59 years of age). No pro-cognitive effect was detected at Day 7 on the exploratory efficacy outcomes.

On the CANTAB Global Composite score, performance was worse than placebo for the 10 mg psilocybin group at Day 7 (p<0.05). However, this result is due in part to the larger improvement in performance from Baseline by the placebo group at Day 7. For the 10 mg group, performance increases again at Day 28 to a level similar to placebo suggesting no adverse effects of the 10 mg dose compared with placebo. The CANTAB cognitive performance results support the safety and tolerability of the administration of a single 10 mg or 25 mg dose of psilocybin.

There was no Visit-Dose effect observed on any of the cognitive outcome measures; PALTEA (episodic memory), SWMBE (working memory), SWMS (executive function and planning), RVPA (sustained attention) and Global Cognitive Composite, suggesting there was no consistent and differential performance changes between the placebo and the 10 mg and 25 mg psilocybin dose groups.

Despite no overall main effect of dose group on RVP performance (cognitive domain of sustained attention), there was a LS mean difference from placebo for both the 10 mg and 25 mg groups at Day 28 (p<0.05), suggesting better performance of subjects in the psilocybin dose groups relative to placebo at Day 28.

PANAS scores, measured immediately post-treatment, showed a reduction in Positive Affect for placebo-treated subjects, which was not observed in the psilocybin groups (p<0.03). PANAS Negative Affect was increased in the 25 mg psilocybin group, compared to a slight decrease in the 10 mg group (p=0.0218) and the placebo group (p=0.0989).

No significant difference in performance was observed between 10 mg psilocybin, 25 mg psilocybin and placebo groups at Day 7 for the exploratory efficacy outcome measures ERTPC (Emotion recognition), OTSPSFC (executive function, planning and working memory) or IEDYERT (rule acquisition and reversal, flexibility of attention).

Example 4: Co-Administration of Psilocybin and a Benzodiazepine

The following example provides details of a study to determine the effects of low and high dose of the benzodiazepine alprazolam on the acute psilocybin experience in healthy volunteers, and to provide an evidence base for the use of benzodiazepines to control anxiety, which may be used to inform future dose and drug selection. This study also seeks to show the dimension of the psychedelic experience affected by GABAergic manipulation, including subjective (11D-ASC) and neurological (fMRA), to help develop an understanding of which aspects are important therapeutically.

In a first dosing session, at t=0; 315 µg/kg psilocybin (PSI) will be administered to a healthy, psychedelic naïve patient (i.e., the patient has no prior experience taking psychedelic drugs). Approximately 4 weeks later, the patient will participate in a second dosing session. In the second dosing session, 315 µg/kg psilocybin will be co-administered to the patient with either (a) a placebo (PSI+PLA), (2) 0.25 mg alprazolam (PSI+0.25 mg), or (3) 1 mg alprazolam (PSI+1 mg) at t=0.

In both dosing sessions, after the patient begins to have a psychedelic experience, the patient will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) and blood cortisol will be evaluated. Longer term effects on wellbeing will also be evaluated after the psychological experience has ended.

Functional mMRI (fMRI) will also be used to measure the effects of low and high dose alprazolam in these patients. Individuals in each group (PSI+PLA, PSA+0.25 mg, PSI+1 mg) will be randomized for resting state fMRI scanning at the peak of the experience. Brain regions associated with fear, panic, and anxiety will be examined. The following comparisons will be performed: (PSI+PLA) vs (PSI+0.25) mg vs (PSI+1 mg). It is hypothesized that activation in fear regions will decrease disproportionately to other neural correlates of the psychedelic state.

Example 5: Co-Administration of Psilocybin and a Benzodiazepine

The following examples 5A and 5B provide details of studies that will be used to determine the effects of low and high dose benzodiazepine (e.g., alprazolam or diazepam) on the acute psilocybin experience in healthy volunteers. The purpose of these studies is to provide an evidence base for the use of benzodiazepines to control psychedelic anxiety, which may be used to inform future dose and drug selection. This study also seeks to show the dimension of the psychedelic experience affected by GABAergic manipulation, including subjective (11 D-ASC) and neurological (fMRI), to help develop an understanding of which aspects are important therapeutically.

Example 5A: Alprazolam

In a first dosing session, at t=0: 315 µg/kg psilocybin (PSI) will be administered to a healthy, psychedelic naïve patient (i.e., the patient has no prior experience taking psychedelic drugs) in an open-label manner.

Approximately 4 weeks later, the patient will participate in a second dosing session. In the second dosing session, 315 µg/kg psilocybin will be co-administered to the patient with either (a) a placebo (PSI+PLA), (2) 0.25 mg alprazolam (PSI+0.25 mg), or (3) 1 mg alprazolam (PSI+1 mg) at t=0.

In both dosing sessions, after the patient begins to have a psychedelic experience, the patient will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) and blood cortisol will be evaluated. Longer term effects on well being will also be evaluated after the psychological experience has ended.

Functional mMRI (fMRI) will also be used to measure the effects of low and high dose alprazolam in these patients. Individuals in each group (PSI+PLA, PSA+0.25 mg, PSI+1 mg) will be randomized for resting state fMRI scanning at the peak of the experience. Brain regions associated with fear, panic, and anxiety will be examined. The following comparisons will be performed: (PSI+PLA) vs (PSI+0.25) mg vs (PSI+1 mg). It is hypothesized that activation in fear regions will decrease disproportionately to other neural correlates of the psychedelic state due to co-administration of alprazolam.

Example 5B: Diazepam

In a first dosing session, at t=0: 25 mg psilocybin (PSI) will be administered to a healthy, psychedelic naïve patient in an open-label manner.

Approximately 4 weeks later, the patient will participate in a second dosing session. In the second dosing session, 25 mg psilocybin will be administered to the patient. Additionally, the patient will also be administered (a) a placebo (PSI+PLA), (2) 2 mg diazepam (PSI+2 mg), (3) 5 mg diazepam (PSI+5 mg), (4) or 10 mg diazepam (PSI+10 mg) at the same time as the psilocybin or at the peak of the psychedelic experience.

In both dosing sessions, after the patient begins to have a psychedelic experience, the patient will be asked to provide a subjective rating approximately every 15 minutes of his or her experience intensity, blissfulness, and anxiety. Heart rate, blood pressure and galvanic skin reaction will also be measured. After each session, 5D-ADC, PANAS, and blood cortisol will be measured. Additionally, a standardized interview will be performed, to discuss the quality of the experience and to get any comments that may be overlooked in the surveys.

Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) and blood cortisol will be evaluated. Longer term effects on wellbeing will also be evaluated after the psychological experience has ended.

Functional mMRI (fMRI) will also be used to measure the effects of low and high dose diazepam in these patients. Individuals in each group (PSI+PLA, PSA+2 mg, PSI+5 mg, PSI+10 mg) will be randomized for resting state fMRI scanning at the peak of the experience. Brain regions associated with fear, panic, and anxiety will be examined. The following comparisons will be performed: (PSI+PLA) vs (PSI+2 mg) vs (PSI+5 mg) vs. (PSI+10 mg). It is hypothesized that activation in fear regions will decrease disproportionately to other neural correlates of the psychedelic state due to co-administration of diazepam.

Example 6: Effect of Alprazolam on 5-HT$_{2A}$ Receptor Binding by Psilocybin

The following example provides details of a study used to determine whether alprazolam-induced changes in subjective experience during psilocybin therapy are due to changes in 5-HT$_{2A}$ occupancy. If not, downstream molecular and cellular effects that may be important in psilocybin's therapeutic effects may be preserved after co-treatment with a benzodiazepine.

In this study, [$^{11}$C]CIMBI-36 (a selective 5-HT$_{2A}$ receptor agonist positron emission tomography (PET) radioligand) will be used to investigate whether 5-HT$_{2A}$ binding is affected by placebo vs. alprazolam.

At time t=0, patients will be administered 25 mg psilocybin (PSI) in combination with either a placebo, or alprazolam. At t=2 hours, patients will be given a tracer dose of [$^{11}$C]CIMBI-36. At t=2-3 hours, a PET scan will be performed, to determine whether 5-HT$_{2A}$ binding is affected by either dose of alprazolam.

This study may optionally be performed using diazepam instead of alprazolam.

Example 7: Co-Administration of Psilocybin and a 5-HT$_{2A}$ Specific Antagonist The following example provides details of a study used to determine the effects of low and high dose of ketanserin, a 5-HT$_{2A}$ specific antagonist on the acute psilocybin experience in healthy volunteers. The purpose of this study is to provide an evidence base for the use of 5-HT$_{2A}$ specific antagonists to control the negative side effects associated with a traumatic psychedelic experience, which may be used to inform future dose and drug selection. This study also seeks to show the dimension of the psychedelic experience affected by GABAergic manipulation, including subjective (11D-ASC) and neurological (fMRI), to help develop an understanding of which aspects are important therapeutically.

In a first dosing session, at t=0: 315 µg/kg psilocybin (PSI) will be administered to a healthy, psychedelic naïve patient (i.e., the patient has no prior experience taking psychedelic drugs). Approximately 4 weeks later, the patient will participate in a second dosing session. In the second dosing session, 315 µg/kg psilocybin will be co-administered to the patient with either (1) a placebo (PSI+PLA), (2) low dose ketanserin (PSI+LD), or (3) high dose ketanserin (PSI+HD) at t=0.

In both dosing sessions, after the patient begins to have a psychedelic experience, the patient will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) and blood cortisol will be evaluated. Longer term effects on well being will also be evaluated after the psychological experience has ended.

Functional mMRI (fMRI) will also be used to measure the effects of low and high dose ketanserin in these patients. Individuals in each group (PSI+PLA, PSA+LD, PSI+HD) will be randomized for resting state fMRI scanning at the peak of the experience. Brain regions associated with fear, panic, and anxiety will be examined. The following comparisons will be performed: (PSI+PLA) vs (PSI+LD) vs (PSI+HD). It is hypothesized that activation in fear regions will decrease disproportionately to other neural correlates of the psychedelic state due to co-administration of ketanserin.

Example 8: Co-Administration of Psilocybin and a 5-HT$_{2A}$ Inverse Agonist

The following example provides details of a study used to determine the effects of low and high dose of pimavanserin, a 5-HT$_{2A}$ inverse agonist on the acute psilocybin experience in healthy volunteers. The purpose of this study is to provide an evidence base for the use of 5-HT$_{2A}$ inverse agonists to control the negative side effects associated with a traumatic psychedelic experience, which may be used to inform future dose and drug selection. This study also seeks to show the dimension of the psychedelic experience affected by GABAergic manipulation, including subjective (11D-ASC) and neurological (fMRIA), to help develop an understanding of which aspects are important therapeutically.

In a first dosing session, at t=0, 315 µg/kg psilocybin (PSI) will be administered to a healthy, psychedelic naïve patient (i.e., the patient has no prior experience taking psychedelic drugs). Approximately 4 weeks later, the patient will participate in a second dosing session. In the second dosing session, 315 µg/kg psilocybin will be co-administered to the patient with either (1) a placebo (PSI+PLA), (2) low dose pimavanserin (PSI+LD), or (3) high dose pimavanserin (PSI+HD) at t=0.

In both dosing sessions, after the patient begins to have a psychedelic experience, the patient will be asked to provide a subjective rating approximately every 20 minutes of his or her experience intensity, blissfulness, and anxiety. Physiological measures of sympathetic simulation will be measured at t=2-3 hours. At t=7 hours, 11D-ASC (11-Dimension Altered States of Consciousness), PANAS (Positive and Negative Affect Schedule), EDI (Ego-Dissolution Inventory) and blood cortisol will be evaluated. Longer term effects on well being will also be evaluated after the psychological experience has ended.

Functional mMRI (fMRI) will also be used to measure the effects of low and high dose pimavanserin in these patients. Individuals in each group (PSI+PLA, PSA+LD, PSI+HD) will be randomized for resting state fMRI scanning at the peak of the experience. Brain regions associated with fear, panic, and anxiety will be examined. The following comparisons will be performed: (PSI+PLA) vs (PSI+LD) vs (PSI+HD). It is hypothesized that activation in fear regions will decrease disproportionately to other neural correlates of the psychedelic state due to co-administration of pimavanserin.

Example 9: Effect of Pimavanserin or Ketanserin on 5-HT$_{2A}$ Receptor Binding by Psilocybin The following example provides details of a study used to determine whether pimavanserin or ketanserin induced changes in subjective experience during psilocybin therapy are due to changes in 5-HT$_{2A}$ occupancy. If not, downstream molecular and cellular effects that may be important in psilocybin's therapeutic effects may be preserved after co-treatment with a 5-HT$_{2A}$ specific antagonist and/or inverse agonist.

In this study, [$^{11}$C]CIMBI-36 (a selective 5-HT$_{2A}$ receptor agonist positron emission tomography (PET) radioligand) will be used to investigate whether 5-HT$_{2A}$ binding is affected by placebo vs. pimavanserin or ketanserin At time t=0, patients will be administered 25 mg psilocybin (PSI) in combination with either a placebo, or a low or high dose of pimavanserin or ketanserin. At t=2 hours, patients will be given a tracer dose of [$^{11}$C]CIMBI-36. At t=2-3 hours, a PET scan will be performed, to determine whether 5-HT$_{2A}$ binding is affected by either dose of pimavanserin or ketanserin.

Example 10: In Vivo Study Investigating Changes in Mouse Protein Expression Levels Associated with the Pathophysiology of Various Diseases, Disorders, and Conditions, Including Inflammation, Alzheimer's Disease, Parkinson's Disease, and Autism Expression level of many proteins, involved in several signaling pathways and processes, has been reported to be altered in patients with various diseases, disorders, and conditions, such as inflammation, Alzheimer's disease, Parkinson's disease and autism, as well as in animal models thereof. The aim the study described below was to evaluate whether psilocybin has the potential to induce a favourable profile of protein expression in those known to participate in the pathophysiology of these diseases, disorders, or conditions. The Olink® panel was used to assess the change in protein expression across time in naïve mice after one administration of psilocybin. Olink® is a proteomics company that developed an easy and convenient exploratory panel simultaneously assessing the expression level of numerous different proteins in rodents. The proteins in this panel are correlated with several biomarkers or dysregulated proteins across various indications.

In this study, three doses of psilocybin (1 mg/kg; 3 mg/kg & 10 mg/kg) were injected into mice, and the vehicle was used as a control (n=10 mice per group). Blood samples were collected at 3 time points post-administration of psilocybin (1 hour, 24 hours, and 8 days). More than 40 μL of each sample were supplied in temperature-resistant, non-protein binding plastics. Samples were shipped on dry ice to Olink®. Samples were randomised by Olink® before the analysis in order to conduct the analysis in a blinded manner.

To analyze the samples, an immunology reaction was performed by preparation of an Incubation mix (containing A- and B-probes, buffer & internal controls) and distribution of three μL of this to the wells of a 96-well PCR (polymerase chain reaction) plate. One μL of each sample; a duplicate of a pooled plasma sample; triplicate wells of interplate control and the negative control, were transferred to the plate in this sequence. The plate was then sealed, centrifuged and incubated at 4° C. overnight. On the following day, an extension- and pre-amplification PCR reaction took place. A proximity extension assay mix was added directly to the samples in the overnight incubation plate and a classical PCR reaction generating a unique PCR target sequence for each biomarker was performed. The resulting DNA sequences were subsequently detected and quantified in a singleplex readout format using the microfluidic real-time PCR instrument (Biomark HD, Fluidigm). The resulting data was quality controlled using RT-PCR Software. Generated Ct-values were exported from the software and imported to Olink® NPX Manager for additional quality control and generation of normalized protein expression (NPX) values.

Assay performance was assessed by measurements of internal and external controls included in all Olink® Panels. The four internal controls (two Incubation controls, one Detection control and one Extension control) were spiked into every sample at an equal level and were used to monitor each step of the reaction. The two external controls (Interplate control and Negative control) were added in triplicate reactions in a separate column of the reaction plate; they were used to minimize plate variation (interplate control) and generate limit of detection (LOD) for each assay (negative control). Each assay run was accepted when QCs were within the predetermined acceptance criteria.

Results from Olink® panels were generated as Ct values from the Fluidigm Biomark. Ct values were then re-calculated to normalized protein expression (NPX) values using Olink® NPX Manager. Results of protein expression levels were reported in normalized protein expression (NPX), Olink®'s arbitrary unit on log 2 scale.

To calculate NPX, the following calculation was performed:

1. Each sample was normalized against the Extension control.

$$Ct_{Analyte} - Ct_{Extension\ Control} = dCt_{Analyte}$$

2. Each assay was normalized against its corresponding interplate control.

$$dCt_{Analyte} - dCt_{Inter-plate\ Control} = ddCt_{Analyte}$$

3. Each assay was adjusted using a pre-determined correction factor, which inverts the values with respect to Ct, so that a high NPX value corresponds to a high protein expression level.

$$\text{Correction factor} - ddCt_{Analyte} = NPX_{Analyte}$$

Psilocybin induced changes in various plasma proteins known to be involved in the pathophysiology of Alzheimer's disease. Specifically, psilocybin induced favorable changes in plasma levels of Glucagon (Gcg, FIG. 50), Receptor protein kinase erbB4 (Erbb4, FIG. 51), Tenascin-R (Tnr, FIG. 52), Transforming growth factor beta receptor type 3 (Tfgbr3, FIG. 53), and Activin A Receptor Type II-like kinase 1 (Acvrl1, FIG. 54). These data suggest that psilocybin favorably impact levels of AD-associated proteins in Alzheimer's disease.

Psilocybin also induced changes in various plasma proteins known to be involved in the pathophysiology of Parkinson's disease. Twenty four hours after administration of 10 mg/kg psilocybin, protein expression of Erbb4 increased (FIG. 51). Twenty four hours after administration of 10 mg/kg psilocybin protein expression of Rgma decreased (FIG. 55). One hour after administration of 10 mg/kg psilocybin, protein expression of Fas increased (FIG. 56). One hour after administration of 10 mg/kg psilocybin, protein expression of glucagon (Gcg) was increased (FIG. 50).

Psilocybin also induced changes in the levels of pro-inflammatory cytokine CXCL1. As shown in FIG. 49, there was a statistically significant reduction in expression of CXCL1 with 10 mg/kg psilocybin vs vehicle at 8 days post administration.

Figure 25:
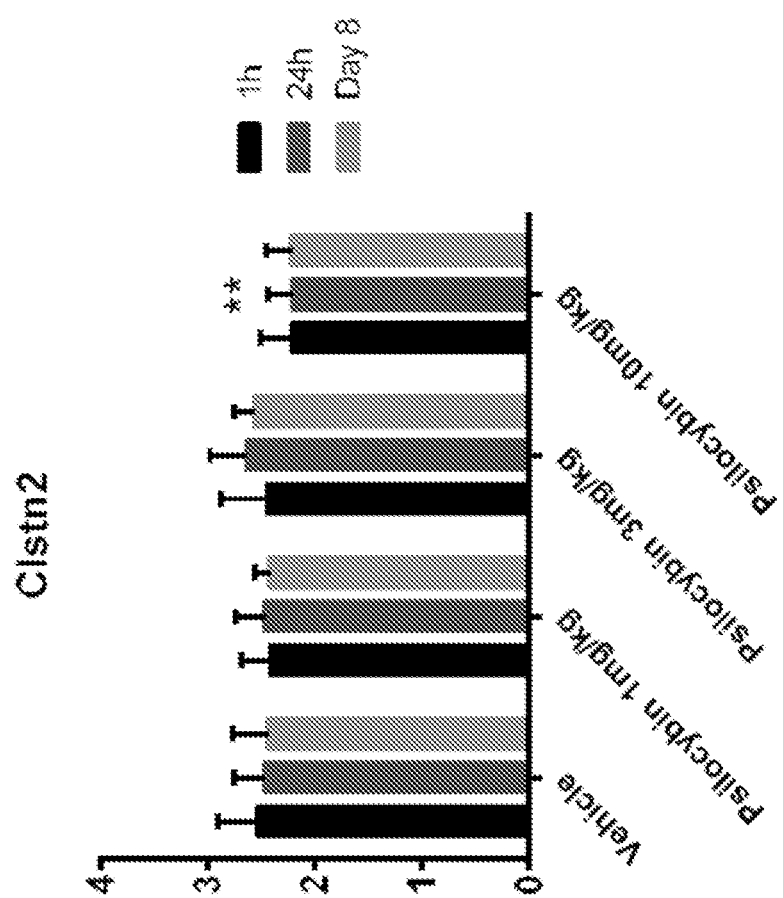
FIG. 25 shows the effect of psilocybin on calsyntenin 2 (Clstn2) expression levels at 1 hour, 24 hours, and on day 8 following a single administration of psilocybin in naïve mice compared to vehicle-treated animals. Two-way ANOVA repeated measures followed by Bonferroni multiple comparison test, *p<0.05, p<0.01, *p<0.001, ****p<0.0001. Data are expressed as mean±standard deviation (sd).
Figure 26:
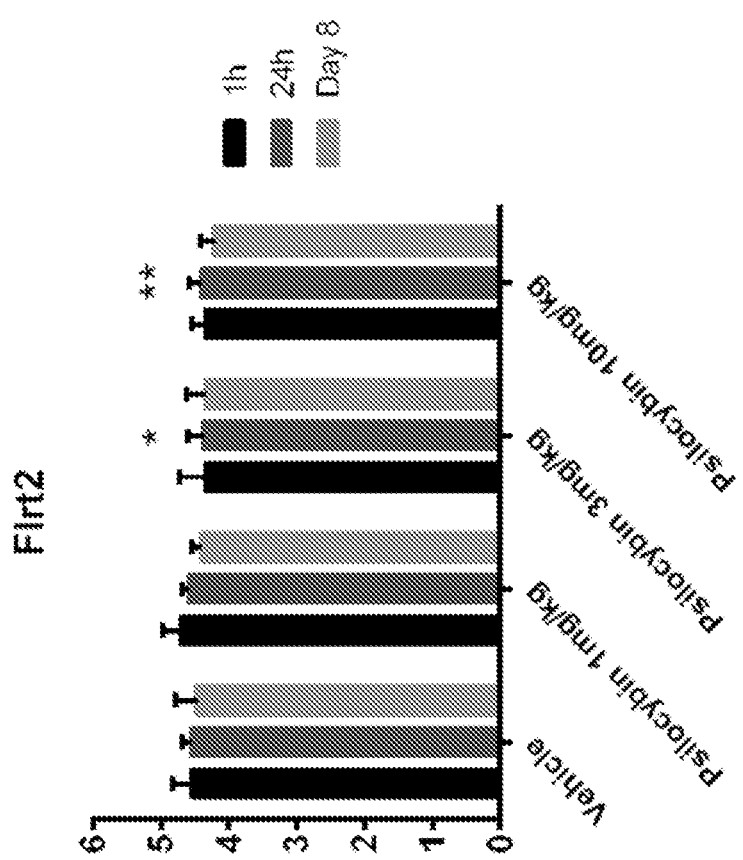
FIG. 26 shows the effect of psilocybin on Fibronectin leucine-rich repeat transmembrane protein 2 (Flrt2) expression levels at 1 hour, 24 hours, and on day 8 following a single administration of psilocybin in naïve mice compared to vehicle-treated animals. Two-way ANOVA repeated measures followed by Bonferroni multiple comparison test, *p<0.05, p<0.01, *p<0.001, ****p<0.0001. Data are expressed as mean±sd.
Figure 27:
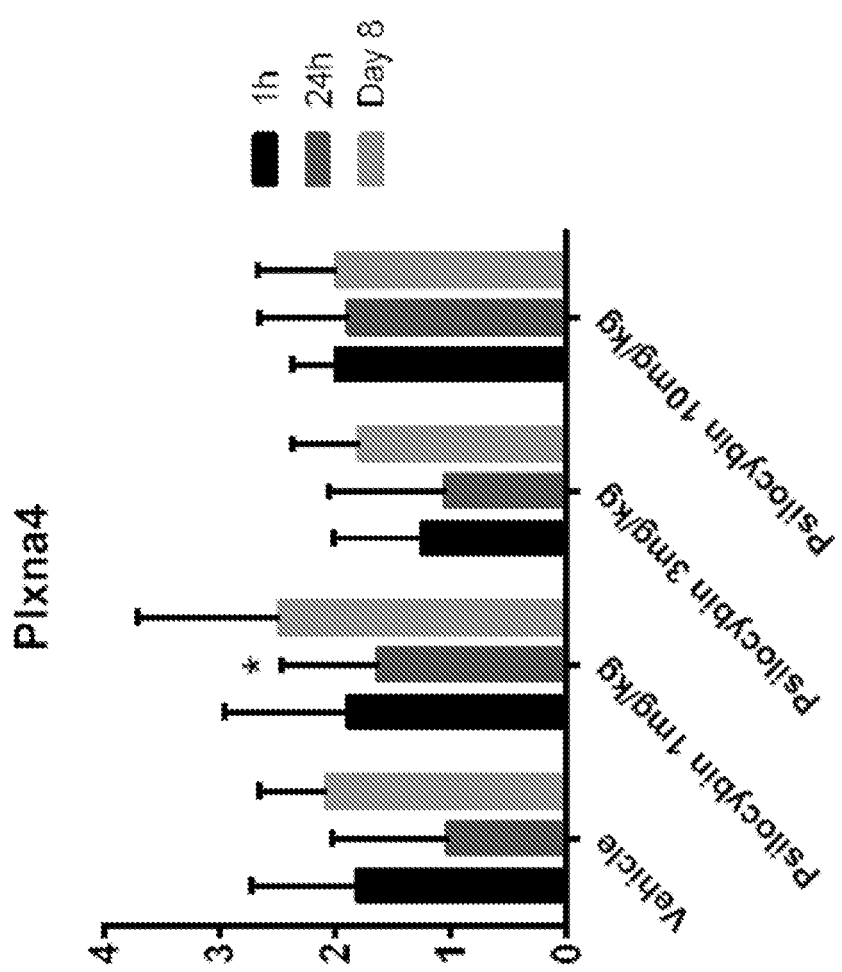
FIG. 27 shows the effect of psilocybin on plexin-A4 (Plxna4) expression levels at 1 hour, 24 hours, and on day 8 following a single administration of psilocybin in naïve mice compared to vehicle-treated animals in an in vivo model. Two-way ANOVA repeated measures followed by Bonferroni multiple comparison test, *p<0.05, p<0.01, *p<0.001, ****p<0.0001. Data are expressed as mean±sd.
Figure 28:
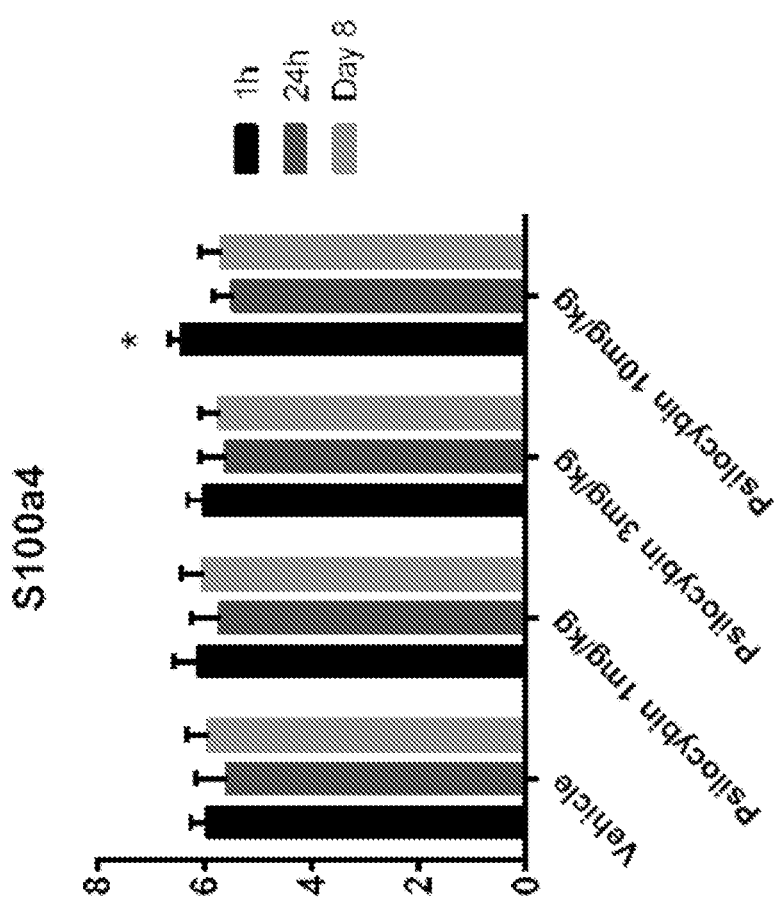
FIG. 28 shows the effect of psilocybin on S100 calcium binding protein A4 (S100a4) expression levels at 1 hour, 24 hours, and on day 8 following a single administration of psilocybin in naïve mice compared to vehicle-treated animals. Two-way ANOVA repeated measures followed by Bonferroni multiple comparison test, *p<0.05, p<0.01, *p<0.001, ****p<0.0001. Data are expressed as mean±sd.
Figure 29:
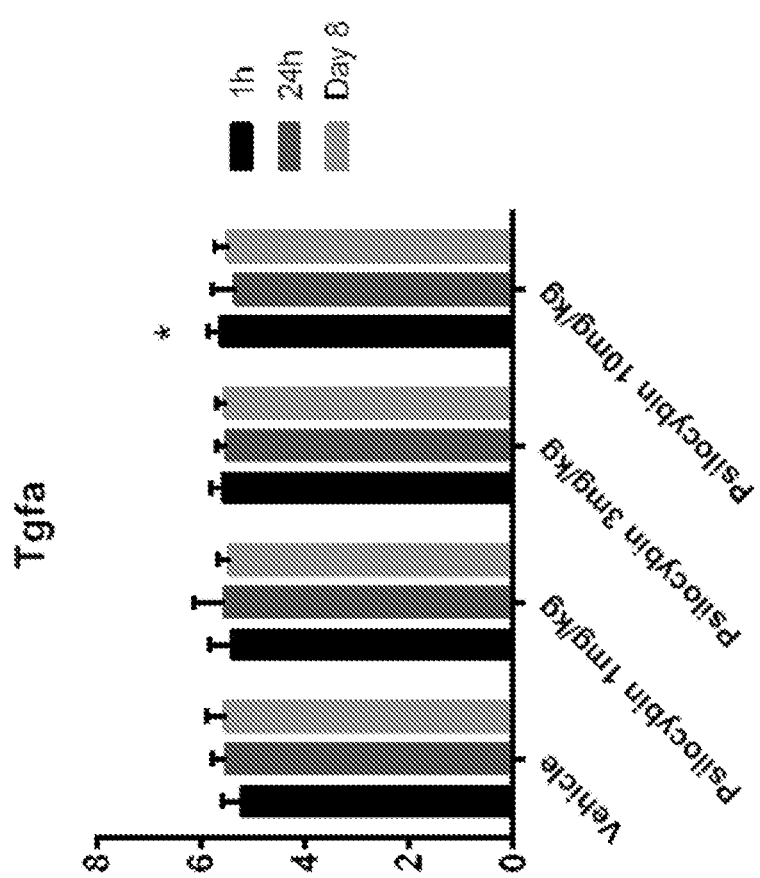
FIG. 29 shows the effect of psilocybin on transforming growth factor alpha (Tgfa) expression levels at 1 hour, 24 hours, and on day 8 following a single administration of psilocybin in naïve mice compared to vehicle-treated animals Two-way ANOVA repeated measures followed by Bonferroni multiple comparison test, *p<0.05. Data are expressed as mean±sd.
Figure 30:
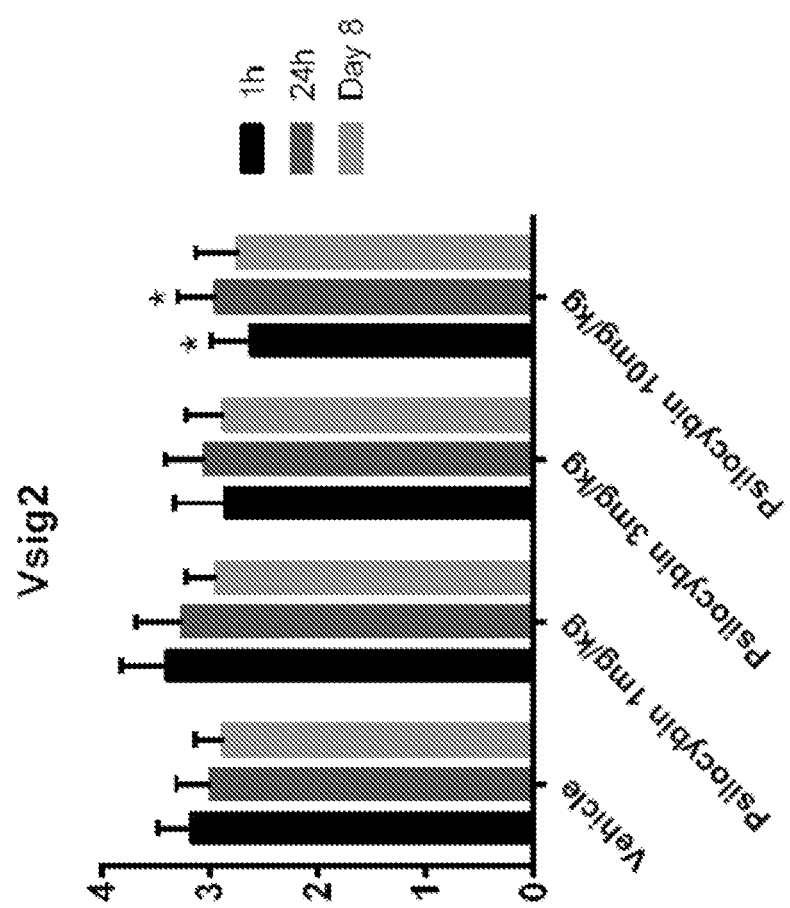
FIG. 30 shows the effect of psilocybin on levels of V-set and immunoglobulin domain containing 2 (Vsig2) expression levels at 1 hour, 24 hours, and on day 8 following a single administration of psilocybin in naïve mice compared to vehicle-treated animals. Two-way ANOVA repeated measures followed by Bonferroni multiple comparison test, *p<0.05, p<0.01, *p<0.001, ****p<0.0001. Data are expressed as mean±sd.

Changes in the levels of various plasma proteins known to be involved in the pathophysiology of autism spectrum disorder were also observed. In addition to Cxcl1 (FIG. 49), Erbb4 (FIG. 51), Fas (FIG. 56), Rgma (FIG. 55), and Tgfbr3 (FIG. 53), described above, Clnstn2 expression levels were significantly decreased 24 hours following a single administration of 10 mg/kg psilocybin in naïve mice (FIG. 25). Flrt2 expression levels were significantly decreased 24 hours following a single administration of 3 mg/kg or 10 mg/kg psilocybin to separate groups of naïve mice (FIG. 26). Plxna4 expression levels were significantly increased 24 hours following a single administration of 1 mg/kg psilocybin in naïve mice (FIG. 27). Rgma expression levels were significantly decreased 24 hours following a single administration of 10 mg/kg psilocybin in naïve mice. S100a4 expression levels were significantly increased 1 hour following a single administration of 10 mg/kg psilocybin in naïve mice (FIG. 28). TGFa expression levels were significantly increased 1 hour following a single administration of 10 mg/kg psilocybin in naïve mice (FIG. 29). Vsig2 expression levels were significantly decreased both 1 and 24 hours (separate groups of animals) following a single administration of 10 mg/kg psilocybin in naïve mice (FIG. 30).

Changes in the levels of various plasma proteins known to be involved in the pathophysiology of inflammatory bowel disease (Cxcl1 (FIG. 49), Erbb4 (FIG. 51), Fas (FIG. 56)), Epilepsy (Cxcl1 (FIG. 49)), Pain (Cxcl1 (FIG. 49), Erbb4 (FIG. 51), Rgma (FIG. 55)), ADHD (Acrvl1 (FIG. 54)), and Sleep-wake disorders (Flrt2 (FIG. 26)).

Example 11: In Vitro Test Assessing the Effect of Psilocin on Damage Induced by Fibrillated Amyloid-β on Cultures of Hippocampal Neurons Amyloid-β toxicity is a hallmark of Alzheimer's disease, and is also frequently seen in multiple sclerosis lesions. In this study, the neuroprotective effect of psilocin on amyloid-β-induced neuronal death in rat primary hippocampal culture was investigated.

Female Wistar rats of 19 days gestation were killed by cervical dislocation and foetuses were removed from the uterus. Their brains were placed in ice-cold medium of Leibovitz (L15, Gibco, Fisher bioblock, France). Hippocampi were carefully removed, and the hippocampal neurons were dissociated by trypsinization for 30 min at 37° C. (trypsin-EDTA, Gibco) in presence of 0.1 mg/ml DNAse I (Roche, France). The reaction was stopped by addition of Dulbecco's Modified Eagle Medium (DMEM; Gibco) with 10% of fetal bovine serum (FBS, Gibco). The suspension was triturated with a 10-ml pipette and using a needle syringe 21 G and centrifuged at 350×g for 10 min at room temperature. The pellet of dissociated cells were resuspended in a medium consisting of Neurobasal (Gibco) supplemented with 2% B27 supplement (Gibco), 0.5 mM L-Glutamine (Gibco), an antibiotic-antimycotic mixture. Viable cells were counted in a Neubauer cytometer using the trypan blue exclusion test (Sigma). Cells were seeded on the basis of 35000 cells per well in 96-well plate (TPP) pre-coated with poly-L-lysine. Half of the medium was replaced by fresh medium at day 3.

The cells were treated with psilocin was tested at the following concentrations: 0.03 µM; 0.1 µM; 0.3 µM; 1 µM; 3 µM & 10 µM. The stock solution was prepared fresh in 100% DMSO at 10 mM.

The protocol shown in Table 34 was performed in three independent cultures. For each culture, each condition was performed six times.

Psilocin was added to cells 10 minutes or 48 hours before amyloid-β intoxication. Neuronal viability was assessed 48 hours after amyloid-β intoxication. Basic fibroblast growth factor (bFGF) was used as a positive control.

For the plate 1, at day 7, the medium was removed and replaced by fresh medium containing test compound (at different concentrations) or bFGF at 10 ng/ml. For the plate 2, at day 9 (10 minutes before the intoxication), the medium was removed and replaced by fresh medium containing test compound (at different concentrations) or bFGF at 10 ng/ml.

At day 9, Aβ 1-40 peptide, previously fibrillated 5 days at 37° C., was added at final concentration of 5 µM in the two plates.

Two days after Aβ exposure (day 11), cell viability was assessed by a measurement of cell metabolic activity using the CellTiter96® non-radioactive kit (MTT, Promega, Charbonnières, France). The CellTiter96® Non-Radioactive Assay is a colorimetric enzymatic assay system which measures the conversion of a tetrazolium salt into a blue formazan product. Media was removed, and cells were incubated 1 hour at 37° C. with fresh medium containing substrate solution. Solubilization solution was added and visible wavelength absorbance data was collected 4 hours later using a 96-well plate reader at 570 nm and 630 nm for non-specific background (Multiskan EX, Thermo Fisher).

Psilocin was found to exert a neuroprotective effect against amyloid-β damage. When applied 10 minutes prior to amyloid-β, psilocin 10 µM increased neuronal viability (FIG. 57). When applied 48 hours prior to amyloid-β, psilocin (0.3, 1, 3 and 10 µM) also increased neuronal viability (FIG. 58).

Example 12: In Vitro Test Investigating the Effect of Psilocin on Neurite Outgrowth in Cultures of Human iPSC-Derived Neurons The neurotrophic effect of psilocin was tested on human iPSC-derived neuronal cultures. Two parameters were evaluated: the average number of neurites per neuron, and the average total neurite length per neuron. Briefly, neurons establish physical connections between them in order to create neuronal networks. The more complex arborization a neuron exhibits, the more likely it is to create neuronal networks with neighboring neurons.

Cryopreserved iCell neurons were thawed and plated according to Cellular Dynamics International instructions. The pharmacological treatments were carried out 2 hours

TABLE 34

Experimental protocol

| Day | Tasks |
| --- | --- |
| 0 | Plating of a primary culture of rat embryo hippocampal cells. This culture contains almost pure neurons. |
| 3 | Renewal of medium. |
| 7 | Compound application (48 h before Aβ administration) for plate 1, renewal of medium for plate 2. |
| 9 | Compound application (10 min before Aβ administration) for plate 2 Aβ injury in presence of compound for plates 1 and 2. |
| 11 (48 h post-Aβ) | Measure of neuronal damage by MTT assay. | after the cell plating. The cells were maintained in a humidified incubator at 37° C. in 5% $CO_2$-95% air atmosphere.

Stock solutions of psilocin were prepared in 100% DMSO at 1000 times the final concentration in the culture media (1000× concentration).

The experiment was performed in two independent cultures, as shown in Table 35. For each culture, each condition was performed in sextuplet.

TABLE 35

Experimental Protocol

| Day | Tasks |
|---|---|
| 0 | Culture initiation using iCell GABA neurons (NRC-100-010, Cellular dynamics) Treatment with test compounds for plate 1 No treatment for plate 2. |
| 3 | Renewal of treatment with test compounds for plate 1. Treatment for plate 2. |
| 7 | Renewal of treatment with test compounds for all plates. |
| 10 | Evaluation of neurite network in tubuline immunostained neurons.. |

Each plate contained two types of other experimental conditions: the control condition treated with vehicle and the culture treated with Brain-derived neutrophic factor (BDNF).

Plate 1 and 2: Cells were treated with psilocin at 3 different concentrations: 0.03 µM, 0.1 µM, 0.3 µM. The stock solution was prepared fresh in 100% DMSO at 10 mM. BDNF was used in parallel.

Ten days after plating, cultures were fixed with paraformaldehyde in PBS (phosphate buffered saline) (4%, Sigma). Then, cells were successively permeabilized, saturated with PBS (containing 3% of BSA) and incubated for 1 h with anti-beta III tubulin antibody (Sigma) at 1/10 000 in PBS containing 0.5% of BSA (bovine serum albumin). Cells were first washed and were then incubated 1 h with goat anti-mouse antibody coupled with AF488 (Invitrogen A11001) diluted at 1/1000 in PBS containing 0.5% of BSA. Finally, nuclei are stained with DAPI 1 mg/ml at 1/1000 in PBS containing 0.5% of BSA. After rinsing them with PBS, the plate was filmed and neurite networks were examined and analyzed using High-Content Screening (CellInsight, Thermo Scientific).

The evaluation of neurite outgrowth was performed using the average number of neurites per neuron and the average of total neurite length per neuron, using Sholl method (Bird & Cuntz, 2019). (See FIG. 59A, FIG. 59B, FIG. 60A, FIG. 60B).

As shown in FIG. 59A, neurons treated at Day 0 (plating day) with psilocin 0.03 µM showed significant increases in the average lengths of neurites. As shown in FIG. 59B, neurons treated at Day 3 with psilocin 0.03 µM showed an increase in both the number of neurites per neurons and the average length of neurites (FIG. 60B). In addition, psilocin 0.1 µM increased the length of neurites.

Example 13: In Vivo Test Investigating the Effect of Psilocybin in a Scopolamine-Induced Cognitive Dysfunction Mouse Model Cognitive impairments are seen in neurocognitive disorders such as Alzheimer's and Parkinson's, as well as other disorders including but limited to attention-deficit disorders, and autism spectrum disorders. In this study, cognitive deficits were induced in mice by scopolamine. Donepezil, a prescribed therapeutic for patients with Alzheimer's disease, was used as a positive control. Working memory was assessed by the number of spontaneous alternations made in a T-maze. More spontaneous alternations exhibited by the animal is interpreted as a better working memory performance (Spowart-Manning & van der Staay, 2004).

This test was divided in two distinct cohort of animals: (1) pre-treatment with psilocybin 1 h before the test (Table 36); (2) pre-treatment with psilocybin 24 h before the test (Table 37). For each cohort, 60 male CD-1 mice (4-5 weeks old) were used. They were randomly distributed to 6 different experimental groups/cohort (10 animals per group).

TABLE 36

Experimental design—cohort tested 1 h after psilocybin administration

| Group | Description | N | Route | Dosage volume | Treatment time |
|---|---|---|---|---|---|
| 1 | Saline/Vehicle | 10 | I.P. | 10 ml/kg | 1 hour |
| 2 | Scopolamine/Vehicle | 10 | I.P. | 10 ml/kg | 1 hour |
| 3 | Scopolamine/Donepezil (0.3 mg/kg) | 10 | P.O. | 10 ml/kg | 1 hour |
| 4 | Scopolamine/Psilocybin (1 mg/kg) | 10 | I.P. | 10 ml/kg | 1 hour |
| 5 | Scopolamine/Psilocybin (3 mg/kg) | 10 | I.P. | 10 ml/kg | 1 hour |
| 6 | Scopolamine/Psilocybin (10 mg/kg) | 10 | I.P. | 10 ml/kg | 1 hour |

I.P. = intraperitoneal; P.O. = per oral

TABLE 37

Experimental design—Cohort tested 24 h after psilocybin administration

| Group | Description | N | Route | Dosage volume | Treatment time |
|---|---|---|---|---|---|
| 1 | Saline/Vehicle | 10 | I.P. | 10 ml/kg | 24 hours |
| 2 | Scopolamine/Vehicle | 10 | I.P. | 10 ml/kg | 24 hours |
| 3 | Scopolamine/Donepezil (0.3 mg/kg) | 10 | P.O. | 10 ml/kg | 1 hours |
| 4 | Scopolamine/Psilocybin (1 mg/kg) | 10 | I.P. | 10 ml/kg | 24 hours |
| 5 | Scopolamine/Psilocybin (3 mg/kg) | 10 | I.P. | 10 ml/kg | 24 hours |
| 6 | Scopolamine/Psilocybin (10 mg/kg) | 10 | I.P. | 10 ml/kg | 24 hours |

I.P. = intraperitoneal; P.O. = per oral

Psilocybin was administered at 1, 3, or 10 mg/kg as outlined in the table above. The oral dosage volume for mice was 10 ml/kg. The vehicle for the test substance was saline (0.9% NaCl), the test formulation was prepared using saline (0.9% NaCl).

Psilocybin was administered as a single dose. The treatment was conducted 1 hour or 24 hours before the T-maze trial. Donepezil (donepezil hydrochloride) was prepared in saline at a concentration of 0.03 mg/ml and was given p.o. at a dosage volume of 10 ml/kg 1 h prior to the T-maze trial. The dose of donepezil was 0.3 mg/kg. Scopolamine (scopolamine hydrochloride) was prepared in a saline vehicle at a concentration of 0.1 mg/ml and was given i.p. at a dosage volume of 10 ml/kg 30 min prior to the T-maze trial start. The dose of scopolamine was of 1 mg/kg.

The T-maze consists of two choice arms and one start arm mounted to a square centre. Sliding doors are provided to close specific arms during the force choice alternation task. During the trials, animal handling and the visibility of the operator were minimized as much as possible.

The experiment consisted of one single session, which started with one "forced-choice" trial, followed by 14 "free-choice" trials. In the first "forced-choice" trial, the animal was confined for 5 seconds in the start arm, which was then released while either the left or right goal arm was blocked by closing the sliding door. After, the animal explored the maze arm and returned to the start position. Immediately after the return of the animal to the start position, the left or right goal door was opened, and the animal can choose freely between the left and right goal arm ("free choice" trials). The animal was considered to have entered an arm when it placed all four paws in the arm. A session was terminated, and the animal was removed from the maze as soon as the 14 "free-choice" trials were performed or 10 min elapsed, whichever circumstance occurred first.

The apparatus was cleaned between each animal using alcohol (70%).

The percent of spontaneous alternations was calculated as number of spontaneous alternations divided by 14 possible free-choices. The T-maze test was performed at 1 hour or 24 hours post-administration of psilocybin (1, 3, or 10 mg/kg), vehicle, or donepezil (which was administered 1 hour prior to the T-maze test in both conditions).

When administered 1 hour prior the test, 10 mg/kg psilocybin showed improvement in cognitive performance when compared to control animals (animal treated with scopolamine alone) (FIG. 61). When administered 24 hours prior the test, 1 mg/kg and 10 mg/kg psilocybin showed improvement in cognitive performance compared to control animals (animal treated with scopolamine alone) (FIG. 62).

Example 14: In Vivo Test Investigating the Effect of Psilocybin on Age-Induced Cognitive Deficits in Mice with the T-Maze Alternation Test Psilocybin was administered to aged mice to assess the pro-cognitive effects of psilocybin. Cognition is naturally impaired in aged animal and was assessed by the spontaneous alternations task in a T-maze. Donepezil, the positive control used here, is a cognitive enhancer and rescues cognitive impairments from aged mice.

The test was divided into two cohorts. The first cohort was tested 1 hour and 1 week after psilocybin treatment (Table 38), and the second cohort 24 hours after psilocybin treatment (Table 39). 60 aged male C57B16 mice (12 months old) and 10 male C57B16 mice (2 months old) were used per cohort. They were randomly distributed to different experimental groups (10 animals per group).

TABLE 38

| | Cohort tested 1 hour and 1 week after psilocybin administration | | | | | |
|---|---|---|---|---|---|---|
| Group | Description | N | Route | Treatment regimen | T-maze time point 1 | T-maze time point 2 |
| 1 | Young mouse/ Vehicle | 10 | I.P. | 7 injections of the vehicle (every 3 days/for 3 weeks) | 1 hour after the last administration | 1 week after the last administration |
| 2 | Aged mouse/ Vehicle | 10 | I.P. | | | |
| 3 | Aged mouse/ Donepezil 0.3 mg/kg | 10 | P.O. | 6 injections of the vehicle + 2 donepezil (every 3 days/for 3 weeks) | 1 hour after the first donepezil treatment | 1 hour after the second donepezil treatment |
| 4 | Aged mouse/ Single dose 1 mg/kg | 10 | I.P. | 6 injections of the vehicle + 1 injection Psilocybin 1 mg/kg (every 3 days/for 3 weeks) | 1 hour after the last administration | 1 week after the last administration |
| 5 | Aged mouse/ Single dose 3 mg/kg | 10 | I.P. | 6 injections of the vehicle + 1 injection of Psilocybin 3 mg/kg (every 3 days/for 3 weeks) | | |
| 6 | Aged mouse/ Chronic dose 1 mg/kg | 10 | I.P. | 7 injections (every 3 days/for 3 weeks) of Psilocybin 1 mg/kg | | |
| 7 | Aged mouse/ Chronic dose 3 mg/kg | 10 | I.P. | 7 injections (every 3 days/for 3 weeks) of Psilocybin 3 mg/kg | | |

I.P. = intraperitoneal; P.O. = per oral

TABLE 39

Cohort treated with psilocybin prior the test

| Group Description | N | Route | Treatment regiment | T-maze time point |
|---|---|---|---|---|
| 1 Young mouse/ Vehicle | 10 | I.P. | 7 injections of the vehicle (every 3 days for 3 weeks) | 24 hours after the last administration |
| 2 Aged mouse/ Vehicle | 10 | I.P. | 7 injections of the vehicle (every 3 days during 3 weeks) | 24 hours after the last administration |
| 3 Aged mouse/ Donepezil 0.3 mg/kg | 10 | P.O. | 6 injections of the vehicle + 1 donepezil (every 3 days for 3 weeks) | 1 hour after donepezil |
| 4 Aged mouse/ Single dose 1 mg/kg | 10 | I.P. | 6 injections of the vehicle + 1 injection Psilocybin 1 mg/kg (every 3 days for 3 weeks) | 24 hours after the last administration |
| 5 Aged mouse/ Single dose 3 mg/kg | 10 | I.P. | 6 injections of the vehicle + 1 injection of Psilocybin 3 mg/kg (every 3 days for 3 weeks) | 24 hours after the last administration |
| 6 Aged mouse/ Chronic dose 1 mg/kg | 10 | I.P. | 7 injections of Psilocybin 1 mg/kg (every 3 days for 3 weeks) | |
| 7 Aged mouse/ Chronic dose 3 mg/kg | 10 | I.P. | 7 injections of Psilocybin 3 mg/kg (every 3 days for 3 weeks) | |

I.P. = intraperitoneal; P.O. = per oral

Psilocybin was administered at 1 or 3 mg/kg I.P., and the dosage volume for mice is 10 ml/kg. The vehicle for the test substance was saline (0.9% NaCl), the test formulation was prepared using saline (0.9% NaCl).

Psilocybin was administered as a single or repeated (7 injections) regimen. To harmonize the number of treatment and handling across the different experimental groups, 6 injections of the vehicle were performed prior to the single dose administration of psilocybin. Repeated injections were carried out every 3 days, for a total of 3 weeks.

The T-maze consists of two choice arms and one start arm mounted to a square centre. Sliding doors are provided to close specific arms during the force choice alternation task.

During the trials, animal handling and the visibility of the operator were minimized as much as possible. The experimental consisted of one single session, which started with one "forced-choice" trial, followed by 14 "free-choice" trials. In the first "forced-choice" trial, the animal was confined for 5 seconds in the start arm, which was then released while either the left or right goal arm is blocked by closing the sliding door. After, the animal explored the maze arm and returned to the start position. Immediately after the return of the animal to the start position, the left or right goal door was opened, and the animal can choose freely between the left and right goal arm ("free choice" trials). The animal was considered to have entered an arm when it placed all four paws in the arm. A session was terminated, and the animal was removed from the maze as soon as the 14 "free-choice" trials were performed or 10 min elapsed, whichever circumstance occurred first. The apparatus was cleaned between each animal using alcohol (70%).

The percent of spontaneous alternations was calculated as number of spontaneous alternations divided by 14 possible free-choices.

The T-maze tests was performed at two timepoints: 1 hour and 1 week after the last treatment for the first cohort, respectively and 24 hours after the last treatment for the second cohort.

Psilocybin rescued cognitive impairments occurring in aged mice when treated 1 hour prior the test (1 and 3 mg/kg, both single administration and chronic administration). See FIG. 63. When treated 24 hours prior to the test, psilocybin also rescued cognitive impairment (3 mg/kg chronic dose). See FIG. 64.

Chronic administration of 3 mg/kg psilocybin rescued in a long-lasting manner cognitive impairment occurring in aged mice when treated 1 week prior the test (1 and 3 mg/kg, both single administration and chronic administration). See FIG. 65.

Example 15: Rapid Visual Information Processing Task in Humans

To assess the effects of psilocybin on cognitive processing, a clinical trial testing psilocybin in healthy participants was performed. Although not exclusively, visual information processing deficits are found in ADHD and autism spectrum disorders, as well as in neurocognitive disorders such as Alzheimer's and Parkinson's. A total of 89 healthy participants were randomised to receive a single oral administration of placebo (n=29), 10 mg psilocybin (n=3 0), or 25 mg psilocybin (n=30). Participants were followed for up to 28 days after administration. Rapid visual information processing (RVP), a sensitive measure of sustained attention, was assessed twice prior to dosing (Day 0): during screening (Day −2) and at baseline (Day −1). Participants were then tested for RVP after drug administration: on Day 7 and Day 28.

RVP provides measures of response accuracy, target sensitivity, and reaction times. During the task, a white box is shown in the centre of a screen, in which single digits appear in a pseudo-random order at a rate of 100 digits per minute. Subjects must detect a series of 3-digit target sequences (e.g., 3-5-7; 2-4-6; 4-6-8) and respond by touching the button at the bottom of the screen when they see the final number of the sequence. Nine target sequences appear every minute.

RVP A Prime (RVPA) is the primary outcome measure for the RVP, where A' (A prime) is the signal detection measure of a subject's sensitivity to the target sequence (string of three numbers), regardless of response tendency (the expected range is 0.00 to 1.00; bad to good). A higher RVPA score indicates better performance, demonstrating that the subject is better at detecting target sequences.

Analysis of the least squares (LS) mean difference revealed a significant separation of the psilocybin treatment groups (10 mg and 25 mg) from the placebo group at Day 28 (10 mg LS Mean difference 0.01096, p-value~0.0376, 25 mg LS Mean difference 0.01225, p-value~0.0234). Differences in LS mean compared to placebo are summarised in Table 40 and illustrated in FIG. 9M.

TABLE 40

Summary of differences of least squares mean compared to placebo group

| Dose | Comparison | Visit | LS mean Estimate | Standard Error | p value | Lower CI | Upper CI |
|---|---|---|---|---|---|---|---|
| 10 mg | Placebo | Treatment V6 Day 28 (remote) | 0.01096 | 0.005243 | 0.04 | 0.001 | 0.021 |
| 25 mg | Placebo | Treatment V6 Day 28 (remote) | 0.01225 | 0.005372 | 0.02 | 0.002 | 0.023 |

Example 16: Effect of Psilocin on Damage Induced by 6-hydroxydopamine (6-OHDA) on Mesencephalic Neuronal Cultures The neuroprotective effect of psilocin against 6-OHDA-mediated injury on mesencephalic neuronal cultures was investigated.

A primary culture of rat embryo mesencephalic cells was plated on a 96-well plate. The cells were maintained at 37° C. in 5% $CO_2$. Half of the medium was changed on day 2.

On day 6, the culture medium was removed and replaced by media containing psilocin (0.03 μM, 0.1 μM, 0.3 μM, 1 μM, 3 μM, or 10 μM), a negative control (saline vehicle, labelled control in FIG. 10), or a positive control (brain-derived neurotrophic factor (BDNF) and glial cell-derived neurotrophic factor (GDNF))). After one hour, 15 μM 6-OHDA was added for 48 hours.

On day 8, immunodetection was used to determine the number of tyrosine hydroxylase positive neurons.

Figure 10:
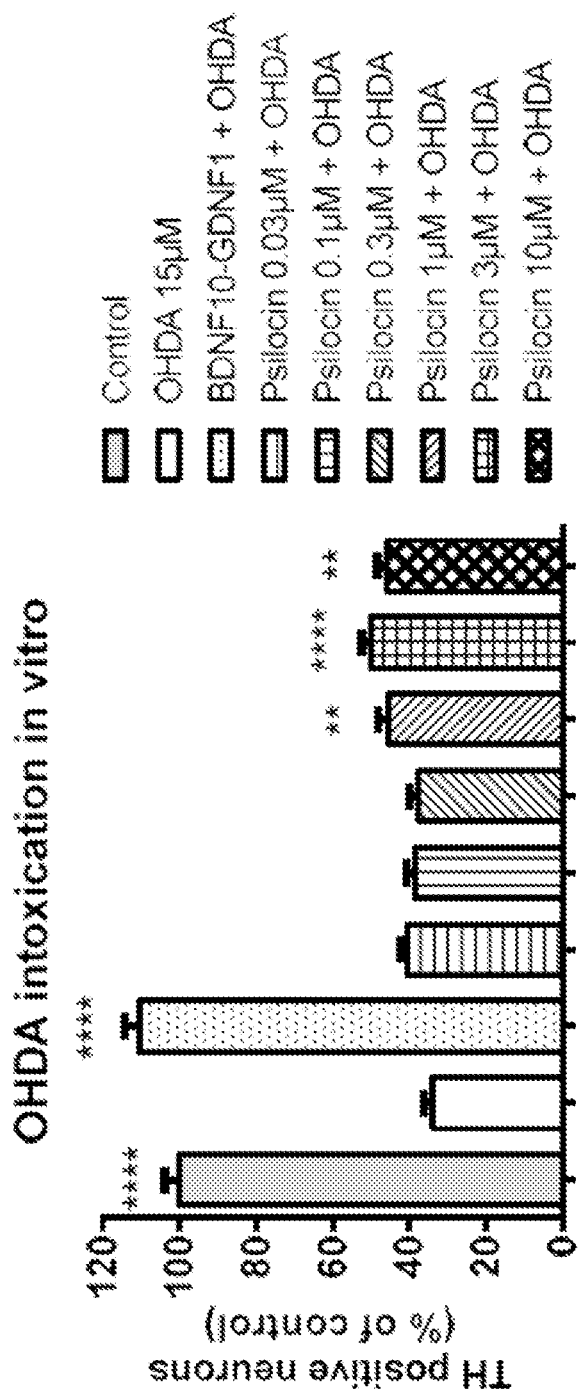
FIG. 10 shows the effect of psilocin on cell viability expressed by the percentage of TH (tyrosine hydroxylase) positive neurons following 6-ODHA (6-hydroxydopamine) intoxication compared to the 15 μM 6-OHDA treated group in an in vitro model. One-way ANOVA followed by Fisher's LSD for pairwise comparison test, $*p<0.05$, $p<0.01$, $*p<0.001$, $****p<0.0001$. Data are expressed as mean±standard error of the mean (sem).

Neuronal viability was assessed 48 hours after 6-OHDA intoxication and measured by the number of TH (tyrosine hydroxylase) positive neurons. The compound 6-OHDA kills specifically dopaminergic neurons, mimicking the cellular pathophysiology of Parkinson's disease. When administered one hour prior to administration of 6-OHDA, 1 μM, 3 μM and 10 μM psilocin increased neuronal viability, suggesting psilocin is protective against 6-OHDA induced neuronal damage (FIG. 10). This result shows that psilocin, the active metabolite of psilocybin, exhibited a neuroprotective effect on dopaminergic neurons, the degeneration of which is central in Parkinson's disease pathology. The result for each well was expressed as a percentage by setting the density of tyrosine hydroxylase positive cells under control conditions to 100%. The result for each condition was reported as mean (±S.E.M.) from 4 independent cultures.

Example 17: In Vivo Study of the Effect of Psilocybin in the 6-OHDA-Induced Parkinson's Disease Model The effect of psilocybin on a 6-OHDA model of Parkinson's disease, which induces depletion of dopaminergic neurons in animals, was investigated.

60 male Sprague Dawley rats were distributed to five different experimental groups (12 animals/group). Table 41 shows the assignment of rats to experimental groups.

TABLE 41

6-OHDA-induced Parkinson's Disease Model Group Assignment

| Group | Description | N | Route | Treatment schedule |
|---|---|---|---|---|
| 1 | Saline/Vehicle | 12 | I.P. | Every 3 days during 3 weeks - |
| 2 | 6-OHDA/Vehicle | 12 | I.P. | First treatment occurs 1 day after |
| 3 | 6-OHDA/Psilocybin (1 mg/kg) | 12 | I.P. | surgery (half of the animals) or 4 |
| 4 | 6-OHDA/Psilocybin (3 mg/kg) | 12 | I.P. | days after surgery (other half of |
| 5 | 6-OHDA/Psilocybin (10 mg/kg) | 12 | I.P. | the animals) |

I.P. = intraperitoneally 1.5 μl of 6-OHDA (2 μg/μl in 0.1% ascorbic acid dissolved in saline preventing heat and light exposure) was injected into the right medial forebrain bundle at 2 injection sites (3 μl total injected volume). Vehicle or psilocybin treatments (1 mg/kg, 3 mg/kg, or 10 mg/kg) were administered as outlined in Table 41. The treatments were administered every 3 days starting the day after the surgery or 4 days after the surgery for three weeks. The vehicle was 0.9% sterile saline solution.

Four weeks after the 6-OHDA injection, the assessment of sensorimotor coordination was performed by placing each rat on a 2 meter long wooden beam, divided into four 50-cm segments, elevated 80 cm above the floor level, and which was in contact with the home cage on one extremity. All rats were trained according to the following protocol. On the first session (day 1), the rats were placed on the beam, 50 cm away from the goal box (i.e., their home cage) on five consecutive occasions. On the next session (day 2), the rats were placed 50, 100, 150 and 200 cm away from the goal box, successively, with only one run allowed for each distance. On the third session (day 3), the rats were twice placed 100 cm away and then twice 200 cm away from the goal box. On the fourth session (day 4), the rats were placed 200 cm away for three consecutive runs. On the next day, all rats were tested for three consecutive trials as in the fourth session, and their performance was rated. For each virtual 50-cm segment of the beam, the experimenter rated the locomotor behavior a score of 1 per segment when the rat traverses the segment with all paws on the upper surface of the beam. Conversely, a score of 0 was given for each segment on which the rat slipped, placed its toes on the side surface of the beam or fall from the beam. The overall score was calculated by adding the scores of the three runs (maximal score=12, i.e., four for each trial), and the interval between each run was of 5 s. In addition, rats that did not move within the 120 seconds after the initiation of the test were considered having delayed motor initiative (limb akinesia). The number of rats with limb akinesia was counted.

Figure 11:
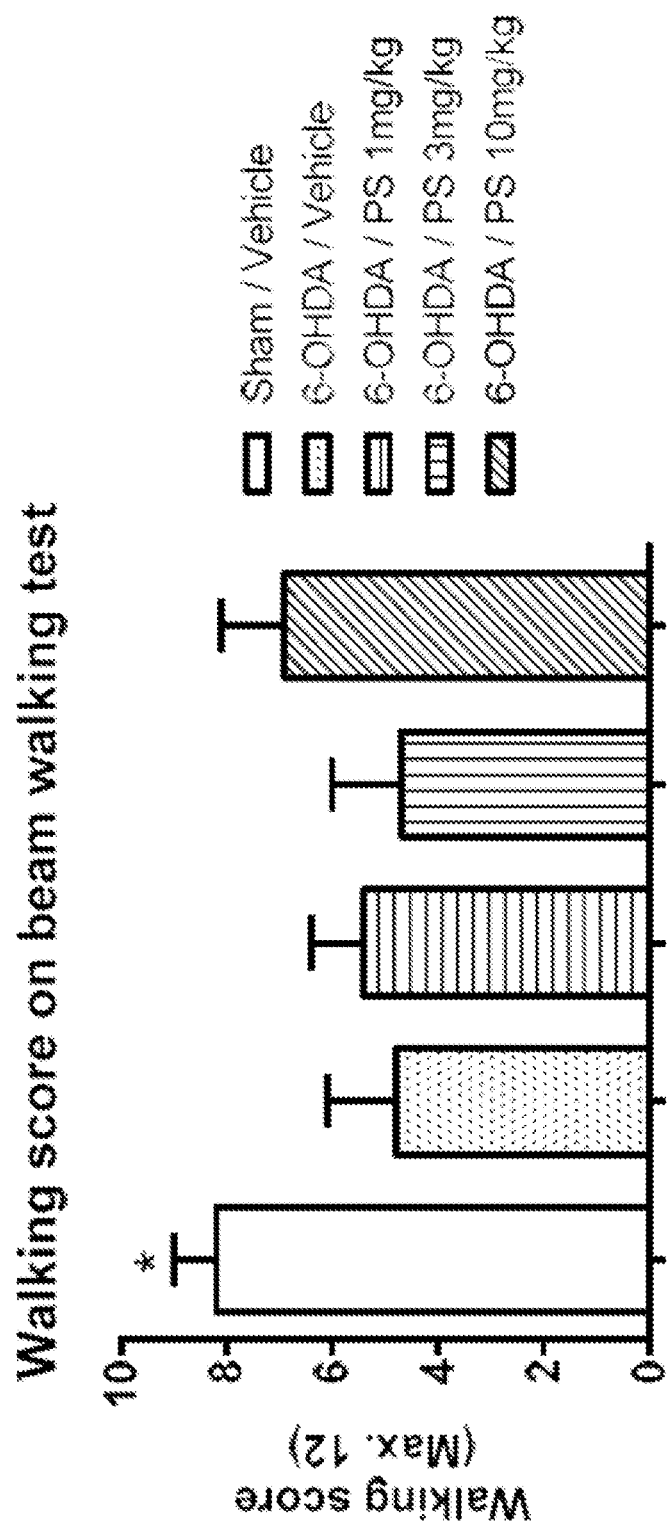
FIG. 11 shows the effect of psilocybin on the walking score on a beam walking test following 6-OHDA intoxication in an in vivo model. One-way ANOVA followed by Fisher's LSD for pairwise comparison test, $*p<0.05$, $**p<0.01$. Data are expressed as mean±sem.
Figure 12:
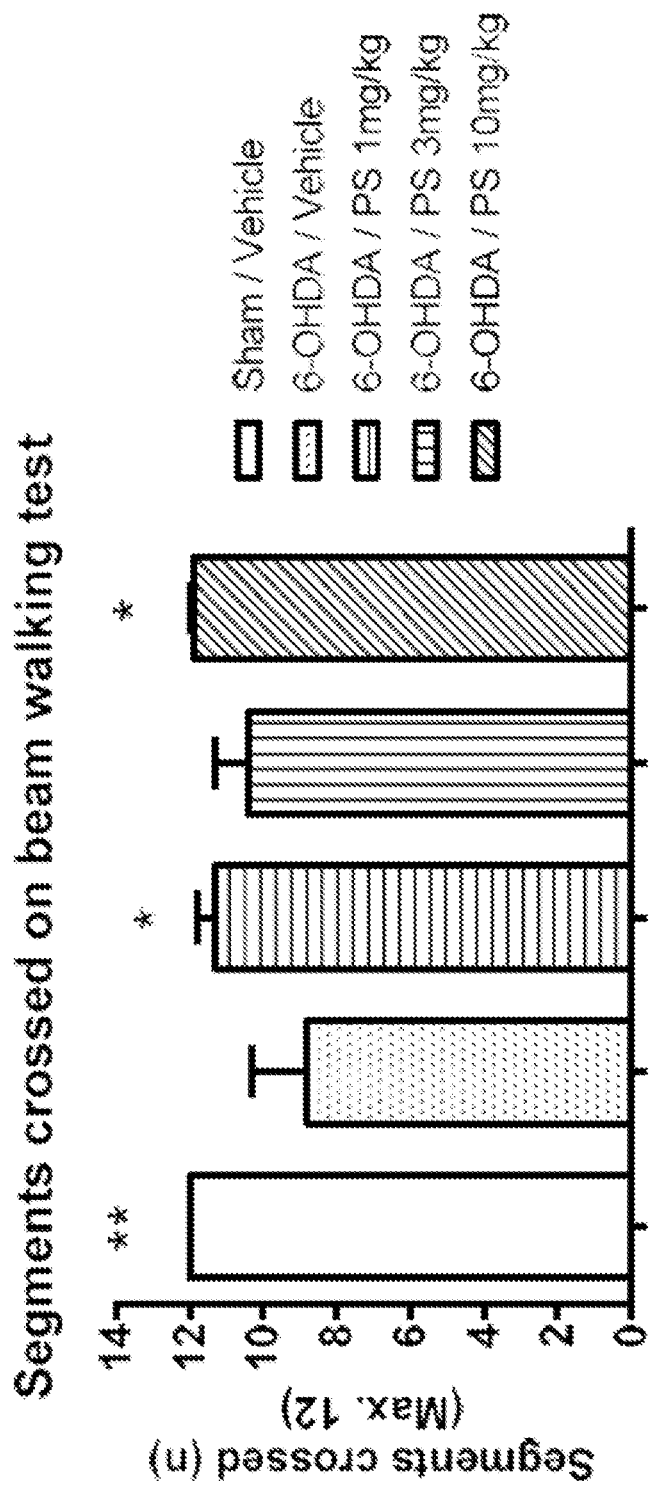
FIG. 12 shows the effect of psilocybin on the number of segments crossed (crossing score) on a beam walking test following 6-OHDA intoxication in an in vivo model. One-way ANOVA followed by Fisher's LSD for pairwise comparison test, $*p<0.05$, $**p<0.01$. Data are expressed as mean±sem.
Figure 13:
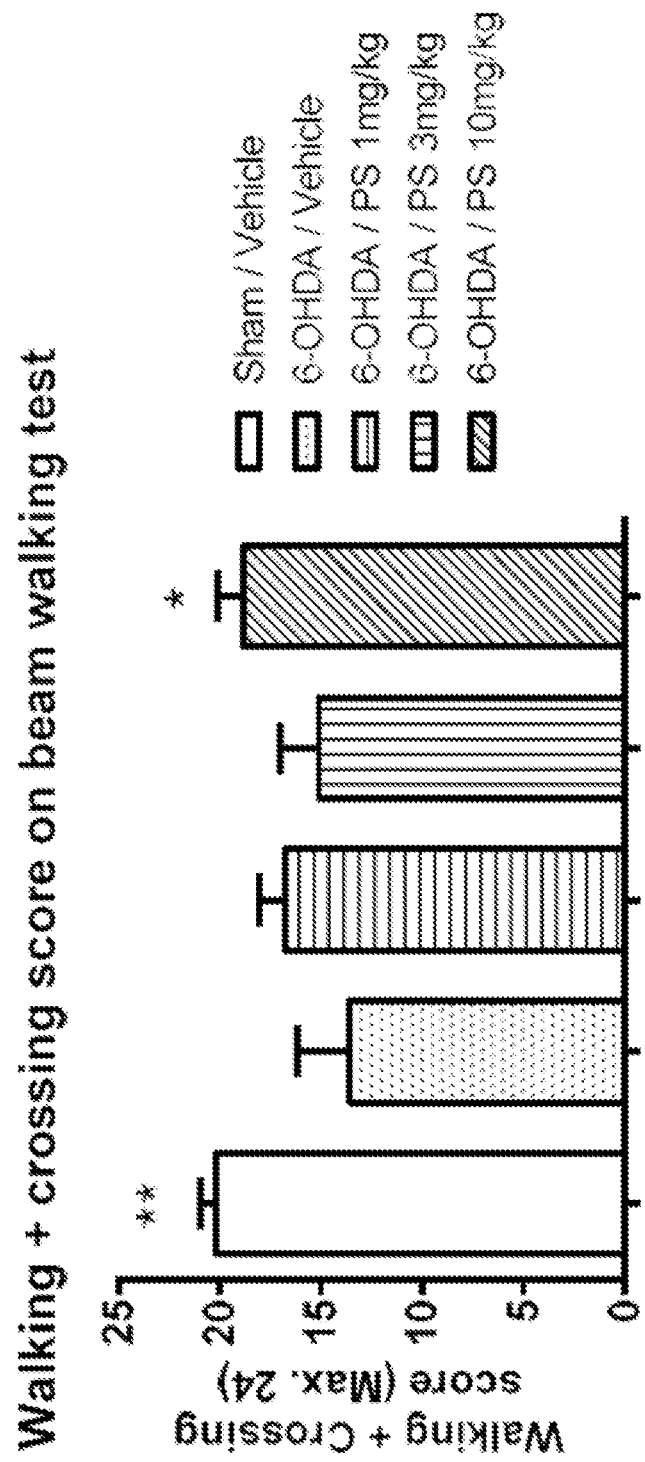
FIG. 13 shows the effect of psilocybin on the walking and crossing score on a beam walking test following 6-OHDA intoxication in an in vivo model. One-way ANOVA followed by Fisher's LSD for pairwise comparison test, $*p<0.05$, $**p<0.01$. Data are expressed as mean±sem.
Figure 14:
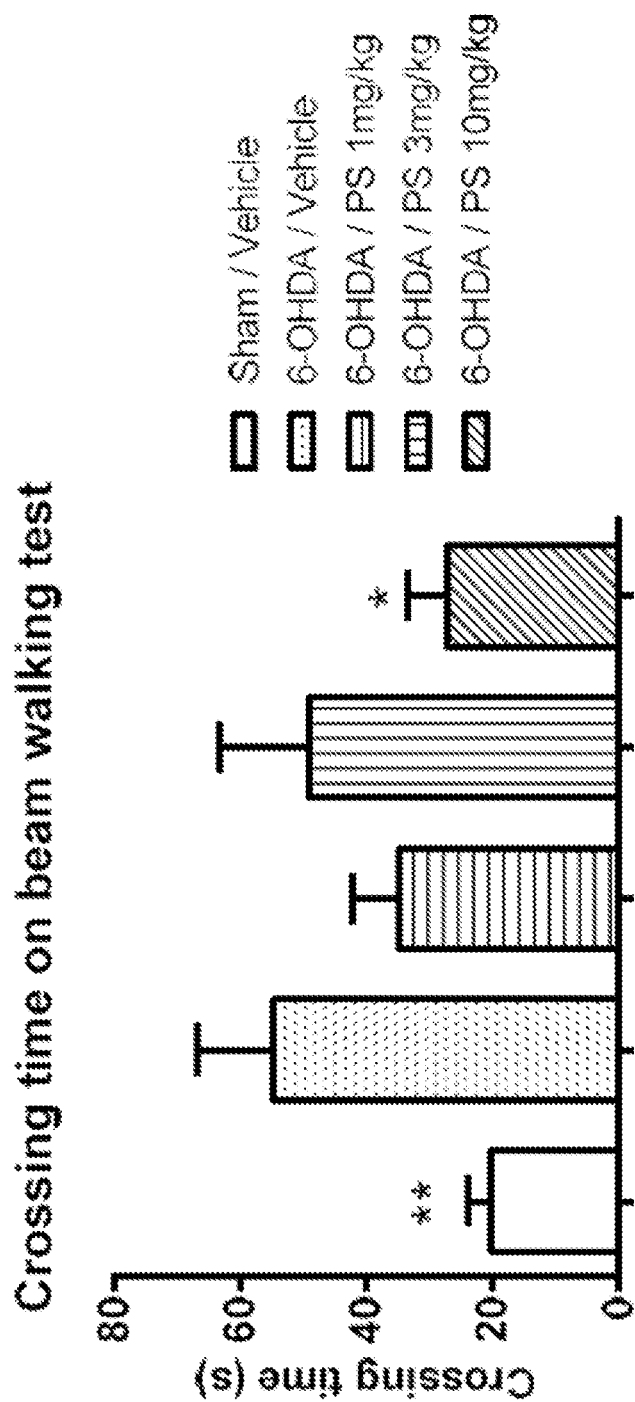
FIG. 14 shows the effect of psilocybin on crossing time on a beam walking test following 6-OHDA intoxication in an in vivo model. One-way ANOVA followed by Fisher's LSD for pairwise comparison test, $*p<0.05$, $**p<0.01$. Data are expressed as mean±sem.

Three parameters were evaluated to assess the sensorimotor functions of the animals on the beam walking test: the walking function (i.e. whether animals are walking properly or are making stumble), the number of segments crossed, and the crossing time across the bar. Treatment with 1 mg/kg psilocybin or 10 mg/kg psilocybin significantly increased the number of segments crossed by the animals (FIG. 12). Treatment with 10 mg/kg psilocybin improved the general physical condition of the animals as shown by the combination of the walking score with the number of segments crossed (FIG. 11, FIG. 13). In addition, treatment with 10 mg/kg psilocybin decreased the time necessary to travel along the beam (FIG. 14).

Example 18: In Vivo Study of the Effect of Psilocybin on the Haloperidol-Induced Catalepsy Model The potential anti-akinetic effect of psilocybin in mice was investigated. Psilocybin (1 mg/kg, 3 mg/kg, or 10 mg/kg), chlorstyril caffeine (CSC), or vehicle was administered one hour, 24 hours, or one week prior to administration of haloperidol.

After administration of haloperidol, a catalepsy test was administered to each mouse. During the test, the forelimbs of the mice were placed on a catalepsy apparatus. The latency time was defined as the time necessary for the mouse to put the forelimbs on the table. The cut off time was set as 3 minutes. Catalepsy was evaluated every 45 minutes for 270 minutes after the Haloperidol injection.

Figure 15:
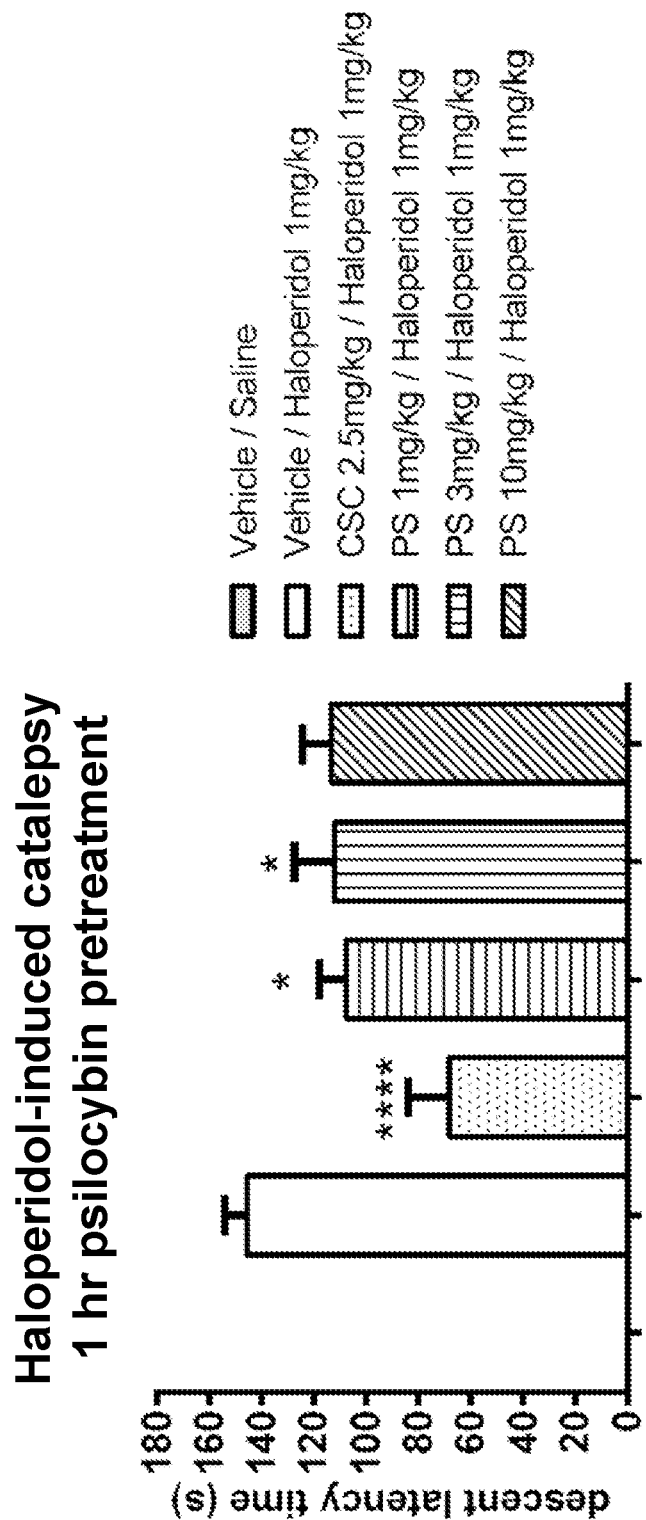
FIG. 15 shows the effect of psilocybin compared to vehicle/haloperidol treatment one hour after administration on the mean descent latency time in a haloperidol-induced catalepsy model. One-way ANOVA followed by Fisher's LSD for pairwise comparison test, $*p<0.05$, $p<0.01$, $*p<0.001$, $****p<0.0001$. Data are expressed as mean±sem.
Figure 16:
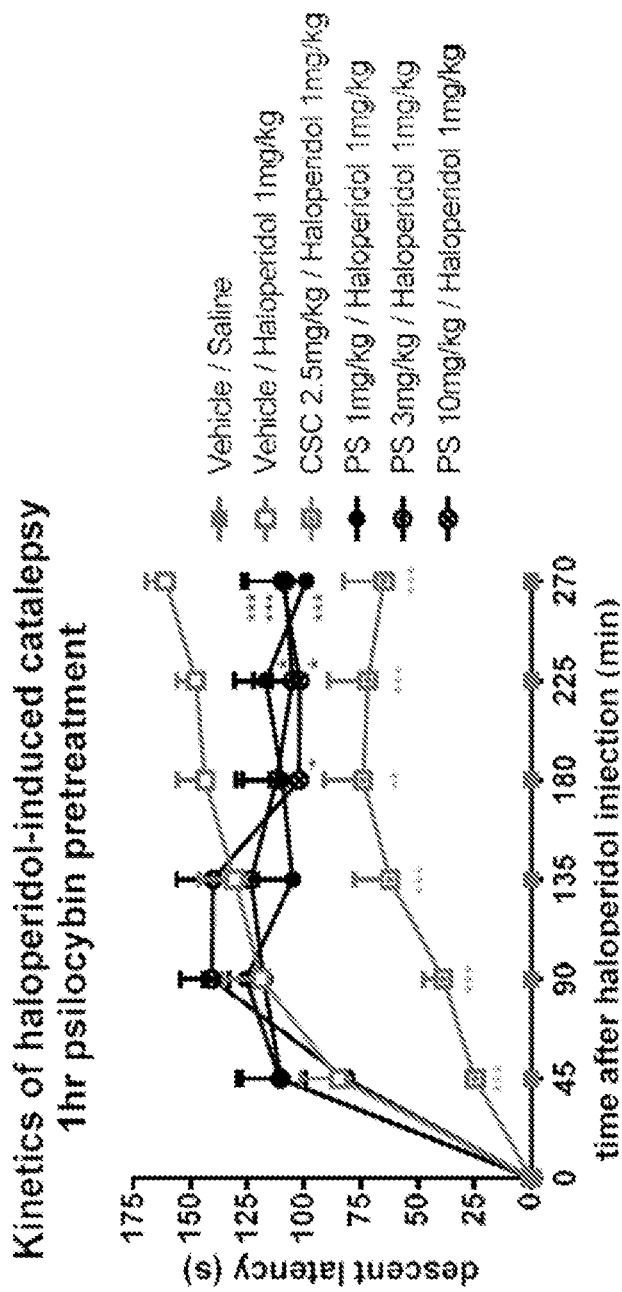
FIG. 16 shows the effect of psilocybin one hour after administration on the kinetics of descent latency in a haloperidol-induced catalepsy model. One-way ANOVA followed by Fisher's LSD for pairwise comparison test, $*p<0.05$, $p<0.01$, $*p<0.001$, $****p<0.0001$. Data are expressed as mean±sem.

When animals are treated one hour prior to the test, the administration of 1 mg/kg psilocybin and 3 mg/kg psilocybin decreased significantly the average descent latency time compared to animals treated with haloperidol alone (FIG. 15). Treatment with 1 mg/kg psilocybin results in a decrease in descent latency compared to the group treated with haloperidol alone at the end of test (270 minutes after haloperidol injection) (FIG. 16). Treatment with 3 mg/kg psilocybin resulted in a significant decrease in descent latency compared to the group treated with haloperidol from 225 minutes post-haloperidol injection onwards (FIG. 16). Treatment with 10 mg/kg psilocybin shows results in a significant decrease in descent latency compared to the group treated with haloperidol alone from 180 minutes post-haloperidol injection onwards (FIG. 16).

Figure 17:
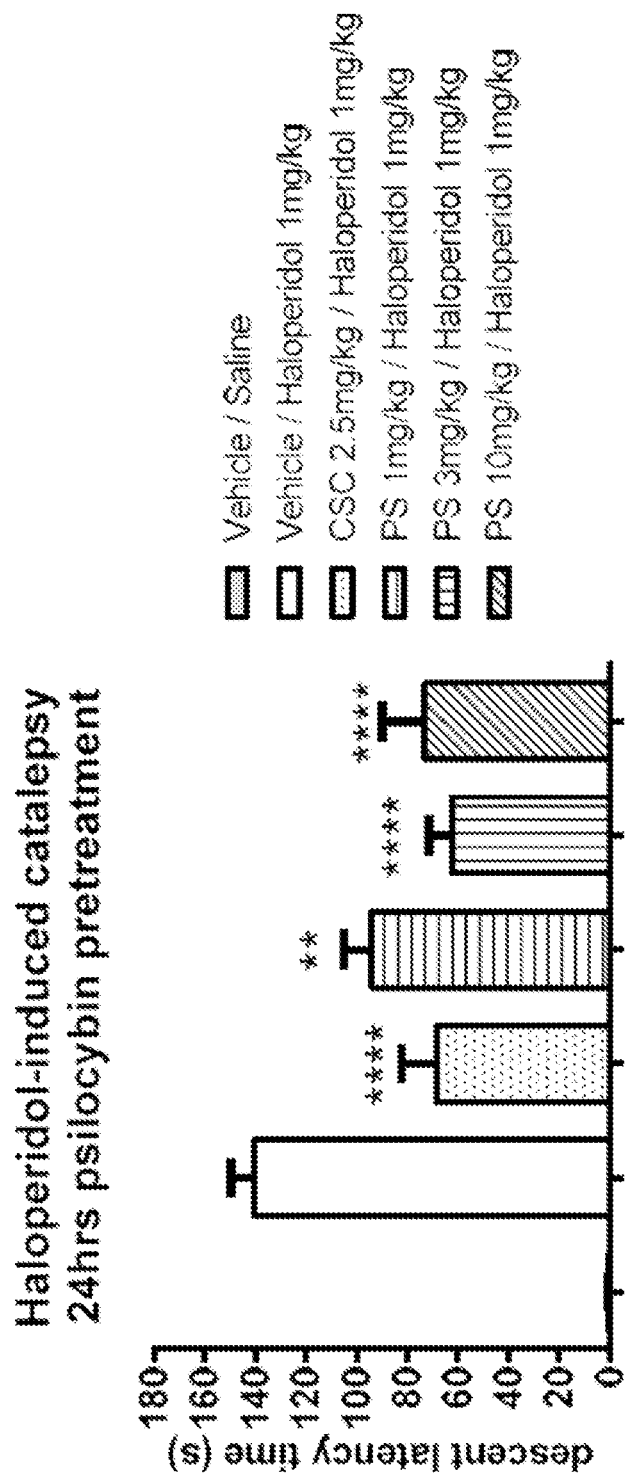
FIG. 17 shows the effect of psilocybin 24 hours after administration on the mean descent latency time in a haloperidol-induced catalepsy model. One-way ANOVA followed by Fisher's LSD for pairwise comparison test, $*p<0.05$, $p<0.01$, $*p<0.001$, $****p<0.0001$. Data are expressed as mean±sem.
Figure 18:
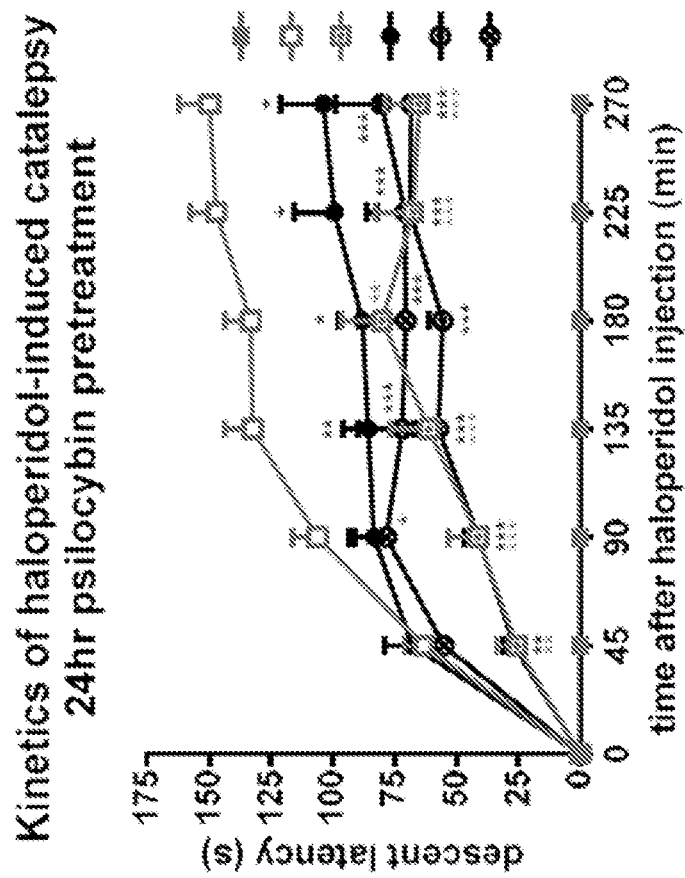
FIG. 18 shows the effect of psilocybin 24 hours after administration on the kinetics of descent latency in a haloperidol-induced catalepsy model. One-way ANOVA followed by Fisher's LSD for pairwise comparison test, $*p<0.05$, $p<0.01$, $*p<0.001$, $****p<0.0001$. Data are expressed as mean±sem.

When animals were treated with psilocybin prior to the test, the three groups treated with psilocybin (1, 3 and 10 mg/kg) showed a significantly reduced haloperidol-induced catalepsy (90 seconds, 60 seconds, 75 seconds with psilocybin 1, 3 and 10 mg/kg respectively) (FIG. 17). Treatment with 3 mg/kg psilocybin induced an early and sustained reduction in descent latency, starting 45 minutes after the administration of haloperidol, and lasting up to the end of the test (270 minutes) (FIG. 18). This effect was similar to the one observed with the positive control CSC. Treatment with 1 mg/kg or 10 mg/kg psilocybin provided a delayed positive effect on catalepsy, starting 135 minutes and 90 minutes after haloperidol administration respectively (FIG. 18). Benefits were sustained up to the end of the test for both groups.

Figure 19:
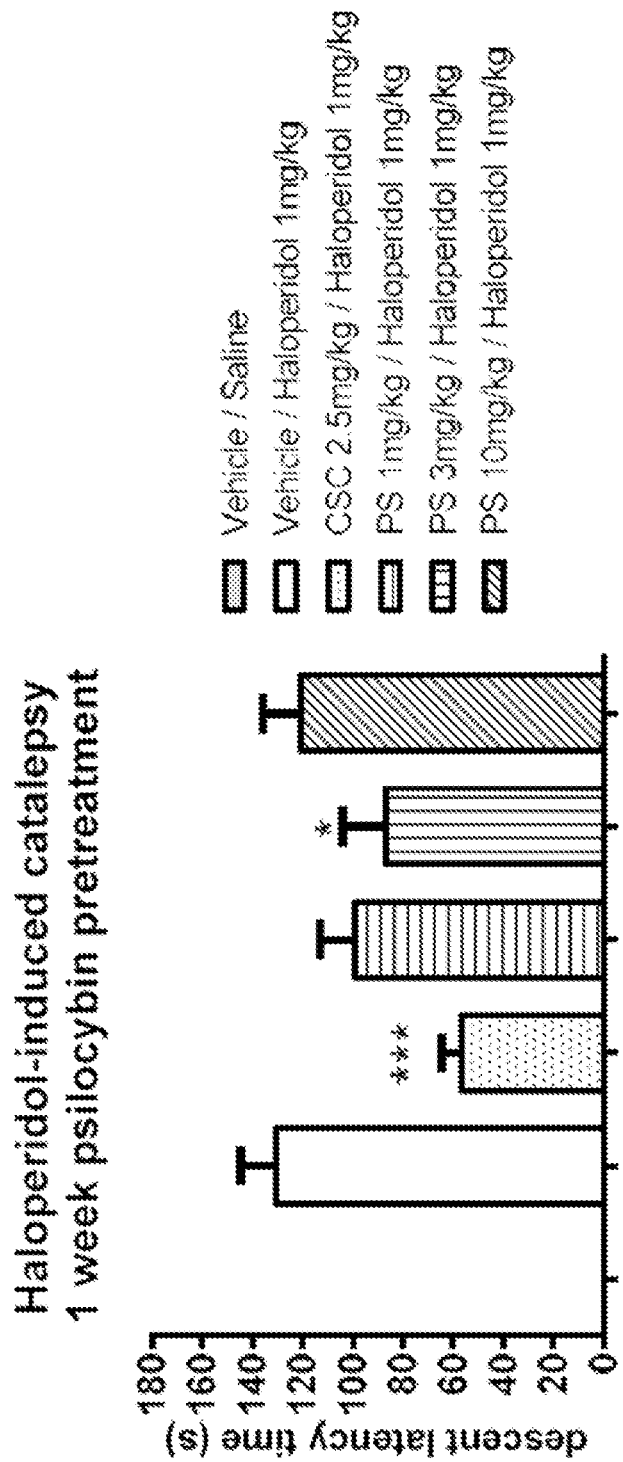
FIG. 19 shows the effect of psilocybin one week after administration on the mean descent latency time in a haloperidol-induced catalepsy model. One-way ANOVA followed by Fisher's LSD for pairwise comparison test, $*p<0.05$, $p<0.01$, $*p<0.001$, $****p<0.0001$. Data are expressed as mean±sem.
Figure 20:
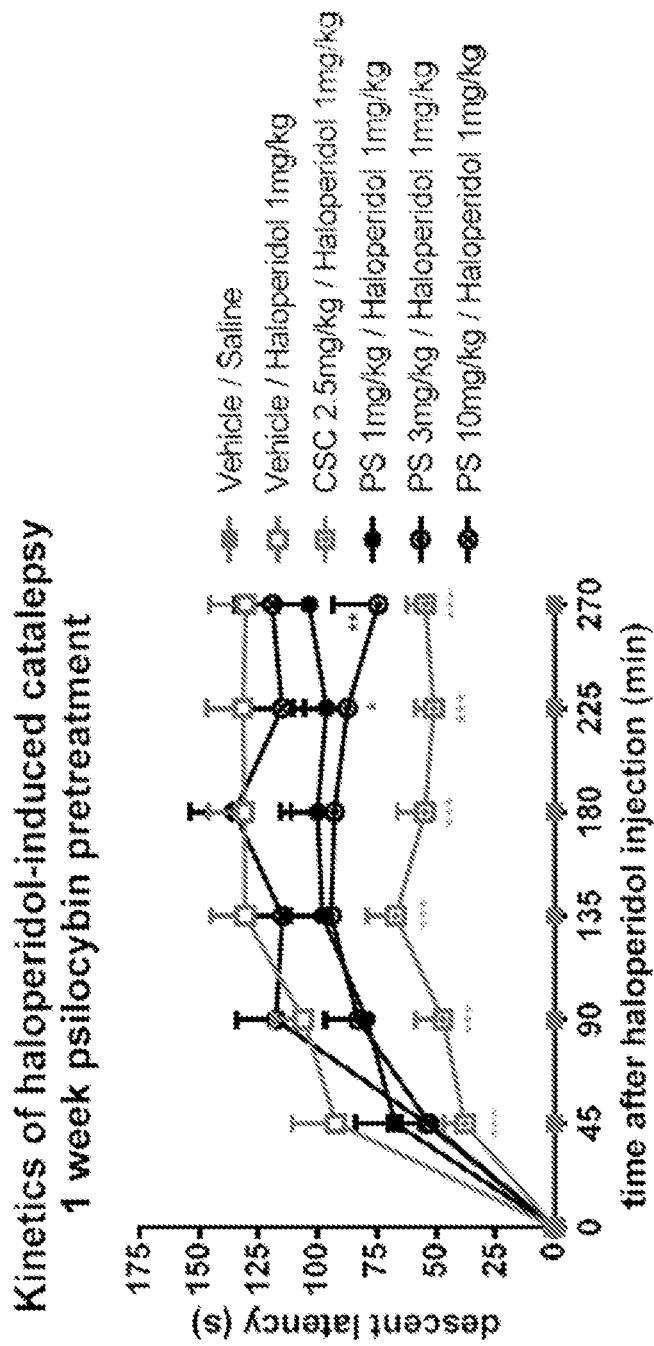
FIG. 20 shows the effect of psilocybin one week after administration on the kinetics of descent latency in a haloperidol-induced catalepsy model. One-way ANOVA followed by Fisher's LSD for pairwise comparison test, *p<0.05, p<0.01, *p<0.001, ****p<0.0001. Data are expressed as mean±sem.

When treated 1 week prior to the test, 3 mg/kg psilocybin results in a significant decrease in descent time latency (FIG. 19). Treatment with 3 mg/kg psilocybin led to a significant decrease in descent latency compared to the group treated with haloperidol alone 224 minutes post-haloperidol administration onwards (FIG. 20).

Example 19. In Vivo Study of the Effect of Psilocybin on CCK-Induced Panic Anxiety One comorbidity associated with, for example Alzheimer's Disease and Parkinson's Disease is anxiety. The aim of this study is to investigate the potential anti-panic/anxiolytic effect of psilocybin on rats after an induced panic anxiety using cholecystokinin tetrapeptide (CCK-4). Peripheral administration of the CCK-4 leads to an anxiogenic-like action in the elevated plus-maze (EPM) model of anxiety in rats. Psilocybin (1 mg/kg, 3 mg/kg, or 10 mg/kg) or saline vehicle were administered to rats two hours or twenty four hours before administration of the EPM test. Diazepam (positive control) was administered to rats one hour before the EPM test. CCK-4 was administered at a dose of 0.2 mg/kg 30 minutes before the EPM test.

The EPM test employed a PVC maze covered with Plexiglas and subdivided into four equal exploratory arms (21×8 cm), which were all interconnected by a small platform (8×8 cm). The apparatus was placed 59 cm above the floor. Two arms were open, and two others were closed with wall (high: 21 cm). After administration of CCK-4, the rat was placed on the platform opposite a closed arm. The number of entries and the time spent in each arm were recorded during a 5 minute period. The animal was considered as entered in an arm when it placed its four paws in the arm.

Figure 21:
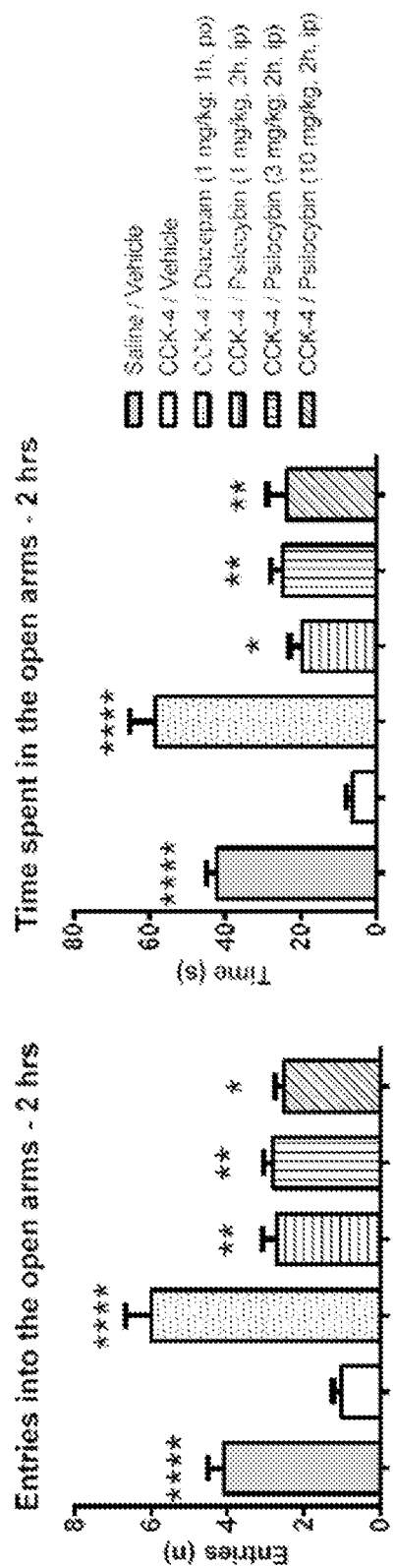
FIG. 21 shows the number of entries into the open arms and the time spent in the open arms two hours post-administration of psilocybin in a CCK-4 (cholecystokinine-4) induced anxiety model. One-way ANOVA followed by Fisher's LSD for pairwise comparison test, *p<0.05, p<0.01, *p<0.001, ****p<0.0001. Data are expressed as mean±sem.
Figure 22:
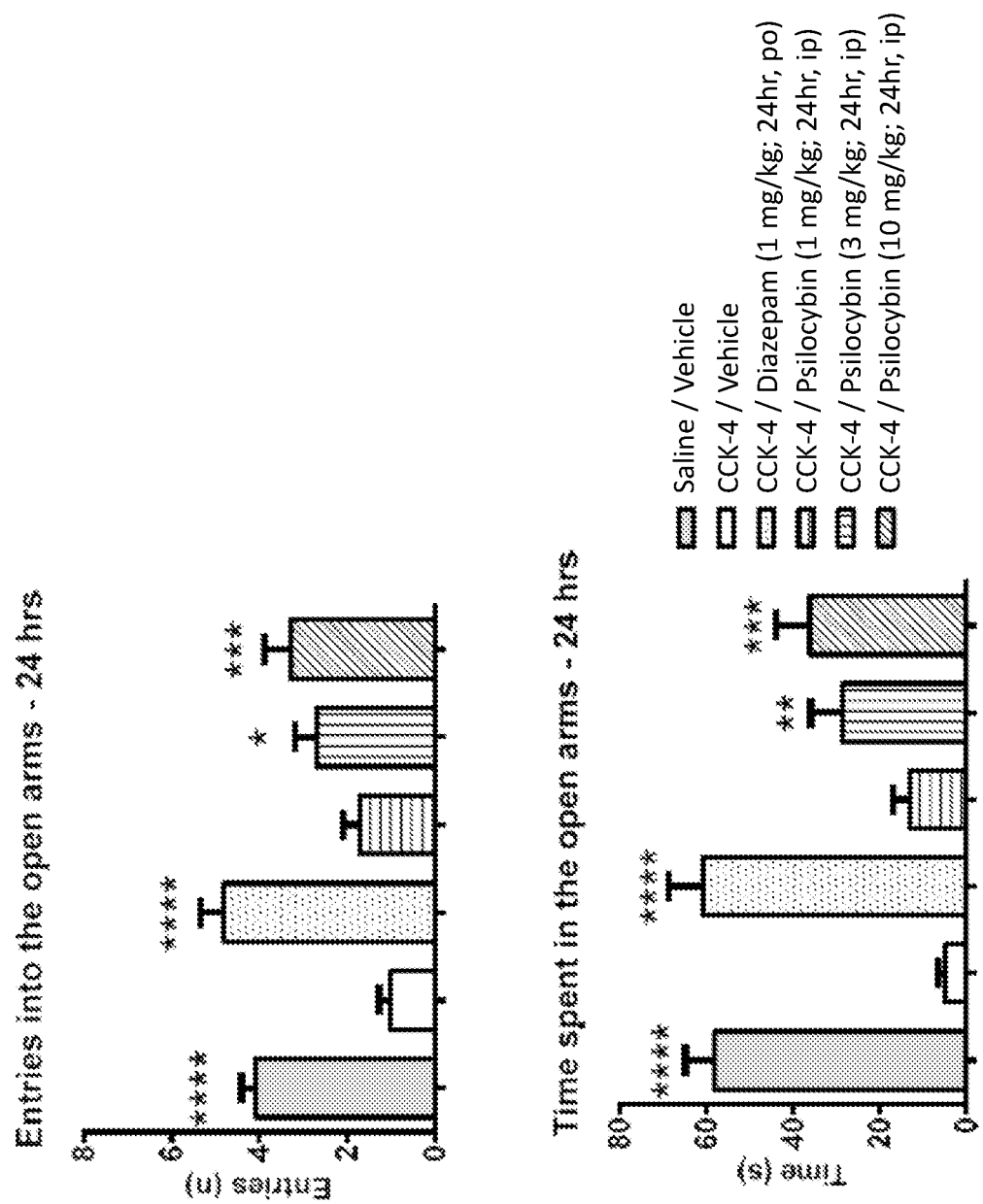
FIG. 22 shows the number of entries into the open arms and the time spent in the open arms 24 hours post-administration of psilocybin in a CCK-4 induced anxiety model. One-way ANOVA followed by Fisher's LSD for pairwise comparison test, *p<0.05, p<0.01, *p<0.001, ****p<0.0001. Data are expressed as mean±sem.

Administration of 1, 3, and 10 mg/kg psilocybin two hours prior to the EPM test led to a significant increase in the number of entries into and the time spent in the open arms compared to vehicle (FIG. 21). Administration of 3 and 10 mg/kg psilocybin 24 hours prior to the EPM test significantly increased the number of entries into and the time spent in the open arms compared to vehicle (FIG. 22).

Example 20. Effect of Psilocybin on Marble Burying (MB) Test in an In Vivo Model The aim of this study was to examine the effects of different doses of psilocybin on the marble burying test.

Mice were intraperitoneally administered either vehicle for fluoxetine (vehicle FL, 0.9% NaCl at 10 ml/kg, group 1), fluoxetine (10 mg/kg, group 2), vehicle for psilocybin (vehicle PS, 0.9% NaCl at 10 ml/kg, group 3) or psilocybin (1 mg/kg, 3 mg/kg, 10 mg/kg IP; groups 4, 5 and 6, respectively). Mice underwent the MB test once; either 30 minutes (vehicle FL and fluoxetine) or 1 hour (vehicle PS and psilocybin) after drug administration.

Animals were placed individually in a clear cage containing 5 cm of wood chip bedding upon which glass marbles were arranged in even rows on the bedding. The number of marbles used was 20. Each animal was allowed a period of 30 minutes in the cage, after which it was removed, and the number of marbles buried was recorded. A buried marble is considered >75% covered by bedding. Marble burying is interpreted as either an anxiety-related or repetitive compulsive-like behavior (as in OCD, autism spectrum disorders, or eating disorders such as anorexia). A greater number of buried marbles represents a higher degree of compulsivity. Two blinded experimenters counted the marbles and data represents an average score of the two counts.

Once the marble assessment was completed, mice were culled. Data were analyzed by comparing treatment groups to control groups (n=9 mice per group). The data from the vehicle FL and fluoxetine groups were expressed as mean±S.E.M. and were statistically analyzed using an unpaired t-test, while data from the vehicle PS and psilocybin groups were statistically analyzed using a one-way ANOVA and Tukey's correction test.

Figure 23:
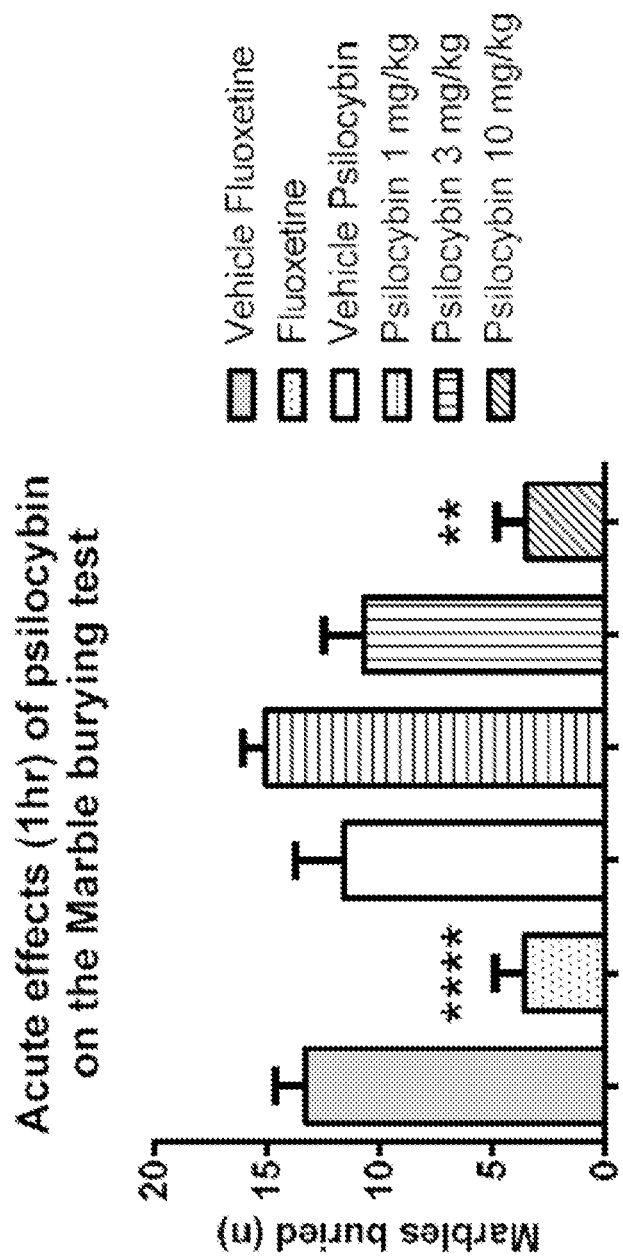
FIG. 23 shows the number of buried marbles 1 hour following psilocybin (PS) treatment. Fluoxetine (Fluox, 30 min pre-treatment) was used as a positive control. Data are expressed as mean±SEM. Statistical significance was determined using an unpaired t-test for vehicle FL and fluoxetine, ***p<0.0001. Statistical significance was determined using one-way ANOVA and Tukey's correction test for vehicle PS and psilocybin, ##p<0.001. FL=fluoxetine; PS=psilocybin.

As shown in FIG. 23, the highest dose of psilocybin (10 mg/kg) significantly reduced the number of marbles buried by mice compared to the vehicle control (vehicle PS, ##p<0.001) 1 hour post-treatment. The effects of the highest dose of psilocybin on marble burying were similar to that of fluoxetine, a selective serotonin reuptake inhibitor (***p<0.0001).

Example 21: In Vivo Study Assessing the Effect of Psilocybin on Social and Repetitive Behaviors The aim of this study was to investigate the pro-social effects of psilocybin in the well-established and well-validated valproic acid (VPA) mouse model of ASD, as well as its ability to reduce repetitive behaviors such as excessive self-grooming, given that social communication deficits and the presence of repetitive behaviors represent two core domains of ASD. 22 animals were treated with VPA and 22 animals served as wild-type controls (n=22) were wild-type controls. Of the VPA mice, ten animals were male and twelve were female. Of wild-type (controls), eleven animals were male and eleven were female. In addition, four male conspecific mice and four conspecific mice were used to interact with the test mice.

Both wild-type and VPA mice were separated into three groups. Wild-type mice received either vehicle (saline, n=6), 1 mg/kg psilocybin (n=8) or 3 mg/kg psilocybin (n=8). VPA mice received either saline (n=7), 1 mg/kg psilocybin (n=7) or 3 mg/kg psilocybin (n=8).

On days 1-3, mice were habituated to the three chamber apparatus for 10 minutes once per day. Test mice were placed one at a time in the middle of the central chamber and allowed to freely explore all three chambers over the course of 10 minutes. Conspecific mice were placed in the interior of a cup inside the apparatus for 10 minutes. All habituation sessions were recorded on video.

On day 3, mice were administered one dose of vehicle, 1 mg/kg psilocybin, or 3 mg/kg psilocybin.

A first experimental arena apparatus was constructed using clear red-tinted acrylic sheets for the walls and matte white plastic sheets for the floor. The total inner measures of the apparatus were 60×40×20 cm. Two clear red acrylic sheets with door cut-outs were used as inner walls, dividing the total space into three 20 cm by 40 cm chambers. The openings between chambers were closed by hinged doors made out of the same material as the walls, and were held lifted by a cord clamped to the top edge of the walls. The wall and floor plates were mounted over 3D-printed base holders and metal columns at the corners. The two cylindrical cups, placed in the center of the right and left chambers contained evenly spaced vertical transparent plastic bars held in place by two 3D-printed rings.

A second experimental arena apparatus, which contained modifications relative to the first experimental arena apparatus, was also constructed. The walls and floor plates, of similar dimensions and materials, were held in place by 3D-printed base holders, with no columns. Two removable acrylic rectangular sheets were used as separators to close the doors when needed.

The cups of the first experimental arena were replaced with cups of a clear acrylic cylinder with bar-shaped cut outs at the bottom half.

For both versions of the setup a CCD camera was placed about one meter above the apparatus. The setup illumination was dim and near-infrared lights were used for video recording.

Three-Chamber Test: On day 4, 24 hours following the administration of psilocybin or vehicle, a 10-minute habituation (with cups present, in which the conspecific animals are situated during the subsequent tests) was first completed. Immediately following this, an unfamiliar mouse (stranger 1) was added to one of the chambers for the 10-minute three-chamber assessment of sociability.

Social Novelty Preference Test: Immediately following the ten minute three-chamber test of sociability, each mouse was further tested in a third 10-minute session to quantify preference for spending time in the chamber containing a novel stranger mouse compared to the familiar mouse. During a two minute interval between tests, a new unfamiliar mouse was placed in the cup that had been empty during the prior 10 minute session. The test mouse had a choice between the first, already-investigated familiar mouse (stranger 1) and the novel unfamiliar mouse (stranger 2). The entire 34 minutes of the experiment were video recorded.

Self-grooming repetitive behavior: Self-grooming behavior of each treatment group was analysed in two minute bins for a total of ten minutes during the habituation period on the test day (day 4), 24 hours following the administration of psilocybin or saline. Notably, an additional three VPA animals treated with vehicle (n=3) and 1 mg/kg psilocybin (n=3) were included in this analysis. Self-grooming behavior was measured by a trained experimenter who was self-blinded to the treatment received by each animal. Total self-grooming time (for all body regions) was recorded manually from videos using a hand-held stopwatch Data Analysis: Time spent in each chamber was analysed using OptiMouse, a MatLab-based tracking and analysis software. This software, which detects the position of the test mouse in each frame, allows to quantify time in each chamber and represent the position data in the form of a heat-map. Nose to nose interactions, along with the total duration of interactions with the social and non-social cups were manually quantified by an eye-trained observer. Analysis was performed using a two-way analysis of variance (ANOVA). A Bonferroni post-hoc test and LSD post-hoc test were performed for the three-chamber and social novelty preference tasks, respectively. For self-grooming repetitive behavior, an unpaired t test and one-way ANOVA were performed for comparison between control and VPA animals and VPA animals treated with psilocybin, respectively. A P value 0.05 was considered statistically significant.

Figure 31:
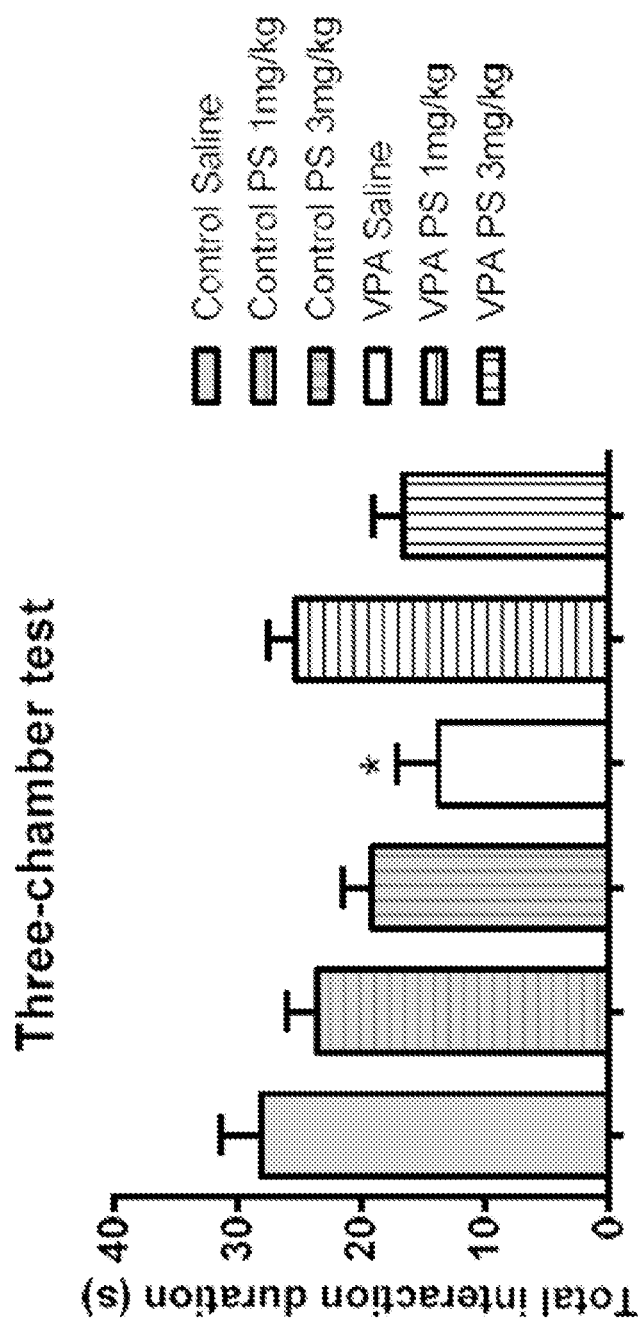
FIG. 31 shows the effect of psilocybin on three-chamber test performance in the valproic acid (VPA) animal model 24 hours post-administration. Two-way ANOVA repeated measures followed by Bonferroni multiple comparison test, *p<0.05. Data are expressed as mean±sem.

The three-chamber task was performed to assess the pro-social behavior of VPA mice, a rodent model of ASD, following a single administration of either 1 mg/kg psilocybin or 3 mg/kg psilocybin. Pro-social behavior was assessed as the total (nose-nose) interaction time between the test and conspecific (cup) animal in the three-chamber task 24 hours following the administration of psilocybin. VPA mice treated with saline (VPA Saline in FIG. 31), as expected, had significantly reduced total interaction time compared to wild-type controls. VPA mice administered 1 mg/kg psilocybin (VPA PS 1 mg/kg in FIG. 31) displayed pro-social behavior as measured by increased total interaction time when compared to VPA mice treated with saline (trend level), towards that of the wild-type control animals treated with saline (FIG. 31).

Figure 32:
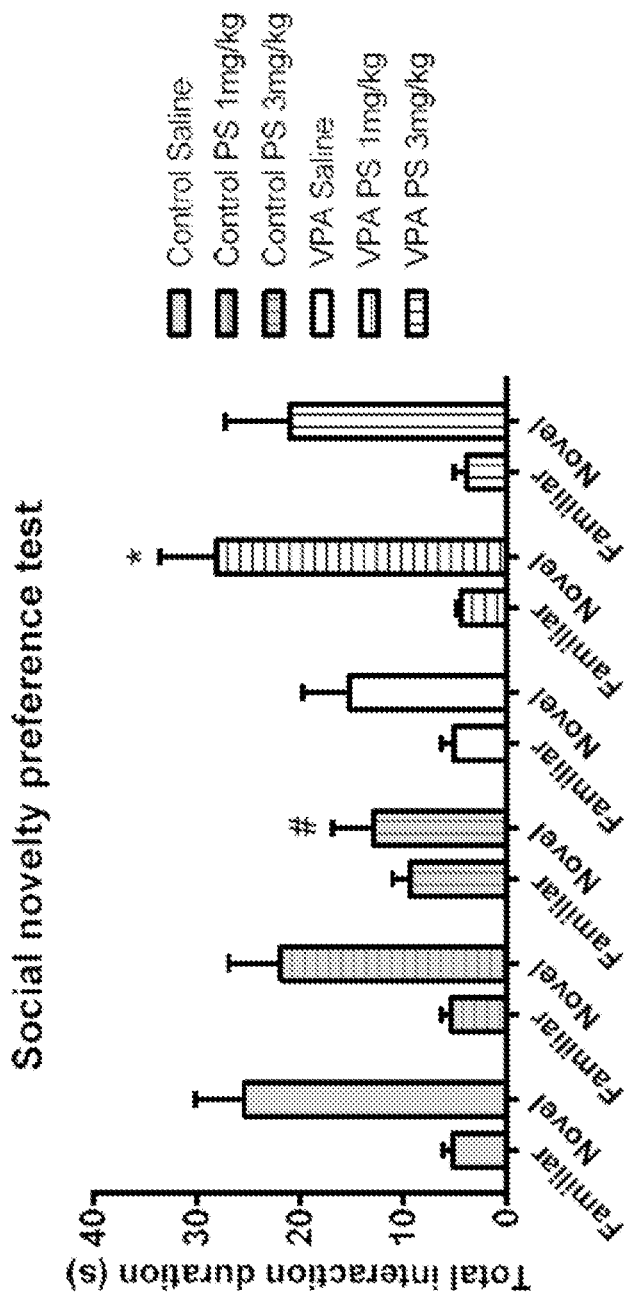
FIG. 32 shows the effect of psilocybin on social novelty preference test performance in the valproic acid (VPA) animal model 24 hours post-administration (* for intra-group and # for inter-group comparison). Two-way ANOVA repeated measures followed by Bonferroni multiple comparison test, *p<0.05, #p<0.05. Data are expressed as mean±sem.

The social novelty preference test was performed immediately following the three chamber task. VPA mice treated with saline showed reduced preference for the novel animal in the three chamber test apparatus, as assessed by total interaction time, when compared to wild-type animals treated with saline (FIG. 32). VPA mice treated with 1 mg/kg psilocybin displayed a stronger preference for social novelty, as assessed by a significantly increased total interaction time with the novel mouse compared to the familiar animal (FIG. 32). A mixed-effects model (REML) analysis also suggested a strong interaction between treatment (psilocybin) and pre-treatment (VPA) for social novelty preference behavior when expressed as a ratio of total interaction time for novel/familiar mouse, this reached a trend towards statistical significance (p value=0.059).

Figure 33:
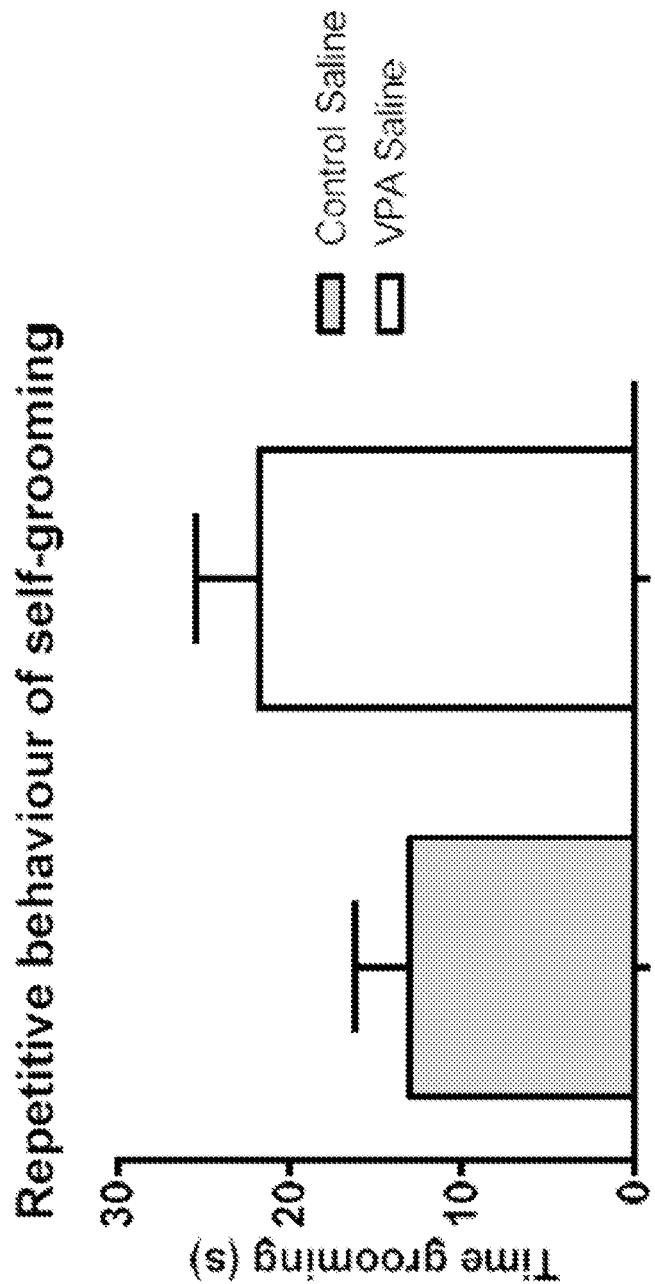
FIG. 33 shows the effect of valproic acid (VPA) pre-treatment on repetitive self-grooming behavior when compared to wild-type control animals. Unpaired t-test. Data are expressed as mean±sem.
Figure 34:
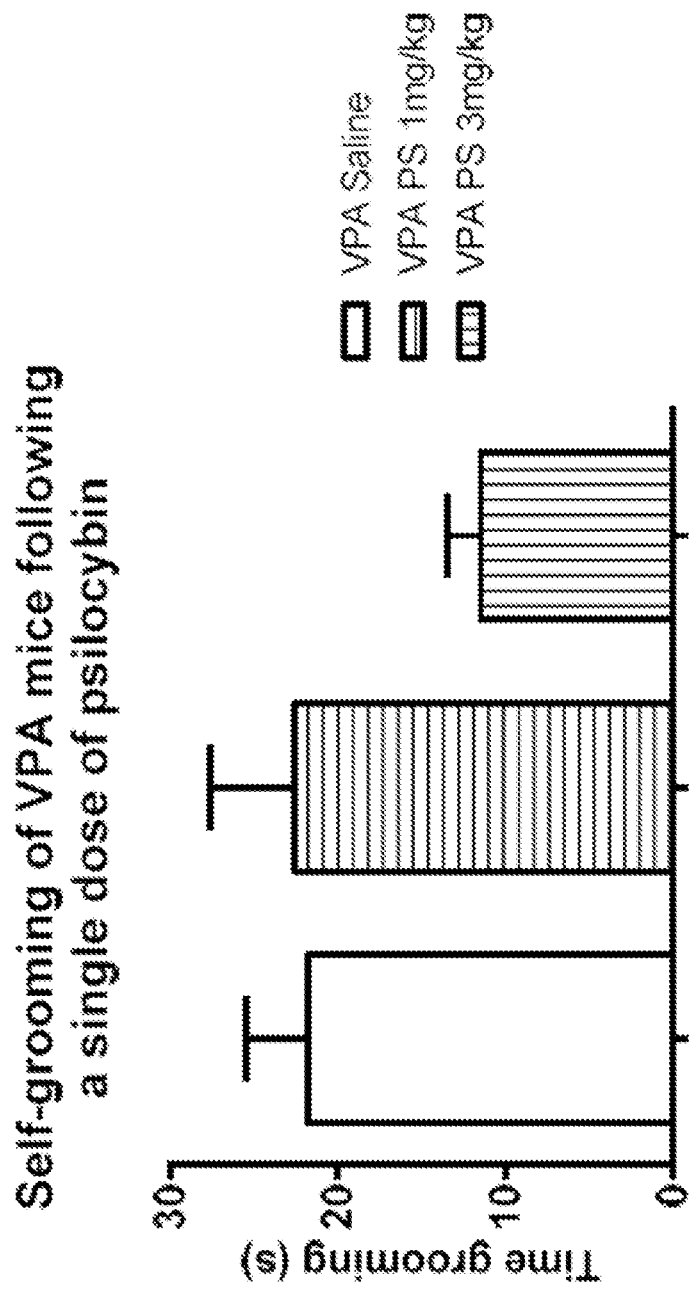
FIG. 34 shows the effect of psilocybin on repetitive self-grooming behavior in the valproic acid (VPA) animal model 24 hours post-administration. One-way ANOVA test. Data are expressed as mean±sem.

Repetitive behavior was assessed as total self-grooming time in the 10 minute habituation period prior to both the three-chamber and social novelty preference task, 24 hours after the administration of psilocybin or saline. As expected, VPA mice treated with saline had increased total self-grooming time compared to wild-type control animals (FIG. 33). VPA mice treated with 3 mg/kg psilocybin showed considerably reduced total self-grooming time compared to VPA animals treated with saline, and reduced this behavior to similar levels to that of wild-type controls (FIG. 34). A mixed-effects model (REML) analysis also suggested a strong interaction between treatment (psilocybin) and pre-treatment (VPA) for repetitive self-grooming behavior that almost reached statistical significance (p value=0.0613).

Example 22: Healthy Volunteer Study Assessing the Acute and Long-Term Effects of Psilocybin on Social Cognition and Behavior This human study in healthy volunteers aimed to assess various psychological and brain measures both acutely and long-term following psilocybin administration. A total of 17 healthy psychedelic-naïve participants were included. All participants underwent two dosing sessions, four weeks apart with doses of 1 mg (first session) and 25 mg psilocybin (second session), each session was followed one day later by an integration therapy session. Three neuroimaging fMRI sessions were conducted: one day before the 1 mg psilocybin session; four weeks after the 1 mg session/one day prior to 25 mg psilocybin session & four weeks after the 25 mg session (key endpoint). Psychological measures including an emotional processing battery (including the facial expression recognition task; emotional categorisation task and emotional recall task) and social connectedness scale were completed by participants at baseline, 2 weeks and 4 weeks following the 1 mg and 25 mg psilocybin dosing sessions.

Social connectedness is the measure of how individuals come together and the experience of feeling close and connected to other people, including feeling cared for, valued, loved, and forms the basis of interpersonal relationships. The social connectedness scale is a well-validated and established, self-administered scale.

The facial expression recognition task (FERT) assessed the interpretation of various facial expressions including those displaying happiness, surprise, sadness, fear, anger and disgust. Examples of each expression with varying intensity are presented to participants and reaction times for correct responses are measured.

Each of the aforementioned scans were 90 minutes and incorporated the following:
(a) 1. A high resolution anatomical scan (e.g. for measuring cortical thickness and for registering functional scans)
(b) 2. A diffusion tensor imaging (DTI) scan (e.g. for measuring fractional anisotropy of white matter)
(c) 3. An eyes-closed resting state blood-oxygen-level-dependent (BOLD) scan (e.g. for measuring resting-state functional connectivity, RSFC)
(d) 4. An eyes-closed resting state BOLD scan with music listening
(e) 5. An emotional faces paradigm (BOLD)

Different versions of the faces were used for each scan, order of their presentation was counterbalanced across the conditions.

Figure 35:
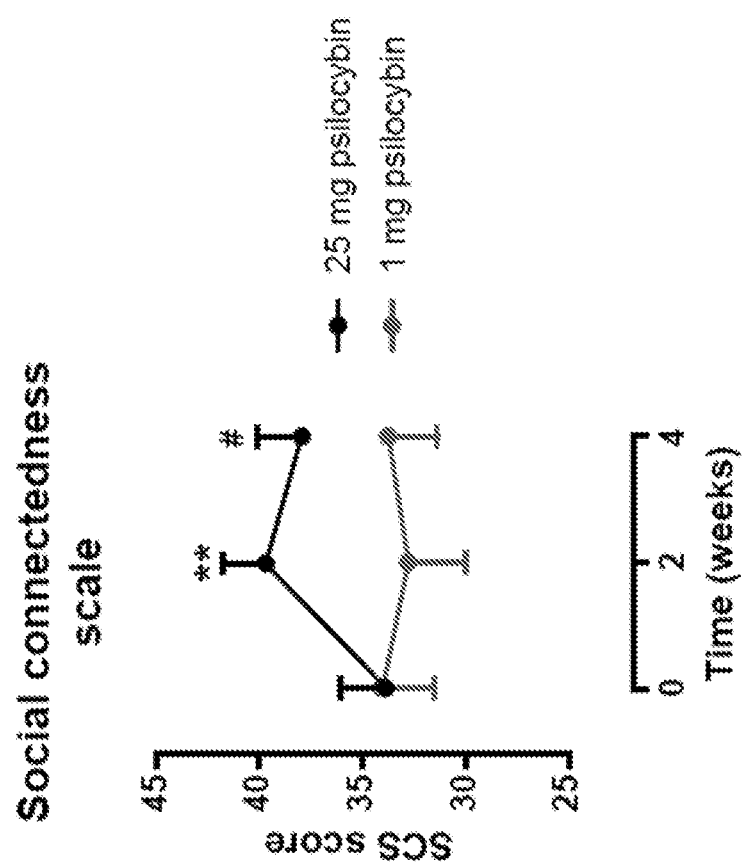
FIG. 35 shows the change in social connectedness scale (SCS) score 2 and 4 weeks following the administration of two doses of psilocybin to healthy human volunteers. Two-way ANOVA repeated measures with Bonferroni correction, **p<0.01, #<0.05. Data are expressed as mean±sem.

Social connectedness, as assessed by the social connectedness scale scores, was significantly increased 2 weeks following the administration of 25 mg psilocybin compared to baseline, this was sustained (at trend level) at week 4 (FIG. 35). Analysis was performed using repeated measures (RM) ANOVA (with Bonferroni correction), with p values<0.05 deemed significant.

Figure 36:
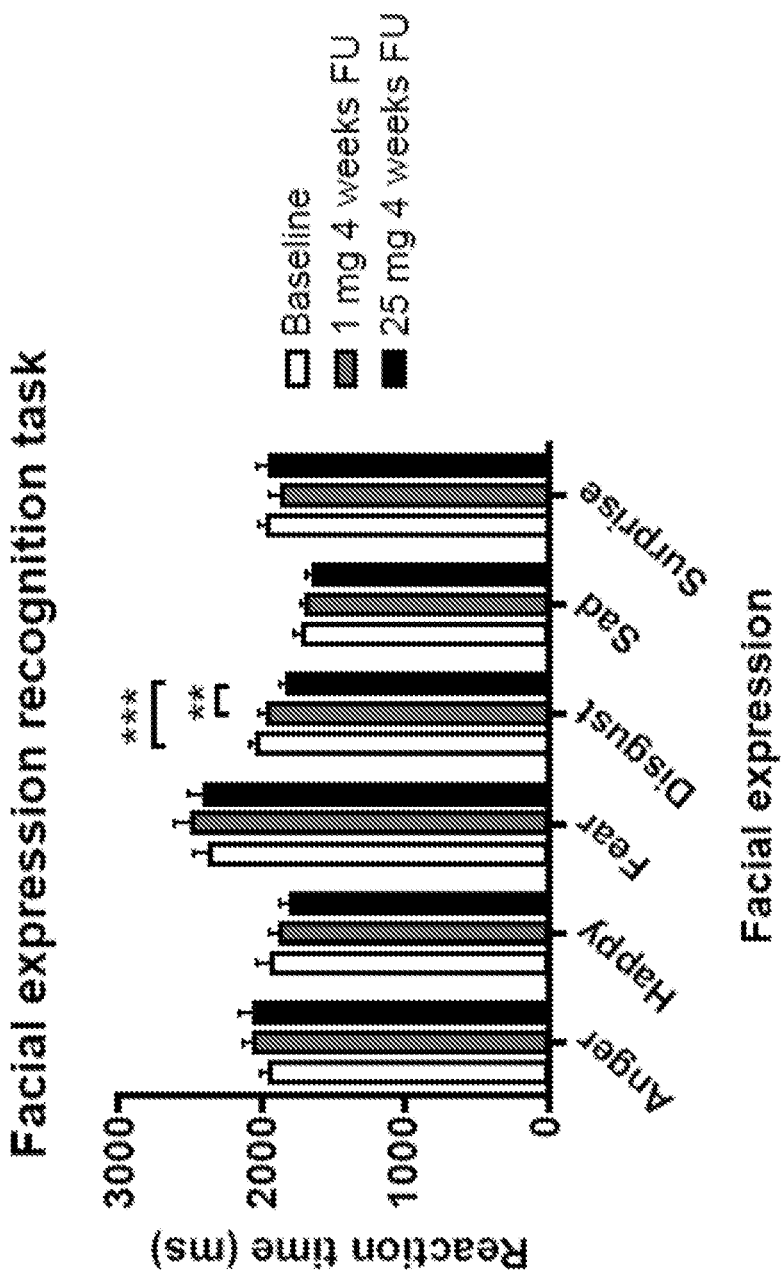
FIG. 36 shows the reaction time of healthy human volunteers in the facial expression recognition task following administration of psilocybin. One-way ANOVA repeated measures, *p<0.05, p<0.01, *p<0.001. Data are expressed as mean±sem.

Participants were significantly faster at recognising the expression of "disgust", as assessed by reaction time to faces displaying this expression, in the facial expression recognition test 4 weeks following the administration of 25 mg of psilocybin when compared to baseline, this was also significantly reduced in 25 mg dose groups at 4 weeks when compared to the very low 1 mg dose. (FIG. 36). Analysis was performed using repeated measures (RM) ANOVA, with p values<0.05 deemed significant.

Figure 37:
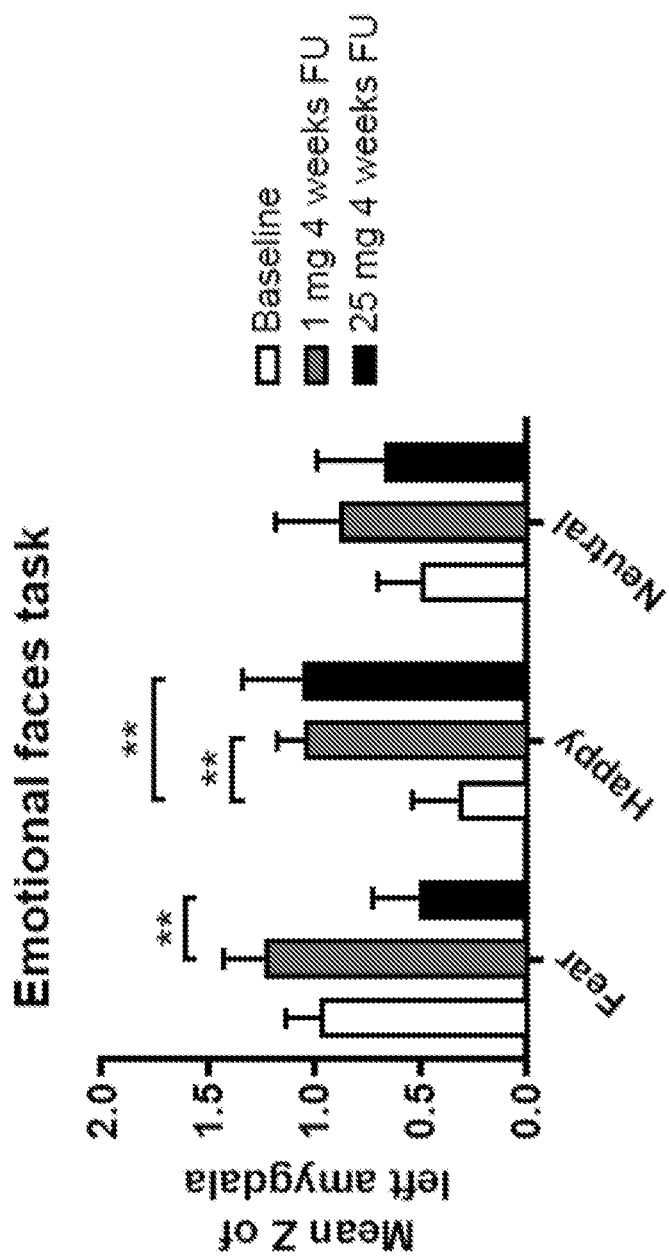
FIG. 37 shows the activation of the left amygdala as represented by the change of mean Z in the left amygdala in healthy volunteers following administration of psilocybin. One-way ANOVA repeated measures, *p<0.05, p<0.01, *p<0.001. Data are expressed as mean±sem.

In the emotional faces task in the fMRI scanner, a significantly decreased (p<0.01) left amygdala responsivity to fearful faces was observed compared to baseline (trend level) and this was also significantly reduced (p<0.01) compared to 4 weeks following a very low dose 1 mg psilocybin administration (FIG. 37). Significantly increased (p<0.01**) left amygdala responsivity to happy faces 4 weeks after both 1 mg and 25 mg psilocybin administration, when compared to baseline (FIG. 37). Analysis was performed using repeated measures (RM) ANOVA, with p values<0.05 deemed significant.

Example 23: Evaluating Psilocybin in Sleep-Wake Disorders

To determine whether psilocybin may treat sleep-wake disorders, and other disorders wherein sleep disruptions are a symptom or comorbidity, various doses of psilocybin were tested in an animal model to determine if psilocybin had an effect on wakefulness, NREM and/or REM sleep, as well as on common electroencephalogram (EEG) frequency bands.

Wistar-Kyoto (WKY) rats exhibit abnormal behavioral, hormonal, neurochemical as well as sleep-wake characteristics that are often associated with depression. Since WKY rats show decreased sensitivity to conventional monoamine-based antidepressant treatment, they are used as a model of TRD. WKY rats are known to exhibit enhanced REM sleep, a common feature in depressed patients.

Male (WKY) rats (200-250 g) were implanted with electroencephalography (EEG) and electromyography (EMG) electrodes and telemetry transmitters under general anaesthesia (2-5% isoflurane in Oxygen). A telemetry transmitter (HD-502, Data Sciences International) was placed in the peritoneal cavity, and the wires of the transmitter were passed through the muscle wall and then sub-dermally to the scalp to act as EEG/EMG electrodes. Two bore holes were made in the skull (Fronto-parietal coordinates; Bregma +2 mm anterior, midline +1.0 mm lateral and Lambda 0 mm, +1.5 mm lateral). The positive EEG electrode was attached to the anterior bore hole and the negative EEG electrode to the posterior bore hole. Both electrodes were secured in place using a suitable adhesive agent (Cyanoacrylate gel, RS components). A second set of electrodes were sutured into the nuchal muscle to act as EMG electrodes. During the post-surgical recovery period (minimum 7 days), the rats received standard post-operative care and no experimental procedures were performed until the pre-operative body weight was regained.

The animals were not drug-naïve at the beginning of the study as they were used in a previous study. The length of the washout period between the two studies was more than 3 months.

Animals were maintained on a 12/12 hour light dark cycle. On study days, the animals were placed in recording boxes and EEG/EMG, locomotor activity, as well as body temperature were recorded for 0.5 h before and 24 h after each dosing. All animals were dosed with saline vehicle first, followed by one of the drug treatments 24 h later. Drug treatments included ketamine (5 and 10 mg/kg) administered subcutaneously (s.c.), s.c.) and psilocybin (1, 3 and 10 mg/kg); administered intraperitoneally (i.p.).

All treatments were administered 2 h after light onset. All animals received all treatment conditions by escalating the doses on a weekly basis, and with a 6 days washout period between a drug treatment and the subsequent vehicle treatment.

EEG, EMG, locomotor activity and body temperature data were acquired for 0.5 hours before and 24 hours after each treatment with Spike2 software (CED, Cambridge UK). EEG/EMG signals were amplified, analogue filtered (0.5-100 Hz), digitized (256 Hz), and then digitally filtered (EEG: 0.5-100 Hz and EMG: 5-100 Hz).

The subsequent EEG/EMG recordings were automatically scored as wake, non-REM (NREM) sleep, or REM sleep in 10 second epochs using SleepSign (Kissei Comtec, Japan).

Power spectral analysis was performed on EEG data recorded over the 0-1 hour, 1-7 hour and 11-19 hour periods post-treatment. EEG power spectra were computed for consecutive 2 second epochs by fast Fourier transformation (Hanning window, 0.5 Hz resolution) between 0.5-100 Hz. Epochs with artefacts (5×STD of RMS) were discarded. Data were presented in 1 Hz bins, and the bins were marked by their upper limits.

Statistical analysis: Repeated measures ANOVA followed by Dunnett post-test was used to compare the different treatment groups (GraphPad, Prism 8).

Figure 39:
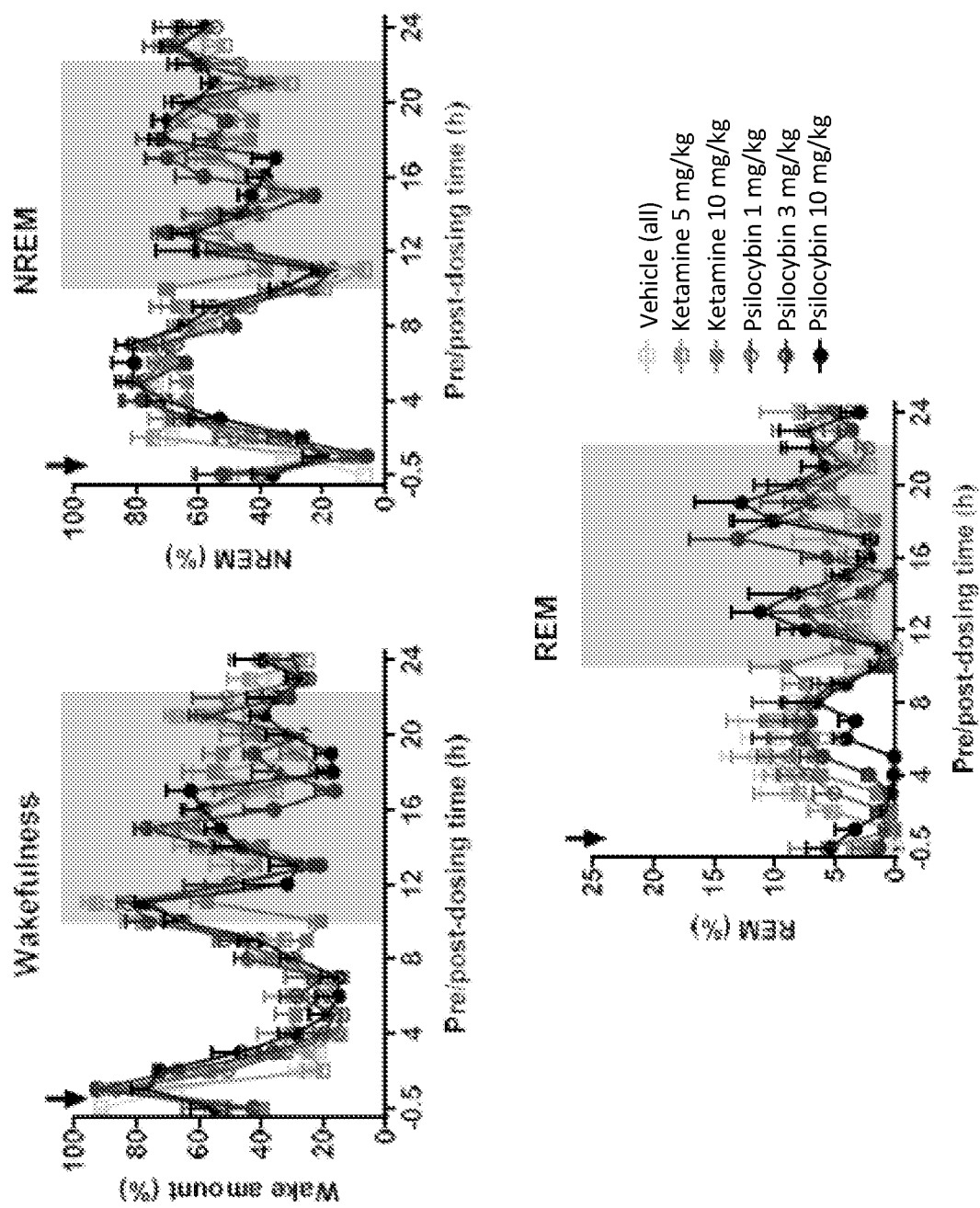
FIG. 39 is a series of graphs showing the changes in amount of wakefulness, non-rapid eye movement (NREM) sleep and rapid eye movement (REM) sleep over 24 hours following psilocybin administration. Black arrow denotes dosing time. Grey background denotes dark phase (i.e., when the rodents are awake).
Figure 40:
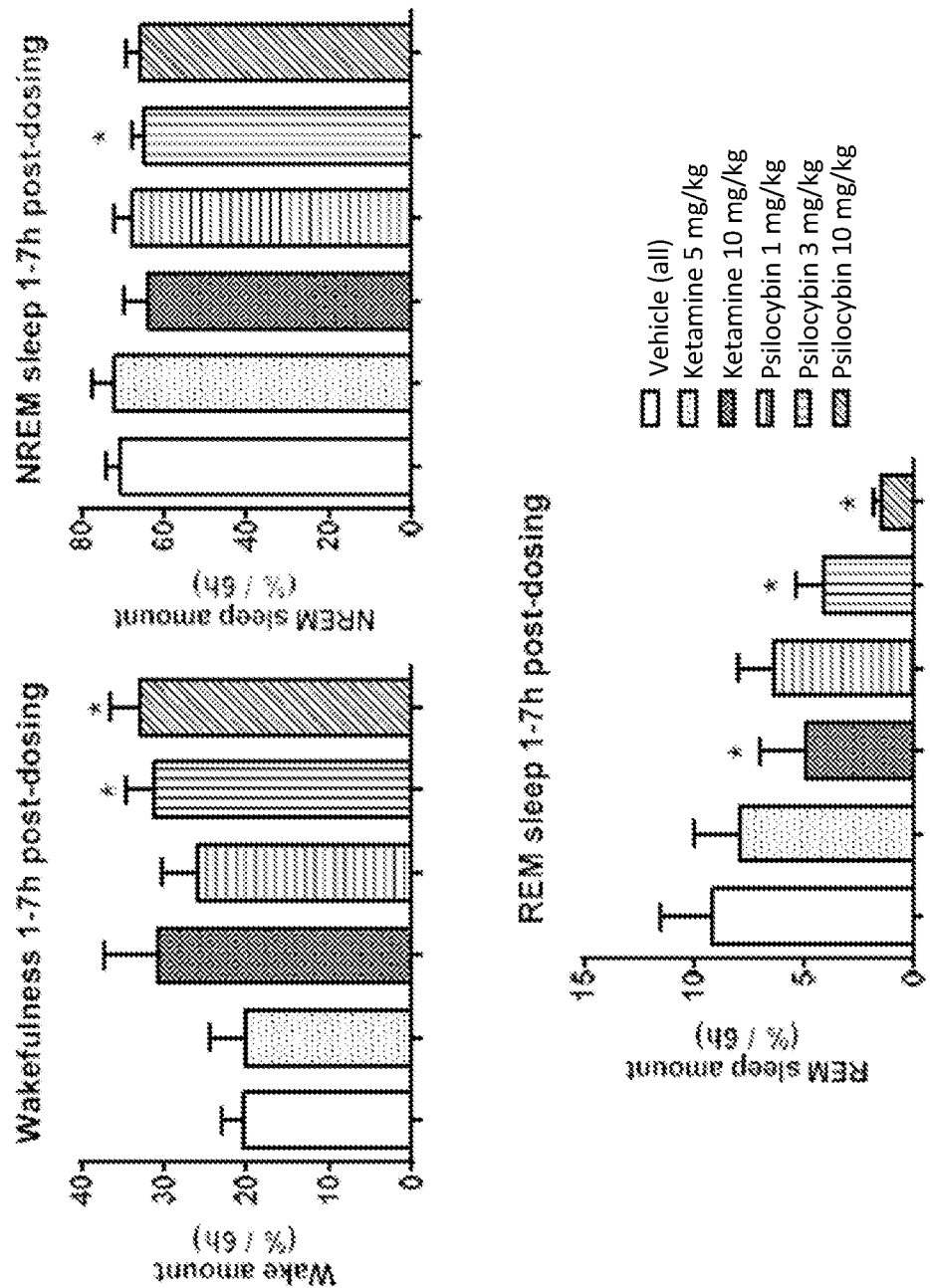
FIG. 40 is a series of graphs showing the amount of wakefulness, NREM sleep and REM sleep 1-7 hours (light phase, i.e., when the rodents are asleep) post-dosing with psilocybin.

In this study, both psilocybin (1 mg/kg, 3 mg/kg, and 10 mg/kg, i.p.) and ketamine (5 mg/kg and 10 mg/kg) decreased the amount of REM sleep in a dose-dependent manner (FIGS. 39 and 40). Notably, abnormally increased amount of REM sleep is observed in some sleep disorders such as narcolepsy, as well as in comorbid conditions including depression and ADHD, among others.

Psilocybin also caused a dose-dependent increase in wake amount and a slight decrease in NREM sleep amount during the light period (FIGS. 39 and 40). This was followed by a slight but significant increase in the amount of NREM sleep at the expense of wakefulness in psilocybin-treated rats during the dark period most likely caused by a rebound effect (FIGS. 39 and 41).

Psilocybin suppressed high-frequency gamma (30-100 Hz) oscillations in the EEG of WKY rats in the 1st hour post-treatment (FIG. 42). In the subsequent part of the light period, psilocybin (1, 3 and 10 mg/kg, i.p.) increased both EEG theta (4-10 Hz) and beta (10-30 Hz) oscillations and suppressed EEG gamma oscillations in WKY rats (FIG. 43). Notably, abnormally enhanced gamma oscillations have been observed in several sleep disorders such as insomnia, as well as in comorbid conditions including anxiety, autism spectrum disorder, epilepsy, ADHD, positive symptoms in schizophrenia, pain, and inflammation, among others.

Example 24: Testing the Analgesic Activity of Psilocybin in a Mouse Model of Chronic Neuropathic Pain To determine whether psilocybin may alleviate chronic neuropathic pain, various doses of psilocybin were tested in a mouse model of chronic constriction injury (CCI).

Male C57BL/6 mice (age 6-7 weeks, source: Charles River UK) were housed in standard caging in groups of 2-4, with free access to food (5CR4, Purina) and water (except during placement in the test box) on a 12/12 light/dark cycle.

All animals underwent behavioral testing of mechanical allodynia on three consecutive days (Day -2, Day-1 and Day 0) prior to surgery in order to determine the baseline withdrawal thresholds. Briefly, Static mechanical (tactile) allodynia was assessed by measurement of withdrawal threshold using calibrated (force; g) von-Frey monofilaments (Touch-Test Sensory Evaluator; Scientific Marketing Associates) applied to the plantar surface of the hind-paw. The animals were placed in individual Perspex boxes on a raised metal mesh for 30-40 minutes before the test. A series of graduated von Frey hairs (0.07, 0.16, 0.4, 0.6 and 1 g) was applied in sequence with a protocol of 1 second on 1 second off, repeated 10 times. Each hair was applied perpendicularly to the center of the ventral surface of the paw until it slightly bends. The force applied to the hind-paw of the animal to induce 5 responses out of 10 trials was recorded as paw withdrawal threshold (PWT). Three baseline paw withdrawal thresholds were taken on ipsilateral paws. The mean of the last two readings used as the baseline withdrawal threshold.

Subsequently, surgery was performed under anesthesia (Isoflurane mixed with oxygen, 3:1, 2 L/min) to tie three loose ligatures of prolene (7-0, Ethicon) around the sciatic nerve, with 1 mm spacing between each. The nerve was then returned below the muscle layer and the wound closed using absorbable sutures (Vicryl).

Following recovery from surgery, Von Frey assessment of mechanical allodynia was taken on days 19 and 22. Animals were then ranked and randomized (based on a Latin square design) to treatment groups according to the percentage change (compared to pre-surgery baseline) of the mean mechanical withdrawal threshold observed on days 19 and 22. Only those animals showing a PWT percentage change of >50% from pre-surgery baseline were included in the study.

On day 23, the animals were dosed with psilocybin (1, 3 or 10 mg/kg by intraperitoneal injection) or vehicle (10 mL/kg by intraperitoneal injection). Nerve pain medication Pregabalin (15 mg/kg administered orally) was also used as a positive control. Allodynia was then assessed at 0.5, 4 and 24 hours post-treatment timepoint (PTT).

Figure 38:
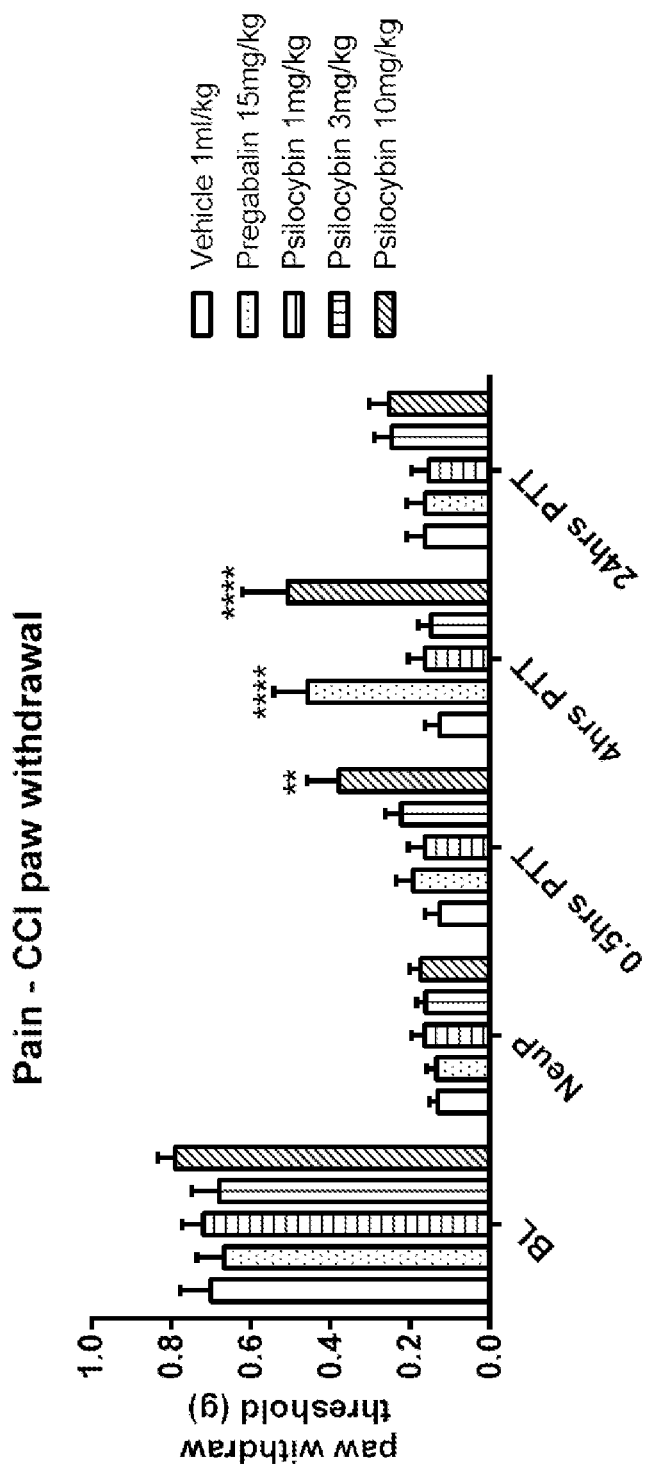
FIG. 38 is a graph showing the effects of psilocybin treatment on paw withdrawal threshold in mice that have undergone ligation of the sciatic nerve in a chronic constriction injury (CCI) model, as compared to vehicle-treated animals. Statistical significance was determined using a Two-way ANOVA repeated measures test followed by Fisher's Least Significant Difference (LSD) for pairwise comparison test. *p<0.05; p<0.01; *p<0.001; ****p<0.0001. Data are expressed as mean±sem. BL=pre-surgery baseline, NeuP=neuropathic baseline, PTT=post-treatment time point.

Data are shown in Table 42 and FIG. 38. Ligation of the sciatic nerve decreased the force-induced paw withdrawal threshold between Days 19-22 in all animals as expected.

The anticipated analgesic activity of pregabalin administered orally at 15 mg/kg was demonstrated by a significant increase in the paw withdrawal threshold 4 hours following administration, as compared to neuropathic baseline measurements. Administration of psilocybin at 10 mg/kg significantly increased the paw withdrawal threshold, at both 30 minutes and 4 hours following administration, as compared to neuropathic baseline measurements.

TABLE 42

Paw withdrawal threshold

Force-induced paw withdrawal (g) ± SEM

| Test day | Vehicle 10 ml/kg IP n = 9 | | Psilocybin 1 mg/kg IP n = 10 | | Psilocybin 3 mg/kg IP n = 10 | | Psilocybin 10 mg/kg IP n = 10 | | Pregabalin 15 mg/kg PO n = 9 | |
|---|---|---|---|---|---|---|---|---|---|---|
| | Mean | sem | mean | sem | mean | sem | mean | sem | mean | sem |
| D-2 D-1 Baseline | 0.7 | 0.08 | 0.72 | 0.05 | 0.68 | 0.07 | 0.79 | 0.04 | 0.67 | 0.07 |
| D19-22 Neuropathic baseline | 0.13 | 0.02 | 0.16 | 0.03 | 0.16 | 0.02 | 0.17 | 0.03 | 0.13 | 0.03 |
| D23 0.5 hours PTT | 0.13 | 0.04 | 0.16 | 0.04 | 0.22 | 0.04 | 0.38* | 0.08 | 0.19 | 0.04 |
| D23 4 hours PTT | 0.13 | 0.04 | 0.16 | 0.04 | 0.15 | 0.03 | 0.51* | 0.11 | 0.46* | 0.09 |
| D24 24 hours PTT | 0.16 | 0.05 | 0.15 | 0.04 | 0.25 | 0.04 | 0.25 | 0.05 | 0.16 | 0.05 |

*P < 0.05
PTT = post-treatment timepoint
IP = intraperitoneal
sem = standard error of the mean Example 25. In Vivo Study Examining Psilocybin for the Treatment of Epilepsy Administration of chemical convulsant agents such as Pentylenetetrazol (PTZ) are used to mimic behavioral aspects of human epilepsy. PTZ causes myoclonic jerking movements, clonic convulsions or forelimb/hindlimb tonic extension in rodents. The PTZ model is primarily used to evaluate anti-convulsant properties of antiepileptic drugs (AED's) by identifying compounds which raise seizure threshold but can also be used to identify pro-convulsant agents that lower seizure threshold. PTZ is a well-established model for acute and repetitive seizures, and is accepted for use for screening AED action. PTZ induces myoclonic and generalized tonic-clonic seizures.

Male CD1 mice (age 6-8 weeks, weight 30.0-42.9 g, source: Charles River UK) were used in this study. The mice were housed in groups of 2-4, in standard caging with free access to food and water on a 12/12 light/dark cycle. Mice were dose with an intraperitoneal (i.p.) injection of either diazepam (10 mg/kg, p.o.) 60 minutes prior to PTZ administration or psilocybin (1, 3, or 10 mg/kg) administered 20 minutes prior to PTZ administration. Following pre-treatment, mice were lightly restrained and injected intravenously using a cannula (size 26G ½ inch) secured to the tail by tape. Via the cannula, the mice received a time-infusion of pentylenetetrazol (8 mg/ml in 0.9% heparinised saline at 0.5 ml/min) up to a cut-off time of 120 seconds. During this time-infusion, mice were individually assessed for the onset of myoclonic, forelimb tonus and hindlimb tonus seizures. The latencies (in seconds) from start of infusion to the appearance of first myoclonus, forelimb tonic and hind limb tonic extension were recorded. Infusions were stopped at the appearance of hindlimb tonic extension (or respiratory arrest) in each animal up to a cut off point of 120 s. For animals reaching this cut off, the dose of PTZ in mg/kg infused over the 120 s was calculated as the threshold dose.

The threshold dose in mg/kg for the appearance of clonic and tonic seizures, based on latencies to first myoclonus, forelimb tonus and hindlimb tonic extension was calculated using the following formula: [time to seizure (s)×concentration of PTZ (mg/mL)×flow rate (mL/min)×1000]/60× body weight of animal (g).

Data was analysed using one way ANOVA in which the dose of PTZ required to induce seizure was compared between each treatment groups and vehicle. This was followed by dunnetts multiple comparison test using Prism. A P score of equal to or below 0.05 was considered significant.

Figure 24:
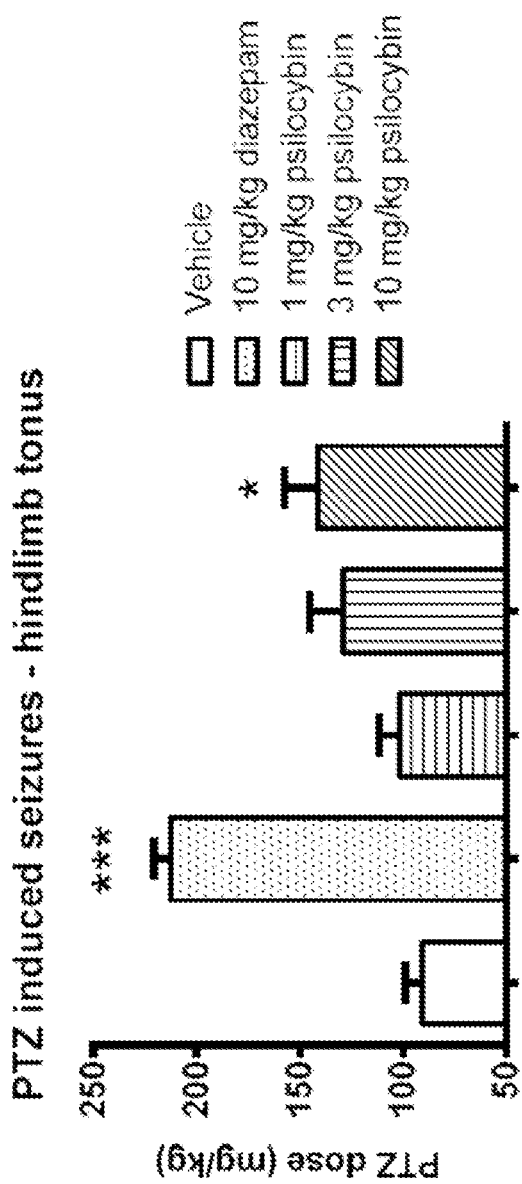
FIG. 24 shows that the PTZ dose required to induce hindlimb tonic seizures in mice administered psilocybin is increased compared to mice administered vehicle. One-way ANOVA followed by Dunnett's multiple comparison test, *p<0.05, ***p<0.001. Data are expressed as mean±sem.

Intravenous infusion of PTZ (8 mg/ml at 0.5 ml/minute) in the mouse induced sequential myoclonic, forelimb and hindlimb tonic seizures as expected. Diazepam administered ip at 10 mg/kg significantly increased the dose of PTZ required to induce myoclonic, forelimb and hindlimb tonic seizures thereby producing the expected broad anticonvulsant effect across different seizure types. Psilocybin administered IP at 10 mg/kg significantly increased the dose of PTZ required to induce hind limb tonic seizures when compared to the vehicle treated group (FIG. 24).

Example 26: Psilocybin Dampens LPS-Induced Cytokine Secretion

In order to determine whether psilocybin has anti-inflammatory effects, lipopolysaccharide (LPS)-induced changes in blood concentrations of TNFα, IL-6, IL1-b and IL-10 were examined when administered alongside vehicle (negative control), dexamethasone (positive control, 1 mg/kg, p.o), or 3 different concentrations of psilocybin (1, 3 and 10 mg/kg, i.p) in rats. Dexamethasone (1 mg/kg) or vehicle (1 ml/kg) was administered 1 hour prior to psilocybin or vehicle administration. LPS or vehicle were administered 1 hour post psilocybin or vehicle administration, with plasma samples collected after another hour for cytokine analysis. A schematic illustrating the dosing and sample collection protocol is shown in FIG. 44. These experiments were performed in accordance with the European Directive 2010/63/EU. The data were analyzed using a one-way Analysis of Variance (ANOVA) to compare the effect of treatment to vehicle, and the effect of LPS (with vehicle) compared with control. Fishers Least Significant Difference (LSD) was performed post-hoc, in Prism® (GraphPad®, USA) ($p<0.05$ considered significant).

Psilocybin pre-treatment caused a slight reduction in LPS-induced TNFα (FIG. 45) and IL-6 (FIG. 46) levels, and a significant reduction in IL-1β (FIG. 47) and IL-10 (FIG. 48) levels.

Example 27: Evaluation of Psilocybin's Efficacy in a Dextran Sodium Sulfate (DSS)-Induced Mouse Model of Ulcerative Colitis Adult male C57BL/6 mice are randomized into experimental groups (n=10 for each group) based on their body-weights and allowed to acclimatize for one week. Psilocybin treatments are administered in accordance with the schedule below by scientific staff blinded to treatment groups. On Day 0, drinking water is replaced by a 5% dextran sodium sulfate (DSS) in tap water. Animals are given ad libitum access to the 5% DSS until disease progression is such that DSS is removed and replaced with drinking water. From Day 0 until the end of the experiment on Day 7, animals are monitored daily for clinical signs of colitis such as bodyweight loss, loose stools and/or diarrhea and presence of occult or gross blood in stools. On Day 7, animals are culled, the colon dissected out and colon length measured. One sample of colon per animal is transferred in tissue fixative then processed for paraffin embedding and stored until histopathology analysis.

The protective effect of the various doses of psilocybin will be evaluated, based on clinical scores of colitis, histopathology analysis of the dissected colons, and differences in colon length observed among the treatment groups.

| Groups | Treatments | | | |
|---|---|---|---|---|
| | Dose | Route | Regimen | Intervention |
| 1 Vehicle (saline) | N/A | IP | Day 0, 3, 6 | DSS 5% in drinking water |
| 2 Psilocybin | 1 mg/kg | | | |
| 3 Psilocybin | 3 mg/kg | | | |
| 4 Psilocybin | 10 mg/kg | | | |

Example 28: In Vitro Study to Assess Psilocin's Effect on Cell Viability Upon Oxygen Glucose Deprivation An in vitro model is used to examine whether psilocybin affects cell viability upon oxygen glucose deprivation (OGD). During stroke, blockage or rupture of a blood vessels disrupts the supply of neurons in oxygen and nutrients such as glucose and leads to cell death. Thus, OGD mimics what happens in the injured part of a brain during a stroke. Cell viability is determined by measuring lactate dehydrogenase (LDH) release.

Briefly, E18 rat embryos are dissected in preparation of cortical cultures. Cortical cultures are treated with vehicle, positive control (MK-801+CNQX (glutamate receptor antagonists)), or psilocin at concentration of 0.1 μM, 0.3 μM, 1 μM, 3 μM, or 10 μM. N=6 for each treatment group.

Subsequently, cortical cultures are exposed to oxygen glucose deprivation, which leads to swelling and neurodegeneration, mimicking the effects of a stroke. LDH release is measured according to a standard assay.

A decrease in LDH release in the psilocybin and positive control group compared to vehicle indicates that psilocybin is protective against cell death caused by OGD.

Example 29: In Vitro Study to Assess Psilocin's Effect on Cell Viability Upon Kainic Acid Treatment An in vitro model is used to examine whether psilocybin affects cell viability upon kainic acid treatment. Kainic Acid (KA) is a potent agonist at glutamate receptors, and excessive KA concentrations can elicit excitotoxicity in spinal motor neurons, causing neuronal death. This neurotoxicity partially mimics the neurodegeneration observed in the pathophysiology of ALS. The present study evaluates the effect of treatment with KA and psilocybin or positive control Cyanquixaline (CNQX) on Lactate dehydrogenase (LDH) release of spinal cord cultures (i.e., a mixture of cells enriched in motor neurons).

Briefly, E15 Wistar rat pups will be dissected for preparation of spinal cord cultures. The cells are cultured under standard conditions.

Cells are treated with either (i) vehicle, (ii) psilocin (0.1 μM, 0.3 μM, 1 μM, 3 μM, or 10 μM), or (iii) CNQX (i.e., a glutamate receptor antagonist used as a positive control). They are then treated with kainic acid and incubated for a predetermined period of time. Cell viability is measured using a standard assay.

A decrease in cell mortality when the cells are treated with the positive control or psilocin indicates that psilocybin is protective against cell death caused by kainic acid.

Example 30: Clinical Study of the Safety and Efficacy of Psilocybin as an Adjunct to Opioid Substitution Therapy in Patients with Opioid Use Disorder Aim of Study:

The aim of this study is to explore the safety and efficacy of psilocybin therapy as an adjunct to opioid substitution therapy (OST) for relapse prevention in patients with Opioid Use Disorder (OUD). A single dose of psilocybin (25 mg) will be administered under supportive conditions as an adjunct to ongoing OST to adult patients with OUD. Data will be gathered on efficacy and adverse events (AEs), changes in vital signs, electrocardiograms (ECGs), clinical laboratory blood tests, and suicidality (Columbia Suicide Severity Rating Scale; C-SSRS). Additional objectives include (i) exploring the efficacy of 25 mg of psilocybin administered under supportive conditions in preventing relapse, improving adherence to ongoing prescribed OST, reducing opioid cravings, use of illicit opioids, and (ii) evaluating the effects of psilocybin on mood, anxiety, quality of life, functioning and associated disability, personality traits, trauma, and role of therapeutic alliance in safety and clinical efficacy of the psilocybin session and feasibility of psilocybin therapy in OUD.

Study Design:

This is a phase II, fixed dose, open label trial to explore the safety, tolerability and efficacy of a 25 mg dose of psilocybin as an adjunct to OST in OUD patients with MDD.

The study population will include adult men and women, 18 years of age or above, currently taking methadone, buprenorphine or naltrexone for OUD diagnosed according to the Structured Clinical Interview for DSM-5 Clinical Trials Version (SCID-5-CT).

Participants will be recruited primarily among patients in treatment for OUD at the study site and through referrals from specialized addictions and psychiatric services.

The majority of participants will have no prior exposure to psilocybin or so-called "magic mushrooms"; however, participants with prior recreational experience with psilocybin or "magic mushrooms" are eligible. Any past exposure to psilocybin, or other psychedelics, should be more than 12 months prior to Screening (V1).

Inclusion Criteria are Listed Below:
- Male or female, 18 years of age or above at Screening (V1)
- Diagnosis of OUD according to DSM-5, measured with the OUD section of the SCID-5-CT Currently prescribed an taking an OST (buprenorphine, naltrexone, suboxone or methadone)
- Either one or more of the following: Recently started an OST (within the past months from Screening [V1]); recent (within months of screening [V1]) use of illicit opioids; reported experiencing the craving criterion within the SCID-5-CT OUD diagnostic assessment
- Adherence to prescribed OST>=75% of time over past month (determined via patient self-report)
- Able to complete all protocol required assessment tools without any assistance or alteration to the copyrighted assessments, and to comply with all study visits
- Has capacity to consent (assessed via investigator judgement)

After signing an informed consent form (ICF), participants will be assessed for their eligibility with the MINI 7.0.2, SCID-5-CT, and the C-SSRS. Additionally, a physical exam, vital signs, review of medical history, prior/concomitant medications, clinical laboratory tests, adverse events/serious adverse events (SAEs), a 12-lead ECG, urinalysis, urine drug screen and a urine pregnancy test (if applicable) and a documentation of the contraceptive method to be used will be undertaken. Those who meet the eligibility criteria will enter the screening period. At the initial Screening Visit (V1), the participant will also be evaluated with the Timeline Followback (TLFB). Once a participant completes all Screening assessments (V1), the investigator(s) will review the results and issue approval, if the participant is eligible.

During the Screening Period all participants will have two pre-administration psychological support sessions with an assigned specially trained study therapist to discuss safety and effects of psilocybin. Each participant will have one pre-administration psychological support session with their dedicated study therapist which will occur shortly after eligibility is confirmed (V1a). At this session the therapist will grant the patient access to online preparatory materials consisting of videos of participants from prior studies sharing their experience, animations of psilocybin's mechanism of action and what to expect during the session, as well as breathing and relaxation exercises. Participants are encouraged to get familiar with these materials.

One pre-administration psychological support session will occur one day prior to the psilocybin session (Baseline, V2, Day −1), and again will be with the participant's assigned study therapist. On this day the participants will also undergo an review of inclusion/exclusion criteria, vital signs, a 12-lead ECG, urinalysis, urine drug screen, urine pregnancy test (if applicable), clinical laboratory tests, review of concomitant therapies, AE/SAEs review, the C-SSRS, the TLFB, Opioid Craving Scale (OCS), Sheehan Disability Scale (SDS), Montgomery Asberg Depression Rating Scale (MADRS), the Euro Quality of Life-5 dimension-5 level (EQ-5D-5L) scale, Stages of Change Readiness and Treatment Eagerness Scale (SOCRATES), Pain VAS, the Trauma History Questionnaire (THQ), Generalized Anxiety Disorder-7 item scale (GAD-7), Severity of Dependence Scale, the Barratt Impulsiveness Scale (BIS-11), the Ten-Item Personality Inventory (TIPI), and the 16 item, Quick Inventory of Depressive Symptomatology Scale, Self-Report (QIDS-SR-16). Both the therapist and the participant will be asked to fill out a therapeutic alliance evaluation questionnaire—the Scale to Assess Therapeutic Relationship (Clinician and Patient version, STAR-C and STAR-P, respectively). A final review of Baseline data will be completed to ensure the participant's continued eligibility. Participants cannot be progressed to V3 until this approval is received.

The psilocybin session (V3, Day 0) will last approximately eight hours. Each participant will be supported by a specially trained dedicated therapist with whom they formed therapeutic alliance in the preparation phase. A review of inclusion/exclusion criteria, AEs, concomitant medications, and vital signs will take place before the psilocybin session begins. Participants will also complete C-SSRS, Pain VAS. The session will be supervised by a trained physician. After the acute effects of psilocybin pass, participants will be evaluated for safety, AEs will be recorded and participants will complete the C-SSRS, a Likert-scale to rate the intensity of the experience, the Five-Dimensional Altered States of Consciousness questionnaire (5D-ASC), Pain VAS, and will then stay in hospital overnight.

On Day 1 (V4), the day following psilocybin administration, participants will be seen in person to complete a safety check, vital signs, 12-lead ECG, urinalysis, urine drug screen, AE and concomitant medication review, C-SSRS, TLFB, OCS, SDS, MADRS, 5D-ASC, Severity of Dependence Scale, BIS-11, TIPI and Pain VAS. A post-administration psychological support session (i.e., an integration session) will also be conducted for participants on Day 1 to discuss their experiences during the psilocybin session with their assigned therapist. Participants will be assessed by a clinician for safety before being discharged.

On Day 7 (V5), participants will be seen in person for a safety check, and completion of assessments including vital signs, 12-lead ECG, urinalysis, urine drug screen, clinical laboratory tests, AEs and concomitant medication review, the C-SSRS, TLFB, OCS, SDS, MADRS, EQ-5D-5L, GAD-7, Severity of Dependence Scale, BIS-11, TIPI and Pain VAS. A post-administration psychological support session (i.e., an integration session) will also be conducted for participants to discuss their experiences during the psilocybin session.

On Day 21 (V6), participants will be seen in person for a safety check, integration, and completion of assessments including vital signs, 12-lead ECG, urinalysis, urine drug screen, AE and concomitant medication review, the C-SSRS, TLFB, OCS, SDS, MADRS, GAD-7, EQ-5D-5L, Severity of Dependence Scale, BIS-11, TIPI and Pain VAS.

On Day 56 (V7), participants will be seen in person for a safety check, and completion of assessments including vital signs, 12-lead ECG, urinalysis, urine drug screen, AE and concomitant medication review, the C-SSRS, TLFB, OCS, SDS, MADRS, QIDS-SR-16, GAD-7, EQ-5D-5L, Severity of Dependence Scale, BIS-11. TIPI and Pain VAS. Participants and clinicians will also be asked to complete a semi-structured qualitative interview at this time point to assess their views and experiences of the treatment.

All sessions between the therapist(s) and the participant(s) will be video and audio recorded for live safety monitoring, adherence monitoring and quality assurance, therapist training, and to ensure that no directive psychotherapy was provided.

Participants will be seen at the clinic for Screening (V1 and Via), Baseline (V2, Day −1), Day 0 (V3, Dosing), Day 1 (V4), Day 7 (V5), Day 21 (V6), and Day 57 (V7) visits. V5, 6 and 7 will be offered remotely if required and at the discretion of the study clinician.

Rescue medications are allowed at any stage of the study as noted in the protocol. Participants who start prohibited medications after the dosing session will not be excluded from the study and will be followed up until the final study visit (V7), unless consent is withdrawn. The reason for starting these medications will be documented.

Study Endpoints are Listed Below:
- Incidence and occurrence of treatment-emergent adverse events (TEAEs) and SAEs from Day of Dosing (Day 0, V3) to Week 12 (V7) and from Day 1 (V4) to Week 12 (V7).
- Incidence of clinically important changes in ECG parameters from Screening (V1) to Week 12 (V6).
- Incidence of clinically important changes in laboratory results from Screening (V1) to Week 12 (V6).
- Incidence of clinically significant changes in vital signs from Screening (V1) to Week 12 (V6).
- Incidence of changes in suicidal ideation/behavior (measured using the C-SSRS) score at all visits from Baseline (Day −1 [V2]) to Week 12 (V7).
- Time to any of the following events related to opioid use relapse from Baseline:
  - Self-reported illicit opioid use on the TLFB.
  - Positive urine drug screen for opioids assessed at day 1, week 1, week 3, or week 12.
  - Overdose of opioids.
  - Hospitalization due to OUD.
  - Need for emergency medical interventions for OUD.
- Number of cumulative opioid abstinent days from Baseline at Week 1 (V5), Week 3 (V6) and week 12 (V7) (determined via TLFB self-report).
- Abstinence from opioids from Baseline at Week 1 (V5), Week 3 (V6), and Week 12 (V7) (determined via urine drugs screening and TLFB self-report).
- Quantity of opioids consumed over 12 weeks (if using, data will be collected via the TLFB and translated by the opioid equivalence chart).
- Number of opioid use days from Baseline to Week 12 compared to the period 3 months prior to baseline.
- Change in self-report adherence to ongoing OST over 12 weeks (expressed as % of estimated days participants took their OST) compared to baseline.
- Time to use of illicit opioids from Baseline (TLFB).
- Time to positive urine screen for illicit opioids from Baseline (urine tests at day 1, Week 1, Week 3 and Week 12).
- Relapse rate, assessed with urine samples for detection of opioids, at Day 1 (V4), Week 1 (V5), Week 3 (V6) and Week 12 (V7).
- Relapse rate as determined by mean number of days of participant opioid use via TLFB from Day 0 to Day 1(V4), Week 1(V5), Week 3 (V6) and Week 12 (V7)
- Change in OCS score from Baseline to Day 1 (V4), Week 1 (V5), Week 3 (V6) and Week 12 (V7).
- Change in Severity of Dependence Scale total score from Baseline to Day 1 (V4), Week 1 (V5), Week 3 (V6) and Week 12 (V7).
- Number and frequency of other illicit drugs used (if any) as assessed using the TLFB at week 1, week 3 and week 12 and compared to Baseline.
- Participant EQ-5D-5L score change from Baseline (Day −1 [V2]) to subsequent follow up visits.
- Change in Pain VAS scores from Baseline (Day −1 [V2]) to Day 0 (V3), Day 1 (V4), Weeks 1 (V5), 3 (V6)), and 8 (V7).
- Change in QIDS-SR-16 total score from Baseline (V2) to Week 12 (V7).
- Change in MADRS total score from Baseline (V2) to Week 1 (V5), Week 3 (V6) and Week 12 (V7).
- Change in GAD-7 total score from Baseline (V2) to Week 1 (V5), Week 3 (V6) and Week 12 (V7).
- SDS score change from Baseline (Day −1 [V2]) to Week 1 (V5), 3 (V6), and 12 (V7)).
- Summary of the 5D-ASC on the day of psilocybin dosing (V3) and Day 1 (V4).
- Links between psychedelic intensity and experience (via the 5D-ASC and intensity Likert ratings), readiness (SOCRATES), change in depression and anxiety severity (MADRS, and GAD-7 respectively), trauma (Trauma History Questionnaire), impulsivity (BIS-11), and personality (TIPI) and efficacy in terms of outcomes related to relapse will be explored.
- Patient experience, feasibility and acceptability of the treatment will be summarized, for example, compliance with the treatment schedule and protocol defined assessments and visits.
- Change in the BIS-11 total score from Baseline (V2) to Day 1 (V4), Week 1 (V5), Week 3 (V6) and Week 12 (V7).
- Change in TIPI Extraversion score from Baseline (V2) to Day 1 (V4), Week 1 (V5), Week 3 (V6) and Week 12 (V7).
- Change in TIPI Agreeableness score from Baseline (V2) to Day 1 (V4), Week 1 (V5), Week 3 (V6) and Week 12 (V7).
- Change in TIPI Conscientiousness score from Baseline (V2) to Day 1 (V4), Week 1 (V5), Week 3 (V6) and Week 12 (V7).
- Change in TIPI Emotional Stability score from Baseline (V2) to Day 1 (V4), Week 1 (V5), Week 3 (V6) and Week 12 (V7).
- Change in TIPI Openness to Experiences score from Baseline (V2) to Day 1 (V4), Week 1 (V5), Week 3 (V6) and Week 12 (V7).
- Therapeutic alliance of the clinician and patient, as rated using the STAR-C and STAR-P respectively will be assessed at Baseline, along with assessing correlations with this measure and primary and secondary outcomes as a possible predictor of response and safety.
- Results of a semi-structured interview on participant and clinician experience and preference in having a second psilocybin session, at Week 12 (V7) post dosing.

Without being bound by any particular mechanism of action, one of skill in the art would understand that the models used to study the efficacy of an active agent in a particular indication, and data obtained using the same, can also be applied to other indications. As such, the following table indicates which models and examples are potentially relevant for the listed indications. This is non-exhaustive, and one of skill in the art would understand that the various examples discussed herein can be used to support the activity of psilocybin, active metabolites of psilocybin, prodrugs of psilocybin, and prodrugs of active metabolites of psilocybin in a variety of indications.

| Study | Relevant indications |
|---|---|
| Example 10<br>In vivo study investigating changes in mouse protein:<br>Increase in receptor protein kinase erbB4 (Erbb4) expression | Alzheimer's<br>Sleep wake disorders<br>Pain<br>Parkinson's<br>Neurodegenerative disorder<br>IBD<br>Inflammation<br>Autism |
| Example 10<br>In vivo study investigating changes in mouse protein:<br>Decrease in calsyntenin 2 (CIstn2) expression | Alzheimer's<br>Autism |
| Example 10<br>In vivo study investigating changes in mouse protein:<br>Increase in glucagon (Gcg) expression | Alzheimer's<br>Sleep wake disorders<br>Pain<br>Parkinson's<br>Neurodegenerative disorder<br>Inflammation |
| Example 10<br>In vivo study investigating changes in mouse protein<br>Increase in plasma levels of tenascin-R (Tnr) | Alzheimer's |
| Example 10<br>In vivo study investigating changes in mouse protein<br>Increase in plasma levels of transforming growth factor beta receptor type 3 (Tfgbr3) | Alzheimer's<br>Autism |
| Example 10<br>In vivo study investigating changes in mouse protein<br>Increase in plasma levels of activin A Receptor Type II-like kinase 1(Acyrl1) | ADHD<br>Alzheimer's |
| Example 10<br>In vivo study investigating changes in mouse protein<br>Decrease in plasma levels of fibronectin leucine-rich repeat transmembrane protein 2 (Flrt2) | Sleep wake disorders<br>Inflammation<br>Autism |
| Example 10<br>In vivo study investigating changes in mouse protein<br>Decrease in repulsive guidance molecule A (Rgma) expression | Sleep wake disorders<br>Pain<br>Parkinson's<br>IBD<br>Inflammation<br>Autism |
| Example 10<br>In vivo study investigating changes in mouse protein<br>Decrease in C-X-C chemokine ligand 1 (Cxcl1) expression | Sleep wake disorders<br>Pain<br>Epilepsy<br>Neurodegenerative disorder<br>IBD<br>Inflammation<br>Autism |
| Example 10<br>In vivo study investigating changes in mouse protein<br>Increase tumor necrosis factor superfamily member 6 (Fas) expression | Parkinson's<br>IBD<br>Inflammation |
| Example 10<br>In vivo study investigating changes in mouse protein<br>Decrease in V-set and immunoglobulin domain containing 2 (Vsig2) expression | Autism |
| Example 10<br>In vivo study investigating changes in mouse protein<br>Increase in S100 calcium binding protein A4 (S100a4) expression | Autism |
| Example 10<br>In vivo study investigating changes in mouse protein<br>Increase in plexin-A4 (Plxna4) expression | Autism |
| Example 10<br>In vivo study investigating changes in mouse protein<br>Increase in transforming growth factor alpha (TGFa) expression | Autism |
| Example 11<br>In vitro test assessing the effect of psilocin on damage induced by fibrillated amyloid-β on cultures of hippocampal neurons | Alzheimer's<br>Multiple sclerosis |
| Example 12<br>In vitro test investigating the effect of psilocin on neurite outgrowth in<br>cultures of human iPSC-derived neurons | Alzheimer's<br>Multiple sclerosis |
| Example 13<br>In vivo test investigating the effect of psilocybin in a scopolamine-induced cognitive dysfunction mouse model | Alzheimer's<br>Parkinson's<br>ADHD<br>Autism |
| Example 14<br>In vivo test investigating the effect of psilocybin on aged-induced cognitive deficits in mice with the T-maze alternation test | Alzheimer's<br>Parkinson's |

| Study | Relevant indications |
|---|---|
| Example 15<br>Rapid visual information processing task in humans | Autism<br>Alzheimer's<br>Parkinson's<br>ADHD<br>Autism |
| Example 16<br>Effect of psilocybin on damage induced by 6-hydroxydopamine (6-OHDA) on mesencephalic neuronal cultures | Parkinson's |
| Example 17<br>In vivo study of the effect of psilocybin in the 6-OHDA-induced Parkinson's Disease Model | Parkinson's |
| Example 18<br>In vivo study of the effect of psilocybin on haloperidol induced catalepsy | Parkinson's |
| Example 19<br>In vivo study of the effect of Psilocybin on CCK-induced panic anxiety | Autism |
| Example 20<br>Effect of Psilocybin on Marble Burying (MB) Test in an in vivo model | Autism |
| Example 21<br>In vivo study assessing the effect of psilocybin on pro-social and repetitive behaviors | Autism<br>Antisocial behavior disorder |
| Example 22<br>Healthy Volunteer Study assessing the acute and long-term effects of psilocybin on social cognition and behavior | Autism<br>Alzheimer's<br>ADHD<br>Sleep disorders |
| Example 23<br>Evaluating psilocybin in sleep-wake disorders | Autism<br>Epilepsy<br>ADHD<br>Pain<br>Epilepsy<br>Inflammation<br>Multiple sclerosis |
| Example 24<br>Testing the analgesic activity of psilocybin in a mouse model of chronic neuropathic pain | Pain<br>Multiple sclerosis |
| Example 25<br>In vivo study examining psilocybin for the treatment of epilepsy | Epilepsy |
| Example 26<br>Psilocybin dampens LPS-induced cytokine secretion | Inflammation<br>Pain<br>Multiple sclerosis |

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The foregoing is illustrative of the present invention, and is not to be construed as limiting thereof. The invention is defined by the following claims, with equivalents of the claims to be included therein.

What is claimed is:

1. A method for treating attention-deficit hyperactivity (ADHD) disorder in a subject in need thereof, the method comprising administering to the subject a therapeutically effective amount of crystalline psilocybin, wherein the crystalline psilocybin is characterized by XRPD peaks at 11.5±0.1, 12.0±0.1, 14.5±0.1, 17.5±0.1 and 19.7±0.1° 2θ, and wherein the crystalline psilocybin has a chemical purity of greater than 97% as determined by HPLC analysis.

2. The method of claim 1, wherein the subject has an attention-deficit hyperactivity subtype selected from predominantly inattentive, predominantly hyperactive/impulsive, or combined presentation.

3. The method of claim 1, wherein the subject has one or more conditions comorbid with ADHD selected from oppositional defiant disorder, learning difficulties, depression, bipolar disorder, substance use disorder, autism spectrum disorder, personality disorder, or obsessive compulsive disorder.

4. The method of claim 3, wherein the one or more conditions comorbid with ADHD is oppositional defiant disorder.

5. The method of claim 1, wherein the subject has a reduced ADHD Rating Scale V score after administration of the crystalline psilocybin.

6. A method for treating an autism spectrum disorder (ASD) or a symptom thereof in a subject in need thereof, the method comprising administering to the subject a therapeutically effective amount of crystalline psilocybin, wherein the crystalline psilocybin is characterized by XRPD peaks at 11.5±0.1, 12.0±0.1, 14.5±0.1, 17.5±0.1 and 19.7±0.1° 2θ, and wherein the crystalline psilocybin has a chemical purity of greater than 97% as determined by HPLC analysis.

7. The method of claim 6, wherein the subject has one or more conditions comorbid with ASD selected from an attention-deficit hyperactivity disorder, a sleep-wake disorder, an impulse-control disorder, disruptive behavior, a conduct disorder, a depressive disorder, obsessive-compulsive disorder, bipolar disorder, or schizophrenia.

8. The method of claim 6, wherein the subject has one or more conditions comorbid with ASD selected from an inflammatory disorder, a gastrointestinal disorder, or epilepsy.

9. The method of claim 6, wherein the subject has depression.

10. The method of claim 6, wherein the subject has a reduced Vineland-II Adaptive Behavior (VABS-2) score after administration of the crystalline psilocybin.

11. The method of claim 6, wherein the subject has a reduced proxy version-t score on the Social Responsiveness Scale, Second Edition (SRS-2) after administration of the crystalline psilocybin.

12. The method of claim 6, wherein the crystalline psilocybin has no single impurity of greater than 1%.

13. The method of claim 6, wherein the crystalline psilocybin is administered in an oral dosage form.

14. The method of claim 6, wherein about 1 mg to about 40 mg of the crystalline psilocybin is administered.

15. The method of claim 6, wherein about 1 mg of the crystalline psilocybin is administered.

16. The method of claim 6, wherein about 5 mg of the crystalline psilocybin is administered.

17. The method of claim 6, wherein about 10 mg of the crystalline psilocybin is administered.

18. The method of claim 6, wherein about 25 mg of the crystalline psilocybin is administered.

19. The method of claim 6, wherein the crystalline psilocybin is further characterized by at least one peak selected from the group consisting of 20.4±0.1, 22.2±0.1, 24.3±0.1, and 25.7±0.1° 2θ.

20. The method of claim 1, wherein the crystalline psilocybin has no single impurity of greater than 1%.

21. The method of claim 1, wherein the crystalline psilocybin is administered in an oral dosage form.

22. The method of claim 1, wherein about 1 mg to about 40 mg of the crystalline psilocybin is administered.

23. The method of claim 1, wherein about 1 mg of the crystalline psilocybin is administered.

24. The method of claim 1, wherein about 5 mg of the crystalline psilocybin is administered.

25. The method of claim 1, wherein about 10 mg of the crystalline psilocybin is administered.

26. The method of claim 1, wherein about 25 mg of the crystalline psilocybin is administered.

27. The method of claim 1, wherein the crystalline psilocybin is further characterized by at least one peak selected from the group consisting of 20.4±0.1, 22.2±0.1, 24.3±0.1, and 25.7±0.1° 2θ.

* * * * *